United States Patent
Haining et al.

(10) Patent No.: US 12,050,219 B2
(45) Date of Patent: Jul. 30, 2024

(54) MODULATING BIOMARKERS SUCH AS SPP TO INCREASE TUMOR IMMUNITY AND IMPROVE THE EFFICACY OF CANCER IMMUNOTHERAPY

(71) Applicant: Dana-Farber Cancer Institute, Inc., Boston, MA (US)

(72) Inventors: William N. Haining, Newton, MA (US); Adrienne Long, Mountain View, CA (US); Robert Manguso, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 260 days.

(21) Appl. No.: 17/421,202

(22) PCT Filed: Jan. 9, 2020

(86) PCT No.: PCT/US2020/012827
§ 371 (c)(1),
(2) Date: Jul. 7, 2021

(87) PCT Pub. No.: WO2020/146563
PCT Pub. Date: Jul. 16, 2020

(65) Prior Publication Data
US 2022/0057403 A1     Feb. 24, 2022

Related U.S. Application Data

(60) Provisional application No. 62/815,507, filed on Mar. 8, 2019, provisional application No. 62/790,758, filed on Jan. 10, 2019.

(51) Int. Cl.
*G01N 33/574*     (2006.01)
*A61K 39/00*     (2006.01)
*A61K 39/395*     (2006.01)
*A61P 35/00*     (2006.01)

(52) U.S. Cl.
CPC .... *G01N 33/57492* (2013.01); *A61K 39/0011* (2013.01); *A61K 39/3955* (2013.01); *A61P 35/00* (2018.01); *A61K 2039/5158* (2013.01); *G01N 2333/96472* (2013.01)

(58) Field of Classification Search
CPC .... G01N 33/57492; G01N 2333/96472; A61P 35/00; A61K 39/0011; A61K 39/3955; A61K 2039/5158
See application file for complete search history.

(56) References Cited

U.S. PATENT DOCUMENTS

| | | |
|---|---|---|
| 2007/0224201 A1 | 9/2007 | Wu et al. |
| 2009/0081243 A1 | 3/2009 | Brandon et al. |
| 2015/0147761 A1 | 5/2015 | Meyer et al. |
| 2017/0058034 A1 | 3/2017 | Jiang et al. |
| 2018/0148378 A1 | 5/2018 | Mayr et al. |

FOREIGN PATENT DOCUMENTS

| | | | | |
|---|---|---|---|---|
| WO | WO-2013190075 A2 | * | 12/2013 | ............. C07K 14/47 |
| WO | WO-2018/148378 A1 | | 8/2018 | |
| WO | WO-2018204661 A1 | * | 11/2018 | ......... A61K 31/4709 |
| WO | WO-2020/146563 A1 | | 7/2020 | |

OTHER PUBLICATIONS

Voss et al (Mechanism, specificity, and physiology of signal peptide peptidase (SPP) and SPP-like proteases, Biochimica et Biophysica Acta 1828 (2013) 2828-2839) (Year: 2013).*
Durgeau et al., "Different expression levels of the TAP peptide transporter lead to recognition of different antigenic peptides by tumor-specific CTL$_+$A3092" $_+$A3098, *The Journal of Immunology* 187.11: 5532-5539 (2011).
Hsu et al., "Signal peptide peptidase-mediated nuclear localization of heme oxygenase-1 promotes cancer cell proliferation and invasion independent of its enzymatic activity", *Oncogene* 34.18: 2360-2370 (2015).
Oliveira et al., "New role of signal peptide peptidase to liberate C-terminal peptides for MHC class I presentation", *The Journal of Immunology* 191.8: 4020-4028 (2013).
International Search Report and Written Opinion for International Application No. PCT/US2020/012827 dated May 27, 2020.
Invitation to Pay Additional Fees for International Application No. PCT/US2020/012827 mailed Apr. 3, 2020.
Wei et al., "Signal peptide peptidase, encoded by HM13, contributes to tumor progression by affecting EGFRvIII secretion profiles in glioblastoma," CNS Neuroscience & Therapeutics, 23(3):257-265 (2017).

* cited by examiner

*Primary Examiner* — Mark Halvorson
*Assistant Examiner* — Dennis J Sullivan
(74) *Attorney, Agent, or Firm* — Foley Hoag LLP; Deann F. Smith; Philip S. Choi

(57) ABSTRACT

The present invention relates, in part, to methods of treating a cancer in a subject comprising administering to the subject a therapeutically effective amount of an agent that modulates one or more biomarkers, such as inhibits one or more biomarkers listed in Table 1 and/or increases one or more biomarkers listed in Table 4, in combination with an immunotherapy.

20 Claims, 32 Drawing Sheets
Specification includes a Sequence Listing.

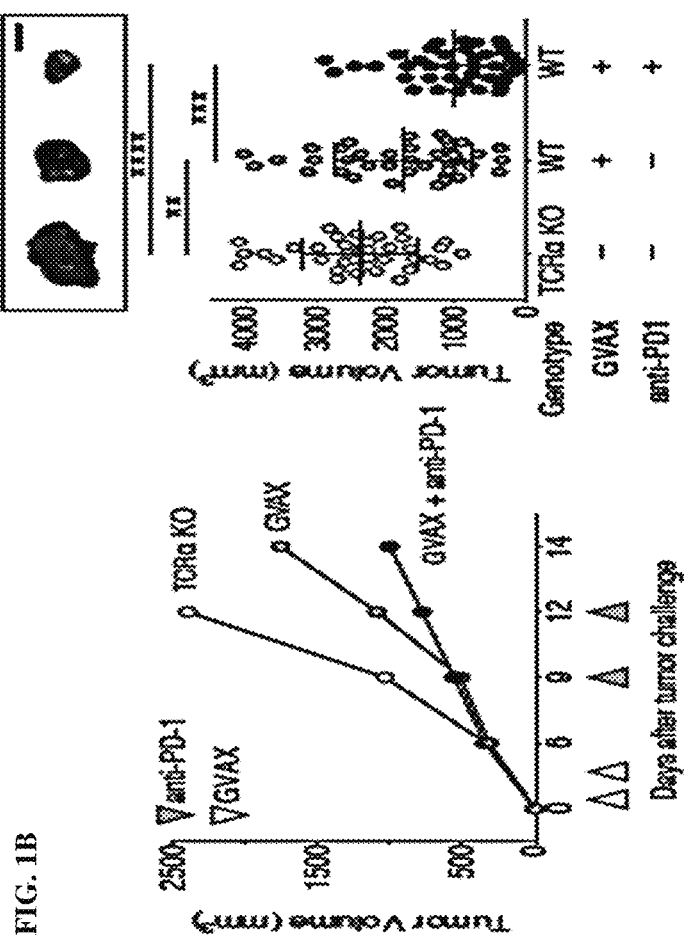
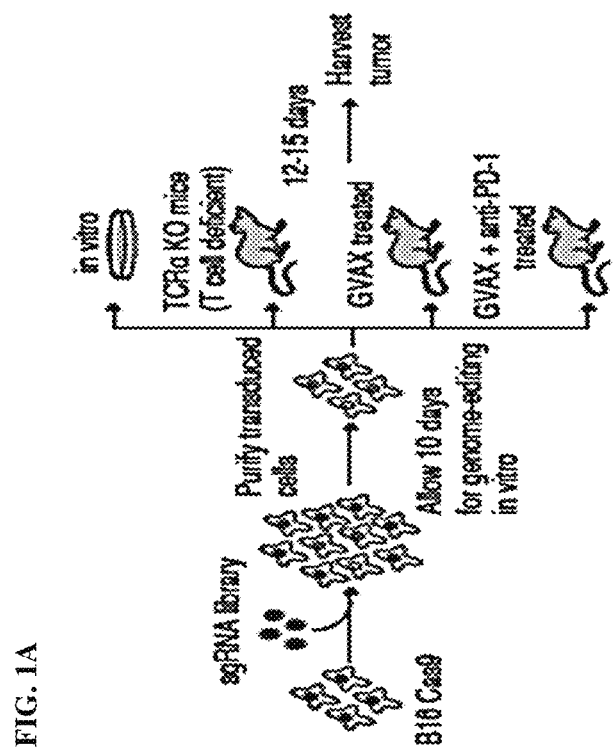
FIG. 1B
FIG. 1A

Signal peptide peptidase (SPP)
H13 (mouse), HM13 (human)

Efficient KO of SPP (qRT=PCR)

SPP knockout

SPP knockout

SEQUENCE LISTING

<160> NUMBER OF SEQ ID NOS: 84

<210> SEQ ID NO 1
<211> LENGTH: 1624
<212> TYPE: DNA
<213> ORGANISM: Homo sapiens

<400> SEQUENCE: 1

| | | | | | |
|---|---|---|---|---|---|
| gtgcgcggcg | cgggcttggg | agggagcacg | tcacttcctg | ttgccttagg | ggaacgtggc | 60 |
| tttccctgca | gagccggtgt | ctccgcctgc | gtccctgctg | cagcaaccgg | agctggagtc | 120 |
| ggatcccgaa | cgcaccctcg | ccatggactc | ggccctcagc | gatccgcata | acggcagtgc | 180 |
| cgaggcaggc | ggccccacca | acagcactac | gcggccgcct | tccacgcccg | agggcatcgc | 240 |
| gctggcctac | ggcagcctcc | tgctcatggc | gctgctgccc | atcttcttcg | gcgccctgcg | 300 |
| ctccgtacgc | tgcgcccgcg | gcaagaatgc | ttcagacatg | cctgaaacaa | tcaccagccg | 360 |
| ggatgccgcc | cgcttcccca | tcatcgccag | ctgcacactc | ttggggctct | acctcttttt | 420 |
| caaaatattc | tcccaggagt | acatcaacct | cctgctgtcc | atgtatttct | tcgtgctggg | 480 |
| aatcctggcc | ctgtcccaca | ccatcagccc | cttcatgaat | aagttttttc | cagccagctt | 540 |
| tccaaatcga | cagtaccagc | tgctcttcac | acagggttct | ggggaaaaca | aggaagagat | 600 |
| catcaattat | gaatttgaca | ccaaggacct | ggtgtgcctg | gcctgagca | gcatcgttgg | 660 |
| cgtctggtac | ctgctgagga | agcactggat | tgccaacaac | cttttttggcc | tggccttctc | 720 |
| ccttaatgga | gtagagctcc | tgcacctcaa | caatgtcagc | actggctgca | tcctgctggg | 780 |
| cggactcttc | atctacgatg | tcttctgggt | atttggcacc | aatgtgatgg | tgacagtggc | 840 |
| caagtccttc | gaggcaccaa | taaaattggt | gtttccccag | gatctgctgg | agaaaggcct | 900 |
| cgaagcaaac | aactttgcca | tgctgggact | tggagatgtc | gtcattccag | ggatcttcat | 960 |
| tgccttgctg | ctgcgctttg | acatcagctt | gaagaagaat | acccacacct | acttctacac | 1020 |
| cagctttgca | gcctacatct | tcggcctggg | ccttaccatc | ttcatcatgc | acatcttcaa | 1080 |
| gcatgctcag | cctgccctcc | tatacctggt | ccccgcctgc | atcggttttc | ctgtcctggt | 1140 |
| ggcgctggcc | aagggagaag | tgacagagat | gttcagttat | gaggagtcaa | atcctaagga | 1200 |
| tccagcggca | gtgacagaat | ccaaagaggg | aacagaggca | tcagcatcga | aggggctgga | 1260 |
| gaagaaagag | aaatgatgca | gctggtgccc | gagcctctca | gggccagacc | agacagatgg | 1320 |
| gggctgggcc | cacacaggcg | tgcaccggta | gagggcacag | gaggccaagg | gcagctccag | 1380 |
| gacagggcag | ggggcagcag | gatacctcca | gccaggcctc | tgtggcctct | gtttccttct | 1440 |
| cccttcttg | gccctcctct | gctcctcccc | acaccctgca | ggcaaaagaa | accccccagct | 1500 |
| tcccccctcc | ccgggagcca | ggtgggaaaa | gtgggtgtga | ttttagatt | ttgtattgtg | 1560 |
| gactgatttt | gcctcacatt | aaaaactcat | cccatggcca | gggcgggcca | ctgtgctcct | 1620 |
| ggaa | | | | | | 1624 |

<210> SEQ ID NO 2
<211> LENGTH: 377
<212> TYPE: PRT
<213> ORGANISM: Homo sapiens

<400> SEQUENCE: 2

Met Asp Ser Ala Leu Ser Asp Pro His Asn Gly Ser Ala Glu Ala Gly
1               5                   10                  15
Gly Pro Thr Asn Ser Thr Thr Arg Pro Pro Ser Thr Pro Glu Gly Ile
            20                  25                  30

Ala Leu Ala Tyr Gly Ser Leu Leu Met Ala Leu Leu Pro Ile Phe
         35                  40                  45

Phe Gly Ala Leu Arg Ser Val Arg Cys Ala Arg Gly Lys Asn Ala Ser
 50                  55                  60

Asp Met Pro Glu Thr Ile Thr Ser Arg Asp Ala Ala Arg Phe Pro Ile
 65                  70                  75                  80

Ile Ala Ser Cys Thr Leu Leu Gly Leu Tyr Leu Phe Phe Lys Ile Phe
                 85                  90                  95

Ser Gln Glu Tyr Ile Asn Leu Leu Ser Met Tyr Phe Phe Val Leu
             100                 105                 110

Gly Ile Leu Ala Leu Ser His Thr Ile Ser Pro Phe Met Asn Lys Phe
             115                 120                 125

Phe Pro Ala Ser Phe Pro Asn Arg Gln Tyr Gln Leu Leu Phe Thr Gln
 130                 135                 140

Gly Ser Gly Glu Asn Lys Glu Ile Ile Asn Tyr Glu Phe Asp Thr
145                 150                 155                 160

Lys Asp Leu Val Cys Leu Gly Leu Ser Ser Ile Val Gly Val Trp Tyr
                 165                 170                 175

Leu Leu Arg Lys His Trp Ile Ala Asn Asn Leu Phe Gly Leu Ala Phe
             180                 185                 190

Ser Leu Asn Gly Val Glu Leu Leu His Leu Asn Asn Val Ser Thr Gly
             195                 200                 205

Cys Ile Leu Leu Gly Gly Leu Phe Ile Tyr Asp Val Phe Trp Val Phe
 210                 215                 220

Gly Thr Asn Val Met Val Thr Val Ala Lys Ser Phe Glu Ala Pro Ile
225                 230                 235                 240

Lys Leu Val Phe Pro Gln Asp Leu Leu Glu Lys Gly Leu Glu Ala Asn
                 245                 250                 255

Asn Phe Ala Met Leu Gly Leu Gly Asp Val Val Ile Pro Gly Ile Phe
             260                 265                 270

Ile Ala Leu Leu Leu Arg Phe Asp Ile Ser Leu Lys Lys Asn Thr His
             275                 280                 285

Thr Tyr Phe Tyr Thr Ser Phe Ala Ala Tyr Ile Phe Gly Leu Gly Leu
 290                 295                 300

Thr Ile Phe Ile Met His Ile Phe Lys His Ala Gln Pro Ala Leu Leu
305                 310                 315                 320

Tyr Leu Val Pro Ala Cys Ile Gly Phe Pro Val Leu Val Ala Leu Ala
                 325                 330                 335

Lys Gly Glu Val Thr Glu Met Phe Ser Tyr Glu Glu Ser Asn Pro Lys
             340                 345                 350

Asp Pro Ala Ala Val Thr Glu Ser Lys Glu Gly Thr Glu Ala Ser Ala
             355                 360                 365

Ser Lys Gly Leu Glu Lys Lys Glu Lys
 370                 375

<210> SEQ ID NO 3
<211> LENGTH: 1827
<212> TYPE: DNA
<213> ORGANISM: Homo sapiens

<400> SEQUENCE: 3
gtgcgcggcg cgggcttggg agggagcacg tcacttcctg ttgccttagg ggaacgtggc    60
tttccctgca gagccggtgt ctccgcctgc gtccctgctg cagcaaccgg agctggagtc   120

-continued

```
ggatcccgaa cgcaccctcg ccatggactc ggccctcagc gatccgcata acggcagtgc    180
cgaggcaggc ggccccacca acagcactac gcggccgcct ccacgcccg agggcatcgc    240 gctggcctac ggcagcctcc tgctcatggc gctgctgccc atcttcttcg gcgccctgcg    300
ctccgtacgc tgcgcccgcg gcaagaatgc ttcagacatg cctgaaacaa tcaccagccg    360
ggatgccgcc cgcttcccca tcatcgccag ctgcacactc ttggggctct acctcttttt    420
caaaatattc tcccaggagt acatcaacct cctgctgtcc atgtatttct tcgtgctggg    480
aatcctggcc ctgtcccaca ccatcagccc cttcatgaat aagttttttc cagccagctt    540
tccaaatcga cagtaccagc tgctcttcac acagggttct ggggaaaaca aggaagagat    600
catcaattat gaatttgaca ccaaggacct ggtgtgcctg ggcctgagca gcatcgttgg    660
cgtctggtac ctgctgagga agcactggat tgccaacaac cttttttggcc tggccttctc    720 ccttaatgga gtagagctcc tgcacctcaa caatgtcagc actggctgca tcctgctggg    780
cggactcttc atctacgatg tcttctgggt atttggcacc aatgtgatgg tgacagtggc    840
caagtccttc gaggcaccaa taaaattggt gtttccccag gatctgctgg agaaaggcct    900
cgaagcaaac aactttgcca tgctgggact tggagatgtc gtcattccag ggatcttcat    960
tgccttgctg ctgcgctttg acatcagctt gaagaagaat acccacacct acttctacac   1020
cagctttgca gcctacatct tcggcctggg ccttaccatc ttcatcatgc acatcttcaa   1080
gcatgctcag cctgccctcc tatacctggt ccccgcctgc atcggttttc ctgtcctggt   1140
ggcgctggcc aagggagaag tgacagagat gttcagctac gagtcctcgg cggaaatcct   1200
gcctcatacc ccgaggctca cccacttccc cacagtctcg ggctccccag ccagcctggc   1260
cgactccatg cagcagaagc tagctggccc tcgccgccgg cgcccgcaga atcccagcgc   1320
catgtaatgc ccagcgggtg cccacctgcc cgcttccccc tactgccccg ggcccaagt    1380 tatgaggagt caaatcctaa ggatccagcg cagtgacag aatccaaaga gggaacagag   1440
gcatcagcat cgaaggggct ggagaagaaa gagaaatgat gcagctggtg cccgagcctc   1500
tcagggccag accagacaga tgggggctgg gcccacacag gcgtgcaccg gtagagggca   1560
caggaggcca agggcagctc caggacaggg caggggcag caggatacct ccagccaggc   1620
ctctgtggcc tctgtttcct tctccctttc ttggccctcc tctgctcctc cccacaccct   1680
gcaggcaaaa gaaccccca gcttccccc tccccgggag ccaggtggga aaagtgggtg   1740 tgattttttag attttgtatt gtggactgat tttgcctcac attaaaaact catcccatgg   1800
ccagggcggg ccactgtgct cctggaa                                       1827
```

<210> SEQ ID NO 4
<211> LENGTH: 394
<212> TYPE: PRT
<213> ORGANISM: Homo sapiens

<400> SEQUENCE: 4

```
Met Asp Ser Ala Leu Ser Asp Pro His Asn Gly Ser Ala Glu Ala Gly
1               5                   10                  15

Gly Pro Thr Asn Ser Thr Thr Arg Pro Pro Ser Thr Pro Glu Gly Ile
            20                  25                  30

Ala Leu Ala Tyr Gly Ser Leu Leu Leu Met Ala Leu Leu Pro Ile Phe
        35                  40                  45

Phe Gly Ala Leu Arg Ser Val Arg Cys Ala Arg Gly Lys Asn Ala Ser
    50                  55                  60
```

Asp Met Pro Glu Thr Ile Thr Ser Arg Asp Ala Ala Arg Phe Pro Ile
65                  70                  75                  80

Ile Ala Ser Cys Thr Leu Leu Gly Leu Tyr Leu Phe Phe Lys Ile Phe
                85                  90                  95

Ser Gln Glu Tyr Ile Asn Leu Leu Ser Met Tyr Phe Phe Val Leu
            100                 105                 110

Gly Ile Leu Ala Leu Ser His Thr Ile Ser Pro Phe Met Asn Lys Phe
            115                 120                 125

Phe Pro Ala Ser Phe Pro Asn Arg Gln Tyr Gln Leu Leu Phe Thr Gln
130                 135                 140

Gly Ser Gly Glu Asn Lys Glu Glu Ile Ile Asn Tyr Glu Phe Asp Thr
145                 150                 155                 160

Lys Asp Leu Val Cys Leu Gly Leu Ser Ser Ile Val Gly Val Trp Tyr
                165                 170                 175

Leu Leu Arg Lys His Trp Ile Ala Asn Asn Leu Phe Gly Leu Ala Phe
            180                 185                 190

Ser Leu Asn Gly Val Glu Leu Leu His Leu Asn Asn Val Ser Thr Gly
            195                 200                 205

Cys Ile Leu Leu Gly Gly Leu Phe Ile Tyr Asp Val Phe Trp Val Phe
210                 215                 220

Gly Thr Asn Val Met Val Thr Val Ala Lys Ser Phe Glu Ala Pro Ile
225                 230                 235                 240

Lys Leu Val Phe Pro Gln Asp Leu Leu Glu Lys Gly Leu Glu Ala Asn
                245                 250                 255

Asn Phe Ala Met Leu Gly Leu Gly Asp Val Val Ile Pro Gly Ile Phe
            260                 265                 270

Ile Ala Leu Leu Leu Arg Phe Asp Ile Ser Leu Lys Lys Asn Thr His
            275                 280                 285

Thr Tyr Phe Tyr Thr Ser Phe Ala Ala Tyr Ile Phe Gly Leu Gly Leu
290                 295                 300

Thr Ile Phe Ile Met His Ile Phe Lys His Ala Gln Pro Ala Leu Leu
305                 310                 315                 320

Tyr Leu Val Pro Ala Cys Ile Gly Phe Pro Val Leu Val Ala Leu Ala
                325                 330                 335

Lys Gly Glu Val Thr Glu Met Phe Ser Tyr Glu Ser Ser Ala Glu Ile
            340                 345                 350

Leu Pro His Thr Pro Arg Leu Thr His Phe Pro Thr Val Ser Gly Ser
            355                 360                 365

Pro Ala Ser Leu Ala Asp Ser Met Gln Gln Lys Leu Ala Gly Pro Arg
370                 375                 380

Arg Arg Arg Pro Gln Asn Pro Ser Ala Met
385                 390

<210> SEQ ID NO 5
<211> LENGTH: 1771
<212> TYPE: DNA
<213> ORGANISM: Homo sapiens

<400> SEQUENCE: 5
gtgcgcggcg cgggcttggg agggagcacg tcacttcctg ttgccttagg ggaacgtggc    60
tttccctgca gagccggtgt ctccgcctgc gtccctgctg cagcaaccgg agctggagtc   120
ggatcccgaa cgcaccctcg ccatggactc ggccctcagc gatccgcata acggcagtgc   180
cgaggcaggc ggccccacca acagcactac gcggccgcct tccacgcccg agggcatcgc   240

```
gctggcctac ggcagcctcc tgctcatggc gctgctgccc atcttcttcg gcgccctgcg    300
ctccgtacgc tgcgcccgcg gcaagaatgc ttcagacatg cctgaaacaa tcaccagccg    360
ggatgccgcc cgcttcccca tcatcgccag ctgcacactc ttggggctct acctcttttt    420
caaaatattc tcccaggagt acatcaacct cctgctgtcc atgtatttct tcgtgctggg    480
aatcctggcc ctgtcccaca ccatcagccc cttcatgaat aagttttttc cagccagctt    540
tccaaatcga cagtaccagc tgctcttcac acagggttct ggggaaaaca aggaagagat    600
catcaattat gaatttgaca ccaaggacct ggtgtgcctg ggcctgagca gcatcgttgg    660
cgtctggtac ctgctgagga agcactggat tgccaacaac cttttttggcc tggccttctc    720 ccttaatgga gtagagctcc tgcacctcaa caatgtcagc actggctgca tcctgctggg    780
cggactcttc atctacgatg tcttctgggt atttggcacc aatgtgatgg tgacagtggc    840
caagtccttc gaggcaccaa taaaattggt gtttccccag gatctgctgg agaaaggcct    900
cgaagcaaac aactttgcca tgctgggact tggagatgtc gtcattccag gatcttcat     960 tgccttgctg ctgcgctttg acatcagctt gaagaagaat cccacacct acttctacac     1020 cagctttgca gcctacatct tcggcctggg ccttaccatc ttcatcatgc acatcttcaa    1080
gcatgctcag cctgccctcc tatacctggt ccccgcctgc atcggttttc ctgtcctggt    1140
ggcgctggcc aagggagaag tgacagagat gttcagctac gagtcctcgg cggaaatcct    1200
gcctcatacc ccgaggctca cccacttccc cacagtctcg ggctccccag ccagcctggc    1260
cgactccatg cagcagaagc tagctggccc tcgccgccgg cgcccgcaga atcccagcgc    1320
catttatgag gagtcaaatc ctaaggatcc agcggcagtg acagaatcca agagggaac    1380 agaggcatca gcatcgaagg ggctggagaa gaaagagaaa tgatgcagct ggtgcccgag    1440
cctctcaggg ccagaccaga cagatggggg ctgggcccac acaggcgtgc accggtagag    1500
ggcacaggag gccaagggca gctccaggac agggcagggg gcagcaggat acctccagcc    1560
aggcctctgt ggcctctgtt tccttctccc tttcttggcc ctcctctgct cctccccaca    1620
ccctgcaggc aaaagaaacc cccagcttcc ccctccccg ggagccaggt gggaaaagtg    1680
ggtgtgattt ttagattttg tattgtggac tgattttgcc tcacattaaa aactcatccc    1740
atggccaggg cgggccactg tgctcctgga a                                   1771
```

<210> SEQ ID NO 6
<211> LENGTH: 426
<212> TYPE: PRT
<213> ORGANISM: Homo sapiens

<400> SEQUENCE: 6

Met Asp Ser Ala Leu Ser Asp Pro His Asn Gly Ser Ala Glu Ala Gly
1               5                   10                  15

Gly Pro Thr Asn Ser Thr Thr Arg Pro Pro Ser Thr Pro Glu Gly Ile
                20                  25                  30

Ala Leu Ala Tyr Gly Ser Leu Leu Leu Met Ala Leu Leu Pro Ile Phe
            35                  40                  45

Phe Gly Ala Leu Arg Ser Val Arg Cys Ala Arg Gly Lys Asn Ala Ser
        50                  55                  60

Asp Met Pro Glu Thr Ile Thr Ser Arg Asp Ala Ala Arg Phe Pro Ile
65                  70                  75                  80

Ile Ala Ser Cys Thr Leu Leu Gly Leu Tyr Leu Phe Phe Lys Ile Phe
                85                  90                  95

```
Ser Gln Glu Tyr Ile Asn Leu Leu Leu Ser Met Tyr Phe Val Leu
            100                 105                 110
Gly Ile Leu Ala Leu Ser His Thr Ile Ser Pro Phe Met Asn Lys Phe
        115                 120                 125
Phe Pro Ala Ser Phe Pro Asn Arg Gln Tyr Gln Leu Leu Phe Thr Gln
    130                 135                 140
Gly Ser Gly Glu Asn Lys Glu Glu Ile Ile Asn Tyr Glu Phe Asp Thr
145                 150                 155                 160
Lys Asp Leu Val Cys Leu Gly Leu Ser Ser Ile Val Gly Val Trp Tyr
                165                 170                 175
Leu Leu Arg Lys His Trp Ile Ala Asn Asn Leu Phe Gly Leu Ala Phe
            180                 185                 190
Ser Leu Asn Gly Val Glu Leu Leu His Leu Asn Asn Val Ser Thr Gly
        195                 200                 205
Cys Ile Leu Leu Gly Gly Leu Phe Ile Tyr Asp Val Phe Trp Val Phe
    210                 215                 220
Gly Thr Asn Val Met Val Thr Val Ala Lys Ser Phe Glu Ala Pro Ile
225                 230                 235                 240
Lys Leu Val Phe Pro Gln Asp Leu Leu Glu Lys Gly Leu Glu Ala Asn
                245                 250                 255
Asn Phe Ala Met Leu Gly Leu Gly Asp Val Val Ile Pro Gly Ile Phe
            260                 265                 270
Ile Ala Leu Leu Leu Arg Phe Asp Ile Ser Leu Lys Lys Asn Thr His
        275                 280                 285
Thr Tyr Phe Tyr Thr Ser Phe Ala Ala Tyr Ile Phe Gly Leu Gly Leu
    290                 295                 300
Thr Ile Phe Ile Met His Ile Phe Lys His Ala Gln Pro Ala Leu Leu
305                 310                 315                 320
Tyr Leu Val Pro Ala Cys Ile Gly Phe Pro Val Leu Val Ala Leu Ala
                325                 330                 335
Lys Gly Glu Val Thr Glu Met Phe Ser Tyr Glu Ser Ser Ala Glu Ile
            340                 345                 350
Leu Pro His Thr Pro Arg Leu Thr His Phe Pro Thr Val Ser Gly Ser
        355                 360                 365
Pro Ala Ser Leu Ala Asp Ser Met Gln Gln Lys Leu Ala Gly Pro Arg
    370                 375                 380
Arg Arg Arg Pro Gln Asn Pro Ser Ala Ile Tyr Glu Glu Ser Asn Pro
385                 390                 395                 400
Lys Asp Pro Ala Ala Val Thr Glu Ser Lys Glu Gly Thr Glu Ala Ser
                405                 410                 415
Ala Ser Lys Gly Leu Glu Lys Lys Glu Lys
            420                 425

<210> SEQ ID NO 7
<211> LENGTH: 2169
<212> TYPE: DNA
<213> ORGANISM: Homo sapiens

<400> SEQUENCE: 7
gtgcgcggcg cgggcttggg agggagcacg tcacttcctg ttgccttagg ggaacgtggc      60
tttccctgca gagccggtgt ctccgcctgc gtccctgctg cagcaaccgg agctggagtc     120
ggatcccgaa cgcaccctcg ccatggactc ggccctcagc gatccgcata acggcagtgc     180
cgaggcaggc ggccccacca acagcactac gcggccgcct tccacgcccg agggcatcgc     240
```

```
gctggcctac ggcagcctcc tgctcatggc gctgctgccc atcttcttcg gcgccctgcg    300
ctccgtacgc tgccgcccgcg gcaagaatgc ttcagacatg cctgaaacaa tcaccagccg    360
ggatgccgcc cgcttcccca tcatcgccag ctgcacactc ttggggctct acctctttt    420 caaaatattc tcccaggagt acatcaacct cctgctgtcc atgtatttct tcgtgctggg    480
aatcctggcc ctgtcccaca ccatcaggtc agaaggcatc tctctgcaac atttgaagca    540
gctttctcgg gaaccagtac agggtcttgg atgagaacat gacttttggc atcattcaga    600
gccaggtttg aatcctggct ataaaactca agggactctt tcccctgcac actgtagatg    660
actaggacaa gaacaatgac ctctctgggc cacagtttcc ttatagacat gatgaggatc    720
tggtgggtgt ttccaccacc acagctgttg ggaaagtgat tgtgagcag taatgtcatg    780 ttagttgtga cagtactcag gtgagtaaca ccagtaccac ctgccgggtg ttgtggccta    840
gctgtgtgct aagtgccatg ttgggctcct cacacatgat cgtgtttcgt aaggagccag    900
aggcagcata gtgaaaagtt aggagcgtgg gctctggcat ttgactacct tactttgagt    960
ccagactctg ccacttaata gctctgtgat cttgggcaag ttacttaatc tctctggcct   1020
caatttcctg gtaatgtgg agaaaaataa tagtgccctt cccatggggt catgtggaaa   1080
gcttttagca cagtatctgg tgatttaaag tgttcagtaa ctattagctg ttactgtcat   1140
tatctgtgtt aacctgccag acaacctat atgggttgct tttgctttca cacctgtatg   1200
atagtcatgg aaactgaagc ccagagaggt taagaaattt gctaggatca caccactaat   1260
aagcaacaga gccaggattc aaacccaggt gtggctccag agcccatcct cttcccactg   1320
ctaccctaac tcaaactgcc acatgctcgt gtcctttcag tggggagagt ggttcattag   1380 aggggggttgc tactttatt ttggacaggc cagttctcca ttctgcagga ctatcccatg   1440
tattacaaac agttggcaac cttgccctgc tcaccaaatg ggagttgcat accagtattc   1500
cccagcttgt gactacagag atgtcccagt atgtttcttt ctgccccgtt gaagaggtgc   1560
agcctcaggc tgagaaacac tgatagacca gaggtggcc agggttccca gaaggaagga   1620
actcaccttg aacttagctt tctttgaagg gtaggaaacc tggaagacgt acaaaggagg   1680
gagaggtcag gtgctagaaa gtttgtgcac attgagggca tgggcagaat ctgctcccaa   1740
aagcattgaa agccaatatg aggccaggtg gtggctcatg cctgtaatcc cagcactttg   1800
ggaggccaag gcaggcggat cacaaggtca ggagattgag accatcctgg ccaacatggt   1860 gaaacccgt ctctactaaa aatacaaaaa aattagctgg gcatggtggt gcatgcctgt   1920
agtcccagct actcaggagg ctgaggtagg agaatcattg aacctgggag gcggaggttg   1980
cagtgagccg agattgcacc actgcattcc agcctggcga cagagtgaga ctccatctca   2040
aaaaaaaaaa aaaagccaat atgaatgtgg cttcattctt ctaggcacac tggcaggaca   2100
gtgtggtagt caggagcaca gggtcaagag gcaggcagcc ttgggacaaa cacctggtgc   2160
tgccagctc                                                          2169
```

<210> SEQ ID NO 8
<211> LENGTH: 143
<212> TYPE: PRT
<213> ORGANISM: Homo sapiens

<400> SEQUENCE: 8

```
Met Asp Ser Ala Leu Ser Asp Pro His Asn Gly Ser Ala Glu Ala Gly
1               5                   10                  15

Gly Pro Thr Asn Ser Thr Thr Arg Pro Pro Ser Thr Pro Glu Gly Ile
            20                  25                  30
```

```
Ala Leu Ala Tyr Gly Ser Leu Leu Met Ala Leu Leu Pro Ile Phe
         35                  40                  45

Phe Gly Ala Leu Arg Ser Val Arg Cys Ala Arg Gly Lys Asn Ala Ser
     50                  55                  60

Asp Met Pro Glu Thr Ile Thr Ser Arg Asp Ala Ala Arg Phe Pro Ile
 65                  70                  75                  80

Ile Ala Ser Cys Thr Leu Leu Gly Leu Tyr Leu Phe Phe Lys Ile Phe
                 85                  90                  95

Ser Gln Glu Tyr Ile Asn Leu Leu Ser Met Tyr Phe Phe Val Leu
                100                 105                 110

Gly Ile Leu Ala Leu Ser His Thr Ile Arg Ser Glu Gly Ile Ser Leu
                115                 120                 125

Gln His Leu Lys Gln Leu Ser Arg Glu Pro Val Gln Gly Leu Gly
        130                 135                 140

<210> SEQ ID NO 9
<211> LENGTH: 5402
<212> TYPE: DNA
<213> ORGANISM: Mus musculus

<400> SEQUENCE: 9
```

| | | | | | |
|---|---|---|---|---|---|
| gggaggcacg | tcacttcctg | tttctttagg | ggaacgtggc | tttccccgca | gtgcctcttc | 60 |
| tccgtctacg | ttcgtgctgc | ggcggccgga | gctggagtcg | gagcccgagc | gcagcctcgc | 120 |
| catggattcg | gctgtcagcg | atccgcacaa | cggcagcgcc | gaggctggca | ccccagccaa | 180 |
| cggcacgacg | cggccgccct | ccacgcccga | gggcatcgcg | ctggcctacg | gcagcctcct | 240 |
| gctcatggcg | ctgctgccca | tcttcttcgg | cgccctgcgc | tcggtgcgct | gcgcccgcgg | 300 |
| caagagctct | tcggacatgc | cagaaaccat | caccagtcga | gatgccgccc | gcttccccat | 360 |
| catcgccagc | tgcacactcc | tggggctcta | cctcttttc  | aaaatattct | cccaggagta | 420 |
| catcaacctc | ttgctgtcca | tgtatttctt | cgtgctgggg | atcctggccc | tgtcacacac | 480 |
| catcagcccc | ttcatgaata | agttttttcc | agccaacttc | ccaaaccgcc | agtatcagct | 540 |
| gctcttcaca | cagggctctg | ggaaaacaa  | agaagagatc | atcaactatg | agtttgacac | 600 |
| taaggacctg | gtgtgcctgg | gcctaagcag | cgtcgttggt | gtctggtacc | ttctgaggaa | 660 |
| gcactggatt | gccaacaacc | tgtttggcct | ggccttctcc | cttaatgggg | tagagctcct | 720 |
| gcacctgaac | aacgtgagca | ctggctgtat | cctgctcgga | ggactcttca | tctatgacat | 780 |
| cttctgggta | ttcggcacca | acgtgatggt | gacagtggcc | aagtcctttg | aggcaccaat | 840 |
| aaaattggtg | ttcccccagg | atctgctgga | gaagggcctt | gaagcagaca | ctttgccat  | 900 |
| gctgggactt | ggagacattg | tcattccagg | gatcttcatt | gccttactgc | ttcgttttga | 960 |
| catcagcttg | aagaagaaca | cgcacaccta | cttctacacc | agcttcgccg | cctacatctt | 1020 |
| cggcctgggt | ctcaccatct | tcatcatgca | catcttcaag | cacgcccagc | cggctctcct | 1080 |
| gtacctggtc | cctgcctgca | tcggcttttcc | tgtcctggtg | cactagcca  | agggagaagt | 1140 |
| ggccgagatg | ttcagctacg | agtcctcggc | cgtaatcctg | cctcatacgc | cgaggctcac | 1200 |
| tcactttccc | acagtctcgg | gctccctgc  | cagcctggcc | gactccatgc | agcagaagct | 1260 |
| agctggccct | cgtcgccggc | gcccgcagaa | tcccagcgcc | atgtagtgcc | cagcaggtgc | 1320 |
| ccacctgccc | gcttcccac  | tgtcctgggc | ctaagttatg | aggagtccaa | ccctaaagat | 1380 |
| ccagcagccg | agactgaatc | caaagaggag | tcaacagagg | cgtcggcatc | gaagaggcta | 1440 |
| gagaagaagg | agaaatgagg | cagcgctgcc | tgacccttga | gggccagatc | ggacaggcag | 1500 |

```
gggatgacct gtgggcgaca cagaagagaa gacacctgca ggaggcgacg gtggccccag    1560
gatggggagc aggcctctgc tgcctgttcc ctctgcccct tctctggctt cctctgctcc    1620
tcctcatccc tgcaggcaaa ggaaaccctc tgctgcttcc ttccccagga gccaggtggg    1680
cactgaatgt ggttttttaga tttttgtatt gtggactgtc tttgcctcat attaaaaact    1740
catcccatgg ccgctaggcc accgtgctcc aagggagctc tcagcagctc tgcctagtgt    1800
ttcgtgctga actcatcggg gctttgcgag taccttcgtg ggtgccaggc cagaagtggg    1860
ttcccatgag cctcctttcc cagccactcc tgggggacag tgaaggtggt gggcgagtgc    1920
ttgctgcgcc ccgctggcct tggtatgaga tgaagagagt gtcacggggc accccgcttc    1980
agcaaaggga cttgtaacta tggacagacg gctccctggg cttgctgtcc atctggctgg    2040
aaatcaaagg tccatctttt ccatccccag gtctcccaaa atacagctca ggtcttcaga    2100
aagcctgccc tggggaggga gcagattcca gagaacagaa gaggccatcc aaggtcaggc    2160
aagagttaga gatcccaaag ccaaagtctc cctcccttcct gaccttcaag cgagtccctaa   2220 aagggcaagg agagggcagc tcatccctcg tccacctgcc caggtggaaa aactgagact    2280
gtggaatggc catgacctgt gagctttccc tggctagggt tcaggttaa tgactaaaat    2340 gaacagattg gaaatggtca gagagcaaag gctgtccaga gcctggggaa taagagtgga    2400
gggaggtgag tgtccccagt ttcagatgta gaccaggtgt gtcgatgcaa gcttcggatc    2460
tgtacttcgg atgctaagct gcgcgtgctt tagcctcgct ctacagagga gggaatgggg    2520
ccgctcaccc ccagacagtg actgcagctc aacatactaa gcactgtgct gtcctcttat    2580
aggaccaaga agtcactgtg gctgctctgc tgggccaccg agtcagccac ccaacttctc    2640
tgggtctaaa agtctggaga ggaaagcctg aaaggctctc taggcagggg gtctctttag    2700
ggccttcttg gatctctgca ggcttgtact gccttcaggg ggaggccatg tggtcctgga    2760
acaaagcccc tctgagggtg gcagatgggg caggcagccc aggcacacag tgtggttggc    2820
tcaacagccc acagcccaca aaggcctcat tgagtcactg ccgacccca gcagaggctg     2880 aggtggcagt ggcgccgggc gcctgccacc taatgaccgt cctggctggg ccagatgttc    2940
cacagacctt gcagcgccga tcagggcctg cctggccaag cagccacaga ggccactcca    3000
gttccaatta accagcttca gctgagcaaa ccacgggcag cagcggggcc cagcctgggc    3060
ggtgggcccg gccggcccg gccggccggc agagcctctg agtctagact ccagatgtga    3120
accgccaccg cctgagcccc atggaaaaat ggcaccaggc cgggcgcgca tcaggcctgc    3180
atactgggag gcgggatggg tggctgggca gggcctcaga tgggactggt gccaggctca    3240
ccctggagtg ggggtggatt cttcggaagc tgctttcaaa cagatttccc ctggtttgtg    3300
gtgtcctctc tgtgccttgg ttttttccagt aggaggaggc tgttagggct taagaccatc    3360
cctgcaagaa accccatact ctatacatgc ttaccgggtt agcatgtggc cagcattgta    3420
gagtgttcta gaagttcttg actatccctg tgtggaatat gcctgccatc ccagcacttg    3480
tagaggcagc aagctgagat aagccttgtc tacatagcaa gtttcaggtc agccagcgct    3540
ccaagataag aattagctta aaaaattaaa aaaaaaaaa gccagattga tccatactgg    3600
tttgtgacta atcttgaacc cgggagactt aagacaggat gatcaattca aagtcccccct   3660 tggctacaaa gagttcaaag ccagagcctg cctctagcca agtggagaga ttaattgtaa    3720
caatcctata tggcacctac catcatcttc acagataagg aatggcaagc aggtctgcac    3780
tgacctgccg gtgtttgacc ttagtgcctg gcttatctaa actcatgttc accactgtgc    3840
```

```
tgaattcctg tttcttgtct ttggggacag catagggatt atggggacag ggagaggatg    3900
acaatggatg gcttccagga tgagatggca gtgtcctgac atctgatccc tttcttcagc    3960
taaaagaggt gagagcatcc tctcacccag ttgccctttg gaaagtcttt ctgtttccat    4020
gcagtgtcag acaccagcta agttgataag gacctaacag ggagcacaaa tggtggctct    4080
ccggagctga catcctgcaa gatggcattc ctctggggag actgacggaa atgactgggt    4140
ggatgtgcca agagatgatg ccacaggaga tgggactcct gccccggtcc tggtgggcaa    4200
agcaagggtc tgtgccatcc agctgcccctt gcacaaaacg acaaactcag tgctcccgcc    4260
accaccccag gaaaaaaaaa gccaggctgg caggggtctc tgcggcagcc tgcgcctcct    4320
tcctgttctc caactatgga ctccccgcgt gactgccggc cacgggagga gcggcatcct    4380
gcggggtgcg ccaggaaggg ccttgcaagc gggaaggaaa gcgccacctc tctcgccccc    4440
gccaaggcca cacctgggct ccgcaggcgg tagcgccggg ccagcgcctg gctccagcga    4500
gtctgggccg ccctccctac gcactgcggg ggccgccagc tggctggtc gctcgcgcag    4560
ctccgcggcc ggaagctgtt cactgggggg cgtggtccgt gttggtccca cccaggaggg    4620
cagggtcact gtagcccaag gacaagcttt ggaatttcgg ctggctttac agtctccatt    4680
tgtgtttttc tttcctccca gtcccagggg accgaaccgt gctaagtgag cgctatatca    4740
ctgagctgta tccccgaaac ccttcacttc gatgttctta cctagaaaat gagggaattg    4800
taccccaccc ccaacacctg gcccagtgca aaatcatgcc ggcactgtgt gtgttaaatg    4860
aatgcatgcg aaggtctaaa acctccctga ggcctggcgt tgtcttgggc aaaaagctcc    4920
ccgcagatga ggaatccttt gtttcatccc tgagctgcgt tttcctcagt cagtggtggc    4980
tgagaagaaa cagtcctcgg aaaacatgga cacctagaat atcctccgta aaagatatgg    5040
aagagtctcc aagatggggc ggggggggggg gggggggaat gtggtagcat actcctgcaa    5100
tcctaaaacc cgagagtaag gcaggaggat cgagagtaag gcaggaggat cgtctagagc    5160
cagctcctga tgcagatttc aaggctagtt tgggctacat aagatcctgt tgtctcaaaa    5220
ctgatatatt tggaggtaaa aatgctcaaa agaattacac ttggaagatt ttgcttttg    5280
gagggtaggg gagtttggag ggagtggggtt gcttgggttt gagattggaa cttgctatgt    5340
aacccaggct ggcccagatg gaactctgta cagcagacta ggattacaag aaactttctc    5400
tg                                                                    5402
```

<210> SEQ ID NO 10
<211> LENGTH: 394
<212> TYPE: PRT
<213> ORGANISM: Mus musculus

<400> SEQUENCE: 10

```
Met Asp Ser Ala Val Ser Asp Pro His Asn Gly Ser Ala Glu Ala Gly
1               5                   10                  15

Thr Pro Ala Asn Gly Thr Thr Arg Pro Pro Ser Thr Pro Glu Gly Ile
            20                  25                  30

Ala Leu Ala Tyr Gly Ser Leu Leu Leu Met Ala Leu Leu Pro Ile Phe
        35                  40                  45

Phe Gly Ala Leu Arg Ser Val Arg Cys Ala Arg Gly Lys Ser Ser Ser
    50                  55                  60

Asp Met Pro Glu Thr Ile Thr Ser Arg Asp Ala Ala Arg Phe Pro Ile
65                  70                  75                  80

Ile Ala Ser Cys Thr Leu Leu Gly Leu Tyr Leu Phe Phe Lys Ile Phe
                85                  90                  95
```

Ser Gln Glu Tyr Ile Asn Leu Leu Ser Met Tyr Phe Phe Val Leu
            100                 105                 110

Gly Ile Leu Ala Leu Ser His Thr Ile Ser Pro Phe Met Asn Lys Phe
            115                 120                 125

Phe Pro Ala Asn Phe Pro Asn Arg Gln Tyr Gln Leu Leu Phe Thr Gln
        130                 135                 140

Gly Ser Gly Glu Asn Lys Glu Ile Ile Asn Tyr Glu Phe Asp Thr
145                 150                 155                 160

Lys Asp Leu Val Cys Leu Gly Leu Ser Ser Val Val Gly Val Trp Tyr
                165                 170                 175

Leu Leu Arg Lys His Trp Ile Ala Asn Asn Leu Phe Gly Leu Ala Phe
            180                 185                 190

Ser Leu Asn Gly Val Glu Leu Leu His Leu Asn Asn Val Ser Thr Gly
            195                 200                 205

Cys Ile Leu Leu Gly Gly Leu Phe Ile Tyr Asp Ile Phe Trp Val Phe
        210                 215                 220

Gly Thr Asn Val Met Val Thr Val Ala Lys Ser Phe Glu Ala Pro Ile
225                 230                 235                 240

Lys Leu Val Phe Pro Gln Asp Leu Leu Glu Lys Gly Leu Glu Ala Asp
                245                 250                 255

Asn Phe Ala Met Leu Gly Leu Gly Asp Ile Val Ile Pro Gly Ile Phe
            260                 265                 270

Ile Ala Leu Leu Leu Arg Phe Asp Ile Ser Leu Lys Lys Asn Thr His
        275                 280                 285

Thr Tyr Phe Tyr Thr Ser Phe Ala Ala Tyr Ile Phe Gly Leu Gly Leu
            290                 295                 300

Thr Ile Phe Ile Met His Ile Phe Lys His Ala Gln Pro Ala Leu Leu
305                 310                 315                 320

Tyr Leu Val Pro Ala Cys Ile Gly Phe Pro Val Leu Val Ala Leu Ala
                325                 330                 335

Lys Gly Glu Val Ala Glu Met Phe Ser Tyr Glu Ser Ser Ala Val Ile
            340                 345                 350

Leu Pro His Thr Pro Arg Leu Thr His Phe Pro Thr Val Ser Gly Ser
        355                 360                 365

Pro Ala Ser Leu Ala Asp Ser Met Gln Gln Lys Leu Ala Gly Pro Arg
370                 375                 380

Arg Arg Arg Pro Gln Asn Pro Ser Ala Met
385                 390

<210> SEQ ID NO 11
<211> LENGTH: 5202
<212> TYPE: DNA
<213> ORGANISM: Mus musculus

<400> SEQUENCE: 11
gggaggcacg tcacttcctg tttctttagg ggaacgtggc tttccccgca gtgcctcttc     60
tccgtctacg ttcgtgctgc ggcggccgga gctggagtcg gagcccgagc gcagcctcgc    120
catggattcg gctgtcagcg atccgcacaa cggcagcgcc gaggctggca ccccagccaa    180
cggcacgacg cggccgccct ccacgcccga gggcatcgcg ctggcctacg cagcctcct    240 gctcatggcg ctgctgccca tcttcttcgg cgccctgcgc tcggtgcgct gcgccgcgg    300 caagagctct tcggacatgc cagaaaccat caccagtcga gatgccgccc gcttccccat    360
catcgccagc tgcacactcc tggggctcta cctctttttc aaaatattct cccaggagta    420

-continued

```
catcaacctc ttgctgtcca tgtatttctt cgtgctgggg atcctggccc tgtcacacac   480
catcagcccc ttcatgaata agttttttcc agccaacttc ccaaaccgcc agtatcagct   540
gctcttcaca cagggctctg gggaaaacaa agaagagatc atcaactatg agtttgacac   600
taaggacctg gtgtgcctgg gcctaagcag cgtcgttggt gtctggtacc ttctgaggaa   660
gcactggatt gccaacaacc tgtttggcct ggccttctcc cttaatgggg tagagctcct   720
gcacctgaac aacgtgagca ctggctgtat cctgctcgga ggactcttca tctatgacat   780
cttctgggta ttcggcacca acgtgatggt gacagtggcc aagtcctttg aggcaccaat   840
aaaattggtg ttcccccagg atctgctgga aagggccttg aagcagaca  actttgccat   900
gctgggactt ggagacattg tcattccagg gatcttcatt gccttactgc ttcgttttga   960
catcagcttg aagaagaaca cgcacaccta cttctacacc agcttcgccg cctacatctt  1020
cggcctgggt ctcaccatct tcatcatgca catcttcaag cacgcccagc cggctctcct  1080
gtacctggtc cctgcctgca tcggcttttcc tgtcctggtg gcactagcca agggagaagt  1140
ggccgagatg ttcagttatg aggagtccaa ccctaaagat ccagcagccg agactgaatc  1200
caaagaggag tcaacagagg cgtcggcatc gaagaggcta gagaagaagg agaaatgagg  1260
cagcgctgcc tgacccttga gggccagatc ggacaggcag gggatgacct gtgggcgaca  1320
cagaagagaa gacacctgca ggaggcgacg gtggccccag gatggggagc aggcctctgc  1380
tgcctgttcc ctctgccctt tctctggctt cctctgctcc tcctcatccc tgcaggcaaa  1440
ggaaaccctc tgctgcttcc ttccccagga gccaggtggg cactgaatgt ggttttttaga  1500
tttttgtatt gtggactgtc tttgcctcat attaaaaact catcccatgg ccgctaggcc  1560
accgtgctcc aagggagctc tcagcagctc tgcctagtgt ttcgtgctga actcatcggg  1620
gctttgcgag taccttcgtg ggtgccaggc cagaagtggg ttcccatgag cctcctttcc  1680
cagccactcc tgggggacag tgaaggtggt gggcgagtgc ttgctgcgcc ccgctggcct  1740
tggtatgaga tgaagagagt gtcacggggc accccgcttc agcaaaggga cttgtaacta  1800
tggacagacg gctccctggg cttgctgtcc atctggctgg aaatcaaagg tccatctttt  1860
ccatcccag gtctcccaaa atacagctca ggtcttcaga aagcctgccc tggggaggga  1920
gcagattcca gagaacagaa gaggccatcc aaggtcaggc aagagttaga gatcccaaag  1980
ccaaagtctc cctccctcct gaccttcaag cgagtccctg aagggcaagg agagggcagc  2040
tcatccctcg tccacctgcc caggtggaaa aactgagact gtggaatggc catgacctgt  2100
gagctttccc tggctagggt tcaggttaa tgactaaaat gaacagattg gaaatggtca  2160
gagagcaaag gctgtccaga gcctggggaa taagagtgga gggaggtgag tgtccccagt  2220
ttcagatgta gaccaggtgt gtcgatgcaa gcttcggatc tgtacttcgg atgctaagct  2280
gcgcgtgctt tagcctcgct ctacagagga gggaatgggg ccgctcaccc ccagacagtg  2340
actgcagctc aacatactaa gcactgtgct gtcctcttat aggaccaaga agtcactgtg  2400
gctgctctgc tgggccaccg agtcagccac ccaacttctc tgggtctaaa agtctggaga  2460
ggaaagcctg aaaggctctc taggcagggg gtctctttag ggccttcttg gatctctgca  2520
ggcttgtact gccttcaggg ggaggccatg tggtcctgga acaaagcccc tctgagggtg  2580
gcagatgggg caggcagccc aggcacacag tgtggttggc tcaacagccc acagcccaca  2640
aaggcctcat tgagtcactg ccgaccccca gcagaggctg aggtggcagt ggcgccgggc  2700
gcctgccacc taatgaccgt cctggctggg ccagatgttc cacagacctt gcagcgccga  2760
```

```
tcagggcctg cctggccaag cagccacaga ggccactcca gttccaatta accagcttca    2820
gctgagcaaa ccacgggcag cagcggggcc cagcctgggc ggtgggcccg gcccggcccg    2880
gccggccggc agagcctctg agtctagact ccagatgtga accgccaccg cctgagcccc    2940
atggaaaaat ggcaccaggc cgggcgcgca tcaggcctgc atactgggag gcgggatggg    3000
tggctgggca gggcctcaga tgggactggt gccaggctca ccctggagtg ggggtggatt    3060
cttcggaagc tgcttttcaaa cagatttccc ctggtttgtg gtgtcctctc tgtgccttgg    3120
tttttccagt aggaggaggc tgttagggct taagaccatc cctgcaagaa accccatact    3180
ctatacatgc ttaccgggtt agcatgtggc cagcattgta gagtgttcta gaagttcttg    3240
actatccctg tgtggaatat gcctgccatc ccagcacttg tagaggcagc aagctgagat    3300
aagccttgtc tacatagcaa gtttcaggtc agccagcgct ccaagataag aattagctta    3360
aaaaattaaa aaaaaaaaa gccagattga tccatactgg tttgtgacta atcttgaacc    3420
cgggagactt aagacaggat gatcaattca aagtccccct tggctacaaa gagttcaaag    3480
ccagagcctg cctctagcca agtggagaga ttaattgtaa caatcctata tggcacctac    3540
catcatcttc acagataagg aatggcaagc aggtctgcac tgacctgccg gtgtttgacc    3600
ttagtgcctg gcttatctaa actcatgttc accactgtgc tgaattcctg tttcttgtct    3660
ttggggacag catagggatt atggggacag ggagaggatg acaatggatg gcttccagga    3720
tgagatggca gtgtcctgac atctgatccc tttcttcagc taaagaggt gagagcatcc    3780
tctcacccag ttgcccttg gaaagtcttt ctgtttccat gcagtgtcag acaccagcta    3840
agttgataag gacctaacag ggagcacaaa tggtggctct ccggagctga catcctgcaa    3900
gatggcattc ctctggggag actgacggaa atgactgggt ggatgtgcca agagatgatg    3960
ccacaggaga tgggactcct gccccggtcc tggtgggcaa agcaagggtc tgtgccatcc    4020
agctgccctt gcacaaaacg acaaactcag tgctcccgcc accacccag gaaaaaaaaa    4080
gccaggctgg caggggtctc tgcggcagcc tgcgcctcct tcctgttctc caactatgga    4140
ctccccgcgt gactgccggc cacgggagga gcggcatcct gcggggtgcg ccaggaaggg    4200
ccttgcaagc gggaaggaaa gcgccacctc tctcgccccc gccaaggcca cacctgggct    4260
ccgcaggcgg tagcgccggg ccagcgcctg gctccagcga gtctgggccg ccctccctac    4320
gcactgcggg ggccgccagc tgggctggtc gctcgcgcag ctccgcggcc ggaagctgtt    4380
cactgggggg cgtggtccgt gttggtccca cccaggaggg cagggtcact gtagcccaag    4440
gacaagcttt ggaatttcgg ctggctttac agtctccatt tgtgttttc tttcctccca    4500
gtcccagggg accgaaccgt gctaagtgag cgctatatca ctgagctgta tccccgaaac    4560
ccttcacttc gatgttctta cctagaaaat gagggaattg taccccaccc ccaacacctg    4620
gcccagtgca aaatcatgcc ggcactgtgt gtgttaaatg aatgcatgcg aaggtctaaa    4680
acctccctga ggcctggcgt tgtcttgggc aaaaagctcc ccgcagatga ggaatccttt    4740
gtttcatccc tgagctgcgt tttcctcagt cagtggtggc tgagaagaaa cagtcctcgg    4800
aaaacatgga cacctagaat atcctccgta aagatatgg aagagtctcc aagatggggc    4860
gggggggggg ggggggaat gtggtagcat actcctgcaa tcctaaaacc cgagagtaag    4920
gcaggaggat cgagagtaag gcaggaggat cgtctagagc cagctcctga tgcagatttc    4980
aaggctagtt tgggctacat aagatcctgt tgtctcaaaa ctgatatatt tggaggtaaa    5040
aatgctcaaa agaattacac ttggaagatt ttgcttttg gagggtaggg gagtttggag    5100
```

```
ggagtgggtt gcttgggttt gagattggaa cttgctatgt aacccaggct ggcccagatg    5160
gaactctgta cagcagacta ggattacaag aaactttctc tg                      5202
```

<210> SEQ ID NO 12
<211> LENGTH: 378
<212> TYPE: PRT
<213> ORGANISM: Mus musculus

<400> SEQUENCE: 12

| Met | Asp | Ser | Ala | Val | Ser | Asp | Pro | His | Asn | Gly | Ser | Ala | Glu | Ala | Gly |
|---|---|---|---|---|---|---|---|---|---|---|---|---|---|---|---|
| 1 | | | | 5 | | | | | 10 | | | | | 15 | |

Thr Pro Ala Asn Gly Thr Thr Arg Pro Pro Ser Thr Pro Glu Gly Ile
            20                  25                  30

Ala Leu Ala Tyr Gly Ser Leu Leu Leu Met Ala Leu Leu Pro Ile Phe
        35                  40                  45

Phe Gly Ala Leu Arg Ser Val Arg Cys Ala Arg Gly Lys Ser Ser Ser
    50                  55                  60

Asp Met Pro Glu Thr Ile Thr Ser Arg Asp Ala Ala Arg Phe Pro Ile
65                  70                  75                  80

Ile Ala Ser Cys Thr Leu Leu Gly Leu Tyr Leu Phe Phe Lys Ile Phe
                85                  90                  95

Ser Gln Glu Tyr Ile Asn Leu Leu Leu Ser Met Tyr Phe Phe Val Leu
            100                 105                 110

Gly Ile Leu Ala Leu Ser His Thr Ile Ser Pro Phe Met Asn Lys Phe
        115                 120                 125

Phe Pro Ala Asn Phe Pro Asn Arg Gln Tyr Gln Leu Leu Phe Thr Gln
    130                 135                 140

Gly Ser Gly Glu Asn Lys Glu Glu Ile Ile Asn Tyr Glu Phe Asp Thr
145                 150                 155                 160

Lys Asp Leu Val Cys Leu Gly Leu Ser Ser Val Val Gly Val Trp Tyr
                165                 170                 175

Leu Leu Arg Lys His Trp Ile Ala Asn Asn Leu Phe Gly Leu Ala Phe
            180                 185                 190

Ser Leu Asn Gly Val Glu Leu Leu His Leu Asn Asn Val Ser Thr Gly
        195                 200                 205

Cys Ile Leu Leu Gly Gly Leu Phe Ile Tyr Asp Ile Phe Trp Val Phe
    210                 215                 220

Gly Thr Asn Val Met Val Thr Val Ala Lys Ser Phe Glu Ala Pro Ile
225                 230                 235                 240

Lys Leu Val Phe Pro Gln Asp Leu Leu Glu Lys Gly Leu Glu Ala Asp
                245                 250                 255

Asn Phe Ala Met Leu Gly Leu Gly Asp Ile Val Ile Pro Gly Ile Phe
            260                 265                 270

Ile Ala Leu Leu Leu Arg Phe Asp Ile Ser Leu Lys Lys Asn Thr His
        275                 280                 285

Thr Tyr Phe Tyr Thr Ser Phe Ala Ala Tyr Ile Phe Gly Leu Gly Leu
    290                 295                 300

Thr Ile Phe Ile Met His Ile Phe Lys His Ala Gln Pro Ala Leu Leu
305                 310                 315                 320

Tyr Leu Val Pro Ala Cys Ile Gly Phe Pro Val Leu Val Ala Leu Ala
                325                 330                 335

Lys Gly Glu Val Ala Glu Met Phe Ser Tyr Glu Glu Ser Asn Pro Lys
            340                 345                 350

Asp Pro Ala Ala Glu Thr Glu Ser Lys Glu Glu Ser Thr Glu Ala Ser
            355                 360                 365

Ala Ser Lys Arg Leu Glu Lys Lys Glu Lys
        370                 375

<210> SEQ ID NO 13
<211> LENGTH: 1112
<212> TYPE: DNA
<213> ORGANISM: Mus musculus

<400> SEQUENCE: 13

| | | | | | |
|---|---|---|---|---|---|
| gggaggcacg | tcacttcctg | tttctttagg | ggaacgtggc | tttccccgca | gtgcctcttc | 60 |
| tccgtctacg | ttcgtgctgc | ggcggccgga | gctggagtcg | gagcccgagc | gcagcctcgc | 120 |
| catggattcg | gctgtcagcg | atccgcacaa | cggcagcgcc | gaggctggca | ccccagccaa | 180 |
| cggcacgacg | cggccgccct | ccacgcccga | gggcatcgcg | ctggcctacg | gcagcctcct | 240 |
| gctcatggcg | ctgctgccca | tcttcttcgg | cgccctgcgc | tcggtgcgct | gcgcccgcgg | 300 |
| caagagctct | tcggacatgc | cagaaaccat | caccagtcga | gatgccgccc | gcttccccat | 360 |
| catcgccagc | tgcacactcc | tggggctcta | cctcttttc  | aaaatattct | cccaggagta | 420 |
| catcaacctc | ttgctgtcca | tgtatttctt | cgtgctgggg | atcctggccc | tgtcacacac | 480 |
| catcagcccc | ttcatgaata | agttttttcc | agccaacttc | ccaaaccgcc | agtatcagct | 540 |
| gctcttcaca | cagggctctg | ggaaaaacaa | agaaggtcag | tgctgcccat | gtccctggg  | 600 |
| gtgtgtcttc | ccctcttgtc | tttctccagt | actgggtttt | ccaaagaaac | gagcactaaa | 660 |
| gacgaaaccg | aatttgtatg | ccctggttc  | atacccagct | tggtcaccac | ctagcaatgg | 720 |
| gaatctgaat | gatcccgttg | tttctgagca | cgggctgttt | ttggaggttt | gttacccat  | 780 |
| ctgtaaaatg | gagtaaacag | taagtaggaa | gcaatcagca | cagtgcctgg | ctcatataag | 840 |
| cccccagtaa | aagctgtacc | agacagctct | tagcgtgcct | atctcgtgat | tgtttcacgt | 900 |
| aagctttgaa | agagataact | atgaagatac | gtacggcatc | atgcggatgc | acacaaggtg | 960 |
| acaagagtaa | cgatgccttg | gactaagtgg | aagctaattc | atacacatga | aatgaatagc | 1020 |
| ctgtgggatg | tattccagtc | tttcctggtt | gtcaagtaca | tctttgccga | ataaataatt | 1080 |
| attggatttt | ttttaaaaaa | aaaaaaaaaa | aa         |            |            | 1112 |

<210> SEQ ID NO 14
<211> LENGTH: 224
<212> TYPE: PRT
<213> ORGANISM: Mus musculus

<400> SEQUENCE: 14

Met Asp Ser Ala Val Ser Asp Pro His Asn Gly Ser Ala Glu Ala Gly
1               5                   10                  15

Thr Pro Ala Asn Gly Thr Thr Arg Pro Pro Ser Thr Pro Glu Gly Ile
            20                  25                  30

Ala Leu Ala Tyr Gly Ser Leu Leu Leu Met Ala Leu Leu Pro Ile Phe
        35                  40                  45

Phe Gly Ala Leu Arg Ser Val Arg Cys Ala Arg Gly Lys Ser Ser
    50                  55                  60

Asp Met Pro Glu Thr Ile Thr Ser Arg Asp Ala Ala Arg Phe Pro Ile
65                  70                  75                  80

Ile Ala Ser Cys Thr Leu Leu Gly Leu Tyr Leu Phe Phe Lys Ile Phe
                85                  90                  95

```
Ser Gln Glu Tyr Ile Asn Leu Leu Ser Met Tyr Phe Val Leu
            100                 105                 110

Gly Ile Leu Ala Leu Ser His Thr Ile Ser Pro Phe Met Asn Lys Phe
            115                 120                 125

Phe Pro Ala Asn Phe Pro Asn Arg Gln Tyr Gln Leu Leu Phe Thr Gln
    130                 135                 140

Gly Ser Gly Glu Asn Lys Glu Gly Gln Cys Cys Pro Cys Pro Leu Gly
145                 150                 155                 160

Cys Val Phe Pro Ser Cys Leu Ser Pro Val Leu Gly Phe Pro Lys Lys
                165                 170                 175

Arg Ala Leu Lys Thr Lys Pro Asn Leu Tyr Gly Pro Gly Ser Tyr Pro
            180                 185                 190

Ala Trp Ser Pro Pro Ser Asn Gly Asn Leu Asn Asp Pro Val Val Ser
        195                 200                 205

Glu His Gly Leu Phe Leu Glu Val Cys Tyr Pro Ile Cys Lys Met Glu
    210                 215                 220

<210> SEQ ID NO 15
<211> LENGTH: 4499
<212> TYPE: DNA
<213> ORGANISM: Mus musculus

<400> SEQUENCE: 15
gggaggcacg tcacttcctg tttctttagg gaacgtggc tttccccgca gtgcctcttc      60
tccgtctacg ttcgtgctgc ggcggccgga gctggagtcg gagcccgagc gcagcctcgc    120
catggattcg gctgtcagcg atccgcacaa cggcagcgcc gaggctggca ccccagccaa    180
cggcacgacg cggccgccct ccacgcccga gggcatcgcg ctggcctacg cagcctcct    240 gctcatggcg ctgctgccca tcttcttcgg cgccctgcgc tcggtgcgct cgcccgcgg    300 caagagctct tcggacatgc cagaaaccat caccagtcga gatgccgccc gcttccccat    360
catcgccagc tgcacactcc tggggctcta cctctttttc aaaatattct cccaggagta    420
catcaacctc ttgctgtcca tgtatttctt cgtgctgggg atcctggccc tgtcacacac    480
catcaggtca gaaggcatct ctcgacagcc tttgaagctg ctttctcagg agccagtaca    540
gggtcttgga tgggaacatg gtcttttgtg tcattcagag ccaggtttaa atcctggctg    600
taaaatccaa gggaatcttc cctcacgtca gcactatacg tgacctagga tggaacccca    660
aacttctcag ggccaccaac tcctaataag gacgtacaag gctatgtatg gtggctctta    720
gtactcaaga ggctgaggca agttcctgag ctaccatata agacccagtc ttcgaaaaaa    780
acctaggcag aagtgtcata gagtcaccac agtgctgatg tgtgtctcat caggaccact    840
tgaagcacga ggcttggctc tcatgggac aggcacctac cagcagaggg ttaggaatgc    900
cttcccttaa atccagtctc tacactccaa gttaacctct ttgacttcag tctccttaag    960
gttgtgtttt gttttttaaaa acaagcaag caaactgatg ccttcatgt agaaaatgtc    1020 tctcagtcaa taagtacaac tgtcaccttt gttaggactg ctgtgatcac ctgtgtcagc    1080
ttgttagaca cccttgactg gctggctctg ggtgttaatc ctgggttagt cagggaagct    1140
gaagttagtg tgtttgagac attcagtaag atcactcagc ccatttctgt ctgcctgttt    1200
gcagtagtcc acagatagac tgaggaatgg ctaggaaaag ttgtccgaag aaaggaacgc    1260
aacgtgacct caggtttgag aggtaggaag cctgggagag gtataaggag agaggtgctg    1320
gtcaggagct tgatgatctc catacagtag ggatcagagc tacacagagc agaatctgca    1380
```

```
ccaaggaaca gtgaggttta ttcctcaggc aagctggcag gatggagaca ggcagagtgg    1440
taggtagcct tggcctctga atatcagtcc gtctgtcccc cgtcgtcatc gtgtgtcccc    1500
ccccaccacc cgaccccac ccggcctgcc gtaaacagta tacaaagtct tcaaacaagc     1560
agaaagtgtc agatgggctg ctgtctccgc tgggacttta gctatgggct ttggagtaaa    1620
tctagcacca tcttgacctg caaaatctta ctctagctgc attgaaagta cggtagccct    1680
tctcagagga tgacttggac ctggcaagca agaatagcag gtccagcact catgaggacc    1740
tgaggcaagg ataggagtca tcgctctgaa actctgggtt tccttctttt ccatgctggc    1800
cagagccatc cagggtctac aagaggtctc ccagttcctc ccatagccta gcttcgccga    1860
tcagggagag cgtgctcttt gaaagcacca ggaacggcat atgcttgaga actaattatt    1920
tcacggtagc ccagcagccc tgcatccaac tgcccacaaa ctgttgtggt ccacatgtct    1980
cagaacaacc aattgtgtct ctacccaact tagaaatgtt agtgatagct attatcaaca    2040
caaaataaag ccagcggtct cctaggaata gagagcttaa tggtaaagcc tggtaagggt    2100
aagaccctgg gtttgatcct agcaccacaa acaaaagtga gcagttaact atgtaggaag    2160
ccaggcagca ctacacacct ctaatcccaa gcactcagga ggaagaggca ggcaaatcac    2220
cagcacggct agctatactg taagaccctg tctccaaaaa agaaagaga acagggaagg    2280 caccggcaag ctgagtgtgt tggctcagcc tttgatccta gtacttggga tgcagaggca    2340
gggagagcag gagctcagag tcccctcag ctgcacagcc aggtcacagc ctattagtta    2400
tatgagacag tgtagcagaa cagtaagggc tacgtggtaa catttgtgag gtagaagctg    2460
gtttggttgt tgtttcctg ctgggtgtta aactacagcc cagtcctaag ttttgttttt    2520
tcttttggtg ttaggaattg aacccagggc cacatataca cacataagcg agtcgtgtgg    2580
tctagcactg acccacctcc ccagccatga gtcattttgt taataaaatc cagagcactg    2640
gtaatgtgct gtggcagtcg ggagcttgag aggctgaggc gtgaggttat cgtgagaaag    2700
aagtaaagcc aatgaatttt attacaagag ggggaagaat ttaaccttt ttttcttttt     2760 agagtgttga tccaaaaatt aaactgactc ttactcactg gaggtgtgtt ttctcaagtc    2820
ttttggtaaa gcaaactaca gtgtttaaga gtttccacga gctgtttata gccacaagtc    2880
agacttcctc tggagttgag ccataaggtc tgaggggatg agacaaggaa gctgaggttc    2940
aaaagaatta ttatggctcc caggattcac agctgagaaa agcagaggcg tttgatccca    3000
gggctctctg accacagtgc tagaattcct tatcactttg tggccaaaat taaggggaag    3060
agagaatttg gagaaaacag actcacctct ccacacatct caaaaatgcc cgctaaagac    3120
tgtaagagcc acatcccagt catggtggcc cagaccacac ccaaatccct ccacctctgt    3180
tgccacccca ctgcctgcct cagaccgac cacagctcac agcgttgcag gcaggtagga    3240
gacatcttgc cttcacctaa tagttaccaa aactccaacc cagccagact ctgcacatcc    3300
tgccagagca gtcgtggcct gttttttatca cctgtggctg agctcttgcc ctactcaagt    3360
ggtccacagc aagaaagccc aagtcgtcta cctcaggaga gcacatcccc aggttcatta    3420
accctcgctg tctaccccag agggagaggc accagaacat ttctcagaag aaaacgagga    3480
actttgtctc ttatgagtca tggagagtca taaaaacact gcccacagta aaagtacaat    3540
cagagcaggc cagcaaactc tgcctggcat ggggcatcga tgagacaggg ccctgccctc    3600
cagttcacag attcacacca gttacatcac actagtcctc ttctgtgttg tatcttacag    3660
cagacccttt tcctcagtgc ttgccttgat cccaactgtt tagagggatt aagacacgag    3720
gatcaaaagc tggaggccag cctgagcaac tgagtgaaac tctatttcaa aatgagtaag    3780
```

-continued

```
gcctaaatgt gtagctcggt ggtatggcac acatacagaa atcagtgcag acatttaaca    3840
cttgaagtgg aagccacggg tgaactcaca agataccaag tattagctta atcctcttcg    3900
agatccctga gagattcaga cttggtgtga gtcctggaat tccagcactt gggagacaga    3960
agcagaagga ttgttgcaaa tttgaggcag gtctgagctg tagagtgaga ctcttagcac    4020
aaacagtaat cctctgagag aggtattaca atatggtgat tgtaataagg tatctaataa    4080
ctcggataca gaaagagttg catggagcag ttgttgtaac tttgccaaga tcatacctct    4140
gagaagtggc agagatggga cttgaaccta ggaatcatgt ctccagtcta ttctgctgat    4200
taaaaacacc gaattctgaa gaggctaggt agggtgagtg ttccagctcc tcacactgct    4260
ctctgctctg cctctgcctg tgtctgcact tgtgccatgc cttcacccctt cctcacattc    4320 agcagactga gcccctcgcc ttggctgtcc tggctgagtc tgccttccgt gggtgctcac    4380
tctatgccct gtaccgtct cttctctgcc tctgataata ttcattatca accacttcac    4440
acagtctgca aaggatcagg cccagaggtg actcttaaat tcctattctc caagccacc    4499
```

<210> SEQ ID NO 16
<211> LENGTH: 173
<212> TYPE: PRT
<213> ORGANISM: Mus musculus

<400> SEQUENCE: 16

```
Met Asp Ser Ala Val Ser Asp Pro His Asn Gly Ser Ala Glu Ala Gly
1               5                   10                  15

Thr Pro Ala Asn Gly Thr Thr Arg Pro Pro Ser Thr Pro Glu Gly Ile
            20                  25                  30

Ala Leu Ala Tyr Gly Ser Leu Leu Leu Met Ala Leu Leu Pro Ile Phe
        35                  40                  45

Phe Gly Ala Leu Arg Ser Val Arg Cys Ala Arg Gly Lys Ser Ser Ser
    50                  55                  60

Asp Met Pro Glu Thr Ile Thr Ser Arg Asp Ala Ala Arg Phe Pro Ile
65                  70                  75                  80

Ile Ala Ser Cys Thr Leu Leu Gly Leu Tyr Leu Phe Phe Lys Ile Phe
                85                  90                  95

Ser Gln Glu Tyr Ile Asn Leu Leu Leu Ser Met Tyr Phe Phe Val Leu
            100                 105                 110

Gly Ile Leu Ala Leu Ser His Thr Ile Arg Ser Glu Gly Ile Ser Arg
        115                 120                 125

Gln Pro Leu Lys Leu Leu Ser Gln Glu Pro Val Gln Gly Leu Gly Trp
    130                 135                 140

Glu His Gly Leu Leu Cys His Ser Glu Pro Gly Leu Asn Pro Gly Cys
145                 150                 155                 160

Lys Ile Gln Gly Asn Leu Pro Ser Arg Gln His Tyr Thr
                165                 170
```

<210> SEQ ID NO 17
<211> LENGTH: 9
<212> TYPE: PRT
<213> ORGANISM: Homo sapiens

<400> SEQUENCE: 17

```
Val Met Ala Pro Arg Thr Leu Leu Leu
1               5
```

<210> SEQ ID NO 18

```
<211> LENGTH: 9
<212> TYPE: PRT
<213> ORGANISM: Homo sapiens

<400> SEQUENCE: 18

Val Met Ala Pro Arg Thr Leu Val Leu
1               5

<210> SEQ ID NO 19
<211> LENGTH: 9
<212> TYPE: PRT
<213> ORGANISM: Homo sapiens

<400> SEQUENCE: 19

Val Met Ala Pro Arg Thr Val Leu Leu
1               5

<210> SEQ ID NO 20
<211> LENGTH: 9
<212> TYPE: PRT
<213> ORGANISM: Homo sapiens

<400> SEQUENCE: 20

Val Met Ala Pro Arg Ala Leu Leu Leu
1               5

<210> SEQ ID NO 21
<211> LENGTH: 9
<212> TYPE: PRT
<213> ORGANISM: Homo sapiens

<400> SEQUENCE: 21

Val Met Ala Pro Arg Thr Leu Ile Leu
1               5

<210> SEQ ID NO 22
<211> LENGTH: 9
<212> TYPE: PRT
<213> ORGANISM: Homo sapiens

<400> SEQUENCE: 22

Val Met Ala Pro Arg Thr Leu Phe Leu
1               5

<210> SEQ ID NO 23
<211> LENGTH: 9
<212> TYPE: PRT
<213> ORGANISM: Mus musculus

<400> SEQUENCE: 23

Ala Met Ala Pro Arg Thr Leu Leu Leu
1               5

<210> SEQ ID NO 24
<211> LENGTH: 9
<212> TYPE: PRT
<213> ORGANISM: Artificial Sequence
<220> FEATURE:
<223> OTHER INFORMATION: /note="Description of Artificial Sequence:
      Synthetic peptide sequence"

<400> SEQUENCE: 24

Val Thr Ala Pro Arg Thr Val Leu Leu
1               5
```

```
<210> SEQ ID NO 25
<211> LENGTH: 9
<212> TYPE: PRT
<213> ORGANISM: Artificial Sequence
<220> FEATURE:
<223> OTHER INFORMATION: /note="Description of Artificial Sequence:
      Synthetic peptide sequence"

<400> SEQUENCE: 25

Gln Met Arg Pro Val Ser Arg Val Leu
1               5

<210> SEQ ID NO 26
<211> LENGTH: 9
<212> TYPE: PRT
<213> ORGANISM: Artificial Sequence
<220> FEATURE:
<223> OTHER INFORMATION: /note="Description of Artificial Sequence:
      Synthetic peptide sequence"

<400> SEQUENCE: 26

Ser Leu Glu Leu Gly Asp Ser Ala Leu
1               5

<210> SEQ ID NO 27
<211> LENGTH: 9
<212> TYPE: PRT
<213> ORGANISM: Artificial Sequence
<220> FEATURE:
<223> OTHER INFORMATION: /note="Description of Artificial Sequence:
      Synthetic peptide sequence"

<400> SEQUENCE: 27

Leu Leu Leu Gly Pro Gly Ser Gly Leu
1               5

<210> SEQ ID NO 28
<211> LENGTH: 9
<212> TYPE: PRT
<213> ORGANISM: Artificial Sequence
<220> FEATURE:
<223> OTHER INFORMATION: /note="Description of Artificial Sequence:
      Synthetic peptide sequence"

<400> SEQUENCE: 28

Ser Gln Ala Pro Leu Pro Cys Val Leu
1               5

<210> SEQ ID NO 29
<211> LENGTH: 10
<212> TYPE: PRT
<213> ORGANISM: Artificial Sequence
<220> FEATURE:
<223> OTHER INFORMATION: /note="Description of Artificial Sequence:
      Synthetic peptide sequence"

<400> SEQUENCE: 29

Tyr Leu Leu Pro Arg Arg Gly Pro Arg Leu
1               5                   10

<210> SEQ ID NO 30
<211> LENGTH: 9
<212> TYPE: PRT
<213> ORGANISM: Artificial Sequence
<220> FEATURE:
<223> OTHER INFORMATION: /note="Description of Artificial Sequence:
      Synthetic peptide sequence"
```

```
<400> SEQUENCE: 30

Gly Met Gln Phe Asp Arg Gly Tyr Leu
1               5

<210> SEQ ID NO 31
<211> LENGTH: 9
<212> TYPE: PRT
<213> ORGANISM: Artificial Sequence
<220> FEATURE:
<223> OTHER INFORMATION: /note="Description of Artificial Sequence:
      Synthetic peptide sequence"

<400> SEQUENCE: 31

Ala Met Leu Gln Asp Ile Ala Thr Leu
1               5

<210> SEQ ID NO 32
<211> LENGTH: 9
<212> TYPE: PRT
<213> ORGANISM: Artificial Sequence
<220> FEATURE:
<223> OTHER INFORMATION: /note="Description of Artificial Sequence:
      Synthetic peptide sequence"

<400> SEQUENCE: 32

Lys Met Leu Arg Gly Val Asn Val Leu
1               5

<210> SEQ ID NO 33
<211> LENGTH: 9
<212> TYPE: PRT
<213> ORGANISM: Artificial Sequence
<220> FEATURE:
<223> OTHER INFORMATION: /note="Description of Artificial Sequence:
      Synthetic peptide sequence"

<400> SEQUENCE: 33

Val Glu Gly Glu Ala Leu Ala Thr Leu
1               5

<210> SEQ ID NO 34
<211> LENGTH: 9
<212> TYPE: PRT
<213> ORGANISM: Artificial Sequence
<220> FEATURE:
<223> OTHER INFORMATION: /note="Description of Artificial Sequence:
      Synthetic peptide sequence"

<400> SEQUENCE: 34

Ala Ala Val Glu Glu Leu Lys Ala Leu
1               5

<210> SEQ ID NO 35
<211> LENGTH: 9
<212> TYPE: PRT
<213> ORGANISM: Artificial Sequence
<220> FEATURE:
<223> OTHER INFORMATION: /note="Description of Artificial Sequence:
      Synthetic peptide sequence"

<400> SEQUENCE: 35

Ala Val Ala Lys Ala Gly Lys Pro Leu
1               5

<210> SEQ ID NO 36
<211> LENGTH: 9
```

<212> TYPE: PRT
<213> ORGANISM: Artificial Sequence
<220> FEATURE:
<223> OTHER INFORMATION: /note="Description of Artificial Sequence:
      Synthetic peptide sequence"

<400> SEQUENCE: 36

Lys Leu Gln Glu Arg Val Ala Lys Leu
1               5

<210> SEQ ID NO 37
<211> LENGTH: 9
<212> TYPE: PRT
<213> ORGANISM: Artificial Sequence
<220> FEATURE:
<223> OTHER INFORMATION: /note="Description of Artificial Sequence:
      Synthetic peptide sequence"

<400> SEQUENCE: 37

Arg Met Pro Pro Leu Gly His Glu Leu
1               5

<210> SEQ ID NO 38
<211> LENGTH: 9
<212> TYPE: PRT
<213> ORGANISM: Artificial Sequence
<220> FEATURE:
<223> OTHER INFORMATION: /note="Description of Artificial Sequence:
      Synthetic peptide sequence"

<400> SEQUENCE: 38

Val Leu Arg Pro Gly Gly His Phe Leu
1               5

<210> SEQ ID NO 39
<211> LENGTH: 9
<212> TYPE: PRT
<213> ORGANISM: Artificial Sequence
<220> FEATURE:
<223> OTHER INFORMATION: /note="Description of Artificial Sequence:
      Synthetic peptide sequence"

<400> SEQUENCE: 39

Val Met Thr Thr Val Leu Ala Thr Leu
1               5

<210> SEQ ID NO 40
<211> LENGTH: 9
<212> TYPE: PRT
<213> ORGANISM: Artificial Sequence
<220> FEATURE:
<223> OTHER INFORMATION: /note="Description of Artificial Sequence:
      Synthetic peptide sequence"

<400> SEQUENCE: 40

Arg Leu Pro Ala Lys Ala Pro Leu Leu
1               5

<210> SEQ ID NO 41
<211> LENGTH: 9
<212> TYPE: PRT
<213> ORGANISM: Artificial Sequence
<220> FEATURE:
<223> OTHER INFORMATION: /note="Description of Artificial Sequence:
      Synthetic peptide sequence"

<400> SEQUENCE: 41

Val Met Ala Thr Arg Arg Asn Val Leu
1               5

<210> SEQ ID NO 42
<211> LENGTH: 9
<212> TYPE: PRT
<213> ORGANISM: Artificial Sequence
<220> FEATURE:
<223> OTHER INFORMATION: /note="Description of Artificial Sequence:
      Synthetic peptide sequence"

<400> SEQUENCE: 42

Val Leu Arg Pro Gly Gly His Phe Leu
1               5

<210> SEQ ID NO 43
<211> LENGTH: 9
<212> TYPE: PRT
<213> ORGANISM: Artificial Sequence
<220> FEATURE:
<223> OTHER INFORMATION: /note="Description of Artificial Sequence:
      Synthetic peptide sequence"

<400> SEQUENCE: 43

Gly Met Lys Phe Asp Arg Gly Tyr Ile
1               5

<210> SEQ ID NO 44
<211> LENGTH: 9
<212> TYPE: PRT
<213> ORGANISM: Artificial Sequence
<220> FEATURE:
<223> OTHER INFORMATION: /note="Description of Artificial Sequence:
      Synthetic peptide sequence"

<400> SEQUENCE: 44

Ala Leu Trp Met Arg Phe Leu Pro Leu
1               5

<210> SEQ ID NO 45
<211> LENGTH: 9
<212> TYPE: PRT
<213> ORGANISM: Artificial Sequence
<220> FEATURE:
<223> OTHER INFORMATION: /note="Description of Artificial Sequence:
      Synthetic peptide sequence"

<400> SEQUENCE: 45

Phe Leu Ala Arg Ser Ala Leu Ile Leu
1               5

<210> SEQ ID NO 46
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA sequence"

<400> SEQUENCE: 46
gcctgctgtc acttgctacg                                              20

<210> SEQ ID NO 47
<211> LENGTH: 20
<212> TYPE: DNA

```
<213> ORGANISM: Artificial Sequence
<220> FEATURE:
<223> OTHER INFORMATION: /note="Description of Artificial Sequence:
      Synthetic sgRNA sequence"

<400> SEQUENCE: 47
aatcaaccag agaatttccg                                             20

<210> SEQ ID NO 48
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA sequence"

<400> SEQUENCE: 48
ggtccagctc ccgttctaca                                             20

<210> SEQ ID NO 49
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA sequence"

<400> SEQUENCE: 49
gtatggcagc aacgtcacga                                             20

<210> SEQ ID NO 50
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA sequence"

<400> SEQUENCE: 50
tatagagctg aaaaaccgca                                             20

<210> SEQ ID NO 51
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA sequence"

<400> SEQUENCE: 51
ccacattacg gacgatgcaa                                             20

<210> SEQ ID NO 52
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA sequence"

<400> SEQUENCE: 52
tcttacgagg aggagaaagg                                             20

<210> SEQ ID NO 53
<211> LENGTH: 20
<212> TYPE: DNA
<213> ORGANISM: Artificial Sequence
```

<220> FEATURE:
<223> OTHER INFORMATION: /note="Description of Artificial Sequence:
      Synthetic sgRNA sequence"

<400> SEQUENCE: 53
gcaagtgtag tttcccacca                                            20

<210> SEQ ID NO 54
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA sequence"

<400> SEQUENCE: 54
gcgaggtatt cggctccgcg                                            20

<210> SEQ ID NO 55
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA sequence"

<400> SEQUENCE: 55
gctttcacgg aggttcgacg                                            20

<210> SEQ ID NO 56
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA sequence"

<400> SEQUENCE: 56
atgttgcagt tcggctcgat                                            20

<210> SEQ ID NO 57
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA sequence"

<400> SEQUENCE: 57
acgtgtaagg cgaacgcctt                                            20

<210> SEQ ID NO 58
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA sequence"

<400> SEQUENCE: 58
attgttcgac cgtctacggg                                            20

<210> SEQ ID NO 59
<211> LENGTH: 20
<212> TYPE: DNA
<213> ORGANISM: Artificial Sequence
<220> FEATURE:

```
<223> OTHER INFORMATION: /note="Description of Artificial Sequence:
      Synthetic sgRNA sequence"

<400> SEQUENCE: 59
tagccgacaa tgatgaaccg                                               20

<210> SEQ ID NO 60
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA sequence"

<400> SEQUENCE: 60
aggcctcctg acaatacccg                                               20

<210> SEQ ID NO 61
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA sequence"

<400> SEQUENCE: 61
ggaacttcag agtaaacctg                                               20

<210> SEQ ID NO 62
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA sequence"

<400> SEQUENCE: 62
actggctgta tcctgctcgg                                               20

<210> SEQ ID NO 63
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA sequence"

<400> SEQUENCE: 63
ggccactgtc accatcacgt                                               20

<210> SEQ ID NO 64
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA sequence"

<400> SEQUENCE: 64
gctgtcagcg atccgcacaa                                               20

<210> SEQ ID NO 65
<211> LENGTH: 20
<212> TYPE: DNA
<213> ORGANISM: Artificial Sequence
```

```
<220> FEATURE:
<223> OTHER INFORMATION: /note="Description of Artificial Sequence:
      Synthetic sgRNA sequence"

<400> SEQUENCE: 65
tccgcacaac ggcagcgccg                                                 20

<210> SEQ ID NO 66
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA sequence"

<400> SEQUENCE: 66
agaaatacat ggacagcaag                                                 20

<210> SEQ ID NO 67
<211> LENGTH: 7483
<212> TYPE: DNA
<213> ORGANISM: Homo sapiens

<400> SEQUENCE: 67
agtgctggct ggacagctgc tctgggcagg agagagaggg agagacaaga gacacacaca     60
gagagacggc gaggaaggga aagacccaga gggacgccta aacgagact tggagccaga    120 cagaggaaga ggggacgtgt gtttgcagac tggctgggcc cgtgacccag cttcctgagt    180
cctccgtgca ggtggcagct gtaccaggct ggcaggtcac tgagagtggg cagctgggcc    240
ccagaactgt gcctggccca gtgggcagca ggagctcctg acttgggacc atggtgattc    300
ttcagcaggg ggaccatgtg tggatggacc tgagattggg gcaggagttc gacgtgccca    360
tcggggcggt ggtgaagctc tgcgactctg gcaggtcca ggtggtggat gatgaagaca    420
atgaacactg gatctctccg cagaacgcaa cgcacatcaa gcctatgcac cccacgtcgg    480
tccacggcgt ggaggacatg atccgcctgg gggacctcaa cgaggcgggc atcttgcgca    540
acctgcttat ccgctaccgg gaccacctca tctacacgta tacgggctcc atcctggtgg    600
ctgtgaaccc ctaccagctg ctctccatct actcgccaga gcacatccgc cagtatacca    660
acaagaagat tgggagatg ccccccaca tctttgccat tgctgacaac tgctacttca    720
acatgaaacg caacagccga gaccagtgct gcatcatcag tgggaatct ggggccggga    780 agacggagag cacaaagctg atcctgcagt tcctggcagc catcagtggg cagcactcgt    840
ggattgagca gcaggtcttg gaggccaccc ccattctgga agcatttggg aatgccaaga    900
ccatccgcaa tgacaactca agccgttttcg gaaagtacat cgacatccac ttcaacaagc    960
ggggcgccat cgagggcgcg aagattgagc agtacctgct ggaaaagtca cgtgtctgtc   1020
gccaggccct ggatgaaagg aactaccacg tgttctactg catgctggag ggtatgagtg   1080
aggatcagaa gaagaagctg ggcttgggcc aggcctctga ctacaactac ttggccatgg   1140
gtaactgcat aacctgtgag ggccgggtgg acagccagga gtacgccaac atccgctccg   1200
ccatgaaggt gctcatgttc actgacaccg agaactggga gatctcgaag ctcctggctg   1260
ccatcctgca cctgggcaac ctgcagtatg aggcacgcac atttgaaaac ctggatgcct   1320
gtgaggttct cttctcccca tcgctggcca cagctgcatc cctgcttgag gtgaaccccc   1380
cagacctgat gagctgcctg actagccgca ccctcatcac ccgcggggag acggtgtcca   1440
ccccactgag cagggaacag gcactggacg tgcgcgacgc cttcgtaaag gggatctacg   1500
```

```
ggcggctgtt cgtgtggatt gtggacaaga tcaacgcagc aatttacaag cctccctccc    1560
aggatgtgaa gaactctcgc aggtccatcg gcctcctgga catctttggg tttgagaact    1620
ttgctgtgaa cagctttgag cagctctgca tcaacttcgc caatgagcac ctgcagcagt    1680
tctttgtgcg gcacgtgttc aagctggagc aggaggaata tgacctggag agcattgact    1740
ggctgcacat cgagttcact gacaaccagg atgccctgga catgattgcc aacaagccca    1800
tgaacatcat ctccctcatc gatgaggaga gcaagttccc caagggcaca gacaccacca    1860
tgttacacaa gctgaactcc cagcacaagc tcaacgccaa ctacatcccc cccaagaaca    1920
accatgagac ccagtttggc atcaaccatt ttgcaggcat cgtctactat gagacccaag    1980
gcttcctgga gaagaaccga gacaccctgc atggggacat tatccagctg gtccactcct    2040
ccaggaacaa gttcatcaag cagatcttcc aggccgatgt cgccatgggc gccgagacca    2100
ggaagcgctc gcccacactt agcagccagt tcaagcggtc actggagctg ctgatgcgca    2160
cgctgggtgc ctgccagccc ttctttgtgc gatgcatcaa gcccaatgag ttcaagaagc    2220
ccatgctgtt cgaccggcac ctgtgcgtgc gccagctgcg gtactcagga atgatggaga    2280
ccatccgaat ccgccgagct ggctacccca tccgctacag cttcgtagag tttgtggagc    2340
ggtaccgtgt gctgctgcca ggtgtgaagc ggcctacaa gcagggcgac ctccgcggga    2400
cttgccagcg catggctgag gctgtgctgg gcacccacga tgactggcag ataggcaaaa    2460
ccaagatctt tctgaaggac caccatgaca tgctgctgga agtggagcgg acaaagcca    2520
tcaccgacag agtcatcctc cttcagaaag tcatccgggg attcaaagac aggtctaact    2580
ttctgaagct gaagaacgct gccacactga tccagaggca ctggcggggt cacaactgta    2640
ggaagaacta cgggctgatg cgtctgggct tcctgcggct gcaggccctg caccgctccc    2700
ggaagctgca ccagcagtac cgcctggccc gccagcgcat catccagttc caggcccgct    2760
gccgcgccta tctggtgcgc aaggccttcc gccaccgcct ctgggctgtg ctcaccgtgc    2820
aggcctatgc ccggggcatg atcgcccgca ggctgcacca acgcctcagg gctgagtatc    2880
tgtggcgcct cgaggctgag aaaatgcggc tggcggagga agagaagctt cggaaggaga    2940
tgagcgccaa gaaggccaag gaggaggccg agcgcaagca tcaggagcgc ctggcccagc    3000
tggctcgtga ggacgctgag cgggagctga aggagaagga ggccgctcgg cggaagaagg    3060
agctcctgga gcagatggaa agggcccgcc atgagcctgt caatcactca gacatggtgg    3120
acaagatgtt tggcttcctg gggacttcag gtggcctgcc aggccaggag ggccaggcac    3180
ctagtggctt tgaggacctg gagcgagggc ggagggagat ggtggaggag gacctggatg    3240
cagccctgcc cctgcctgac gaggatgagg aggacctctc tgagtataaa tttgccaagt    3300
tcgcggccac ctacttccag gggacaacca cgcactccta cacccggcgg ccactcaaac    3360
agccactgct ctaccatgac gacgagggtg accagctggc agccctggcg gtctggatca    3420
ccatcctccg cttcatgggg gacctccctg agcccaagta ccacacagcc atgagtgatg    3480
gcagtgagaa gatccctgtg atgaccaaga tttatgagac cctgggcaag aagacgtaca    3540
agagggagct gcaggccctg caggcgaggc gcgaggccca gctccccgag ggccagaaga    3600
agagcagtgt gaggcacaag ctggtgcatt tgactctgaa aaagaagtcc aagctcacag    3660
aggaggtgac caagaggctg catgacgggg agtccacagt gcagggcaac agcatgctgg    3720
aggaccggcc cacctccaac ctggagaagc tgcacttcat catcggcaat ggcatcctgc    3780
ggccagcact ccgggacgag atctactgcc agatcagcaa gcagctgacc cacaacccct    3840
ccaagagcag ctatgcccgg ggctggatta tcgtgtctct ctgcgtgggc tgtttcgccc    3900
```

```
cctccgagaa gtttgtcaag tacctgcgga acttcatcca cggggcccg cccggctacg    3960
ccccgtactg tgaggagcgc ctgagaagga cctttgtcaa tgggacacgg acacagccgc    4020
ccagctggct ggagctgcag gccaccaagt ccaagaagcc aatcatgttg cccgtgacat    4080
tcatggatgg gaccaccaag accctgctga cggactcggc aaccacggcc aaggagctct    4140
gcaacgcgct ggccgacaag atctctctca aggaccggtt cggggttctcc ctctacattg    4200
ccctgtttga caaggtgtcc tccctgggca gcggcagtga ccacgtcatg gacgccatct    4260
cccagtgcga gcagtacgcc aaggagcagg gcgcccagga gcgcaacgcc cctggaggc    4320
tcttcttccg caaagaggtc ttcacgcccc ggcacagccc ctccgaggac aacgtggcca    4380
ccaacctcat ctaccagcag gtggtgcgag gagtcaagtt tggggagtac aggtgtgaga    4440
aggaggacga cctggctgag ctggcctccc agcagtactt tgtagactat ggctctgaga    4500
tgatcctgga gcgcctcctg aacctcgtgc ccacctacat ccccgaccgc gagatcacgc    4560
ccctgaagac gctggagaag tgggcccagc tggccatcgc cgcccacaag aagggggattt    4620
atgcccagag gagaactgat gcccagaagg tcaaagagga tgtggtcagt tatgcccgct    4680
tcaagtggcc ccttgctcttc tccaggtttt atgaagccta caaattctca ggccccagtc    4740
tccccaagaa cgacgtcatc gtggccgtca actggacggg tgtgtacttt gtggatgagc    4800
aggagcaggt acttctggag ctgtccttcc cagagatcat ggccgtgtcc agcagcaggg    4860
agtgccgtgt ctggctctca ctgggctgct ctgatcttgg ctgtgctgcg cctcactcag    4920
gctgggcagg actgaccccg gcggggccct gttctccgtg ttggtcctgc aggggagcga    4980
aaacgacggc cccagcttc acgctggcca ccatcaaggg ggacgaatac accttcacct    5040
ccagcaatgc tgaggacatt cgtgacctgg tggtcacctt cctagagggg ctccggaaga    5100
gatctaagta tgttgtggcc ctgcaggata accccaaccc cgcaggcgag gagtcaggct    5160
tcctcagctt tgccaaggga gacctcatca tcctggacca tgacacgggc gagcaggtca    5220
tgaactcggg ctgggccaac ggcatcaatg agaggaccaa gcagcgtggg gacttcccca    5280
ccgacagtgt gtacgtcatg cccactgtca ccatgccacc gcgggagatt gtggccctgg    5340
tcaccatgac tcccgatcag aggcaggacg ttgtccggct cttgcagctg cgaacggcgg    5400
agcccgaggt gcgtgccaag ccctacacgc tggaggagtt ttcctatgac tacttcaggc    5460
ccccacccaa gcacacgctg agccgtgtca tggtgtccaa ggcccgaggc aaggaccggc    5520
tgtggagcca cacgcgggaa ccgctcaagc aggcgctgct caagaagctc ctgggcagtg    5580
aggagctctc gcaggaggcc tgcctggcct tcattgctgt gctcaagtac atgggcgact    5640
acccgtccaa gaggacacgc tccgtcaacg agctcaccga ccagatcttt gagggtcccc    5700
tgaaagccga gccctgaag gacgaggcat atgtgcagat cctgaagcag ctgaccgaca    5760
accacatcag gtacagcgag gagcggggtt gggagctgct ctggctgtgc acgggccttt    5820
tcccacccag caacatcctc ctgccccacg tgcagcgctt cctgcagtcc cgaaagcact    5880
gcccactcgc catcgactgc ctgcaacggc tccagaaagc cctgagaaac gggtcccgga    5940
agtaccctcc gcacctggtg gaggtggagg ccatccagca aagaccacc cagatttttcc    6000
acaaagtcta cttccctgat gacactgacg aggccttcga agtggagtcc agcaccaagg    6060
ccaaggactt ctgccagaac atcgccacca ggctgctcct caagtcctca gagggattca    6120
gcctcttttgt caaaattgca gacaaggtcc tcagcgttcc tgagaatgac ttcttctttg    6180
actttgttcg acacttgaca gactggataa agaaagctcg gccccatcaag gacggaattg    6240
```

```
tgccctcact cacctaccag gtgttcttca tgaagaagct gtggaccacc acggtgccag    6300
ggaaggatcc catggccgat tccatcttcc actattacca ggagttgccc aagtatctcc    6360
gaggctacca caagtgcacg cgggaggagg tgctgcagct gggggcgctg atctacaggg    6420
tcaagttcga ggaggacaag tcctacttcc ccagcatccc caagctgctg cgggagctgg    6480
tgccccagga ccttatccgg caggtctcac ctgatgactg gaagcggtcc atcgtcgcct    6540
acttcaacaa gcacgcaggg aagtccaagg aggaggccaa gctggccttc ctgaagctca    6600
tcttcaagtg gcccaccttt ggctcagcct tcttcgaggt gaagcaaact acggagccaa    6660
acttccctga gatcctccta attgccatca caagtatgg ggtcagcctc atcgatccca    6720
aaacgaagga tatcctcacc actcatccct tcaccaagat ctccaactgg agcagcggca    6780
acacctactt ccatcatcacc attgggaact tggtgcgcgg gagcaaactg ctctgcgaga    6840
cgtcactggg ctacaagatg gatgacctcc tgacttccta cattagccag atgctcacag    6900
ccatgagcaa acagcgggc tccaggagcg gcaagtgaac agtcacgggg aggtgctggt    6960
tccatgcctg ctctcgaggc agcagtgggt tcaggcccat cagctacccc tgcagctggg    7020
gaagacttat gccatcccgg cagcgaggct gggctggcca gccaccactg actataccaa    7080
ctgggcctct gatgttcttc cagtgaggca tctctctggg atgcagaact tccctccatc    7140
cacccctctg gcacctgggt tggtctaatc ctagtttgct gtggccttcc cggttgtgag    7200
agcctgtgat cctagatgt gtctcctgtt tcagaccagc cccaccatgc aacttccttt    7260
gactttctgt gtaccactgg gatagaggaa tcaagaggac aatctagctc tccatacttt    7320
gaacaaccaa atgtgcattg aatactctga aaccgaaggg actggatctg caggtgggat    7380
gagggagaca gaccactttt ctatattgca gtgtgaatgc tgggcccctg ctcaagtcta    7440
ccctgatcac ctcagggcat aaagcatgtt tcattctctg gcc                     7483

<210> SEQ ID NO 68
<211> LENGTH: 2215
<212> TYPE: PRT
<213> ORGANISM: Homo sapiens

<400> SEQUENCE: 68

Met Val Ile Leu Gln Gln Gly Asp His Val Trp Met Asp Leu Arg Leu
1               5                   10                  15

Gly Gln Glu Phe Asp Val Pro Ile Gly Ala Val Val Lys Leu Cys Asp
            20                  25                  30

Ser Gly Gln Val Gln Val Val Asp Asp Glu Asp Asn Glu His Trp Ile
        35                  40                  45

Ser Pro Gln Asn Ala Thr His Ile Lys Pro Met His Pro Thr Ser Val
    50                  55                  60

His Gly Val Glu Asp Met Ile Arg Leu Gly Leu Asn Glu Ala Gly
65                  70                  75                  80

Ile Leu Arg Asn Leu Leu Ile Arg Tyr Arg Asp His Leu Ile Tyr Thr
                85                  90                  95

Tyr Thr Gly Ser Ile Leu Val Ala Val Asn Pro Tyr Gln Leu Leu Ser
            100                 105                 110

Ile Tyr Ser Pro Glu His Ile Arg Gln Tyr Thr Asn Lys Lys Ile Gly
        115                 120                 125

Glu Met Pro Pro His Ile Phe Ala Ile Ala Asp Asn Cys Tyr Phe Asn
    130                 135                 140

Met Lys Arg Asn Ser Arg Asp Gln Cys Cys Ile Ile Ser Gly Glu Ser
145                 150                 155                 160
```

```
Gly Ala Gly Lys Thr Glu Ser Thr Lys Leu Ile Leu Gln Phe Leu Ala
            165                 170                 175
Ala Ile Ser Gly Gln His Ser Trp Ile Glu Gln Gln Val Leu Glu Ala
            180                 185                 190
Thr Pro Ile Leu Glu Ala Phe Gly Asn Ala Lys Thr Ile Arg Asn Asp
            195                 200                 205
Asn Ser Ser Arg Phe Gly Lys Tyr Ile Asp Ile His Phe Asn Lys Arg
            210                 215                 220
Gly Ala Ile Glu Gly Ala Lys Ile Glu Gln Tyr Leu Leu Glu Lys Ser
225                 230                 235                 240
Arg Val Cys Arg Gln Ala Leu Asp Glu Arg Asn Tyr His Val Phe Tyr
            245                 250                 255
Cys Met Leu Glu Gly Met Ser Glu Asp Gln Lys Lys Lys Leu Gly Leu
            260                 265                 270
Gly Gln Ala Ser Asp Tyr Asn Tyr Leu Ala Met Gly Asn Cys Ile Thr
            275                 280                 285
Cys Glu Gly Arg Val Asp Ser Gln Glu Tyr Ala Asn Ile Arg Ser Ala
            290                 295                 300
Met Lys Val Leu Met Phe Thr Asp Thr Glu Asn Trp Glu Ile Ser Lys
305                 310                 315                 320
Leu Leu Ala Ala Ile Leu His Leu Gly Asn Leu Gln Tyr Glu Ala Arg
            325                 330                 335
Thr Phe Glu Asn Leu Asp Ala Cys Glu Val Leu Phe Ser Pro Ser Leu
            340                 345                 350
Ala Thr Ala Ala Ser Leu Leu Glu Val Asn Pro Pro Asp Leu Met Ser
            355                 360                 365
Cys Leu Thr Ser Arg Thr Leu Ile Thr Arg Gly Glu Thr Val Ser Thr
            370                 375                 380
Pro Leu Ser Arg Glu Gln Ala Leu Asp Val Arg Asp Ala Phe Val Lys
385                 390                 395                 400
Gly Ile Tyr Gly Arg Leu Phe Val Trp Ile Val Asp Lys Ile Asn Ala
            405                 410                 415
Ala Ile Tyr Lys Pro Pro Ser Gln Asp Val Lys Asn Ser Arg Arg Ser
            420                 425                 430
Ile Gly Leu Leu Asp Ile Phe Gly Phe Glu Asn Phe Ala Val Asn Ser
            435                 440                 445
Phe Glu Gln Leu Cys Ile Asn Phe Ala Asn Glu His Leu Gln Gln Phe
            450                 455                 460
Phe Val Arg His Val Phe Lys Leu Glu Gln Glu Glu Tyr Asp Leu Glu
465                 470                 475                 480
Ser Ile Asp Trp Leu His Ile Glu Phe Thr Asp Asn Gln Asp Ala Leu
            485                 490                 495
Asp Met Ile Ala Asn Lys Pro Met Asn Ile Ile Ser Leu Ile Asp Glu
            500                 505                 510
Glu Ser Lys Phe Pro Lys Gly Thr Asp Thr Thr Met Leu His Lys Leu
            515                 520                 525
Asn Ser Gln His Lys Leu Asn Ala Asn Tyr Ile Pro Pro Lys Asn Asn
            530                 535                 540
His Glu Thr Gln Phe Gly Ile Asn His Phe Ala Gly Ile Val Tyr Tyr
545                 550                 555                 560
Glu Thr Gln Gly Phe Leu Glu Lys Asn Arg Asp Thr Leu His Gly Asp
            565                 570                 575
```

```
Ile Ile Gln Leu Val His Ser Ser Arg Asn Lys Phe Ile Lys Gln Ile
            580                 585                 590

Phe Gln Ala Asp Val Ala Met Gly Ala Glu Thr Arg Lys Arg Ser Pro
        595                 600                 605

Thr Leu Ser Ser Gln Phe Lys Arg Ser Leu Glu Leu Leu Met Arg Thr
    610                 615                 620

Leu Gly Ala Cys Gln Pro Phe Phe Val Arg Cys Ile Lys Pro Asn Glu
625                 630                 635                 640

Phe Lys Lys Pro Met Leu Phe Asp Arg His Leu Cys Val Arg Gln Leu
                645                 650                 655

Arg Tyr Ser Gly Met Met Glu Thr Ile Arg Ile Arg Arg Ala Gly Tyr
            660                 665                 670

Pro Ile Arg Tyr Ser Phe Val Glu Phe Val Glu Arg Tyr Arg Val Leu
        675                 680                 685

Leu Pro Gly Val Lys Pro Ala Tyr Lys Gln Gly Asp Leu Arg Gly Thr
    690                 695                 700

Cys Gln Arg Met Ala Glu Ala Val Leu Gly Thr His Asp Asp Trp Gln
705                 710                 715                 720

Ile Gly Lys Thr Lys Ile Phe Leu Lys Asp His His Asp Met Leu Leu
                725                 730                 735

Glu Val Glu Arg Asp Lys Ala Ile Thr Asp Arg Val Ile Leu Leu Gln
            740                 745                 750

Lys Val Ile Arg Gly Phe Lys Asp Arg Ser Asn Phe Leu Lys Leu Lys
        755                 760                 765

Asn Ala Ala Thr Leu Ile Gln Arg His Trp Arg Gly His Asn Cys Arg
    770                 775                 780

Lys Asn Tyr Gly Leu Met Arg Leu Gly Phe Leu Arg Leu Gln Ala Leu
785                 790                 795                 800

His Arg Ser Arg Lys Leu His Gln Gln Tyr Arg Leu Ala Arg Gln Arg
                805                 810                 815

Ile Ile Gln Phe Gln Ala Arg Cys Arg Ala Tyr Leu Val Arg Lys Ala
            820                 825                 830

Phe Arg His Arg Leu Trp Ala Val Leu Thr Val Gln Ala Tyr Ala Arg
        835                 840                 845

Gly Met Ile Ala Arg Arg Leu His Gln Arg Leu Arg Ala Glu Tyr Leu
    850                 855                 860

Trp Arg Leu Glu Ala Glu Lys Met Arg Leu Ala Glu Glu Lys Leu
865                 870                 875                 880

Arg Lys Glu Met Ser Ala Lys Lys Ala Lys Glu Glu Ala Glu Arg Lys
                885                 890                 895

His Gln Glu Arg Leu Ala Gln Leu Ala Arg Glu Asp Ala Glu Arg Glu
            900                 905                 910

Leu Lys Glu Lys Glu Ala Ala Arg Arg Lys Lys Glu Leu Leu Glu Gln
        915                 920                 925

Met Glu Arg Ala Arg His Glu Pro Val Asn His Ser Asp Met Val Asp
    930                 935                 940

Lys Met Phe Gly Phe Leu Gly Thr Ser Gly Gly Leu Pro Gly Gln Glu
945                 950                 955                 960

Gly Gln Ala Pro Ser Gly Phe Glu Asp Leu Glu Arg Gly Arg Arg Glu
                965                 970                 975

Met Val Glu Glu Asp Leu Asp Ala Ala Leu Pro Leu Pro Asp Glu Asp
            980                 985                 990
```

```
Glu Glu Asp Leu Ser Glu Tyr Lys  Phe Ala Lys Phe Ala  Ala Thr Tyr
         995                1000                 1005

Phe Gln Gly Thr Thr Thr His  Ser Tyr Thr Arg Arg  Pro Leu Lys
   1010                1015                1020

Gln Pro Leu Leu Tyr His Asp  Asp Glu Gly Asp Gln  Leu Ala Ala
   1025                1030                1035

Leu Ala Val Trp Ile Thr Ile  Leu Arg Phe Met Gly  Asp Leu Pro
   1040                1045                1050

Glu Pro Lys Tyr His Thr Ala  Met Ser Asp Gly Ser  Glu Lys Ile
   1055                1060                1065

Pro Val Met Thr Lys Ile Tyr  Glu Thr Leu Gly Lys  Lys Thr Tyr
   1070                1075                1080

Lys Arg Glu Leu Gln Ala Leu  Gln Gly Glu Gly Glu  Ala Gln Leu
   1085                1090                1095

Pro Glu Gly Gln Lys Lys Ser  Ser Val Arg His Lys  Leu Val His
   1100                1105                1110

Leu Thr Leu Lys Lys Lys Ser  Lys Leu Thr Glu Glu  Val Thr Lys
   1115                1120                1125

Arg Leu His Asp Gly Glu Ser  Thr Val Gln Gly Asn  Ser Met Leu
   1130                1135                1140

Glu Asp Arg Pro Thr Ser Asn  Leu Glu Lys Leu His  Phe Ile Ile
   1145                1150                1155

Gly Asn Gly Ile Leu Arg Pro  Ala Leu Arg Asp Glu  Ile Tyr Cys
   1160                1165                1170

Gln Ile Ser Lys Gln Leu Thr  His Asn Pro Ser Lys  Ser Ser Tyr
   1175                1180                1185

Ala Arg Gly Trp Ile Leu Val  Ser Leu Cys Val Gly  Cys Phe Ala
   1190                1195                1200

Pro Ser Glu Lys Phe Val Lys  Tyr Leu Arg Asn Phe  Ile His Gly
   1205                1210                1215

Gly Pro Pro Gly Tyr Ala Pro  Tyr Cys Glu Glu Arg  Leu Arg Arg
   1220                1225                1230

Thr Phe Val Asn Gly Thr Arg  Thr Gln Pro Pro Ser  Trp Leu Glu
   1235                1240                1245

Leu Gln Ala Thr Lys Ser Lys  Lys Pro Ile Met Leu  Pro Val Thr
   1250                1255                1260

Phe Met Asp Gly Thr Thr Lys  Thr Leu Leu Thr Asp  Ser Ala Thr
   1265                1270                1275

Thr Ala Lys Glu Leu Cys Asn  Ala Leu Ala Asp Lys  Ile Ser Leu
   1280                1285                1290

Lys Asp Arg Phe Gly Phe Ser  Leu Tyr Ile Ala Leu  Phe Asp Lys
   1295                1300                1305

Val Ser Ser Leu Gly Ser Gly  Ser Asp His Val Met  Asp Ala Ile
   1310                1315                1320

Ser Gln Cys Glu Gln Tyr Ala  Lys Glu Gln Gly Ala  Gln Glu Arg
   1325                1330                1335

Asn Ala Pro Trp Arg Leu Phe  Phe Arg Lys Glu Val  Phe Thr Pro
   1340                1345                1350

Trp His Ser Pro Ser Glu Asp  Asn Val Ala Thr Asn  Leu Ile Tyr
   1355                1360                1365

Gln Gln Val Val Arg Gly Val  Lys Phe Gly Glu Tyr  Arg Cys Glu
   1370                1375                1380
```

```
Lys Glu Asp Asp Leu Ala Glu Leu Ala Ser Gln Gln Tyr Phe Val
    1385                1390                1395

Asp Tyr Gly Ser Glu Met Ile Leu Glu Arg Leu Leu Asn Leu Val
    1400                1405                1410

Pro Thr Tyr Ile Pro Asp Arg Glu Ile Thr Pro Leu Lys Thr Leu
    1415                1420                1425

Glu Lys Trp Ala Gln Leu Ala Ile Ala Ala His Lys Lys Gly Ile
    1430                1435                1440

Tyr Ala Gln Arg Arg Thr Asp Ala Gln Lys Val Lys Glu Asp Val
    1445                1450                1455

Val Ser Tyr Ala Arg Phe Lys Trp Pro Leu Leu Phe Ser Arg Phe
    1460                1465                1470

Tyr Glu Ala Tyr Lys Phe Ser Gly Pro Ser Leu Pro Lys Asn Asp
    1475                1480                1485

Val Ile Val Ala Val Asn Trp Thr Gly Val Tyr Phe Val Asp Glu
    1490                1495                1500

Gln Glu Gln Val Leu Leu Glu Leu Ser Phe Pro Glu Ile Met Ala
    1505                1510                1515

Val Ser Ser Ser Arg Glu Cys Arg Val Trp Leu Ser Leu Gly Cys
    1520                1525                1530

Ser Asp Leu Gly Cys Ala Ala Pro His Ser Gly Trp Ala Gly Leu
    1535                1540                1545

Thr Pro Ala Gly Pro Cys Ser Pro Cys Trp Ser Cys Arg Gly Ala
    1550                1555                1560

Lys Thr Thr Ala Pro Ser Phe Thr Leu Ala Thr Ile Lys Gly Asp
    1565                1570                1575

Glu Tyr Thr Phe Thr Ser Ser Asn Ala Glu Asp Ile Arg Asp Leu
    1580                1585                1590

Val Val Thr Phe Leu Glu Gly Leu Arg Lys Arg Ser Lys Tyr Val
    1595                1600                1605

Val Ala Leu Gln Asp Asn Pro Asn Pro Ala Gly Glu Glu Ser Gly
    1610                1615                1620

Phe Leu Ser Phe Ala Lys Gly Asp Leu Ile Ile Leu Asp His Asp
    1625                1630                1635

Thr Gly Glu Gln Val Met Asn Ser Gly Trp Ala Asn Gly Ile Asn
    1640                1645                1650

Glu Arg Thr Lys Gln Arg Gly Asp Phe Pro Thr Asp Ser Val Tyr
    1655                1660                1665

Val Met Pro Thr Val Thr Met Pro Pro Arg Glu Ile Val Ala Leu
    1670                1675                1680

Val Thr Met Thr Pro Asp Gln Arg Gln Asp Val Val Arg Leu Leu
    1685                1690                1695

Gln Leu Arg Thr Ala Glu Pro Glu Val Arg Ala Lys Pro Tyr Thr
    1700                1705                1710

Leu Glu Glu Phe Ser Tyr Asp Tyr Phe Arg Pro Pro Lys His
    1715                1720                1725

Thr Leu Ser Arg Val Met Val Ser Lys Ala Arg Gly Lys Asp Arg
    1730                1735                1740

Leu Trp Ser His Thr Arg Glu Pro Leu Lys Gln Ala Leu Leu Lys
    1745                1750                1755

Lys Leu Leu Gly Ser Glu Glu Leu Ser Gln Glu Ala Cys Leu Ala
    1760                1765                1770
```

Phe Ile Ala Val Leu Lys Tyr Met Gly Asp Tyr Pro Ser Lys Arg
1775                1780                1785

Thr Arg Ser Val Asn Glu Leu Thr Asp Gln Ile Phe Glu Gly Pro
1790                1795                1800

Leu Lys Ala Glu Pro Leu Lys Asp Glu Ala Tyr Val Gln Ile Leu
1805                1810                1815

Lys Gln Leu Thr Asp Asn His Ile Arg Tyr Ser Glu Glu Arg Gly
1820                1825                1830

Trp Glu Leu Leu Trp Leu Cys Thr Gly Leu Phe Pro Pro Ser Asn
1835                1840                1845

Ile Leu Leu Pro His Val Gln Arg Phe Leu Gln Ser Arg Lys His
1850                1855                1860

Cys Pro Leu Ala Ile Asp Cys Leu Gln Arg Leu Gln Lys Ala Leu
1865                1870                1875

Arg Asn Gly Ser Arg Lys Tyr Pro Pro His Leu Val Glu Val Glu
1880                1885                1890

Ala Ile Gln His Lys Thr Thr Gln Ile Phe His Lys Val Tyr Phe
1895                1900                1905

Pro Asp Asp Thr Asp Glu Ala Phe Glu Val Glu Ser Ser Thr Lys
1910                1915                1920

Ala Lys Asp Phe Cys Gln Asn Ile Ala Thr Arg Leu Leu Leu Lys
1925                1930                1935

Ser Ser Glu Gly Phe Ser Leu Phe Val Lys Ile Ala Asp Lys Val
1940                1945                1950

Leu Ser Val Pro Glu Asn Asp Phe Phe Phe Asp Phe Val Arg His
1955                1960                1965

Leu Thr Asp Trp Ile Lys Lys Ala Arg Pro Ile Lys Asp Gly Ile
1970                1975                1980

Val Pro Ser Leu Thr Tyr Gln Val Phe Phe Met Lys Lys Leu Trp
1985                1990                1995

Thr Thr Thr Val Pro Gly Lys Asp Pro Met Ala Asp Ser Ile Phe
2000                2005                2010

His Tyr Tyr Gln Glu Leu Pro Lys Tyr Leu Arg Gly Tyr His Lys
2015                2020                2025

Cys Thr Arg Glu Glu Val Leu Gln Leu Gly Ala Leu Ile Tyr Arg
2030                2035                2040

Val Lys Phe Glu Glu Asp Lys Ser Tyr Phe Pro Ser Ile Pro Lys
2045                2050                2055

Leu Leu Arg Glu Leu Val Pro Gln Asp Leu Ile Arg Gln Val Ser
2060                2065                2070

Pro Asp Asp Trp Lys Arg Ser Ile Val Ala Tyr Phe Asn Lys His
2075                2080                2085

Ala Gly Lys Ser Lys Glu Glu Ala Lys Leu Ala Phe Leu Lys Leu
2090                2095                2100

Ile Phe Lys Trp Pro Thr Phe Gly Ser Ala Phe Phe Glu Val Lys
2105                2110                2115

Gln Thr Thr Glu Pro Asn Phe Pro Glu Ile Leu Leu Ile Ala Ile
2120                2125                2130

Asn Lys Tyr Gly Val Ser Leu Ile Asp Pro Lys Thr Lys Asp Ile
2135                2140                2145

Leu Thr Thr His Pro Phe Thr Lys Ile Ser Asn Trp Ser Ser Gly
2150                2155                2160

| | | | | | | | | | | | |
|---|---|---|---|---|---|---|---|---|---|---|---|
| Asn | Thr | Tyr | Phe | His | Ile | Thr | Ile | Gly | Asn | Leu | Val | Arg | Gly | Ser |
| | 2165 | | | | | 2170 | | | | | 2175 | | | |
| Lys | Leu | Leu | Cys | Glu | Thr | Ser | Leu | Gly | Tyr | Lys | Met | Asp | Asp | Leu |
| 2180 | | | | | | 2185 | | | | | | 2190 | | |
| Leu | Thr | Ser | Tyr | Ile | Ser | Gln | Met | Leu | Thr | Ala | Met | Ser | Lys | Gln |
| | 2195 | | | | | 2200 | | | | | 2205 | | | |
| Arg | Gly | Ser | Arg | Ser | Gly | Lys | | | | | | | | |
| | 2210 | | | | | 2215 | | | | | | | | |

<210> SEQ ID NO 69
<211> LENGTH: 7339
<212> TYPE: DNA
<213> ORGANISM: Homo sapiens

<400> SEQUENCE: 69

```
ggcaggagag agagggagag acaagagaca cacacagaga gacggcgagg aagggaaaga      60
cccagaggga cgcctagaac gagacttgga gccagacaga ggaagagggg acgtgtgttt     120
gcagactggc tgggcccgtg acccagcttc ctgagtcctc cgtgcaggtg cagctgtac     180
caggctggca ggtcactgag agtgggcagc tgggccccag aactgtgcct ggcccagtgg     240
gcagcaggag ctcctgactt gggaccatga tgattcttca gcaggggac catgtgtgga     300
tggacctgag attggggcag gagttcgacg tgcccatcgg ggcggtggtg aagctctgcg     360
actctgggca ggtccaggtg gtggatgatg aagacaatga acactggatc tctccgcaga     420
acgcaacgca catcaagcct atgcacccca cgtcggtcca cggcgtggag acatgatcc     480
gcctggggga cctcaacgag gcgggcatct tgcgcaacct gcttatccgc taccgggacc     540
acctcatcta cacgtatacg ggctccatcc tggtggctgt gaaccctac cagctgctct     600
ccatctactc gccagagcac atccgccagt ataccaacaa gagattggg gagatgcccc     660
cccacatctt tgccattgct gacaactgct acttcaacat gaaacgcaac agccgagacc     720
agtgctgcat catcagtggg gaatctgggg ccgggaagac ggagagcaca aagctgatcc     780
tgcagttcct ggcagccatc agtgggcagc actcgtggat tgagcagcag gtcttggagg     840
ccaccccat tctggaagca tttgggaatg ccaagaccat ccgcaatgac aactcaagcc     900
gtttcggaaa gtacatcgac atccacttca caagcgggg cgccatcgag ggcgcgaaga     960
ttgagcagta cctgctggaa aagtcacgtg tctgtcgcca ggccctggat gaaaggaact    1020
accacgtgtt ctactgcatg ctggagggta tgagtgagga tcagaagaag aagctgggct    1080
gggccaggc tctgactac aactacttgg ccatgggtaa ctgcataacc tgtgagggcc    1140
gggtggacag ccaggagtac gccaacatcc gctccgccat gaaggtgctc atgttcactg    1200
acaccgagaa ctgggagatc tcgaagctcc tggctgccat cctgcacctg gcaacctgc    1260
agtatgaggc acgcacattt gaaaacctgg atgcctgtga ggttctcttc tccccatcgc    1320
tggccacagc tgcatccctg cttgaggtga cccccccaga cctgatgagc tgcctgacta    1380
gccgcaccct catcacccgc ggggagacgg tgtccacccc actgagcagg gaacaggcac    1440
tggacgtgcg cgacgccttc gtaaagggga tctacgggcg gctgttcgtg tggattgtgg    1500
acaagatcaa cgcagcaatt tacaagcctc cctcccagga tgtgaagaac tctcgcaggt    1560
ccatcggcct cctggacatc tttgggtttg agaactttgc tgtgaacagc tttgagcagc    1620
tctgcatcaa cttcgccaat gagcacctgc agcagttctt tgtgcggcac gtgttcaagc    1680
tggagcagga ggaatatgac ctggagagca ttgactggct gcacatcgag ttcactgaca    1740
accaggatgc cctggacatg attgccaaca agcccatgaa catcatctcc ctcatcgatg    1800
```

```
aggagagcaa gttccccaag ggcacagaca ccaccatgtt acacaagctg aactcccagc    1860
acaagctcaa cgccaactac atcccccca agaacaacca tgagacccag tttggcatca    1920
accattttgc aggcatcgtc tactatgaga cccaaggctt cctggagaag aaccgagaca    1980
ccctgcatgg ggacattatc cagctggtcc actcctccag gaacaagttc atcaagcaga    2040
tcttccaggc cgatgtcgcc atgggcgccg agaccaggaa gcgctcgccc acacttagca    2100
gccagttcaa gcggtcactg gagctgctga tgcgcacgct gggtgcctgc cagcccttct    2160
ttgtgcgatg catcaagccc aatgagttca gaagcccat gctgttcgac cggcacctgt    2220
gcgtgcgcca gctgcggtac tcaggaatga tggagaccat ccgaatccgc cgagctggct    2280
accccatccg ctacagcttc gtagagtttg tggagcggta ccgtgtgctg ctgccaggtg    2340
tgaagccggc ctacaagcag gcgacctcc gcgggacttg ccagcgcatg gctgaggctg    2400
tgctgggcac ccacgatgac tggcagatag gcaaaaccaa gatctttctg aaggaccacc    2460
atgacatgct gctggaagtg gagcgggaca aagccatcac cgacagagtc atcctccttc    2520
agaaagtcat ccggggattc aaagacaggt ctaactttct gaagctgaag aacgctgcca    2580
cactgatcca gaggcactgg cggggtcaca actgtaggaa gaactacggg ctgatgcgtc    2640
tgggcttcct gcggctgcag gccctgcacc gctcccggaa gctgcaccag cagtaccgcc    2700
tggcccgcca gcgcatcatc cagttccagg cccgctgccg cgcctatctg gtgcgcaagg    2760
ccttccgcca ccgcctctgg gctgtgctca ccgtgcaggc ctatgcccgg gcatgatcg    2820 cccgcaggct gcaccaacgc ctcagggctg agtatctgtg gcgcctcgag gctgagaaaa    2880
tgcggctggc ggaggaagag aagcttcgga aggagatgag cgccaagaag gccaaggagg    2940
aggccgagcg caagcatcag gagcgcctgg cccagctggc tcgtgaggac gctgagcggg    3000
agctgaagga gaaggaggcc gctcggcgga agaaggagct cctggagcag atggaaaggg    3060
cccgccatga gcctgtcaat cactcagaca tggtgggaca agatgtttggc ttcctgggga    3120 cttcaggtgg cctgccaggc caggagggcc aggcacctag tggctttgag gacctggagc    3180
gagggcggag ggagatggtg gaggaggacc tggatgcagc cctgccctg cctgacgagg    3240 atgaggagga cctctctgag tataaatttg ccaagttcgc ggccacctac ttccagggga    3300
caaccacgca ctcctacacc cggcggccac tcaaacagcc actgctctac catgacgacg    3360
agggtgacca gctggcagcc ctggcggtct ggatcaccat cctccgcttc atggggacc    3420 tccctgagcc caagtaccac acagccatga gtgatggcag tgagaagatc cctgtgatga    3480
ccaagattta tgagaccctg gcaagaaga cgtacaagag ggagctgcag gccctgcagg    3540
gcgagggcga ggcccagctc cccgagggcc agaagaagag cagtgtgagg cacaagctgg    3600
tgcatttgac tctgaaaaag aagtccaagc tcacagagga ggtgaccaag aggctgcatg    3660
acggggagtc cacagtgcag ggcaacagca tgctggagga ccggcccacc tccaacctgg    3720
agaagctgca cttcatcatc ggcaatggca tcctgcggcc agcactccgg gacgagatct    3780
actgccagat cagcaagcag ctgacccaca accctccaa gagcagctat gcccggggct    3840
ggattctcgt gtctctctgc gtgggctgtt tcgccccctc cgagaagttt gtcaagtacc    3900
tgcggaactt catccacggg ggcccgcccg gctacgcccc gtactgtgag gagcgcctga    3960
gaaggacctt tgtcaatggg acacggacac agccgcccag ctggctggag ctgcaggcca    4020
ccaagtccaa gaagccaatc atgttgcccg tgacattcat ggatgggacc accaagaccc    4080
tgctgacgga ctcggcaacc acggccaagg agctctgcaa cgcgctggcc gacaagatct    4140
```

```
ctctcaagga ccggttcggg ttctccctct acattgccct gtttgacaag gtgtcctccc      4200
tgggcagcgg cagtgaccac gtcatggacg ccatctccca gtgcgagcag tacgccaagg      4260
agcagggcgc ccaggagcgc aacgccccct ggaggctctt cttccgcaaa gaggtcttca      4320
cgccctggca cagcccctcc gaggacaacg tggccaccaa cctcatctac cagcaggtgg      4380
tgcgaggagt caagtttggg gagtacaggt gtgagaagga ggacgacctg gctgagctgg      4440
cctcccagca gtactttgta gactatggct ctgagatgat cctggagcgc ctcctgaacc      4500
tcgtgcccac ctacatcccc gaccgcgaga tcacgcccct gaagacgctg gagaagtggg      4560
cccagctggc catcgccgcc cacaagaagg ggatttatgc ccagaggaga actgatgccc      4620
agaaggtcaa agaggatgtg gtcagttatg cccgcttcaa gtggcccttg ctcttctcca      4680
ggttttatga agcctacaaa ttctcaggcc ccagtctccc caagaacgac gtcatcgtgg      4740
ccgtcaactg gacgggtgtg tactttgtgg atgagcagga gcaggtactt ctggagctgt      4800
ccttcccaga gatcatggcc gtgtccagca gcagggagc gaaaacgacg gcccccagct      4860
tcacgctggc caccatcaag ggggacgaat acaccttcac ctccagcaat gctgaggaca      4920
ttcgtgacct ggtggtcacc ttcctagagg ggctccggaa gagatctaag tatgttgtgg      4980
ccctgcagga taaccccaac cccgcaggcg aggagtcagg cttcctcagc tttgccaagg      5040
gagacctcat catcctggac catgacacgg gcgagcaggt catgaactcg ggctgggcca      5100
acggcatcaa tgagaggacc aagcagcgtg gggacttccc caccgacagt gtgtacgtca      5160
tgcccactgt caccatgcca ccgcgggaga ttgtggccct ggtcaccatg actcccgatc      5220
agaggcagga cgttgtccgg ctcttgcagc tgcgaacggc ggagcccgag gtgcgtgcca      5280
agccctacac gctggaggag ttttcctatg actacttcag gcccccaccc aagcacacgc      5340
tgagccgtgt catggtgtcc aaggcccgag gcaaggaccg gctgtggagc cacacgcggg      5400
aaccgctcaa gcaggcgctg ctcaagaagc tcctgggcag tgaggagctc tcgcaggagg      5460
cctgcctggc cttcattgct gtgctcaagt acatgggcga ctacccgtcc aagaggacac      5520
gctccgtcaa cgagctcacc gaccagatct ttgagggtcc cctgaaagcc gagcccctga      5580
aggacgaggc atatgtgcag atcctgaagc agctgaccga caaccacatc aggtacagcg      5640
aggagcgggg ttgggagctg ctctggctgt gcacgggcct ttcccacccc agcaacatcc      5700
tcctgcccca cgtgcagcgc ttcctgcagt cccgaaagca ctgccactc gccatcgact      5760 gcctgcaacg gctccagaaa gccctgagaa acgggtcccg gaagtaccct ccgcacctgg      5820
tggaggtgga ggccatccag cacaagacca cccagatttt ccacaaagtc tacttccctg      5880
atgacactga cgaggccttc gaagtggagt ccagcaccaa ggccaaggac ttctgccaga      5940
acatcgccac caggctgctc ctcaagtcct cagagggatt cagcctcttt gtcaaaattg      6000
cagacaaggt cctcagcgtt cctgagaatg acttcttctt tgactttgtt cgacacttga      6060
cagactggat aaagaaagct cggcccatca aggacgaat tgtgccctca ctcacctacc      6120
aggtgttctt catgaagaag ctgtggacca ccacggtgcc agggaaggat cccatggccg      6180
attccatctt ccactattac caggagttgc ccaagtatct ccgaggctac cacaagtgca      6240
cgcgggagga ggtgctgcag ctgggggcgc tgatctacag ggtcaagttc gaggaggaca      6300
agtcctactt ccccagcatc cccaagctgc tgcgggagct ggtgccccag gaccttatcc      6360
ggcaggtctc acctgatgac tggaagcggt ccatcgtcgc ctacttcaac aagcacgcag      6420
ggaagtccaa ggaggaggcc aagctggcct tcctgaagct catcttcaag tggcccacct      6480
ttggctcagc cttcttcgag caaactacgg agccaaactt ccctgagatc ctcctaattg      6540
```

-continued

```
ccatcaacaa gtatgggtc agcctcatcg atcccaaaac gaaggatatc ctcaccactc    6600
atcccttcac caagatctcc aactggagca gcggcaacac ctacttccac atcaccattg    6660
ggaacttggt gcgcgggagc aaactgctct gcgagacgtc actgggctac aagatggatg    6720
acctcctgac ttcctacatt agccagatgc tcacagccat gagcaaacag cggggctcca    6780
ggagcggcaa gtgaacagtc acggggaggt gctggttcca tgcctgctct cgaggcagca    6840
gtgggttcag gcccatcagc taccctgca gctggggaag acttatgcca tcccggcagc    6900
gaggctgggc tggccagcca ccactgacta taccaactgg gcctctgatg ttcttccagt    6960
gaggcatctc tctgggatgc agaacttccc tccatccacc cctctggcac tgggttggt    7020
ctaatcctag tttgctgtgg ccttcccggt tgtgagagcc tgtgatcctt agatgtgtct    7080
cctgtttcag accagcccca ccatgcaact tcctttgact ttctgtgtac cactgggata    7140
gaggaatcaa gaggacaatc tagctctcca tactttgaac aaccaaatgt gcattgaata    7200
ctctgaaacc gaagggactg gatctgcagg tgggatgagg gagacagacc acttttctat    7260
attgcagtgt gaatgctggg cccctgctca agtctaccct gatcacctca gggcataaag    7320
catgtttcat tctctggcc                                                7339
```

<210> SEQ ID NO 70
<211> LENGTH: 2175
<212> TYPE: PRT
<213> ORGANISM: Homo sapiens

<400> SEQUENCE: 70

```
Met Val Ile Leu Gln Gln Gly Asp His Val Trp Met Asp Leu Arg Leu
1               5                   10                  15

Gly Gln Glu Phe Asp Val Pro Ile Gly Ala Val Val Lys Leu Cys Asp
            20                  25                  30

Ser Gly Gln Val Gln Val Val Asp Asp Glu Asp Asn Glu His Trp Ile
        35                  40                  45

Ser Pro Gln Asn Ala Thr His Ile Lys Pro Met His Pro Thr Ser Val
    50                  55                  60

His Gly Val Glu Asp Met Ile Arg Leu Gly Asp Leu Asn Glu Ala Gly
65                  70                  75                  80

Ile Leu Arg Asn Leu Leu Ile Arg Tyr Arg Asp His Leu Ile Tyr Thr
                85                  90                  95

Tyr Thr Gly Ser Ile Leu Val Ala Val Asn Pro Tyr Gln Leu Leu Ser
            100                 105                 110

Ile Tyr Ser Pro Glu His Ile Arg Gln Tyr Thr Asn Lys Lys Ile Gly
        115                 120                 125

Glu Met Pro Pro His Ile Phe Ala Ile Ala Asp Asn Cys Tyr Phe Asn
    130                 135                 140

Met Lys Arg Asn Ser Arg Asp Gln Cys Cys Ile Ile Ser Gly Glu Ser
145                 150                 155                 160

Gly Ala Gly Lys Thr Glu Ser Thr Lys Leu Ile Leu Gln Phe Leu Ala
                165                 170                 175

Ala Ile Ser Gly Gln His Ser Trp Ile Glu Gln Gln Val Leu Glu Ala
            180                 185                 190

Thr Pro Ile Leu Glu Ala Phe Gly Asn Ala Lys Thr Ile Arg Asn Asp
        195                 200                 205

Asn Ser Ser Arg Phe Gly Lys Tyr Ile Asp Ile His Phe Asn Lys Arg
    210                 215                 220
```

```
Gly Ala Ile Glu Gly Ala Lys Ile Glu Gln Tyr Leu Leu Glu Lys Ser
225                 230                 235                 240

Arg Val Cys Arg Gln Ala Leu Asp Glu Arg Asn Tyr His Val Phe Tyr
            245                 250                 255

Cys Met Leu Glu Gly Met Ser Glu Asp Gln Lys Lys Lys Leu Gly Leu
                260                 265                 270

Gly Gln Ala Ser Asp Tyr Asn Tyr Leu Ala Met Gly Asn Cys Ile Thr
            275                 280                 285

Cys Glu Gly Arg Val Asp Ser Gln Glu Tyr Ala Asn Ile Arg Ser Ala
290                 295                 300

Met Lys Val Leu Met Phe Thr Asp Thr Glu Asn Trp Glu Ile Ser Lys
305                 310                 315                 320

Leu Leu Ala Ala Ile Leu His Leu Gly Asn Leu Gln Tyr Glu Ala Arg
                325                 330                 335

Thr Phe Glu Asn Leu Asp Ala Cys Glu Val Leu Phe Ser Pro Ser Leu
                340                 345                 350

Ala Thr Ala Ala Ser Leu Leu Glu Val Asn Pro Pro Asp Leu Met Ser
            355                 360                 365

Cys Leu Thr Ser Arg Thr Leu Ile Thr Arg Gly Glu Thr Val Ser Thr
370                 375                 380

Pro Leu Ser Arg Glu Gln Ala Leu Asp Val Arg Asp Ala Phe Val Lys
385                 390                 395                 400

Gly Ile Tyr Gly Arg Leu Phe Val Trp Ile Val Asp Lys Ile Asn Ala
                405                 410                 415

Ala Ile Tyr Lys Pro Pro Ser Gln Asp Val Lys Asn Ser Arg Arg Ser
                420                 425                 430

Ile Gly Leu Leu Asp Ile Phe Gly Phe Glu Asn Phe Ala Val Asn Ser
            435                 440                 445

Phe Glu Gln Leu Cys Ile Asn Phe Ala Asn Glu His Leu Gln Gln Phe
450                 455                 460

Phe Val Arg His Val Phe Lys Leu Glu Gln Glu Glu Tyr Asp Leu Glu
465                 470                 475                 480

Ser Ile Asp Trp Leu His Ile Glu Phe Thr Asp Asn Gln Asp Ala Leu
                485                 490                 495

Asp Met Ile Ala Asn Lys Pro Met Asn Ile Ile Ser Leu Ile Asp Glu
            500                 505                 510

Glu Ser Lys Phe Pro Lys Gly Thr Asp Thr Thr Met Leu His Lys Leu
            515                 520                 525

Asn Ser Gln His Lys Leu Asn Ala Asn Tyr Ile Pro Pro Lys Asn Asn
530                 535                 540

His Glu Thr Gln Phe Gly Ile Asn His Phe Ala Gly Ile Val Tyr Tyr
545                 550                 555                 560

Glu Thr Gln Gly Phe Leu Glu Lys Asn Arg Asp Thr Leu His Gly Asp
                565                 570                 575

Ile Ile Gln Leu Val His Ser Ser Arg Asn Lys Phe Ile Lys Gln Ile
                580                 585                 590

Phe Gln Ala Asp Val Ala Met Gly Ala Glu Thr Arg Lys Arg Ser Pro
            595                 600                 605

Thr Leu Ser Ser Gln Phe Lys Arg Ser Leu Glu Leu Leu Met Arg Thr
            610                 615                 620

Leu Gly Ala Cys Gln Pro Phe Phe Val Arg Cys Ile Lys Pro Asn Glu
625                 630                 635                 640
```

```
Phe Lys Lys Pro Met Leu Phe Asp Arg His Leu Cys Val Arg Gln Leu
                645             650                 655

Arg Tyr Ser Gly Met Met Glu Thr Ile Arg Ile Arg Ala Gly Tyr
                660             665                 670

Pro Ile Arg Tyr Ser Phe Val Glu Phe Val Glu Arg Tyr Arg Val Leu
                675             680                 685

Leu Pro Gly Val Lys Pro Ala Tyr Lys Gln Gly Asp Leu Arg Gly Thr
            690             695             700

Cys Gln Arg Met Ala Glu Ala Val Leu Gly Thr His Asp Trp Gln
705             710             715                 720

Ile Gly Lys Thr Lys Ile Phe Leu Lys Asp His His Asp Met Leu Leu
                725             730                 735

Glu Val Glu Arg Asp Lys Ala Ile Thr Asp Arg Val Ile Leu Leu Gln
                740             745                 750

Lys Val Ile Arg Gly Phe Lys Asp Arg Ser Asn Phe Leu Lys Leu Lys
                755             760                 765

Asn Ala Ala Thr Leu Ile Gln Arg His Trp Arg Gly His Asn Cys Arg
770             775             780

Lys Asn Tyr Gly Leu Met Arg Leu Gly Phe Leu Arg Leu Gln Ala Leu
785             790             795                 800

His Arg Ser Arg Lys Leu His Gln Gln Tyr Arg Leu Ala Arg Gln Arg
                805             810                 815

Ile Ile Gln Phe Gln Ala Arg Cys Arg Ala Tyr Leu Val Arg Lys Ala
                820             825             830

Phe Arg His Arg Leu Trp Ala Val Leu Thr Val Gln Ala Tyr Ala Arg
                835             840             845

Gly Met Ile Ala Arg Arg Leu His Gln Arg Leu Arg Ala Glu Tyr Leu
850             855             860

Trp Arg Leu Glu Ala Glu Lys Met Arg Leu Ala Glu Glu Lys Leu
865             870             875             880

Arg Lys Glu Met Ser Ala Lys Lys Ala Lys Glu Glu Ala Glu Arg Lys
                885             890             895

His Gln Glu Arg Leu Ala Gln Leu Ala Arg Glu Asp Ala Glu Arg Glu
            900             905             910

Leu Lys Glu Lys Glu Ala Ala Arg Arg Lys Lys Glu Leu Leu Glu Gln
                915             920             925

Met Glu Arg Ala Arg His Glu Pro Val Asn His Ser Asp Met Val Asp
930             935             940

Lys Met Phe Gly Phe Leu Gly Thr Ser Gly Gly Leu Pro Gly Gln Glu
945             950             955             960

Gly Gln Ala Pro Ser Gly Phe Glu Asp Leu Glu Arg Gly Arg Arg Glu
                965             970             975

Met Val Glu Glu Asp Leu Asp Ala Ala Leu Pro Leu Pro Asp Glu Asp
            980             985             990

Glu Glu Asp Leu Ser Glu Tyr Lys  Phe Ala Lys Phe Ala  Ala Thr Tyr
            995             1000            1005

Phe Gln  Gly Thr Thr Thr His  Ser Tyr Thr Arg Arg  Pro Leu Lys
    1010             1015              1020

Gln Pro  Leu Leu Tyr His Asp  Asp Glu Gly Asp Gln  Leu Ala Ala
    1025             1030             1035

Leu Ala  Val Trp Ile Thr Ile  Leu Arg Phe Met Gly  Asp Leu Pro
    1040             1045             1050
```

-continued

Glu Pro Lys Tyr His Thr Ala Met Ser Asp Gly Ser Glu Lys Ile
1055                1060                1065

Pro Val Met Thr Lys Ile Tyr Glu Thr Leu Gly Lys Lys Thr Tyr
1070                1075                1080

Lys Arg Glu Leu Gln Ala Leu Gln Gly Glu Gly Glu Ala Gln Leu
1085                1090                1095

Pro Glu Gly Gln Lys Lys Ser Ser Val Arg His Lys Leu Val His
1100                1105                1110

Leu Thr Leu Lys Lys Lys Ser Lys Leu Thr Glu Glu Val Thr Lys
1115                1120                1125

Arg Leu His Asp Gly Glu Ser Thr Val Gln Gly Asn Ser Met Leu
1130                1135                1140

Glu Asp Arg Pro Thr Ser Asn Leu Glu Lys Leu His Phe Ile Ile
1145                1150                1155

Gly Asn Gly Ile Leu Arg Pro Ala Leu Arg Asp Glu Ile Tyr Cys
1160                1165                1170

Gln Ile Ser Lys Gln Leu Thr His Asn Pro Ser Lys Ser Ser Tyr
1175                1180                1185

Ala Arg Gly Trp Ile Leu Val Ser Leu Cys Val Gly Cys Phe Ala
1190                1195                1200

Pro Ser Glu Lys Phe Val Lys Tyr Leu Arg Asn Phe Ile His Gly
1205                1210                1215

Gly Pro Pro Gly Tyr Ala Pro Tyr Cys Glu Glu Arg Leu Arg Arg
1220                1225                1230

Thr Phe Val Asn Gly Thr Arg Thr Gln Pro Pro Ser Trp Leu Glu
1235                1240                1245

Leu Gln Ala Thr Lys Ser Lys Lys Pro Ile Met Leu Pro Val Thr
1250                1255                1260

Phe Met Asp Gly Thr Thr Lys Thr Leu Leu Thr Asp Ser Ala Thr
1265                1270                1275

Thr Ala Lys Glu Leu Cys Asn Ala Leu Ala Asp Lys Ile Ser Leu
1280                1285                1290

Lys Asp Arg Phe Gly Phe Ser Leu Tyr Ile Ala Leu Phe Asp Lys
1295                1300                1305

Val Ser Ser Leu Gly Ser Gly Ser Asp His Val Met Asp Ala Ile
1310                1315                1320

Ser Gln Cys Glu Gln Tyr Ala Lys Glu Gln Gly Ala Gln Glu Arg
1325                1330                1335

Asn Ala Pro Trp Arg Leu Phe Phe Arg Lys Glu Val Phe Thr Pro
1340                1345                1350

Trp His Ser Pro Ser Glu Asp Asn Val Ala Thr Asn Leu Ile Tyr
1355                1360                1365

Gln Gln Val Val Arg Gly Val Lys Phe Gly Glu Tyr Arg Cys Glu
1370                1375                1380

Lys Glu Asp Asp Leu Ala Glu Leu Ala Ser Gln Gln Tyr Phe Val
1385                1390                1395

Asp Tyr Gly Ser Glu Met Ile Leu Glu Arg Leu Leu Asn Leu Val
1400                1405                1410

Pro Thr Tyr Ile Pro Asp Arg Glu Ile Thr Pro Leu Lys Thr Leu
1415                1420                1425

Glu Lys Trp Ala Gln Leu Ala Ile Ala Ala His Lys Lys Gly Ile
1430                1435                1440

```
Tyr Ala Gln Arg Arg Thr Asp Ala Gln Lys Val Lys Glu Asp Val
    1445                1450                1455

Val Ser Tyr Ala Arg Phe Lys Trp Pro Leu Leu Phe Ser Arg Phe
    1460                1465                1470

Tyr Glu Ala Tyr Lys Phe Ser Gly Pro Ser Leu Pro Lys Asn Asp
    1475                1480                1485

Val Ile Val Ala Val Asn Trp Thr Gly Val Tyr Phe Val Asp Glu
    1490                1495                1500

Gln Glu Gln Val Leu Leu Glu Leu Ser Phe Pro Glu Ile Met Ala
    1505                1510                1515

Val Ser Ser Ser Arg Gly Ala Lys Thr Thr Ala Pro Ser Phe Thr
    1520                1525                1530

Leu Ala Thr Ile Lys Gly Asp Glu Tyr Thr Phe Thr Ser Ser Asn
    1535                1540                1545

Ala Glu Asp Ile Arg Asp Leu Val Val Thr Phe Leu Glu Gly Leu
    1550                1555                1560

Arg Lys Arg Ser Lys Tyr Val Val Ala Leu Gln Asp Asn Pro Asn
    1565                1570                1575

Pro Ala Gly Glu Glu Ser Gly Phe Leu Ser Phe Ala Lys Gly Asp
    1580                1585                1590

Leu Ile Ile Leu Asp His Asp Thr Gly Glu Gln Val Met Asn Ser
    1595                1600                1605

Gly Trp Ala Asn Gly Ile Asn Glu Arg Thr Lys Gln Arg Gly Asp
    1610                1615                1620

Phe Pro Thr Asp Ser Val Tyr Val Met Pro Thr Val Thr Met Pro
    1625                1630                1635

Pro Arg Glu Ile Val Ala Leu Val Thr Met Thr Pro Asp Gln Arg
    1640                1645                1650

Gln Asp Val Val Arg Leu Leu Gln Leu Arg Thr Ala Glu Pro Glu
    1655                1660                1665

Val Arg Ala Lys Pro Tyr Thr Leu Glu Glu Phe Ser Tyr Asp Tyr
    1670                1675                1680

Phe Arg Pro Pro Pro Lys His Thr Leu Ser Arg Val Met Val Ser
    1685                1690                1695

Lys Ala Arg Gly Lys Asp Arg Leu Trp Ser His Thr Arg Glu Pro
    1700                1705                1710

Leu Lys Gln Ala Leu Leu Lys Leu Leu Gly Ser Glu Glu Leu
    1715                1720                1725

Ser Gln Glu Ala Cys Leu Ala Phe Ile Ala Val Leu Lys Tyr Met
    1730                1735                1740

Gly Asp Tyr Pro Ser Lys Arg Thr Arg Ser Val Asn Glu Leu Thr
    1745                1750                1755

Asp Gln Ile Phe Glu Gly Pro Leu Lys Ala Glu Pro Leu Lys Asp
    1760                1765                1770

Glu Ala Tyr Val Gln Ile Leu Lys Gln Leu Thr Asp Asn His Ile
    1775                1780                1785

Arg Tyr Ser Glu Glu Arg Gly Trp Glu Leu Leu Trp Leu Cys Thr
    1790                1795                1800

Gly Leu Phe Pro Pro Ser Asn Ile Leu Leu Pro His Val Gln Arg
    1805                1810                1815

Phe Leu Gln Ser Arg Lys His Cys Pro Leu Ala Ile Asp Cys Leu
    1820                1825                1830
```

```
Gln Arg Leu Gln Lys Ala Leu Arg Asn Gly Ser Arg Lys Tyr Pro
    1835                1840                1845

Pro His Leu Val Glu Val Glu Ala Ile Gln His Lys Thr Thr Gln
    1850                1855                1860

Ile Phe His Lys Val Tyr Phe Pro Asp Asp Thr Asp Glu Ala Phe
    1865                1870                1875

Glu Val Glu Ser Ser Thr Lys Ala Lys Asp Phe Cys Gln Asn Ile
    1880                1885                1890

Ala Thr Arg Leu Leu Leu Lys Ser Ser Glu Gly Phe Ser Leu Phe
    1895                1900                1905

Val Lys Ile Ala Asp Lys Val Leu Ser Val Pro Glu Asn Asp Phe
    1910                1915                1920

Phe Phe Asp Phe Val Arg His Leu Thr Asp Trp Ile Lys Lys Ala
    1925                1930                1935

Arg Pro Ile Lys Asp Gly Ile Val Pro Ser Leu Thr Tyr Gln Val
    1940                1945                1950

Phe Phe Met Lys Lys Leu Trp Thr Thr Thr Val Pro Gly Lys Asp
    1955                1960                1965

Pro Met Ala Asp Ser Ile Phe His Tyr Tyr Gln Glu Leu Pro Lys
    1970                1975                1980

Tyr Leu Arg Gly Tyr His Lys Cys Thr Arg Glu Glu Val Leu Gln
    1985                1990                1995

Leu Gly Ala Leu Ile Tyr Arg Val Lys Phe Glu Glu Asp Lys Ser
    2000                2005                2010

Tyr Phe Pro Ser Ile Pro Lys Leu Leu Arg Glu Leu Val Pro Gln
    2015                2020                2025

Asp Leu Ile Arg Gln Val Ser Pro Asp Asp Trp Lys Arg Ser Ile
    2030                2035                2040

Val Ala Tyr Phe Asn Lys His Ala Gly Lys Ser Lys Glu Glu Ala
    2045                2050                2055

Lys Leu Ala Phe Leu Lys Leu Ile Phe Lys Trp Pro Thr Phe Gly
    2060                2065                2070

Ser Ala Phe Phe Glu Gln Thr Thr Glu Pro Asn Phe Pro Glu Ile
    2075                2080                2085

Leu Leu Ile Ala Ile Asn Lys Tyr Gly Val Ser Leu Ile Asp Pro
    2090                2095                2100

Lys Thr Lys Asp Ile Leu Thr Thr His Pro Phe Thr Lys Ile Ser
    2105                2110                2115

Asn Trp Ser Ser Gly Asn Thr Tyr Phe His Ile Thr Ile Gly Asn
    2120                2125                2130

Leu Val Arg Gly Ser Lys Leu Leu Cys Glu Thr Ser Leu Gly Tyr
    2135                2140                2145

Lys Met Asp Asp Leu Leu Thr Ser Tyr Ile Ser Gln Met Leu Thr
    2150                2155                2160

Ala Met Ser Lys Gln Arg Gly Ser Arg Ser Gly Lys
    2165                2170                2175

<210> SEQ ID NO 71
<211> LENGTH: 7481
<212> TYPE: DNA
<213> ORGANISM: Mus musculus
```

<400> SEQUENCE: 71

```
agtgcaggct ggacagctgc cctgaacaga aagaaagagt gacccaggga gacaagaaac    60
agagtagccc aagggaagcc cacagcagca gcagatcaag gctcaagctg gagctgaaaa   120
tttgcaggct ccagcctcag cttccagagt cctcctgacc tgtgacccct ggctcctggc   180
tgggaggtgg tgactcggag ggtgtggata aacccagag ctgtgtctgg tcactccggc    240
aggtgtgctg acgtagaagc atggttattc tgcagaaggg ggactatgta tggatggacc   300
tgaagtcagg ccaggagttt gatgtgccca tcggggccgt ggtgaagctc tgcgactcgg   360
gccagatcca ggtggtggat gatgaagaca atgaacactg gatatcccct cagaatgcca   420
cgcacatcaa gccaatgcac cccacatcgg tgcacggcgt ggaggacatg atccgcctgg   480
gggatctcaa cgaggcaggc atccttcgaa accttctcat tcgctaccgg gaccacctca   540
tctatacgta cacaggttcc atcctggtgg ccgtgaaccc ctaccagctg ctctccatct   600
actcgccaga gcatccgc cagtacacca acaagaagat aggggagatg cccccccaca    660
tcttcgccat tgctgacaac tgctacttca acatgaaacg caacaaccgg gaccagtgct   720
gtattatcag cggggagtcg ggagctggca agacagagag cacaaagttg atcctgcagt   780
tcctggcagc catcagtgga cagcactcat ggatcgagca gcaggtgctg gaggccaccc   840
cgatcctgga agcatttggg aacgccaaga ccatccgcaa cgacaactct agccgctttg   900
gcaagtacat tgacatccac tttaacaagc gtggtgccat cgagggcgcc aaaatagagc   960
aatacctgct ggagaagtca cgtgtctgcc gccaggcccc tgacgagagg aactatcacg  1020
tgttctactg tatgctggag ggcatgaatg aggaggagaa gaagaaactg ggcctaggcc  1080
aggccgctga ctacaactac ttggccatgg gtaactgcat cacctgtgag ggccgcgtgg  1140
acagtcagga gtatgccaac atccgctctg ccatgaaggt tctcatgttc acagacacgg  1200
agaactggga gatctcgaag cttctggctg ccatcctaca catgggcaat ctgcagtatg  1260
aggcccggac atttgagaac ttggatgcgt gtgaagtcct cttctcccca tcgctggcca  1320
cggcagcttc tctgctcgag gtgaaccccc cagacctgat gagctgcctc accagccgca  1380
ccctcatcac ccgtggggag acggtgtcca ccccctctcag cagggaacag gcgctggatg  1440
tgcgagatgc cttttgtcaag ggcatctatg gcggctctt tgtgtggatt gtggagaaga  1500
tcaacgcagc aatctacaag ccaccccccc tggaagtgaa gaactctcgc ggtccatcg    1560
gtctcctgga catctttgga tttgagaact tcactgtgaa cagcttcgag cagctctgca  1620
ttaactttgc caatgagcac ctgcagcaat tcttcgtgcg gcacgtgttc aagctggagc  1680
aggaggagta cgacctggag agcatcgact ggttgcacat tgagttcact gacaaccagg  1740
aagcactgga catgattgcc aaccggccta tgaacgtcat ctccctcatc gatgaggaga  1800
gcaagttccc caagggcacg gatgccacca tgctgcataa gctgaactca cagcacaagc  1860
tcaatgccaa ctacgtgcca cccaagaaca gccacgagac ccagtttgga atcaaccact  1920
ttgcgggtgt tgtctattat gagagtcaag gcttcctgga agaaccgga gacaccctgc   1980
atggggacat catccagctg gtccactctt cccggaacaa gttcataaag cagatttttcc  2040
aagctgacgt tgccatgggt gccgagacca ggaagcgctc gcctacactc agcagccagt  2100
tcaagcggtc tctggagctg ctgatgcgca cactgggcgc ctgccagccc ttcttttgtgc  2160
gttgtatcaa acccaatgag ttcaagaagc ccatgtctct tgaccggcac ttgtgtgtac  2220
gccagctgcg atattcgggc atgatggaga caatccgcat ccgccacgca ggctacccca  2280
```

-continued

```
ttcgctacag ctttgtggag tttgtggagc gctaccgggt actgctgcct ggtgtgaagc    2340
cagcatacaa gcagggtgac ctccgaggga catgccagcg catggctgag gctgtgctgg    2400
gcacgcacga tgactggcag attggcaaaa ccaagatctt tctgaaggac caccatgaca    2460
tgttgctgga ggtggagcgg acaaggcca tcacagacag agtcattctc ctccagaagg     2520
ttatccgggg cttcaaagac aggtccaact tcctgagact gaagagtgct gccacactga    2580
tccagaggca ctggcgggc caccactgta ggaaaaacta tgagctgatt cgtcttggct     2640
tcctgcggct gcaggccctg caccgctccc ggaagctgca caagcagtac cgcctggcca    2700
gacagcgcat aatagagttc caggcccgct gccgggccta tctggtgcgc aaggccttcc    2760
gccaccgcct ctgggccgtg atcaccgtgc aggcctatgc ccgaggcatg attgcccgcc    2820
ggctacaccg ccgcctccgg gttgagtacc agcggcgcct cgaggcagag aggatgcgtc    2880
tggcagagga ggagaaactc cgaaaggaga tgagtgccaa gaaggccaaa gaggaggctg    2940
agcgcaagca tcaggagcgc ctggctcagc tagcccgcga ggatgcggag cgggaactga    3000
aggagaagga ggaggctcgg aggaagaagg aactgctgga gcagatggag aaggcccgcc    3060
acgaacccat caaccactca gatatggtgg acaagatgtt tggcttcctg gggacttcag    3120
gcagcctgcc aggccaggaa ggccaggcgc ctagtggctt tgaggaccta gagcgcggac    3180
ggagggagat ggtggaagag gatgttgacg ctgccctgcc cctgcctgat gaagacgagg    3240 aggaccttc tgagtacaaa ttcgccaagt ttgctgccac ctacttccag ggcacaacca    3300
cacactccta cacccggagg cctctcaagc agccgctgct ctaccacgac gatgagggtg    3360
accagctggc ggcgctggct gtctggatca ccatcctccg gttcatgggg gacctcccag    3420
agcccaagta ccacacagcc atgagcgacg gcagtgagaa gatcccagtg atgactaaga    3480
tctacgagac cctaggcaag aagacatata agagggagct gcaggccttg cagggcgagg    3540
gcgagaccca gctccctgag gggcagaaga agaccagtgt gagacacaag ttggtacact    3600
tgacactgaa gaaaaagtcc aaactcacag aagaggtgac caagaggctg aacgatgggg    3660
aatccacggt acagggcaac agcatgctgg aggatcggcc cacctcaaat ctagagaagc    3720
tgcacttcat catcggcaac ggcatcctgc ggctgcgct gcgggacgag atttactgcc    3780
agatcagtaa gcagctcaca cacaacccat ccaagagcag ctatgccagg ggctggatcc    3840
tcgtgtcgct ctgtgtgggc tgcttcgccc cctctgagaa gttcgttaag tacctgcgga    3900
acttcatcca cggaggccca cctggctatg ctccttactg tgaggagcgc ctgaggagga    3960
cctttgtcaa cggaactcgg acacagccac ccagctggct ggagctgcag gccaccaagt    4020
ccaagaagcc catcatgttg cccgtgacct tcatggatgg gaccaccaag accctgctaa    4080
cagattcagc aactacagcc agggagctgt gcaatgctct ggctgacaag atctcactca    4140
aggaccgctt tggcttctcc ctctacatcg ctctgttcga taaggtgtcc tccctgggca    4200
gcggcagtga ccatgtcatg gatgccatct ctcagtgtga gcagtacgcc aaggagcagg    4260
gtgctcagga gcgcaacgcc ccatggaggc tcttctttag aaaggaggtc ttcacaccct    4320
ggcacaaccc ctcggaggac aacgtggcca cgaacctcat ctaccagcag gtggtgcgag    4380
gagtcaagtt tggggagtac aggtgtgaga aggaggacga cctggctgag ctggcttctc    4440
agcagtactt tgtggactat ggttctgaga tgattctgga gcgcctgctg agcctcgtgc    4500
ccacttacat ccctgaccgt gagatcacac cgctgaagaa tcttgagaag tgggcacagc    4560
tggccattgc tgcccacaag aagggaattt atgcccagag gaaactgac tcccagaagg     4620 tcaaagagga tgtggtcaat tatgcccgtt tcaagtggcc cttgctcttc tccaggtttt    4680
```

```
acgaagctta caaattctca ggccctcccc tccccaagag cgacgtcatc gtggctgtca    4740
actggacggg tgtgtacttc gtggacgagc aggagcaggt gcttctggag ctgtccttcc    4800
cggagatcat ggctgtgtcc agcagtaggg agtgccgcgt cttgctctca ctgggctgct    4860
ctgacttggg ctgtgctact tgtcaatcgg gccgggcagg gctgaccccg gctggaccct    4920
gttctccgtg ttggtcctgt aggggaacaa agatgatggc ccccagcttt accctggcca    4980
ccatcaaagg agatgagtac accttcacat ccagcaatgc tgaggacatc cgtgacctgg    5040
tggtcacctt tctggagggg ctacggaaga ggtctaagta tgtggtggca ctgcaggaca    5100
atcctaaccc tgctggtgag gagtcaggct cctcagcctt cgccaaggga gacctcatca    5160
tccttgacca tgatactggt gagcaggtca tgaactcagg ctgggccaac ggcatcaacg    5220
agaggaccaa gcagcgcggc gacttcccca ctgactgtgt atacgtcatg cccactgtca    5280
ccttgccacc aagggagatt gtggccctgg tcactatgac cccagaccag aggcaggatg    5340
tcgtccggct cctgcagctt cgcacagcag agccagaggt gcgcgccaag ccctacacgc    5400
tagaggagtt ctcctacgac tacttcaggc ccccacccaa gcacacgctg agccgtgtca    5460
tggtgtccaa ggcccgcggt aaggacaggc tgtggagcca cacacgagag cccctcaagc    5520
aggccctgct caagaagatc ctgggcagtg aagaactctc ccaggaagcc tgcatggcct    5580
ttgtagctgt gctcaagtac atgggcgact acccatccaa gaggatgcga tccgtcaatg    5640
agctcactga ccagatcttt gagtgggcac tcaaggctga gcccctcaag gatgaggcct    5700
acgtgcagat cctgaagcag ctgactgaca atcacatcag gtacagcgaa gagaggggct    5760
gggaactgct gtggctgtgc acgggcctct tcccgcccag caacatcctc ctgcctcatg    5820
ttcagcggtt tctgcagtcc cgcaagcact gtcctcttgc cattgactgc ctgcagaggc    5880
tccagaaagc cctgagaaat ggctcccgga agtaccctcc gcacctggtg gaggtggagg    5940
ccatccaaca taagactacc cagatcttcc acaaggtcta cttccccgat gacacggacg    6000
aggcttttga ggtggagtcc agcaccaagg ccaaggactt ctgccagaac atcgccagcc    6060
ggctgctgct caagtcttcc gagggattca gccttttttgt caaaatcgca gataaggtca    6120
tcagcgtccc agagaatgat ttcttctttg actttgtccg acacctgaca gactggataa    6180
agaaagcacg gcccatcaag gacggaatcg tgccctcact aacctaccag gtgttcttca    6240
tgaagaagct gtggaccacc acagtgccgg gcaaggaccc catggctgac tccatcttcc    6300
actattacca ggaactgccc aaatatctcc gaggctacca caagtgcacc cgggaggagg    6360
tgctgcagct gggcgcactc atctacaggg tcaagtttga ggaggacaaa tcctacttcc    6420
ctagcatccc caagttgctg agggagctgg taccccagga cctaatccgg caggtctcac    6480
ctgatgactg gaaacggtct attgtcgcct acttcaacaa acatgcgggg aagtccaagg    6540
aggaagccaa gctggccttc ctcaaactca tcttcaagtg gcccaccttt ggctcagcct    6600
tctttgaggt gaagcaaact acagaaccaa acttcccaga gattctctta attgccatca    6660
acaagtacgg ggtcagcctc atcgatccca gaaccaagga catcctgact actcacccct    6720
tcaccaagat ctccaactgg agtagtggca cacctactt ccacatcacc attgggaact    6780
tggtccgtgg gagcaaactg ctctgtgaga catcgctggg atacaaaatg gatgatcttc    6840
tgacttccta catcagccag atgctcacag ccatgagcaa gcagaggaac tccaggagtg    6900
gaaggtgaac ctcagaggag acgctggctc aggccttggc cctctaggca gggaagctgg    6960
actgaccata tctgctgggc atctgatctg cctgccacga ggtccagact cttctgcatc    7020
```

-continued

```
cacctatggc atctgggttt gctgtcaccc tactttgttg tggccttcct ggtgtaagag      7080
tctgtgttcc ttggtcacct ctcctgattc agaccagctc catcaagcaa cctcttttga      7140
ctttctgtat atggatggca cagaggaatc aaggacaact tagctctctg catacttgga      7200
acaaccaaac tatttgtaca ttgaacggat gctctgaaac ccaagggact gggctcaggg      7260
tcctcagcac tggcccctgt cataagcact accactaagg actctctgga ggactcctca      7320
gtatcatctg ctccaggaag cccctagac tacctcctga gtctggacaa agcctcctga       7380
ttctacctgg atcactcctg ttatgtgaca gttatgtggt gggtccctgc taaaatctcc      7440
ctgaccacct gagggcataa agcatgtgtc ttattctctg g                          7481
```

<210> SEQ ID NO 72
<211> LENGTH: 2215
<212> TYPE: PRT
<213> ORGANISM: Mus musculus

<400> SEQUENCE: 72

| Met | Val | Ile | Leu | Gln | Lys | Gly | Asp | Tyr | Val | Trp | Met | Asp | Leu | Lys | Ser |
|---|---|---|---|---|---|---|---|---|---|---|---|---|---|---|---|
| 1 | | | | 5 | | | | | 10 | | | | | 15 | |

| Gly | Gln | Glu | Phe | Asp | Val | Pro | Ile | Gly | Ala | Val | Val | Lys | Leu | Cys | Asp |
|---|---|---|---|---|---|---|---|---|---|---|---|---|---|---|---|
| | | | 20 | | | | | 25 | | | | | 30 | | |

| Ser | Gly | Gln | Ile | Gln | Val | Val | Asp | Asp | Glu | Asp | Asn | Glu | His | Trp | Ile |
|---|---|---|---|---|---|---|---|---|---|---|---|---|---|---|---|
| | | 35 | | | | | 40 | | | | | 45 | | | |

| Ser | Pro | Gln | Asn | Ala | Thr | His | Ile | Lys | Pro | Met | His | Pro | Thr | Ser | Val |
|---|---|---|---|---|---|---|---|---|---|---|---|---|---|---|---|
| | 50 | | | | | 55 | | | | | 60 | | | | |

| His | Gly | Val | Glu | Asp | Met | Ile | Arg | Leu | Gly | Asp | Leu | Asn | Glu | Ala | Gly |
|---|---|---|---|---|---|---|---|---|---|---|---|---|---|---|---|
| 65 | | | | | 70 | | | | | 75 | | | | | 80 |

| Ile | Leu | Arg | Asn | Leu | Leu | Ile | Arg | Tyr | Arg | Asp | His | Leu | Ile | Tyr | Thr |
|---|---|---|---|---|---|---|---|---|---|---|---|---|---|---|---|
| | | | | 85 | | | | | 90 | | | | | 95 | |

| Tyr | Thr | Gly | Ser | Ile | Leu | Val | Ala | Val | Asn | Pro | Tyr | Gln | Leu | Leu | Ser |
|---|---|---|---|---|---|---|---|---|---|---|---|---|---|---|---|
| | | | 100 | | | | | 105 | | | | | 110 | | |

| Ile | Tyr | Ser | Pro | Glu | His | Ile | Arg | Gln | Tyr | Thr | Asn | Lys | Lys | Ile | Gly |
|---|---|---|---|---|---|---|---|---|---|---|---|---|---|---|---|
| | | 115 | | | | | 120 | | | | | 125 | | | |

| Glu | Met | Pro | Pro | His | Ile | Phe | Ala | Ile | Ala | Asp | Asn | Cys | Tyr | Phe | Asn |
|---|---|---|---|---|---|---|---|---|---|---|---|---|---|---|---|
| | 130 | | | | | 135 | | | | | 140 | | | | |

| Met | Lys | Arg | Asn | Asn | Arg | Asp | Gln | Cys | Cys | Ile | Ile | Ser | Gly | Glu | Ser |
|---|---|---|---|---|---|---|---|---|---|---|---|---|---|---|---|
| 145 | | | | | 150 | | | | | 155 | | | | | 160 |

| Gly | Ala | Gly | Lys | Thr | Glu | Ser | Thr | Lys | Leu | Ile | Leu | Gln | Phe | Leu | Ala |
|---|---|---|---|---|---|---|---|---|---|---|---|---|---|---|---|
| | | | | 165 | | | | | 170 | | | | | 175 | |

| Ala | Ile | Ser | Gly | Gln | His | Ser | Trp | Ile | Glu | Gln | Gln | Val | Leu | Glu | Ala |
|---|---|---|---|---|---|---|---|---|---|---|---|---|---|---|---|
| | | | 180 | | | | | 185 | | | | | 190 | | |

| Thr | Pro | Ile | Leu | Glu | Ala | Phe | Gly | Asn | Ala | Lys | Thr | Ile | Arg | Asn | Asp |
|---|---|---|---|---|---|---|---|---|---|---|---|---|---|---|---|
| | | 195 | | | | | 200 | | | | | 205 | | | |

| Asn | Ser | Ser | Arg | Phe | Gly | Lys | Tyr | Ile | Asp | Ile | His | Phe | Asn | Lys | Arg |
|---|---|---|---|---|---|---|---|---|---|---|---|---|---|---|---|
| | 210 | | | | | 215 | | | | | 220 | | | | |

| Gly | Ala | Ile | Glu | Gly | Ala | Lys | Ile | Glu | Gln | Tyr | Leu | Leu | Glu | Lys | Ser |
|---|---|---|---|---|---|---|---|---|---|---|---|---|---|---|---|
| 225 | | | | | 230 | | | | | 235 | | | | | 240 |

| Arg | Val | Cys | Arg | Gln | Ala | Pro | Asp | Glu | Arg | Asn | Tyr | His | Val | Phe | Tyr |
|---|---|---|---|---|---|---|---|---|---|---|---|---|---|---|---|
| | | | | 245 | | | | | 250 | | | | | 255 | |

| Cys | Met | Leu | Glu | Gly | Met | Asn | Glu | Glu | Glu | Lys | Lys | Lys | Leu | Gly | Leu |
|---|---|---|---|---|---|---|---|---|---|---|---|---|---|---|---|
| | | | 260 | | | | | 265 | | | | | 270 | | |

| Gly | Gln | Ala | Ala | Asp | Tyr | Asn | Tyr | Leu | Ala | Met | Gly | Asn | Cys | Ile | Thr |
|---|---|---|---|---|---|---|---|---|---|---|---|---|---|---|---|
| | | 275 | | | | | 280 | | | | | 285 | | | |

```
Cys Glu Gly Arg Val Asp Ser Gln Glu Tyr Ala Asn Ile Arg Ser Ala
    290                 295                 300

Met Lys Val Leu Met Phe Thr Asp Thr Glu Asn Trp Glu Ile Ser Lys
305                 310                 315                 320

Leu Leu Ala Ala Ile Leu His Met Gly Asn Leu Gln Tyr Glu Ala Arg
                325                 330                 335

Thr Phe Glu Asn Leu Asp Ala Cys Glu Val Leu Phe Ser Pro Ser Leu
            340                 345                 350

Ala Thr Ala Ala Ser Leu Leu Glu Val Asn Pro Pro Asp Leu Met Ser
        355                 360                 365

Cys Leu Thr Ser Arg Thr Leu Ile Thr Arg Gly Glu Thr Val Ser Thr
    370                 375                 380

Pro Leu Ser Arg Glu Gln Ala Leu Asp Val Arg Asp Ala Phe Val Lys
385                 390                 395                 400

Gly Ile Tyr Gly Arg Leu Phe Val Trp Ile Val Glu Lys Ile Asn Ala
                405                 410                 415

Ala Ile Tyr Lys Pro Pro Leu Glu Val Lys Asn Ser Arg Arg Ser
                420                 425                 430

Ile Gly Leu Leu Asp Ile Phe Gly Phe Glu Asn Phe Thr Val Asn Ser
            435                 440                 445

Phe Glu Gln Leu Cys Ile Asn Phe Ala Asn Glu His Leu Gln Gln Phe
    450                 455                 460

Phe Val Arg His Val Phe Lys Leu Glu Gln Glu Glu Tyr Asp Leu Glu
465                 470                 475                 480

Ser Ile Asp Trp Leu His Ile Glu Phe Thr Asp Asn Gln Glu Ala Leu
                485                 490                 495

Asp Met Ile Ala Asn Arg Pro Met Asn Val Ile Ser Leu Ile Asp Glu
            500                 505                 510

Glu Ser Lys Phe Pro Lys Gly Thr Asp Ala Thr Met Leu His Lys Leu
        515                 520                 525

Asn Ser Gln His Lys Leu Asn Ala Asn Tyr Val Pro Pro Lys Asn Ser
    530                 535                 540

His Glu Thr Gln Phe Gly Ile Asn His Phe Ala Gly Val Val Tyr Tyr
545                 550                 555                 560

Glu Ser Gln Gly Phe Leu Glu Lys Asn Arg Asp Thr Leu His Gly Asp
                565                 570                 575

Ile Ile Gln Leu Val His Ser Ser Arg Asn Lys Phe Ile Lys Gln Ile
            580                 585                 590

Phe Gln Ala Asp Val Ala Met Gly Ala Glu Thr Arg Lys Arg Ser Pro
    595                 600                 605

Thr Leu Ser Ser Gln Phe Lys Arg Ser Leu Glu Leu Leu Met Arg Thr
610                 615                 620

Leu Gly Ala Cys Gln Pro Phe Phe Val Arg Cys Ile Lys Pro Asn Glu
625                 630                 635                 640

Phe Lys Lys Pro Met Leu Phe Asp Arg His Leu Cys Val Arg Gln Leu
                645                 650                 655

Arg Tyr Ser Gly Met Met Glu Thr Ile Arg Ile Arg His Ala Gly Tyr
            660                 665                 670

Pro Ile Arg Tyr Ser Phe Val Glu Phe Val Glu Arg Tyr Arg Val Leu
        675                 680                 685

Leu Pro Gly Val Lys Pro Ala Tyr Lys Gln Gly Asp Leu Arg Gly Thr
    690                 695                 700
```

```
Cys Gln Arg Met Ala Glu Ala Val Leu Gly Thr His Asp Asp Trp Gln
705                 710                 715                 720

Ile Gly Lys Thr Lys Ile Phe Leu Lys Asp His His Asp Met Leu Leu
            725                 730                 735

Glu Val Glu Arg Asp Lys Ala Ile Thr Asp Arg Val Ile Leu Leu Gln
                740                 745                 750

Lys Val Ile Arg Gly Phe Lys Asp Arg Ser Asn Phe Leu Arg Leu Lys
            755                 760                 765

Ser Ala Ala Thr Leu Ile Gln Arg His Trp Arg Gly His His Cys Arg
770                 775                 780

Lys Asn Tyr Glu Leu Ile Arg Leu Gly Phe Leu Arg Leu Gln Ala Leu
785                 790                 795                 800

His Arg Ser Arg Lys Leu His Lys Gln Tyr Arg Leu Ala Arg Gln Arg
                805                 810                 815

Ile Ile Glu Phe Gln Ala Arg Cys Arg Ala Tyr Leu Val Arg Lys Ala
                820                 825                 830

Phe Arg His Arg Leu Trp Ala Val Ile Thr Val Gln Ala Tyr Ala Arg
            835                 840                 845

Gly Met Ile Ala Arg Arg Leu His Arg Arg Leu Arg Val Glu Tyr Gln
850                 855                 860

Arg Arg Leu Glu Ala Glu Arg Met Arg Leu Ala Glu Glu Lys Leu
865                 870                 875                 880

Arg Lys Glu Met Ser Ala Lys Lys Ala Lys Glu Glu Ala Glu Arg Lys
                885                 890                 895

His Gln Glu Arg Leu Ala Gln Leu Ala Arg Glu Asp Ala Glu Arg Glu
                900                 905                 910

Leu Lys Glu Lys Glu Ala Arg Lys Lys Glu Leu Leu Glu Gln
                915                 920                 925

Met Glu Lys Ala Arg His Glu Pro Ile Asn His Ser Asp Met Val Asp
930                 935                 940

Lys Met Phe Gly Phe Leu Gly Thr Ser Gly Ser Leu Pro Gly Gln Glu
945                 950                 955                 960

Gly Gln Ala Pro Ser Gly Phe Glu Asp Leu Glu Arg Gly Arg Arg Glu
                965                 970                 975

Met Val Glu Glu Asp Val Asp Ala Ala Leu Pro Leu Pro Glu Asp
                980                 985                 990

Glu Glu Asp Leu Ser Glu Tyr Lys Phe Ala Lys Phe Ala Ala Thr Tyr
                995                 1000                1005

Phe Gln Gly Thr Thr Thr His Ser Tyr Thr Arg Arg Pro Leu Lys
    1010                1015                1020

Gln Pro Leu Leu Tyr His Asp Asp Glu Gly Asp Gln Leu Ala Ala
    1025                1030                1035

Leu Ala Val Trp Ile Thr Ile Leu Arg Phe Met Gly Asp Leu Pro
    1040                1045                1050

Glu Pro Lys Tyr His Thr Ala Met Ser Asp Gly Ser Glu Lys Ile
    1055                1060                1065

Pro Val Met Thr Lys Ile Tyr Glu Thr Leu Gly Lys Lys Thr Tyr
    1070                1075                1080

Lys Arg Glu Leu Gln Ala Leu Gln Gly Glu Gly Glu Thr Gln Leu
    1085                1090                1095

Pro Glu Gly Gln Lys Lys Thr Ser Val Arg His Lys Leu Val His
    1100                1105                1110
```

-continued

```
Leu Thr Leu Lys Lys Lys Ser Lys Leu Thr Glu Glu Val Thr Lys
    1115                1120                1125

Arg Leu Asn Asp Gly Glu Ser Thr Val Gln Gly Asn Ser Met Leu
    1130                1135                1140

Glu Asp Arg Pro Thr Ser Asn Leu Glu Lys Leu His Phe Ile Ile
    1145                1150                1155

Gly Asn Gly Ile Leu Arg Pro Ala Leu Arg Asp Glu Ile Tyr Cys
    1160                1165                1170

Gln Ile Ser Lys Gln Leu Thr His Asn Pro Ser Lys Ser Ser Tyr
    1175                1180                1185

Ala Arg Gly Trp Ile Leu Val Ser Leu Cys Val Gly Cys Phe Ala
    1190                1195                1200

Pro Ser Glu Lys Phe Val Lys Tyr Leu Arg Asn Phe Ile His Gly
    1205                1210                1215

Gly Pro Pro Gly Tyr Ala Pro Tyr Cys Glu Glu Arg Leu Arg Arg
    1220                1225                1230

Thr Phe Val Asn Gly Thr Arg Thr Gln Pro Pro Ser Trp Leu Glu
    1235                1240                1245

Leu Gln Ala Thr Lys Ser Lys Lys Pro Ile Met Leu Pro Val Thr
    1250                1255                1260

Phe Met Asp Gly Thr Thr Lys Thr Leu Leu Thr Asp Ser Ala Thr
    1265                1270                1275

Thr Ala Arg Glu Leu Cys Asn Ala Leu Ala Asp Lys Ile Ser Leu
    1280                1285                1290

Lys Asp Arg Phe Gly Phe Ser Leu Tyr Ile Ala Leu Phe Asp Lys
    1295                1300                1305

Val Ser Ser Leu Gly Ser Gly Ser Asp His Val Met Asp Ala Ile
    1310                1315                1320

Ser Gln Cys Glu Gln Tyr Ala Lys Glu Gln Gly Ala Gln Glu Arg
    1325                1330                1335

Asn Ala Pro Trp Arg Leu Phe Phe Arg Lys Glu Val Phe Thr Pro
    1340                1345                1350

Trp His Asn Pro Ser Glu Asp Asn Val Ala Thr Asn Leu Ile Tyr
    1355                1360                1365

Gln Gln Val Val Arg Gly Val Lys Phe Gly Glu Tyr Arg Cys Glu
    1370                1375                1380

Lys Glu Asp Asp Leu Ala Glu Leu Ala Ser Gln Gln Tyr Phe Val
    1385                1390                1395

Asp Tyr Gly Ser Glu Met Ile Leu Glu Arg Leu Leu Ser Leu Val
    1400                1405                1410

Pro Thr Tyr Ile Pro Asp Arg Glu Ile Thr Pro Leu Lys Asn Leu
    1415                1420                1425

Glu Lys Trp Ala Gln Leu Ala Ile Ala Ala His Lys Lys Gly Ile
    1430                1435                1440

Tyr Ala Gln Arg Arg Thr Asp Ser Gln Lys Val Lys Glu Asp Val
    1445                1450                1455

Val Asn Tyr Ala Arg Phe Lys Trp Pro Leu Leu Phe Ser Arg Phe
    1460                1465                1470

Tyr Glu Ala Tyr Lys Phe Ser Gly Pro Pro Leu Pro Lys Ser Asp
    1475                1480                1485

Val Ile Val Ala Val Asn Trp Thr Gly Val Tyr Phe Val Asp Glu
    1490                1495                1500
```

```
Gln Glu Gln Val Leu Leu Glu Leu Ser Phe Pro Glu Ile Met Ala
1505                1510                1515

Val Ser Ser Ser Arg Glu Cys Arg Val Leu Leu Ser Leu Gly Cys
1520                1525                1530

Ser Asp Leu Gly Cys Ala Thr Cys Gln Ser Gly Arg Ala Gly Leu
1535                1540                1545

Thr Pro Ala Gly Pro Cys Ser Pro Cys Trp Ser Cys Arg Gly Thr
1550                1555                1560

Lys Met Met Ala Pro Ser Phe Thr Leu Ala Thr Ile Lys Gly Asp
1565                1570                1575

Glu Tyr Thr Phe Thr Ser Ser Asn Ala Glu Asp Ile Arg Asp Leu
1580                1585                1590

Val Val Thr Phe Leu Glu Gly Leu Arg Lys Arg Ser Lys Tyr Val
1595                1600                1605

Val Ala Leu Gln Asp Asn Pro Asn Pro Ala Gly Glu Glu Ser Gly
1610                1615                1620

Phe Leu Ser Phe Ala Lys Gly Asp Leu Ile Ile Leu Asp His Asp
1625                1630                1635

Thr Gly Glu Gln Val Met Asn Ser Gly Trp Ala Asn Gly Ile Asn
1640                1645                1650

Glu Arg Thr Lys Gln Arg Gly Asp Phe Pro Thr Asp Cys Val Tyr
1655                1660                1665

Val Met Pro Thr Val Thr Leu Pro Pro Arg Glu Ile Val Ala Leu
1670                1675                1680

Val Thr Met Thr Pro Asp Gln Arg Gln Asp Val Val Arg Leu Leu
1685                1690                1695

Gln Leu Arg Thr Ala Glu Pro Glu Val Arg Ala Lys Pro Tyr Thr
1700                1705                1710

Leu Glu Glu Phe Ser Tyr Asp Tyr Phe Arg Pro Pro Lys His
1715                1720                1725

Thr Leu Ser Arg Val Met Val Ser Lys Ala Arg Gly Lys Asp Arg
1730                1735                1740

Leu Trp Ser His Thr Arg Glu Pro Leu Lys Gln Ala Leu Leu Lys
1745                1750                1755

Lys Ile Leu Gly Ser Glu Glu Leu Ser Gln Glu Ala Cys Met Ala
1760                1765                1770

Phe Val Ala Val Leu Lys Tyr Met Gly Asp Tyr Pro Ser Lys Arg
1775                1780                1785

Met Arg Ser Val Asn Glu Leu Thr Asp Gln Ile Phe Glu Trp Ala
1790                1795                1800

Leu Lys Ala Glu Pro Leu Lys Asp Glu Ala Tyr Val Gln Ile Leu
1805                1810                1815

Lys Gln Leu Thr Asp Asn His Ile Arg Tyr Ser Glu Glu Arg Gly
1820                1825                1830

Trp Glu Leu Leu Trp Leu Cys Thr Gly Leu Phe Pro Pro Ser Asn
1835                1840                1845

Ile Leu Leu Pro His Val Gln Arg Phe Leu Gln Ser Arg Lys His
1850                1855                1860

Cys Pro Leu Ala Ile Asp Cys Leu Gln Arg Leu Gln Lys Ala Leu
1865                1870                1875

Arg Asn Gly Ser Arg Lys Tyr Pro Pro His Leu Val Glu Val Glu
1880                1885                1890
```

```
Ala Ile Gln His Lys Thr Thr Gln Ile Phe His Lys Val Tyr Phe
1895                1900                1905

Pro Asp Asp Thr Asp Glu Ala Phe Glu Val Glu Ser Ser Thr Lys
1910                1915                1920

Ala Lys Asp Phe Cys Gln Asn Ile Ala Ser Arg Leu Leu Leu Lys
1925                1930                1935

Ser Ser Glu Gly Phe Ser Leu Phe Val Lys Ile Ala Asp Lys Val
1940                1945                1950

Ile Ser Val Pro Glu Asn Asp Phe Phe Asp Phe Val Arg His
1955                1960                1965

Leu Thr Asp Trp Ile Lys Lys Ala Arg Pro Ile Lys Asp Gly Ile
1970                1975                1980

Val Pro Ser Leu Thr Tyr Gln Val Phe Phe Met Lys Lys Leu Trp
1985                1990                1995

Thr Thr Thr Val Pro Gly Lys Asp Pro Met Ala Asp Ser Ile Phe
2000                2005                2010

His Tyr Tyr Gln Glu Leu Pro Lys Tyr Leu Arg Gly Tyr His Lys
2015                2020                2025

Cys Thr Arg Glu Glu Val Leu Gln Leu Gly Ala Leu Ile Tyr Arg
2030                2035                2040

Val Lys Phe Glu Glu Asp Lys Ser Tyr Phe Pro Ser Ile Pro Lys
2045                2050                2055

Leu Leu Arg Glu Leu Val Pro Gln Asp Leu Ile Arg Gln Val Ser
2060                2065                2070

Pro Asp Asp Trp Lys Arg Ser Ile Val Ala Tyr Phe Asn Lys His
2075                2080                2085

Ala Gly Lys Ser Lys Glu Glu Ala Lys Leu Ala Phe Leu Lys Leu
2090                2095                2100

Ile Phe Lys Trp Pro Thr Phe Gly Ser Ala Phe Phe Glu Val Lys
2105                2110                2115

Gln Thr Thr Glu Pro Asn Phe Pro Glu Ile Leu Leu Ile Ala Ile
2120                2125                2130

Asn Lys Tyr Gly Val Ser Leu Ile Asp Pro Arg Thr Lys Asp Ile
2135                2140                2145

Leu Thr Thr His Pro Phe Thr Lys Ile Ser Asn Trp Ser Ser Gly
2150                2155                2160

Asn Thr Tyr Phe His Ile Thr Ile Gly Asn Leu Val Arg Gly Ser
2165                2170                2175

Lys Leu Leu Cys Glu Thr Ser Leu Gly Tyr Lys Met Asp Asp Leu
2180                2185                2190

Leu Thr Ser Tyr Ile Ser Gln Met Leu Thr Ala Met Ser Lys Gln
2195                2200                2205

Arg Asn Ser Arg Ser Gly Arg
2210                2215

<210> SEQ ID NO 73
<211> LENGTH: 7361
<212> TYPE: DNA
<213> ORGANISM: Mus musculus

<400> SEQUENCE: 73
agtgcaggct ggacagctgc cctgaacaga aagaaagagt gacccaggga gacaagaaac      60
agagtagccc aagggaagcc cacagcagca gcagatcaag gctcaagctg gagctgaaaa     120
```

-continued

| | |
|---|---|
| tttgcaggct ccagcctcag cttccagagt cctcctgacc tgtgacccct ggctcctggc | 180 |
| tgggaggtgg tgactcggag ggtgtggata aacccagag ctgtgtctgg tcactccggc | 240 |
| aggtgtgctg acgtagaagc atggttattc tgcagaaggg ggactatgta tggatggacc | 300 |
| tgaagtcagg ccaggagttt gatgtgccca tcggggccgt ggtgaagctc tgcgactcgg | 360 |
| gccagatcca ggtggtggat gatgaagaca atgaacactg gatatcccct cagaatgcca | 420 |
| cgcacatcaa gccaatgcac cccacatcgg tgcacggcgt ggaggacatg atccgcctgg | 480 |
| gggatctcaa cgaggcaggc atccttcgaa accttctcat tcgctaccgg gaccacctca | 540 |
| tctatacgta cacaggttcc atcctggtgg ccgtgaaccc ctaccagctg ctctccatct | 600 |
| actcgccaga gcacatccgc cagtacacca acaagaagat aggggagatg cccccccaca | 660 |
| tcttcgccat tgctgacaac tgctacttca acatgaaacg caacaaccgg gaccagtgct | 720 |
| gtattatcag cggggagtcg ggagctggca agacagagag cacaaagttg atcctgcagt | 780 |
| tcctggcagc catcagtgga cagcactcat ggatcgagca gcaggtgctg gaggccaccc | 840 |
| cgatcctgga agcatttggg aacgccaaga ccatccgcaa cgacaactct agccgctttg | 900 |
| gcaagtacat tgacatccac tttaacaagc gtggtgccat cgagggcgcc aaaatagagc | 960 |
| aatacctgct ggagaagtca cgtgtctgcc gccaggcccc tgacgagagg aactatcacg | 1020 |
| tgttctactg tatgctggag ggcatgaatg aggaggagaa gaagaaactg gcctaggcc | 1080 |
| aggccgctga ctacaactac ttggccatgg gtaactgcat cacctgtgag ggccgcgtgg | 1140 |
| acagtcagga gtatgccaac atccgctctg ccatgaaggt tctcatgttc acagacacgg | 1200 |
| agaactggga gatctcgaag cttctggctg ccatcctaca catgggcaat ctgcagtatg | 1260 |
| aggcccggac atttgagaac ttggatgcgt gtgaagtcct cttctcccca tcgctggcca | 1320 |
| cggcagcttc tctgctcgag gtgaaccccc cagacctgat gagctgcctc accagccgca | 1380 |
| ccctcatcac ccgtggggag acggtgtcca cccctctcag cagggaacag gcgctggatg | 1440 |
| tgcgagatgc ctttgtcaag ggcatctatg gcggctctt tgtgtggatt gtggagaaga | 1500 |
| tcaacgcagc aatctacaag ccaccccccc tggaagtgaa gaactctcgc cggtccatcg | 1560 |
| gtctcctgga catctttgga tttgagaact tcactgtgaa cagcttcgag cagctctgca | 1620 |
| ttaactttgc caatgagcac ctgcagcaat tcttcgtgcg gcacgtgttc aagctggagc | 1680 |
| aggaggagta cgacctggag agcatcgact ggttgcacat tgagttcact gacaaccagg | 1740 |
| aagcactgga catgattgcc aaccggccta tgaacgtcat ctccctcatc gatgaggaga | 1800 |
| gcaagttccc caagggcacg gatgccacca tgctgcataa gctgaactca cagcacaagc | 1860 |
| tcaatgccaa ctacgtgcca cccaagaaca gccacgagac ccagtttgga atcaaccact | 1920 |
| ttgcgggtgt tgtctattat gagagtcaag gcttcctgga gaagaaccga gacaccctgc | 1980 |
| atggggacat catccagctg gtccactctt cccggaacaa gttcataaag cagattttcc | 2040 |
| aagctgacgt tgccatgggt gccgagacca ggaagcgctc gcctacactc agcagccagt | 2100 |
| tcaagcggtc tctggagctg ctgatgcgca cactgggcgc ctgccagccc ttctttgtgc | 2160 |
| gttgtatcaa acccaatgag ttcaagaagc ccatgctctt cgaccggcac ttgtgtgtac | 2220 |
| gccagctgcg atattcgggc atgatggaga caatccgcat ccgccacgca ggctacccca | 2280 |
| ttcgctacag cttttgtggag tttgtggagc gctaccgggt actgctgcct ggtgtgaagc | 2340 |
| cagcatacaa gcagggtgac ctccgaggga catgccagcg catggctgag gctgtgctgg | 2400 |
| gcacgcacga tgactggcag attggcaaaa ccaagatctt tctgaaggac caccatgaca | 2460 |
| tgttgctgga ggtggagcgg gacaaggcca tcacagacag agtcattctc ctccagaagg | 2520 |

```
ttatccgggg cttcaaagac aggtccaact tcctgagact gaagagtgct gccacactga    2580
tccagaggca ctggcggggc caccactgta ggaaaaacta tgagctgatt cgtcttggct    2640
tcctgcggct gcaggccctg caccgctccc ggaagctgca caagcagtac cgcctggcca    2700
gacagcgcat aatagagttc caggcccgct gccgggccta tctggtgcgc aaggccttcc    2760
gccaccgcct ctgggccgtg atcaccgtgc aggcctatgc ccgaggcatg attgcccgcc    2820
ggctacaccg ccgcctccgg gttgagtacc agcggcgcct cgaggcagag aggatgcgtc    2880
tggcagagga ggagaaactc cgaaaggaga tgagtgccaa gaaggccaaa gaggaggctg    2940
agcgcaagca tcaggagcgc ctggctcagc tagcccgcga ggatgcggag cgggaactga    3000
aggagaagga ggaggctcgg aggaagaagg aactgctgga gcagatggag aaggcccgcc    3060
acgaacccat caaccactca gatatggtgg acaagatgtt tggcttcctg ggacttcag    3120 gcagcctgcc aggccaggaa ggccaggcgc ctagtggctt tgaggaccta gagcgcggac    3180
ggagggagat ggtggaagag gatgttgacg ctgccctgcc cctgcctgat gaagacgagg    3240
aggacctttc tgagtacaaa ttcgccaagt ttgctgccac ctacttccag ggcacaacca    3300
cacactccta cacccggagg cctctcaagc agccgctgct ctaccacgac gatgagggtg    3360
accagctggc ggcgctggct gtctggatca ccatcctccg gttcatgggg gacctcccag    3420
agcccaagta ccacacagcc atgagcgacg gcagtgagaa gatcccagtg atgactaaga    3480
tctacgagac cctaggcaag aagacatata agagggagct gcaggccttg cagggcgagg    3540
gcgagaccca gctccctgag gggcagaaga agaccagtgt gagacacaag ttggtacact    3600
tgacactgaa gaaaaagtcc aaactcacag aagaggtgac caagaggctg aacgatgggg    3660
aatccacggt acagggcaac agcatgctgg aggatcggcc cacctcaaat ctagagaagc    3720
tgcacttcat catcggcaac ggcatcctgc ggcctgcgct gcgggacgag atttactgcc    3780
agatcagtaa gcagctcaca cacaacccat ccaagagcag ctatgccagg gctggatcc    3840 tcgtgtcgct ctgtgtgggc tgcttcgccc cctctgagaa gttcgttaag tacctgcgga    3900
acttcatcca cggaggccca cctggctatg ctccttactg tgaggagcgc ctgaggagga    3960
cctttgtcaa cggaactcgg acacagccac ccagctggct ggagctgcag gccaccaagt    4020
ccaagaagcc catcatgttg cccgtgacct tcatggatgg gaccaccaag accctgctaa    4080
cagattcagc aactacagcc agggagctgt gcaatgctct ggctgacaag atctcactca    4140
aggaccgctt tggcttctcc ctctacatcg ctctgttcga taaggtgtcc tccctgggca    4200
gcggcagtga ccatgtcatg gatgccatct ctcagtgtga cagtacgcc aaggagcagg    4260 gtgctcagga gcgcaacgcc ccatggaggc tcttctttag aaaggaggtc ttcacaccct    4320
ggcacaaccc ctcggaggac aacgtggcca cgaacctcat ctaccagcag gtggtgcgag    4380
gagtcaagtt tgggagtac aggtgtgaga aggaggacga cctggctgag ctggcttctc    4440
agcagtactt tgtggactat ggttctgaga tgattctgga gcgcctgctg agcctcgtgc    4500
ccacttacat ccctgaccgt gagatcacac cgctgaagaa tcttgagaag tgggcacagc    4560
tggccattgc tgcccacaag aagggaattt atgcccagag gagaactgac tcccagaagg    4620
tcaaagagga tgtggtcaat tatgcccgtt tcaagtggcc cttgctcttc tccaggtttt    4680
acgaagctta caaattctca ggccctcccc tccccaagag cgacgtcatc gtggctgtca    4740
actggacggg tgtgtacttc gtggacgagc aggagcaggt gcttctggag ctgtccttcc    4800
cggagatcat ggctgtgtcc agcagtaggg gaacaaagat gatggccccc agctttaccc    4860
```

-continued

```
tggccaccat caaaggagat gagtacacct tcacatccag caatgctgag gacatccgtg    4920
acctggtggt caccttctg gaggggctac ggaagaggtc taagtatgtg gtggcactgc    4980
aggacaatcc taaccctgct ggtgaggagt caggcttcct cagcttcgcc aagggagacc    5040
tcatcatcct tgaccatgat actggtgagc aggtcatgaa ctcaggctgg gccaacggca    5100
tcaacgagag gaccaagcag cgcggcgact cccccactga ctgtgtatac gtcatgccca    5160
ctgtcacctt gccaccaagg gagattgtgg ccctggtcac tatgacccca gaccagaggc    5220
aggatgtcgt ccggctcctg cagcttcgca cagcagagcc agaggtgcgc gccaagccct    5280
acacgctaga ggagttctcc tacgactact tcaggccccc acccaagcac acgctgagcc    5340
gtgtcatggt gtccaaggcc cgcggtaagg acaggctgtg gagccacaca cgagagcccc    5400
tcaagcaggc cctgctcaag aagatcctgg gcagtgaaga actctcccag gaagcctgca    5460
tggcctttgt agctgtgctc aagtacatgg gcgactaccc atccaagagg atgcgatccg    5520
tcaatgagct cactgaccag atctttgagt gggcactcaa ggctgagccc ctcaaggatg    5580
aggcctacgt gcagatcctg aagcagctga ctgacaatca catcaggtac agcgaagaga    5640
ggggctggga actgctgtgg ctgtgcacgg gcctcttccc gcccagcaac atcctcctgc    5700
ctcatgttca gcggttttctg cagtcccgca agcactgtcc tcttgccatt gactgcctgc    5760
agaggctcca gaaagccctg agaaatggct cccggaagta ccctccgcac ctggtggagg    5820
tggaggccat ccaacataag actacccaga tcttccacaa ggtctacttc cccgatgaca    5880
cggacgaggc ttttgaggtg gagtccagca ccaaggccaa ggacttctgc agaacatcg    5940
ccagccggct gctgctcaag tcttccgagg gattcagcct ttttgtcaaa atcgcagata    6000
aggtcatcag cgtcccagag aatgatttct tctttgactt tgtccgacac ctgacagact    6060
ggataaagaa agcacggccc atcaaggacg gaatcgtgcc ctcactaacc taccaggtgt    6120
tcttcatgaa gaagctgtgg accaccacag tgccgggcaa ggaccccatg gctgactcca    6180
tcttccacta ttaccaggaa ctgcccaaat atctccgagg ctaccacaag tgcacccggg    6240
aggaggtgct gcagctgggc gcactcatct acagggtcaa gtttgaggag gacaaatcct    6300
acttccctag catccccaag ttgctgaggg agctggtacc ccaggaccta atccggcagg    6360
tctcacctga tgactggaaa cggtctattg tcgcctactt caacaaacat gcggggaagt    6420
ccaaggagga agccaagctg gccttcctca aactcatctt caagtggccc accttttggct   6480
cagccttctt tgaggtgaag caaactacag aaccaaactt cccagagatt ctcttaattg    6540
ccatcaacaa gtacgggtc agcctcatcg atcccgaaac caaggacatc ctgactactc    6600
accccttcac caagatctcc aactggagta gtggcaacac ctacttccac atcaccattg    6660
ggaacttggt ccgtgggagc aaactgctct gtgagacatc gctgggatac aaaatggatg    6720
atcttctgac ttcctacatc agccagatgc tcacagccat gagcaagcag aggaactcca    6780
ggagtggaag gtgaacctca gaggagacgc tggctcaggc cttggccctc taggcaggga    6840
agctggactg accatatctg ctgggcatct gatctgcctg ccacgaggtc cagactcttc    6900
tgcatccacc tatggcatct gggtttgctg tcaccctact ttgttgtggc cttcctggtg    6960
taagagtctg tgttccttgg tcacctctcc tgattcagac cagctccatc aagcaacctc    7020
ttttgacttt ctgtatatgg atggcacaga ggaatcaagg acaacttagc tctctgcata    7080
cttggaacaa ccaaactatt tgtacattga acggatgctc tgaaacccaa gggactgggc    7140
tcagggtcct cagcactggc ccctgtcata agcactacca ctaaggactc tctggaggac    7200
tcctcagtat catctgctcc aggaagcccc ctagactacc tcctgagtct ggacaaagcc    7260
```

```
tcctgattct acctggatca ctcctgttat gtgacagtta tgtggtgggt ccctgctaaa    7320
atctccctga ccacctgagg gcataaagca tgtgtcttat t                        7361
```

<210> SEQ ID NO 74
<211> LENGTH: 2177
<212> TYPE: PRT
<213> ORGANISM: Mus musculus

<400> SEQUENCE: 74

| | | | | | | | | | | | | | | |
|---|---|---|---|---|---|---|---|---|---|---|---|---|---|---|
| Met | Val | Ile | Leu | Gln | Lys | Gly | Asp | Tyr | Val | Trp | Met | Asp | Leu | Lys | Ser |
| 1 | | | | 5 | | | | | 10 | | | | | 15 | |
| Gly | Gln | Glu | Phe | Asp | Val | Pro | Ile | Gly | Ala | Val | Val | Lys | Leu | Cys | Asp |
| | | | 20 | | | | | 25 | | | | | 30 | | |
| Ser | Gly | Gln | Ile | Gln | Val | Asp | Asp | Glu | Asp | Asn | Glu | His | Trp | Ile |
| | | 35 | | | | | 40 | | | | | 45 | | |
| Ser | Pro | Gln | Asn | Ala | Thr | His | Ile | Lys | Pro | Met | His | Pro | Thr | Ser | Val |
| | 50 | | | | | 55 | | | | | 60 | | | | |
| His | Gly | Val | Glu | Asp | Met | Ile | Arg | Leu | Gly | Asp | Leu | Asn | Glu | Ala | Gly |
| 65 | | | | | 70 | | | | | 75 | | | | | 80 |
| Ile | Leu | Arg | Asn | Leu | Leu | Ile | Arg | Tyr | Arg | Asp | His | Leu | Ile | Tyr | Thr |
| | | | | 85 | | | | | 90 | | | | | 95 | |
| Tyr | Thr | Gly | Ser | Ile | Leu | Val | Ala | Val | Asn | Pro | Tyr | Gln | Leu | Leu | Ser |
| | | | 100 | | | | | 105 | | | | | 110 | | |
| Ile | Tyr | Ser | Pro | Glu | His | Ile | Arg | Gln | Tyr | Thr | Asn | Lys | Lys | Ile | Gly |
| | | | 115 | | | | | 120 | | | | | 125 | | |
| Glu | Met | Pro | Pro | His | Ile | Phe | Ala | Ile | Ala | Asp | Asn | Cys | Tyr | Phe | Asn |
| | | 130 | | | | | 135 | | | | | 140 | | | |
| Met | Lys | Arg | Asn | Asn | Arg | Asp | Gln | Cys | Cys | Ile | Ile | Ser | Gly | Glu | Ser |
| 145 | | | | | 150 | | | | | 155 | | | | | 160 |
| Gly | Ala | Gly | Lys | Thr | Glu | Ser | Thr | Lys | Leu | Ile | Leu | Gln | Phe | Leu | Ala |
| | | | | 165 | | | | | 170 | | | | | 175 | |
| Ala | Ile | Ser | Gly | Gln | His | Ser | Trp | Ile | Glu | Gln | Gln | Val | Leu | Glu | Ala |
| | | | 180 | | | | | 185 | | | | | 190 | | |
| Thr | Pro | Ile | Leu | Glu | Ala | Phe | Gly | Asn | Ala | Lys | Thr | Ile | Arg | Asn | Asp |
| | | 195 | | | | | 200 | | | | | 205 | | | |
| Asn | Ser | Ser | Arg | Phe | Gly | Lys | Tyr | Ile | Asp | Ile | His | Phe | Asn | Lys | Arg |
| | 210 | | | | | 215 | | | | | 220 | | | | |
| Gly | Ala | Ile | Glu | Gly | Ala | Lys | Ile | Glu | Gln | Tyr | Leu | Leu | Glu | Lys | Ser |
| 225 | | | | | 230 | | | | | 235 | | | | | 240 |
| Arg | Val | Cys | Arg | Gln | Ala | Pro | Asp | Glu | Arg | Asn | Tyr | His | Val | Phe | Tyr |
| | | | | 245 | | | | | 250 | | | | | 255 | |
| Cys | Met | Leu | Glu | Gly | Met | Asn | Glu | Glu | Glu | Lys | Lys | Lys | Leu | Gly | Leu |
| | | | 260 | | | | | 265 | | | | | 270 | | |
| Gly | Gln | Ala | Ala | Asp | Tyr | Asn | Tyr | Leu | Ala | Met | Gly | Asn | Cys | Ile | Thr |
| | | 275 | | | | | 280 | | | | | 285 | | | |
| Cys | Glu | Gly | Arg | Val | Asp | Ser | Gln | Glu | Tyr | Ala | Asn | Ile | Arg | Ser | Ala |
| | | 290 | | | | | 295 | | | | | 300 | | | |
| Met | Lys | Val | Leu | Met | Phe | Thr | Asp | Thr | Glu | Asn | Trp | Glu | Ile | Ser | Lys |
| 305 | | | | | 310 | | | | | 315 | | | | | 320 |
| Leu | Leu | Ala | Ala | Ile | Leu | His | Met | Gly | Asn | Leu | Gln | Tyr | Glu | Ala | Arg |
| | | | | 325 | | | | | 330 | | | | | 335 | |
| Thr | Phe | Glu | Asn | Leu | Asp | Ala | Cys | Glu | Val | Leu | Phe | Pro | Ser | Leu |
| | | | 340 | | | | | 345 | | | | | 350 | | |

```
Ala Thr Ala Ala Ser Leu Leu Glu Val Asn Pro Pro Asp Leu Met Ser
            355                 360                 365

Cys Leu Thr Ser Arg Thr Leu Ile Thr Arg Gly Glu Thr Val Ser Thr
370                 375                 380

Pro Leu Ser Arg Glu Gln Ala Leu Asp Val Arg Asp Ala Phe Val Lys
385                 390                 395                 400

Gly Ile Tyr Gly Arg Leu Phe Val Trp Ile Val Glu Lys Ile Asn Ala
            405                 410                 415

Ala Ile Tyr Lys Pro Pro Leu Glu Val Lys Asn Ser Arg Arg Ser
            420                 425                 430

Ile Gly Leu Leu Asp Ile Phe Gly Phe Glu Asn Phe Thr Val Asn Ser
            435                 440                 445

Phe Glu Gln Leu Cys Ile Asn Phe Ala Asn Glu His Leu Gln Gln Phe
            450                 455                 460

Phe Val Arg His Val Phe Lys Leu Glu Gln Glu Glu Tyr Asp Leu Glu
465                 470                 475                 480

Ser Ile Asp Trp Leu His Ile Glu Phe Thr Asp Asn Gln Glu Ala Leu
            485                 490                 495

Asp Met Ile Ala Asn Arg Pro Met Asn Val Ile Ser Leu Ile Asp Glu
            500                 505                 510

Glu Ser Lys Phe Pro Lys Gly Thr Asp Ala Thr Met Leu His Lys Leu
            515                 520                 525

Asn Ser Gln His Lys Leu Asn Ala Asn Tyr Val Pro Pro Lys Asn Ser
            530                 535                 540

His Glu Thr Gln Phe Gly Ile Asn His Phe Ala Gly Val Val Tyr Tyr
545                 550                 555                 560

Glu Ser Gln Gly Phe Leu Glu Lys Asn Arg Asp Thr Leu His Gly Asp
                565                 570                 575

Ile Ile Gln Leu Val His Ser Ser Arg Asn Lys Phe Ile Lys Gln Ile
            580                 585                 590

Phe Gln Ala Asp Val Ala Met Gly Ala Glu Thr Arg Lys Arg Ser Pro
            595                 600                 605

Thr Leu Ser Ser Gln Phe Lys Arg Ser Leu Glu Leu Leu Met Arg Thr
            610                 615                 620

Leu Gly Ala Cys Gln Pro Phe Phe Val Arg Cys Ile Lys Pro Asn Glu
625                 630                 635                 640

Phe Lys Lys Pro Met Leu Phe Asp Arg His Leu Cys Val Arg Gln Leu
                645                 650                 655

Arg Tyr Ser Gly Met Met Glu Thr Ile Arg Ile Arg His Ala Gly Tyr
                660                 665                 670

Pro Ile Arg Tyr Ser Phe Val Glu Phe Val Glu Arg Tyr Arg Val Leu
            675                 680                 685

Leu Pro Gly Val Lys Pro Ala Tyr Lys Gln Gly Asp Leu Arg Gly Thr
            690                 695                 700

Cys Gln Arg Met Ala Glu Ala Val Leu Gly Thr His Asp Asp Trp Gln
705                 710                 715                 720

Ile Gly Lys Thr Lys Ile Phe Leu Lys Asp His His Asp Met Leu Leu
                725                 730                 735

Glu Val Glu Arg Asp Lys Ala Ile Thr Asp Arg Val Ile Leu Leu Gln
                740                 745                 750

Lys Val Ile Arg Gly Phe Lys Asp Arg Ser Asn Phe Leu Arg Leu Lys
            755                 760                 765
```

```
Ser Ala Ala Thr Leu Ile Gln Arg His Trp Arg Gly His Cys Arg
    770                 775                 780

Lys Asn Tyr Glu Leu Ile Arg Leu Gly Phe Leu Arg Leu Gln Ala Leu
785                 790                 795                 800

His Arg Ser Arg Lys Leu His Lys Gln Tyr Arg Leu Ala Arg Gln Arg
            805                 810                 815

Ile Ile Glu Phe Gln Ala Arg Cys Arg Ala Tyr Leu Val Arg Lys Ala
                820                 825                 830

Phe Arg His Arg Leu Trp Ala Val Ile Thr Val Gln Ala Tyr Ala Arg
            835                 840                 845

Gly Met Ile Ala Arg Arg Leu His Arg Arg Leu Arg Val Glu Tyr Gln
    850                 855                 860

Arg Arg Leu Glu Ala Glu Arg Met Arg Leu Ala Glu Glu Lys Leu
865                 870                 875                 880

Arg Lys Glu Met Ser Ala Lys Lys Ala Lys Glu Glu Ala Glu Arg Lys
                885                 890                 895

His Gln Glu Arg Leu Ala Gln Leu Ala Arg Glu Asp Ala Glu Arg Glu
                900                 905                 910

Leu Lys Glu Lys Glu Ala Arg Arg Lys Lys Glu Leu Leu Glu Gln
915                 920                 925

Met Glu Lys Ala Arg His Glu Pro Ile Asn His Ser Asp Met Val Asp
    930                 935                 940

Lys Met Phe Gly Phe Leu Gly Thr Ser Gly Ser Leu Pro Gly Gln Glu
945                 950                 955                 960

Gly Gln Ala Pro Ser Gly Phe Glu Asp Leu Glu Arg Gly Arg Arg Glu
                965                 970                 975

Met Val Glu Glu Asp Val Asp Ala Ala Leu Pro Leu Pro Asp Glu Asp
            980                 985                 990

Glu Glu Asp Leu Ser Glu Tyr Lys Phe Ala Lys Phe Ala Ala Thr Tyr
                995                1000                1005

Phe Gln Gly Thr Thr Thr His Ser Tyr Thr Arg Arg Pro Leu Lys
1010                1015                1020

Gln Pro Leu Leu Tyr His Asp Asp Glu Gly Asp Gln Leu Ala Ala
1025                1030                1035

Leu Ala Val Trp Ile Thr Ile Leu Arg Phe Met Gly Asp Leu Pro
1040                1045                1050

Glu Pro Lys Tyr His Thr Ala Met Ser Asp Gly Ser Glu Lys Ile
1055                1060                1065

Pro Val Met Thr Lys Ile Tyr Glu Thr Leu Gly Lys Lys Thr Tyr
1070                1075                1080

Lys Arg Glu Leu Gln Ala Leu Gln Gly Glu Gly Glu Thr Gln Leu
1085                1090                1095

Pro Glu Gly Gln Lys Lys Thr Ser Val Arg His Lys Leu Val His
1100                1105                1110

Leu Thr Leu Lys Lys Lys Ser Lys Leu Thr Glu Glu Val Thr Lys
1115                1120                1125

Arg Leu Asn Asp Gly Glu Ser Thr Val Gln Gly Asn Ser Met Leu
1130                1135                1140

Glu Asp Arg Pro Thr Ser Asn Leu Glu Lys Leu His Phe Ile Ile
1145                1150                1155

Gly Asn Gly Ile Leu Arg Pro Ala Leu Arg Asp Glu Ile Tyr Cys
1160                1165                1170
```

```
Gln Ile Ser Lys Gln Leu Thr His Asn Pro Ser Lys Ser Ser Tyr
1175                1180                1185

Ala Arg Gly Trp Ile Leu Val Ser Leu Cys Val Gly Cys Phe Ala
1190                1195                1200

Pro Ser Glu Lys Phe Val Lys Tyr Leu Arg Asn Phe Ile His Gly
1205                1210                1215

Gly Pro Pro Gly Tyr Ala Pro Tyr Cys Glu Glu Arg Leu Arg Arg
1220                1225                1230

Thr Phe Val Asn Gly Thr Arg Thr Gln Pro Pro Ser Trp Leu Glu
1235                1240                1245

Leu Gln Ala Thr Lys Ser Lys Lys Pro Ile Met Leu Pro Val Thr
1250                1255                1260

Phe Met Asp Gly Thr Thr Lys Thr Leu Leu Thr Asp Ser Ala Thr
1265                1270                1275

Thr Ala Arg Glu Leu Cys Asn Ala Leu Ala Asp Lys Ile Ser Leu
1280                1285                1290

Lys Asp Arg Phe Gly Phe Ser Leu Tyr Ile Ala Leu Phe Asp Lys
1295                1300                1305

Val Ser Ser Leu Gly Ser Gly Ser Asp His Val Met Asp Ala Ile
1310                1315                1320

Ser Gln Cys Glu Gln Tyr Ala Lys Glu Gln Gly Ala Gln Glu Arg
1325                1330                1335

Asn Ala Pro Trp Arg Leu Phe Phe Arg Lys Glu Val Phe Thr Pro
1340                1345                1350

Trp His Asn Pro Ser Glu Asp Asn Val Ala Thr Asn Leu Ile Tyr
1355                1360                1365

Gln Gln Val Val Arg Gly Val Lys Phe Gly Glu Tyr Arg Cys Glu
1370                1375                1380

Lys Glu Asp Asp Leu Ala Glu Leu Ala Ser Gln Gln Tyr Phe Val
1385                1390                1395

Asp Tyr Gly Ser Glu Met Ile Leu Glu Arg Leu Leu Ser Leu Val
1400                1405                1410

Pro Thr Tyr Ile Pro Asp Arg Glu Ile Thr Pro Leu Lys Asn Leu
1415                1420                1425

Glu Lys Trp Ala Gln Leu Ala Ile Ala Ala His Lys Lys Gly Ile
1430                1435                1440

Tyr Ala Gln Arg Arg Thr Asp Ser Gln Lys Val Lys Glu Asp Val
1445                1450                1455

Val Asn Tyr Ala Arg Phe Lys Trp Pro Leu Leu Phe Ser Arg Phe
1460                1465                1470

Tyr Glu Ala Tyr Lys Phe Ser Gly Pro Pro Leu Pro Lys Ser Asp
1475                1480                1485

Val Ile Val Ala Val Asn Trp Thr Gly Val Tyr Phe Val Asp Glu
1490                1495                1500

Gln Glu Gln Val Leu Leu Glu Leu Ser Phe Pro Glu Ile Met Ala
1505                1510                1515

Val Ser Ser Arg Gly Thr Lys Met Met Ala Pro Ser Phe Thr
1520                1525                1530

Leu Ala Thr Ile Lys Gly Asp Glu Tyr Thr Phe Thr Ser Ser Asn
1535                1540                1545

Ala Glu Asp Ile Arg Asp Leu Val Val Thr Phe Leu Glu Gly Leu
1550                1555                1560
```

```
Arg Lys Arg Ser Lys Tyr Val Val Ala Leu Gln Asp Asn Pro Asn
1565                1570                1575

Pro Ala Gly Glu Glu Ser Gly Phe Leu Ser Phe Ala Lys Gly Asp
1580                1585                1590

Leu Ile Ile Leu Asp His Asp Thr Gly Glu Gln Val Met Asn Ser
1595                1600                1605

Gly Trp Ala Asn Gly Ile Asn Glu Arg Thr Lys Gln Arg Gly Asp
1610                1615                1620

Phe Pro Thr Asp Cys Val Tyr Val Met Pro Thr Val Thr Leu Pro
1625                1630                1635

Pro Arg Glu Ile Val Ala Leu Val Thr Met Thr Pro Asp Gln Arg
1640                1645                1650

Gln Asp Val Val Arg Leu Leu Gln Leu Arg Thr Ala Glu Pro Glu
1655                1660                1665

Val Arg Ala Lys Pro Tyr Thr Leu Glu Glu Phe Ser Tyr Asp Tyr
1670                1675                1680

Phe Arg Pro Pro Lys His Thr Leu Ser Arg Val Met Val Ser
1685                1690                1695

Lys Ala Arg Gly Lys Asp Arg Leu Trp Ser His Thr Arg Glu Pro
1700                1705                1710

Leu Lys Gln Ala Leu Leu Lys Lys Ile Leu Gly Ser Glu Glu Leu
1715                1720                1725

Ser Gln Glu Ala Cys Met Ala Phe Val Ala Val Leu Lys Tyr Met
1730                1735                1740

Gly Asp Tyr Pro Ser Lys Arg Met Arg Ser Val Asn Glu Leu Thr
1745                1750                1755

Asp Gln Ile Phe Glu Trp Ala Leu Lys Ala Glu Pro Leu Lys Asp
1760                1765                1770

Glu Ala Tyr Val Gln Ile Leu Lys Gln Leu Thr Asp Asn His Ile
1775                1780                1785

Arg Tyr Ser Glu Glu Arg Gly Trp Glu Leu Leu Trp Leu Cys Thr
1790                1795                1800

Gly Leu Phe Pro Pro Ser Asn Ile Leu Leu Pro His Val Gln Arg
1805                1810                1815

Phe Leu Gln Ser Arg Lys His Cys Pro Leu Ala Ile Asp Cys Leu
1820                1825                1830

Gln Arg Leu Gln Lys Ala Leu Arg Asn Gly Ser Arg Lys Tyr Pro
1835                1840                1845

Pro His Leu Val Glu Val Glu Ala Ile Gln His Lys Thr Thr Gln
1850                1855                1860

Ile Phe His Lys Val Tyr Phe Pro Asp Asp Thr Asp Glu Ala Phe
1865                1870                1875

Glu Val Glu Ser Ser Thr Lys Ala Lys Asp Phe Cys Gln Asn Ile
1880                1885                1890

Ala Ser Arg Leu Leu Leu Lys Ser Ser Glu Gly Phe Ser Leu Phe
1895                1900                1905

Val Lys Ile Ala Asp Lys Val Ile Ser Val Pro Glu Asn Asp Phe
1910                1915                1920

Phe Phe Asp Phe Val Arg His Leu Thr Asp Trp Ile Lys Lys Ala
1925                1930                1935

Arg Pro Ile Lys Asp Gly Ile Val Pro Ser Leu Thr Tyr Gln Val
1940                1945                1950
```

| | | | | | | | | | | | | |
|---|---|---|---|---|---|---|---|---|---|---|---|---|
|Phe|Phe|Met|Lys|Lys|Leu|Trp|Thr|Thr|Thr|Val|Pro|Gly|Lys|Asp|
| |1955| | | |1960| | | |1965| | | | | |

Phe Phe Met Lys Lys Leu Trp Thr Thr Thr Val Pro Gly Lys Asp
    1955                1960                1965

Pro Met Ala Asp Ser Ile Phe His Tyr Tyr Gln Glu Leu Pro Lys
    1970                1975                1980

Tyr Leu Arg Gly Tyr His Lys Cys Thr Arg Glu Glu Val Leu Gln
    1985                1990                1995

Leu Gly Ala Leu Ile Tyr Arg Val Lys Phe Glu Glu Asp Lys Ser
    2000                2005                2010

Tyr Phe Pro Ser Ile Pro Lys Leu Leu Arg Glu Leu Val Pro Gln
    2015                2020                2025

Asp Leu Ile Arg Gln Val Ser Pro Asp Asp Trp Lys Arg Ser Ile
    2030                2035                2040

Val Ala Tyr Phe Asn Lys His Ala Gly Lys Ser Lys Glu Glu Ala
    2045                2050                2055

Lys Leu Ala Phe Leu Lys Leu Ile Phe Lys Trp Pro Thr Phe Gly
    2060                2065                2070

Ser Ala Phe Phe Glu Val Lys Gln Thr Thr Glu Pro Asn Phe Pro
    2075                2080                2085

Glu Ile Leu Leu Ile Ala Ile Asn Lys Tyr Gly Val Ser Leu Ile
    2090                2095                2100

Asp Pro Arg Thr Lys Asp Ile Leu Thr Thr His Pro Phe Thr Lys
    2105                2110                2115

Ile Ser Asn Trp Ser Ser Gly Asn Thr Tyr Phe His Ile Thr Ile
    2120                2125                2130

Gly Asn Leu Val Arg Gly Ser Lys Leu Leu Cys Glu Thr Ser Leu
    2135                2140                2145

Gly Tyr Lys Met Asp Asp Leu Leu Thr Ser Tyr Ile Ser Gln Met
    2150                2155                2160

Leu Thr Ala Met Ser Lys Gln Arg Asn Ser Arg Ser Gly Arg
    2165                2170                2175

<210> SEQ ID NO 75
<211> LENGTH: 7214
<212> TYPE: DNA
<213> ORGANISM: Mus musculus

<400> SEQUENCE: 75

```
ggcgctaggc tgtgagatca tcagaggact ccgttaccca cacagctgcc agaggggagt    60
tgtcaaagtg aaaccccagg gactgggggt gtagtttgtg gggtcagggg gactatgtat   120
ggatggacct gaagtcaggc caggagtttg atgtgcccat cggggccgtg gtgaagctct   180
gcgactcggg ccagatccag gtggtggatg atgaagacaa tgaacactgg atatcccctc   240
agaatgccac gcacatcaag ccaatgcacc ccacatcggt gcacggcgtg gaggacatga   300
tccgcctggg ggatctcaac gaggcaggca tccttcgaaa ccttctcatt cgctaccggg   360
accacctcat ctataccagc tgtggaggac ggacgtacac aggttccatc ctggtggccg   420
tgaaccccta ccagctgctc tccatctact cgccagagca catccgccag tacaccaaca   480
agaagatagg ggagatgccc ccccacatct tcgccattgc tgacaactgc tacttcaaca   540
tgaaacgcaa caaccgggac cagtgctgta ttatcagcgg ggagtcggga ctggcaagaa   600
cagagagcac aaagttgatc ctgcagttcc tggcagccat cagtggacag cactcatgga   660
tcgagcagca ggtgctggag gccaccccga tcctggaagc atttgggaac gccaagacca   720
tccgcaacga caactctagc cgctttggca agtacattga catccacttt aacaagcgtg   780
```

```
gtgccatcga gggcgccaaa atagagcaat acctgctgga gaagtcacgt gtctgccgcc      840
aggcccctga cgagaggaac tatcacgtgt tctactgtat gctggagggc atgaatgagg      900
aggagaagaa gaaactgggc ctaggccagg ccgctgacta caactacttg gccatgggta      960
actgcatcac ctgtgagggc cgcgtggaca gtcaggagta tgccaacatc cgctctgcca     1020
tgaaggttct catgttcaca gacacggaga actgggagat ctcgaagctt ctggctgcca     1080
tcctacacat gggcaatctg cagtatgagg cccggacatt tgagaacttg gatgcgtgtg     1140
aagtcctctt ctccccatcg ctggccacgg cagcttctct gctcgaggtg aacccccag      1200 acctgatgag ctgcctcacc agccgcaccc tcatcacccg tggggagacg gtgtccaccc     1260
ctctcagcag ggaacaggcg ctggatgtgc gagatgcctt tgtcaagggc atctatgggc     1320
ggctctttgt gtggattgtg gagaagatca acgcagcaat ctacaagcca ccccccctgg     1380
aagtgaagaa ctctcgccgg tccatcggtc tcctggacat cttttggattt gagaacttca    1440 ctgtgaacag cttcgagcag ctctgcatta actttgccaa tgagcacctg cagcaattct     1500
tcgtgcggca cgtgttcaag ctggagcagg aggagtacga cctggagagc atcgactggt     1560
tgcacattga gttcactgac aaccaggaag cactggacat gattgccaac cggcctatga     1620
acgtcatctc cctcatcgat gaggagagca agttcccccaa gggcacggat gccaccatgc    1680
tgcataagct gaactcacag cacaagctca tgccaactac gtgccaccc aagaacagcc      1740 acgagaccca gtttggaatc aaccactttg cgggtgttgt ctattatgag agtcaaggct     1800
tcctggagaa gaaccgagac accctgcatg gggacatcat ccagctggtc cactcttccc    1860
ggaacaagtt cataaagcag attttccaag ctgacgttgc catgggtgcc gagaccagga    1920
agcgctcgcc tacactcagc agccagttca gcggtctctc tggagctgctg atgcgcacac    1980 tgggcgcctg ccagcccttc tttgtgcgtt gtatcaaacc caatgagttc aagaagccca     2040
tgctcttcga ccggcacttg tgtgtacgcc agctgcgata ttcgggcatg atggagacaa     2100
tccgcatccg ccacgcaggc tacccccattc gctacagctt tgtggagttt gtggagcgct    2160
accgggtact gctgcctggt gtgaagccag catacaagca gggtgacctc cgagggacat     2220
gccagcgcat ggctgaggct gtgctgggca cgcacgatga ctggcagatt ggcaaaacca     2280
agatctttct gaaggaccac catgacatgt tgctggaggt ggagcgggac aaggccatca     2340
cagacagagt cattctcctc cagaaggtta tccggggctt caaagacagg tccaacttcc     2400
tgagactgaa gagtgctgcc acactgatcc agaggcactg gcggggccac cactgtagga    2460
aaaactatga gctgattcgt cttggcttcc tgcggctgca ggccctgcac cgctcccgga    2520
agctgcacaa gcagtaccgc ctggccagac agcgcataat agagttccag gcccgctgcc    2580
gggcctatct ggtgcgcaag gccttccgcc accgcctctg ggccgtgatc accgtgcagg     2640
cctatgcccg aggcatgatt gcccgccggc tacaccgccg cctccgggtt gagtaccagc    2700
ggcgcctcga ggcagagagg atgcgtctgg cagaggagga gaaactccga aaggagatga    2760
gtgccaagaa ggccaaagag gaggctgagc gcaagcatca ggagcgcctg gctcagctag    2820
cccgcgagga tgcggagcgg gaactgaagg agaaggagga ggctcggagg aagaaggaac    2880
tgctggagca gatggagaag gcccgccacg aacccatcaa ccactcagat atggtggaca    2940
agatgtttgg cttcctgggg acttcaggca gcctgccagg ccaggaaggc caggcgccta    3000
gtggctttga ggacctagag cgcggacgga gggagatggt ggaagaggat gttgacgctg     3060 ccctgccccct gcctgatgaa gacgaggagg accttttctga gtacaaattc gccaagtttg    3120
ctgccaccta cttccagggc acaaccacac actcctacac ccggaggcct ctcaagcagc     3180
```

```
cgctgctcta ccacgacgat gagggtgacc agctggcggc gctggctgtc tggatcacca    3240
tcctccggtt catggggac ctcccagagc ccaagtacca cacagccatg agcgacggca      3300
gtgagaagat cccagtgatg actaagatct acgagaccct aggcaagaag acatataaga    3360
gggagctgca ggccttgcag ggcgaggcg agacccagct ccctgagggg cagaagaaga     3420
ccagtgtgag acacaagttg gtacacttga cactgaagaa aaagtccaaa ctcacagaag    3480
aggtgaccaa gaggctgaac gatggggaat ccacggtaca gggcaacagc atgctggagg    3540
atcggcccac ctcaaatcta gagaagctgc acttcatcat cggcaacggc atcctgcggc    3600
ctgcgctgcg ggacgagatt tactgccaga tcagtaagca gctcacacac aacccatcca    3660
agagcagcta tgccaggggc tggatcctcg tgtcgctctg tgtgggctgc ttcgcccct     3720 ctgagaagtt cgttaagtac ctgcggaact tcatccacgg aggcccacct ggctatgctc    3780
cttactgtga ggagcgcctg aggaggacct tgtcaacgg aactcggaca cagccaccca    3840
gctggctgga gctgcaggcc accaagtcca agaagcccat catgttgccc gtgaccttca    3900
tggatgggac caccaagacc ctgctaacag attcagcaac tacagccagg gagctgtgca    3960
atgctctggc tgacaagatc tcactcaagg accgctttgg cttctccctc tacatcgctc    4020
tgttcgataa ggtgtcctcc ctgggcagcg gcagtgacca tgtcatggat gccatctctc    4080
agtgtgagca gtacgccaag gagcagggtg ctcaggagcg caacgcccca tggaggctct    4140
tctttagaaa ggaggtcttc acaccctggc acaaccctc ggaggacaac gtggccacga     4200
acctcatcta ccagcaggtg gtgcgaggag tcaagtttgg ggagtacagg tgtgagaagg    4260
aggacgacct ggctgagctg gcttctcagc agtactttgt ggactatggt tctgagatga    4320
ttctggagcg cctgctgagc ctcgtgccca cttacatccc tgaccgtgag atcacaccgc    4380
tgaagaatct tgagaagtgg gcacagctgg ccattgctgc ccacaagaag gaatttatg     4440 cccagaggag aactgactcc cagaaggtca agaggatgt ggtcaattat gcccgtttca     4500
agtggccctt gctcttctcc aggttttacg aagcttacaa attctcaggc cctccctcc     4560 ccaagagcga cgtcatcgtg gctgtcaact ggacgggtgt gtacttcgtg gacgagcagg    4620
agcaggtgct tctggagctg tccttcccgg agatcatggc tgtgtccagc agtagggaa     4680 caaagatgat ggccccagc tttaccctgg ccaccatcaa aggagatgag tacaccttca     4740
catccagcaa tgctgaggac atccgtgacc tggtggtcac ctttctggag gggctacgga    4800
agaggtctaa gtatgtggtg gcactgcagg acaatcctaa ccctgctggt gaggagtcag    4860
gcttcctcag cttcgccaag ggagacctca tcatccttga ccatgatact ggtgagcagg    4920
tcatgaactc aggctgggcc aacggcatca cgagaggac caagcagcgc ggcgacttcc     4980
ccactgactg tgtatacgtc atgccactg tcaccttgcc accaagggag attgtggccc     5040
tggtcactat gacccagac cagaggcagg atgtcgtccg gctcctgcag cttcgcacag     5100
cagagccaga ggtgcgcgcc aagccctaca cgctagagga gttctcctac gactacttca    5160
ggcccccacc caagcacacg ctgagccgtg tcatggtgtc caaggcccgc ggtaaggaca    5220
ggctgtggag ccacacacga gagccctca agcaggccct gctcaagaag atcctgggca    5280
gtgaagaact ctcccaggaa gcctgcatgg cctttgtagc tgtgctcaag tacatgggcg    5340
actacccatc caagaggatg cgatccgtca atgagctcac tgaccagatc tttgagtggg    5400
cactcaaggc tgagccctc aaggatgagg cctacgtgca gatcctgaag cagctgactg     5460
acaatcacat caggtacagc gaagagaggg gctgggaact gctgtggctg tgcacgggcc    5520
```

| | |
|---|---|
| tcttcccgcc cagcaacatc ctcctgcctc atgttcagcg gtttctgcag tcccgcaagc | 5580 |
| actgtcctct tgccattgac tgcctgcaga ggctccagaa agccctgaga aatggctccc | 5640 |
| ggaagtaccc tccgcacctg gtggaggtgg aggccatcca acataagact acccagatct | 5700 |
| tccacaaggt ctacttcccc gatgacacgg acgaggcttt tgaggtggag tccagcacca | 5760 |
| aggccaagga cttctgccag aacatcgcca gccggctgct gctcaagtct tccgagggat | 5820 |
| tcagccfttt tgtcaaaatc gcagataagg tcatcagcgt cccagagaat gatttcttct | 5880 |
| ttgactttgt ccgacacctg acagactgga taaagaaagc acggcccatc aaggacggaa | 5940 |
| tcgtgccctc actaacctac caggtgttct tcatgaagaa gctgtggacc accacagtgc | 6000 |
| cgggcaagga ccccatggct gactccatct tccactatta ccaggaactg cccaaatatc | 6060 |
| tccgaggcta ccacaagtgc acccgggagg aggtgctgca gctgggcgca ctcatctaca | 6120 |
| gggtcaagtt tgaggaggac aaatcctact tccctagcat ccccaagttg ctgagggagc | 6180 |
| tggtacccca ggacctaatc cggcaggtct cacctgatga ctggaaacgg tctattgtcg | 6240 |
| cctacttcaa caaacatgcg gggaagtcca aggaggaagc caagctggcc ttcctcaaac | 6300 |
| tcatcttcaa gtggcccacc tttggctcag ccttctttga ggtgaagcaa actacagaac | 6360 |
| caaacttccc agagattctc ttaattgcca tcaacaagta cggggtcagc ctcatcgatc | 6420 |
| ccagaaccaa ggacatcctg actactcacc ccttcaccaa gatctccaac tggagtagtg | 6480 |
| gcaacaccta cttccacatc accattggga acttggtccg tgggagcaaa ctgctctgtg | 6540 |
| agacatcgct gggatacaaa atggatgatc ttctgacttc ctacatcagc cagatgctca | 6600 |
| cagccatgag caagcagagg aactccagga gtggaaggtg aacctcagag gagacgctgg | 6660 |
| ctcaggcctt ggccctctag gcagggaagc tggactgacc atatctgctg ggcatctgat | 6720 |
| ctgcctgcca cgaggtccag actcttctgc atccacctat ggcatctggg tttgctgtca | 6780 |
| ccctactttg ttgtggcctt cctggtgtaa gagtctgtgt tccttggtca cctctcctga | 6840 |
| ttcagaccag ctccatcaag caacctcttt tgactttctg tatatggatg cacagagga | 6900 |
| atcaaggaca acttagctct ctgcatactt ggaacaacca aactatttgt acattgaacg | 6960 |
| gatgctctga aacccaaggg actgggctca gggtcctcag cactggcccc tgtcataagc | 7020 |
| actaccacta aggactctct ggaggactcc tcagtatcat ctgctccagg aagcccccta | 7080 |
| gactacctcc tgagtctgga caaagcctcc tgattctacc tggatcactc ctgttatgtg | 7140 |
| acagttatgt ggtgggtccc tgctaaaatc tccctgacca cctgagggca taaagcatgt | 7200 |
| gtcttattct ctgg | 7214 |

<210> SEQ ID NO 76
<211> LENGTH: 2172
<212> TYPE: PRT
<213> ORGANISM: Mus musculus

<400> SEQUENCE: 76

```
Met Asp Leu Lys Ser Gly Gln Glu Phe Asp Val Pro Ile Gly Ala Val
1               5                   10                  15

Val Lys Leu Cys Asp Ser Gly Gln Ile Gln Val Asp Asp Glu Asp
            20                  25                  30

Asn Glu His Trp Ile Ser Pro Gln Asn Ala Thr His Ile Lys Pro Met
        35                  40                  45

His Pro Thr Ser Val His Gly Val Glu Asp Met Ile Arg Leu Gly Asp
    50                  55                  60
```

```
Leu Asn Glu Ala Gly Ile Leu Arg Asn Leu Leu Ile Arg Tyr Arg Asp
 65                  70                  75                  80

His Leu Ile Tyr Thr Ser Cys Gly Gly Arg Thr Tyr Thr Gly Ser Ile
                 85                  90                  95

Leu Val Ala Val Asn Pro Tyr Gln Leu Leu Ser Ile Tyr Ser Pro Glu
                100                 105                 110

His Ile Arg Gln Tyr Thr Asn Lys Lys Ile Gly Glu Met Pro Pro His
            115                 120                 125

Ile Phe Ala Ile Ala Asp Asn Cys Tyr Phe Asn Met Lys Arg Asn Asn
130                 135                 140

Arg Asp Gln Cys Cys Ile Ile Ser Gly Glu Ser Gly Ala Gly Lys Thr
145                 150                 155                 160

Glu Ser Thr Lys Leu Ile Leu Gln Phe Leu Ala Ala Ile Ser Gly Gln
                165                 170                 175

His Ser Trp Ile Glu Gln Gln Val Leu Glu Ala Thr Pro Ile Leu Glu
            180                 185                 190

Ala Phe Gly Asn Ala Lys Thr Ile Arg Asn Asp Asn Ser Ser Arg Phe
            195                 200                 205

Gly Lys Tyr Ile Asp Ile His Phe Asn Lys Arg Gly Ala Ile Glu Gly
210                 215                 220

Ala Lys Ile Glu Gln Tyr Leu Leu Glu Lys Ser Arg Val Cys Arg Gln
225                 230                 235                 240

Ala Pro Asp Glu Arg Asn Tyr His Val Phe Tyr Cys Met Leu Glu Gly
                245                 250                 255

Met Asn Glu Glu Glu Lys Lys Lys Leu Gly Leu Gly Gln Ala Ala Asp
            260                 265                 270

Tyr Asn Tyr Leu Ala Met Gly Asn Cys Ile Thr Cys Glu Gly Arg Val
            275                 280                 285

Asp Ser Gln Glu Tyr Ala Asn Ile Arg Ser Ala Met Lys Val Leu Met
290                 295                 300

Phe Thr Asp Thr Glu Asn Trp Glu Ile Ser Lys Leu Leu Ala Ala Ile
305                 310                 315                 320

Leu His Met Gly Asn Leu Gln Tyr Glu Ala Arg Thr Phe Glu Asn Leu
                325                 330                 335

Asp Ala Cys Glu Val Leu Phe Ser Pro Ser Leu Ala Thr Ala Ala Ser
            340                 345                 350

Leu Leu Glu Val Asn Pro Pro Asp Leu Met Ser Cys Leu Thr Ser Arg
            355                 360                 365

Thr Leu Ile Thr Arg Gly Glu Thr Val Ser Thr Pro Leu Ser Arg Glu
            370                 375                 380

Gln Ala Leu Asp Val Arg Asp Ala Phe Val Lys Gly Ile Tyr Gly Arg
385                 390                 395                 400

Leu Phe Val Trp Ile Val Glu Lys Ile Asn Ala Ala Ile Tyr Lys Pro
                405                 410                 415

Pro Pro Leu Glu Val Lys Asn Ser Arg Arg Ser Ile Gly Leu Leu Asp
            420                 425                 430

Ile Phe Gly Phe Glu Asn Phe Thr Val Asn Ser Phe Glu Gln Leu Cys
            435                 440                 445

Ile Asn Phe Ala Asn Glu His Leu Gln Gln Phe Phe Val Arg His Val
450                 455                 460

Phe Lys Leu Glu Gln Glu Glu Tyr Asp Leu Glu Ser Ile Asp Trp Leu
465                 470                 475                 480
```

-continued

His Ile Glu Phe Thr Asp Asn Gln Glu Ala Leu Asp Met Ile Ala Asn
                485                 490                 495
Arg Pro Met Asn Val Ile Ser Leu Ile Asp Glu Glu Ser Lys Phe Pro
            500                 505                 510
Lys Gly Thr Asp Ala Thr Met Leu His Lys Leu Asn Ser Gln His Lys
            515                 520                 525
Leu Asn Ala Asn Tyr Val Pro Pro Lys Asn Ser His Glu Thr Gln Phe
        530                 535                 540
Gly Ile Asn His Phe Ala Gly Val Val Tyr Glu Ser Gln Gly Phe
545                 550                 555                 560
Leu Glu Lys Asn Arg Asp Thr Leu His Gly Asp Ile Ile Gln Leu Val
                565                 570                 575
His Ser Ser Arg Asn Lys Phe Ile Lys Gln Ile Phe Gln Ala Asp Val
            580                 585                 590
Ala Met Gly Ala Glu Thr Arg Lys Arg Ser Pro Thr Leu Ser Ser Gln
            595                 600                 605
Phe Lys Arg Ser Leu Glu Leu Leu Met Arg Thr Leu Gly Ala Cys Gln
610                 615                 620
Pro Phe Phe Val Arg Cys Ile Lys Pro Asn Glu Phe Lys Lys Pro Met
625                 630                 635                 640
Leu Phe Asp Arg His Leu Cys Val Arg Gln Leu Arg Tyr Ser Gly Met
                645                 650                 655
Met Glu Thr Ile Arg Ile Arg His Ala Gly Tyr Pro Ile Arg Tyr Ser
            660                 665                 670
Phe Val Glu Phe Val Glu Arg Tyr Arg Val Leu Leu Pro Gly Val Lys
            675                 680                 685
Pro Ala Tyr Lys Gln Gly Asp Leu Arg Gly Thr Cys Gln Arg Met Ala
            690                 695                 700
Glu Ala Val Leu Gly Thr His Asp Asp Trp Gln Ile Gly Lys Thr Lys
705                 710                 715                 720
Ile Phe Leu Lys Asp His His Asp Met Leu Leu Glu Val Glu Arg Asp
                725                 730                 735
Lys Ala Ile Thr Asp Arg Val Ile Leu Leu Gln Lys Val Ile Arg Gly
            740                 745                 750
Phe Lys Asp Arg Ser Asn Phe Leu Arg Leu Lys Ser Ala Ala Thr Leu
            755                 760                 765
Ile Gln Arg His Trp Arg Gly His His Cys Arg Lys Asn Tyr Glu Leu
            770                 775                 780
Ile Arg Leu Gly Phe Leu Arg Leu Gln Ala Leu His Arg Ser Arg Lys
785                 790                 795                 800
Leu His Lys Gln Tyr Arg Leu Ala Arg Gln Arg Ile Ile Glu Phe Gln
                805                 810                 815
Ala Arg Cys Arg Ala Tyr Leu Val Arg Lys Ala Phe Arg His Arg Leu
            820                 825                 830
Trp Ala Val Ile Thr Val Gln Ala Tyr Ala Arg Gly Met Ile Ala Arg
            835                 840                 845
Arg Leu His Arg Arg Leu Arg Val Glu Tyr Gln Arg Arg Leu Glu Ala
            850                 855                 860
Glu Arg Met Arg Leu Ala Glu Glu Lys Leu Arg Lys Glu Met Ser
865                 870                 875                 880
Ala Lys Lys Ala Lys Glu Glu Ala Glu Arg Lys His Gln Glu Arg Leu
            885                 890                 895

-continued

```
Ala Gln Leu Ala Arg Glu Asp Ala Glu Arg Glu Leu Lys Glu Lys Glu
            900                 905                 910

Glu Ala Arg Arg Lys Glu Leu Glu Gln Met Glu Lys Ala Arg
            915                 920                 925

His Glu Pro Ile Asn His Ser Asp Met Val Asp Lys Met Phe Gly Phe
            930                 935                 940

Leu Gly Thr Ser Gly Ser Leu Pro Gly Gln Glu Gly Gln Ala Pro Ser
945                 950                 955                 960

Gly Phe Glu Asp Leu Glu Arg Gly Arg Arg Glu Met Val Glu Glu Asp
                965                 970                 975

Val Asp Ala Ala Leu Pro Leu Pro Asp Glu Asp Glu Asp Leu Ser
            980                 985                 990

Glu Tyr Lys Phe Ala Lys Phe Ala  Ala Thr Tyr Phe Gln  Gly Thr Thr
            995                 1000                1005

Thr His Ser Tyr Thr Arg Arg  Pro Leu Lys Gln Pro  Leu Leu Tyr
        1010                1015                1020

His Asp Asp Glu Gly Asp Gln  Leu Ala Ala Leu Ala  Val Trp Ile
        1025                1030                1035

Thr Ile Leu Arg Phe Met Gly  Asp Leu Pro Glu Pro  Lys Tyr His
        1040                1045                1050

Thr Ala Met Ser Asp Gly Ser  Glu Lys Ile Pro Val  Met Thr Lys
        1055                1060                1065

Ile Tyr Glu Thr Leu Gly Lys  Lys Thr Tyr Lys Arg  Glu Leu Gln
        1070                1075                1080

Ala Leu Gln Gly Glu Gly Glu  Thr Gln Leu Pro Glu  Gly Gln Lys
        1085                1090                1095

Lys Thr Ser Val Arg His Lys  Leu Val His Leu Thr  Leu Lys Lys
        1100                1105                1110

Lys Ser Lys Leu Thr Glu Glu  Val Thr Lys Arg Leu  Asn Asp Gly
        1115                1120                1125

Glu Ser Thr Val Gln Gly Asn  Ser Met Leu Glu Asp  Arg Pro Thr
        1130                1135                1140

Ser Asn Leu Glu Lys Leu His  Phe Ile Ile Gly Asn  Gly Ile Leu
        1145                1150                1155

Arg Pro Ala Leu Arg Asp Glu  Ile Tyr Cys Gln Ile  Ser Lys Gln
        1160                1165                1170

Leu Thr His Asn Pro Ser Lys  Ser Ser Tyr Ala Arg  Gly Trp Ile
        1175                1180                1185

Leu Val Ser Leu Cys Val Gly  Cys Phe Ala Pro Ser  Glu Lys Phe
        1190                1195                1200

Val Lys Tyr Leu Arg Asn Phe  Ile His Gly Gly Pro  Pro Gly Tyr
        1205                1210                1215

Ala Pro Tyr Cys Glu Glu Arg  Leu Arg Arg Thr Phe  Val Asn Gly
        1220                1225                1230

Thr Arg Thr Gln Pro Pro Ser  Trp Leu Glu Leu Gln  Ala Thr Lys
        1235                1240                1245

Ser Lys Lys Pro Ile Met Leu  Pro Val Thr Phe Met  Asp Gly Thr
        1250                1255                1260

Thr Lys Thr Leu Leu Thr Asp  Ser Ala Thr Thr Ala  Arg Glu Leu
        1265                1270                1275

Cys Asn Ala Leu Ala Asp Lys  Ile Ser Leu Lys Asp  Arg Phe Gly
        1280                1285                1290
```

```
Phe Ser Leu Tyr Ile Ala Leu Phe Asp Lys Val Ser Ser Leu Gly
1295                 1300                1305

Ser Gly Ser Asp His Val Met Asp Ala Ile Ser Gln Cys Glu Gln
1310                1315                1320

Tyr Ala Lys Glu Gln Gly Ala Gln Glu Arg Asn Ala Pro Trp Arg
1325                1330                1335

Leu Phe Phe Arg Lys Glu Val Phe Thr Pro Trp His Asn Pro Ser
1340                1345                1350

Glu Asp Asn Val Ala Thr Asn Leu Ile Tyr Gln Gln Val Val Arg
1355                1360                1365

Gly Val Lys Phe Gly Glu Tyr Arg Cys Glu Lys Glu Asp Asp Leu
1370                1375                1380

Ala Glu Leu Ala Ser Gln Gln Tyr Phe Val Asp Tyr Gly Ser Glu
1385                1390                1395

Met Ile Leu Glu Arg Leu Leu Ser Leu Val Pro Thr Tyr Ile Pro
1400                1405                1410

Asp Arg Glu Ile Thr Pro Leu Lys Asn Leu Glu Lys Trp Ala Gln
1415                1420                1425

Leu Ala Ile Ala Ala His Lys Lys Gly Ile Tyr Ala Gln Arg Arg
1430                1435                1440

Thr Asp Ser Gln Lys Val Lys Glu Asp Val Val Asn Tyr Ala Arg
1445                1450                1455

Phe Lys Trp Pro Leu Leu Phe Ser Arg Phe Tyr Glu Ala Tyr Lys
1460                1465                1470

Phe Ser Gly Pro Pro Leu Pro Lys Ser Asp Val Ile Val Ala Val
1475                1480                1485

Asn Trp Thr Gly Val Tyr Phe Val Asp Glu Gln Glu Gln Val Leu
1490                1495                1500

Leu Glu Leu Ser Phe Pro Glu Ile Met Ala Val Ser Ser Ser Arg
1505                1510                1515

Gly Thr Lys Met Met Ala Pro Ser Phe Thr Leu Ala Thr Ile Lys
1520                1525                1530

Gly Asp Glu Tyr Thr Phe Thr Ser Ser Asn Ala Glu Asp Ile Arg
1535                1540                1545

Asp Leu Val Val Thr Phe Leu Glu Gly Leu Arg Lys Arg Ser Lys
1550                1555                1560

Tyr Val Val Ala Leu Gln Asp Asn Pro Asn Pro Ala Gly Glu Glu
1565                1570                1575

Ser Gly Phe Leu Ser Phe Ala Lys Gly Asp Leu Ile Ile Leu Asp
1580                1585                1590

His Asp Thr Gly Glu Gln Val Met Asn Ser Gly Trp Ala Asn Gly
1595                1600                1605

Ile Asn Glu Arg Thr Lys Gln Arg Gly Asp Phe Pro Thr Asp Cys
1610                1615                1620

Val Tyr Val Met Pro Thr Val Thr Leu Pro Pro Arg Glu Ile Val
1625                1630                1635

Ala Leu Val Thr Met Thr Pro Asp Gln Arg Gln Asp Val Val Arg
1640                1645                1650

Leu Leu Gln Leu Arg Thr Ala Glu Pro Glu Val Arg Ala Lys Pro
1655                1660                1665

Tyr Thr Leu Glu Glu Phe Ser Tyr Asp Tyr Phe Arg Pro Pro Pro
1670                1675                1680
```

```
Lys His Thr Leu Ser Arg Val Met Val Ser Lys Ala Arg Gly Lys
1685                1690                1695

Asp Arg Leu Trp Ser His Thr Arg Glu Pro Leu Lys Gln Ala Leu
1700                1705                1710

Leu Lys Lys Ile Leu Gly Ser Glu Glu Leu Ser Gln Glu Ala Cys
1715                1720                1725

Met Ala Phe Val Ala Val Leu Lys Tyr Met Gly Asp Tyr Pro Ser
1730                1735                1740

Lys Arg Met Arg Ser Val Asn Glu Leu Thr Asp Gln Ile Phe Glu
1745                1750                1755

Trp Ala Leu Lys Ala Glu Pro Leu Lys Asp Glu Ala Tyr Val Gln
1760                1765                1770

Ile Leu Lys Gln Leu Thr Asp Asn His Ile Arg Tyr Ser Glu Glu
1775                1780                1785

Arg Gly Trp Glu Leu Leu Trp Leu Cys Thr Gly Leu Phe Pro Pro
1790                1795                1800

Ser Asn Ile Leu Leu Pro His Val Gln Arg Phe Leu Gln Ser Arg
1805                1810                1815

Lys His Cys Pro Leu Ala Ile Asp Cys Leu Gln Arg Leu Gln Lys
1820                1825                1830

Ala Leu Arg Asn Gly Ser Arg Lys Tyr Pro Pro His Leu Val Glu
1835                1840                1845

Val Glu Ala Ile Gln His Lys Thr Thr Gln Ile Phe His Lys Val
1850                1855                1860

Tyr Phe Pro Asp Asp Thr Asp Glu Ala Phe Glu Val Glu Ser Ser
1865                1870                1875

Thr Lys Ala Lys Asp Phe Cys Gln Asn Ile Ala Ser Arg Leu Leu
1880                1885                1890

Leu Lys Ser Ser Glu Gly Phe Ser Leu Phe Val Lys Ile Ala Asp
1895                1900                1905

Lys Val Ile Ser Val Pro Glu Asn Asp Phe Phe Phe Asp Phe Val
1910                1915                1920

Arg His Leu Thr Asp Trp Ile Lys Lys Ala Arg Pro Ile Lys Asp
1925                1930                1935

Gly Ile Val Pro Ser Leu Thr Tyr Gln Val Phe Phe Met Lys Lys
1940                1945                1950

Leu Trp Thr Thr Thr Val Pro Gly Lys Asp Pro Met Ala Asp Ser
1955                1960                1965

Ile Phe His Tyr Tyr Gln Glu Leu Pro Lys Tyr Leu Arg Gly Tyr
1970                1975                1980

His Lys Cys Thr Arg Glu Glu Val Leu Gln Leu Gly Ala Leu Ile
1985                1990                1995

Tyr Arg Val Lys Phe Glu Glu Asp Lys Ser Tyr Phe Pro Ser Ile
2000                2005                2010

Pro Lys Leu Leu Arg Glu Leu Val Pro Gln Asp Leu Ile Arg Gln
2015                2020                2025

Val Ser Pro Asp Asp Trp Lys Arg Ser Ile Val Ala Tyr Phe Asn
2030                2035                2040

Lys His Ala Gly Lys Ser Lys Glu Glu Ala Lys Leu Ala Phe Leu
2045                2050                2055

Lys Leu Ile Phe Lys Trp Pro Thr Phe Gly Ser Ala Phe Phe Glu
2060                2065                2070
```

```
Val Lys Gln Thr Thr Glu Pro Asn Phe Pro Glu Ile Leu Leu Ile
    2075                2080                2085
Ala Ile Asn Lys Tyr Gly Val Ser Leu Ile Asp Pro Arg Thr Lys
    2090                2095                2100
Asp Ile Leu Thr Thr His Pro Phe Thr Lys Ile Ser Asn Trp Ser
    2105                2110                2115
Ser Gly Asn Thr Tyr Phe His Ile Thr Ile Gly Asn Leu Val Arg
    2120                2125                2130
Gly Ser Lys Leu Leu Cys Glu Thr Ser Leu Gly Tyr Lys Met Asp
    2135                2140                2145
Asp Leu Leu Thr Ser Tyr Ile Ser Gln Met Leu Thr Ala Met Ser
    2150                2155                2160
Lys Gln Arg Asn Ser Arg Ser Gly Arg
    2165                2170

<210> SEQ ID NO 77
<211> LENGTH: 7196
<212> TYPE: DNA
<213> ORGANISM: Mus musculus

<400> SEQUENCE: 77
ggcgctaggc tgtgagatca tcagaggact ccgttaccca cacagctgcc agaggggagt      60
tgtcaaagtg aaaccccagg gactgggggt gtagtttgtg gggtcagggg gactatgtat     120
ggatggacct gaagtcaggc caggagtttg atgtgcccat cggggccgtg gtgaagctct     180
gcgactcggg ccagatccag gtggtggatg atgaagacaa tgaacactgg atatcccctc     240
agaatgccac gcacatcaag ccaatgcacc ccacatcggt gcacggcgtg gaggacatga     300
tccgcctggg ggatctcaac gaggcaggca tccttcgaaa ccttctcatt cgctaccggg     360
accacctcat ctatacgtac acaggttcca tcctggtggc cgtgaacccc taccagctgc     420
tctccatcta ctcgccagag cacatccgcc agtacaccaa caagaagata ggggagatgc     480
ccccccacat cttcgccatt gctgacaact gctacttcaa catgaaacgc aacaaccggg     540
accagtgctg tattatcagc ggggagtcgg gagctggcaa gacagagagc acaaagttga     600
tcctgcagtt cctggcagcc atcagtggac agcactcatg gatcgagcag caggtgctgg     660
aggccacccc gatcctggaa gcatttggga cgccaagac catccgcaac gacaactcta     720
gccgctttgg caagtacatt gacatccact ttaacaagcg tggtgccatc gagggcgcca     780
aaatagagca atacctgctg gagaagtcac gtgtctgccg ccaggcccct gacgagagga     840
actatcacgt gttctactgt atgctggagg gcatgaatga ggaggagaag aagaaactgg     900
gcctaggcca ggccgctgac tacaactact ggccatgggt aactgcatc acctgtgagg     960 gccgcgtgga cagtcaggag tatgccaaca tccgctctgc catgaaggtt ctcatgttca    1020
cagacacgga gaactgggag atctcgaagc ttctggctgc catcctacac atgggcaatc    1080
tgcagtatga ggcccggaca tttgagaact ggatgcgtg tgaagtcctc ttctccccat    1140
cgctggccac ggcagcttct ctgctcgagg tgaaccccc agacctgatg agctgcctca    1200
ccagccgcac cctcatcacc cgtgggagga cggtgtccac ccctctcagc agggaacagg    1260
cgctggatgt gcgagatgcc tttgtcaagg gcatctatgg gcggctcttt gtgtggattg    1320
tggagaagat caacgcagca atctacaagc acccccccct ggaagtgaag aactctcgcc    1380
ggtccatcgg tctcctggac atctttggat tgagaacctt cactgtgaac agcttcgagc    1440
agctctgcat taactttgcc aatgagcacc tgcagcaatt cttcgtgcgg cacgtgttca    1500
```

```
agctggagca ggaggagtac gacctggaga gcatcgactg gttgcacatt gagttcactg    1560
acaaccagga agcactggac atgattgcca accggcctat gaacgtcatc tccctcatcg    1620
atgaggagag caagttcccc aagggcacgg atgccaccat gctgcataag ctgaactcac    1680
agcacaagct caatgccaac tacgtgccac ccaagaacag ccacgagacc cagtttggaa    1740
tcaaccactt tgcgggtgtt gtctattatg agagtcaagg cttcctggag aagaaccgag    1800
acaccctgca tggggacatc atccagctgg tccactcttc ccggaacaag ttcataaagc    1860
agattttcca agctgacgtt gccatggggtg ccgagaccag gaagcgctcg cctacactca    1920
gcagccagtt caagcggtct ctggagctgc tgatgcgcac actgggcgcc tgccagccct    1980
tctttgtgcg ttgtatcaaa cccaatgagt tcaagaagcc catgctcttc gaccggcact    2040
tgtgtgtacg ccagctgcga tattcgggca tgatggagac aatccgcatc cgccacgcag    2100
gctaccccat tcgctacagc tttgtggagt ttgtggagcg ctaccgggta ctgctgcctg    2160
gtgtgaagcc agcatacaag cagggtgacc tccgagggac atgccagcgc atggctgagg    2220
ctgtgctggg cacgcacgat gactggcaga ttggcaaaac caagatcttt ctgaaggacc    2280
accatgacat gttgctggag gtggagcggg acaaggccat cacagacaga gtcattctcc    2340
tccagaaggt tatccggggc ttcaaagaca ggtccaactt cctgagactg aagagtgctg    2400
ccacactgat ccagaggcac tggcggggcc accactgtag gaaaaactat gagctgattc    2460
gtcttggctt cctgcggctg caggccctgc accgctcccg gaagctgcac aagcagtacc    2520
gcctggccag acagcgcata atagagttcc aggcccgctg ccgggcctat ctggtgcgca    2580
aggccttccg ccaccgcctc tgggccgtga tcaccgtgca ggcctatgcc cgaggcatga    2640
ttgcccgccg gctacaccgc cgcctccggg ttgagtacca gcggcgcctc gaggcagaga    2700
ggatgcgtct ggcagaggag gagaaactcc gaaaggagag gagtgccaag aaggccaaag    2760
aggaggctga gcgcaagcat caggagcgcc tggctcagct agcccgcgag gatgcggagc    2820
gggaactgaa ggagaaggag gaggctcgga ggaagaagga actgctggag cagatggaga    2880
aggcccgcca cgaacccatc aaccactcag atatggtgga caagatgttt ggcttcctgg    2940
ggacttcagg cagcctgcca ggccaggaag gccaggcgcc tagtggcttt gaggacctag    3000
agcgcggacg gagggagatg gtggaagagg atgttgacgc tgccctgccc ctgcctgatg    3060
aagacgagga ggacctttct gagtacaaat cgccaagtt tgctgccacc tacttccagg    3120
gcacaaccac acactcctac acccggaggc ctctcaagca gccgctgctc taccacgacg    3180
atgagggtga ccagctggcg gcgctggctg tctggatcac catcctccgg ttcatggggg    3240
acctcccaga gcccaagtac cacacagcca tgagcgacgg cagtgagaag atcccagtga    3300
tgactaagat ctacgagacc ctaggcaaga agacatataa gagggagctg caggccttgc    3360
agggcgaggg cgagacccag ctccctgagg ggcagaagaa gaccagtgtg agacacaagt    3420
tggtacactt gacactgaag aaaaagtcca actcacaga agaggtgacc aagaggctga    3480
acgatgggga atccacggta cagggcaaca gcatgctgga ggatcggccc acctcaaatc    3540
tagagaagct gcacttcatc atcggcaacg gcatcctgcg gcctgcgctg cgggacgaga    3600
tttactgcca gatcagtaag cagctcacac acaacccatc caagagcagc tatgccaggg    3660
gctggatcct cgtgtcgctc tgtgtgggct gcttcgcccc ctctgagaag ttcgttaagt    3720
acctgcggaa cttcatccac ggaggcccac ctggctatgc tccttactgt gaggagcgcc    3780
tgaggaggac ctttgtcaac ggaactcgga cacagccacc cagctggctg agctgcagg    3840
ccaccaagtc caagaagccc atcatgttgc ccgtgacctt catggatggg accaccaaga    3900
```

```
ccctgctaac agattcagca actacagcca gggagctgtg caatgctctg gctgacaaga   3960
tctcactcaa ggaccgcttt ggcttctccc tctacatcgc tctgttcgat aaggtgtcct   4020
ccctgggcag cggcagtgac catgtcatgg atgccatctc tcagtgtgag cagtacgcca   4080
aggagcaggg tgctcaggag cgcaacgccc catggaggct cttctttaga aaggaggtct   4140
tcacaccctg gcacaacccc tcggaggaca acgtggccac gaacctcatc taccagcagg   4200
tggtgcgagg agtcaagttt ggggagtaca ggtgtgagaa ggaggacgac ctggctgagc   4260
tggcttctca gcagtacttt gtggactatg gttctgagat gattctggag cgcctgctga   4320
gcctcgtgcc cacttacatc cctgaccgtg agatcacacc gctgaagaat cttgagaagt   4380
gggcacagct ggccattgct gcccacaaga agggaattta tgcccagagg agaactgact   4440
cccagaaggt caaagaggat gtggtcaatt atgcccgttt caagtggccc ttgctcttct   4500
ccaggtttta cgaagcttac aaattctcag gccctcccct ccccaagagc gacgtcatcg   4560
tggctgtcaa ctggacgggt gtgtacttcg tggacgagca ggagcaggtg cttctggagc   4620
tgtccttccc ggagatcatg gctgtgtcca gcagtagggg aacaaagatg atggccccca   4680
gctttaccct ggccaccatc aaaggagatg agtacacctt cacatccagc aatgctgagg   4740
acatccgtga cctggtggtc acctttctgg aggggctacg gaagaggtct aagtatgtgg   4800
tggcactgca ggacaatcct aaccctgctg gtgaggagtc aggcttcctc agcttcgcca   4860
agggagacct catcatcctt gaccatgata ctggtgagca ggtcatgaac tcaggctggg   4920
ccaacggcat caacgagagg accaagcagc gcggcgactt ccccactgac tgtgtatacg   4980
tcatgcccac tgtcaccttg ccaccaaggg agattgtggc cctggtcact atgaccccag   5040
accagaggca ggatgtcgtc cggctcctgc agcttcgcac agcagagcca gaggtgcgcg   5100
ccaagcccta cacgctagag gagttctcct acgactactt caggccccca cccaagcaca   5160
cgctgagccg tgtcatggtg tccaaggccc gcggtaagga caggctgtgg agccacacac   5220
gagagcccct caagcaggcc ctgctcaaga agatcctggg cagtgaagaa ctctcccagg   5280
aagcctgcat ggcctttgta gctgtgctca agtacatggg cgactaccca tccaagagga   5340
tgcgatccgt caatgagctc actgaccaga tctttgagtg ggcactcaag gctgagcccc   5400
tcaaggatga ggcctacgtg cagatcctga agcagctgac tgacaatcac atcaggtaca   5460
gcgaagagag gggctgggaa ctgctgtggc tgtgcacggg cctcttcccg cccagcaaca   5520
tcctcctgcc tcatgttcag cggtttctgc agtcccgcaa gcactgtcct cttgccattg   5580
actgcctgca gaggctccag aaagccctga gaaatggctc ccggaagtac cctccgcacc   5640
tggtggaggt ggaggccatc aacataaga ctacccagat cttccacaag gtctacttcc   5700
ccgatgacac ggacgaggct tttgaggtgg agtccagcac caaggccaag gacttctgcc   5760
agaacatcgc cagccggctg ctgctcaagt cttccgaggg attcagccctt tttgtcaaaa   5820 tcgcagataa ggtcatcagc gtcccagaga atgatttctt cttttgacttt gtccgacacc   5880 tgacagactg gataaagaaa gcacggccca tcaaggacgg aatcgtgccc tcactaacct   5940
accaggtgtt cttcatgaag aagctgtgga ccaccacagt gccgggcaag gaccccatgg   6000
ctgactccat cttccactat taccaggaac tgcccaaata tctccgaggc taccacaagt   6060
gcacccggga ggaggtgctg cagctgggcg cactcatcta cagggtcaag tttgaggagg   6120
acaaatccta cttccctagc atccccaagt tgctgaggga gctggtaccc caggacctaa   6180
tccggcaggt ctcacctgat gactggaaac ggtctattgt cgcctacttc aacaaacatg   6240
```

-continued

```
cggggaagtc caaggaggaa gccaagctgg ccttcctcaa actcatcttc aagtggccca    6300
cctttggctc agccttcttt gaggtgaagc aaactacaga accaaacttc ccagagattc    6360
tcttaattgc catcaacaag tacggggtca gcctcatcga tcccagaacc aaggacatcc    6420
tgactactca ccccttcacc aagatctcca actggagtag tggcaacacc tacttccaca    6480
tcaccattgg gaacttggtc cgtgggagca aactgctctg tgagacatcg ctgggataca    6540
aaatggatga tcttctgact tcctacatca gccagatgct cacagccatg agcaagcaga    6600
ggaactccag gagtggaagg tgaacctcag aggagacgct ggctcaggcc ttggccctct    6660
aggcagggaa gctggactga ccatatctgc tgggcatctg atctgcctgc cacgaggtcc    6720
agactcttct gcatccacct atggcatctg ggtttgctgt caccctactt tgttgtggcc    6780
ttcctggtgt aagagtctgt gttccttggt cacctctcct gattcagacc agctccatca    6840
agcaacctct tttgactttc tgtatatgga tggcacagag gaatcaagga caacttagct    6900
ctctgcatac ttggaacaac caaactattt gtacattgaa cggatgctct gaaacccaag    6960
ggactgggct cagggtcctc agcactggcc cctgtcataa gcactaccac taaggactct    7020
ctggaggact cctcagtatc atctgctcca ggaagccccc tagactacct cctgagtctg    7080
gacaaagcct cctgattcta cctggatcac tcctgttatg tgacagttat gtggtgggtc    7140
cctgctaaaa tctccctgac cacctgaggg cataaagcat gtgtcttatt ctctgg       7196
```

<210> SEQ ID NO 78
<211> LENGTH: 2166
<212> TYPE: PRT
<213> ORGANISM: Mus musculus

<400> SEQUENCE: 78

```
Met Asp Leu Lys Ser Gly Gln Glu Phe Asp Val Pro Ile Gly Ala Val
1               5                   10                  15

Val Lys Leu Cys Asp Ser Gly Gln Ile Gln Val Val Asp Asp Glu Asp
            20                  25                  30

Asn Glu His Trp Ile Ser Pro Gln Asn Ala Thr His Ile Lys Pro Met
        35                  40                  45

His Pro Thr Ser Val His Gly Val Glu Asp Met Ile Arg Leu Gly Asp
    50                  55                  60

Leu Asn Glu Ala Gly Ile Leu Arg Asn Leu Leu Ile Arg Tyr Arg Asp
65                  70                  75                  80

His Leu Ile Tyr Thr Tyr Thr Gly Ser Ile Leu Val Ala Val Asn Pro
                85                  90                  95

Tyr Gln Leu Leu Ser Ile Tyr Ser Pro Glu His Ile Arg Gln Tyr Thr
            100                 105                 110

Asn Lys Lys Ile Gly Glu Met Pro Pro His Ile Phe Ala Ile Ala Asp
        115                 120                 125

Asn Cys Tyr Phe Asn Met Lys Arg Asn Asn Arg Asp Gln Cys Cys Ile
    130                 135                 140

Ile Ser Gly Glu Ser Gly Ala Gly Lys Thr Glu Ser Thr Lys Leu Ile
145                 150                 155                 160

Leu Gln Phe Leu Ala Ala Ile Ser Gly Gln His Ser Trp Ile Glu Gln
                165                 170                 175

Gln Val Leu Glu Ala Thr Pro Ile Leu Glu Ala Phe Gly Asn Ala Lys
            180                 185                 190

Thr Ile Arg Asn Asp Asn Ser Ser Arg Phe Gly Lys Tyr Ile Asp Ile
        195                 200                 205
```

-continued

His Phe Asn Lys Arg Gly Ala Ile Glu Gly Ala Lys Ile Glu Gln Tyr
    210                 215                 220

Leu Leu Glu Lys Ser Arg Val Cys Arg Gln Ala Pro Asp Glu Arg Asn
225                 230                 235                 240

Tyr His Val Phe Tyr Cys Met Leu Glu Gly Met Asn Glu Glu Glu Lys
                245                 250                 255

Lys Lys Leu Gly Leu Gly Gln Ala Ala Asp Tyr Asn Tyr Leu Ala Met
            260                 265                 270

Gly Asn Cys Ile Thr Cys Glu Gly Arg Val Asp Ser Gln Glu Tyr Ala
            275                 280                 285

Asn Ile Arg Ser Ala Met Lys Val Leu Met Phe Thr Asp Thr Glu Asn
    290                 295                 300

Trp Glu Ile Ser Lys Leu Leu Ala Ala Ile Leu His Met Gly Asn Leu
305                 310                 315                 320

Gln Tyr Glu Ala Arg Thr Phe Glu Asn Leu Asp Ala Cys Glu Val Leu
                325                 330                 335

Phe Ser Pro Ser Leu Ala Thr Ala Ala Ser Leu Leu Glu Val Asn Pro
            340                 345                 350

Pro Asp Leu Met Ser Cys Leu Thr Ser Arg Thr Leu Ile Thr Arg Gly
            355                 360                 365

Glu Thr Val Ser Thr Pro Leu Ser Arg Glu Gln Ala Leu Asp Val Arg
370                 375                 380

Asp Ala Phe Val Lys Gly Ile Tyr Gly Arg Leu Phe Val Trp Ile Val
385                 390                 395                 400

Glu Lys Ile Asn Ala Ala Ile Tyr Lys Pro Pro Pro Leu Glu Val Lys
                405                 410                 415

Asn Ser Arg Arg Ser Ile Gly Leu Leu Asp Ile Phe Gly Phe Glu Asn
            420                 425                 430

Phe Thr Val Asn Ser Phe Glu Gln Leu Cys Ile Asn Phe Ala Asn Glu
            435                 440                 445

His Leu Gln Gln Phe Phe Val Arg His Val Phe Lys Leu Glu Gln Glu
    450                 455                 460

Glu Tyr Asp Leu Glu Ser Ile Asp Trp Leu His Ile Glu Phe Thr Asp
465                 470                 475                 480

Asn Gln Glu Ala Leu Asp Met Ile Ala Asn Arg Pro Met Asn Val Ile
                485                 490                 495

Ser Leu Ile Asp Glu Glu Ser Lys Phe Pro Lys Gly Thr Asp Ala Thr
            500                 505                 510

Met Leu His Lys Leu Asn Ser Gln His Lys Leu Asn Ala Asn Tyr Val
            515                 520                 525

Pro Pro Lys Asn Ser His Glu Thr Gln Phe Gly Ile Asn His Phe Ala
    530                 535                 540

Gly Val Val Tyr Tyr Glu Ser Gln Gly Phe Leu Glu Lys Asn Arg Asp
545                 550                 555                 560

Thr Leu His Gly Asp Ile Ile Gln Leu Val His Ser Ser Arg Asn Lys
                565                 570                 575

Phe Ile Lys Gln Ile Phe Gln Ala Asp Val Ala Met Gly Ala Glu Thr
            580                 585                 590

Arg Lys Arg Ser Pro Thr Leu Ser Ser Gln Phe Lys Arg Ser Leu Glu
            595                 600                 605

Leu Leu Met Arg Thr Leu Gly Ala Cys Gln Pro Phe Phe Val Arg Cys
610                 615                 620

```
Ile Lys Pro Asn Glu Phe Lys Pro Met Leu Phe Asp Arg His Leu
625                 630                 635                 640

Cys Val Arg Gln Leu Arg Tyr Ser Gly Met Met Glu Thr Ile Arg Ile
                645                 650                 655

Arg His Ala Gly Tyr Pro Ile Arg Tyr Ser Phe Val Glu Phe Val Glu
                660                 665                 670

Arg Tyr Arg Val Leu Leu Pro Gly Val Lys Pro Ala Tyr Lys Gln Gly
        675                 680                 685

Asp Leu Arg Gly Thr Cys Gln Arg Met Ala Glu Ala Val Leu Gly Thr
    690                 695                 700

His Asp Asp Trp Gln Ile Gly Lys Thr Lys Ile Phe Leu Lys Asp His
705                 710                 715                 720

His Asp Met Leu Leu Glu Val Glu Arg Asp Lys Ala Ile Thr Asp Arg
                725                 730                 735

Val Ile Leu Leu Gln Lys Val Ile Arg Gly Phe Lys Asp Arg Ser Asn
                740                 745                 750

Phe Leu Arg Leu Lys Ser Ala Ala Thr Leu Ile Gln Arg His Trp Arg
        755                 760                 765

Gly His His Cys Arg Lys Asn Tyr Glu Leu Ile Arg Leu Gly Phe Leu
    770                 775                 780

Arg Leu Gln Ala Leu His Arg Ser Arg Lys Leu His Lys Gln Tyr Arg
785                 790                 795                 800

Leu Ala Arg Gln Arg Ile Ile Glu Phe Gln Ala Arg Cys Arg Ala Tyr
                805                 810                 815

Leu Val Arg Lys Ala Phe Arg His Arg Leu Trp Ala Val Ile Thr Val
        820                 825                 830

Gln Ala Tyr Ala Arg Gly Met Ile Ala Arg Arg Leu His Arg Arg Leu
    835                 840                 845

Arg Val Glu Tyr Gln Arg Arg Leu Glu Ala Glu Arg Met Arg Leu Ala
850                 855                 860

Glu Glu Glu Lys Leu Arg Lys Glu Met Ser Ala Lys Lys Ala Lys Glu
865                 870                 875                 880

Glu Ala Glu Arg Lys His Gln Glu Arg Leu Ala Gln Leu Ala Arg Glu
                885                 890                 895

Asp Ala Glu Arg Glu Leu Lys Glu Lys Glu Ala Arg Arg Lys Lys
                900                 905                 910

Glu Leu Leu Glu Gln Met Glu Lys Ala Arg His Glu Pro Ile Asn His
    915                 920                 925

Ser Asp Met Val Asp Lys Met Phe Gly Phe Leu Gly Thr Ser Gly Ser
930                 935                 940

Leu Pro Gly Gln Glu Gly Gln Ala Pro Ser Gly Phe Glu Asp Leu Glu
945                 950                 955                 960

Arg Gly Arg Arg Glu Met Val Glu Glu Asp Val Asp Ala Ala Leu Pro
                965                 970                 975

Leu Pro Asp Glu Asp Glu Asp Leu Ser Glu Tyr Lys Phe Ala Lys
                980                 985                 990

Phe Ala Ala Thr Tyr Phe Gln Gly Thr Thr Thr His Ser Tyr Thr Arg
        995                 1000                1005

Arg Pro Leu Lys Gln Pro Leu Leu Tyr His Asp Asp Glu Gly Asp
        1010                1015                1020

Gln Leu Ala Ala Leu Ala Val Trp Ile Thr Ile Leu Arg Phe Met
        1025                1030                1035
```

```
Gly Asp Leu Pro Glu Pro Lys Tyr His Thr Ala Met Ser Asp Gly
1040                 1045                 1050

Ser Glu Lys Ile Pro Val Met Thr Lys Ile Tyr Glu Thr Leu Gly
1055                 1060                 1065

Lys Lys Thr Tyr Lys Arg Glu Leu Gln Ala Leu Gln Gly Glu Gly
1070                 1075                 1080

Glu Thr Gln Leu Pro Glu Gly Gln Lys Lys Thr Ser Val Arg His
1085                 1090                 1095

Lys Leu Val His Leu Thr Leu Lys Lys Lys Ser Lys Leu Thr Glu
1100                 1105                 1110

Glu Val Thr Lys Arg Leu Asn Asp Gly Glu Ser Thr Val Gln Gly
1115                 1120                 1125

Asn Ser Met Leu Glu Asp Arg Pro Thr Ser Asn Leu Glu Lys Leu
1130                 1135                 1140

His Phe Ile Ile Gly Asn Gly Ile Leu Arg Pro Ala Leu Arg Asp
1145                 1150                 1155

Glu Ile Tyr Cys Gln Ile Ser Lys Gln Leu Thr His Asn Pro Ser
1160                 1165                 1170

Lys Ser Ser Tyr Ala Arg Gly Trp Ile Leu Val Ser Leu Cys Val
1175                 1180                 1185

Gly Cys Phe Ala Pro Ser Glu Lys Phe Val Lys Tyr Leu Arg Asn
1190                 1195                 1200

Phe Ile His Gly Gly Pro Pro Gly Tyr Ala Pro Tyr Cys Glu Glu
1205                 1210                 1215

Arg Leu Arg Arg Thr Phe Val Asn Gly Thr Arg Thr Gln Pro Pro
1220                 1225                 1230

Ser Trp Leu Glu Leu Gln Ala Thr Lys Ser Lys Lys Pro Ile Met
1235                 1240                 1245

Leu Pro Val Thr Phe Met Asp Gly Thr Thr Lys Thr Leu Leu Thr
1250                 1255                 1260

Asp Ser Ala Thr Thr Ala Arg Glu Leu Cys Asn Ala Leu Ala Asp
1265                 1270                 1275

Lys Ile Ser Leu Lys Asp Arg Phe Gly Phe Ser Leu Tyr Ile Ala
1280                 1285                 1290

Leu Phe Asp Lys Val Ser Ser Leu Gly Ser Gly Ser Asp His Val
1295                 1300                 1305

Met Asp Ala Ile Ser Gln Cys Glu Gln Tyr Ala Lys Glu Gln Gly
1310                 1315                 1320

Ala Gln Glu Arg Asn Ala Pro Trp Arg Leu Phe Phe Arg Lys Glu
1325                 1330                 1335

Val Phe Thr Pro Trp His Asn Pro Ser Glu Asp Asn Val Ala Thr
1340                 1345                 1350

Asn Leu Ile Tyr Gln Gln Val Val Arg Gly Val Lys Phe Gly Glu
1355                 1360                 1365

Tyr Arg Cys Glu Lys Glu Asp Asp Leu Ala Glu Leu Ala Ser Gln
1370                 1375                 1380

Gln Tyr Phe Val Asp Tyr Gly Ser Glu Met Ile Leu Glu Arg Leu
1385                 1390                 1395

Leu Ser Leu Val Pro Thr Tyr Ile Pro Asp Arg Glu Ile Thr Pro
1400                 1405                 1410

Leu Lys Asn Leu Glu Lys Trp Ala Gln Leu Ala Ile Ala Ala His
1415                 1420                 1425
```

```
Lys Lys Gly Ile Tyr Ala Gln Arg Arg Thr Asp Ser   Gln Lys Val
    1430            1435                1440

Lys Glu Asp Val Val Asn Tyr Ala Arg Phe Lys Trp   Pro Leu Leu
    1445            1450                1455

Phe Ser Arg Phe Tyr Glu Ala Tyr Lys Phe Ser Gly   Pro Pro Leu
    1460            1465                1470

Pro Lys Ser Asp Val Ile Val Ala Val Asn Trp Thr   Gly Val Tyr
    1475            1480                1485

Phe Val Asp Glu Gln Glu Gln Val Leu Leu Glu Leu   Ser Phe Pro
    1490            1495                1500

Glu Ile Met Ala Val Ser Ser Arg Gly Thr Lys Met   Met Ala
    1505            1510                1515

Pro Ser Phe Thr Leu Ala Thr Ile Lys Gly Asp Glu   Tyr Thr Phe
    1520            1525                1530

Thr Ser Ser Asn Ala Glu Asp Ile Arg Asp Leu Val   Val Thr Phe
    1535            1540                1545

Leu Glu Gly Leu Arg Lys Arg Ser Lys Tyr Val Val   Ala Leu Gln
    1550            1555                1560

Asp Asn Pro Asn Pro Ala Gly Glu Glu Ser Gly Phe   Leu Ser Phe
    1565            1570                1575

Ala Lys Gly Asp Leu Ile Ile Leu Asp His Asp Thr   Gly Glu Gln
    1580            1585                1590

Val Met Asn Ser Gly Trp Ala Asn Gly Ile Asn Glu   Arg Thr Lys
    1595            1600                1605

Gln Arg Gly Asp Phe Pro Thr Asp Cys Val Tyr Val   Met Pro Thr
    1610            1615                1620

Val Thr Leu Pro Pro Arg Glu Ile Val Ala Leu Val   Thr Met Thr
    1625            1630                1635

Pro Asp Gln Arg Gln Asp Val Val Arg Leu Leu Gln   Leu Arg Thr
    1640            1645                1650

Ala Glu Pro Glu Val Arg Ala Lys Pro Tyr Thr Leu   Glu Glu Phe
    1655            1660                1665

Ser Tyr Asp Tyr Phe Arg Pro Pro Pro Lys His Thr   Leu Ser Arg
    1670            1675                1680

Val Met Val Ser Lys Ala Arg Gly Lys Asp Arg Leu   Trp Ser His
    1685            1690                1695

Thr Arg Glu Pro Leu Lys Gln Ala Leu Leu Lys Lys   Ile Leu Gly
    1700            1705                1710

Ser Glu Glu Leu Ser Gln Glu Ala Cys Met Ala Phe   Val Ala Val
    1715            1720                1725

Leu Lys Tyr Met Gly Asp Tyr Pro Ser Lys Arg Met   Arg Ser Val
    1730            1735                1740

Asn Glu Leu Thr Asp Gln Ile Phe Glu Trp Ala Leu   Lys Ala Glu
    1745            1750                1755

Pro Leu Lys Asp Glu Ala Tyr Val Gln Ile Leu Lys   Gln Leu Thr
    1760            1765                1770

Asp Asn His Ile Arg Tyr Ser Glu Glu Arg Gly Trp   Glu Leu Leu
    1775            1780                1785

Trp Leu Cys Thr Gly Leu Phe Pro Pro Ser Asn Ile   Leu Leu Pro
    1790            1795                1800

His Val Gln Arg Phe Leu Gln Ser Arg Lys His Cys   Pro Leu Ala
    1805            1810                1815
```

```
Ile Asp Cys Leu Gln Arg Leu Gln Lys Ala Leu Arg Asn Gly Ser
1820                1825                1830

Arg Lys Tyr Pro Pro His Leu Val Glu Val Glu Ala Ile Gln His
1835                1840                1845

Lys Thr Thr Gln Ile Phe His Lys Val Tyr Phe Pro Asp Asp Thr
1850                1855                1860

Asp Glu Ala Phe Glu Val Glu Ser Ser Thr Lys Ala Lys Asp Phe
1865                1870                1875

Cys Gln Asn Ile Ala Ser Arg Leu Leu Leu Lys Ser Ser Glu Gly
1880                1885                1890

Phe Ser Leu Phe Val Lys Ile Ala Asp Lys Val Ile Ser Val Pro
1895                1900                1905

Glu Asn Asp Phe Phe Phe Asp Phe Val Arg His Leu Thr Asp Trp
1910                1915                1920

Ile Lys Lys Ala Arg Pro Ile Lys Asp Gly Ile Val Pro Ser Leu
1925                1930                1935

Thr Tyr Gln Val Phe Phe Met Lys Lys Leu Trp Thr Thr Thr Val
1940                1945                1950

Pro Gly Lys Asp Pro Met Ala Asp Ser Ile Phe His Tyr Tyr Gln
1955                1960                1965

Glu Leu Pro Lys Tyr Leu Arg Gly Tyr His Lys Cys Thr Arg Glu
1970                1975                1980

Glu Val Leu Gln Leu Gly Ala Leu Ile Tyr Arg Val Lys Phe Glu
1985                1990                1995

Glu Asp Lys Ser Tyr Phe Pro Ser Ile Pro Lys Leu Leu Arg Glu
2000                2005                2010

Leu Val Pro Gln Asp Leu Ile Arg Gln Val Ser Pro Asp Asp Trp
2015                2020                2025

Lys Arg Ser Ile Val Ala Tyr Phe Asn Lys His Ala Gly Lys Ser
2030                2035                2040

Lys Glu Glu Ala Lys Leu Ala Phe Leu Lys Leu Ile Phe Lys Trp
2045                2050                2055

Pro Thr Phe Gly Ser Ala Phe Phe Glu Val Lys Gln Thr Thr Glu
2060                2065                2070

Pro Asn Phe Pro Glu Ile Leu Leu Ile Ala Ile Asn Lys Tyr Gly
2075                2080                2085

Val Ser Leu Ile Asp Pro Arg Thr Lys Asp Ile Leu Thr Thr His
2090                2095                2100

Pro Phe Thr Lys Ile Ser Asn Trp Ser Ser Gly Asn Thr Tyr Phe
2105                2110                2115

His Ile Thr Ile Gly Asn Leu Val Arg Gly Ser Lys Leu Leu Cys
2120                2125                2130

Glu Thr Ser Leu Gly Tyr Lys Met Asp Asp Leu Leu Thr Ser Tyr
2135                2140                2145

Ile Ser Gln Met Leu Thr Ala Met Ser Lys Gln Arg Asn Ser Arg
2150                2155                2160

Ser Gly Arg
2165

<210> SEQ ID NO 79
<211> LENGTH: 6807
<212> TYPE: DNA
<213> ORGANISM: Rattus norvegicus
```

<400> SEQUENCE: 79

```
ggccggtgcc attgcaggct ggacagctgc cccgaacaga gagaaagagt gacccaggga      60
gacaagaaac agagtagccc aagggaaccc cacagcaaca tcagagcaag actcaagctg     120
gggcaaagta tttgcaggct ccagcctcag cttccagagt cctccagacc tgtgacccct     180
ggcctgaggc tggggggtg gtgacccaga gggtgtggat aagacccaga acggtgtctg      240
gtcactcagg caggtgctct gacgtagaac catggttatt ctacaaaagg gggactacgt     300
gtggatggac ctgaagtcgg gccaggagtt cgatgtgccc atcggggcca tggtaaagct     360
ctgtgagtct gggcagatcc aggtggtgga tgatgaaggc aatgaacact ggatttcccc     420
tcaaaatgcc acgcacatca agccaatgca ccccacatcg gtgcatggtg tggaggacat     480
gatccgcctg ggggatctca acgaggcagg cattcttcga aaccttctca ttcgctaccg     540
ggaccatctc atctacacat acacgggttc catcctggtg gccgtgaacc cctaccagct     600
gctgtccatc tactcgtcag agcacatccg ccagtatacc aacaagaaga tagggggagat    660
gcccccccac atctttgcca ttgccgacaa ttgctacttc aacatgaaac gcaacaaccg     720
ggaccagtgc tgtatcatca gcggggaatc aggagctggc aagacagaga gcacaaagct     780
gatcctgcag ttcctggcgg ctatcagtgg acagcactca tggatcgagc agcaggtgct     840
ggaggccacc ccgatcctgg aagcatttgg gaatgccaag accatccgca atgcaactc      900
cagccgcttt ggcaagtaca ttgacatcca ctttaacaag cgtggtgcca ttgagggcgc     960
aaaaatagag cagtacctgc tggagaagtc acgagtctgc cgccaggccc ctgatgagag    1020
gaactatcac gtgttctact gtatgctgga gggcatgaat gaggaggaga agaagaagct    1080
aggcctaggc caggccgctg actacaacta tttggcaatg ggtaactgca tcacctgtga    1140
gggccgtgtg gacagtcagg agtatgccaa catccgctca gccatgaagg tgctcatgtt    1200
cacagacacg gagaactggg agatcttgaa gcttctggcc gccatcctac acatgggcaa    1260
tctgcagtac gaggcccgta cgtttgagaa cttggatgcg tgcgaagtcc tcttctcccc    1320
atcgctggcc acggcagctt ctcatctcga ggtgaatccc ccagacctga tgagctgcct    1380
caccagccgc accctcatca cccgtgggga acggtctcc accctctca gcagggagca     1440
ggcgctggat gtgcgagatg cctttgtcaa gggcatctat gggcggctct ttgtatggat    1500
tgtggagaag atcaatgcag caatctacaa accaccctct caggaagtga cgaactctcg    1560
ccggtccatc ggtctcctgg acattttggg gtttgagaac ttcaccgtga acagctttga    1620
gcagctctgc attaactttg ccaatgagca cctgcagcag ttttcgtgc gacacgtgtt     1680
caagttggag caggaggagt atgacttgga gagcattgac tggctgcaca tcgagttcac    1740
tgacaaccag gaggccctgg acatgatcgc caaccggcct atgaacgtca tctccctcat    1800
tgacgaagag agcaagttcc ccaagggcac ggatgccacc atgctgcata gttgaactc     1860
acagcacagg ctcaatgcca actacgtccc acccaagaac agccatgaga cccagttggg    1920
aatcaaccac tttgcgggca ttgtctacta tgagagtcaa ggcttcctgg agaagaacag    1980
agacacctg catggggaca tcatccagct ggtccactct tcccggaaca gtttgtaaa      2040
gcagattttc caggccgacg ttgctatggg tgcagagacc aggaagcgct cgcctacact    2100
cagcagccag ttcaagcggt ctctggagct gctgatgcgc acactgggcg cctgccagcc    2160
cttcttgta cgatgcatca aacccaatga gttcaagaag cccatgctct cgaccggca     2220
cctgtgtgta cgccagctgc gctattcggg catgatggag actatccgca tccgccacgc    2280
```

```
aggctacccc attcgctaca gctttgtgga gtttgtggag cgctaccgcg tgctgctgcc    2340
tggggtgaaa ccagcataca agcaggatga cctccaaggg acatgccagc gcatggctga    2400
ggccgtgctg ggcactcacg atgactggca gattggcaaa accaagatct ttctgaagga    2460
ccaccatgac atgttgctgg aggtggagcg ggacaaggcc atcacagaca gagtcattct    2520
cctccagaag gtcatccggg gcttcaaaga caggtccaac ttcctgagat tgaagagtgc    2580
agccacactg atccagaggc attggcgggg ccaccactgt aggaaaaact atgagctgat    2640
tcgtcttggc ttcctgcggt tgcaggccct gcaccgctcc cggaaactgc acaaacagta    2700
ccgcctggcc agacagcgca taataaagtt ccaggcccgc tgccgggcct acctggtgcg    2760
cagggccttc cgccaccgcc tctgggccgt gatcaccgtg caggcctatg cccggggcat    2820
gattgcgcgc cggctacacc ggcgcctccg agttgagtac tggcggcgcc ttgaggcaga    2880
gaggatgcgg ctggcagagg aggagaagct aagaaaggag atgagtgcca agaaggccaa    2940
ggaggaggcg gagcgcaagc atcaggagcg cctggcccag ctagcccgcg aggatgcaga    3000
gcgggaactg aaggagaagg aagaggctcg gcggaagaag gagctgttac agcagatgga    3060
gagggcccgc catgagccta tcaaccactc agatatggtg gacaagatgt ttggcttcct    3120
ggggacttca gtggcctgc caggccagga gggccaggca cctagtggct ttgaggacct    3180
ggagcgaggg cggagggaga tggtggaaga ggatgtcgat gctgccctgc ccctgcctga    3240
cgaggatgag gaggaccttt ctgagtacaa attcgccaaa tttgctgcca cctacttcca    3300
gggcacaacc acacactcct acacccggag gcccctcaag cagccactgc tctaccacga    3360
tgatgagggt gaccagctgg cggcactggc tgtctggatc accatcctcc ggttcatggg    3420
ggacctccca gagcccaagt accacacagc catgagcgat ggcagtgaga agatccctgt    3480
gatgactaag atctatgaga ccctgggcaa gaagacatac aagagggagc tgcaggccct    3540
gcagggcgag ggcgaggccc agctctctga ggggcagaag aagaccagtg tgaaacacaa    3600
gttggtacac ttgacactga agaagaagtc caaactcaca gaagaggtga ccaagaggct    3660
gcatgatggg gagtccatgg tacagggcaa cagcatgctg gaggaccggc ccacctcaaa    3720
tctagagaag ctgcacttca tcattggcaa cggtatcctg cgacctgcac tgcgggatga    3780
gatttactgc cagatcagca agcaactcac acacaaccca tccaagagca gctatgccag    3840
gggctggatc cttgtgtctc tgtgtgtggg atgcttcgcc ccttctgaga gtttgttaa    3900 gtacctacgg aacttcatcc atggaggccc accggctat gcccctact gtgaggagcg    3960 cctgagaagg acctttgtca atggaactcg gacacagcca cccagttggc tggaactgca    4020
ggccaccaag tccaagaagc ccatcatgtt gcccgtgacc ttcatggacg ggaccactaa    4080
gaccctgcta gcagattcag caaccacagc caaggaacta tgcaatgctc tggctgacaa    4140
gatctcactc aaggaccgct ttggcttctc cctctacatt gctctgttcg ataaggtatc    4200
ctccctgggc agtggcagtg accacgtcat ggacgcaatc tcccagtgcg agcagtatgc    4260
caaggagcag ggtgcacagg agcgcaacgc cccctggagg ctcttcttca gaaaggaggt    4320
cttcacaccc tggcacaacc cctcggagga caacgtggcc accaacctca tctaccagca    4380
ggtggtgcga ggagtcaagt ttgggagta caggtgtgag aaggaggatg acctggccga    4440
gttggcctcc cagcagtact ttgtggacta tggttctgag atgattctgg agcgtctgct    4500
gagcctcgtg cccacttaca ttcctgaccg tgagatcaca ccgctaaaga atcttgagaa    4560
gtgggcacag ctggctattg ctgcccacaa gaagggaatt tatgcccaga ggagaactga    4620
tgcccagaag gtcaaacagg atgtggtcaa ttatgcccgt ttcaagtggc ccttgctctt    4680
```

```
ttccaggttt tatgaagcct acaaattctc aggccctccc ctccctaaga gtgacgtcat    4740
cgtggctgtg aactggacgg gcgtctactt cgtggacgag caggagcagg tgcttctgga    4800
gctgtccttt ccggagatca tggctgtgtc cagcagtagg ggagcaaaac tgatggcccc    4860
cagctttaca ctggccacca tcaaagggga tgagtacacc ttcacatcta gcaatgctga    4920
ggacatccgt gacctggtgg tcacctttct ggaggggctc cggaagaggt ctaagtatgt    4980
ggtggcactg caggacaatc ccaaccctgc tggtgaggag tcgggcttcc tcagctttgc    5040
caagggagac ctcatcattc tcgaccatga taccggcgag caggtcatga attcaggctg    5100
ggccaatggc atcaacgaga gaaccaagca gcgtggagac ttccccaccg actgtgtcta    5160
cgtcatgccc actgtcacct tgccacccag ggaaattgtg ccctggtca ctatgacccc     5220
agaccagagg caggatgttg tccggcttct gcagctgcgc acagcagagc cagaggtgcg    5280
caccaagccc tacacgctgg aggagttctc ctatgactac ttcaggtccc cacccaagca    5340
cacgctgagc cgtgtcatgg tgtccaaggc ccgagggaag gaccgactgt ggagtcacac    5400
acgagagccc ctcaagcagg ccctgctcaa gaagatcgtg ggcagcgagg aactctccca    5460
ggaagcctgc atgtccttca tagctgtgct caagtacatg ggtgactacc atccaagag     5520
gacacgctct gtcaatgagc tcactgacca gatcttcgag tgggcagtga aggccgagcc    5580
cctcaaagat gaggcctacg tgcagatcct gaagcagctg actgacaatc atatcaggta    5640
cagcgaagag aagggttggg agctgctgtg gctgtgcaca ggcctcttcc cacccagcaa    5700
catcctcctg cctcatgttc agcgtttcct gcagtcccgc aaacactgtc ctcttgccat    5760
tgactgccta caaaggctcc agaaagccct gagaaacggg tcccggaagt accctccaca    5820
cctggtggag gtagaggcca tccagcacaa gactacccag attttccaca aggtctactt    5880
ccctgacgac acggatgagg cttttgaggt agagtccagc accaaggcca aggacttctg    5940
ccagaacatc gccagccggc tgctcctcaa gtcttctgag ggattcagcc ttttgtcaa     6000
aatcgcagat aaggtcatca gcgtccctga gaatgacttc ttctttgact tgttcgaca    6060
cctgacagac tggataaaga aggcacggcc catcaaggat ggaatcgtgc cctcactgac    6120
ctaccaggtg ttcttcatga agaagctgtg gaccaccacc gtgcctggca aggacccat     6180
ggccgactcc atattccact attaccagga actgcccaag tatctccgag gctaccacaa    6240
gtgcacccgg gaggaggtgc tacagctggg cgcgctcatc tacagggtca agtttgagga    6300
ggacaaatcc tacttcccta gcatccccaa gttgctgagg gagctggtgc cccaggacct    6360
aatccggcag gtctcacctg atgactggaa acggtctatt gtcgcctact caacaagca    6420
tgcagggaag tccaaggagg aggccaagct ggccttcctc aagctcatct tcaagtggcc    6480
caccttttgga tcagccttct ttgaggtgaa gcaaacgaca gaaccaaact cccagagat    6540
tctcttaatt gccatcaaca agtatgggat cagcctcatc gatcccagaa ccaaggacat    6600
cttgactact caccccttca ccaagatctc caactggagt agtggcaaca cctacttcca    6660
catcaccatt gggaacttgg tccgtgggag caaactgctc tgtgagacat cactgggata    6720
caaaatggat gatcttctga cttcctacat cagccagatg ctcactgcca tgagcaaaca    6780
gaggaactcc aggagcggga ggtgaac                                        6807
```

<210> SEQ ID NO 80
<211> LENGTH: 2177
<212> TYPE: PRT
<213> ORGANISM: Rattus norvegicus

<400> SEQUENCE: 80

```
Met Val Ile Leu Gln Lys Gly Asp Tyr Val Trp Met Asp Leu Lys Ser
1               5                   10                  15

Gly Gln Glu Phe Asp Val Pro Ile Gly Ala Met Val Lys Leu Cys Glu
            20                  25                  30

Ser Gly Gln Ile Gln Val Val Asp Asp Glu Gly Asn Glu His Trp Ile
        35                  40                  45

Ser Pro Gln Asn Ala Thr His Ile Lys Pro Met His Pro Thr Ser Val
50                  55                  60

His Gly Val Glu Asp Met Ile Arg Leu Gly Asp Leu Asn Glu Ala Gly
65                  70                  75                  80

Ile Leu Arg Asn Leu Leu Ile Arg Tyr Arg Asp His Leu Ile Tyr Thr
                85                  90                  95

Tyr Thr Gly Ser Ile Leu Val Ala Val Asn Pro Tyr Gln Leu Leu Ser
            100                 105                 110

Ile Tyr Ser Ser Glu His Ile Arg Gln Tyr Thr Asn Lys Lys Ile Gly
        115                 120                 125

Glu Met Pro Pro His Ile Phe Ala Ile Ala Asp Asn Cys Tyr Phe Asn
130                 135                 140

Met Lys Arg Asn Asn Arg Asp Gln Cys Cys Ile Ile Ser Gly Glu Ser
145                 150                 155                 160

Gly Ala Gly Lys Thr Glu Ser Thr Lys Leu Ile Leu Gln Phe Leu Ala
                165                 170                 175

Ala Ile Ser Gly Gln His Ser Trp Ile Glu Gln Gln Val Leu Glu Ala
            180                 185                 190

Thr Pro Ile Leu Glu Ala Phe Gly Asn Ala Lys Thr Ile Arg Asn Asp
        195                 200                 205

Asn Ser Ser Arg Phe Gly Lys Tyr Ile Asp Ile His Phe Asn Lys Arg
210                 215                 220

Gly Ala Ile Glu Gly Ala Lys Ile Glu Gln Tyr Leu Leu Glu Lys Ser
225                 230                 235                 240

Arg Val Cys Arg Gln Ala Pro Asp Glu Arg Asn Tyr His Val Phe Tyr
                245                 250                 255

Cys Met Leu Glu Gly Met Asn Glu Glu Glu Lys Lys Lys Leu Gly Leu
            260                 265                 270

Gly Gln Ala Ala Asp Tyr Asn Tyr Leu Ala Met Gly Asn Cys Ile Thr
        275                 280                 285

Cys Glu Gly Arg Val Asp Ser Gln Glu Tyr Ala Asn Ile Arg Ser Ala
290                 295                 300

Met Lys Val Leu Met Phe Thr Asp Thr Glu Asn Trp Glu Ile Leu Lys
305                 310                 315                 320

Leu Leu Ala Ala Ile Leu His Met Gly Asn Leu Gln Tyr Glu Ala Arg
                325                 330                 335

Thr Phe Glu Asn Leu Asp Ala Cys Glu Val Leu Phe Ser Pro Ser Leu
            340                 345                 350

Ala Thr Ala Ala Ser His Leu Glu Val Asn Pro Pro Asp Leu Met Ser
        355                 360                 365

Cys Leu Thr Ser Arg Thr Leu Ile Thr Arg Gly Glu Thr Val Ser Thr
370                 375                 380

Pro Leu Ser Arg Glu Gln Ala Leu Asp Val Arg Asp Ala Phe Val Lys
385                 390                 395                 400

Gly Ile Tyr Gly Arg Leu Phe Val Trp Ile Val Glu Lys Ile Asn Ala
                405                 410                 415
```

```
Ala Ile Tyr Lys Pro Pro Ser Gln Glu Val Thr Asn Ser Arg Arg Ser
            420                 425                 430

Ile Gly Leu Leu Asp Ile Phe Gly Phe Glu Asn Phe Thr Val Asn Ser
            435                 440                 445

Phe Glu Gln Leu Cys Ile Asn Phe Ala Asn Glu His Leu Gln Gln Phe
        450                 455                 460

Phe Val Arg His Val Phe Lys Leu Glu Gln Glu Glu Tyr Asp Leu Glu
465                 470                 475                 480

Ser Ile Asp Trp Leu His Ile Glu Phe Thr Asp Asn Gln Glu Ala Leu
                485                 490                 495

Asp Met Ile Ala Asn Arg Pro Met Asn Val Ile Ser Leu Ile Asp Glu
            500                 505                 510

Glu Ser Lys Phe Pro Lys Gly Thr Asp Ala Thr Met Leu His Lys Leu
        515                 520                 525

Asn Ser Gln His Arg Leu Asn Ala Asn Tyr Val Pro Pro Lys Asn Ser
    530                 535                 540

His Glu Thr Gln Phe Gly Ile Asn His Phe Ala Gly Ile Val Tyr Tyr
545                 550                 555                 560

Glu Ser Gln Gly Phe Leu Glu Lys Asn Arg Asp Thr Leu His Gly Asp
                565                 570                 575

Ile Ile Gln Leu Val His Ser Ser Arg Asn Lys Phe Val Lys Gln Ile
            580                 585                 590

Phe Gln Ala Asp Val Ala Met Gly Ala Glu Thr Arg Lys Arg Ser Pro
        595                 600                 605

Thr Leu Ser Ser Gln Phe Lys Arg Ser Leu Glu Leu Leu Met Arg Thr
    610                 615                 620

Leu Gly Ala Cys Gln Pro Phe Phe Val Arg Cys Ile Lys Pro Asn Glu
625                 630                 635                 640

Phe Lys Lys Pro Met Leu Phe Asp Arg His Leu Cys Val Arg Gln Leu
                645                 650                 655

Arg Tyr Ser Gly Met Met Glu Thr Ile Arg Ile Arg His Ala Gly Tyr
            660                 665                 670

Pro Ile Arg Tyr Ser Phe Val Glu Phe Val Glu Arg Tyr Arg Val Leu
        675                 680                 685

Leu Pro Gly Val Lys Pro Ala Tyr Lys Gln Asp Asp Leu Gln Gly Thr
    690                 695                 700

Cys Gln Arg Met Ala Glu Ala Val Leu Gly Thr His Asp Asp Trp Gln
705                 710                 715                 720

Ile Gly Lys Thr Lys Ile Phe Leu Lys Asp His His Asp Met Leu Leu
                725                 730                 735

Glu Val Glu Arg Asp Lys Ala Ile Thr Asp Arg Val Ile Leu Leu Gln
            740                 745                 750

Lys Val Ile Arg Gly Phe Lys Asp Arg Ser Asn Phe Leu Arg Leu Lys
        755                 760                 765

Ser Ala Ala Thr Leu Ile Gln Arg His Trp Arg Gly His His Cys Arg
    770                 775                 780

Lys Asn Tyr Glu Leu Ile Arg Leu Gly Phe Leu Arg Leu Gln Ala Leu
785                 790                 795                 800

His Arg Ser Arg Lys Leu His Lys Gln Tyr Arg Leu Ala Arg Gln Arg
                805                 810                 815

Ile Ile Lys Phe Gln Ala Arg Cys Arg Ala Tyr Leu Val Arg Arg Ala
            820                 825                 830
```

```
Phe Arg His Arg Leu Trp Ala Val Ile Thr Val Gln Ala Tyr Ala Arg
            835                 840                 845

Gly Met Ile Ala Arg Arg Leu His Arg Leu Arg Val Glu Tyr Trp
    850                 855                 860

Arg Arg Leu Glu Ala Glu Arg Met Arg Leu Ala Glu Glu Lys Leu
865                 870                 875                 880

Arg Lys Glu Met Ser Ala Lys Lys Ala Lys Glu Ala Glu Arg Lys
                885                 890                 895

His Gln Glu Arg Leu Ala Gln Leu Ala Arg Glu Asp Ala Glu Arg Glu
                900                 905                 910

Leu Lys Glu Lys Glu Ala Arg Arg Lys Lys Glu Leu Leu Gln Gln
            915                 920                 925

Met Glu Arg Ala Arg His Glu Pro Ile Asn His Ser Asp Met Val Asp
    930                 935                 940

Lys Met Phe Gly Phe Leu Gly Thr Ser Ser Gly Leu Pro Gly Gln Glu
945                 950                 955                 960

Gly Gln Ala Pro Ser Gly Phe Glu Asp Leu Glu Arg Gly Arg Arg Glu
                965                 970                 975

Met Val Glu Glu Asp Val Asp Ala Ala Leu Pro Leu Pro Asp Glu Asp
            980                 985                 990

Glu Glu Asp Leu Ser Glu Tyr Lys Phe Ala Lys Phe Ala Ala Thr Tyr
        995                 1000                1005

Phe Gln Gly Thr Thr Thr His Ser Tyr Thr Arg Arg Pro Leu Lys
    1010                1015                1020

Gln Pro Leu Leu Tyr His Asp Asp Glu Gly Asp Gln Leu Ala Ala
    1025                1030                1035

Leu Ala Val Trp Ile Thr Ile Leu Arg Phe Met Gly Asp Leu Pro
    1040                1045                1050

Glu Pro Lys Tyr His Thr Ala Met Ser Asp Gly Ser Glu Lys Ile
    1055                1060                1065

Pro Val Met Thr Lys Ile Tyr Glu Thr Leu Gly Lys Lys Thr Tyr
    1070                1075                1080

Lys Arg Glu Leu Gln Ala Leu Gln Gly Glu Gly Glu Ala Gln Leu
    1085                1090                1095

Ser Glu Gly Gln Lys Lys Thr Ser Val Lys His Lys Leu Val His
    1100                1105                1110

Leu Thr Leu Lys Lys Lys Ser Lys Leu Thr Glu Glu Val Thr Lys
    1115                1120                1125

Arg Leu His Asp Gly Glu Ser Met Val Gln Gly Asn Ser Met Leu
    1130                1135                1140

Glu Asp Arg Pro Thr Ser Asn Leu Glu Lys Leu His Phe Ile Ile
    1145                1150                1155

Gly Asn Gly Ile Leu Arg Pro Ala Leu Arg Asp Glu Ile Tyr Cys
    1160                1165                1170

Gln Ile Ser Lys Gln Leu Thr His Asn Pro Ser Lys Ser Ser Tyr
    1175                1180                1185

Ala Arg Gly Trp Ile Leu Val Ser Leu Cys Val Gly Cys Phe Ala
    1190                1195                1200

Pro Ser Glu Lys Phe Val Lys Tyr Leu Arg Asn Phe Ile His Gly
    1205                1210                1215

Gly Pro Pro Gly Tyr Ala Pro Tyr Cys Glu Glu Arg Leu Arg Arg
    1220                1225                1230
```

-continued

```
Thr Phe Val Asn Gly Thr Arg Thr Gln Pro Pro Ser Trp Leu Glu
    1235            1240                1245

Leu Gln Ala Thr Lys Ser Lys Lys Pro Ile Met Leu Pro Val Thr
    1250            1255                1260

Phe Met Asp Gly Thr Thr Lys Thr Leu Leu Ala Asp Ser Ala Thr
    1265            1270                1275

Thr Ala Lys Glu Leu Cys Asn Ala Leu Ala Asp Lys Ile Ser Leu
    1280            1285                1290

Lys Asp Arg Phe Gly Phe Ser Leu Tyr Ile Ala Leu Phe Asp Lys
    1295            1300                1305

Val Ser Ser Leu Gly Ser Gly Ser Asp His Val Met Asp Ala Ile
    1310            1315                1320

Ser Gln Cys Glu Gln Tyr Ala Lys Glu Gln Gly Ala Gln Glu Arg
    1325            1330                1335

Asn Ala Pro Trp Arg Leu Phe Phe Arg Lys Glu Val Phe Thr Pro
    1340            1345                1350

Trp His Asn Pro Ser Glu Asp Asn Val Ala Thr Asn Leu Ile Tyr
    1355            1360                1365

Gln Gln Val Val Arg Gly Val Lys Phe Gly Glu Tyr Arg Cys Glu
    1370            1375                1380

Lys Glu Asp Asp Leu Ala Glu Leu Ala Ser Gln Gln Tyr Phe Val
    1385            1390                1395

Asp Tyr Gly Ser Glu Met Ile Leu Glu Arg Leu Leu Ser Leu Val
    1400            1405                1410

Pro Thr Tyr Ile Pro Asp Arg Glu Ile Thr Pro Leu Lys Asn Leu
    1415            1420                1425

Glu Lys Trp Ala Gln Leu Ala Ile Ala Ala His Lys Lys Gly Ile
    1430            1435                1440

Tyr Ala Gln Arg Arg Thr Asp Ala Gln Lys Val Lys Gln Asp Val
    1445            1450                1455

Val Asn Tyr Ala Arg Phe Lys Trp Pro Leu Leu Phe Ser Arg Phe
    1460            1465                1470

Tyr Glu Ala Tyr Lys Phe Ser Gly Pro Pro Leu Pro Lys Ser Asp
    1475            1480                1485

Val Ile Val Ala Val Asn Trp Thr Gly Val Tyr Phe Val Asp Glu
    1490            1495                1500

Gln Glu Gln Val Leu Leu Glu Leu Ser Phe Pro Glu Ile Met Ala
    1505            1510                1515

Val Ser Ser Ser Arg Gly Ala Lys Leu Met Ala Pro Ser Phe Thr
    1520            1525                1530

Leu Ala Thr Ile Lys Gly Asp Glu Tyr Thr Phe Thr Ser Ser Asn
    1535            1540                1545

Ala Glu Asp Ile Arg Asp Leu Val Val Thr Phe Leu Glu Gly Leu
    1550            1555                1560

Arg Lys Arg Ser Lys Tyr Val Val Ala Leu Gln Asp Asn Pro Asn
    1565            1570                1575

Pro Ala Gly Glu Glu Ser Gly Phe Leu Ser Phe Ala Lys Gly Asp
    1580            1585                1590

Leu Ile Ile Leu Asp His Asp Thr Gly Glu Gln Val Met Asn Ser
    1595            1600                1605

Gly Trp Ala Asn Gly Ile Asn Glu Arg Thr Lys Gln Arg Gly Asp
    1610            1615                1620
```

```
Phe Pro Thr Asp Cys Val Tyr Val Met Pro Thr Val Thr Leu Pro
1625                1630                1635

Pro Arg Glu Ile Val Ala Leu Val Thr Met Thr Pro Asp Gln Arg
1640                1645                1650

Gln Asp Val Val Arg Leu Leu Gln Leu Arg Thr Ala Glu Pro Glu
1655                1660                1665

Val Arg Thr Lys Pro Tyr Thr Leu Glu Glu Phe Ser Tyr Asp Tyr
1670                1675                1680

Phe Arg Ser Pro Pro Lys His Thr Leu Ser Arg Val Met Val Ser
1685                1690                1695

Lys Ala Arg Gly Lys Asp Arg Leu Trp Ser His Thr Arg Glu Pro
1700                1705                1710

Leu Lys Gln Ala Leu Leu Lys Lys Ile Val Gly Ser Glu Glu Leu
1715                1720                1725

Ser Gln Glu Ala Cys Met Ser Phe Ile Ala Val Leu Lys Tyr Met
1730                1735                1740

Gly Asp Tyr Pro Ser Lys Arg Thr Arg Ser Val Asn Glu Leu Thr
1745                1750                1755

Asp Gln Ile Phe Glu Trp Ala Val Lys Ala Glu Pro Leu Lys Asp
1760                1765                1770

Glu Ala Tyr Val Gln Ile Leu Lys Gln Leu Thr Asp Asn His Ile
1775                1780                1785

Arg Tyr Ser Glu Glu Lys Gly Trp Glu Leu Leu Trp Leu Cys Thr
1790                1795                1800

Gly Leu Phe Pro Pro Ser Asn Ile Leu Leu Pro His Val Gln Arg
1805                1810                1815

Phe Leu Gln Ser Arg Lys His Cys Pro Leu Ala Ile Asp Cys Leu
1820                1825                1830

Gln Arg Leu Gln Lys Ala Leu Arg Asn Gly Ser Arg Lys Tyr Pro
1835                1840                1845

Pro His Leu Val Glu Val Glu Ala Ile Gln His Lys Thr Thr Gln
1850                1855                1860

Ile Phe His Lys Val Tyr Phe Pro Asp Asp Thr Asp Glu Ala Phe
1865                1870                1875

Glu Val Glu Ser Ser Thr Lys Ala Lys Asp Phe Cys Gln Asn Ile
1880                1885                1890

Ala Ser Arg Leu Leu Leu Lys Ser Ser Glu Gly Phe Ser Leu Phe
1895                1900                1905

Val Lys Ile Ala Asp Lys Val Ile Ser Val Pro Glu Asn Asp Phe
1910                1915                1920

Phe Phe Asp Phe Val Arg His Leu Thr Asp Trp Ile Lys Lys Ala
1925                1930                1935

Arg Pro Ile Lys Asp Gly Ile Val Pro Ser Leu Thr Tyr Gln Val
1940                1945                1950

Phe Phe Met Lys Lys Leu Trp Thr Thr Thr Val Pro Gly Lys Asp
1955                1960                1965

Pro Met Ala Asp Ser Ile Phe His Tyr Tyr Gln Glu Leu Pro Lys
1970                1975                1980

Tyr Leu Arg Gly Tyr His Lys Cys Thr Arg Glu Glu Val Leu Gln
1985                1990                1995

Leu Gly Ala Leu Ile Tyr Arg Val Lys Phe Glu Glu Asp Lys Ser
2000                2005                2010
```

```
Tyr Phe Pro Ser Ile Pro Lys Leu Leu Arg Glu Leu Val Pro Gln
    2015                2020                2025

Asp Leu Ile Arg Gln Val Ser Pro Asp Asp Trp Lys Arg Ser Ile
    2030                2035                2040

Val Ala Tyr Phe Asn Lys His Ala Gly Lys Ser Lys Glu Glu Ala
    2045                2050                2055

Lys Leu Ala Phe Leu Lys Leu Ile Phe Lys Trp Pro Thr Phe Gly
    2060                2065                2070

Ser Ala Phe Phe Glu Val Lys Gln Thr Thr Glu Pro Asn Phe Pro
    2075                2080                2085

Glu Ile Leu Leu Ile Ala Ile Asn Lys Tyr Gly Ile Ser Leu Ile
    2090                2095                2100

Asp Pro Arg Thr Lys Asp Ile Leu Thr Thr His Pro Phe Thr Lys
    2105                2110                2115

Ile Ser Asn Trp Ser Ser Gly Asn Thr Tyr Phe His Ile Thr Ile
    2120                2125                2130

Gly Asn Leu Val Arg Gly Ser Lys Leu Leu Cys Glu Thr Ser Leu
    2135                2140                2145

Gly Tyr Lys Met Asp Asp Leu Leu Thr Ser Tyr Ile Ser Gln Met
    2150                2155                2160

Leu Thr Ala Met Ser Lys Gln Arg Asn Ser Arg Ser Gly Arg
    2165                2170                2175

<210> SEQ ID NO 81
<211> LENGTH: 9
<212> TYPE: PRT
<213> ORGANISM: Artificial Sequence
<220> FEATURE:
<223> OTHER INFORMATION: /note="Description of Artificial Sequence:
      Synthetic peptide sequence"

<400> SEQUENCE: 81

Ala Ile Thr Asp Arg Val Ile Leu Leu
1               5

<210> SEQ ID NO 82
<211> LENGTH: 9
<212> TYPE: PRT
<213> ORGANISM: Artificial Sequence
<220> FEATURE:
<223> OTHER INFORMATION: /note="Description of Artificial Sequence:
      Synthetic peptide sequence"

<400> SEQUENCE: 82

Tyr Leu Ser Gly Ile Ala His Phe Leu
1               5

<210> SEQ ID NO 83
<211> LENGTH: 9
<212> TYPE: PRT
<213> ORGANISM: Artificial Sequence
<220> FEATURE:
<223> OTHER INFORMATION: /note="Description of Artificial Sequence:
      Synthetic peptide sequence"

<400> SEQUENCE: 83

Leu Leu Pro Glu His Phe Leu Phe Leu
1               5

<210> SEQ ID NO 84
<211> LENGTH: 9
```

```
<212> TYPE: PRT
<213> ORGANISM: Artificial Sequence
<220> FEATURE:
<223> OTHER INFORMATION: /note="Description of Artificial Sequence:
      Synthetic peptide sequence"

<400> SEQUENCE: 84

Ala Ile Ile Glu Ser Thr Pro Glu Leu
1               5
```

MODULATING BIOMARKERS SUCH AS SPP TO INCREASE TUMOR IMMUNITY AND IMPROVE THE EFFICACY OF CANCER IMMUNOTHERAPY

CROSS-REFERENCE TO RELATED APPLICATIONS

This application is the U.S. national phase of International Patent Application No. PCT/US20/12827, filed on 9 Jan. 2020, which claims the benefit of priority to U.S. Provisional Application Ser. No. 62/790,758, filed on 10 Jan. 2019; and U.S. Provisional Application Ser. No. 62/815,507, filed on 8 Mar. 2019; the entire contents of each of said applications are incorporated herein in their entirety by this reference.

BACKGROUND OF THE INVENTION

The striking clinical success of cancer immunotherapy with checkpoint blockade suggests it is likely to form the foundation of curative therapy for many malignancies (Reck et al. (2016) *N. Engl. J. Med.* 375:1823-1833; Hodi et al. (2010) *N. Engl. J. Med.* 363:711-723; Postow et al. (2015) *N. Engl. J. Med.* 372:2006-2017; Wolchok et al. (2013) *N. Engl. J. Med.* 369:122-133; Ferris et al. (2016) *N. Engl. J. Med.* 375:1856-1867; Brahmer et al. (2012) *N. Engl. J. Med.* 366:2455-2465; Nghiem et al. (2016) *N. Engl. J. Med.* 374:2542-2552; Topalian et al. (2012) *N. Engl. J. Med.* 366:2443-2454); Motzer et al. (2015) *N. Eng. J. Med.* 373:1803-1813). However, despite these successes, checkpoint blockade does not achieve sustained clinical response in most patients (Tumeh et al. (2014) *Nature* 515:568-571; Kelderman et al. (2014) *Mol. Oncol.* 8:1132-1139; Zaretsky et al. (2016) *N. Engl. J. Med.* 375:819-829). Additional therapeutic strategies are therefore needed to increase the clinical efficacy of immunotherapy. Moreover, the optimal strategy for combining emerging cancer immunotherapies with checkpoint blockade remains uncertain.

A relatively small number of genes, such as PD-L1, that enable tumors to evade the immune system have been discovered and most of these are already the focus of intense efforts to develop new immunotherapies (Freeman et al. (2000) *J. Exp. Med.* 192:1027-1034; Hirano et al. (2005) *Cancer Res.* 65:1089-1096; Dong et al. (2002) *Nat. Med.* 8:793-800; Balachandran et al. (2011) *Nat. Med.* 17:1094-1100; Spranger et al. (2013) *Sci Transl Med.* 5:200ra116; Holmgaard et al. (2013) *J. Exp. Med.* 210:1389-1402; Sockolosky et al. (2016) *Proc. Nat. Acad. Sci. U.S.A.* 113:E2646-654; Liu et al. (2015) *Nat. Med.* 21:1209-1215; Weiskopf et al. (2016) *J. Clin. Invest.* 126:2610-2620; Tseng et al. (2013) *Proc. Nat. Acad. Sci. U.S.A.* 110: 11103-11108; Sica et al. (2003) *Immunity* 18:849-861; Zang et al. (2007) *Proc. Nat. Acad. Sci. U.S.A.* 104, 19458-19463). Although cancer cells could, in theory, express many more genes that regulate their response or resistance to tumor immunity, strategies to systematically discover such genes are lacking.

Loss-of-function genetic screens have been increasingly used to study the functional consequences of gene deletion on tumor cells (Howard et al. (2016) Functional Genomic Characterization of Cancer Genomes. *Cold Spring Harb. Symp. Quant. Biol.* (2016); Ebert et al. (2008) *Nature* 451:335-339; Cowley et al. (2014) *Scientific Data* 1:article number 140035). These approaches include pooled genetic screens using CRISPR-Cas9-mediated genome editing that simultaneously test the role of a large number of genes on tumor cell growth, viability or drug resistance (Wang et al. (2014) *Science* 343:80-84; Shalem et al. (2014) *Science* 343:84-87). However, these screens have generally been conducted in vitro, where the contribution of the immune system is absent, or have studied phenotypes such as metastasis that do not directly evaluate the role of tumor immunity (Hart et al. (2015) *Cell* 163:1515-1526; Yu et al. (2016) *Nat. Biotechnol.* 34:419-423; Chen et al. (2015) *Cell* 160:1246-1260).

Despite the dramatic clinical success of cancer immunotherapy with immunotherapy, such as PD-1 checkpoint blockade, most patients do not experience sustained clinical benefit from treatment. Accordingly a great need in the art exists for additional therapeutic strategies.

SUMMARY OF THE INVENTION

The present invention is based, at least in part, on the discovery that inhibiting or blocking one or more biomarkers listed in Table 1, such as signal peptide peptidase (SPP), in combination with an immunotherapy, results in a synergistic therapeutic benefit for treating cancers that is unexpected given the lack of such benefit observed for the immunotherapy alone. The present invention involves the inhibition of SPP to improve anti-tumor immunity in cancer patients. Using an in vivo CRISPR/Cas9-based high throughput screening system, SPP has been identified as a candidate molecule, that when inhibited, sensitizes tumors to immunotherapy. It is demonstrated herein that mice bearing SPP-deficient tumors have an improved response to immunotherapy (anti-PD-1 treatment and GM-CSF expressing tumor cell vaccination) and prolonged survival, compared to treated mice bearing wild-type tumors. To date, SPP has not been demonstrated as a target for cancer in combination with immunotherapy. Functional data validating that SPP-deficiency can increase the efficacy of immunotherapy is presented herein for the first time. Accordingly, SPP-inhibitors will be useful for systemic or local delivery for use to improve anti-tumor immunity in patients, including those afflicted with cancer, and represents a novel strategy for treating cancer in the setting of concurrent immunotherapy.

In one aspect, a method of treating a subject afflicted with a cancer comprising administering to the subject a therapeutically effective amount of (1) one or more agents that inhibit the copy number, the expression level, and/or the activity of one or more biomarkers listed in Table 1 or a fragment thereof, in combination with an immunotherapy; and/or (2) one or more agents that increase the copy number, the expression level, and/or the activity of one or more biomarkers listed in Table 4 or a fragment thereof, in combination with an immunotherapy., is provided.

Numerous embodiments are further provided that can be applied to any aspect of the present invention and/or combined with any other embodiment described herein. In particular, claims and description provided below in the summary of the invention, as well as throughout the instant specification, for assessing, diagnosing, prognosing, modulating, etc. a biomarker listed in Table 1 also apply to a biomarker listed in Table 4 and generally in the opposite direction of each other. In one embodiment, the method comprises an agent that decreases the copy number, the expression level, and/or the activity of signal peptide peptidase (SPP); and/or increases the copy number, the expression level, and/or the activity of Myo7a. In another embodiment, the agent selectively decreases the amount and/or activity of Qdm-associated HLA-E; and/or increases the amount and/or activity of Myo7a-associated HLA-E. In yet another embodiment, the agent decreases the copy number, the expression level, and/or the activity of the one or more Qdm peptides, optionally wherein the agent blocks the production of one or more Qdm peptides; and/or wherein the agent increases the copy number, the expression level, and/or the activity of the HLA-E-associated peptides that are not Qdm peptides. In still another embodiment, the agent decreases inhibition of natural killer (NK) cells or T cells, optionally wherein the agent decreases CD94/NKG2A-mediated inhibition of NK cells or T cells; and/or wherein the agent decreases HLA-E-mediated inhibition of NK cells or T cells. In another embodiment, the agent increases HLA-E-mediated killing of cancer cells by CD8+ T cells, optionally wherein the agent promotes the interaction between HLA-E and T cell receptors. In one embodiment, the agent is a small molecule inhibitor, CRISPR single-guide RNA (sgRNA), RNA interfering agent, antisense oligonucleotide, peptide or peptidomimetic inhibitor, aptamer, antibody, or intrabody. In another embodiment, the RNA interfering agent is a small interfering RNA (siRNA), CRISPR RNA (crRNA), a small hairpin RNA (shRNA), a microRNA (miRNA), or a piwi-interacting RNA (piRNA). In another embodiment, the RNA interfering agent is a CRISPR single-guide RNA (sgRNA). In yet another embodiment, the sgRNA comprises a nucleic acid sequence selected from the group consisting of nucleic acid sequence listed in Table 3. In another embodiment, the agent comprises an intrabody, or an antigen binding fragment thereof, which specifically binds to SPP and/or a substrate of SPP. In another embodiment, the intrabody, or antigen binding fragment thereof, is murine, chimeric, humanized, composite, or human. In still another embodiment, the intrabody, or antigen binding fragment thereof, is detectably labeled, comprises an effector domain, comprises an Fc domain, and/or is selected from the group consisting of Fv, Fav, F(ab')2, Fab', dsFv, scFv, sc(Fv)2, and diabodies fragments. In another embodiment, the intrabody, or antigen binding fragment thereof, is conjugated to a cytotoxic agent. In one embodiment, the cytotoxic agent is selected from the group consisting of a chemotherapeutic agent, a biologic agent, a toxin, and a radioactive isotope. In another embodiment, the agent increases the sensitivity of the cancer cells to an immunotherapy, optionally wherein the immunotherapy is T-cell-mediated. In one embodiment, the immunotherapy and/or a cancer therapy is administered before, after, or concurrently with the agent. In another embodiment, the immunotherapy comprises an anti-cancer vaccine and/or virus. In yet another embodiment, the immunotherapy is cell-based. In still another embodiment, the immunotherapy inhibits an immune checkpoint. In one embodiment, the immune checkpoint is selected from the group consisting of CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRP, CD47, CD48, 2B4 (CD244), B7.1, B7.2, ILT-2, ILT-4, TIGIT, HHLA2, butyrophilins, IDO, CD39, CD73 and A2aR. In another embodiment, the immune checkpoint is selected from the group consisting of PD-1, PD-L1, and PD-L2, optionally wherein the immune checkpoint is PD-1. In one embodiment, the cancer therapy is selected from the group consisting of immunotherapy, targeted therapy, chemotherapy, radiation therapy, hormonal therapy, an anti-cancer vaccine, an anti-cancer virus, a checkpoint inhibitor, a radiosensitizer, an immunogenic chemotherapy, interferon, an interferon-inducing agent, an inflammatory agent, and a TLR agonist. In one embodiment, the biomarker comprises a nucleic acid sequence having at least 95% identity to a nucleic acid sequence listed in Table 1 and/or encodes an amino acid sequence having at least 95% identity to an amino acid sequence listed in Table 1. In one embodiment, the one or more biomarkers are human, mouse, chimeric, or a fusion. In another embodiment, the SPP comprises an amino acid sequence listed in Table 1, optionally wherein the amino acid sequence is selected from the group consisting of SEQ ID NOs: 2, 4, 6, 8, 10, 12, 14, and 16. In another embodiment, the SPP is encoded by a nucleic acid comprising the sequence listed in Table 1, optionally wherein the nucleic acid sequence is selected from the group consisting of SEQ ID NOs: 1, 3, 5, 7, 9, 11, 13, and 15. In one embodiment, the agent decreases the number of proliferating cells in the cancer and/or decreases the volume or size of a tumor comprising the cancer cells. In another embodiment, the agent increases the amount of CD8+ T cells or NK cells in a tumor comprising the cancer cells. In yet another embodiment, the cancer is selected from the group consisting of melanoma, glioblastoma, lung cancer, prostate cancer, squamous cell carcinoma, adenocarcinoma, cervical carcinoma, head and neck carcinoma, and gastric cancer. In still another embodiment, the cancer is melanoma. In one embodiment, the subject is an animal model of the cancer, preferably a mouse model, or a human. In another embodiment, the method further comprises administering to the subject at least one additional cancer therapy or regimen, optionally wherein the at least one additional cancer therapy or regimen is administered before, after, or concurrently with the agent and/or the immunotherapy. In another embodiment, the agent is administered in a pharmaceutically acceptable formulation. In one embodiment, the agent inhibits gamma secretase, optionally wherein the agent is selected from YO-01027, GSI XXI (also known as Compound E), R04929097, GSI II (also known as MW167 or DFK167), L-685458, LY411575, and (Z-LL)$_2$.

In one aspect, a method of killing cancer cells comprising contacting the cancer cells with an agent that inhibits the copy number, the expression level, and/or the activity of one or more biomarkers listed in Table 1 or a fragment thereof, in combination with an immunotherapy, is provided.

As described above, numerous embodiments are further provided that can be applied to any aspect of the present invention and/or combined with any other embodiment described herein. For example, in one embodiment, the method comprises an agent that decreases the copy number, the expression level, and/or the activity of SPP. In another embodiment, the agent selectively decreases the catalytic activity and/or the substrate binding activity of SPP, optionally the protease activity of SPP. In still another embodiment, the agent decreases the copy number, the expression level, and/or the activity of one or more Qdm peptides, optionally wherein the agent blocks the production of one or more Qdm peptides; and/or the agent increases the copy number, the expression level, and/or the activity of the HLA-E-associated peptides that are not Qdm peptides. In still another embodiment, the agent decreases inhibition of natural killer (NK) cells or T cells, optionally wherein the agent decreases CD94/NKG2A-mediated inhibition of NK cells or T cells; and/or wherein the agent decreases HLA-E-mediated inhibition of NK cells or T cells. In another embodiment, the agent increases HLA-E-mediated killing of cancer cells by CD8+ T cells, optionally wherein the agent promotes the interaction between HLA-E and T cell receptors. In one embodiment, the agent is a small molecule inhibitor, CRISPR single-guide RNA (sgRNA), RNA interfering agent, antisense oligonucleotide, peptide or peptidomimetic inhibitor, aptamer, antibody, or intrabody. In another embodiment, the RNA interfering agent is a small interfering RNA (siRNA), CRISPR RNA (crRNA), a small hairpin RNA (shRNA), a microRNA (miRNA), or a piwi-interacting RNA (piRNA). In another embodiment, the RNA interfering agent is a CRISPR single-guide RNA (sgRNA). In yet another embodiment, the sgRNA comprises a nucleic acid sequence selected from the group consisting of nucleic acid sequence listed in Table 3. In another embodiment, the agent comprises an intrabody, or an antigen binding fragment thereof, which specifically binds to SPP and/or a substrate of SPP. In another embodiment, the intrabody, or antigen binding fragment thereof, is murine, chimeric, humanized, composite, or human. In still another embodiment, the intrabody, or antigen binding fragment thereof, is detectably labeled, comprises an effector domain, comprises an Fc domain, and/or is selected from the group consisting of Fv, Fav, F(ab')2, Fab', dsFv, scFv, sc(Fv)2, and diabodies fragments. In another embodiment, the intrabody, or antigen binding fragment thereof, is conjugated to a cytotoxic agent. In one embodiment, the cytotoxic agent is selected from the group consisting of a chemotherapeutic agent, a biologic agent, a toxin, and a radioactive isotope. In another embodiment, the agent increases the sensitivity of the cancer cells to an immunotherapy, optionally wherein the immunotherapy is T-cell-mediated. In one embodiment, the cancer cells are contacted with an immunotherapy and/or a cancer therapy before, after, or concurrently with the agent. In another embodiment, the immunotherapy comprises an anti-cancer vaccine and/or virus. In yet another embodiment, the immunotherapy is cell-based. In still another embodiment, the immunotherapy inhibits an immune checkpoint. In one embodiment, the immune checkpoint is selected from the group consisting of CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRP, CD47, CD48, 2B4 (CD244), B7.1, B7.2, ILT-2, ILT-4, TIGIT, HHLA2, butyrophilins, IDO, CD39, CD73 and A2aR. In another embodiment, the immune checkpoint is selected from the group consisting of PD-1, PD-L1, and PD-L2, optionally wherein the immune checkpoint is PD-1. In one embodiment, the cancer therapy is selected from the group consisting of immunotherapy, targeted therapy, chemotherapy, radiation therapy, hormonal therapy, an anti-cancer vaccine, an anti-cancer virus, a checkpoint inhibitor, a radiosensitizer, an immunogenic chemotherapy, interferon, an interferon-inducing agent, an inflammatory agent, and a TLR agonist. In one embodiment, the biomarker comprises a nucleic acid sequence having at least 95% identity to a nucleic acid sequence listed in Table 1 and/or encodes an amino acid sequence having at least 95% identity to an amino acid sequence listed in Table 1. In one embodiment, the one or more biomarkers are human, mouse, chimeric, or a fusion. In another embodiment, the SPP comprises an amino acid sequence listed in Table 1, optionally wherein the amino acid sequence is selected from the group consisting of SEQ ID NOs: 2, 4, 6, 8, 10, 12, 14, and 16. In another embodiment, the SPP is encoded by a nucleic acid comprising the sequence listed in Table 1, optionally wherein the nucleic acid sequence is selected from the group consisting of SEQ ID NOs: 1, 3, 5, 7, 9, 11, 13, and 15. In one embodiment, the agent decreases the number of proliferating cells in the cancer and/or decreases the volume or size of a tumor comprising the cancer cells. In another embodiment, the agent increases the amount of CD8+ T cells or NK cells in a tumor comprising the cancer cells. In yet another embodiment, the cancer is selected from the group consisting of melanoma, glioblastoma, lung cancer, prostate cancer, squamous cell carcinoma, adenocarcinoma, cervical carcinoma, head and neck carcinoma, and gastric cancer. In still another embodiment, the cancer is melanoma. In another embodiment, the agent is administered in a pharmaceutically acceptable formulation. In another embodiment, the method further comprises contacting the cancer cells with at least one additional agent that inhibits proliferation of the cancer cells. In one embodiment, the cancer is in a subject and the subject is a mammal. In another embodiment, the mammal is a mouse or a human. In yet another embodiment, the mammal is a human. In one embodiment, the agent inhibits gamma secretase, optionally wherein the agent is selected from YO-01027, GSI XXI (also known as Compound E), R04929097, GSI II (also known as MW167 or DFK167), L-685458, LY411575, and (Z-LL)$_2$.

In another aspect, a method of determining whether a subject afflicted with a cancer or at risk for developing a cancer would benefit from inhibiting the copy number, amount, and/or activity of at least one biomarker listed in Table 1, the method comprising: a) determining the copy number, amount, and/or activity of the at least one biomarker listed in Table 1 in a biological sample from a subject; b) determining the copy number, amount, and/or activity of the at least one biomarker listed in Table 1 in a control; and c) comparing the copy number, amount, and/or activity of the at least one biomarker listed in Table 1 detected in steps a) and b); wherein the presence of, or a significant increase in, the copy number, amount, and/or activity of the at least one biomarker listed in Table 1 in the subject sample relative to the control copy number, amount, and/or activity of the at least one biomarker indicates that the subject afflicted with the cancer or at risk for developing the cancer would benefit from inhibiting the copy number, amount, and/or activity of the at least one biomarker listed in Table 1.

As described above numerous embodiments are further provided that can be applied to any aspect of the present invention and/or combined with any other embodiment described herein. For example, in one embodiment, the method further comprises recommending, prescribing, or administering an agent that inhibits the at least one biomarker listed in Table 1 if the cancer is determined to benefit from the agent, optionally further administering at least one additional cancer therapy. In another embodiment, the method further comprises recommending, prescribing, or administering cancer therapy other than an agent that inhibits the at least one biomarker listed in Table 1 if the cancer is determined to not benefit from the agent. In yet one embodiment, the cancer therapy is selected from the group consisting of immunotherapy, targeted therapy, chemotherapy, radiation therapy, hormonal therapy, an anti-cancer vaccine, an anti-cancer virus, a checkpoint inhibitor, a radiosensitizer, an immunogenic chemotherapy, interferon, an interferon-inducing agent, and a TLR agonist. In one embodiment, the control sample is determined from a cancerous or non-cancerous sample from either the patient or a member of the same species to which the patient belongs. In another embodiment, the control sample comprises cells. In one embodiment, the sample comprises cells, serum, peritumoral tissue, and/or intratumoral tissue obtained from the subject. In another embodiment, the one or more biomarkers listed in Table 1 comprise SPP. In another embodiment, the one or more biomarkers comprise a nucleic acid sequence having at least 95% identity to a nucleic acid sequence listed in Table 1 and/or encode an amino acid sequence having at least 95% identity to an amino acid sequence listed in Table 1. In yet another embodiment, the SPP comprises an amino acid sequence listed in Table 1, optionally wherein the amino acid sequence is selected from the group consisting of SEQ ID NOs: 2, 4, 6, 8, 10, 12, 14, and 16. In still another embodiment, the SPP is encoded by a nucleic acid sequence listed in Table 1, optionally wherein the nucleic acid sequence is selected from the group consisting of SEQ ID NOs: 1, 3, 5, 7, 9, 11, 13, and 15. In one embodiment, the cancer is selected from the group consisting of melanoma, glioblastoma, lung cancer, prostate cancer, squamous cell carcinoma, adenocarcinoma, cervical carcinoma, head and neck carcinoma, and gastric cancer. In another embodiment, the cancer is melanoma. In one embodiment, the cancer is in a subject and the subject is a mammal. In another embodiment, the mammal is a mouse or a human. In yet another embodiment, the mammal is a human.

In another aspect, a method for predicting the clinical outcome of a subject afflicted with a cancer expressing one or more biomarkers listed in Table 1 or a fragment thereof, is provided herein, the method comprising: a) determining the copy number, amount, and/or activity of at least one biomarker listed in Table 1 in a subject sample; b) determining the copy number, amount, and/or activity of the at least one biomarker in a control having a good clinical outcome; and c) comparing the copy number, amount, and/or activity of the at least one biomarker in the subject sample and in the control; wherein the presence of, or a significant increase in, the copy number, amount, and/or activity of, the at least one biomarker listed in Table 1 in the subject sample as compared to the copy number, amount and/or activity in the control, is an indication that the subject has a poor clinical outcome.

Numerous embodiments are further provided that can be applied to any aspect of the present invention and/or combined with any other embodiment described herein. For example, in one embodiment, the sample comprises cells, serum, peritumoral tissue, and/or intratumoral tissue obtained from the subject. In another embodiment, the one or more biomarkers listed in Table 1 comprise SPP. In another embodiment, the one or more biomarkers comprise a nucleic acid sequence having at least 95% identity to a nucleic acid sequence listed in Table 1 and/or encode an amino acid sequence having at least 95% identity to an amino acid sequence listed in Table 1. In yet another embodiment, the SPP comprises an amino acid sequence listed in Table 1, optionally wherein the amino acid sequence is selected from the group consisting of SEQ ID NOs: 2, 4, 6, 8, 10, 12, 14, and 16. In still another embodiment, the SPP is encoded by a nucleic acid sequence listed in Table 1, optionally wherein the nucleic acid sequence is selected from the group consisting of SEQ ID NOs: 1, 3, 5, 7, 9, 11, 13, and 15. In one embodiment, the cancer is selected from the group consisting of melanoma, glioblastoma, lung cancer, prostate cancer, squamous cell carcinoma, adenocarcinoma, cervical carcinoma, head and neck carcinoma, and gastric cancer. In another embodiment, the cancer is melanoma. In one embodiment, the cancer is in a subject and the subject is a mammal. In another embodiment, the mammal is a mouse or a human. In yet another embodiment, the mammal is a human.

In yet another aspect, a method for monitoring the progression of a cancer in a subject, wherein the subject is administered a therapeutically effective amount of an agent that inhibits the copy number, amount, and/or activity of at least one biomarker listed in Table 1, the method comprising: a) detecting in a subject sample at a first point in time the copy number, amount, and/or activity of the at least one biomarker listed in Table 1; b) repeating step a) at a subsequent point in time; and c) comparing the amount or activity of the at least one biomarker listed in Table 1 detected in steps a) and b) to monitor the progression of the cancer in the subject.

Numerous embodiments are further provided that can be applied to any aspect of the present invention and/or combined with any other embodiment described herein. For example, in one embodiment, between the first point in time and the subsequent point in time, the subject has undergone treatment, completed treatment, and/or is in remission for the cancer. In another embodiment, the cancer treatment is selected from the group consisting of immunotherapy, targeted therapy, chemotherapy, radiation therapy, hormonal therapy, an anti-cancer vaccine, an anti-cancer virus, a checkpoint inhibitor, a radiosensitizer, an immunogenic chemotherapy, interferon, an interferon-inducing agent, an inflammatory agent, and a TLR agonist. In yet another embodiment, the first and/or at least one subsequent sample is selected from the group consisting of ex vivo and in vivo samples. In still another embodiment, the first and/or at least one subsequent sample is a portion of a single sample or pooled samples obtained from the subject. In one embodiment, the sample comprises cells, serum, peritumoral tissue, and/or intratumoral tissue obtained from the subject. In another embodiment, the one or more biomarkers listed in Table 1 comprise SPP. In another embodiment, the one or more biomarkers comprise a nucleic acid sequence having at least 95% identity to a nucleic acid sequence listed in Table 1 and/or encode an amino acid sequence having at least 95% identity to an amino acid sequence listed in Table 1. In yet another embodiment, the SPP comprises an amino acid sequence listed in Table 1, optionally wherein the amino acid sequence is selected from the group consisting of SEQ ID NOs: 2, 4, 6, 8, 10, 12, 14, and 16. In still another embodiment, the SPP is encoded by a nucleic acid sequence listed in Table 1, optionally wherein the nucleic acid sequence is selected from the group consisting of SEQ ID NOs: 1, 3, 5, 7, 9, 11, 13, and 15. In one embodiment, the cancer is selected from the group consisting of melanoma, glioblastoma, lung cancer, prostate cancer, squamous cell carcinoma, adenocarcinoma, cervical carcinoma, head and neck carcinoma, and gastric cancer. In another embodiment, the cancer is melanoma. In one embodiment, the cancer is in a subject and the subject is a mammal. In another embodiment, the mammal is a mouse or a human. In yet another embodiment, the mammal is a human.

In another aspect, a method of assessing the efficacy of an agent that inhibits the copy number, amount, and/or activity of at least one biomarker listed in Table 1 for treating a cancer in a subject, comprising: a) detecting in a subject sample at a first point in time the copy number, amount, and/or or activity of the at least one biomarker listed in Table 1; b) repeating step a) during at least one subsequent point in time after administration of the agent; and c) comparing the copy number, amount, and/or activity detected in steps a) and b), wherein the absence of, or a significant decrease in, the copy number, amount, and/or activity of, the at least one biomarker listed in Table 1, in the subsequent sample as compared to the copy number, amount, and/or activity in the sample at the first point in time, indicates that the agent treats the cancer in the subject.

Numerous embodiments are further provided that can be applied to any aspect of the present invention and/or combined with any other embodiment described herein. For example, in one embodiment, between the first point in time and the subsequent point in time, the subject has undergone treatment, completed treatment, and/or is in remission for the cancer. In another embodiment, the cancer treatment is selected from the group consisting of immunotherapy, targeted therapy, chemotherapy, radiation therapy, hormonal therapy, an anti-cancer vaccine, an anti-cancer virus, a checkpoint inhibitor, a radiosensitizer, an immunogenic chemotherapy, interferon, an interferon-inducing agent, an inflammatory agent, and a TLR agonist. In yet another embodiment, the first and/or at least one subsequent sample is selected from the group consisting of ex vivo and in vivo samples. In still another embodiment, the first and/or at least one subsequent sample is a portion of a single sample or pooled samples obtained from the subject. In one embodiment, the sample comprises cells, serum, peritumoral tissue, and/or intratumoral tissue obtained from the subject. In another embodiment, the one or more biomarkers listed in Table 1 comprise SPP. In another embodiment, the one or more biomarkers comprise a nucleic acid sequence having at least 95% identity to a nucleic acid sequence listed in Table 1 and/or encode an amino acid sequence having at least 95% identity to an amino acid sequence listed in Table 1. In yet another embodiment, the SPP comprises an amino acid sequence listed in Table 1, optionally wherein the amino acid sequence is selected from the group consisting of SEQ ID NOs: 2, 4, 6, 8, 10, 12, 14, and 16. In still another embodiment, the SPP is encoded by a nucleic acid sequence listed in Table 1, optionally wherein the nucleic acid sequence is selected from the group consisting of SEQ ID NOs: 1, 3, 5, 7, 9, 11, 13, and 15. In one embodiment, the cancer is selected from the group consisting of melanoma, glioblastoma, lung cancer, prostate cancer, squamous cell carcinoma, adenocarcinoma, cervical carcinoma, head and neck carcinoma, and gastric cancer. In another embodiment, the cancer is melanoma. In one embodiment, the cancer is in a subject and the subject is a mammal. In another embodiment, the mammal is a mouse or a human. In yet another embodiment, the mammal is a human.

Representative examples of additional embodiments that are further provided and can be applied to any aspect of the present invention and/or combined with any other embodiment described herein include, for example, wherein the agent selectively (1) increases the activity of Myo7a, or a fragment thereof, in binding HLA-E, or orghologs thereof; (2) increases the copy number of Myo7a, or a fragment thereof; and/or (3) increases the amount of the Myo7a-associated HLA-E, or orthologs thereof. In another embodiment, the agent can selectively decreases the biological activity and/or the substrate binding activity of SPP, optionally the protease activity of SPP. In still another embodiment, the agent selectively decreases the amount and/or activity of Qdm-associated HLA-E; and/or increases the amount and/or activity of Myo7a-associated HLA-E. In yet another embodiment, the agent increases the immune response to tumors, optionally wherein the immune response is a proliferation of CD8+ T cells.

BRIEF DESCRIPTION OF THE DRAWINGS

FIG. 1A-FIG. 1F show that in vivo pooled loss-of-function screening using CRISPR/Cas9 in tumor cells recovers known mediators of immune evasion. FIG. 1A shows a schematic diagram of the in vivo screening system using the B16 transplantable tumor model. Tumor volumes (in mm$^3$) were compared under each conditions, averaged for each group at each time point (FIG. 1B, left) or for individual animals on the day of sacrifice (FIG. 1B, right). Bars represent means, while whiskers represent standard deviation. Enrichment analysis was carried out using a hypergeometric test to show functional classes of genes, (from the Gene Ontology Consortium database (GO)) targeted by sgRNAs, that were enriched or depleted in tumors in animals, including animals treated with irradiated tumor cell vaccine (GVAX) and anti-PD-1 antibody and the TCRα$^{-/-}$ animals (FIG. 1C). Frequency histogram (FIG. 1D, top) and collapsed histograms (FIG. 1D, middle) of enrichment or depletion (normalized as Z scores) are shown for all 9,992 sgRNAs screened. Enrichment/depletion scores are averaged from 10 mice per condition. sgRNAs targeting PD-L1 are indicated by the red lines (FIG. 1D, middle). PD-L1 expression is compared among Cas9-expressing B16 tumor cells transfected with one of the four sgRNAs targeting PD-L1 (red) or a control sgRNA (grey) (FIG. 1D, bottom). Similar to FIG. 1D, FIG. 1E shows the depletion of CD47 by its specific sgRNAs (indicated in red (top and middle) and CD47 expression after CRISPR editing with sgRNAs targeting CD47 (bottom). FIG. 1F compares tumor volumes over time between CD47 null (red) and control (grey) tumors growing in mice treated with GVAX and PD-1 blockade (average and standard error of the mean; n=10 animals per group).  $p<0.01$; * $p<0.001$; **** $p<0.0001$.

FIG. 2A shows Western blot of B16 cell lysate for Cas9 and β-ACTIN with or without transduction with a lentiviral vector encoding Cas9. A pie chart shows the fraction of genes targeted in the screening in each of the GO term categories indicated (FIG. 2B). Two-dimensional histograms show the pair-wise distribution of sgRNAs abundance (averaged for each condition) (FIG. 2C). Saturation analysis of animal replicates from the three in vivo screening conditions is shown in FIG. 2D. Pearson correlations are calculated for the library distribution in one animal vs. any other animal, then for two animals averaged versus any other two averaged, and so on. Saturation approaches $r=0.95$. A matrix of the Pearson correlations of the library distribution from one animal compared to any other animal for B16 Pool 1 is shown (FIG. 2E). Expression of CD47 by B16 cells transfected with either CD47-targeting (red) or control (grey) sgRNA is compared (FIG. 2F).

FIG. 5A is adapted from Schroder et al. (2010) *Biochem J.* 427:e1-e3.

FIG. 6A and FIG. 6E show efficient CRISPR mediated SPP knock out in the B16 melanoma cell line by quantitative reverse transcription PCR. FIG. 6B and FIG. 6D show schematic diagrams of test animals transplanted with tumor cells with or without the SPP deletion. FIG. 6C and FIG. 6F show the efficacy data of tumor-bearing animals treated with PD-1 blockade and GM-CSF expressing tumor cell vaccine (GVAX). Animals bearing the SPP knockout show complete tumor regression. FIG. 6G shows efficacy data of NOD scid gamma (NSG) mice bearing SPP knockout tumors. The data show that the anti-tumor effect of the SPP deletion requires immune response. The data further show that SPP is involved in the function of non-classical MHC molecule Qa-1b. Tumor volumes (in $mm^3$) were compared under each conditions, averaged for each group at each time point. Triangles under the X-axis show administration of the indicated immunotherapy. Bars represent standard error of the mean.

FIG. 7A and FIG. 7C show schematic diagrams depicting a role of Qa-1b (Qa-1b in mice; HLA-E in humans) in inhibiting the activity of NK cells and CD8+ T cells. SPP facilitates the activity of Qa-1b by producing Qa-1b-associated peptide (Qdm peptide). Qa-1b, upon binding the peptide, inhibits the activity of NK cells and CD8+ cells via its interaction with the CD94/NKG2A receptor. FIG. 7B shows a schematic diagram comparing classical and non-classical MHC molecules. FIG. 7D shows that SPP generates Qdm, which is a predominant peptide displayed by Qa-1b. Specifically, FIG. 7D shows a membrane-bound signal peptide peptidase (SPP) cleaveing a nascent transcript to generate the Qdm peptide. Over 90% of the peptides presented by Qa-1b is Qdm, which is required for the interaction between Qa-1b and NKG2A. FIG. 7E shows a flow chart depicting a mechanism by which the SPP deletion promotes NK cell- and T cell-mediated killing of tumor cells via Qa-1b. Qdm facilitates the interaction between Qa-1b on tumor cells and NKG2A on NK cells and T cells. This interaction inhibits the cytotoxic killing of the tumor cells by NK cells and T cells. When SPP is deleted, such inhibition of immune response is relieved, allowing NK cells and T cells to kill the tumor cells. Overall, these diagrams demonstrate a mechanism by which the SPP deletion promotes eradication of tumors.

FIG. 8A shows the first mechanism, that SPP deletion blocks the production of Qdm peptide, which is the peptide that preferentially binds to Qa-1b. Without the SPP-generated Qdm peptide, Qa-1b cannot engage the CD94/NKG2A receptor and transmit inhibitory signals to immune cells. Thus, the deletion of SPP removes the immune inhibitory signal of Qa-1b. FIG. 8B shows the second mechanism, that without the presence of SPP-generated Qdm peptide, Qa-1b can now present other peptides that allow Qa-1b to engage the T-cell receptor and trigger the activity of CD8+ T cell. The combined effects of both mechanisms result in enhanced killing of tumor cells.

FIG. 9A shows efficient CRISPR mediated Qa1-b knock out in the B16 melanoma cell line by flow cytometry. FIG. 9B shows a schematic diagram of test animals transplanted with tumor cells with or without the Qa-1b deletion. FIG. 9C shows the efficacy data of tumor-bearing animals treated with PD-1 blockade and GVAX. Animals bearing the Qa-1b deletion show complete tumor regression. FIG. 9D shows efficacy data of mice bearing the tumors containing the SPP deletion (SPP KO), the Qa-1b deletion (Qa-1b KO), or the double deletion of both SPP and Qa-1b (Dbl KO). The efficacy data show a lack of synergism between the SPP deletion and Qa-1b deletion, indicating that they function in the same pathway. Tumor volumes (in $mm^3$) were compared under each conditions, averaged for each group at each time point. Triangles under the X-axis show administration of the indicated immunotherapy. Bars represent standard deviation.

FIG. 11A shows that the SPP deletion does not affect Qa-1b expression on tumor cells, indicating that Qa-1b associates with other peptides that stabilize Qa-1b expression. FIG. 11B shows that SPP deletion alters peptide repertoire displayed on Qa-1b. FIG. 11C shows a mass spectrometry-based method to identify additional peptides that are associated with Qa-1b in the SPP-deleted tumors. FIG. 11D demonstrates that Qa-1b can be efficiently and purely isolated by immunoprecipitation techniques using an HA-tagged re-expressed version of the Qa-1b molecule. FIG. 11E shows that Qa-1b predominantly associates with Qdm peptide in tumors with a wild-type copy of SPP. However, in tumors with SPP deletion, the Qa-1b-associated peptide repertoire becomes more heterogeneous. Importantly, a significant number of Qa-1b molecules associates with Myo7a in tumors with SPP deletion, indicating that it plays an important role in sensitizing the tumors to immune therapy.

DETAILED DESCRIPTION OF THE INVENTION

Figure 1D:
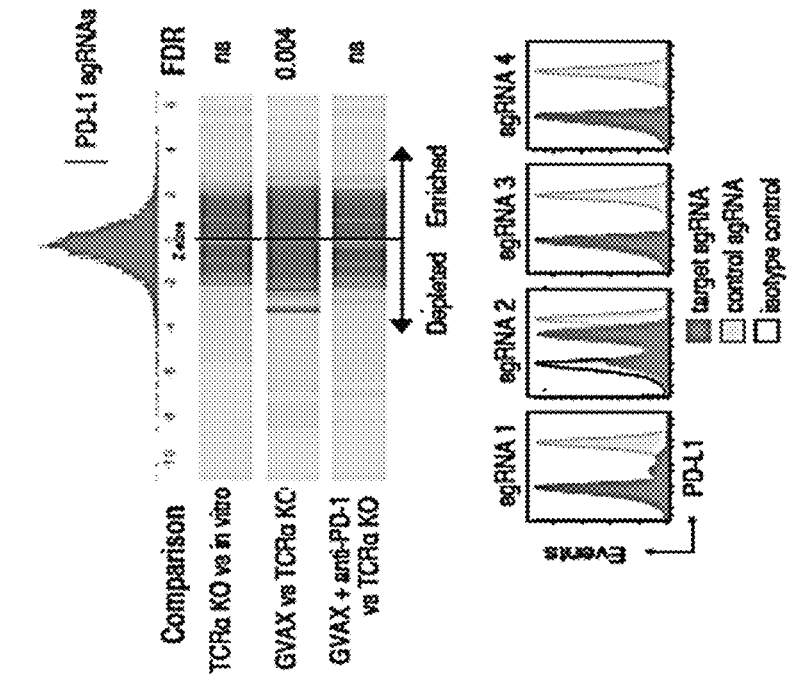

It has been determined herein that negative regulators of one or more biomarkers listed in Table 1, such as SPP, can be used to augment tumor immunity and immunotherapies. Thus, the instant disclosure provides at least a method of treating cancers, e.g., those cancer types otherwise not responsive or weakly responsive to immunotherapies, with a combination of a negative regulator of one or more biomarkers listed in Table 1, and another immunotherapy. The results described herein are unexpected given that analyses of such regulator function has heretofore been largely confined to hematopoietic cells and not examined in cancer cells, as well as the fact that modulating sensitivity to interferon signaling is critical for immunotherapy effects rather than simply modulating interferon availability since interferon therapy is known to not significantly augment immunotherapy effects. Accordingly, the present invention provides exemplary RNA interfering agents inhibiting such regulators, which may be used in the combination therapy and other methods described herein, such as agents that inhibit the function and/or its ability of one or more biomarkers listed in Table 1 to interact/bind to its substrates described herein, or by increasing its degradation and/or stability and/or interaction/binding to its inhibitors. Similarly, methods of screening for inhibitors of such regulators and methods of diagnosing, prognosing, and monitoring cancer involving such inhibitors/immunotherapy combination therapies are provided.

I. Definitions

The articles "a" and "an" are used herein to refer to one or to more than one (i.e. to at least one) of the grammatical object of the article. By way of example, "an element" means one element or more than one element.

The term "altered amount" or "altered level" refers to increased or decreased copy number (e.g., germline and/or somatic) of a biomarker nucleic acid, e.g., increased or decreased expression level in a cancer sample, as compared to the expression level or copy number of the biomarker nucleic acid in a control sample. The term "altered amount" of a biomarker also includes an increased or decreased protein level of a biomarker protein in a sample, e.g., a cancer sample, as compared to the corresponding protein level in a normal, control sample. Furthermore, an altered amount of a biomarker protein may be determined by detecting posttranslational modification such as methylation status of the marker, which may affect the expression or activity of the biomarker protein.

The amount of a biomarker in a subject is "significantly" higher or lower than the normal amount of the biomarker, if the amount of the biomarker is greater or less, respectively, than the normal level by an amount greater than the standard error of the assay employed to assess amount, and preferably at least 20%, 30%, 40%, 50%, 60%, 70%, 80%, 90%, 100%, 150%, 200%, 300%, 350%, 400%, 500%, 600%, 700%, 800%, 900%, 1000% or than that amount. Alternately, the amount of the biomarker in the subject can be considered "significantly" higher or lower than the normal amount if the amount is at least about two, and preferably at least about three, four, or five times, higher or lower, respectively, than the normal amount of the biomarker. Such "significance" can also be applied to any other measured parameter described herein, such as for expression, inhibition, cytotoxicity, cell growth, and the like.

The term "altered level of expression" of a biomarker refers to an expression level or copy number of the biomarker in a test sample, e.g., a sample derived from a patient suffering from cancer, that is greater or less than the standard error of the assay employed to assess expression or copy number, and is preferably at least twice, and more preferably three, four, five or ten or more times the expression level or copy number of the biomarker in a control sample (e.g., sample from a healthy subjects not having the associated disease) and preferably, the average expression level or copy number of the biomarker in several control samples. The altered level of expression is greater or less than the standard error of the assay employed to assess expression or copy number, and is preferably at least 20%, 30%, 40%, 50%, 60%, 70%, 80%, 90%, 100%, 150%, 200%, 300%, 350%, 400%, 500%, 600%, 700%, 800%, 900%, 1000% or more times the expression level or copy number of the biomarker in a control sample (e.g., sample from a healthy subjects not having the associated disease) and preferably, the average expression level or copy number of the biomarker in several control samples. In some embodiments, the level of the biomarker refers to the level of the biomarker itself, the level of a modified biomarker (e.g., phosphorylated biomarker), or to the level of a biomarker relative to another measured variable, such as a control (e.g., phosphorylated biomarker relative to an unphosphorylated biomarker).

The term "altered activity" of a biomarker refers to an activity of the biomarker which is increased or decreased in a disease state, e.g., in a cancer sample, as compared to the activity of the biomarker in a normal, control sample. Altered activity of the biomarker may be the result of, for example, altered expression of the biomarker, altered protein level of the biomarker, altered structure of the biomarker, or, e.g., an altered interaction with other proteins involved in the same or different pathway as the biomarker or altered interaction with transcriptional activators or inhibitors.

The term "altered structure" of a biomarker refers to the presence of mutations or allelic variants within a biomarker nucleic acid or protein, e.g., mutations which affect expression or activity of the biomarker nucleic acid or protein, as compared to the normal or wild-type gene or protein. For example, mutations include, but are not limited to substitutions, deletions, or addition mutations. Mutations may be present in the coding or non-coding region of the biomarker nucleic acid.

Unless otherwise specified here within, the terms "antibody" and "antibodies" refers to antigen-binding portions adaptable to be expressed within cells as "intracellular antibodies." (Chen et al. (1994) *Human Gene Ther.* 5:595-601). Methods are well-known in the art for adapting antibodies to target (e.g., inhibit) intracellular moieties, such as the use of single-chain antibodies (scFvs), modification of immunoglobulin VL domains for hyperstability, modification of antibodies to resist the reducing intracellular environment, generating fusion proteins that increase intracellular stability and/or modulate intracellular localization, and the like. Intracellular antibodies can also be introduced and expressed in one or more cells, tissues or organs of a multicellular organism, for example for prophylactic and/or therapeutic purposes (e.g., as a gene therapy) (see, at least PCT Publs. WO 08/020079, WO 94/02610, WO 95/22618, and WO 03/014960; U.S. Pat. No. 7,004,940; Cattaneo and Biocca (1997) *Intracellular Antibodies: Development and Applications* (Landes and Springer-Verlag publs.); Kontermann (2004) *Methods* 34:163-170; Cohen et al. (1998) *Oncogene* 17:2445-2456; Auf der Maur et al. (2001) *FEBS Lett.* 508:407-412; Shaki-Loewenstein et al. (2005) *J. Immunol. Meth.* 303:19-39).

Antibodies may be polyclonal or monoclonal; xenogeneic, allogeneic, or syngeneic; or modified forms thereof (e.g. humanized, chimeric, etc.). Antibodies may also be fully human. Preferably, antibodies of the present invention bind specifically or substantially specifically to a biomarker polypeptide or fragment thereof. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

Antibodies may also be "humanized", which is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the present invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

The term "assigned score" refers to the numerical value designated for each of the biomarkers after being measured in a patient sample. The assigned score correlates to the absence, presence or inferred amount of the biomarker in the sample. The assigned score can be generated manually (e.g., by visual inspection) or with the aid of instrumentation for image acquisition and analysis. In certain embodiments, the assigned score is determined by a qualitative assessment, for example, detection of a fluorescent readout on a graded scale, or quantitative assessment. In one embodiment, an "aggregate score," which refers to the combination of assigned scores from a plurality of measured biomarkers, is determined. In one embodiment the aggregate score is a summation of assigned scores. In another embodiment, combination of assigned scores involves performing mathematical operations on the assigned scores before combining them into an aggregate score. In certain, embodiments, the aggregate score is also referred to herein as the "predictive score."

The term "biomarker" refers to a measurable entity of the present invention that has been determined to be predictive of effects of combinatorial therapies comprising one or more inhibitors of one or more biomarkers listed in Table 1, such SPP, HLA-E, and/or HLA-E-associated peptide, and immunotherapy (e.g., immune checkpoint inhibitors) on a cancer. Biomarkers can include, without limitation, nucleic acids and proteins, including those shown in the Tables, the Examples, the Figures, and otherwise described herein. As described herein, any relevant characteristic of a biomarker can be used, such as the copy number, amount, activity, location, modification (e.g., phosphorylation), and the like.

A "blocking" antibody or an antibody "antagonist" is one which inhibits or reduces at least one biological activity of the antigen(s) it binds. In certain embodiments, the blocking antibodies or antagonist antibodies or fragments thereof described herein substantially or completely inhibit a given biological activity of the antigen(s).

The term "body fluid" refers to fluids that are excreted or secreted from the body as well as fluids that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit).

The terms "cancer" or "tumor" or "hyperproliferative" refer to the presence of cells possessing characteristics typical of cancer-causing cells, such as uncontrolled proliferation, immortality, metastatic potential, rapid growth and proliferation rate, and certain characteristic morphological features. Unless otherwise stated, the terms include metaplasias. In some embodiments, such cells exhibit such characteristics in part or in full due to the expression and activity of signaling pathways regulated by one or more biomarkers listed in Table 1. In some embodiments, the cancer cells described herein are not sensitive to at least one of immunotherapies. In some embodiments, the cancer cells are treatable with an agent capable of antagonizing regulators of the biomarkers described herein, such as inhibiting expression and/or function, as described herein.

Cancer cells are often in the form of a tumor, but such cells may exist alone within an animal, or may be a non-tumorigenic cancer cell, such as a leukemia cell. As used herein, the term "cancer" includes premalignant as well as malignant cancers. Cancers include, but are not limited to, B cell cancer, e.g., multiple myeloma, Waldenström's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematologic tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, cancers are epithlelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated.

In certain embodiments, the cancer encompasses melanoma. The term "melanoma" as used herein, is generally meant to include cancers that develop from the pigment-containing cells, known as melanocytes, in the basal layer of the epidermis. Melanomas typically occur in the skin but may rarely occur in the mouth, intestines, or eye. In women they most commonly occur on the legs, while in men they are most common on the back. Sometimes they develop from a mole with concerning changes including an increase in size, irregular edges, change in color, itchiness, or skin breakdown. Thus, the term "melanoma" also includes cancers developing from these cells, tissues, and organs.

Melanomas are among the most dangerous forms of skin cancer and develop when unrepaired DNA damage to skin cells (most often caused by ultraviolet radiation from sunshine or tanning beds) triggers gene mutations that lead the skin cells to multiply rapidly and form malignant tumors. The primary cause of melanoma is ultraviolet light (UV) exposure in those with low levels of skin pigment. Melanomas often resemble moles; some develop from moles. Those with many moles, a history of affected family members, and who have poor immune function are at greater risk. A number of rare genetic defects such as xeroderma pigmentosum also increase risk (Azoury and Lange, 2014 *Surg Clin North Am.* 2014 94:945-962).

Melanoma can be divided into different types, including, at least, lentigo maligna, lentigo maligna melanoma, superficial spreading melanoma, acral lentiginous melanoma, mucosal melanoma, nodular melanoma, polypoid melanoma, desmoplastic melanoma, amelanotic melanoma, soft-tissue melanoma, melanoma with small nevus-like cells, melanoma with features of a Spitz nevus, uveal melanoma, etc. (see James, et al., 2006 *Andrews' Diseases of the Skin: clinical Dermatology.* Saunders Elsevier. pp. 694-9) Diagnosis is by biopsy of any concerning skin lesion, including, at least, shave (tangential) biopsy, punch biopsy, incisional and excisional biopsies, "optical" biopsies (e.g., by reflectance confocal microscopy (RCM)), fine needle aspiration (FNA) biopsy, surgical lymph node biopsy, sentinel lymph node biopsy, etc. In addition, visual inspection may also be used for diagnosis, such as a popular method for the signs and symptoms of melanoma as mnemonic "ABCDE": Asymmetrical skin lesion, Border of the lesion is irregular, Color: melanomas usually have multiple colors, Diameter: moles greater than 6 mm are more likely to be melanomas than smaller moles, and Enlarging: Enlarging or evolving. Another method as the "ugly duckling sign" is also known in the art (Mascaro and Mascaro, 1998 *Arch Dermatol.* 134: 1484-1485).

Treatment of melanoma includes surgery, chemotherapy (such as temozolomide, dacarbazine (also termed DTIC), etc.), radiation therapy, oncolytic virotherapy (e.g., see Forbes et al., 2013 *Front. Genet.* 4:184), and immunotherapy (e.g., interleukin-2 (IL-2), interferon, etc.). Targeted therapies (e.g., as in Maverakis et al., 2015 *Acta Derm Venereol.* 95: 516-524) may include: 1) adoptive cell therapy (ACT) using TILs immune cells (tumor infiltrating lymphocytes) isolated from a person's own melanoma tumor). Cells are grown in large numbers in a laboratory and returned to the patient after a treatment that temporarily reduces normal T cells in the patient's body. TIL therapy following lymphodepletion can result in durable complete response in a variety of setups (Besser et al., 2010 *Clin. Cancer Res.* 16:2646-2655); and 2) adoptive transfer of genetically altered (expressing T cell receptors (TCRs)) autologous lymphocytes into patient's lymphocytes, where the altered lymphocytes recognize and bind to the surface of melanoma cells and kill them. Other therapies include, at least, B-Raf inhibitors (such as vemurafenib, see Chapman et al., 2011 *N. Engl. J Med.* 364:2507-2516) and ipilimumab (alone or in combination with dacarbazine, see, e.g., Robert et al. (2011) *N. Engl. J. Med.* 364:2517-2526).

The term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

The term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control cancer patient (can be stored sample or previous sample measurement) with a known outcome; normal tissue or cells isolated from a subject, such as a normal patient or the cancer patient, cultured primary cells/ tissues isolated from a subject such as a normal subject or the cancer patient, adjacent normal cells/tissues obtained from the same organ or body location of the cancer patient, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment (for example, standard of care cancer therapy). It will be understood by those of skill in the art that such control samples and reference standard expression product levels can be used in combination as controls in the methods of the present invention. In one embodiment, the control may comprise normal or non-cancerous cell/ tissue sample. In another preferred embodiment, the control may comprise an expression level for a set of patients, such as a set of cancer patients, or for a set of cancer patients receiving a certain treatment, or for a set of patients with one outcome versus another outcome. In the former case, the specific expression product level of each patient can be assigned to a percentile level of expression, or expressed as either higher or lower than the mean or average of the reference standard expression level. In another preferred embodiment, the control may comprise normal cells, cells from patients treated with combination chemotherapy, and cells from patients having benign cancer. In another embodiment, the control may also comprise a measured value for example, average level of expression of a particular gene in a population compared to the level of expression of a housekeeping gene in the same population. Such a population may comprise normal subjects, cancer patients who have not undergone any treatment (i.e., treatment naive), cancer patients undergoing standard of care therapy, or patients having benign cancer. In another preferred embodiment, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with cancer. In one embodiment a control expression product level is established wherein higher or lower levels of expression product relative to, for instance, a particular percentile, are used as the basis for predicting outcome. In another preferred embodiment, a control expression product level is established using expression product levels from cancer control patients with a known outcome, and the expression product levels from the test sample are compared to the control expression product level as the basis for predicting outcome. As demonstrated by the data below, the methods of the present invention are not limited to use of a specific cut-point in comparing the level of expression product in the test sample to the control.

The "copy number" of a biomarker nucleic acid refers to the number of DNA sequences in a cell (e.g., germline and/or somatic) encoding a particular gene product. Generally, for a given gene, a mammal has two copies of each gene. The copy number can be increased, however, by gene amplification or duplication, or reduced by deletion. For example, germline copy number changes include changes at one or more genomic loci, wherein said one or more genomic loci are not accounted for by the number of copies in the normal complement of germline copies in a control (e.g., the normal copy number in germline DNA for the same species as that from which the specific germline DNA and corresponding copy number were determined). Somatic copy number changes include changes at one or more genomic loci, wherein said one or more genomic loci are not accounted for by the number of copies in germline DNA of a control (e.g., copy number in germline DNA for the same subject as that from which the somatic DNA and corresponding copy number were determined).

The "normal" copy number (e.g., germline and/or somatic) of a biomarker nucleic acid or "normal" level of expression of a biomarker nucleic acid or protein is the activity/level of expression or copy number in a biological sample, e.g., a sample containing tissue, whole blood, serum, plasma, buccal scrape, saliva, cerebrospinal fluid, urine, stool, and bone marrow, from a subject, e.g., a human, not afflicted with cancer, or from a corresponding non-cancerous tissue in the same subject who has cancer.

As used herein, the term "costimulate" with reference to activated immune cells includes the ability of a costimulatory molecule to provide a second, non-activating receptor mediated signal (a "costimulatory signal") that induces proliferation or effector function. For example, a costimulatory signal can result in cytokine secretion, e.g., in a T cell that has received a T cell-receptor-mediated signal. Immune cells that have received a cell-receptor mediated signal, e.g., via an activating receptor are referred to herein as "activated immune cells."

The term "determining a suitable treatment regimen for the subject" is taken to mean the determination of a treatment regimen (i.e., a single therapy or a combination of different therapies that are used for the prevention and/or treatment of the cancer in the subject) for a subject that is started, modified and/or ended based or essentially based or at least partially based on the results of the analysis according to the present invention. One example is starting an adjuvant therapy after surgery whose purpose is to decrease the risk of recurrence, another would be to modify the dosage of a particular chemotherapy. The determination can, in addition to the results of the analysis according to the present invention, be based on personal characteristics of the subject to be treated. In most cases, the actual determination of the suitable treatment regimen for the subject will be performed by the attending physician or doctor.

The term "diagnosing cancer" includes the use of the methods, systems, and code of the present invention to determine the presence or absence of a cancer or subtype thereof in an individual. The term also includes methods, systems, and code for assessing the level of disease activity in an individual.

A molecule is "fixed" or "affixed" to a substrate if it is covalently or non-covalently associated with the substrate such that the substrate can be rinsed with a fluid (e.g. standard saline citrate, pH 7.4) without a substantial fraction of the molecule dissociating from the substrate.

The term "expression signature" or "signature" refers to a group of one or more coordinately expressed biomarkers related to a measured phenotype. For example, the genes, proteins, metabolites, and the like making up this signature may be expressed in a specific cell lineage, stage of differentiation, or during a particular biological response. The biomarkers can reflect biological aspects of the tumors in which they are expressed, such as the cell of origin of the cancer, the nature of the non-malignant cells in the biopsy, and the oncogenic mechanisms responsible for the cancer. Expression data and gene expression levels can be stored on computer readable media, e.g., the computer readable medium used in conjunction with a microarray or chip reading device. Such expression data can be manipulated to generate expression signatures.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

The term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes.

The term "immunotherapy" or "immunotherapies" refer to any treatment that uses certain parts of a subject's immune system to fight diseases such as cancer. The subject's own immune system is stimulated (or suppressed), with or without administration of one or more agent for that purpose. Immunotherapies that are designed to elicit or amplify an immune response are referred to as "activation immunotherapies." Immunotherapies that are designed to reduce or suppress an immune response are referred to as "suppression immunotherapies." Any agent believed to have an immune system effect on the genetically modified transplanted cancer cells can be assayed to determine whether the agent is an immunotherapy and the effect that a given genetic modification has on the modulation of immune response. In some embodiments, the immunotherapy is cancer cell-specific. In some embodiments, immunotherapy can be "untargeted," which refers to administration of agents that do not selectively interact with immune system cells, yet modulates immune system function. Representative examples of untargeted therapies include, without limitation, chemotherapy, gene therapy, and radiation therapy.

Immunotherapy is one form of targeted therapy that may comprise, for example, the use of cancer vaccines and/or sensitized antigen presenting cells. For example, an oncolytic virus is a virus that is able to infect and lyse cancer cells, while leaving normal cells unharmed, making them potentially useful in cancer therapy. Replication of oncolytic viruses both facilitates tumor cell destruction and also produces dose amplification at the tumor site. They may also act as vectors for anticancer genes, allowing them to be specifically delivered to the tumor site. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). For example, anti-VEGF and mTOR inhibitors are known to be effective in treating renal cell carcinoma. Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer.

Immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer.

The term "immunogenic chemotherapy" refers to any chemotherapy that has been demonstrated to induce immunogenic cell death, a state that is detectable by the release of one or more damage-associated molecular pattern (DAMP) molecules, including, but not limited to, calreticulin, ATP and HMGB1 (Kroemer et al. (2013), *Annu. Rev. Immunol.*, 31:51-72). Specific representative examples of consensus immunogenic chemotherapies include 5'-fluorouracil, anthracyclines, such as doxorubicin, and the platinum drug, oxaliplatin, among others.

In some embodiments, immunotherapy comprises inhibitors of one or more immune checkpoints. The term "immune checkpoint" refers to a group of molecules on the cell surface of CD4+ and/or CD8+ T cells that fine-tune immune responses by down-modulating or inhibiting an anti-tumor immune response. Immune checkpoint proteins are well-known in the art and include, without limitation, CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRP, CD47, CD48, 2B4 (CD244), B7.1, B7.2, ILT-2, ILT-4, TIGIT, HHLA2, butyrophilins, IDO, CD39, CD73 and A2aR (see, for example, WO 2012/177624). The term further encompasses biologically active protein fragment, as well as nucleic acids encoding full-length immune checkpoint proteins and biologically active protein fragments thereof. In some embodiment, the term further encompasses any fragment according to homology descriptions provided herein. In one embodiment, the immune checkpoint is PD-1.

Immune checkpoints and their sequences are well-known in the art and representative embodiments are described below. For example, the term "PD-1" refers to a member of the immunoglobulin gene superfamily that functions as a coinhibitory receptor having PD-L1 and PD-L2 as known ligands. PD-1 was previously identified using a subtraction cloning based approach to select for genes upregulated during TCR-induced activated T cell death. PD-1 is a member of the CD28/CTLA-4 family of molecules based on its ability to bind to PD-L1. Like CTLA-4, PD-1 is rapidly induced on the surface of T-cells in response to anti-CD3 (Agata et al. 25 (1996) *Int. Immunol.* 8:765). In contrast to CTLA-4, however, PD-1 is also induced on the surface of B-cells (in response to anti-IgM). PD-1 is also expressed on a subset of thymocytes and myeloid cells (Agata et al. (1996) supra; Nishimura et al. (1996) *Int. Immunol.* 8:773).

The nucleic acid and amino acid sequences of a representative human PD-1 biomarker is available to the public at the GenBank database under NM_005018.2 and NP_005009.2 and is shown in Table 1 (see also Ishida et al. (1992) 20 *EMBO J* 11:3887; Shinohara et al. (1994) *Genomics* 23:704; U.S. Pat. No. 5,698,520). PD-1 has an extracellular region containing immunoglobulin superfamily domain, a transmembrane domain, and an intracellular region including an immunoreceptor tyrosine-based inhibitory motif (ITIM) (Ishida et al. (1992) *EMBO J.* 11:3887; Shinohara et al. (1994) *Genomics* 23:704; and U.S. Pat. No. 5,698,520) and an immunoreceptor tyrosine-based switch motif (ITSM). These features also define a larger family of polypeptides, called the immunoinhibitory receptors, which also includes gp49B, PIR-B, and the killer inhibitory receptors (KIRs) (Vivier and Daeron (1997) *Immunol. Today* 18:286). It is often assumed that the tyrosyl phosphorylated ITIM and ITSM motif of these receptors interacts with SH2-domain containing phosphatases, which leads to inhibitory signals. A subset of these immunoinhibitory receptors bind to MHC polypeptides, for example the KIRs, and CTLA4 binds to B7-1 and B7-2. It has been proposed that there is a phylogenetic relationship between the MHC and B7 genes (Henry et al. (1999) *Immunol. Today* 20(6):285-8). Nucleic acid and polypeptide sequences of PD-1 orthologs in organisms other than humans are well-known and include, for example, mouse PD-1 (NM 008798.2 and NP_032824.1), rat PD-1 (NM_001106927.1 and NP_001100397.1), dog PD-1 (XM_543338.3 and XP_543338.3), cow PD-1 (NM_001083506.1 and NP_001076975.1), and chicken PD-1 (XM_422723.3 and XP_422723.2).

PD-1 polypeptides are inhibitory receptors capable of transmitting an inhibitory signal to an immune cell to thereby inhibit immune cell effector function, or are capable of promoting costimulation (e.g., by competitive inhibition) of immune cells, e.g., when present in soluble, monomeric form. Preferred PD-1 family members share sequence identity with PD-1 and bind to one or more B7 family members, e.g., B7-1, B7-2, PD-1 ligand, and/or other polypeptides on antigen presenting cells.

The term "PD-1 activity," includes the ability of a PD-1 polypeptide to modulate an inhibitory signal in an activated immune cell, e.g., by engaging a natural PD-1 ligand on an antigen presenting cell. Modulation of an inhibitory signal in an immune cell results in modulation of proliferation of, and/or cytokine secretion by, an immune cell. Thus, the term "PD-1 activity" includes the ability of a PD-1 polypeptide to bind its natural ligand(s), the ability to modulate immune cell costimulatory or inhibitory signals, and the ability to modulate the immune response.

The term "PD-1 ligand" refers to binding partners of the PD-1 receptor and includes both PD-L1 (Freeman et al. (2000) *J. Exp. Med.* 192:1027-1034) and PD-L2 (Latchman et al. (2001) *Nat. Immunol.* 2:261). At least two types of human PD-1 ligand polypeptides exist. PD-1 ligand proteins comprise a signal sequence, and an IgV domain, an IgC domain, a transmembrane domain, and a short cytoplasmic tail. Both PD-L1 (See Freeman et al. (2000) for sequence data) and PD-L2 (See Latchman et al. (2001) *Nat. Immunol.* 2:261 for sequence data) are members of the B7 family of polypeptides. Both PD-L1 and PD-L2 are expressed in placenta, spleen, lymph nodes, thymus, and heart. Only PD-L2 is expressed in pancreas, lung and liver, while only PD-L1 is expressed in fetal liver. Both PD-1 ligands are upregulated on activated monocytes and dendritic cells, although PD-L1 expression is broader. For example, PD-L1 is known to be constitutively expressed and upregulated to higher levels on murine hematopoietic cells (e.g., T cells, B cells, macrophages, dendritic cells (DCs), and bone marrow-derived mast cells) and non-hematopoietic cells (e.g., endothelial, epithelial, and muscle cells), whereas PD-L2 is inducibly expressed on DCs, macrophages, and bone marrow-derived mast cells (see Butte et al. (2007) *Immunity* 27:111).

PD-1 ligands comprise a family of polypeptides having certain conserved structural and functional features. The term "family" when used to refer to proteins or nucleic acid molecules, is intended to mean two or more proteins or nucleic acid molecules having a common structural domain or motif and having sufficient amino acid or nucleotide sequence homology, as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics. PD-1 ligands are members of the B7 family of polypeptides. The term "B7 family" or "B7 polypeptides" as used herein includes costimulatory polypeptides that share sequence homology with B7 polypeptides, e.g., with B7-1, B7-2, B7h (Swallow et al. (1999) *Immunity* 11:423), and/or PD-1 ligands (e.g., PD-L1 or PD-L2). For example, human B7-1 and B7-2 share approximately 26% amino acid sequence identity when compared using the BLAST program at NCBI with the default parameters (Blosum62 matrix with gap penalties set at existence 11 and extension 1 (See the NCBI website). The term B7 family also includes variants of these polypeptides which are capable of modulating immune cell function. The B7 family of molecules share a number of conserved regions, including signal domains, IgV domains and the IgC domains. IgV domains and the IgC domains are art-recognized Ig superfamily member domains. These domains correspond to structural units that have distinct folding patterns called Ig folds. Ig folds are comprised of a sandwich of two β sheets, each consisting of anti-parallel β strands of 5-10 amino acids with a conserved disulfide bond between the two sheets in most, but not all, IgC domains of Ig, TCR, and MIIC molecules share the same types of sequence patterns and are called the C1-set within the Ig superfamily. Other IgC domains fall within other sets. IgV domains also share sequence patterns and are called V set domains. IgV domains are longer than IgC domains and contain an additional pair of β strands.

Preferred B7 polypeptides are capable of providing costimulatory or inhibitory signals to immune cells to thereby promote or inhibit immune cell responses. For example, B7 family members that bind to costimulatory receptors increase T cell activation and proliferation, while B7 family members that bind to inhibitory receptors reduce costimulation. Moreover, the same B7 family member may increase or decrease T cell costimulation. For example, when bound to a costimulatory receptor, PD-1 ligand can induce costimulation of immune cells or can inhibit immune cell costimulation, e.g., when present in soluble form. When bound to an inhibitory receptor, PD-1 ligand polypeptides can transmit an inhibitory signal to an immune cell. Preferred B7 family members include B7-1, B7-2, B7h, PD-L1 or PD-L2 and soluble fragments or derivatives thereof. In one embodiment, B7 family members bind to one or more receptors on an immune cell, e.g., CTLA4, CD28, ICOS, PD-1 and/or other receptors, and, depending on the receptor, have the ability to transmit an inhibitory signal or a costimulatory signal to an immune cell, preferably a T cell.

Modulation of a costimulatory signal results in modulation of effector function of an immune cell. Thus, the term "PD-1 ligand activity" includes the ability of a PD-1 ligand polypeptide to bind its natural receptor(s) (e.g. PD-1 or B7-1), the ability to modulate immune cell costimulatory or inhibitory signals, and the ability to modulate the immune response.

The term "PD-L1" refers to a specific PD-1 ligand. Two forms of human PD-L1 molecules have been identified. One form is a naturally occurring PD-L1 soluble polypeptide, i.e., having a short hydrophilic domain and no transmembrane domain, and is referred to herein as PD-L1S. The second form is a cell-associated polypeptide, i.e., having a transmembrane and cytoplasmic domain, referred to herein as PD-L1M. The nucleic acid and amino acid sequences of representative human PD-L1 biomarkers regarding PD-L1M are also available to the public at the GenBank database under NM_014143.3 and NP_054862.1. PD-L1 proteins comprise a signal sequence, and an IgV domain and an IgC domain. The signal sequence of PD-L1S is shown from about amino acid 1 to about amino acid 18. The signal sequence of PD-L1M is shown:from about amino acid 1 to about amino acid 18. The IgV domain of PD-L1S is shown from about amino acid 19 to about amino acid 134 and the IgV domain of PD-L1M is shown from about amino acid 19 to about amino acid 134. The IgC domain of PD-L1S is shown from about amino acid 135 to about amino acid 227 and the IgC domain of PD-L1M is shown from about amino acid 135 to about amino acid 227. The hydrophilic tail of the PD-L1 exemplified in PD-L1S comprises a hydrophilic tail shown from about amino acid 228 to about amino acid 245. The PD-L1 polypeptide exemplified in PD-L1M comprises a transmembrane domain shown from about amino acids 239 to about amino acid 259 and a cytoplasmic domain shown from about 30 amino acid 260 to about amino acid 290. In addition, nucleic acid and polypeptide sequences of PD-L1 orthologs in organisms other than humans are well-known and include, for example, mouse PD-L1 (NM_021893.3 and NP_068693.1), rat PD-L1 (NM_001191954.1 and NP_001178883.1), dog PD-L1 (XM_541302.3 and XP_541302.3), cow PD-L1 (NM_001163412.1 and NP_001156884.1), and chicken PD-L1 (XM_424811.3 and XP_424811.3).

The term "PD-L2" refers to another specific PD-1 ligand. PD-L2 is a B7 family member expressed on various APCs, including dendritic cells, macrophages and bone-marrow derived mast cells (Zhong et al. (2007) Eur. J. Immunol. 37:2405). APC-expressed PD-L2 is able to both inhibit T cell activation through ligation of PD-1 and costimulate T cell activation, through a PD-1 independent mechanism (Shin et al. (2005) J. Exp. Med. 201:1531). In addition, ligation of dendritic cell-expressed PD-L2 results in enhanced dendritic cell cytokine expression and survival (Radhakrishnan et al. (2003) J. Immunol. 37:1827; Nguyen et al. (2002) J. Exp. Med. 196:1393). The nucleic acid and amino acid sequences of representative human PD-L2 biomarkers are well-known in the art and are also available to the public at the GenBank database under NM_025239.3 and NP_079515.2. PD-L2 proteins are characterized by common structural elements. In some embodiments, PD-L2 proteins include at least one or more of the following domains: a signal peptide domain, a transmembrane domain, an IgV domain, an IgC domain, an extracellular domain, a transmembrane domain, and a cytoplasmic domain. For example, amino acids 1-19 of PD-L2 comprises a signal sequence. As used herein, a "signal sequence" or "signal peptide" serves to direct a polypeptide containing such a sequence to a lipid bilayer, and is cleaved in secreted and membrane bound polypeptides and includes a peptide containing about 15 or more amino acids which occurs at the N-terminus of secretory and membrane bound polypeptides and which contains a large number of hydrophobic amino acid residues. For example, a signal sequence contains at least about 10-30 amino acid residues, preferably about 15-25 amino acid residues, more preferably about 18-20 amino acid residues, and even more preferably about 19 amino acid residues, and has at least about 35-65%, preferably about 38-50%, and more preferably about 40-45% hydrophobic amino acid residues (e.g., valine, leucine, isoleucine or phenylalanine). In another embodiment, amino acid residues 220-243 of the native human PD-L2 polypeptide and amino acid residues 201-243 of the mature polypeptide comprise a transmembrane domain. As used herein, the term "transmembrane domain" includes an amino acid sequence of about 15 amino acid residues in length which spans the plasma membrane. More preferably, a transmembrane domain includes about at least 20, 25, 30, 35, 40, or 45 amino acid residues and spans the plasma membrane. Transmembrane domains are rich in hydrophobic residues, and typically have an alpha-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta, W. N. et al. (1996) Annu. Rev. Neurosci. 19: 235-263. In still another embodiment, amino acid residues 20-120 of the native human PD-L2 polypeptide and amino acid residues 1-101 of the mature polypeptide comprise an IgV domain. Amino acid residues 121-219 of the native human PD-L2 polypeptide and amino acid residues 102-200 of the mature polypeptide comprise an IgC domain. As used herein, IgV and IgC domains are recognized in the art as Ig superfamily member domains. These domains correspond to structural units that have distinct folding patterns called Ig folds. Ig folds are comprised of a sandwich of two ß sheets, each consisting of antiparallel (3 strands of 5-10 amino acids with a conserved disulfide bond between the two sheets in most, but not all, domains. IgC domains of Ig, TCR, and MHC molecules share the same types of sequence patterns and are called the Cl set within the Ig superfamily. Other IgC domains fall within other sets. IgV domains also share sequence patterns and are called V set domains. IgV domains are longer than C-domains and form an additional pair of strands. In yet another embodiment, amino acid residues 1-219 of the native human PD-L2 polypeptide and amino acid residues 1-200 of the mature polypeptide comprise an extracellular domain. As used herein, the term "extracellular domain" represents the N-terminal amino acids which extend as a tail from the surface of a cell. An extracellular domain of the present invention includes an IgV domain and an IgC domain, and may include a signal peptide domain. In still another embodiment, amino acid residues 244-273 of the native human PD-L2 polypeptide and amino acid residues 225-273 of the mature polypeptide comprise a cytoplasmic domain. As used herein, the term "cytoplasmic domain" represents the C-terminal amino acids which extend as a tail into the cytoplasm of a cell. In addition, nucleic acid and polypeptide sequences of PD-L2 orthologs in organisms other than humans are well-known and include, for example, mouse PD-L2 (NM_021396.2 and NP_067371.1), rat PD-L2 (NM_001107582.2 and NP_001101052.2), dog PD-L2 (XM_847012.2 and XP_852105.2), cow PD-L2 (XM_586846.5 and XP_586846.3), and chimpanzee PD-L2 (XM_001140776.2 and XP_001140776.1).

The term "PD-L2 activity," "biological activity of PD-L2," or "functional activity of PD-L2," refers to an activity exerted by a PD-L2 protein, polypeptide or nucleic acid molecule on a PD-L2-responsive cell or tissue, or on a PD-L2 polypeptide binding partner, as determined in vivo, or in vitro, according to standard techniques. In one embodiment, a PD-L2 activity is a direct activity, such as an association with a PD-L2 binding partner. As used herein, a "target molecule" or "binding partner" is a molecule with which a PD-L2 polypeptide binds or interacts in nature, such that PD-L2-mediated function is achieved. In an exemplary embodiment, a PD-L2 target molecule is the receptor RGMb. Alternatively, a PD-L2 activity is an indirect activity, such as a cellular signaling activity mediated by interaction of the PD-L2 polypeptide with its natural binding partner (i.e., physiologically relevant interacting macromolecule involved in an immune function or other biologically relevant function), e.g., RGMb. The biological activities of PD-L2 are described herein. For example, the PD-L2 polypeptides of the present invention can have one or more of the following activities: 1) bind to and/or modulate the activity of the receptor RGMb, PD-1, or other PD-L2 natural binding partners, 2) modulate intra-or intercellular signaling, 3) modulate activation of immune cells, e.g., T lymphocytes, and 4) modulate the immune response of an organism, e.g., a mouse or human organism.

"Anti-immune checkpoint therapy" refers to the use of agents that inhibit immune checkpoint nucleic acids and/or proteins. Inhibition of one or more immune checkpoints can block or otherwise neutralize inhibitory signaling to thereby upregulate an immune response in order to more efficaciously treat cancer. Exemplary agents useful for inhibiting immune checkpoints include antibodies, small molecules, peptides, peptidomimetics, natural ligands, and derivatives of natural ligands, that can either bind and/or inactivate or inhibit immune checkpoint proteins, or fragments thereof; as well as RNA interference, antisense, nucleic acid aptamers, etc. that can downregulate the expression and/or activity of immune checkpoint nucleic acids, or fragments thereof. Exemplary agents for upregulating an immune response include antibodies against one or more immune checkpoint proteins block the interaction between the proteins and its natural receptor(s); a non-activating form of one or more immune checkpoint proteins (e.g., a dominant negative polypeptide); small molecules or peptides that block the interaction between one or more immune checkpoint proteins and its natural receptor(s); fusion proteins (e.g. the extracellular portion of an immune checkpoint inhibition protein fused to the Fc portion of an antibody or immunoglobulin) that bind to its natural receptor(s); nucleic acid molecules that block immune checkpoint nucleic acid transcription or translation; and the like. Such agents can directly block the interaction between the one or more immune checkpoints and its natural receptor(s) (e.g., antibodies) to prevent inhibitory signaling and upregulate an immune response. Alternatively, agents can indirectly block the interaction between one or more immune checkpoint proteins and its natural receptor(s) to prevent inhibitory signaling and upregulate an immune response. For example, a soluble version of an immune checkpoint protein ligand such as a stabilized extracellular domain can bind to its receptor to indirectly reduce the effective concentration of the receptor to bind to an appropriate ligand. In one embodiment, anti-PD-1 antibodies, anti-PD-L1 antibodies, and/or anti-PD-L2 antibodies, either alone or in combination, are used to inhibit immune checkpoints. These embodiments are also applicable to specific therapy against particular immune checkpoints, such as the PD-1 pathway (e.g., anti-PD-1 pathway therapy, otherwise known as PD-1 pathway inhibitor therapy).

The term "SPP," also known as Signal Peptide Peptidase, Histocompatibility Minor 13 (HM13), or H13, refers to a member of a group of proteins known as GxGD-type aspartyl intramembrane-cleaving proteases (I-CLiPs) selective for substrates with a type II membrane topology. SPP is a homolog of presenilins, the catalytic component of gamma secretases (Mentrup et al. (2017) *Eur. J. CellBiol.* 96:372-382). All such members of the GxGD protease family share a conserved GxGD motif within their catalytic center. SPP is actively retained in the endoplasmic reticulum membrane due to its KKXX retention signal in animals (Krawitz et al. (2005) *J. Biol. Chem.* 280:39515-39523). A splice isoform of SPP found in mice lacks the retention signal and is observed at the plasma membrane (Urny et al. (2006) *Biochim. Biophys. Acta* 1759:159-165). SPP is conserved across mouse, human, and malaria.

SPP protein catalyzes intramembrane proteolysis of peptides residing in the endoplasmic reticulum membrane. Known functions of Spp include the cleavage and maturation of the hepatitis C virus core protein (McLauchlan et al. (2002) *EMBO J* 21:3980-8) and nuclear localization of hemeoxygenase-1 (HO-1) (Hsu et al. (2015) *Oncogene* 34:2360-2370). SPP is essential for the intramembrane proteolysis of signal peptides after they have been initially cleaved from a preprotein by signal peptidase. This results in the release of signal-peptide derived fragments from the ER membrane into the cytoplasm and the ER lumen. Theses resultant peptide fragments often are subsequently degraded, however can also bind to MHC molecules that are subsequently displayed on the cell surface and play an active role in immune modulation and immunosurveillance. Notably, SPP cleavage of signal peptides derived from MHC class I molecules produces the dominant peptide that binds to the non-polymorphic MHC molecule HLA-E. This peptide, referred to as the "Qa1 determining peptide", or Qdm, is required for HLA-E the interaction between HLA-E and its receptor CD94/NKG2A, which is found on NK cells and T cells. By producing the HLA-E-associated Qdm peptide via its protease activity, SPP facilitates the interaction between HLA-E and CD94/NKG2A, which subsequently leads to the inhibition of the cytotoxic activity of NK cells and T cells, and allows immune escape of cancer cells. Additionally, SPP is implicated in generating other peptides presented on classical MHC class I and, in some circumstances, the non-classical HLA-E molecules, contributing to immunosurveillance (Hage et al. (2008) *Proc. Natl. Acad. Sci. U.S.A.* 105:10119-10124). Overall, to this date, SPP is not believed to be shown as a target for a cancer therapy, let alone as a target for a cancer therapy in combination with the immunotherapy.

The term "SPP" is intended to include fragments, variants (e.g., allelic variants) and derivatives thereof. The tertiary structure of a homologue from the archaean *Methanoculleus marisnigri* has been solved and shows a unique fold which includes nine transmembrane segments that form a horseshoe shape (Moliaka et al. (2004) *FEBS Letters* 557:185-191). SPPs do not require cofactors as demonstrated by expression in bacteria and purification of a proteolytically active form. The C-terminal region defines the functional domain, which is in itself sufficient for proteolytic activity (Narayanan et al. (2007) *J. Biol. Chem.* 282:20172-9). Aspartic peptidases, also known as aspartyl proteases, are widely distributed proteolytic enzymes (Davies (1990) *Annu. Rev. Biophy. Biophysical Chem.* 19:189-215) known to exist in vertebrates, fungi, plants, protozoa, bacteria, archaea, retroviruses and some plant viruses. All known aspartic peptidases are endopeptidases. A water molecule, activated by two aspartic acid residues, acts as the nucleophile in catalysis. Aspartic peptidases can be grouped into five clans, each of which shows a unique structural fold (Rawlings et al. (1993) *Biochem. J.* 290:205-218). The nucleic acid and amino acid sequences of a representative human SPP is available to the public at the GenBank database (Gene ID 81502) and is shown in Table 1. SPP is enclosed by HM13 in human, and by H13 in mice. Multiple transcript variants encoding several different isoforms have been found for SPP. Human SPP variants include the transcript variant 1 encoding isoform 1 (NM_030789.3 and NP_110416.1), the transcript variant 2 encoding isoform 2 (NM_178580.2 and NP_848695.1), the transcript variant 3 encoding isoform 3 (NM_178581.2 and NP_848696.1), and the transcript variant 4 encoding isoform 4 (NM_178582.2 and NP_848697.1).

Nucleic acid and polypeptide sequences of SPP orthologs in organisms other than humans are well known and include, for example, chimpanzee SPP (XM_016937630.1 and XP_016793119.1; XM_016937632.1 and XP_016793121.1; XM_016937631.1 and XP_016793120.1; XM_016937634.1 and XP_016793123.1; XM_016937633.2 and XP_016793122.1), dog SPP (XM_022408849.1 and XP_022264557.1; XM_845723.5 and XP_850816.1; XM_857030.6 and XP_862123.1), cattle SPP (NM_001046124.2 and NP_001039589.2; XM_025000521.1 and XP_024856289.1; XM_025000524.1 and XP_024856292.1; XM_025000519.1 and XP_024856287.1; XM_005214665.4 and XP_005214722.1; XM_005214664.4 and XP_005214721.1; XM_005214663.4 and XP_005214720.1; XM_025000522.1 and XP_024856290.1; XM_025000525.1 and XP_024856293.1; XM_025000523.1 and XP_024856291.1), mouse SPP (NM_001159551.1 and NP_001153023.1; NM_001159552.1 and NP_001153024.1; NM_001159553.1 and NP_001153025.1; NM_010376.4 and NP_034506.1; XM_006498783.3 and XP_006498846.1; XM_017315666.1 and XP_017171155.1), rat SPP (NM_001107789.1 and NP_001101259.1; XM_006235268.1 and XP_006235330.1; XM_008762330.1 and XP_008760552.1; XM_006235269.1 and XP_006235331.1), chicken SPP (XM_004947155.3 and XP_004947212.2; XM_003642489.4 and XP_003642537.3), zebrafish SPP (NM 212572.2 and NP_997737.2; XM_005161890.4 and XP_005161947.1), fruit fly SPP (NM_078720.3 and NP_523444.1), mosquito SPP (XM_319582.4 and XP_319582.4), and rice SPP (XM_015784530.1 and XP_015640016.1).

The term "SPP activity" includes the ability of an SPP polypeptide (and its fragments, domains, and/or motifs thereof, discussed herein) to bind its substrate and/or catalyze the protease activity. SPP cleaves signal peptides in the ER membrane. Following synthesis at the ER membrane, nascent proteins that are either secreted or express on the cell are translocated into the ER lumen through the translocon and signal peptides are removed by signal peptidase. Subsequently, signal peptides are cleaved by SPP within the lipid bilayer and the respective signal peptide fragments are released from the ER membrane into cytosol and ER lumen. SPP activity may also include one or more of functions, such as those disclosed herein in the immune response and antigen processing. For example, SPP is required for the synthesis of the HLA-E-associated peptide Qdm, which is crucial in facilitating the interaction between HLA-E and CD94/NKG2A, and inhibition of NK cells and T cells. Accordingly, SPP activity includes inhibition of NK cells and T cells, and keeping the tumor cells resistant to immunotherapy. SPP may interact with various proteins disclosed herein, such as the HLA-E-associated peptide, a precursor thereof, and other binding partners for it functions in regulation of the proteins (e.g., secreted proteins), immune response, and antigen processing. SPP may also be proteolyticly modified, be glycosylated, or otherwise disclosed herein, for it functions.

The term "SPP substrate(s)" refers to binding partners of a SPP polypeptide (and its fragments, domains, and/or motifs thereof, discussed herein), e.g., the proteins listed herein, including P4HB, DERL1, RNF139, ABCE1, XBP1 (isoform 1) and ABHD16A. Furthermore, SPP substrates may refer to downstream members in the signaling pathways where SPP has a functional role.

The term "SPP-regulated pathway(s)" includes pathways in which SPP (and its fragments, domains, and/or motifs thereof, discussed herein) binds to at least one of its substrate, through which at least one cellular function and/or activity and/or cellular protein profiles is changed (e.g., proteolytic modification of proteins and antigen processing). In some embodiments, SPP promotes antigen processing and presentation for at least one of its substrates (e.g., antigens) which bind to it. SPP-regulated pathways include at least those described herein, such as regulation and proteolytic processing of proteins in ER, and/or antigen processing such as the production of the HLA-E-associated peptides, etc. Furthermore, SPP-regulated pathways include facilitating the interaction between HLA-E and CD94/NKG2A, and inhibition of NK cells and T cells.

The term "SPP inhibitor(s)" includes any natural or non-natural agent prepared, synthesized, manufactured, and/or purified by human that is capable of reducing, inhibiting, blocking, preventing, and/or that inhibits the ability of a SPP polypeptide (and its fragments, domains, and/or motifs thereof, discussed herein). In one embodiment, such inhibitors may reduce or inhibit the binding/interaction between SPP and its substrates or other binding partners. In another embodiment, such inhibitors may reduce or inhibit SPP as a peptidase/protease for antigen processing and/or other immune responses. In still another embodiment, such inhibitors may increase or promote the turnover rate, reduce or inhibit the expression and/or the stability (e.g., the half-life), and/or change the cellular localization of SPP, resulting in at least a decrease in SPP levels and/or activity. In yet another embodiment, such inhibitors may impair the catalytic activity of SPP. In still another embodiment, the inhibitors inhibit the proteolytic activity of SPP. Such inhibitors may be any molecule, including but not limited to small molecule compounds, antibodies or intrabodies, RNA interfereing (RNAi) agents (including at least siRNAs, shRNAs, microRNAs (miRNAs), piwi, and other well-known agents). Such inhibitors may be specific to SPP or also inhibit at least one of the binding partners. The inhibitors of SPP may also inhibit gamma-secretases due to extensive structural homology between SPP and gamma-secretases. Such inhibitors may include YO-01027 with the dibenoazepine structure (Hirano et al. (2017) *Proc. Natl. Acad. Sci. U.S.A.* 114:e10782-e10791) and the like. Such inhibitors may also include GSI XXI (also known as Compound E), GSI II (also known as MW167 or DFK167), and (Z-LL)2-ketone (Lemberg et al. (2001) *J. Immunol.* 167:6441-6446). Inhibition of SPP by various gamma secretase inhibitors has been previously demonstrated (Ran et al. (2015) *PLOS ONE* 10:e0128619). Certain inhibitors of SPP and gamma secretase are commercially available from Selleckchem (at world wide web selleckchem.com), including R04929097 (Cat. #S1575), Semagacestat (also known as LY450139; Cat. #S1594), MK-0752 (Cat. #S2660), Avagacestat (also known as BMS-708163; Cat. #S1262), NGP555 (Cat. #S8603), YO-01027 (Cat. #S2711), LY411575 (Cat. #S2714), Nirogacestat (also known as PF-03084014 or PF-3084014; Cat. #S8018), and L-685458 (Cat. #S7673). RNA interference for SPP polypepitdes are well known and commercially available (e.g., human, rat, or mouse shRNA/siRNA products (Cat. #TL500903, TF304082, TR304082, TL304082V, TL500903V, TG500903, TF500903, TG304082, TL304082, TR500903, TR706338, TL706338V, TL706338, TF706338, TG706338, and SR325168) from Origene (Rockville, MD), siRNA/shRNA products (Cat. #sc-45549, sc-45550, and others) and human or mouse gene knockout kit via CRISPR (Cat. #sc-405271, and sc-420752) from Santa Cruz Biotechonology (Dallas, Texas), and Ready-to-package AAV shRNA clones from Vigene Biosciences (Rockville, MD, Cat. #SH871995, SH804900, SH846606, and SH889432), etc.). Methods for detection, purification, and/or inhibition of SPP (e.g., by anti-SPP antibodies) are also well known and commercially available (e.g., multiple SPP antibodies from Origene (Cat. #TA339562), Sigma Aldrich (St. Louis, MO; Cat. #SAB1300769), Novus Biologicals (Littleton, CO, Cat. #NBP2-32276, NBP2-54935, etc.), abcam (Cambridge, MA, Cat. #ab190253, ab113872, and others), etc.). SPP knockout human cell lines are also well known and available at the Horizon (Cambridge, UK, Cat. #HZGHC81502).

The term "Myo7a," also known as Myosin VIIA or Usher Syndrome 1B, is an actin-based motor molecule with ATPase activity. Myosins are mechanochemical proteins characterized by the presence of a motor domain, an actin-binding domain, a neck domain that interacts with other proteins, and a tail domain that serves as an anchor. The MYO7A gene encodes an unconventional myosin with a very short tail. Unconventional myosins serve in intracellular movements. Their highly divergent tails bind to membranous compartments, which are then moved relative to actin filaments. In the retina, Myo7a plays an important role in the renewal of the outer photoreceptor disks. It also plays an important role in the distribution and migration of retinal pigment epithelial (RPE) melanosomes and phagosomes, and in the regulation of opsin transport in retinal photoreceptors. In the inner ear, Myo7a plays an important role in differentiation, morphogenesis and organization of cochlear hair cell bundles. It is involved in hair-cell vesicle trafficking of aminoglycosides, which are known to induce ototoxicity. Motor protein that is a part of the functional network formed by USH1C, USH1G, CDH23 and MYO7A that mediates mechanotransduction in cochlear hair cells. It is required for normal hearing. Defects in Myo7a are associated with the mouse shaker-1 phenotype and the human Usher syndrome 1B which are characterized by deafness, reduced vestibular function, and in human, retinal degeneration. Alternative splicing results in multiple transcript variants. Silencing Myo7a by means of RNAi inhibits melanoma cell growth through upregulation of cell cycle regulator p21 (also known as CDKN1A) and suppressed melanoma cell migration and invasion through downregulation of RhoGDI2 (also known as ARHGDIB) and MMP9 (Liu et al. (2018) *J Cell Sci* 131:1-13). In addition, Myo7a depletion suppress melanoma cell metastases to the lung, kidney and bone in mice, while overexpression of Myo7a promoted melanoma xenograft growth and lung metastasis. Myo7a levels are also elevated in human melanoma patients. However, to this date, Myo7a is not believed to be shown as a target for a cancer therapy in combination with the immunotherapy.

The term "Myo7a" is intended to include fragments, variants (e.g., allelic variants) and derivatives thereof. Myo7a characterized by a kinesin and myosin motor domain, an actin-binding domain, calmodulin-binding region, P-loop containing nucleoside triphosphate hydrolase region, MyTH4 domain, FERM domain, and SH3 domain. Myo7a also has a SAH (single alpha-helix) domain characterized by a high content of charged residues that are predicted to stabilize the alpha-helical structure by ionic bonds. Myo7a belongs to TRAFAC class myosin-kinetic ATPase superfamily. The nucleic acid and amino acid sequences of a representative human Myo7a is available to the public at the GenBank database (Gene ID 4647) and is shown in Table 4. Multiple transcript variants encoding several different isoforms have been found for Myo7a, including at least 8 different human transcript variants generated by alternative splicing (see World Wide Web at uniprot.org/uniprot/Q13402). Human Myo7a variants include the transcript variant 1 encoding isoform 1 (NM_000260.4 and NP_000251.3) and the transcript variant 2 encoding isoform 2 (NM_001127180.1 and NP_001120652.1).

Nucleic acid and polypeptide sequences of Myo7a orthologs in organisms other than humans are well known and include, for example, mouse Myo7a (NM_001256081.1 and NP_001243010.1; NM_001256082.1 and NP_001243011.1; NM_001256083.1 and NP_001243012.1; NM_008663.2 and NP_032689.2), rat Myo7a (NM_153473.1 and NP_703203.1), dog Myo7a (XM_014122712.2 and XP_013978187.1; XM_022407643.1 and XP_022263351.1; XM_022407642.1 and XP_022263350.1; XM_022407646.1 and XP_022263354.1; XM_022407644.1 and XP_022263352.1; XM_022407647.1 and XP_022263355.1; XM_022407649.1 and XP_022263357.1; XM_022407648.1 and XP_022263356.1), and horse Myo7a (XM_023645658.1 and XP_023501426.1; XM_023645656.1 and XP_023501424.1; XM_023645659.1 and XP_023501427.1; XM_023645657.1 and XP_023501425.1; XM_023645660.1 and XP_023501428.1).

The term "Myo7a activity" includes the ability of an Myo7a polypeptide (and its fragments, domains, and/or motifs thereof, discussed herein) to bind its substrates, and/or mediate its ATPase activity and/or motor activity.

Such activity includes previously known activities such as an actin-binding activity and/or calmodulin-binding activity. The Myo7a activity also includes the activities that are discovered herein, such as the ability its fragments to bind Qa-1b, and/or their ability to facilitate interaction between Qa-1b and T cell receptors. Such activity also includes the anti-tumor activity by inducing CD8+ T cells to kill the tumor cells.

The term "Myo7a substrate(s)" refers to binding partners of a Myo7a polypeptide (and its fragments, domains, and/or motifs thereof, discussed herein), e.g., the proteins listed herein, including Myo7a itself (homodimerization), USH1C, USH1G, MYRIP, RPE65, CIB2, CALM, WHRN, PLEKHB1 (e.g., via PH domain), PCDH15, TWF2, MYH9, ADGRV1, USH2A, and PDZD7. Importantly, Myo7a substrates include Qa-1b, T cell receptors, and their orthologs.

The term "Myo7a-regulated pathway(s)" includes pathways in which Myo7a (and its fragments, domains, and/or motifs thereof, discussed herein) binds to at least one of its substrate, through which at least one cellular function and/or activity and/or cellular protein profiles is changed. Myo7a-regulated pathways include at least those described herein, such as positive or negative regulation of interaction between Qa-1b and T cell receptors. Myo7a-regulated pathways also include facilitating and/or promoting immune response to tumor cells. In some embodiments, the pathway promotes the cytotoxic activity of CD8+ T cells on tumor cells. In addition, Myo7a-regulated pathways include indirectly stabilizing the expression of Qa-1b via Myo7a's association with the Qa-1b protein. Furthermore, Myo7a-regulated pathways include the pathway that generates the fragments of Myo7a that bind to Qa-1b.

The term "agents that increase the copy number, the expression level, and/or the activity of Myo7a," or the term "agents that increase the amount and/or activity of Myo7a-associated HLA-E" encompasses any natural or non-natural agent prepared, synthesized, manufactured, and/or purified by human that is capable of increasing the expression level and/or activity of a Myo7a polypeptide (and its fragments, domains, and/or motifs thereof, discussed herein). In some embodiments, the agent may increase the binding/interaction between Myo7a and its substrates or other binding partners. For example, the agent may increase the recognition and/or binding of Myo7a to proteases thereby increasing the production of the Myo7a fragments that bind to Qa-1b and its orthologs. Alternatively, the agent may increase the binding of Myo7a fragments to Qa-1b and its orthologs. In other embodiments, the agent may increase the expression of a Myo7a polypeptide. In yet other embodiments, such agent may increase Myo7a's activity in enhancing the immune response against tumors. In still other embodiments, such inhibitors may decrease the turnover rate, increase the expression and/or the stability (e.g., the half-life), and/or change the cellular localization of Myo7a, resulting in at least an increase in Myo7a levels and/or activity. Such agents may be any molecule, including but not limited to small molecule compounds, antibodies or intrabodies, RNA interfereing (RNAi) agents (including at least siRNAs, shRNAs, microRNAs (miRNAs), piwi, and other well-known agents), purified Myo7a polypeptide, purified and/or synthesized Myo7a fragment peptides, and gene constructs that allow endogenous production of Myo7a or its fragments inside cancer cells. Such agents may be specific to Myo7a or also to at least one of the binding partners, including but not limited to Qa-1b. Purified recombinant Myo7a proteins and peptides are well known and commercially available (Cat. #H00004647-QO1, NBP1-84266PEP, H00053904-QO1, H00053904-P01 (Novus Biologicals); Cat. #ab152555; ab4996 (Abcam)). Methods for production and purification of synthetic peptides are well known in the art. cDNA clones or expression vectors, as well as lentiviral particles for expressing human, mouse, or rat Myo7a are also commercially available (Cat. #RC224736L1V, RC224736, MR226682, MR231926, RC226361L3, RG224736, MR231933, RC226361L4, RC226476, RG226476, RR213648, MR231922, MG226682, RG226476, RR213648 (OriGene)). Antibodies for detection of Myo7a are commercially available (Cat. #TA351421 (OriGene); ab3481, ab150386, ab92996, ab92996, ab155984, ab230631 (Abcam)). In addition, human MYO7A knockout cell line is commercially available from Horizon (Cambridge, UK, Cat. #HZGHC4647).

The term "HLA-E," also known as "Qa-1b", or HLA class I histocompatibility antigen (alpha chain E) and Major Histocompatibility Complex (MHC) class I antigen E, refers to a member of a group of proteins in the non-classical MHC class I that are characterized by a limited polymorphism and a lower cell surface expression than the classical paralogues. The functional homolog in mice is called Qa-1b, officially known as H2-T23. HLA-E has a very specialized role in cell recognition by natural killer cells (NK cells) (Braud et al. (1998) *Nature* 391:795-799). HLA-E binds a restricted subset of peptides derived from signal peptides of classical MHC class I molecules, namely HLA-A, B, C, G, termed Qdm peptides (Braud et al. (1997) *Eur. J. Immunol.* 27:1164-1169). These peptides are released from the membrane of the endoplasmic reticulum (ER) by the signal peptide peptidase and trimmed by the cytosolic proteasome (Lemberg et al. (2001) *J. Immunol.* 167:6441-6446; Bland et al. (2003) *J. Biol. Chem.* 278:33747-33752). Upon transport into the ER lumen by the transporter associated with antigen processing (TAP), these peptides bind to a peptide binding groove on the HLA-E molecule (Braud et al. (1998) *Curr. Biol.* 8:1-10). This allows HLA-E to assemble correctly and to be expressed on the cell surface. NK cells recognize the HLA-E+Qdm complex using the heterodimeric inhibitory receptor CD94/NKG2A/B/C (Braud et al. (1998) *Nature* 391:795-799). When CD94/NKG2A or CD94/NKG2B is engaged, it produces an inhibitory effect on the cytotoxic activity of the NK cell to prevent cell lysis. However, binding of HLA-E to CD94/NKG2C results in NK cell activation. This interaction has been shown to trigger expansion of NK cell subsets in antiviral responses (Rölle et al. (2014) *J. Clin. Invest.* 124:5305-5316). The binding affinity of HLA-E+Qdm to CD94/NKG2A is significantly higher than that to CD94/NKG2C. HLA-E is involved in pathways such as allograft rejection (e.g., Type I diabetes mellitus, graft-versus-host disease, autoimmune thyroid disease, viral myocarditis, viral carcinogenesis, viral infection (such as Epstein-Barr virus infection, herpes simplex infection, HTLV-I infection, etc.), interferon gamma signaling, CTL-mediated apoptosis, antigen processing and presentation, etc.), immune response role of DAP12 receptors in NK cells (e.g., CD16 signaling in NK cells, NK cell-mediated cytotoxicity, etc.), antigen processing-cross presentation (e.g., ER-phagosome pathway, endosomal/vacuolar pathway, etc.), class I MHC mediated antigen processing and presentation, and RET signaling (e.g., DAP12 signaling, etc.). HLA-E preferably binds to a peptide derived from the signal sequence of most HLA-A, —B, —C and -G molecules, as well as beta-2-microglobulin (B2M), NK cell lectin-like receptor, and other peptide antigens.

The nucleic acid and amino acid sequences of a representative human HLA-E is available to the public at the GenBank database (Gene ID 3133) and is shown in Table 1 (e.g., GenBank database numbers NM_005516.5 and NP_005507.3). HLA-E belongs to the HLA class I heavy chain paralogues. This class I molecule is a heterodimer consisting of a heavy chain and a light chain (beta-2 microglobulin). The heavy chain is anchored in the membrane. HLA-E binds a restricted subset of peptides derived from the leader peptides of other class I molecules. The heavy chain is approximately 45 kDa and its gene contains 8 exons. Exon one encodes the leader peptide, exons 2 and 3 encode the alpha1 and alpha2 domains, which both bind the peptide, exon 4 encodes the alpha3 domain, exon 5 encodes the transmembrane region, and exons 6 and 7 encode the cytoplasmic tail. The domain structure of HLA-E polypeptide is well known and accessible in UniProtKB database under the accession number P13747, including, in the order from the 5' terminus to the 3' terminus, a signal peptide comprising, e.g., amino acid positions 1-21 of NP_005507.3, an extracellular domain comprising, e.g., amino acid positions 22-305 of NP_005507.3, a transmembrane domain comprising, e.g., amino acid positions 306-329 of NP_005507.3, and a cytoplasmic domain comprising, e.g., amino acid positions 330-358 of NP_005507.3. The extracellular domain further comprises an Alpha-1 region (e.g., amino acid positions 22-111 of NP_005507.3), an Alpha-2 region (e.g., amino acid positions 112-203 of NP_005507.3), an Alpha-3 region (e.g., amino acid positions 204-295 of NP_005507.3, including an Ig-like C1-type domain comprising, e.g., amino acid positions 206-294 of NP_005507.3), and a connecting peptide (e.g., amino acid positions 296-305 of NP_005507.3).

Nucleic acid and polypeptide sequences of HLA-E orthologs in organisms other than humans are well-known and include, for example, chimpanzee (Pan troglodytes) PATR-E (NM_001045498.1 and NP_001038963.1), Rhesus monkey MAMU-E (NM_001114966.1 and NP_001108438.1), mouse H2-T23 (NM_010398.3 and NP_034528.1, and NM_001271005.1 and NP_001257934.1), and Norway rat (*Rattus norvegicus*) RT1-S3 (NM_001008886.2 and NP_001008886.2).

The term "HLA-E activity" includes the ability of a HLA-E polypeptide (and its fragments, domains, and/or motifs thereof, discussed herein) to bind its substrate and/or reduce or inhibit the cytotoxic activity of NK cells or T cells. HLA-E activity may also include one or more of functions, such as those disclosed herein in the NF-κB pathway, autoimmune response, antigen presentation, and viral infection. For example, HLA-E may interact with various proteins disclosed herein, such as HLA-A, —B, —C and -G molecules and other binding partners including multiple antigens and receptors, for it functions in signalings. HLA-E may also be proteolyticly modified, such as being glycosylated, or otherwise disclosed herein, for it functions.

The term "HLA-E substrate(s)" refers to binding partners of a HLA-E polypeptide (and its fragments, domains, and/or motifs thereof, discussed herein), e.g., the proteins listed herein. Furthermore, HLA-E substrates may refer to downstream members in the signaling pathways where HLA-E has a functional role.

The term "HLA-E-regulated signaling pathway(s)" includes signaling pathways in which HLA-E (and its fragments, domains, and/or motifs thereof, discussed herein) binds to at least one of its substrate, through which at least one cellular function and/or activity and/or cellular protein profiles is changed (e.g., antigen processing and presentation). In some embodiments, HLA-E promotes antigen presentation (including autoimmune responses) for at least one of its substrates (e.g., antigens) which bind to it. HLA-E-regulated signaling pathways include at least those described herein, such as allograft rejection, antigen processing-cross presentation, class I MHC mediated antigen processing and presentation, and RET signaling, etc.

The term "HLA-E inhibitor(s)" includes any natural or non-natural agent prepared, synthesized, manufactured, and/or purified by human that is capable of reducing, inhibiting, blocking, preventing, and/or that inhibits the ability of a HLA-E polypeptide (and its fragments, domains, and/or motifs thereof, discussed herein). In one embodiment, such inhibitors may reduce or inhibit the binding/interaction between HLA-E and its substrates or other binding partners. In another embodiment, such inhibitors may reduce or inhibit HLA-E as an MHC molecule for antigen presentation and/or other immune responses. In still another embodiment, such inhibitors may increase or promote the turnover rate, reduce or inhibit the expression and/or the stability (e.g., the half-life), and/or change the cellular localization of HLA-E, resulting in at least a decrease in HLA-E levels and/or activity. Such inhibitors may be any molecule, including but not limited to small molecule compounds, antibodies or intrabodies, RNA interfereing (RNAi) agents (including at least siRNAs, shRNAs, microRNAs (miRNAs), piwi, and other well-known agents). Such inhibitors may be specific to HLA-E or also inhibit at least one of its substrates or binding partners. RNA interference for HLA-E polypepitdes are well known and commercially available (e.g., human or mouse shRNA (Cat. #TF312402, TG312402, TL312402, TL312402V, and TR312402) products from Origene (Rockville, MD), siRNA/shRNA products (Cat. #sc-62470, sc-62471, and sc-42922) and human or mouse gene knockout kit via CRISPR (Cat. #sc-403124 and sc-437133) from Santa Cruz Biotechonology (Dallas, Texas), and Ready-to-package AAV shRNA clones from Vigene Biosciences (Rockville, MD, Cat. #SH888322), etc.). Methods for detection, purification, and/or inhibition of HLA-E (e.g., by anti-HLA-E antibodies) are also well known and commercially available (e.g., multiple anti-HLA-E antibodies from Origene (Cat. #TA320346, AM03010BT-N, SM3053P, SM3053A, and others), Novus Biologicals (Littleton, CO, Cat. #NBP2-47435, NBP1-43124, NB500-310, etc.), abcam (Cambridge, MA, Cat. #ab2216, ab11820, ab11821, ab88090, ab203082, etc.), Santa Cruz Biotechnology (Cat. #sc-71262, sc-51621, sc-51622, and sc-51624), etc.). HLA-E knockout human cell lines are also well known and available at the Horizon (Cambridge, UK, Cat. #HZGHC3133).

The term "HLA-E-associated peptide(s)," refers to any epitope or peptide that associates with HLA-E. The peptide may be of human, mouse, viral, bacterial, synthetic, chimeric, fusion, or conjugated. For example, HLA-E-associated peptides are known to be generated from the leader sequences of MHC class I molecules, such as HLA-A, —B, —C, and -G, which is specifically termed the Qdm peptides and have amino acid sequence of VMAPRTLLL, VMAPRTLVL, VMAPRTVLL, VMAPRALLL, VMAPRTLIL, or VMAPRTLFL. In mouse, the Qdm peptide refers to a peptide with an amino acid sequence of AMAPRTLLL (Kurepa et al. (1998) *J. Exp. Med.* 188:973-978). Both human HLA-E and a mouse homolog, Qa-1b, were shown to bind the Qdm peptides with similar affinity and specificity (Miller et al. (2003) *J. Immunology* 171:1369-1375). In addition, HLA-E-associated peptides may be generated from an endogenous protein, such as Hsp60 or insulin (Lo et al. (2000) *Nat. Med.* 6:215-218; Chun et al. (1998) *Immunology* 94:64-71), or exogenous protein from viral and bacterial pathogens. HLA-E-associated peptides comprise, for example, an amino acid sequence listed in Tables 1 and 2, such as an amino acid sequence selected from the group consisting of SEQ ID NOs: 17-49. The peptides with the amino acid sequences of SEQ ID NOs: 17-49 provide representative examples of HLA-E-associated peptides, and are not meant to be a comprehensive list. Accordingly, HLA-E-associated peptides include many variation of peptides listed herein. In particular, HLA-E-associated peptides may be polymorphic, and comprise 1-3 amino acid substitutions in the amino acid sequences in SEQ ID NOs: 17-49. Alternatively, a HLA-E-associated peptide may comprise 2 amino acid substitutions in the amino acid sequences in SEQ ID NOs: 17-49, and so on. The HLA-E-associated Qdm peptides are required for the interaction of HLA-E and CD94/NKG2 receptors on NK cells or T cells. Such interaction leads to modulation of the cytotoxicity of NK cells and T cells. Other HLA-E-associated peptides are required for the interaction of HLA-E with T-cell receptors on T cells.

The term "HLA-E-Qdm inhibitory activity" includes the ability of the Qdm peptide (and its precursors) to bind its binding partner and/or facilitate interaction between HLA-E and NKG2, particularly CD94/NKG2A. HLA-E-Qdm inhibitory activity may also include one or more functions, such as inhibition of the cytotoxic activity and other functions of NK cells or T cells. In some embodiments, other peptides, such as those described herein, can have binding properties or activity similar to the Qdm peptide.

The term "HLA-E-associated peptide substrate(s)" includes binding partners of a HLA-E-associated peptide, e.g., the proteins listed herein. Furthermore, HLA-E-associated peptide substrates may refer to downstream members in the pathways where HLA-E-associated peptides have a functional role.

The term "HLA-E-associated peptide regulated pathway(s)" includes signaling pathways in which HLA-E-associated peptide binds to at least one of its substrate, through which at least one cellular function and/or activity and/or cellular protein profiles is changed (e.g., activity of NK cells or T cells). In some embodiments, HLA-E-associated peptide promotes interaction between HLA-E and CD94/NKG2A. In another embodiment, HLA-E-associated peptide promotes inhibition of NK cells or T cells. In another embodiment, HLA-E-associated peptide promotes interaction between HLA-E and T cell receptors. In another embodiment, HLA-E-associated peptide promotes killing cancer cells, or sensitizing cancer cells to immunotherapy.

The term "immune response" includes T cell mediated and/or B cell mediated immune responses. Exemplary immune responses include T cell responses, e.g., cytokine production and cellular cytotoxicity. In addition, the term immune response includes immune responses that are indirectly effected by T cell activation, e.g., antibody production (humoral responses) and activation of cytokine responsive cells, e.g., macrophages.

The term "immunotherapeutic agent" can include any molecule, peptide, antibody or other agent which can stimulate a host immune system to generate an immune response to a tumor or cancer in the subject. Various immunotherapeutic agents are useful in the compositions and methods described herein.

The term "inhibit" includes the reduce, decrease, limitation, or blockage, of, for example a particular action, function, or interaction. In some embodiments, cancer is "inhibited" if at least one symptom of the cancer is alleviated, terminated, slowed, or prevented. As used herein, cancer is also "inhibited" if recurrence or metastasis of the cancer is reduced, slowed, delayed, or prevented.

The term "interaction", when referring to an interaction between two molecules, refers to the physical contact (e.g., binding) of the molecules with one another. Generally, such an interaction results in an activity (which produces a biological effect) of one or both of said molecules.

An "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of a biomarker polypeptide or fragment thereof, in which the protein is separated from cellular components of the cells from which it is isolated or recombinantly produced. In one embodiment, the language "substantially free of cellular material" includes preparations of a biomarker protein or fragment thereof, having less than about 30% (by dry weight) of non-biomarker protein (also referred to herein as a "contaminating protein"), more preferably less than about 20% of non-biomarker protein, still more preferably less than about 10% of non-biomarker protein, and most preferably less than about 5% non-biomarker protein. When antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

As used herein, the term "isotype" refers to the antibody class (e.g., IgM, IgG1, IgG2C, and the like) that is encoded by heavy chain constant region genes.

As used herein, the term "$K_D$" is intended to refer to the dissociation equilibrium constant of a particular antibody-antigen interaction. The binding affinity of antibodies of the disclosed invention may be measured or determined by standard antibody-antigen assays, for example, competitive assays, saturation assays, or standard immunoassays such as ELISA or RIA.

A "kit" is any manufacture (e.g. a package or container) comprising at least one reagent, e.g. a probe or small molecule, for specifically detecting and/or affecting the expression of a marker of the present invention. The kit may be promoted, distributed, or sold as a unit for performing the methods of the present invention. The kit may comprise one or more reagents necessary to express a composition useful in the methods of the present invention. In certain embodiments, the kit may further comprise a reference standard, e.g., a nucleic acid encoding a protein that does not affect or regulate signaling pathways controlling cell growth, division, migration, survival or apoptosis. One skilled in the art can envision many such control proteins, including, but not limited to, common molecular tags (e.g., green fluorescent protein and beta-galactosidase), proteins not classified in any of pathway encompassing cell growth, division, migration, survival or apoptosis by GeneOntology reference, or ubiquitous housekeeping proteins. Reagents in the kit may be provided in individual containers or as mixtures of two or more reagents in a single container. In addition, instructional materials which describe the use of the compositions within the kit can be included.

The term "neoadjuvant therapy" refers to a treatment given before the primary treatment. Examples of neoadjuvant therapy can include chemotherapy, radiation therapy, and hormone therapy. For example, in treating breast cancer, neoadjuvant therapy can allows patients with large breast cancer to undergo breast-conserving surgery.

The "normal" level of expression of a biomarker is the level of expression of the biomarker in cells of a subject, e.g., a human patient, not afflicted with a cancer. An "over-expression" or "significantly higher level of expression" of a biomarker refers to an expression level in a test sample that is greater than the standard error of the assay employed to assess expression, and is preferably at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples.

An "over-expression" or "significantly higher level of expression" of a biomarker refers to an expression level in a test sample that is greater than the standard error of the assay employed to assess expression, and is preferably at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples.

The term "pre-determined" biomarker amount and/or activity measurement(s) may be a biomarker amount and/or activity measurement(s) used to, by way of example only, evaluate a subject that may be selected for a particular treatment, evaluate a response to a treatment such as inhibitor(s) of the regulators of one or more biomarkers listed in Table 1, in combination with an immunotherapy, and/or evaluate the disease state. A pre-determined biomarker amount and/or activity measurement(s) may be determined in populations of patients with or without cancer. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements. In another embodiment, the amounts determined and/or compared in a method described herein are based on relative measurements, such as ratios (e.g., serum biomarker normalized to the expression of housekeeping or otherwise generally constant biomarker). The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

The term "predictive" includes the use of a biomarker nucleic acid and/or protein status, e.g., over- or under-activity, emergence, expression, growth, remission, recurrence or resistance of tumors before, during or after therapy, for determining the likelihood of response of a cancer to inhibitor(s) of one or more biomarkers listed in Table 1, in combination with an immunotherapy (e.g., treatment with a combination of such inhibitor and an immunotherapy, such as an immune checkpoint inhibitor). Such predictive use of the biomarker may be confirmed by, e.g., (1) increased or decreased copy number (e.g., by FISH, FISH plus SKY, single-molecule sequencing, e.g., as described in the art at least at J. Biotechnol., 86:289-301, or qPCR), overexpression or underexpression of a biomarker nucleic acid (e.g., by ISH, Northern Blot, or qPCR), increased or decreased biomarker protein (e.g., by IHC), or increased or decreased activity, e.g., in more than about 5%, 6%, 7%, 8%, 9%, 10%, 11%, 12%, 13%, 14%, 15%, 20%, 25%, 30%, 40%, 50%, 60%, 70%, 80%, 90%, 95%, 100%, or more of assayed human cancers types or cancer samples; (2) its absolute or relatively modulated presence or absence in a biological sample, e.g., a sample containing tissue, whole blood, serum, plasma, buccal scrape, saliva, cerebrospinal fluid, urine, stool, or bone marrow, from a subject, e.g. a human, afflicted with cancer; (3) its absolute or relatively modulated presence or absence in clinical subset of patients with cancer (e.g., those responding to a particular inhibitor/immunotherapy combination therapy or those developing resistance thereto).

The term "pre-malignant lesions" as described herein refers to a lesion that, while not cancerous, has potential for becoming cancerous. It also includes the term "pre-malignant disorders" or "potentially malignant disorders." In particular this refers to a benign, morphologically and/or histologically altered tissue that has a greater than normal risk of malignant transformation, and a disease or a patient's habit that does not necessarily alter the clinical appearance of local tissue but is associated with a greater than normal risk of precancerous lesion or cancer development in that tissue (leukoplakia, erythroplakia, erytroleukoplakia lichen planus (lichenoid reaction) and any lesion or an area which histological examination showed atypia of cells or dysplasia. In one embodiment, a metaplasia is a pre-malignant lesion.

The terms "prevent," "preventing," "prevention," "prophylactic treatment," and the like refer to reducing the probability of developing a disease, disorder, or condition in a subject, who does not have, but is at risk of or susceptible to developing a disease, disorder, or condition.

The term "probe" refers to any molecule which is capable of selectively binding to a specifically intended target molecule, for example, a nucleotide transcript or protein encoded by or corresponding to a biomarker nucleic acid. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

The term "prognosis" includes a prediction of the probable course and outcome of cancer or the likelihood of recovery from the disease. In some embodiments, the use of statistical algorithms provides a prognosis of cancer in an individual. For example, the prognosis can be surgery, development of a clinical subtype of cancer (e.g., solid tumors, such as esophageal cancer and gastric cancer), development of one or more clinical factors, or recovery from the disease.

The term "response to immunotherapy" or "response to inhibitor(s) of one or more biomarkers listed in Table 1, in combination with an immunotherapy" relates to any response of the hyperproliferative disorder (e.g., cancer) to an anti-cancer agent, such as an inhibitor of one or more biomarkers listed in Table 1, and an immunotherapy, preferably to a change in tumor mass and/or volume after initiation of neoadjuvant or adjuvant therapy. Hyperproliferative disorder response may be assessed, for example for efficacy or in a neoadjuvant or adjuvant situation, where the size of a tumor after systemic intervention can be compared to the initial size and dimensions as measured by CT, PET, mammogram, ultrasound or palpation. Responses may also be assessed by caliper measurement or pathological examination of the tumor after biopsy or surgical resection. Response may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of hyperproliferative disorder response may be done early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed. This is typically three months after initiation of neoadjuvant therapy. In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular cancer therapeutic regimen is at least 25%, 30%, 35%, 40%, 45%, 50%, 55%, 60%, 65%, 70%, 75%, 80%, 85%, or more. Additional criteria for evaluating the response to cancer therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence. For example, in order to determine appropriate threshold values, a particular cancer therapeutic regimen can be administered to a population of subjects and the outcome can be correlated to biomarker measurements that were determined prior to administration of any cancer therapy. The outcome measurement may be pathologic response to therapy given in the neoadjuvant setting. Alternatively, outcome measures, such as overall survival and disease-free survival can be monitored over a period of time for subjects following cancer therapy for which biomarker measurement values are known. In certain embodiments, the doses administered are standard doses known in the art for cancer therapeutic agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of a cancer therapy can be determined using well-known methods in the art, such as those described in the Examples section.

The term "resistance" refers to an acquired or natural resistance of a cancer sample or a mammal to a cancer therapy (i.e., being nonresponsive to or having reduced or limited response to the therapeutic treatment), such as having a reduced response to a therapeutic treatment by 25% or more, for example, 30%, 40%, 50%, 60%, 70%, 80%, or more, to 2-fold, 3-fold, 4-fold, 5-fold, 10-fold, 15-fold, 20-fold or more. The reduction in response can be measured by comparing with the same cancer sample or mammal before the resistance is acquired, or by comparing with a different cancer sample or a mammal that is known to have no resistance to the therapeutic treatment. A typical acquired resistance to chemotherapy is called "multidrug resistance." The multidrug resistance can be mediated by P-glycoprotein or can be mediated by other mechanisms, or it can occur when a mammal is infected with a multi-drug-resistant microorganism or a combination of microorganisms. The determination of resistance to a therapeutic treatment is routine in the art and within the skill of an ordinarily skilled clinician, for example, can be measured by cell proliferative assays and cell death assays as described herein as "sensitizing." In some embodiments, the term "reverses resistance" means that the use of a second agent in combination with a primary cancer therapy (e.g., chemotherapeutic or radiation therapy) is able to produce a significant decrease in tumor volume at a level of statistical significance (e.g., $p<0.05$) when compared to tumor volume of untreated tumor in the circumstance where the primary cancer therapy (e.g., chemotherapeutic or radiation therapy) alone is unable to produce a statistically significant decrease in tumor volume compared to tumor volume of untreated tumor. This generally applies to tumor volume measurements made at a time when the untreated tumor is growing log rhythmically.

The terms "response" or "responsiveness" refers to an anti-cancer response, e.g. in the sense of reduction of tumor size or inhibiting tumor growth. The terms can also refer to an improved prognosis, for example, as reflected by an increased time to recurrence, which is the period to first recurrence censoring for second primary cancer as a first event or death without evidence of recurrence, or an increased overall survival, which is the period from treatment to death from any cause. To respond or to have a response means there is a beneficial endpoint attained when exposed to a stimulus. Alternatively, a negative or detrimental symptom is minimized, mitigated or attenuated on exposure to a stimulus. It will be appreciated that evaluating the likelihood that a tumor or subject will exhibit a favorable response is equivalent to evaluating the likelihood that the tumor or subject will not exhibit favorable response (i.e., will exhibit a lack of response or be non-responsive).

An "RNA interfering agent" as used herein, is defined as any agent which interferes with or inhibits expression of a target biomarker gene by RNA interference (RNAi). Such RNA interfering agents include, but are not limited to, nucleic acid molecules including RNA molecules which are homologous to the target biomarker gene of the present invention, or a fragment thereof, short interfering RNA (siRNA), and small molecules which interfere with or inhibit expression of a target biomarker nucleic acid by RNA interference (RNAi).

"RNA interference (RNAi)" is an evolutionarily conserved process whereby the expression or introduction of RNA of a sequence that is identical or highly similar to a target biomarker nucleic acid results in the sequence specific degradation or specific post-transcriptional gene silencing (PTGS) of messenger RNA (mRNA) transcribed from that targeted gene (see Coburn and Cullen (2002) *J. Virol.* 76:9225), thereby inhibiting expression of the target biomarker nucleic acid. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs or RNA interfering agents, to inhibit or silence the expression of target biomarker nucleic acids. As used herein, "inhibition of target biomarker nucleic acid expression" or "inhibition of marker gene expression" includes any decrease in expression or protein activity or level of the target biomarker nucleic acid or protein encoded by the target biomarker nucleic acid. The decrease may be of at least 30%, 40%, 50%, 60%, 70%, 80%, 90%, 95% or 99% or more as compared to the expression of a target biomarker nucleic acid or the activity or level of the protein encoded by a target biomarker nucleic acid which has not been targeted by an RNA interfering agent.

The term "sample" used for detecting or determining the presence or level of at least one biomarker is typically brain tissue, cerebrospinal fluid, whole blood, plasma, serum, saliva, urine, stool (e.g., feces), tears, and any other bodily fluid (e.g., as described above under the definition of "body fluids"), or a tissue sample (e.g., biopsy) such as a small intestine, colon sample, or surgical resection tissue. In certain instances, the method of the present invention further comprises obtaining the sample from the individual prior to detecting or determining the presence or level of at least one marker in the sample.

The term "sensitize" means to alter cancer cells or tumor cells in a way that allows for more effective treatment of the associated cancer with a cancer therapy (e.g., anti-immune checkpoint, chemotherapeutic, and/or radiation therapy). In some embodiments, normal cells are not affected to an extent that causes the normal cells to be unduly injured by the therapies. An increased sensitivity or a reduced sensitivity to a therapeutic treatment is measured according to a known method in the art for the particular treatment and methods described herein below, including, but not limited to, cell proliferative assays (Tanigawa N, Kern D H, Kikasa Y, Morton D L, Cancer Res 1982; 42: 2159-2164), cell death assays (Weisenthal L M, Shoemaker R H, Marsden J A, Dill P L, Baker J A, Moran E M, Cancer Res 1984; 94: 161-173; Weisenthal L M, Lippman M E, Cancer Treat Rep 1985; 69: 615-632; Weisenthal L M, In: Kaspers G J L, Pieters R, Twentyman P R, Weisenthal L M, Veerman A J P, eds. Drug Resistance in Leukemia and Lymphoma. Langhorne, P A: Harwood Academic Publishers, 1993: 415-432; Weisenthal L M, Contrib Gynecol Obstet 1994; 19: 82-90). The sensitivity or resistance may also be measured in animal by measuring the tumor size reduction over a period of time, for example, 6 month for human and 4-6 weeks for mouse. A composition or a method sensitizes response to a therapeutic treatment if the increase in treatment sensitivity or the reduction in resistance is 25% or more, for example, 30%, 40%, 50%, 60%, 70%, 80%, or more, to 2-fold, 3-fold, 4-fold, 5-fold, 10-fold, 15-fold, 20-fold or more, compared to treatment sensitivity or resistance in the absence of such composition or method. The determination of sensitivity or resistance to a therapeutic treatment is routine in the art and within the skill of an ordinarily skilled clinician. It is to be understood that any method described herein for enhancing the efficacy of a cancer therapy can be equally applied to methods for sensitizing hyperproliferative or otherwise cancerous cells (e.g., resistant cells) to the cancer therapy.

"Short interfering RNA" (siRNA), also referred to herein as "small interfering RNA" is defined as an agent which functions to inhibit expression of a target biomarker nucleic acid, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

In another embodiment, an siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) *RNA* April; 9(4):493-501 incorporated by reference herein).

RNA interfering agents, e.g., siRNA molecules, may be administered to a patient having or at risk for having cancer, to inhibit expression of a biomarker gene which is overexpressed in cancer and thereby treat, prevent, or inhibit cancer in the subject.

The term "small molecule" is a term of the art and includes molecules that are less than about 1000 molecular weight or less than about 500 molecular weight. In one embodiment, small molecules do not exclusively comprise peptide bonds. In another embodiment, small molecules are not oligomeric. Exemplary small molecule compounds which can be screened for activity include, but are not limited to, peptides, peptidomimetics, nucleic acids, carbohydrates, small organic molecules (e.g., polyketides) (Cane et al. (1998) *Science* 282:63), and natural product extract libraries. In another embodiment, the compounds are small, organic non-peptidic compounds. In a further embodiment, a small molecule is not biosynthetic.

The term "specific binding" refers to antibody binding to a predetermined antigen. Typically, the antibody binds with an affinity ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE® assay instrument using an antigen of interest as the analyte and the antibody as the ligand, and binds to the predetermined antigen with an affinity that is at least 1.1-, 1.2-, 1.3-, 1.4-, 1.5-, 1.6-, 1.7-, 1.8-, 1.9-, 2.0-, 2.5-, 3.0-, 3.5-, 4.0-, 4.5-, 5.0-, 6.0-, 7.0-, 8.0-, 9.0-, or 10.0-fold or greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen." Selective binding is a relative term refering to the ability of an antibody to discriminate the binding of one antigen over another.

The term "subject" refers to any healthy animal, mammal or human, or any animal, mammal or human afflicted with a cancer, e.g., brain, lung, ovarian, pancreatic, liver, breast, prostate, and/or colorectal cancers, melanoma, multiple myeloma, and the like. The term "subject" is interchangeable with "patient."

The term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of tumor recurrence.

The term "synergistic effect" refers to the combined effect of two or more anti-cancer agents (e.g., inhibitor(s) of one or more biomarkers listed in Table 1, in combination with an immunotherapy) can be greater than the sum of the separate effects of the anti-cancer agents/therapies alone.

The term "T cell" includes CD4$^+$ T cells and CD8$^+$ T cells. The term T cell also includes both T helper 1 type T cells and T helper 2 type T cells. The term "antigen presenting cell" includes professional antigen presenting cells (e.g., B lymphocytes, monocytes, dendritic cells, Langerhans cells), as well as other antigen presenting cells (e.g., keratinocytes, endothelial cells, astrocytes, fibroblasts, and oligodendrocytes).

The term "therapeutic effect" refers to a local or systemic effect in animals, particularly mammals, and more particularly humans, caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically effective amount of a compound will depend on its therapeutic index, solubility, and the like. For example, certain compounds discovered by the methods of the present invention may be administered in a sufficient amount to produce a reasonable benefit/risk ratio applicable to such treatment.

The terms "therapeutically-effective amount" and "effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment. Toxicity and therapeutic efficacy of subject compounds may be determined by standard pharmaceutical procedures in cell cultures or experimental animals, e.g., for determining the $LD_{50}$ and the $ED_{50}$. Compositions that exhibit large therapeutic indices are preferred. In some embodiments, the $LD_{50}$ (lethal dosage) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more reduced for the agent relative to no administration of the agent. Similarly, the $ED_{50}$ (i.e., the concentration which achieves a half-maximal inhibition of symptoms) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. Also, Similarly, the $IC_{50}$ (i.e., the concentration which achieves half-maximal cytotoxic or cytostatic effect on cancer cells) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. In some embodiments, cancer cell growth in an assay can be inhibited by at least about 10%, 15%, 20%, 25%, 30%, 35%, 40%, 45%, 50%, 55%, 60%, 65%, 70%, 75%, 80%, 85%, 90%, 95%, or even 100%. In another embodiment, at least about a 10%, 15%, 20%, 25%, 30%, 35%, 40%, 45%, 50%, 55%, 60%, 65%, 70%, 75%, 80%, 85%, 90%, 95%, or even 100% decrease in a solid malignancy can be achieved.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a biomarker nucleic acid and normal post-transcriptional processing (e.g. splicing), if any, of the RNA transcript, and reverse transcription of the RNA transcript.

As used herein, the term "unresponsiveness" includes refractivity of cancer cells to therapy or refractivity of therapeutic cells, such as immune cells, to stimulation, e.g., stimulation via an activating receptor or a cytokine. Unresponsiveness can occur, e.g., because of exposure to immunosuppressants or exposure to high doses of antigen. As used herein, the term "anergy" or "tolerance" includes refractivity to activating receptor-mediated stimulation. Such refractivity is generally antigen-specific and persists after exposure to the tolerizing antigen has ceased. For example, anergy in T cells (as opposed to unresponsiveness) is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory polypeptide) results in failure to produce cytokines and, thus, failure to proliferate. Anergic T cells can, however, proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the AP1 sequence that can be found within the enhancer (Kang et al. (1992) *Science* 257:1134).

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well-known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA encoding a biomarker nucleic acid (or any portion thereof) can be used to derive the polypeptide amino acid sequence, using the genetic code to translate the DNA or RNA into an amino acid sequence. Likewise, for polypeptide amino acid sequence, corresponding nucleotide sequences that can encode the polypeptide can be deduced from the genetic code (which, because of its redundancy, will produce multiple nucleic acid sequences for any given amino acid sequence). Thus, description and/or disclosure herein of a nucleotide sequence which encodes a polypeptide should be considered to also include description and/or disclosure of the amino acid sequence encoded by the nucleotide sequence. Similarly, description and/or disclosure of a polypeptide amino acid sequence herein should be considered to also include description and/or disclosure of all possible nucleotide sequences that can encode the amino acid sequence.

Finally, nucleic acid and amino acid sequence information for the loci and biomarkers of the present invention (e.g., biomarkers listed in Tables 1 and 2) are well-known in the art and readily available on publicly available databases, such as the National Center for Biotechnology Information (NCBI). For example, exemplary nucleic acid and amino acid sequences derived from publicly available sequence databases are provided below and include, for example, PCT Publ. WO 2014/022759, which is incorporated herein in its entirety by this reference.

TABLE 1

SEQ ID NO: 1 Human HM13 Transcript Variant 1 cDNA sequence
(NM 030789.3, CDS region from position 143-1276)
```
   1 gtgcgcggcg cgggcttggg agggagcacg tcacttcctg ttgccttagg ggaacgtggc
  61 tttccctgca gagccggtgt ctccgcctgc gtccctgctg cagcaaccgg agctggagtc
 121 ggatcccgaa cgcaccctcg ccatggactc ggccctcagc gatccgcata acggcagtgc
 181 cgaggcaggc ggccccacca acagcactac gcggccgcct tccacgcccg agggcatcgc
 241 gctggcctac ggcagcctcc tgctcatggc gctgctgccc atcttcttcg gcgcccctgcg
 301 ctccgtacgc tgcgcccgcg gcaagaatgc ttcagacatg cctgaaacaa tcaccagccg
 361 ggatgccgcc cgcttcccca tcatcgcag ctgcacactc ttggggctct acctcttttt
 421 caaaatattc tcccaggagt acatcaacct cctgctgtcc atgtatttct tcgtgctggg
 481 aatcctggcc ctgtcccaca ccatcagccc cttcatgaat aagttttttc cagccagctt
 541 tccaaatcga cagtaccagc tgctcttcac acagggttct ggggaaaaca aggaagagat
 601 catcaattat gaatttgaca ccaaggacct ggtgtgcctg ggcctgagca gcatcgttgg
 661 cgtctggtac ctgctgagga agcactggat tgccaacaac cttttttggcc tggccttctc
 721 ccttaatgga gtagagctcc tgcacctcaa caatgtcagc actggctgca tcctgctggg
 781 cggactcttc atctacgatg tcttctgggt atttggcacc aatgtgatgg tgacagtggc
 841 caagtccttc gaggcaccaa taaaattggt gtttccccag gatctgctgg agaaaggcct
 901 cgaagcaaac aactttgcca tgctgggact tggagatgtc gtcattccag ggatcttcat
 961 tgccttgctg ctgcgctttg acatcagctt gaagaagaat acccacacct acttctacac
1021 cagctttgca gcctacatct tcggcctggg ccttaccatc ttcatcatgc acatcttcaa
1081 gcatgctcag cctgccctcc tatacctggt ccccgcctgc atcggttttc ctgtcctggt
1141 ggcgctggcc aagggagaag tgacagagat gttcagttat gaggagtcaa atcctaagga
1201 tccagcggca gtgacagaat ccaaagaggg aacagaggca tcagcatcga aggggctgga
1261 gaagaaagag aaatgatgca gctggtgccc gagcctctca gggccagacc agacagatgg
1321 gggctgggcc cacacaggcg tgcaccggta gagggcacag gaggccaagg gcagctccag
1381 gacagggcag ggggcagcag gatacctcca gccaggcctc tgtggcctct gtttccttct
1441 cccttttcttg gccctcctct gctcctcccc acaccctgca ggcaaaagaa accccccagct
1501 tccccctcc ccgggagcca ggtgggaaaa gtgggtgtga tttttagatt ttgtattgtg
1561 gactgatttt gcctcacatt aaaaactcat cccatggcca ggggggccca ctgtgctcct
1621 ggaa
```

SEQ ID NO: 2 Human HM13 Isoform 1 (Encoded by Transcript Variant 1)
Amino Acid Sequence (NP 110416.1)
```
   1 mdsalsdphn gsaeaggptn sttrppstpe gialaygsll lmallpiffg alrsvrcarg
  61 knasdmpeti tsrdaarfpi iasctllgly lffkifsqey inlllsmyff vlgilalsht
 121 ispfmnkffp asfpnrqyql lftqgsgenk eeiinyefdt kdlvclglss ivgvwyllrk
 181 hwiannlfgl afslngvell hlnnvstgci llgglfiydv fwvfgtnvmv tvaksfeapi
 241 klvfpqdlle kgleannfam lglgdvvipg ifialllrfd islkknthty fytsfaayif
 301 glgltifimh ifkhaqpall ylvpacigfp vlvalakgev temfsyeesn pkdpaavtes
 361 kegteasask glekkek
```

SEQ ID NO: 3 Human HM13 Transcript Variant 2 cDNA sequence
(NM 178580.2, CDS region from position 143-1327)
```
   1 gtgcgcggcg cgggcttggg agggagcacg tcacttcctg ttgccttagg ggaacgtggc
  61 tttccctgca gagccggtgt ctccgcctgc gtccctgctg cagcaaccgg agctggagtc
 121 ggatcccgaa cgcaccctcg ccatggactc ggccctcagc gatccgcata acggcagtgc
 181 cgaggcaggc ggccccacca acagcactac gcggccgcct tccacgcccg agggcatcgc
 241 gctggcctac ggcagcctcc tgctcatggc gctgctgccc atcttcttcg gcgcccctgcg
 301 ctccgtacgc tgcgcccgcg gcaagaatgc ttcagacatg cctgaaacaa tcaccagccg
 361 ggatgccgcc cgcttcccca tcatcgcag ctgcacactc ttggggctct acctcttttt
 421 caaaatattc tcccaggagt acatcaacct cctgctgtcc atgtatttct tcgtgctggg
 481 aatcctggcc ctgtcccaca ccatcagccc cttcatgaat aagttttttc cagccagctt
 541 tccaaatcga cagtaccagc tgctcttcac acagggttct ggggaaaaca aggaagagat
 601 catcaattat gaatttgaca ccaaggacct ggtgtgcctg ggcctgagca gcatcgttgg
 661 cgtctggtac ctgctgagga agcactggat tgccaacaac cttttttggcc tggccttctc
 721 ccttaatgga gtagagctcc tgcacctcaa caatgtcagc actggctgca tcctgctggg
 781 cggactcttc atctacgatg tcttctgggt atttggcacc aatgtgatgg tgacagtggc
 841 caagtccttc gaggcaccaa taaaattggt gtttccccag gatctgctgg agaaaggcct
 901 cgaagcaaac aactttgcca tgctgggact tggagatgtc gtcattccag ggatcttcat
 961 tgccttgctg ctgcgctttg acatcagctt gaagaagaat acccacacct acttctacac
1021 cagctttgca gcctacatct tcggcctggg ccttaccatc ttcatcatgc acatcttcaa
1081 gcatgctcag cctgccctcc tatacctggt ccccgcctgc atcggttttc ctgtcctggt
1141 ggcgctggcc aagggagaag tgacagagat gttcagctac gagtcctcgg cggaaatcct
1201 gcctcatacc ccgaggctca cccacttccc cacagtctcg ggctcccag ccagcctggc
1261 cgactccatg cagcagaagc tagctggccc tcgccgccgg cgcccgcaga tcccagcgc
1321 catgtaatgc ccagcgggtg cccacctgcc cgcttccccc tactgccccg ggccccaagt
1381 tatgaggagt caaatcctaa ggatccagcg gcagtgacaa aatccaaaga gggaacagag
1441 gcatcagcat cgaaggggct ggagaagaaa gagaaatgat gcagctggtg cccgagcctc
1501 tcagggccag accagacaga tggggggctgg gcccacacag gcgtgcaccg gtagagggca
1561 caggaggcca agggcagctc caggacaggg caggggggcag caggatacct ccagccaggc
1621 ctctgtgtgcc tctgtttcct tctcccttttc ttggccctcc tctgctcctc cccacacctt
1681 gcaggcaaaa gaaaccccca gcttccccccc tccccgggag ccaggtggga aaagtgggtg
1741 tgattttttag attttgtatt gtggactgat tttgcctcac attaaaaact catcccatgg
1801 ccaggggggg ccactgtgct cctggaa
```

SEQ ID NO: 4 Human HM13 Isoform 2 (Encoded by Transcript Variant 2)
Amino Acid Sequence (NP 848695.1)
```
   1 mdsalsdphn gsaeaggptn sttrppstpe gialaygsll lmallpiffg alrsvrcarg
  61 knasdmpeti tsrdaarfpi iasctllgly lffkifsqey inlllsmyff vlgilalsht
 121 ispfmnkffp asfpnrqyql lftqgsgenk eeiinyefdt kdlvclglss ivgvwyllrk
```

TABLE 1-continued

```
181 hwiannlfgl afslngvell hlnnvstgci llgglfiydv fwvfgtnvmv tvaksfeapi
241 klvfpqdlle kgleannfam lglgdvvipg ifialllrfd islkknthty fytsfaayif
301 glgltifimh ifkhaqpall ylvpacigfp vlvalakgev temfsyessa eilphtprlt
361 hfptvsgspa sladsmqqkl agprrrrpqn psam
```

SEQ ID NO: 5 Human HM13 Transcript Variant 3 cDNA sequence (NM 178581.2, CDS region from position 143-1423)

```
   1 gtgcgcggcg cgggcttggg agggagcacg tcacttcctg ttgccttagg ggaacgtggc
  61 tttccctgca gagccggtgt ctccgcctgc gtccctgctg cagcaaccgg agctggagtc
 121 ggatcccgaa cgcaccctcg ccatggactc ggccctcagc gatccgcata acggcagtgc
 181 cgaggcaggc ggcccccacca acagcactac gcggccgcct tccacgcccg agggcatcgc
 241 gctggcctac ggcagcctcc tgctcatggc gctgctgccc atcttcttcg gcgccctgcg
 301 ctccgtacgc tgcgcccgcg gcaagaatgc ttcagacatg cctgaaacaa tcaccagccg
 361 ggatgccgcc cgcttcccca tcatcgccag ctgcacactc ttggggctct acctcttttt
 421 caaaatattc tcccaggagt acatcaacct cctgctgtcc atgtatttct tcgtgctggg
 481 aatcctggcc ctgtcccaca ccatcagccc cttcatgaat aagttttttc cagccagctt
 541 tccaaatcga cagtaccagc tgctcttcac acagggttcg ggggaaaaca aggaagagat
 601 catcaattat gaatttgaca ccaaggacct ggtgtgcctg ggcctgagca gcatcgttgg
 661 cgtctggtac ctgctgagga agcactggat tgccaacaac ctttttggcc tggccttctc
 721 ccttaatgga gtagagctcc tgcacctcaa caatgtcagc actggctgca tcctgctggg
 781 cggactcttc atctacgatg tcttctgggt atttggcacc aatgtgatgg tgacagtggc
 841 caagtccttc gaggcaccaa taaaattggt gtttccccag gatctgctgg agaaaggcct
 901 cgaagcaaac aactttgcca tgctgggact tggagatgtc gtcattccag gatcttcat
 961 tgccttgctg ctgcgctttg acatcagctt gaagaagaat acccacacct acttctacac
1021 cagctttgca gcctacatct tcggcctggg ccttaccatc ttcatcatgc acatcttcaa
1081 gcatgctcag cctgccctcc tatacctggt ccccgcctgc atcggttttc ctgtcctggt
1141 ggcgctggcc aagggagaag tgacagagat gttcagctac gagtcctcgg cggaaatcct
1201 gcctcatacc ccgaggctca cccacttccc cacagtctcg ggctcccag ccagcctggc
1261 cgactccatg cagcagaagc tagctggccc tcgccgccgg cgccgcagag atcccgacgc
1321 catttatgag gagtcaaatc ctaaggatcc agcggcagtg acagaatcca aagagggaac
1381 agaggcatca gcatcgaagg ggctggagaa gaaagagaaa tgatgcagct ggtgcccgag
1441 cctctcaggg ccagaccaga cagatggggg ctgggcccac acaggcgtgc accggtagag
1501 ggcacaggag gccaagggca gctccaggac agggcagggg gcagcaggat acctccagcc
1561 aggcctctgt ggcctctgtt tccttctccc tttcttggcc ctcctctgct cctccccaca
1621 ccctgcaggc aaaagaaacc cccagcttcc cccctcccg ggagccaggt gggaaaagtg
1681 ggtgtgattt tagatttttg tattgtggac tgattttgcc tcacattaaa aactcatccc
1741 atggccaggg cgggccactg tgctcctgga a
```

SEQ ID NO: 6 Human HM13 Isoform 3 (Encoded by Transcript Variant 3) Amino Acid Sequence (NP 848696.1)

```
   1 mdsalsdphn gsaeaggptn sttrppstpe gialaygsll lmallpiffg alrsvrcarg
  61 knasdmpeti tsrdaarfpi iasctllgly lffkifsqey iinlllsmyff vlgilalsht
 121 ispfmnkffp asfpnrqyql lftqggsenk eeiinyefdt kdlvclglss ivgvwyllrk
 181 hwiannlfgl afslngvell hlnnvstgci llgglfiydv fwvfgtnvmv tvaksfeapi
 241 klvfpqdlle kgleannfam lglgdvvipg ifialllrfd islkknthty fytsfaayif
 301 glgltifimh ifkhaqpall ylvpacigfp vlvalakgev temfsyessa eilphtprlt
 361 hfptvsgspa sladsmqqkl agprrrrpqn psaiyeesnp kdpaavtesk egteasaskg
 421 lekkek
```

SEQ ID NO: 7 Human HM13 Transcript Variant 4 cDNA sequence (NM 178582.2, CDS region from position 143-574)

```
   1 gtgcgcggcg cgggcttggg agggagcacg tcacttcctg ttgccttagg ggaacgtggc
  61 tttccctgca gagccggtgt ctccgcctgc gtccctgctg cagcaaccgg agctggagtc
 121 ggatcccgaa cgcaccctcg ccatggactc ggccctcagc gatccgcata acggcagtgc
 181 cgaggcaggc ggcccccacca acagcactac gcggccgcct tccacgcccg agggcatcgc
 241 gctggcctac ggcagcctcc tgctcatggc gctgctgccc atcttcttcg gcgccctgcg
 301 ctccgtacgc tgcgcccgcg gcaagaatgc ttcagacatg cctgaaacaa tcaccagccg
 361 ggatgccgcc cgcttcccca tcatcgccag ctgcacactc ttggggctct acctcttttt
 421 caaaatattc tcccaggagt acatcaacct cctgctgtcc atgtatttct tcgtgctggg
 481 aatcctggcc ctgtcccaca ccatcaggtc agaaggcatc tctctgcaac atttgaagca
 541 gctttctcgg gaaccagtac agggtcttgg atgagaacat gacttttggc atcattcaga
 601 gccaggtttg aatcctggct ataaaactca agggactctt tcccctgcac actgtagatg
 661 actaggacaa gaaccaatgac ctctctgggc cacagtttcc ttatagacat gttttcttga
 721 tggtgggtgt ttccaccacc acagctgttg ggaaagtgat ttgtgagcag taatgtcatg
 781 ttagttgtga cagtactcag gtgagtaaca ccagtaccac ctgccgggtg ttgtggccta
 841 gctgtgtgct aagtgccatg ttgggctcct cacacatgat cgtgtttcgt aaggagccag
 901 aggcagcata gtgaaaagtt aggacgctgg gctctgaagt ttgactacct tactttgagt
 961 ccagactctg ccacttaata gctctgtgat cttgggcaag ttacttaatc tctctggcct
1021 caatttcctg gtgaatgtgg agaaaaataa tagtgcccctt cccatggggt catgtggaaa
1081 gcttttagca cagtatctgg tgatttaaag tgttcagtaa ctattagctg ttactgtcat
1141 tatctgtgtt aacctgccag acaaccttat atggggttgct tttgctttca cacctgtatg
1201 atagtcatgg aaactgaagc ccagagaggt taagaaattt gctaggatca caccactaat
1261 aagcaacaga gccaggattc aaacccaggt gtggctccag agccatcct cttcccactg
1321 ctaccctaac tcaaactgcc acatgctcgt gtcctttcag tggggagagt ggttcattag
1381 aggggggttgc tactttttatt ttggacaggc cagttctcca ttgcagga ctatcccatg
1441 tattacaaac agttggcaac cttgccctgc tcaccaaatg ggagttgcat accagtattc
1501 cccagcttgt gactacagag atgtcccagt atgtttcttt ctgccccgtt gaagaggtgc
1561 agcctcaggc tgagaaacac tgatagacca agaggtggcc agggttccca gaaggaagga
1621 actcaccttg aacttagctt tctttgaagg gtaggaaacc tggaagacgt acaaaggagg
1681 gagaggtcag gtgctagaaa gtttgtgcac attgagggca tgggcagaat ctgctcccaa
```

TABLE 1-continued

```
1741 aagcattgaa agccaatatg aggccaggtg gtggctcatg cctgtaatcc cagcactttg
1801 ggaggccaag gcaggcggat cacaaggtca ggagattgag accatcctgg ccaacatggt
1861 gaaaccccgt ctctactaaa aatacaaaaa aattagctgg gcatggtggt gcatgcctgt
1921 agtcccagct actcaggagg ctgaggtagg agaatcattg aacctgggag gcggaggttg
1981 cagtgagccg agattgcacc actgcattcc agcctggcga cagagtgaga ctccatctca
2041 aaaaaaaaaa aaaagccaat atgaatgtgg cttcattctt ctaggcacac tggcaggaca
2101 gtgtggtagt caggagcaca gggtcaagag gcaggcagcc ttgggacaaa cacctggtgc
2161 tgccagctc
```

SEQ ID NO: 8 Human HM13 Transcript Variant 4 (Encoded by Transcript Variant 4) Amino Acid Sequence (NP 848697.1)
```
  1 mdsalsdphn gsaeaggptn sttrppstpe gialaygsll lmallpiffg alrsvrcarg
 61 knasdmpeti tsrdaarfpi iasctllgly lffkifsqey inlllsmyff vlgilalsht
121 irsegislqh lkqlsrepvq glg
```

SEQ ID NO: 9 Mouse H13 Transcript Variant 1 cDNA sequence
(NM 001159551.1, CDS region from position 122-1306)
```
   1 gggaggcacg tcacttcctg tttctttagg ggaacgtggc tttccccgca gtgcctcttc
  61 tccgtctacg ttcgtgctgc ggcggccgga gctggagtcg gagcccgagc gcagcctcgc
 121 catggattcg gctgtcagcg atccgcacaa cggcagcgcc gaggctggca ccccagccaa
 181 cggcacgacg cggccgccct ccacgcccga gggcatcgcc ctggcctacg gcagcctcct
 241 gctcatggcg ctgctgccca tcttcttcgg cgccctgcgc tcggtgcgct cgcgcccgcg
 301 caagagctct tcggacatgc cagaaaccat caccagtcga gatgccgccc gcttccccat
 361 catcgccagc tgcacactcc tggggctcta cctcttttc aaaatattct cccaggagta
 421 catcaacctc ttgctgtcca tgtatttctt cgtgctgggg atcctggcc tgtcacacac
 481 catcagcccc ttcatgaata gttttttcc agccaacttc ccaaaccgcc agtatcagct
 541 gctcttcaca cagggctctg ggaaaacaa agaagagatc atcaactatg agtttgacac
 601 taaggacctg gtgtgcctgg gcctaagcag cgtcgttggt gtctggtacc ttctgaggaa
 661 gcactggatt gccaacaacc tgtttggcct ggccttctcc cttaatgggg tagagctcct
 721 gcacctgaac aacgtgagca ctggctgtat cctgctcgga ggactcttca tctatgacat
 781 cttctgggta ttcggcacca acgtgatggt gacagtggcc aagtcctttg aggcaccaat
 841 aaaaattggtg ttcccccagg atctgctgga aagggcctt gaagcagaca actttgccat
 901 gctgggactt ggagacattg tcattccagg gatcttcatt gccttactgc ttcgttttga
 961 catcagcttg aagaagaaca cgcacaccta cttctacacc agcttcgccg cctacatctt
1021 cggcctgggt ctcaccatct tcatcatgca catcttcaag cacgcccagc cggctctcct
1081 gtacctggtc cctgcctgca tcggctttcc tgtcctggtg gcactagcca agggagaagt
1141 ggccgagatg ttcagctacg agtcctcggc cgtaatcctg cctcatacgc cgaggctcac
1201 tcactttccc acagtctcgg gctcccctgc cagcctggcc gactccatgc agcagaagct
1261 agctggccct cgtcgccggc gcccgcagaa tccagccgc atgtagtgcc cagcaggtgc
1321 ccacctgccc gcttccccac tgtcctgggc ctaagttatg aggagtccaa ccctaaagat
1381 ccagcagccg agactgaatc caaagaggag tcaacagagg cgtcggcatc gaagaggcta
1441 gagaagaagg agaaatgagg cagcgctgcc tgacccttga gggccagatc ggacaggcag
1501 gggatgacct gtgggcgaca cagaagagaa gacacctgca ggaggcgacg gtggccccag
1561 gatggggagc aggcctctgc tgcctgttcc ctctgccctt tctctggctt cctctgctcc
1621 tcctcatccc tgcaggcaaa ggaaaccctc tgctgcttcc ttcccagga gccaggtggg
1681 cactgaatgt ggttttaga tttttgtatt gtggactgtc tttgcctcat attaaaaact
1741 catcccatgg ccgctaggcc accgtgctcc aagggagctc tcagcagctc tgcctagtgt
1801 ttcgtgctga actcatcggg gctttgcgag taccttcgtg ggtgccaggc cagaagtggg
1861 ttcccatgag cctcctttcc cagccactcc tggggggacag tgaaggtggt gggcgagtgc
1921 ttgctgcgcc ccgctggcct tggtatgaga tgaagagagt gtcacggggc accccgcttc
1981 agcaaaggga cttgtaacta tggacagacg gctccctggg cttgctgtcc atctggctgg
2041 aaatcaaagg tccatctttt ccatcccccag gtctcccaaa atacagctca ggtcttcaga
2101 aagcctgccc tggggaggga gcagattcca gagaacagaa gaggccatcc aaggtcaggc
2161 aagagttaga gatcccaaag ccaaagtctc cctccctcct gaccttcaag cgagtcccta
2221 aagggcaagg agagggcagc tcatccctcg tccacctgcc caggtggaaa aactgagact
2281 gtggaatggc catgacctgt gagctttccc tggctagggt tcagggttaa tgactaaaat
2341 gaacagattg gaaatggtca gagagcaaag gctgtccaga gcctggggaa taagagtgga
2401 gggaggtgag tgtccccagt ttcagatgta gaccaggtgt gtcgatgcaa gcttcggatc
2461 tgtacttcgg atgctaagct gcgcgtgctt tagcctcgct ctacagagga gggaatgggg
2521 ccgctcaccc ccagacagtg actgcagctc aacatactaa gcactgtgct gtcctcttat
2581 aggaccaaga agtcactgtg gctgctctgc tgggccaccg agtcagccac ccaacttctc
2641 tgggtctaaa agtctggaga ggaaagcctg aaaggctctc taggcagggg gtctctttag
2701 ggccttcttg gatctctgca ggcttgtact gccttcaggg ggaggccatg tggtcctcaga
2761 acaaagcccc tctgagggtg gcagatgggg caggcagccc aggcacacag tgtggttggc
2821 tcaacagcccc acagcccaca aaggcctcat tgagtcactg ccgaccccca gcagaggctg
2881 aggtggcagt ggcgccgggc gcctgccacc taatgaccgt cctggctggg ccagatgttc
2941 cacagacctt cgcagcgccga tcagggcctg cctggccaga cagccacaga ggccactcca
3001 gttccaatta accagcttca gctgagcaaa ccacgggcag cagcggggcc cagcctggcc
3061 ggtgggcccg gccggcccg gccggccggc agagcctctg agtctagact ccagatgtga
3121 accgccaccg cctgagcccc atggaaaaat ggcaccaggc cgggcgcgca tcaggcctgc
3181 atactgggag gcgggatggg tggctgggca gggcctcaga tgggactggt gccaggctca
3241 ccctggagtg ggggtggatt cttcggaagc tgctttcaaa cagatttccc ctggttttgtg
3301 gtgtcctctc tgtgccttgg ttttttccagt aggaggaggc tgttagggct taagaccatc
3361 cctgcaagaa acccccatact ctatacatgc ttaccgggtt agcatgtggc cagcattgta
3421 gagtgttcta gaagttcttg actatccctg tgtggaatat gcctgccatc ccagcacttg
3481 tagaggcagc aagctgagat aagccttgtc tacatagcaa gtttcaggtc agccagcgct
3541 ccaagataag aattagctta aaaaattaaa aaaaaaaaa gccagattga tccatactgg
3601 tttgtgacta atcttgaacc cgggagactt aagacaggat gatcaattca aagtccccct
3661 tggctacaaa gagttcaaag ccagagcctg cctcagcca agtggagaga ttaattgtaa
3721 caatcctata tggcacctac catcatcttc acagataagg aatggcaagc aggtctgcac
```

TABLE 1-continued

```
3781 tgacctgccg gtgtttgacc ttagtgcctg gcttatctaa actcatgttc accactgtgc
3841 tgaattcctg tttcttgtct ttggggacag catagggatt atgggacag ggagaggatg
3901 acaatggatg gcttccagga tgagatggca gtgtcctgac atctgatccc tttcttcagc
3961 taaaagaggt gagagcatcc tctcacccag ttgcccttg gaaagtcttt ctgtttccat
4021 gcagtgtcag acaccagcta agttgataag gacctaacag ggagcacaaa tggtggctca
4081 ccggagctga catcctgcaa gatggcattc ctctggggag actgacggaa atgactgggt
4141 ggatgtgcca agagatgatg ccacaggaga tgggactcct gccccggtcc tggtgggcaa
4201 agcaagggtc tgtgccatcc agctgcccct gcacaaaacg acaaactcag tgctcccgcc
4261 accacccag gaaaaaaaaa gccaggctgg caggggtctc tgcggcagcc tgcgcctcct
4321 tcctgttctc caactatgga ctccccgcgt gactgccggc cacggagga cggcatcct
4381 gcggggtgcg ccaggaaggg ccttgcaagc gggaaggaaa cgccacctc tctcgcccc
4441 gccaaggcca cacctgggct ccgcaggcgg tagcgccggg ccagcgcctg gctccagcga
4501 gtctgggccg ccctccctac gcactgcggg ggccgccagc tgggctggtc gctcgcgcag
4561 ctccgcggcc ggaagctgtt cactgggggg cgtggtccgt gttggtccca cccaggaggg
4621 cagggtcact gtagcccaag gacaagcttt ggaatttcgg ctggctttac agtctccatt
4681 tgtgttttc tttcctccca gtcccagggg accgaaccgt gctaagtgag cgctatatca
4741 ctgagctgta tccccgaaac cctccacttc gatgttctta cctagaaaat gagggaattg
4801 taccccacc ccaacacctg gcccagtgca aaatcatgcc ggcactgtgt gtgttaaatg
4861 aatgcatgcg aaggtctaaa acctccctga ggcctggcgt tgtcttgggc aaaaagctcc
4921 ccgcagatga ggaatccttt gtttcatccc tgagctgcgt tttcctcagt cagtggtggc
4981 tgagaagaaa cagtcctcgg aaaacatgga cacctagaat atcctccgta aaagatatgg
5041 aagagtctcc aagatgggc gggggggggg ggggggggaat gtggtagcat actcctgcaa
5101 tcctaaaacc cgagagtaag gcaggaggat cgagagtaag gcaggaggat cgtctagagc
5161 cagctcctga tgcagatttc aaggctagtt tgggctacaa aagatcctgt tgtctcaaaa
5221 ctgatatatt tggaggtaaa aatgctcaaa agaattacac ttggaagatt ttgcttttg
5281 gagggtaggg gagtttggag ggagtgggtt gcttgggttt gagattggaa cttgctatgt
5341 aacccaggct ggcccagatg gaactctgta cagcagacta ggattacaag aaactttctc
5401 tg SEQ ID NO: 10 Mouse H13 Isoform 1 (Encoded by Transcript Variant 1)
Amino Acid Sequence (NP 001153023.1)
   1 mdsavsdphn gsaeagtpan gttrppstpe gialaygsll lmallpiffg alrsvrcarg
  61 ksssdmpeti tsrdaarfpi iasctllgly lffkifsqey inlllsmyff vlgilalsht
 121 ispfmnkffp anfpnrqyql lftqgsgenk eeiinyefdt kdlvclglss vvgvwyllrk
 181 hwiannlfgl afslngvell hlnnvstgci llgglfiydi fwvfgtnvmv tvaksfeapi
 241 klvfpqdlle kgleadnfam lglgdivipg ifialllrfd islkknthty fytsfaayif
 301 glgltifimh ifkhaqpall ylvpacigfp vlvalakgev aemfsyessa vilphtprlt
 361 hfptvsgspa sladsmqqkl agprrrrpqn psam SEQ ID NO: 11 Mouse H13 Transcript Variant 2 cDNA sequence (NM 010376.4,
CDS region from position 122-1258)
   1 gggaggcacg tcacttcctg tttctttagg ggaacgtggc tttccccgca gtgcctcttc
  61 tccgtctacg ttcgtgctgc ggcggccgga gctggagtcg gagcccgagc gcagcctcgc
 121 catggattcg gctgtcagcg atccgcacaa cggcagcgcc gaggctggca ccccagccaa
 181 cggcacgacg cggccgccct ccacgcccga gggcatcgcg ctggcctacg gcagcctcct
 241 gctcatggcg ctgctgccca tcttcttcgg cgccctgcgc tcggtgcgct gccgccggcg
 301 caagagctct tcggacatgc cagaaaccat caccagtcga gatgccgccc gcttccccat
 361 catcgccagc tgcacactcc tggggctcta cctctttttc aaaatattct cccaggagta
 421 catcaacctc ttgctgtcca tgtatttctt cgtgctgggg atcctggccc tgtcacacac
 481 catcagcccc ttcatgaata gttttttcc agccaacttc ccaaaccgac agtatcagct
 541 gctcttcaca cagggctctg gggaaaacaa agaagagatc atcaactatg agtttgacac
 601 taaggacctg gtgtgcctgg gcctaagcag cgtcgttggt gtctggtacc ttctgaggaa
 661 gcactggatt gccaacaacc tgtttggcct ggccttctcc cttaatgggg tagagctcct
 721 gcacctgaac aacgtgagca ctggctgtat cctgctcgga ggactcttca tctatgacat
 781 cttctgggta ttcggcacca acgtgatggt gacagtggcc aagtcctttg aggcaccaat
 841 aaaattggtg ttccccag atctgctgga agggccttt gaagcagaca actttgccat
 901 gctgggactt ggagacattg tcattccagg gatcttcatt gccttactgc ttcgttttga
 961 catcagcttg aagaagaaca cgcacaccta cttctacacc agcttcgccg cctacatctt
1021 cggcctgggt ctcaccatct tcatcatgca catcttcaag cacgcccagc ctgctctcta
1081 gtacctggtc cctgcctgca tcggctttcc tgtcctggtg gcactagcca agggagaagt
1141 ggccgagatg ttcagttatg aggagtccaa ccctaaagat ccagcagccg agactgaatc
1201 caaagaggag tcaacagagg cgtcggcatc gaagaggcta gagaagaagg agaaatgagg
1261 cagcgctgcc tgaccttga gggcagatc ggacaggcag ggatgacct gtggggcaca
1321 cagaagagaa gacacctgca ggaggcgacg gtgccccag gatggggagc aggcctctgc
1381 tgcctgttcc ctctgcccctt tctctggctt cctctgctcc tcctcatccc tgcaggcaaa
1441 ggaaccctc tgctgcttcc ttccccagga gccaggtggg cactgaatgt ggttttaga
1501 tttttgtatt gtggactgtc tttgcctcat attaaaaact catcccatgg ccgctcaggcc
1561 accgtgctcc aagggagctc tcagcagctc tgcctagtgt ttcgtgctga actcatcggg
1621 gctttgcgag taccttcgtg ggtgccaggc cagaagtggg ttcccatgag cctcctttcc
1681 cagccactcc tgggggacag tgaaggtggt gggcgagtgc ttgctgcgcc ccgctggcct
1741 tggtatgaga tgaagagagt gtcacggggc accccgcttc agcaaagga cttgtaacta
1801 tggacagacg gctccctggg cttgctgtcc atctggctgg aaatcaaagg tccatctttt
1861 ccatccccag gtctcccaaa atacagctca ggtcttcaga aagcctgccc tggggaggga
1921 gcagattcca gagaacagaa gaggccatcc aaggtcaggc aagagttaga gatcccaaag
1981 ccaaagtctc cctccctcct gaccttcaag cgagtcctca aaggcaagg agagggcagg
2041 tcatccctcg tccacctgcc caggtgaaaa aactgagact gtggaatggc catgacctgt
2101 gagctttccc tggctagggt tcaggttaa tgactaaaat gaacagattg gaaatggtca
2161 gagagcaaag gctgtccaga gcctggggaa taagagtgga gggaggtgag tgtcccagt
2221 ttcagatgta gaccaggtgt gtcgatgcaa gcttcggatc tgtacttcgg atgctaagct
2281 gcgcgtgctt tagcctcgct ctacagagga gggaatgggg ccgctcaccc ccagacagtg
```

TABLE 1-continued

```
2341 actgcagctc aacatactaa gcactgtgct gtcctcttat aggaccaaga agtcactgtg
2401 gctgctctgc tgggccaccg agtcagccac ccaacttctc tgggtctaaa agtctggaga
2461 ggaaagcctg aaaggctctc taggcagggg gtctctttag ggccttcttg gatctctgca
2521 ggcttgtact gccttcaggg ggaggccatg tggtcctgga acaaagcccc tctgagggtg
2581 gcagatgggg caggcagccc aggcacacag tgtggttggc tcaacagccc acagcccaca
2641 aaggcctcat tgagtcactg ccgaccccca gcagaggctg aggtggcagt ggcgccgggc
2701 gcctgccacc taatgaccgt cctggctggg ccagatgttc cacagacctt gcagcgccga
2761 tcagggcctg cctggccaag cagccacaga ggccactcca gttccaatta accagcttca
2821 gctgagcaaa ccacgggcag cagcggggcc cagcctgggc ggtgggcccg gcccggcccg
2881 gccggccggc agagcctctg agtctagact ccagatgtga accgccaccg cctgagcccc
2941 atggaaaaat ggcaccaggc cgggcgcgca tcaggcctgc atactgggag gcgggatggg
3001 tggctgggca gggcctcaga tgggactggt gccaggctca ccctggagtg ggggtggatt
3061 cttcggaagc tgctttcaaa cagatttccc ctggtttgtg gtgtcctctc tgtgccttgg
3121 tttttccagt aggaggaggc tgttagggct taagaccatc cctgcaagaa accccatact
3181 ctatacatgc ttaccgggtt agcatgtggc cagcattgta gagtgttcta gaagttcttg
3241 actatccctg tgtggaatat gcctgccatc ccagcacttg tagaggcagc aagctgagat
3301 aagccttgtc tacatagcaa gtttcaggtc agccagcgct ccaagataag aattagctta
3361 aaaaattaaa aaaaaaaaaa gccagattga tccatactgg tttgtgacta atcttgaacc
3421 cgggagactt aagacaggat gatcaattca aagtcccct tggctacaaa gagttcaaag
3481 ccagagcctg cctctagcca agtggagaga ttaattgtaa caatcctata tggcacctac
3541 catcatcttc acagataagg aatggcaagc aggtctgcac tgacctgccg gtgtttgacc
3601 ttagtgcctg gcttatctaa actcatgttc accactgtgc tgaattcctg tttcttgtct
3661 ttggggacag catagggatt atggggacag ggagaggatg acaatggatg gcttccagga
3721 tgagatggca gtgtcctgac atctgatccc tttcttcagc taaagaggt gagagcatcc
3781 tctcacccag ttgcccttg gaaagtcttt ctgtttccat gcagtgtcag acaccagcta
3841 agttgataag gacctaacag ggagcacaaa tggtggtctct ccggagctga catcctgcaa
3901 gatggcattc ctctggggag actgacggaa atgactgggt ggatgtgcca agagatgatg
3961 ccacaggaga tgggactcct gccccggtcc tggtgggcaa agcaagggtc tgtgccatcc
4021 agctgcccctt gcacaaaacg acaaactcag tgctcccgcc accaccccag gaaaaaaaaa
4081 gccaggctgg caggggtctc tgcggcagcc tgcgcctcct tcctgttctc caactatgga
4141 ctccccgcgt gactgccggc cacgggagga gcggcatcct gggggtgcg ccaggaaggg
4201 ccttgcaagc gggaaggaaa gcgccacctc tctcgccccc gccaaggcca cacctgggct
4261 ccgcaggcgg tagcgccggg ccagcgcctg gctccagcga gtctgggccg ccctccctac
4321 gcactgcggg ggccgccagc tgggctggtc gctcgcggcc ggaagctgtt
4381 cactgggggg cgtggtccgt gttggtccca cccaggaggg cagggtcact gtagcccaag
4441 gacaagcttt ggaatttcgg ctggctttac agtctccatt tgtgttttc ttcctccca
4501 gtcccagggg accgaaccgt gctaagtgag cgctatatca ctgagctgta tccccgaaac
4561 ccttcacttc gatgttctta cctagaaaat gagggaattg tacccaccc ccaacacctg
4621 gcccagtgca aaatcatgcc ggcactgtgt gtgttaaatg aatgcatgcg aaggtctaaa
4681 acctccctga ggcctggcgt tgtcttgggc aaaaagctcc ccgcagatga ggaatccttt
4741 gtttcatccc tgagctgcgt tttcctcagt cagtggtggc tgagaagaaa cagtcctcgg
4801 aaaacatgga cacctagaat atcctccgta aaagatatgg aagagtcctcc aaagatgggc
4861 ggggggggg ggggggaat gtggtagcat actcctgcaa tcctaaaacc cgagagtaag
4921 gcaggaggat cgagagtaag gcaggaggat cgtctagagc cagctcctga tgcagatttc
4981 aaggctagtt tgggctacat aagatcctgt tgtctcaaaa ctgatatatt tggaggtaaa
5041 aatgctcaaa agaattacac ttggaagatt ttgcttttg gagggtaggg gagtttggag
5101 ggagtgggtt gcttgggtt gagattggaa cttgctatgt aacccaggct ggcccagatg
5161 gaactgggta cagcagacta ggattacaag aaactttctc tg
```

SEQ ID NO: 12 Mouse H13 Isoform 2 (Encoded by Transcript Variant 2)
Amino Acid Sequence (NP 034506.1)
```
  1 mdsavsdphn gsaeagtpan gttrppstpe gialaygsll lmallpiffg alrsvrcarg
 61 ksssdmpeti tsrdaarfpi iasctllgly lffkifsqey inlllsmyff vlgilalsht
121 ispfmnkffp anfpnrqyql lftqgsgenk eeiinyefdt kdlvclglss vvgvwyllrk
181 hwiannlfgl afslngvell hlnnvstgci llgglfiydi fwvfgtnvmv tvaksfeapi
241 klvfpqdlle kgleadnfam lglgdivipg ifialllrfd islkknthty fytsfaayif
301 glgltifimh ifkhaqpall ylvpacigfp vlvalakgev aemfsyeesn pkdpaaetes
361 keesteasas krlekkek
```

SEQ ID NO: 13 Mouse H13 Transcript Variant 3 cDNA sequence
(NM 001159552.1, CDS region from position 122-796)
```
  1 ggaggcacg tcacttcctg tttctttagg ggaacgtggc tttccccgca gtgcctcttc
 61 tccgtctacg ttcgtgctgc ggcggccgga gctggagtcg gagcccgagc gcagcctcgc
121 catggattcg gctgtcagcg atccgcacaa cggcagcgcc gaggctggca ccccagccaa
181 cggcacgacg cggccgccct ccacgcccga gggcatcgcg ctggcctacg gcagcctcct
241 gctcatggcc ctgctgccca tcttcttcgg cgccctgcgc tcggtgcgct gcgcccgcgg
301 caagagctct tcggacatgc cagaaaccat caccagtcga gatgccgccc gcttcccat
361 catcgccagc tgcacactcc tgggctcta cctcttttc aaaatattct cccaggagta
421 catcaacctc ttgctgtcca tgtatttctt cgtgctgggg atcctggccc tgtcacacac
481 catcagcccc ttcatgaata agttttttcc agccaacttc ccaaaccgcc agtatcagct
541 gctcttcaca cagggctctg gggaaaacaa agaaggtcag tgctgcccat gtccccctgga
601 gtgtgtcttc ccctcttgtc tttctccagt actgggtttt ccaaagaaac gagcactaaa
661 gacgaaaccg aatttgtatg gccctggttc ataccccagct tggtcaccac ctagcaatgg
721 gaatctgaat gatcccgttg tttctgagca cgggctgttt ttggaggttt gttaccccat
781 ctgtaaaatg gagtaaacag taagtaggaa ggcaatgaca cagtgcctgg ctcatataag
841 cccccagtaa aagctgtacc agacagctct tagcgtgcct atctcgtgat tgtttcacgt
901 aagctttgaa agagataact atgaagatac gtacggcatc atgcggatgc acacaaggtg
961 acaagagtaa cgatgccttg gactaagtgg aagctaattc atacacatga aatgaatagc
1021 ctgtgggatg tattccagtc tttcctggtt gtcaagtaca tctttgccga ataaataatt
1081 attggatttt tttaaaaaa aaaaaaaaaa aa
```

TABLE 1-continued

SEQ ID NO: 14 Mouse H13 Isoform 3 (Encoded by Transcript Variant 3)
Amino Acid Sequence (NP 001153024.1)
```
   1 mdsavsdphn gsaeagtpan gttrppstpe gialaygsll lmallpiffg alrsvrcarg
  61 ksssdmpeti tsrdaarfpi iasctllgly lffkifsqey inlllsmyff vlgilalsht
 121 ispfmnkffp anfpnrqyql lftqgsgenk egqccpcplg cvfpsclspv lgfpkkralk
 181 tkpnlygpgs ypawsppsng nlndpvvseh glflevcypi ckme
```

SEQ ID NO: 15 Mouse H13 Transcript Variant 4 cDNA sequence
(NM 001159553.1, CDS region from position 122-643)
```
    1 gggaggcacg tcacttcctg tttcttragg ggaacgtggc tttccccgca gtgcctcttc
   61 tccgtctacg ttcgtgctgc ggcggccgga gctggagtcg gagcccgagc gcagcctcgc
  121 catggattcg gctgtcagcg atccgcacaa cggcagcgcc gaggctggca ccccagccaa
  181 cggcacgacg cggccgccct ccacgcccga gggcatcgcg ctggcctacg gcagcctcct
  241 gctcatggcg ctgctgccca tcttcttcgg cgccctgcgc tcgtgcgct gcgcccgcgg
  301 caagagctct tcggacatgc cagaaaccat caccagtcga gatgccgccc gcttccccat
  361 catcgccagc tgcacactcc tggggctcta cctcttttc aaaatattct cccaggagta
  421 catcaacctc ttgctgtcca tgtatttctt cgtgctgggg atcctggccc tgtcacacac
  481 catcaggtca aaggcatct ctcgacagcc tttgaagctg ctttctcagg agccagtaca
  541 gggtcttgga tgggaacatg gtcttttgtg tcattcagag ccaggtttaa atcctggctg
  601 taaaatccaa gggaatcttc cctcacgtca gcactatacg tgacctagga tggaaccca
  661 aacttctcag ggccaccaac tcctaataag gacgtacaag gctatgtatg gtggctctta
  721 gtactcaaga ggctgaggca agttcctgag ctaccatata agacccagtc ttcgaaaaaa
  781 acctaggcag aagtgtcata gagtcaccac agtgctgatg tgtgtctcat caggaccact
  841 tgaagcacga ggcttggctc ctcatggac aggcacctac cagcagaggg ttaggaatgc
  901 cttcccttaa atccagtctc tacactccaa gttaacctct ttgacttcag tctccttaag
  961 gttgtgtttt gttttaaaa acaagcaag caaactgatg gccttcatgt agaaaatgtc
 1021 tctcagtcaa taagtacaac tgtcaccttt gttaggactg ctgtgatcac ctgtgtcagc
 1081 ttgttagaca cccttgactg gctggctctg ggtgttaatc ctgggttagt cagggaagct
 1141 gaagttagtg tgtttgagac attcagtaag atcactcagc ccatttctgt ctgcctgttt
 1201 gcagtagtcc acagatagac tgaggaatgg ctaggaaaag ttgtccgaag aaaggaacgc
 1261 aacgtgacct caggtttgag aggtaggaag cctgggagag tataaggag agaggtgctg
 1321 gtcaggagct tgatgatctc catacagtag ggatcagagc tacacagagc agaatctgca
 1381 ccaaggaaca gtgaggttta ttcctcaggc aagctggcag gatggagaca gcagagtgg
 1441 taggtagcct tggcctctga atatcagtcc gtctgtcccc cgtcgtcatc gtgtgtcccc
 1501 ccccaccacc cgaccccac ccggcctgcc gtaaacagta tacaaagtct tcaaacaagc
 1561 agaaagtgtc agatgggctg ctgtctccgc tgggacttta gctatgggct ttggagtaaa
 1621 tctagcacca tcttgacctg caaaatctta ctctagctgc attgaaagta cggtagccct
 1681 tctcagagga tgacttggac ctggcaagca agaatagcag gtccagcact catgaggacc
 1741 tgaggcaagg ataggagtca tcgctctgaa actctgggtt tccttctttt ccatgctggc
 1801 cagagccatc cagggtctac aagaggtctc ccagttcctc ccatagccta gcttcgccga
 1861 tcagggagag cgtgctctt gaaagcacca ggaacgacat atgcttgaga actaattatt
 1921 tcacggtagc ccagcagccc tgcatccaac tgcccacaaa ctgttgtggt ccacatgtct
 1981 cagaacaaca aattgtgtct ctacccaact tagaaatgtt agtgatagct attatcaaca
 2041 caaaataaag ccagcggtct cctaggaata gagagcttaa tggtaaagcc tggtaagggt
 2101 aagaccctgg gtttgatcct agcaccacaa acaaaagtga gcagttaact atgtaggaag
 2161 ccaggcagca ctacacacct ctaatcccaa gcactcagga ggaagaggca ggcaaatcac
 2221 cagcacggct agctatactg taagaccctg tctccaaaaa aagaaagaga acagggaagg
 2281 caccggcaag ctgagtgtgt tggctcagcc tttgatccta gtacttggga tgcagaggca
 2341 gggagagcag gagctcagag tcccctcag ctgcacagcc aggtcacagc ctattagtta
 2401 tatgagacag tgtagcagaa cagtaagggc tacggtaa catttgtgag gtagaagctg
 2461 gtttggttgt tgttttcctg ctgggtgtta aactacagcc cagtcctaag ttttgttttt
 2521 tcttttggtg ttaggaattg aacccagggc cacatataca cataagcg agtcgtgtgg
 2581 tctagcactg acccacctcc ccagccatga gtcatttttgt taataaaatc cagagcactg
 2641 gtaatgtgct gtggcagtcg ggagcttgag aggctgaggc gtgaggttat cgtgagaaag
 2701 aagtaaagcc aatgaatttt attacaagag ggggaagaat ttaacctttt ttttctttt
 2761 agagtgttga tccaaaaatt aaactgactc ttactcactg gaggtgtgtt ttctcaagtc
 2821 ttttggtaaa gcaaactaca gtgtttaaga gtttccacga gctgtttata gccacaagtc
 2881 agacttcctc tggagttgag ccataaggtc tgaggggatg agacaaggaa gctgaggttc
 2941 aaaagaatta ttatgctcc caggattcac agctgagaaa agcagaggcg tttgatccca
 3001 gggctctctg accacagtgc tagaattcct tatcactttg tggccaaaat taaggggaag
 3061 agagaatttg gagaaaacag actcacctct ccacacatct caaaaatgcc cgctaaagac
 3121 tgtaagagcc acatcccagt catggtggcc cagaccacac ccaaatcct ccacctctgt
 3181 tgccaccca ctgcctgcct cagaccagac cacagctcac agcgttgcag gcaggtagga
 3241 gacatcttgc cttcacctaa tagttaccaa aactccaacc cagccagact ctgcacatcc
 3301 tgccagagca gtcgtggcct gttttcatca cctgtggctg agctcttgcc ctactcaagt
 3361 ggtccacagc aagaaagccc aagtcgtcta cctcagagga gcacatccca aggttcatta
 3421 accctcgctg tctaccccag agggagaggc accagaacat ttctcagaag aaaacgagga
 3481 actttgtctc ttatgagtca tggagagtca taaaaacact gcccacagta aaagtacaat
 3541 cagagcaggc cagcaaactc tgcctggcat ggggcatcga tgacaggg ccctgccctc
 3601 cagttcacag attcacacca gttacatcac actagtcctc ttctgtgttg tatcttcag
 3661 cagaccctt tcctcagtgc ttgcttgat cccaactgtt tagagggatt aagacacgag
 3721 gatcaaaagc tggaggccag cctgagcaac tgagtgaaac tctatttcaa aatgagtaag
 3781 gcctaaatgt gtagctcggt ggtatggcac acatacagaa atcagtgcag acatttaaca
 3841 cttgaagtgg aagccacggg tgaactcaca agataccaag tattagctta atcctcttcg
 3901 agatccctga gagattcaga cttggtgtga gtcctggaat tccagcactt gggagacaga
 3961 agcagaagga ttgttgcaaa tttgaggcag gtctgagctg tagagtgaga ctcttagcac
 4021 aaacagtaat cctctgagag aggtattaca atatggtgat tgtaataagg tatctaataa
 4081 ctcggataca gaaagagttg catggagcag ttgttgtaac tttgccaaga tcataccctct
 4141 gagaagtggc agagatggga cttgaaccta ggaatcatgt ctccagtcta ttctgctgat
```

TABLE 1-continued

```
4201 taaaaacacc gaattctgaa gaggctaggt agggtgagtg ttccagctcc tcacactgct
4261 ctctgctctg cctctgcctg tgtctgcact tgtgccatgc cttcaccctt cctcacattc
4321 agcagactga gcccctcgcc ttggctgtcc tggctgagtc tgccttccgt gggtgctcac
4381 tctatgccct gtaccgtct cttctctgcc tctgataata ttcattatca accacttcac
4441 acagtctgca aaggatcagg cccagaggtg actcttaaat tcctattctc caagccacc
```

SEQ ID NO: 16 Mouse H13 Isoform 4 (Encoded by Transcript Variant 4)
Amino Acid Sequence (NP 001153025.1)
```
  1 mdsavsdphn gsaeagtpan gttrppstpe gialaygsll lmallpiffg alrsvrcarg
 61 ksssdmpeti tsrdaarfpi iasctllgly lffkifsqey inlllsmyff vlgilalsht
121 irsegisrqp lkllsqepvq glgwehgllc hsepglnpgc kiqgnlpsrq hyt
```

SEQ ID NOs: 17-22 Human Qdm Peptides
VMAPRTLLL
VMAPRTLVL
VMAPRTVLL
VMAPRALLL
VMAPRTLIL
VMAPRTLFL SEQ ID NO: 23 Mouse Qdm Peptide
AMAPRTLLL Binding of HLA-E to Qdm peptides allows HLA-E to bind to NKG2A.

* Included in Table 1 are RNA nucleic acid molecules (e.g., thymines replaced with uridines), nucleic acid molecules encoding orthologs of the encoded proteins, as well as DNA or RNA nucleic acid sequences comprising a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with the nucleic acid sequence of any SEQ ID NO listed in Table 1, or a portion thereof. Such nucleic acid molecules can have a function of the full-length nucleic acid as described further herein.

* Included in Table 1 are orthologs of the proteins, as well as polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of any SEQ ID NO listed in Table 1, or a portion thereof. Such polypeptides can have a function of the full-length polypeptide as described further herein.

TABLE 2

SEQ ID NOs: 24-49 Representative examples of
peptides other than Qdm that bind to HLA-E (SEQ
ID NOs: 24-45) or peptides other than Qdm that
bind to Qa1 (SEQ ID NOs: 46-49)
Representative peptides other than Qdm that bind
to HLA-E include:
VTAPRTVLL
QMRPVSRVL
SLELGDSAL
LLLGPGSGL
SQAPLPCVL
YLLPRRGPRL
GMQFDRGYL
AMLQDIATL
KMLRGVNVL
VEGEALATL
AAVEELKAL
AVAKAGKPL
KLQERVAKL
RMPPLGHEL
VLRPGGHFL
VMTTVLATL
RLPAKAPLL
VMATRRNVL TABLE 2-continued VLRPGGHFL
GMKFDRGYI
ALWMRFLPL
FLARSALIL
(Lemberg et al. (2001) J. Immunol. 167: 6441-6446;
Romagnani et al. (2002) Proc. Natl. Acad. Sci.
U.S.A. 99: 11328-33; Yu et al. (2018) Oncology
Letters 15: 8187-8194; Lo et al. (2000) Nat. Med.
6: 215-218; Chun et al. (1998) Immunology 94:
64-71; Zeng et al. (2012) J. Immunol. 188: 302-
310)

Representative peptides that bind to Qa1 identifed
in an SPP knockout B16 melanoma cell line model
described herein and identified by mass
spectrometry of immunoprecipitated Qa1 include:
AITDRVILL
YLSGIAHFL
LLPEHFLFL
AIIESTPEL Binding of HLA-E to peptides other than Qdm allows HLA-E to bind to the T cell receptor, rather than NKG2A.

II. Subjects

In one embodiment, the subject for whom predicted likelihood of efficacy of an inhibitor of one or more biomarkers listed in Table 1, and an immunotherapy combination treatment is determined, is a mammal (e.g., mouse, rat, primate, non-human mammal, domestic animal, such as a dog, cat, cow, horse, and the like), and is preferably a human. In another embodiment, the subject is an animal model of cancer. For example, the animal model can be an orthotopic xenograft animal model of a human-derived cancer.

In another embodiment of the methods of the present invention, the subject has not undergone treatment, such as chemotherapy, radiation therapy, targeted therapy, and/or immunotherapies. In still another embodiment, the subject has undergone treatment, such as chemotherapy, radiation therapy, targeted therapy, and/or immunotherapies.

In certain embodiments, the subject has had surgery to remove cancerous or precancerous tissue. In other embodiments, the cancerous tissue has not been removed, e.g., the cancerous tissue may be located in an inoperable region of the body, such as in a tissue that is essential for life, or in a region where a surgical procedure would cause considerable risk of harm to the patient.

The methods of the present invention can be used to determine the responsiveness to inhibitor(s) of one or more biomarkers listed in Table 1, and immunotherapy combination treatment of many different cancers in subjects such as those described herein.

III. Sample Collection, Preparation and Separation

In some embodiments, biomarker amount and/or activity measurement(s) in a sample from a subject is compared to a predetermined control (standard) sample. The sample from the subject is typically from a diseased tissue, such as cancer cells or tissues. The control sample can be from the same subject or from a different subject. The control sample is typically a normal, non-diseased sample. However, in some embodiments, such as for staging of disease or for evaluating the efficacy of treatment, the control sample can be from a diseased tissue. The control sample can be a combination of samples from several different subjects. In some embodiments, the biomarker amount and/or activity measurement(s) from a subject is compared to a pre-determined level. This pre-determined level is typically obtained from normal samples. As described herein, a "pre-determined" biomarker amount and/or activity measurement(s) may be a biomarker amount and/or activity measurement(s) used to, by way of example only, evaluate a subject that may be selected for treatment (e.g., based on the number of genomic mutations and/or the number of genomic mutations causing non-functional proteins for DNA repair genes), evaluate a response to an inhibitor of one or more biomarkers listed in Table 1, and an immunotherapy combination treatment, and/or evaluate a response to an inhibitor of one or more biomarkers listed in Table 1, and an immunotherapy combination treatment with one or more additional anti-cancer therapies. A pre-determined biomarker amount and/or activity measurement(s) may be determined in populations of patients with or without cancer. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements.

In another embodiment, the amounts determined and/or compared in a method described herein are based on relative measurements, such as ratios (e.g., biomarker copy numbers, level, and/or activity before a treatment vs. after a treatment, such biomarker measurements relative to a spiked or man-made control, such biomarker measurements relative to the expression of a housekeeping gene, and the like). For example, the relative analysis can be based on the ratio of pre-treatment biomarker measurement as compared to post-treatment biomarker measurement. Pre-treatment biomarker measurement can be made at any time prior to initiation of anti-cancer therapy. Post-treatment biomarker measurement can be made at any time after initiation of anti-cancer therapy. In some embodiments, post-treatment biomarker measurements are made 1, 2, 3, 4, 5, 6, 7, 8, 9, 10, 11, 12, 13, 14, 15, 16, 17, 18, 19, 20 weeks or more after initiation of anti-cancer therapy, and even longer toward indefinitely for continued monitoring. Treatment can comprise anti-cancer therapy, such as a therapeutic regimen comprising one or more inhibitors of one or more biomarkers listed in Table 1, and immunotherapy combination treatment alone or in combination with other anti-cancer agents, such as with immune checkpoint inhibitors.

The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

In some embodiments of the present invention the change of biomarker amount and/or activity measurement(s) from the pre-determined level is about 0.1, 0.2, 0.3, 0.4, 0.5, 0.6, 0.7, 0.8, 0.9, 1.0, 1.5, 2.0, 2.5, 3.0, 3.5, 4.0, 4.5, or 5.0 fold or greater, or any range in between, inclusive. Such cutoff values apply equally when the measurement is based on relative changes, such as based on the ratio of pre-treatment biomarker measurement as compared to post-treatment biomarker measurement.

Biological samples can be collected from a variety of sources from a patient including a body fluid sample, cell sample, or a tissue sample comprising nucleic acids and/or proteins. "Body fluids" refer to fluids that are excreted or secreted from the body as well as fluids that are normally not (e.g., amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit). In a preferred embodiment, the subject and/or control sample is selected from the group consisting of cells, cell lines, histological slides, paraffin embedded tissues, biopsies, whole blood, nipple aspirate, serum, plasma, buccal scrape, saliva, cerebrospinal fluid, urine, stool, and bone marrow. In one embodiment, the sample is serum, plasma, or urine. In another embodiment, the sample is serum.

The samples can be collected from individuals repeatedly over a longitudinal period of time (e.g., once or more on the order of days, weeks, months, annually, biannually, etc.). Obtaining numerous samples from an individual over a period of time can be used to verify results from earlier detections and/or to identify an alteration in biological pattern as a result of, for example, disease progression, drug treatment, etc. For example, subject samples can be taken and monitored every month, every two months, or combinations of one, two, or three month intervals according to the present invention. In addition, the biomarker amount and/or activity measurements of the subject obtained over time can be conveniently compared with each other, as well as with those of normal controls during the monitoring period, thereby providing the subject's own values, as an internal, or personal, control for long-term monitoring.

Sample preparation and separation can involve any of the procedures, depending on the type of sample collected and/or analysis of biomarker measurement(s). Such procedures include, by way of example only, concentration, dilution, adjustment of pH, removal of high abundance polypeptides (e.g., albumin, gamma globulin, and transferrin, etc.), addition of preservatives and calibrants, addition of protease inhibitors, addition of denaturants, desalting of samples, concentration of sample proteins, extraction and purification of lipids.

The sample preparation can also isolate molecules that are bound in non-covalent complexes to other protein (e.g., carrier proteins). This process may isolate those molecules bound to a specific carrier protein (e.g., albumin), or use a more general process, such as the release of bound molecules from all carrier proteins via protein denaturation, for example using an acid, followed by removal of the carrier proteins.

Removal of undesired proteins (e.g., high abundance, uninformative, or undetectable proteins) from a sample can be achieved using high affinity reagents, high molecular weight filters, ultracentrifugation and/or electrodialysis. High affinity reagents include antibodies or other reagents (e.g., aptamers) that selectively bind to high abundance proteins. Sample preparation could also include ion exchange chromatography, metal ion affinity chromatography, gel filtration, hydrophobic chromatography, chromatofocusing, adsorption chromatography, isoelectric focusing and related techniques. Molecular weight filters include membranes that separate molecules on the basis of size and molecular weight. Such filters may further employ reverse osmosis, nanofiltration, ultrafiltration and microfiltration.

Ultracentrifugation is a method for removing undesired polypeptides from a sample. Ultracentrifugation is the centrifugation of a sample at about 15,000-60,000 rpm while monitoring with an optical system the sedimentation (or lack thereof) of particles. Electrodialysis is a procedure which uses an electromembrane or semipermeable membrane in a process in which ions are transported through semi-permeable membranes from one solution to another under the influence of a potential gradient. Since the membranes used in electrodialysis may have the ability to selectively transport ions having positive or negative charge, reject ions of the opposite charge, or to allow species to migrate through a semipermeable membrane based on size and charge, it renders electrodialysis useful for concentration, removal, or separation of electrolytes.

Separation and purification in the present invention may include any procedure known in the art, such as capillary electrophoresis (e.g., in capillary or on-chip) or chromatography (e.g., in capillary, column or on a chip). Electrophoresis is a method which can be used to separate ionic molecules under the influence of an electric field. Electrophoresis can be conducted in a gel, capillary, or in a microchannel on a chip. Examples of gels used for electrophoresis include starch, acrylamide, polyethylene oxides, agarose, or combinations thereof. A gel can be modified by its cross-linking, addition of detergents, or denaturants, immobilization of enzymes or antibodies (affinity electrophoresis) or substrates (zymography) and incorporation of a pH gradient. Examples of capillaries used for electrophoresis include capillaries that interface with an electrospray.

Capillary electrophoresis (CE) is preferred for separating complex hydrophilic molecules and highly charged solutes. CE technology can also be implemented on microfluidic chips. Depending on the types of capillary and buffers used, CE can be further segmented into separation techniques such as capillary zone electrophoresis (CZE), capillary isoelectric focusing (CIEF), capillary isotachophoresis (cITP) and capillary electrochromatography (CEC). An embodiment to couple CE techniques to electrospray ionization involves the use of volatile solutions, for example, aqueous mixtures containing a volatile acid and/or base and an organic such as an alcohol or acetonitrile.

Capillary isotachophoresis (cITP) is a technique in which the analytes move through the capillary at a constant speed but are nevertheless separated by their respective mobilities. Capillary zone electrophoresis (CZE), also known as free-solution CE (FSCE), is based on differences in the electrophoretic mobility of the species, determined by the charge on the molecule, and the frictional resistance the molecule encounters during migration which is often directly proportional to the size of the molecule. Capillary isoelectric focusing (CIEF) allows weakly-ionizable amphoteric molecules, to be separated by electrophoresis in a pH gradient. CEC is a hybrid technique between traditional high performance liquid chromatography (HPLC) and CE.

Separation and purification techniques used in the present invention include any chromatography procedures known in the art. Chromatography can be based on the differential adsorption and elution of certain analytes or partitioning of analytes between mobile and stationary phases. Different examples of chromatography include, but not limited to, liquid chromatography (LC), gas chromatography (GC), high performance liquid chromatography (HPLC), etc.

IV. Biomarker Nucleic Acids and Polypeptides

One aspect of the present invention pertains to the use of isolated nucleic acid molecules that correspond to biomarker nucleic acids that encode a biomarker polypeptide or a portion of such a polypeptide. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

A biomarker nucleic acid molecule of the present invention can be isolated using standard molecular biology techniques and the sequence information in the database records described herein. Using all or a portion of such nucleic acid sequences, nucleic acid molecules of the present invention can be isolated using standard hybridization and cloning techniques (e.g., as described in Sambrook et al., ed., *Molecular Cloning: A Laboratory Manual,* 2nd ed., Cold Spring Harbor Laboratory Press, Cold Spring Harbor, N Y, 1989).

A nucleic acid molecule of the present invention can be amplified using cDNA, mRNA, or genomic DNA as a template and appropriate oligonucleotide primers according to standard PCR amplification techniques. The nucleic acid molecules so amplified can be cloned into an appropriate vector and characterized by DNA sequence analysis. Furthermore, oligonucleotides corresponding to all or a portion of a nucleic acid molecule of the present invention can be prepared by standard synthetic techniques, e.g., using an automated DNA synthesizer.

Moreover, a nucleic acid molecule of the present invention can comprise only a portion of a nucleic acid sequence, wherein the full length nucleic acid sequence comprises a marker of the present invention or which encodes a polypeptide corresponding to a marker of the present invention. Such nucleic acid molecules can be used, for example, as a probe or primer. The probe/primer typically is used as one or more substantially purified oligonucleotides. The oligonucleotide typically comprises a region of nucleotide sequence that hybridizes under stringent conditions to at least about 7, preferably about 15, more preferably about 25, 50, 75, 100, 125, 150, 175, 200, 250, 300, 350, or 400 or more consecutive nucleotides of a biomarker nucleic acid sequence. Probes based on the sequence of a biomarker nucleic acid molecule can be used to detect transcripts or genomic sequences corresponding to one or more markers of the present invention. The probe comprises a label group attached thereto, e.g., a radioisotope, a fluorescent compound, an enzyme, or an enzyme co-factor.

A biomarker nucleic acid molecules that differ, due to degeneracy of the genetic code, from the nucleotide sequence of nucleic acid molecules encoding a protein which corresponds to the biomarker, and thus encode the same protein, are also contemplated.

In addition, it will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

The term "allele," which is used interchangeably herein with "allelic variant," refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene or allele. For example, biomarker alleles can differ from each other in a single nucleotide, or several nucleotides, and can include substitutions, deletions, and insertions of nucleotides. An allele of a gene can also be a form of a gene containing one or more mutations.

The term "allelic variant of a polymorphic region of gene" or "allelic variant", used interchangeably herein, refers to an alternative form of a gene having one of several possible nucleotide sequences found in that region of the gene in the population. As used herein, allelic variant is meant to encompass functional allelic variants, non-functional allelic variants, SNPs, mutations and polymorphisms.

The term "single nucleotide polymorphism" (SNP) refers to a polymorphic site occupied by a single nucleotide, which is the site of variation between allelic sequences. The site is usually preceded by and followed by highly conserved sequences of the allele (e.g., sequences that vary in less than $1/100$ or $1/1000$ members of a population). A SNP usually arises due to substitution of one nucleotide for another at the polymorphic site. SNPs can also arise from a deletion of a nucleotide or an insertion of a nucleotide relative to a reference allele. Typically the polymorphic site is occupied by a base other than the reference base. For example, where the reference allele contains the base "T" (thymidine) at the polymorphic site, the altered allele can contain a "C" (cytidine), "G" (guanine), or "A" (adenine) at the polymorphic site. SNP's may occur in protein-coding nucleic acid sequences, in which case they may give rise to a defective or otherwise variant protein, or genetic disease. Such a SNP may alter the coding sequence of the gene and therefore specify another amino acid (a "missense" SNP) or a SNP may introduce a stop codon (a "nonsense" SNP). When a SNP does not alter the amino acid sequence of a protein, the SNP is called "silent." SNP's may also occur in noncoding regions of the nucleotide sequence. This may result in defective protein expression, e.g., as a result of alternative splicing, or it may have no effect on the function of the protein.

As used herein, the terms "gene" and "recombinant gene" refer to nucleic acid molecules comprising an open reading frame encoding a polypeptide corresponding to a marker of the present invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the present invention.

In another embodiment, a biomarker nucleic acid molecule is at least 7, 15, 20, 25, 30, 40, 60, 80, 100, 150, 200, 250, 300, 350, 400, 450, 550, 650, 700, 800, 900, 1000, 1100, 1200, 1300, 1400, 1500, 1600, 1700, 1800, 1900, 2000, 2200, 2400, 2600, 2800, 3000, 3500, 4000, 4500, or more nucleotides in length and hybridizes under stringent conditions to a nucleic acid molecule corresponding to a marker of the present invention or to a nucleic acid molecule encoding a protein corresponding to a marker of the present invention. As used herein, the term "hybridizes under stringent conditions" is intended to describe conditions for hybridization and washing under which nucleotide sequences at least 60% (65%, 70%, 75%, 80%, preferably 85%) identical to each other typically remain hybridized to each other. Such stringent conditions are known to those skilled in the art and can be found in sections 6.3.1-6.3.6 of *Current Protocols in Molecular Biology,* John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50-65° C.

In addition to naturally-occurring allelic variants of a nucleic acid molecule of the present invention that can exist in the population, the skilled artisan will further appreciate that sequence changes can be introduced by mutation thereby leading to changes in the amino acid sequence of the encoded protein, without altering the biological activity of the protein encoded thereby. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, another aspect of the present invention pertains to nucleic acid molecules encoding a polypeptide of the present invention that contain changes in amino acid residues that are not essential for activity. Such polypeptides differ in amino acid sequence from the naturally-occurring proteins which correspond to the markers of the present invention, yet retain biological activity. In one embodiment, a biomarker protein has an amino acid sequence that is at least about 40% identical, 50%, 60%, 70%, 75%, 80%, 83%, 85%, 87.5%, 90%, 91%, 92%, 93%, 94%, 95%, 96%, 97%, 98%, 99% or identical to the amino acid sequence of a biomarker protein described herein.

An isolated nucleic acid molecule encoding a variant protein can be created by introducing one or more nucleotide substitutions, additions or deletions into the nucleotide sequence of nucleic acids of the present invention, such that one or more amino acid residue substitutions, additions, or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

In some embodiments, the present invention further contemplates the use of anti-biomarker antisense nucleic acid molecules, i.e., molecules which are complementary to a sense nucleic acid of the present invention, e.g., complementary to the coding strand of a double-stranded cDNA molecule corresponding to a marker of the present invention or complementary to an mRNA sequence corresponding to a marker of the present invention. Accordingly, an antisense nucleic acid molecule of the present invention can hydrogen bond to (i.e. anneal with) a sense nucleic acid of the present invention. The antisense nucleic acid can be complementary to an entire coding strand, or to only a portion thereof, e.g., all or part of the protein coding region (or open reading frame). An antisense nucleic acid molecule can also be antisense to all or part of a non-coding region of the coding strand of a nucleotide sequence encoding a polypeptide of the present invention. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45, or 50 or more nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been sub-cloned in an antisense orientation (i.e., RNA transcribed from the inserted nucleic acid will be of an antisense orientation to a target nucleic acid of interest, described further in the following subsection).

The antisense nucleic acid molecules of the present invention are typically administered to a subject or generated in situ such that they hybridize with or bind to cellular mRNA and/or genomic DNA encoding a polypeptide corresponding to a selected marker of the present invention to thereby inhibit expression of the marker, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. Examples of a route of administration of antisense nucleic acid molecules of the present invention includes direct injection at a tissue site or infusion of the antisense nucleic acid into a blood- or bone marrow-associated body fluid. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the present invention can be an α-anomeric nucleic acid molecule. An α-anomeric nucleic acid molecule forms specific double-stranded hybrids with complementary RNA in which, contrary to the usual α-units, the strands run parallel to each other (Gaultier et al., 1987, Nucleic Acids Res. 15:6625-6641). The antisense nucleic acid molecule can also comprise a 2'-o-methylribonucleotide (Inoue et al., 1987, Nucleic Acids Res. 15:6131-6148) or a chimeric RNA-DNA analogue (Inoue et al., 1987, FEBS Lett. 215:327-330).

The present invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes as described in Haselhoff and Gerlach, 1988, Nature 334:585-591) can be used to catalytically cleave mRNA transcripts to thereby inhibit translation of the protein encoded by the mRNA. A ribozyme having specificity for a nucleic acid molecule encoding a polypeptide corresponding to a marker of the present invention can be designed based upon the nucleotide sequence of a cDNA corresponding to the marker. For example, a derivative of a Tetrahymena L-19 IVS RNA can be constructed in which the nucleotide sequence of the active site is complementary to the nucleotide sequence to be cleaved (see Cech et al. U.S. Pat. No. 4,987,071; and Cech et al. U.S. Pat. No. 5,116,742). Alternatively, an mRNA encoding a polypeptide of the present invention can be used to select a catalytic RNA having a specific ribonuclease activity from a pool of RNA molecules (see, e.g., Bartel and Szostak, 1993, Science 261:1411-1418).

The present invention also encompasses nucleic acid molecules which form triple helical structures. For example, expression of a biomarker protein can be inhibited by targeting nucleotide sequences complementary to the regulatory region of the gene encoding the polypeptide (e.g., the promoter and/or enhancer) to form triple helical structures that prevent transcription of the gene in target cells. See generally Helene (1991) Anticancer Drug Des. 6(6):569-84; Helene (1992) Ann. N.Y. Acad. Sci. 660:27-36; and Maher (1992) Bioassays 14(12):807-15.

In various embodiments, the nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acid molecules (see Hyrup et al., 1996, Bioorganic & Medicinal Chemistry 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) Proc. Natl. Acad. Sci. U.S.A. 93:14670-675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup, 1996, supra; Perry-O'Keefe et al., 1996, Proc. Natl. Acad. Sci. U.S.A. 93:14670-675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNASE H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup (1996), supra, and Finn et al. (1996) Nucleic Acids Res. 24(17):3357-63. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al., 1989, Nucleic Acids Res. 17:5973-88). PNA monomers are then coupled in a step-wise manner to produce a chimeric molecule with a 5' PNA segment and a 3' DNA segment (Finn et al., 1996, Nucleic Acids Res. 24(17):3357-63). Alternatively, chimeric molecules can be synthesized with a 5' DNA segment and a 3' PNA segment (Peterser et al., 1975, Bioorganic Med. Chem. Lett. 5:1119-11124).

In other embodiments, the oligonucleotide can include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553-6556; Lemaitre et al., 1987, Proc. Natl. Acad. Sci. U.S.A. 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al., 1988, Bio Techniques 6:958-976) or intercalating agents (see, e.g., Zon, 1988, Pharm. Res. 5:539-549). To this end, the oligonucleotide can be conjugated to another molecule, e.g., a peptide, hybridization triggered cross-linking agent, transport agent, hybridization-triggered cleavage agent, etc.

Another aspect of the present invention pertains to the use of biomarker proteins and biologically active portions thereof. In one embodiment, the native polypeptide corresponding to a marker can be isolated from cells or tissue sources by an appropriate purification scheme using standard protein purification techniques. In another embodiment, polypeptides corresponding to a marker of the present invention are produced by recombinant DNA techniques. Alternative to recombinant expression, a polypeptide corresponding to a marker of the present invention can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a biomarker polypeptide include polypeptides comprising amino acid sequences sufficiently identical to or derived from a biomarker protein amino acid sequence described herein, but which includes fewer amino acids than the full length protein, and exhibit at least one activity of the corresponding full-length protein. Typically, biologically active portions comprise a domain or motif with at least one activity of the corresponding protein. A biologically active portion of a protein of the present invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide of the present invention.

Preferred polypeptides have an amino acid sequence of a biomarker protein encoded by a nucleic acid molecule described herein. Other useful proteins are substantially identical (e.g., at least about 40%, preferably 50%, 60%, 70%, 75%, 80%, 83%, 85%, 88%, 90%, 91%, 92%, 93%, 94%, 95%, 96%, 97%, 98%, or 99%) to one of these sequences and retain the functional activity of the protein of the corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) Proc. Natl. Acad. Sci. U.S.A. 87:2264-2268, modified as in Karlin and Altschul (1993) Proc. Natl. Acad. Sci. U.S.A. 90:5873-5877. Such an algorithm is incorporated into the NBLAST and XBLAST programs of Altschul, et al. (1990) J. Mol. Biol. 215:403-410. BLAST nucleotide searches can be performed with the NBLAST program, score=100, wordlength=12 to obtain nucleotide sequences homologous to a nucleic acid molecules of the present invention. BLAST protein searches can be performed with the XBLAST program, score=50, wordlength=3 to obtain amino acid sequences homologous to a protein molecules of the present invention. To obtain gapped alignments for comparison purposes, Gapped BLAST can be utilized as described in Altschul et al. (1997) Nucleic Acids Res. 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, (1988) Comput Appl Biosci, 4:11-7. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) Proc. Natd. Acad. Sci. U.S.A. 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

The present invention also provides chimeric or fusion proteins corresponding to a biomarker protein. As used herein, a "chimeric protein" or "fusion protein" comprises all or part (preferably a biologically active part) of a polypeptide corresponding to a marker of the present invention operably linked to a heterologous polypeptide (i.e., a polypeptide other than the polypeptide corresponding to the marker). Within the fusion protein, the term "operably linked" is intended to indicate that the polypeptide of the present invention and the heterologous polypeptide are fused in-frame to each other. The heterologous polypeptide can be fused to the amino-terminus or the carboxyl-terminus of the polypeptide of the present invention.

One useful fusion protein is a GST fusion protein in which a polypeptide corresponding to a marker of the present invention is fused to the carboxyl terminus of GST sequences. Such fusion proteins can facilitate the purification of a recombinant polypeptide of the present invention.

In another embodiment, the fusion protein contains a heterologous signal sequence, immunoglobulin fusion protein, toxin, or other useful protein sequence. Chimeric and fusion proteins of the present invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the present invention can be cloned into such an expression vector such that the fusion moiety is linked in-frame to the polypeptide of the present invention.

A signal sequence can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the present invention pertains to the described polypeptides having a signal sequence, as well as to polypeptides from which the signal sequence has been proteolytically cleaved (i.e., the cleavage products). In one embodiment, a nucleic acid sequence encoding a signal sequence can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

The present invention also pertains to variants of the biomarker polypeptides described herein. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a biomarker protein which function as either agonists (mimetics) or as antagonists can be identified by screening combinatorial libraries of mutants, e.g., truncation mutants, of the protein of the present invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the present invention from a degenerate oligonucleotide sequence. Methods for synthesizing degenerate oligonucleotides are known in the art (see, e.g., Narang, 1983, *Tetrahedron* 39:3; Itakura et al., 1984, *Annu. Rev. Biochem.* 53:323; Itakura et al., 1984, *Science* 198:1056; Ike et al., 1983 *Nucleic Acid Res.* 11:477).

In addition, libraries of fragments of the coding sequence of a polypeptide corresponding to a marker of the present invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes amino terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the present invention (Arkin and Yourvan, 1992, *Proc. Natl. Acad. Sci. U.S.A.* 89:7811-7815; Delgrave et al., 1993, *Protein Engineering* 6(3):327-331).

An isolated polypeptide or a fragment thereof (or a nucleic acid encoding such a polypeptide) corresponding to one or more biomarkers of the invention, including the biomarkers listed in Table 1 or fragments thereof, can be used as an immunogen to generate antibodies that bind to said immunogen, using standard techniques for polyclonal and monoclonal antibody preparation according to well-known methods in the art. An antigenic peptide comprises at least 8 amino acid residues and encompasses an epitope present in the respective full length molecule such that an antibody raised against the peptide forms a specific immune complex with the respective full length molecule. Preferably, the antigenic peptide comprises at least 10 amino acid residues. In one embodiment such epitopes can be specific for a given polypeptide molecule from one species, such as mouse or human (i.e., an antigenic peptide that spans a region of the polypeptide molecule that is not conserved across species is used as immunogen; such non conserved residues can be determined using an alignment such as that provided herein).

In some embodiments, the immunotherapy utilizes an inhibitor of at least one immune checkpoint, such as an antibody binds substantially specifically to an immune checkpoint, such as PD-1, and inhibits or blocks its immunoinhibitory function, such as by interrupting its interaction with a binding partner of the immune checkpoint, such as PD-L1 and/or PD-L2 binding partners of PD-1. In one embodiment, an antibody, especially an intrabody, binds substantially specifically to one or more biomarkers listed in Table 1, and inhibits or blocks its biological function. In another embodiment, an antibody, especially an intrabody, binds substantially specifically to the binding partner(s) of one or more biomarkers listed in Table 1, such as substrates of such one or more biomarkers described herein, and inhibits or blocks its biological function, such as by interrupting its interaction to one or more biomarkers listed in Table 1.

For example, a polypeptide immunogen typically is used to prepare antibodies by immunizing a suitable subject (e.g., rabbit, goat, mouse or other mammal) with the immunogen. A preferred animal is a mouse deficient in the desired target antigen. For example, a PD-1 knockout mouse if the desired antibody is an anti-PD-1 antibody, may be used. This results in a wider spectrum of antibody recognition possibilities as antibodies reactive to common mouse and human epitopes are not removed by tolerance mechanisms. An appropriate immunogenic preparation can contain, for example, a recombinantly expressed or chemically synthesized molecule or fragment thereof to which the immune response is to be generated. The preparation can further include an adjuvant, such as Freund's complete or incomplete adjuvant, or similar immunostimulatory agent. Immunization of a suitable subject with an immunogenic preparation induces a polyclonal antibody response to the antigenic peptide contained therein.

Polyclonal antibodies can be prepared as described above by immunizing a suitable subject with a polypeptide immunogen. The polypeptide antibody titer in the immunized subject can be monitored over time by standard techniques, such as with an enzyme linked immunosorbent assay (ELISA) using immobilized polypeptide. If desired, the antibody directed against the antigen can be isolated from the mammal (e.g., from the blood) and further purified by well-known techniques, such as protein A chromatography, to obtain the IgG fraction. At an appropriate time after immunization, e.g., when the antibody titers are highest, antibody-producing cells can be obtained from the subject and used to prepare monoclonal antibodies by standard techniques, such as the hybridoma technique (originally described by Kohler and Milstein (1975) Nature 256:495-497) (see also Brown et al. (1981) J. Immunol. 127:539-46; Brown et al. (1980) J. Biol. Chem. 255:4980-83; Yeh et al. (1976) Proc. Natd. Acad. Sci. 76:2927-31; Yeh et al. (1982) Int. J. Cancer 29:269-75), the more recent human B cell hybridoma technique (Kozbor et al. (1983) Immunol. Today 4:72), the EBV-hybridoma technique (Cole et al. (1985) Monoclonal Antibodies and Cancer Therapy, Alan R. Liss, Inc., pp. 77-96) or trioma techniques. The technology for producing monoclonal antibody hybridomas is well-known (see generally Kenneth, R. H. in Monoclonal Antibodies: A New Dimension In Biological Analyses, Plenum Publishing Corp., New York, New York (1980); Lerner, E. A. (1981) Yale J. Biol. Med. 54:387-402; Gefter, M. L. et al. (1977) Somatic Cell Genet. 3:231-36). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds to the polypeptide antigen, preferably specifically. In some embodiments, the immunization is performed in a cell or animal host that has a knockout of a target antigen of interest (e.g., does not produce the antigen prior to immunization).

Any of the many well-known protocols used for fusing lymphocytes and immortalized cell lines can be applied for the purpose of generating a monoclonal antibody against one or more biomarkers of the invention, including the biomarkers listed in Table 1, or a fragment thereof (see, e.g., Galfre, G. et al. (1977) Nature 266:55052; Gefter et al. (1977) supra; Lerner (1981) supra; Kenneth (1980) supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Agl4 myeloma lines. These myeloma lines are available from the American Type Culture Collection (ATCC), Rockville, MD. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind a given polypeptide, e.g., using a standard ELISA assay.

As an alternative to preparing monoclonal antibody-secreting hybridomas, a monoclonal specific for one of the above described polypeptides can be identified and isolated by screening a recombinant combinatorial immunoglobulin library (e.g., an antibody phage display library) with the appropriate polypeptide to thereby isolate immunoglobulin library members that bind the polypeptide. Kits for generating and screening phage display libraries are commercially available (e.g., the Pharmacia Recombinant Phage Antibody System, Catalog No. 27-9400-01; and the Stratagene SurfZAP™ Phage Display Kitz, Catalog No. 240612). Additionally, examples of methods and reagents particularly amenable for use in generating and screening an antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) Biotechnology (NY) 9:1369-1372; Hay et al. (1992) Hum. Antibod. Hybridomas 3:81-85; Huse et al. (1989) Science 246:1275-1281; Griffiths et al. (1993) EMBO J. 12:725-734; Hawkins et al. (1992) J. Mol. Biol. 226:889-896; Clarkson et al. (1991) Nature 352:624-628; Gram et al. (1992) Proc. Natl. Acad. Sci. U.S.A. 89:3576-3580; Garrard et al. (1991) Biotechnology (NY) 9:1373-1377; Hoogenboom et al. (1991) *Nucleic Acids Res.* 19:4133-4137; Barbas et al. (1991) *Proc. Natl. Acad. Sci. U.S.A.* 88:7978-7982; and McCafferty et al. (1990) *Nature* 348:552-554.

Since it is well-known in the art that antibody heavy and light chain CDR3 domains play a particularly important role in the binding specificity/affinity of an antibody for an antigen, the recombinant monoclonal antibodies of the present invention prepared as set forth above preferably comprise the heavy and light chain CDR3s of variable regions of the antibodies described herein and well-known in the art. Similarly, the antibodies can further comprise the CDR2s of variable regions of said antibodies. The antibodies can further comprise the CDR1s of variable regions of said antibodies. In other embodiments, the antibodies can comprise any combinations of the CDRs.

The CDR1, 2, and/or 3 regions of the engineered antibodies described above can comprise the exact amino acid sequence(s) as those of variable regions of the present invention described herein. However, the ordinarily skilled artisan will appreciate that some deviation from the exact CDR sequences may be possible while still retaining the ability of the antibody, especially an introbody, to bind a desired target, such as one or more biomarkers listed in Table 1, and/or a binding partner thereof, either alone or in combination with an immunotherapy, such as the one or more biomarkers, the binding partners/substrates of such biomarkers, or an immunotherapy effectively (e.g., conservative sequence modifications). Accordingly, in another embodiment, the engineered antibody may be composed of one or more CDRs that are, for example, 50%, 60%, 70%, 80%, 85%, 90%, 91%, 92%, 93%, 94%, 95%, 96%, 97%, 98%, 99%, or 99.5% identical to one or more CDRs of the present invention described herein or otherwise publicly available.

For example, the structural features of non-human or human antibodies (e.g., a rat anti-mouse/anti-human antibody) can be used to create structurally related human antibodies, especially introbodies, that retain at least one functional property of the antibodies of the present invention, such as binding to one or more biomarkers listed in Table 1, the binding partners/substrates of such one or more biomarkers, and/or an immune checkpoint. Another functional property includes inhibiting binding of the original known, non-human or human antibodies in a competition ELISA assay.

Antibodies, immunoglobulins, and polypeptides of the invention can be used in an isolated (e.g., purified) form or contained in a vector, such as a membrane or lipid vesicle (e.g. a liposome). Moreover, amino acid sequence modification(s) of the antibodies described herein are contemplated. For example, it may be desirable to improve the binding affinity and/or other biological properties of the antibody. It is known that when a humanized antibody is produced by simply grafting only CDRs in VH and VL of an antibody derived from a non-human animal in FRs of the VH and VL of a human antibody, the antigen binding activity is reduced in comparison with that of the original antibody derived from a non-human animal. It is considered that several amino acid residues of the VH and VL of the non-human antibody, not only in CDRs but also in FRs, are directly or indirectly associated with the antigen binding activity. Hence, substitution of these amino acid residues with different amino acid residues derived from FRs of the VH and VL of the human antibody would reduce binding activity and can be corrected by replacing the amino acids with amino acid residues of the original antibody derived from a non-human animal.

Similarly, modifications and changes may be made in the structure of the antibodies described herein, and in the DNA sequences encoding them, and still obtain a functional molecule that encodes an antibody and polypeptide with desirable characteristics. For example, antibody glycosylation patterns can be modulated to, for example, increase stability. By "altering" is meant deleting one or more carbohydrate moieties found in the antibody, and/or adding one or more glycosylation sites that are not present in the antibody. Glycosylation of antibodies is typically N-linked. "N-linked" refers to the attachment of the carbohydrate moiety to the side chain of an asparagine residue. The tripeptide sequences asparagine-X-serine and asparagines-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites). Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, orhydroxyproline, (e) aromatic residues such as those of phenylalanine, tyrosine, or tryptophan, or (f) the amide group of glutamine. For example, such methods are described in WO87/05330.

Similarly, removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Sojahr et al. (1987) and by Edge et al. (1981). Enzymatic cleavage of carbohydrate moieties on antibodies can be achieved by the use of a variety of endo- and exo-glycosidases as described by Thotakura et al. (1987).

Other modifications can involve the formation of immunoconjugates. For example, in one type of covalent modification, antibodies or proteins are covalently linked to one of a variety of non proteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Conjugation of antibodies or other proteins of the present invention with heterologous agents can be made using a variety of bifunctional protein coupling agents including but not limited to N-succinimidyl (2-pyridyldithio) propionate (SPDP), succinimidyl (N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6diisocyanate), and bis-active fluorine compounds (such as 1,5-difluoro-2,4-dinitrobenzene). For example, carbon labeled 1-isothiocyanatobenzyl methyldiethylene triaminepentaacetic acid (MX-DTPA) is an exemplary chelating agent for conjugation of radionucleotide to the antibody (WO 94/11026).

In another aspect, the present invention features antibodies conjugated to a therapeutic moiety, such as a cytotoxin, a drug, and/or a radioisotope. When conjugated to a cytotoxin, these antibody conjugates are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). An antibody of the present invention can be conjugated to a radioisotope, e.g., radioactive iodine, to generate cytotoxic radiopharmaceuticals for treating a related disorder, such as a cancer.

Conjugated antibodies, in addition to therapeutic utility, can be useful for diagnostically or prognostically to monitor polypeptide levels in tissue as part of a clinical testing procedure, e.g., to determine the efficacy of a given treatment regimen. Detection can be facilitated by coupling (i e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include a flag tag, a myc tag, an hemagglutinin (HA) tag, streptavidin/biotin and avidin/biotin; examples of suitable fluorescent materials include umbelliferone, fluorescein, fluorescein isothiocyanate (FITC), rhodamine, dichlorotriazinylamine fluorescein, dansyl chloride or phycoerythrin (PE); an example of a luminescent material includes luminol; examples of bioluminescent materials include luciferase, luciferin, and aequorin, and examples of suitable radioactive material include $^{125}I$, $^{131}I$, $^{35}S$, or $^3H$. As used herein, the term "labeled", with regard to the antibody, is intended to encompass direct labeling of the antibody by coupling (i.e., physically linking) a detectable substance, such as a radioactive agent or a fluorophore (e.g. fluorescein isothiocyanate (FITC) or phycoerythrin (PE) or Indocyanine (Cy5)) to the antibody, as well as indirect labeling of the antibody by reactivity with a detectable substance.

The antibody conjugates of the present invention can be used to modify a given biological response. The therapeutic moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *Pseudomonas* exotoxin, or diphtheria toxin; a protein such as tumor necrosis factor or interferon-.gamma.; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other cytokines or growth factors.

In one embodiment, an antibody for use in the instant invention is a bispecific or multispecific antibody. A bispecific antibody has binding sites for two different antigens within a single antibody polypeptide. Antigen binding may be simultaneous or sequential. Triomas and hybrid hybridomas are two examples of cell lines that can secrete bispecific antibodies. Examples of bispecific antibodies produced by a hybrid hybridoma or a trioma are disclosed in U.S. Pat. No. 4,474,893. Bispecific antibodies have been constructed by chemical means (Staerz et al. (1985) *Nature* 314:628, and Perez et al. (1985) *Nature* 316:354) and hybridoma technology (Staerz and Bevan (1986) *Proc. Natl. Acad. Sci. U.S.A.*, 83:1453, and Staerz and Bevan (1986) *Immunol. Today* 7:241). Bispecific antibodies are also described in U.S. Pat. No. 5,959,084. Fragments of bispecific antibodies are described in U.S. Pat. No. 5,798,229.

Bispecific agents can also be generated by making heterohybridomas by fusing hybridomas or other cells making different antibodies, followed by identification of clones producing and co-assembling both antibodies. They can also be generated by chemical or genetic conjugation of complete immunoglobulin chains or portions thereof such as Fab and Fv sequences. The antibody component can bind to a polypeptide or a fragment thereof of one or more biomarkers of the invention, including one or more biomarkers listed in Table 1, or a fragment thereof. In one embodiment, the bispecific antibody could specifically bind to both a polypeptide or a fragment thereof and its natural binding partner(s) or a fragment(s) thereof.

Techniques for modulating antibodies, such as humanization, conjugation, recombinant techniques, and the like are well-known in the art.

In another aspect of this invention, peptides or peptide mimetics can be used to antagonize the activity of one or more biomarkers of the invention, including one or more biomarkers listed in Table 1, or a fragment(s) thereof. In one embodiment, variants of one or more biomarkers listed in Table 1 which function as a modulating agent for the respective full length protein, can be identified by screening combinatorial libraries of mutants, e.g., truncation mutants, for antagonist activity. In one embodiment, a variegated library of variants is generated by combinatorial mutagenesis at the nucleic acid level and is encoded by a variegated gene library. A variegated library of variants can be produced, for instance, by enzymatically ligating a mixture of synthetic oligonucleotides into gene sequences such that a degenerate set of potential polypeptide sequences is expressible as individual polypeptides containing the set of polypeptide sequences therein. There are a variety of methods which can be used to produce libraries of polypeptide variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential polypeptide sequences. Methods for synthesizing degenerate oligonucleotides are known in the art (see, e.g., Narang, S. A. (1983) *Tetrahedron* 39:3;

Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a polypeptide coding sequence can be used to generate a variegated population of polypeptide fragments for screening and subsequent selection of variants of a given polypeptide. In one embodiment, a library of coding sequence fragments can be generated by treating a double stranded PCR fragment of a polypeptide coding sequence with a nuclease under conditions wherein nicking occurs only about once per polypeptide, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the polypeptide.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of polypeptides. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of interest (Arkin and Youvan (1992) *Proc. Natl. Acad. Sci. U.S.A.* 89:7811-7815; Delagrave et al. (1993) *Protein Eng.* 6(3):327-331). In one embodiment, cell based assays can be exploited to analyze a variegated polypeptide library. For example, a library of expression vectors can be transfected into a cell line which ordinarily synthesizes one or more biomarkers of the invention, including one or more biomarkers listed in Table 1, or a fragment thereof. The transfected cells are then cultured such that the full length polypeptide and a particular mutant polypeptide are produced and the effect of expression of the mutant on the full length polypeptide activity in cell supernatants can be detected, e.g., by any of a number of functional assays. Plasmid DNA can then be recovered from the cells which score for inhibition, or alternatively, potentiation of full length polypeptide activity, and the individual clones further characterized.

Systematic substitution of one or more amino acids of a polypeptide amino acid sequence with a D-amino acid of the same type (e.g., D-lysine in place of L-lysine) can be used to generate more stable peptides. In addition, constrained peptides comprising a polypeptide amino acid sequence of interest or a substantially identical sequence variation can be generated by methods known in the art (Rizo and Gierasch (1992) *Annu. Rev. Biochem.* 61:387, incorporated herein by reference); for example, by adding internal cysteine residues capable of forming intramolecular disulfide bridges which cyclize the peptide.

The amino acid sequences described herein will enable those of skill in the art to produce polypeptides corresponding peptide sequences and sequence variants thereof. Such polypeptides can be produced in prokaryotic or eukaryotic host cells by expression of polynucleotides encoding the peptide sequence, frequently as part of a larger polypeptide. Alternatively, such peptides can be synthesized by chemical methods. Methods for expression of heterologous proteins in recombinant hosts, chemical synthesis of polypeptides, and in vitro translation are well-known in the art and are described further in Maniatis et al. *Molecular Cloning: A Laboratory Manual* (1989), 2nd Ed., Cold Spring Harbor, N.Y.; Berger and Kimmel, Methods in Enzymology, Volume 152, *Guide to Molecular Cloning Techniques* (1987), Academic Press, Inc., San Diego, Calif.; Merrifield, J. (1969) *J. Am. Chem. Soc.* 91:501; Chaiken I. M. (1981) *CRC Crit. Rev. Biochem.* 11: 255; Kaiser et al. (1989) *Science* 243:187; Merrifield, B. (1986) *Science* 232:342; Kent, S. B. H. (1988) *Annu. Rev. Biochem.* 57:957; and Offord, R. E. (1980) *Semisynthetic Proteins*, Wiley Publishing, which are incorporated herein by reference).

Peptides can be produced, typically by direct chemical synthesis. Peptides can be produced as modified peptides, with nonpeptide moieties attached by covalent linkage to the N-terminus and/or C-terminus. In certain preferred embodiments, either the carboxy-terminus or the amino-terminus, or both, are chemically modified. The most common modifications of the terminal amino and carboxyl groups are acetylation and amidation, respectively. Amino-terminal modifications such as acylation (e.g., acetylation) or alkylation (e.g., methylation) and carboxy-terminal-modifications such as amidation, as well as other terminal modifications, including cyclization, can be incorporated into various embodiments of the invention. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others. Peptides described herein can be used therapeutically to treat disease, e.g., by altering costimulation in a patient.

Peptidomimetics (Fauchere (1986) *Adv. Drug Res.* 15:29; Veber and Freidinger (1985) TINS p. 392; and Evans et al. (1987) *J. Med. Chem.* 30:1229, which are incorporated herein by reference) are usually developed with the aid of computerized molecular modeling. Peptide mimetics that are structurally similar to therapeutically useful peptides can be used to produce an equivalent therapeutic or prophylactic effect. Generally, peptidomimetics are structurally similar to a paradigm polypeptide (i.e., a polypeptide that has a biological or pharmacological activity), but have one or more peptide linkages optionally replaced by a linkage selected from the group consisting of: —CH2NH—, —CH$_2$S—, —CH2-CH2-, —CH=CH— (cis and trans), —COCH2-, —CH(OH)CH2-, and —CH2SO—, by methods known in the art and further described in the following references: Spatola, A. F. in "*Chemistry and Biochemistry of Amino Acids, Peptides, and Proteins*" Weinstein, B., ed., Marcel Dekker, New York, p. 267 (1983); Spatola, A. F., Vega Data (March 1983), Vol. 1, Issue 3, "Peptide Backbone Modifications" (general review); Morley, J. S. (1980) *Trends Pharm. Sci.* pp. 463-468 (general review); Hudson, D. et al. (1979) *Int. J. Pept. Prot. Res.* 14:177-185 (—CH2NH—, CH2CH2-); Spatola, A. F. et al. (1986) *Life Sci.* 38:1243-1249 (—CH2-S); Hann, M. M. (1982) *J. Chem. Soc. Perkin Trans. I* 307-314 (—CH—CH—, cis and trans); Almquist, R. G. et al. (190) *J. Med. Chem.* 23:1392-1398 (—COCH2-); Jennings-White, C. et al. (1982) *Tetrahedron Lett.* 23:2533 (—COCH2-); Szelke, M. et al. *European*

*Appln.* EP 45665 (1982) CA: 97:39405 (1982)(—CH(OH) CH2-); Holladay, M. W. et al. (1983) *Tetrahedron Lett.* (1983) 24:4401-4404 (—C(OH)CH2-); and Hruby, V. J. (1982) *Life Sci.* (1982) 31:189-199 (—CH2-S—); each of which is incorporated herein by reference. A particularly preferred non-peptide linkage is —CH2NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macropolypeptides(s) to which the peptidomimetic binds to produce the therapeutic effect. Derivatization (e.g., labeling) of peptidomimetics should not substantially interfere with the desired biological or pharmacological activity of the peptidomimetic.

Also encompassed by the present invention are small molecules which can modulate (either enhance or inhibit) interactions, e.g., between biomarkers described herein or listed in Table 1 and their natural binding partners. The small molecules of the present invention can be obtained using any of the numerous approaches in combinatorial library methods known in the art, including: spatially addressable parallel solid phase or solution phase libraries; synthetic library methods requiring deconvolution; the 'one-bead one-compound' library method; and synthetic library methods using affinity chromatography selection. (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. U.S.A.* 91:11422; Zuckermann et al. (1994) *J. Med Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner USP '409), plasmids (Cull et al. (1992) *Proc. Natl. Acad. Sci. U.S.A.* 89:1865-1869) or on phage (Scott and Smith (1990) *Science* 249:386-390); (Devlin (1990) *Science* 249:404-406); (Cwirla et al. (1990) *Proc. Natl. Acad. Sci. U.S.A.* 87:6378-6382); (Felici (1991) *J. Mol. Biol.* 222:301-310); (Ladner supra.). Compounds can be screened in cell based or non-cell based assays. Compounds can be screened in pools (e.g. multiple compounds in each testing sample) or as individual compounds.

Chimeric or fusion proteins can be prepared for the inhibitor(s) of one or more biomarkers listed in Table 1, and/or agents for the immunotherapies described herein, such as inhibitors to the biomarkers of the invention, including the biomarkers listed in Table 1, or fragments thereof. As used herein, a "chimeric protein" or "fusion protein" comprises one or more biomarkers of the invention, including one or more biomarkers listed in Table 1, or a fragment thereof, operatively linked to another polypeptide having an amino acid sequence corresponding to a protein which is not substantially homologous to the respective biomarker. In a preferred embodiment, the fusion protein comprises at least one biologically active portion of one or more biomarkers of the invention, including one or more biomarkers listed in Table 1, or fragments thereof. Within the fusion protein, the term "operatively linked" is intended to indicate that the biomarker sequences and the non-biomarker sequences are fused in-frame to each other in such a way as to preserve functions exhibited when expressed independently of the fusion. The "another" sequences can be fused to the N-terminus or C-terminus of the biomarker sequences, respectively.

Such a fusion protein can be produced by recombinant expression of a nucleotide sequence encoding the first peptide and a nucleotide sequence encoding the second peptide. The second peptide may optionally correspond to a moiety that alters the solubility, affinity, stability or valency of the first peptide, for example, an immunoglobulin constant region. In another preferred embodiment, the first peptide consists of a portion of a biologically active molecule (e.g. the extracellular portion of the polypeptide or the ligand binding portion). The second peptide can include an immunoglobulin constant region, for example, a human $C\gamma1$ domain or $C\gamma4$ domain (e.g., the hinge, CH2 and CH3 regions of human $IgC\gamma 1$, or human $IgC\gamma4$, see e.g., Capon et al. U.S. Pat. Nos. 5,116,964; 5,580,756; 5,844,095 and the like, incorporated herein by reference). Such constant regions may retain regions which mediate effector function (e.g. Fc receptor binding) or may be altered to reduce effector function. A resulting fusion protein may have altered solubility, binding affinity, stability and/or valency (i.e., the number of binding sites available per polypeptide) as compared to the independently expressed first peptide, and may increase the efficiency of protein purification. Fusion proteins and peptides produced by recombinant techniques can be secreted and isolated from a mixture of cells and medium containing the protein or peptide. Alternatively, the protein or peptide can be retained cytoplasmically and the cells harvested, lysed and the protein isolated. A cell culture typically includes host cells, media and other byproducts. Suitable media for cell culture are well-known in the art. Protein and peptides can be isolated from cell culture media, host cells, or both using techniques known in the art for purifying proteins and peptides. Techniques for transfecting host cells and purifying proteins and peptides are known in the art.

Preferably, a fusion protein of the invention is produced by standard recombinant DNA techniques. For example, DNA fragments coding for the different polypeptide sequences are ligated together in-frame in accordance with conventional techniques, for example employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992).

The fusion proteins of the invention can be used as immunogens to produce antibodies in a subject. Such antibodies may be used to purify the respective natural polypeptides from which the fusion proteins were generated, or in screening assays to identify polypeptides which inhibit the interactions between one or more biomarkers polypeptide or a fragment thereof and its natural binding partner(s) or a fragment(s) thereof.

Also provided herein are compositions comprising one or more nucleic acids comprising or capable of expressing at least 1, 2, 3, 4, 5, 10, 20 or more small nucleic acids or antisense oligonucleotides or derivatives thereof, wherein said small nucleic acids or antisense oligonucleotides or derivatives thereof in a cell specifically hybridize (e.g., bind) under cellular conditions, with cellular nucleic acids (e.g., small non-coding RNAS such as miRNAs, pre-miRNAs, pri-miRNAs, miRNA*, anti-miRNA, a miRNA binding site, a variant and/or functional variant thereof, cellular mRNAs or a fragments thereof). In one embodiment, expression of the small nucleic acids or antisense oligonucleotides or derivatives thereof in a cell can inhibit expression or biological activity of cellular nucleic acids and/or proteins, e.g., by inhibiting transcription, translation and/or small nucleic acid processing of, for example, one or more biomarkers of the invention, including one or more biomarkers listed in Table 1, or fragment(s) thereof. In one embodiment, the small nucleic acids or antisense oligonucleotides or derivatives thereof are small RNAs (e.g., microRNAs) or complements of small RNAs. In another embodiment, the small nucleic acids or antisense oligonucleotides or derivatives thereof can be single or double stranded and are at least six nucleotides in length and are less than about 1000, 900, 800, 700, 600, 500, 400, 300, 200, 100, 50, 40, 30, 25, 24, 23, 22, 21, 20, 19, 18, 17, 16, 15, or 10 nucleotides in length. In another embodiment, a composition may comprise a library of nucleic acids comprising or capable of expressing small nucleic acids or antisense oligonucleotides or derivatives thereof, or pools of said small nucleic acids or antisense oligonucleotides or derivatives thereof. A pool of nucleic acids may comprise about 2-5, 5-10, 10-20, 10-30 or more nucleic acids comprising or capable of expressing small nucleic acids or antisense oligonucleotides or derivatives thereof.

In one embodiment, binding may be by conventional base pair complementarity, or, for example, in the case of binding to DNA duplexes, through specific interactions in the major groove of the double helix. In general, "antisense" refers to the range of techniques generally employed in the art, and includes any process that relies on specific binding to oligonucleotide sequences.

It is well-known in the art that modifications can be made to the sequence of a miRNA or a pre-miRNA without disrupting miRNA activity. As used herein, the term "functional variant" of a miRNA sequence refers to an oligonucleotide sequence that varies from the natural miRNA sequence, but retains one or more functional characteristics of the miRNA (e.g. cancer cell proliferation inhibition, induction of cancer cell apoptosis, enhancement of cancer cell susceptibility to chemotherapeutic agents, specific miRNA target inhibition). In some embodiments, a functional variant of a miRNA sequence retains all of the functional characteristics of the miRNA. In certain embodiments, a functional variant of a miRNA has a nucleobase sequence that is a least about 60%, 65%, 70%, 75%, 80%, 85%, 90%, 91%, 92%, 93%, 94%, 95%, 96%, 97%, 98% or 99% identical to the miRNA or precursor thereof over a region of about 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleobases, or that the functional variant hybridizes to the complement of the miRNA or precursor thereof under stringent hybridization conditions. Accordingly, in certain embodiments the nucleobase sequence of a functional variant is capable of hybridizing to one or more target sequences of the miRNA.

miRNAs and their corresponding stem-loop sequences described herein may be found in miRBase, an online searchable database of miRNA sequences and annotation, found on the world wide web at microrna.sanger.ac.uk. Entries in the miRBase Sequence database represent a predicted hairpin portion of a miRNA transcript (the stem-loop), with information on the location and sequence of the mature miRNA sequence. The miRNA stem-loop sequences in the database are not strictly precursor miRNAs (pre-miRNAs), and may in some instances include the pre-miRNA and some flanking sequence from the presumed primary transcript. The miRNA nucleobase sequences described herein encompass any version of the miRNA, including the sequences described in Release 10.0 of the miRBase sequence database and sequences described in any earlier Release of the miRBase sequence database. A sequence database release may result in the re-naming of certain miRNAs. A sequence database release may result in a variation of a mature miRNA sequence.

In some embodiments, miRNA sequences of the invention may be associated with a second RNA sequence that may be located on the same RNA molecule or on a separate RNA molecule as the miRNA sequence. In such cases, the miRNA sequence may be referred to as the active strand, while the second RNA sequence, which is at least partially complementary to the miRNA sequence, may be referred to as the complementary strand. The active and complementary strands are hybridized to create a double-stranded RNA that is similar to a naturally occurring miRNA precursor. The activity of a miRNA may be optimized by maximizing uptake of the active strand and minimizing uptake of the complementary strand by the miRNA protein complex that regulates gene translation. This can be done through modification and/or design of the complementary strand.

In some embodiments, the complementary strand is modified so that a chemical group other than a phosphate or hydroxyl at its 5' terminus. The presence of the 5' modification apparently eliminates uptake of the complementary strand and subsequently favors uptake of the active strand by the miRNA protein complex. The 5' modification can be any of a variety of molecules known in the art, including $NH_2$, $NHCOCH_3$, and biotin.

In another embodiment, the uptake of the complementary strand by the miRNA pathway is reduced by incorporating nucleotides with sugar modifications in the first 2-6 nucleotides of the complementary strand. It should be noted that such sugar modifications can be combined with the 5' terminal modifications described above to further enhance miRNA activities.

In some embodiments, the complementary strand is designed so that nucleotides in the 3' end of the complementary strand are not complementary to the active strand. This results in double-strand hybrid RNAs that are stable at the 3' end of the active strand but relatively unstable at the 5' end of the active strand. This difference in stability enhances the uptake of the active strand by the miRNA pathway, while reducing uptake of the complementary strand, thereby enhancing miRNA activity.

Small nucleic acid and/or antisense constructs of the methods and compositions presented herein can be delivered, for example, as an expression plasmid which, when transcribed in the cell, produces RNA which is complementary to at least a unique portion of cellular nucleic acids (e.g., small RNAs, mRNA, and/or genomic DNA). Alternatively, the small nucleic acid molecules can produce RNA which encodes mRNA, miRNA, pre-miRNA, pri-miRNA, miRNA*, anti-miRNA, or a miRNA binding site, or a variant thereof.

For example, selection of plasmids suitable for expressing the miRNAs, methods for inserting nucleic acid sequences into the plasmid, and methods of delivering the recombinant plasmid to the cells of interest are within the skill in the art. See, for example, Zeng et al. (2002) *Mol. Cell* 9:1327-1333; Tuschl (2002), *Nat. Biotechnol.* 20:446-448; Brummelkamp et al. (2002) *Science* 296:550-553; Miyagishi et al. (2002) *Nat. Biotechnol.* 20:497-500; Paddison et al. (2002) *Genes Dev.* 16:948-958; Lee et al. (2002) *Nat. Biotechnol.* 20:500-505; and Paul et al. (2002) *Nat. Biotechnol.* 20:505-508, the entire disclosures of which are herein incorporated by reference.

Alternatively, small nucleic acids and/or antisense constructs are oligonucleotide probes that are generated ex vivo and which, when introduced into the cell, results in hybridization with cellular nucleic acids. Such oligonucleotide probes are preferably modified oligonucleotides that are resistant to endogenous nucleases, e.g., exonucleases and/or endonucleases, and are therefore stable in vivo. Exemplary nucleic acid molecules for use as small nucleic acids and/or antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) BioTechniques 6:958-976; and Stein et al. (1988) Cancer Res 48:2659-2668.

Antisense approaches may involve the design of oligonucleotides (either DNA or RNA) that are complementary to cellular nucleic acids (e.g., complementary to biomarkers listed in Table 1). Absolute complementarity is not required. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a nucleic acid (e.g., RNA) it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the mRNA, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well (Wagner (1994) *Nature* 372: 333). Therefore, oligonucleotides complementary to either the 5' or 3' untranslated, non-coding regions of genes could be used in an antisense approach to inhibit translation of endogenous mRNAs. Oligonucleotides complementary to the 5' untranslated region of the mRNA may include the complement of the AUG start codon. Antisense oligonucleotides complementary to mRNA coding regions are less efficient inhibitors of translation but could also be used in accordance with the methods and compositions presented herein. Whether designed to hybridize to the 5', 3' or coding region of cellular mRNAs, small nucleic acids and/or antisense nucleic acids should be at least six nucleotides in length, and can be less than about 1000, 900, 800, 700, 600, 500, 400, 300, 200, 100, 50, 40, 30, 25, 24, 23, 22, 21, 20, 19, 18, 17, 16, 15, or 10 nucleotides in length.

Regardless of the choice of target sequence, it is preferred that in vitro studies are first performed to quantitate the ability of the antisense oligonucleotide to inhibit gene expression. In one embodiment these studies utilize controls that distinguish between antisense gene inhibition and non-specific biological effects of oligonucleotides. In another embodiment these studies compare levels of the target nucleic acid or protein with that of an internal control nucleic acid or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

Small nucleic acids and/or antisense oligonucleotides can be DNA or RNA or chimeric mixtures or derivatives or modified versions thereof, single-stranded or double-stranded. Small nucleic acids and/or antisense oligonucleotides can be modified at the base moiety, sugar moiety, or phosphate backbone, for example, to improve stability of the molecule, hybridization, etc., and may include other appended groups such as peptides (e.g., for targeting host cell receptors), or agents facilitating transport across the cell membrane (see, e.g., Letsinger et al. (1989) *Proc. Natl. Acad. Sci. U.S.A.* 86:6553-6556; Lemaitre et al. (1987) *Proc. Natl. Acad. Sci. U.S.A.* 84:648-652; PCT Publication No. WO88/09810) or the blood-brain barrier (see, e.g., PCT Publication No. WO89/10134), hybridization-triggered cleavage agents. (See, e.g., Krol et al. (1988) *BioTech.* 6:958-976) or intercalating agents. (See, e.g., Zon (1988) *Pharm. Res.* 5:539-549). To this end, small nucleic acids and/or antisense oligonucleotides may be conjugated to another molecule, e.g., a peptide, hybridization triggered cross-linking agent, transport agent, hybridization-triggered cleavage agent, etc.

Small nucleic acids and/or antisense oligonucleotides may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxytiethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Small nucleic acids and/or antisense oligonucleotides may also comprise at least one modified sugar moiety selected from the group including but not limited to arabinose, 2-fluoroarabinose, xylulose, and hexose.

In certain embodiments, a compound comprises an oligonucleotide (e.g., a miRNA or miRNA encoding oligonucleotide) conjugated to one or more moieties which enhance the activity, cellular distribution or cellular uptake of the resulting oligonucleotide. In certain such embodiments, the moiety is a cholesterol moiety (e.g., antagomirs) or a lipid moiety or liposome conjugate. Additional moieties for conjugation include carbohydrates, phospholipids, biotin, phenazine, folate, phenanthridine, anthraquinone, acridine, fluoresceins, rhodamines, coumarins, and dyes. In certain embodiments, a conjugate group is attached directly to the oligonucleotide. In certain embodiments, a conjugate group is attached to the oligonucleotide by a linking moiety selected from amino, hydroxyl, carboxylic acid, thiol, unsaturations (e.g., double or triple bonds), 8-amino-3,6-dioxaoctanoic acid (ADO), succinimidyl 4-(N-maleimidomethyl) cyclohexane-1-carboxylate (SMCC), 6-aminohexanoic acid (AHEX or AHA), substituted C1-C10 alkyl, substituted or unsubstituted C2-C10 alkenyl, and substituted or unsubstituted C2-C10 alkynyl. In certain such embodiments, a substituent group is selected from hydroxyl, amino, alkoxy, carboxy, benzyl, phenyl, nitro, thiol, thioalkoxy, halogen, alkyl, aryl, alkenyl and alkynyl.

In certain such embodiments, the compound comprises the oligonucleotide having one or more stabilizing groups that are attached to one or both termini of the oligonucleotide to enhance properties such as, for example, nuclease stability. Included in stabilizing groups are cap structures. These terminal modifications protect the oligonucleotide from exonuclease degradation, and can help in delivery and/or localization within a cell. The cap can be present at the 5'-terminus (5'-cap), or at the 3'-terminus (3'-cap), or can be present on both termini. Cap structures include, for example, inverted deoxy abasic caps.

Suitable cap structures include a 4',5'-methylene nucleotide, a 1-(beta-D-erythrofuranosyl) nucleotide, a 4'-thio nucleotide, a carbocyclic nucleotide, a 1,5-anhydrohexitol nucleotide, an L-nucleotide, an alpha-nucleotide, a modified base nucleotide, a phosphorodithioate linkage, a threo-pentofuranosyl nucleotide, an acyclic 3',4'-seco nucleotide, an acyclic 3,4-dihydroxybutyl nucleotide, an acyclic 3,5-dihydroxypentyl nucleotide, a 3'-3'-inverted nucleotide moiety, a 3'-3'-inverted abasic moiety, a 3'-2'-inverted nucleotide moiety, a 3'-2'-inverted abasic moiety, a 1,4-butanediol phosphate, a 3'-phosphoramidate, a hexylphosphate, an aminohexyl phosphate, a 3'-phosphate, a 3'-phosphorothioate, a phosphorodithioate, a bridging methylphosphonate moiety, and a non-bridging methylphosphonate moiety 5'-aminoalkyl phosphate, a 1,3-diamino-2-propyl phosphate, 3-aminopropyl phosphate, a 6-aminohexyl phosphate, a 1,2-aminododecyl phosphate, a hydroxypropyl phosphate, a 5'-5'-inverted nucleotide moiety, a 5'-5'-inverted abasic moiety, a 5'-phosphoramidate, a 5'-phosphorothioate, a 5'-amino, a bridging and/or non-bridging 5'-phosphoramidate, a phosphorothioate, and a 5'-mercapto moiety.

Small nucleic acids and/or antisense oligonucleotides can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, small nucleic acids and/or antisense oligonucleotides comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In a further embodiment, small nucleic acids and/or antisense oligonucleotides are α-anomeric oligonucleotides.

An α-anomeric oligonucleotide forms specific double-stranded hybrids with complementary RNA in which, contrary to the usual b-units, the strands run parallel to each other (Gautier et al. (1987) Nucl. Acids Res. 15:6625-6641). The oligonucleotide is a 2'-O-methylribonucleotide (Inoue et al. (1987) Nucl. Acids Res. 15:6131-6148), or a chimeric RNA-DNA analogue (Inoue et al. (1987) FEBS Lett. 215: 327-330).

Small nucleic acids and/or antisense oligonucleotides of the methods and compositions presented herein may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988) Nucl. Acids Res. 16:3209, methylphosphonate oligonucleotides can be prepared by use of controlled pore glass polymer supports (Sarin et al. (1988) Proc. Natl. Acad. Sci. U.S.A. 85:7448-7451), etc. For example, an isolated miRNA can be chemically synthesized or recombinantly produced using methods known in the art. In some instances, miRNA are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., U.S.A.), Pierce Chemical (part of Perbio Science, Rockford, Ill., U.S.A.), Glen Research (Sterling, Va., U.S.A.), ChemGenes (Ashland, Mass., U.S.A.), Cruachem (Glasgow, UK), and Exiqon (Vedbaek, Denmark).

Small nucleic acids and/or antisense oligonucleotides can be delivered to cells in vivo. A number of methods have been developed for delivering small nucleic acids and/or antisense oligonucleotides DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

In one embodiment, small nucleic acids and/or antisense oligonucleotides may comprise or be generated from double stranded small interfering RNAs (siRNAs), in which sequences fully complementary to cellular nucleic acids (e.g. mRNAs) sequences mediate degradation or in which sequences incompletely complementary to cellular nucleic acids (e.g., mRNAs) mediate translational repression when expressed within cells, or piwiRNAs. In another embodiment, double stranded siRNAs can be processed into single stranded antisense RNAs that bind single stranded cellular RNAs (e.g., microRNAs) and inhibit their expression. RNA interference (RNAi) is the process of sequence-specific, post-transcriptional gene silencing in animals and plants, initiated by double-stranded RNA (dsRNA) that is homologous in sequence to the silenced gene. in vivo, long dsRNA is cleaved by ribonuclease III to generate 21- and 22-nucleotide siRNAs. It has been shown that 21-nucleotide siRNA duplexes specifically suppress expression of endogenous and heterologous genes in different mammalian cell lines, including human embryonic kidney (293) and HeLa cells (Elbashir et al. (2001) Nature 411:494-498). Accordingly, translation of a gene in a cell can be inhibited by contacting the cell with short double stranded RNAs having a length of about 15 to 30 nucleotides or of about 18 to 21 nucleotides or of about 19 to 21 nucleotides. Alternatively, a vector encoding for such siRNAs or short hairpin RNAs (shRNAs) that are metabolized into siRNAs can be introduced into a target cell (see, e.g., McManus et al. (2002) RNA 8:842; Xia et al. (2002) *Nat. Biotechnol.* 20:1006; and Brummelkamp et al. (2002) *Science* 296:550). Vectors that can be used are commercially available, e.g., from OligoEngine under the name pSuper RNAi System™.

Ribozyme molecules designed to catalytically cleave cellular mRNA transcripts can also be used to prevent translation of cellular mRNAs and expression of cellular polypeptides, or both (See, e.g., PCT International Publication WO90/11364, published Oct. 4, 1990; Sarver et al. (1990) *Science* 247:1222-1225 and U.S. Pat. No. 5,093,246). While ribozymes that cleave mRNA at site specific recognition sequences can be used to destroy cellular mRNAs, the use of hammerhead ribozymes is preferred.

Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well-known in the art and is described more fully in Haseloff and Gerlach (1988) *Nature* 334:585-591. The ribozyme may be engineered so that the cleavage recognition site is located near the 5' end of cellular mRNAs; i.e., to increase efficiency and minimize the intracellular accumulation of non-functional mRNA transcripts.

The ribozymes of the methods presented herein also include RNA endoribonucleases (hereinafter "Cech-type ribozymes") such as the one which occurs naturally in *Tetrahymena thermophila* (known as the IVS, or L-19 IVS RNA) and which has been extensively described by Thomas Cech and collaborators (Zaug et al. (1984) *Science* 224:574-578; Zaug et al. (1986) *Science* 231:470-475; Zaug et al. (1986) *Nature* 324:429-433; WO 88/04300; and Been et al. (1986) *Cell* 47:207-216). The Cech-type ribozymes have an eight base pair active site which hybridizes to a target RNA sequence whereafter cleavage of the target RNA takes place. The methods and compositions presented herein encompasses those Cech-type ribozymes which target eight base-pair active site sequences that are present in cellular genes.

As in the antisense approach, the ribozymes can be composed of modified oligonucleotides (e.g., for improved stability, targeting, etc.). A preferred method of delivery involves using a DNA construct "encoding" the ribozyme under the control of a strong constitutive pol III or pol II promoter, so that transfected cells will produce sufficient quantities of the ribozyme to destroy endogenous cellular messages and inhibit translation. Because ribozymes unlike antisense molecules, are catalytic, a lower intracellular concentration is required for efficiency.

Nucleic acid molecules to be used in triple helix formation for the inhibition of transcription of cellular genes are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

Small nucleic acids (e.g., miRNAs, pre-miRNAs, pri-miRNAs, miRNA*, anti-miRNA, or a miRNA binding site, or a variant thereof), antisense oligonucleotides, ribozymes, and triple helix molecules of the methods and compositions presented herein may be prepared by any method known in the art for the synthesis of DNA and RNA molecules. These include techniques for chemically synthesizing oligodeoxyribonucleotides and oligoribonucleotides well-known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone. One of skill in the art will readily understand that polypeptides, small nucleic acids, and antisense oligonucleotides can be further linked to another peptide or polypeptide (e.g., a heterologous peptide), e.g., that serves as a means of protein detection. Non-limiting examples of label peptide or polypeptide moieties useful for detection in the invention include, without limitation, suitable enzymes such as horseradish peroxidase, alkaline phosphatase, beta-galactosidase, or acetylcholinesterase; epitope tags, such as FLAG, MYC, HA, or HIS tags; fluorophores such as green fluorescent protein; dyes; radioisotopes; digoxygenin; biotin; antibodies; polymers; as well as others known in the art, for example, in Principles of Fluorescence Spectroscopy, Joseph R. Lakowicz (Editor), Plenum Pub Corp, 2nd edition (July 1999).

The modulatory agents described herein (e.g., antibodies, small molecules, peptides, fusion proteins, or small nucleic acids) can be incorporated into pharmaceutical compositions and administered to a subject in vivo. The compositions may contain a single such molecule or agent or any combination of agents described herein. "Single active agents" described herein can be combined with other pharmacologically active compounds ("second active agents") known in the art according to the methods and compositions provided herein.

The production and use of biomarker nucleic acid and/or biomarker polypeptide molecules described herein can be facilitated by using standard recombinant techniques. In some embodiments, such techniques use vectors, preferably expression vectors, containing a nucleic acid encoding a biomarker polypeptide or a portion of such a polypeptide. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, namely expression vectors, are capable of directing the expression of genes to which they are operably linked. In general, expression vectors of utility in recombinant DNA techniques are often in the form of plasmids (vectors). However, the present invention is intended to include such other forms of expression vectors, such as viral vectors (e.g., replication defective retroviruses, adenoviruses and adeno-associated viruses), which serve equivalent functions.

The recombinant expression vectors of the present invention comprise a nucleic acid of the present invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Methods in Enzymology: Gene Expression Technology* vol. 185, Academic Press, San Diego, CA (1991). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the present invention can be introduced into host cells to thereby produce proteins or peptides, including fusion proteins or peptides, encoded by nucleic acids as described herein.

The recombinant expression vectors for use in the present invention can be designed for expression of a polypeptide corresponding to a marker of the present invention in prokaryotic (e.g., *E. coli*) or eukaryotic cells (e.g., insect cells {using baculovirus expression vectors}, yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, *Gene* 67:31-40), pMAL (New England Biolabs, Beverly, MA) and pRIT5 (Pharmacia, Piscataway, NJ) which fuse glutathione S-transferase (GST), maltose E binding protein, or protein A, respectively, to the target recombinant protein.

Examples of suitable inducible non-fusion *E. coli* expression vectors include pTrc (Amann et al., 1988, *Gene* 69:301-315) and pET 11d (Studier et al., p. 60-89, In *Gene Expression Technology: Methods in Enzymology* vol. 185, Academic Press, San Diego, CA, 1991). Target biomarker nucleic acid expression from the pTrc vector relies on host RNA polymerase transcription from a hybrid trp-lac fusion promoter. Target biomarker nucleic acid expression from the pET 11d vector relies on transcription from a T7 gn10-lac fusion promoter mediated by a co-expressed viral RNA polymerase (T7 gn1). This viral polymerase is supplied by host strains BL21 (DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacterium with an impaired capacity to proteolytically cleave the recombinant protein (Gottesman, p. 119-128, In *Gene Expression Technology: Methods in Enzymology* vol. 185, Academic Press, San Diego, CA, 1990. Another strategy is to alter the nucleic acid sequence of the nucleic acid to be inserted into an expression vector so that the individual codons for each amino acid are those preferentially utilized in *E. coli* (Wada et al., 1992, *Nucleic Acids Res.* 20:2111-2118). Such alteration of nucleic acid sequences of the present invention can be carried out by standard DNA synthesis techniques.

In another embodiment, the expression vector is a yeast expression vector. Examples of vectors for expression in yeast *S. cerevisiae* include pYepSec1 (Baldari et al., 1987, *EMBO J.* 6:229-234), pMFa (Kurjan and Herskowitz, 1982, *Cell* 30:933-943), pJRY88 (Schultz et al., 1987, *Gene* 54:113-123), pYES2 (Invitrogen Corporation, San Diego, CA), and pPicZ (Invitrogen Corp, San Diego, CA).

Alternatively, the expression vector is a baculovirus expression vector. Baculovirus vectors available for expression of proteins in cultured insect cells (e.g., Sf 9 cells) include the pAc series (Smith et al., 1983, *Mol. Cell Biol.* 3:2156-2165) and the pVL series (Lucklow and Summers, 1989, *Virology* 170:31-39).

In yet another embodiment, a nucleic acid of the present invention is expressed in mammalian cells using a mammalian expression vector. Examples of mammalian expression vectors include pCDM8 (Seed, 1987, *Nature* 329:840) and pMT2PC (Kaufman et al., 1987, *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, *Genes Dev.* 1:268-277), lymphoid-specific promoters (Calame and Eaton, 1988, *Adv. Immunol.* 43:235-275), in particular promoters of T cell receptors (Winoto and Baltimore, 1989, *EMBO J.* 8:729-733) and immunoglobulins (Banerji et al., 1983, *Cell* 33:729-740; Queen and Baltimore, 1983, *Cell* 33:741-748), neuron-specific promoters (e.g., the neurofilament promoter; Byrne and Ruddle, 1989, *Proc. Natl. Acad. Sci. U.S.A.* 86:5473-5477), pancreas-specific promoters (Edlund et al., 1985, *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss, 1990, *Science* 249:374-379) and the α-fetoprotein promoter (Camper and Tilghman, 1989, *Genes Dev.* 3:537-546).

The present invention further provides a recombinant expression vector comprising a DNA molecule cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the present invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue-specific or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes (see Weintraub et al., 1986, *Trends in Genetics*, Vol. 1(1)).

Another aspect of the present invention pertains to host cells into which a recombinant expression vector of the present invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

V. Analyzing Biomarker Nucleic Acids and Polypeptides

Biomarker nucleic acids and/or biomarker polypeptides can be analyzed according to the methods described herein and techniques known to the skilled artisan to identify such genetic or expression alterations useful for the present invention including, but not limited to, 1) an alteration in the level of a biomarker transcript or polypeptide, 2) a deletion or addition of one or more nucleotides from a biomarker gene, 4) a substitution of one or more nucleotides of a biomarker gene, 5) aberrant modification of a biomarker gene, such as an expression regulatory region, and the like.

a. Methods for Detection of Copy Number

Methods of evaluating the copy number of a biomarker nucleic acid are well-known to those of skill in the art. The presence or absence of chromosomal gain or loss can be evaluated simply by a determination of copy number of the regions or markers identified herein.

In one embodiment, a biological sample is tested for the presence of copy number changes in genomic loci containing the genomic marker. A copy number of at least 3, 4, 5, 6, 7, 8, 9, or 10 is predictive of poorer outcome of inhibitor(s) of one or more biomarkers listed in Table 1, and immunotherapy combination treatments.

Methods of evaluating the copy number of a biomarker locus include, but are not limited to, hybridization-based assays. Hybridization-based assays include, but are not limited to, traditional "direct probe" methods, such as Southern blots, in situ hybridization (e.g., FISH and FISH plus SKY) methods, and "comparative probe" methods, such as comparative genomic hybridization (CGH), e.g., cDNA-based or oligonucleotide-based CGH. The methods can be used in a wide variety of formats including, but not limited to, substrate (e.g. membrane or glass) bound methods or array-based approaches.

In one embodiment, evaluating the biomarker gene copy number in a sample involves a Southern Blot. In a Southern Blot, the genomic DNA (typically fragmented and separated on an electrophoretic gel) is hybridized to a probe specific for the target region. Comparison of the intensity of the hybridization signal from the probe for the target region with control probe signal from analysis of normal genomic DNA (e.g., a non-amplified portion of the same or related cell, tissue, organ, etc.) provides an estimate of the relative copy number of the target nucleic acid. Alternatively, a Northern blot may be utilized for evaluating the copy number of encoding nucleic acid in a sample. In a Northern blot, mRNA is hybridized to a probe specific for the target region. Comparison of the intensity of the hybridization signal from the probe for the target region with control probe signal from analysis of normal RNA (e.g., a non-amplified portion of the same or related cell, tissue, organ, etc.) provides an estimate of the relative copy number of the target nucleic acid. Alternatively, other methods well-known in the art to detect RNA can be used, such that higher or lower expression relative to an appropriate control (e.g., a non-amplified portion of the same or related cell tissue, organ, etc.) provides an estimate of the relative copy number of the target nucleic acid.

An alternative means for determining genomic copy number is in situ hybridization (e.g., Angerer (1987) *Meth. Enzymol* 152: 649). Generally, in situ hybridization comprises the following steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application. In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained. The probes are typically labeled, e.g., with radioisotopes or fluorescent reporters. In one embodiment, probes are sufficiently long so as to specifically hybridize with the target nucleic acid(s) under stringent conditions. Probes generally range in length from about 200 bases to about 1000 bases. In some applications it is necessary to block the hybridization capacity of repetitive sequences. Thus, in some embodiments, tRNA, human genomic DNA, or Cot-I DNA is used to block non-specific hybridization.

An alternative means for determining genomic copy number is comparative genomic hybridization. In general, genomic DNA is isolated from normal reference cells, as well as from test cells (e.g., tumor cells) and amplified, if necessary. The two nucleic acids are differentially labeled and then hybridized in situ to metaphase chromosomes of a reference cell. The repetitive sequences in both the reference and test DNAs are either removed or their hybridization capacity is reduced by some means, for example by prehybridization with appropriate blocking nucleic acids and/or including such blocking nucleic acid sequences for said repetitive sequences during said hybridization. The bound, labeled DNA sequences are then rendered in a visualizable form, if necessary. Chromosomal regions in the test cells which are at increased or decreased copy number can be identified by detecting regions where the ratio of signal from the two DNAs is altered. For example, those regions that have decreased in copy number in the test cells will show relatively lower signal from the test DNA than the reference compared to other regions of the genome. Regions that have been increased in copy number in the test cells will show relatively higher signal from the test DNA. Where there are chromosomal deletions or multiplications, differences in the ratio of the signals from the two labels will be detected and the ratio will provide a measure of the copy number. In another embodiment of CGH, array CGH (aCGH), the immobilized chromosome element is replaced with a collection of solid support bound target nucleic acids on an array, allowing for a large or complete percentage of the genome to be represented in the collection of solid support bound targets. Target nucleic acids may comprise cDNAs, genomic DNAs, oligonucleotides (e.g., to detect single nucleotide polymorphisms) and the like. Array-based CGH may also be performed with single-color labeling (as opposed to labeling the control and the possible tumor sample with two different dyes and mixing them prior to hybridization, which will yield a ratio due to competitive hybridization of probes on the arrays). In single color CGH, the control is labeled and hybridized to one array and absolute signals are read, and the possible tumor sample is labeled and hybridized to a second array (with identical content) and absolute signals are read. Copy number difference is calculated based on absolute signals from the two arrays. Methods of preparing immobilized chromosomes or arrays and performing comparative genomic hybridization are well-known in the art (see, e.g., U.S. Pat. Nos. 6,335, 167; 6,197,501; 5,830,645; and 5,665,549 and Albertson (1984) *EMBO J.* 3: 1227-1234; Pinkel (1988) *Proc. Natl. Acad. Sci. U.S.A.* 85: 9138-9142; EPO Pub. No. 430,402; Methods in Molecular Biology, Vol. 33: In situ Hybridization Protocols, Choo, ed., Humana Press, Totowa, N.J. (1994), etc.) In another embodiment, the hybridization protocol of Pinkel, et al. (1998) *Nature Genetics* 20: 207-211, or of Kallioniemi (1992) *Proc. Natl Acad Sci U.S.A.* 89:5321-5325 (1992) is used.

In still another embodiment, amplification-based assays can be used to measure copy number. In such amplification-based assays, the nucleic acid sequences act as a template in an amplification reaction (e.g., Polymerase Chain Reaction (PCR). In a quantitative amplification, the amount of amplification product will be proportional to the amount of template in the original sample. Comparison to appropriate controls, e.g. healthy tissue, provides a measure of the copy number.

Methods of "quantitative" amplification are well-known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols, *A Guide to Methods and Applications*, Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods of the present invention. In fluorogenic quantitative PCR, quantitation is based on amount of fluorescence signals, e.g., TaqMan and SYBR green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. U.S.A.* 86: 1173), self-sustained sequence replication (Guatelli, et al. (1990) *Proc. Nat. Acad. Sci. U.S.A.* 87: 1874), dot PCR, and linker adapter PCR, etc.

Loss of heterozygosity (LOH) and major copy proportion (MCP) mapping (Wang, Z. C., et al. (2004) *Cancer Res* 64(1):64-71; Seymour, A. B., et al. (1994) *Cancer Res* 54, 2761-4; Hahn, S. A., et al. (1995) *Cancer Res* 55, 4670-5; Kimura, M., et al. (1996) *Genes Chromosomes Cancer* 17, 88-93; Li et al., (2008) *MBC Bioinform.* 9, 204-219) may also be used to identify regions of amplification or deletion.

b. Methods for Detection of Biomarker Nucleic Acid Expression

Biomarker expression may be assessed by any of a wide variety of well-known methods for detecting expression of a transcribed molecule or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In preferred embodiments, activity of a particular gene is characterized by a measure of gene transcript (e.g. mRNA), by a measure of the quantity of translated protein, or by a measure of gene product activity. Marker expression can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In another embodiment, detecting or determining expression levels of a biomarker and functionally similar homologs thereof, including a fragment or genetic alteration thereof (e.g., in regulatory or promoter regions thereof) comprises detecting or determining RNA levels for the marker of interest. In one embodiment, one or more cells from the subject to be tested are obtained and RNA is isolated from the cells. In a preferred embodiment, a sample of breast tissue cells is obtained from the subject.

In one embodiment, RNA is obtained from a single cell. For example, a cell can be isolated from a tissue sample by laser capture microdissection (LCM). Using this technique, a cell can be isolated from a tissue section, including a stained tissue section, thereby assuring that the desired cell is isolated (see, e.g., Bonner et al. (1997) *Science* 278: 1481; Emmert-Buck et al. (1996) *Science* 274:998; Fend et al. (1999) *Am. J. Path.* 154: 61 and Murakami et al. (2000) *Kidney Int.* 58:1346). For example, Murakami et al., supra, describe isolation of a cell from a previously immunostained tissue section.

It is also be possible to obtain cells from a subject and culture the cells in vitro, such as to obtain a larger population of cells from which RNA can be extracted. Methods for establishing cultures of non-transformed cells, i.e., primary cell cultures, are known in the art.

When isolating RNA from tissue samples or cells from individuals, it may be important to prevent any further changes in gene expression after the tissue or cells has been removed from the subject. Changes in expression levels are known to change rapidly following perturbations, e.g., heat shock or activation with lipopolysaccharide (LPS) or other reagents. In addition, the RNA in the tissue and cells may quickly become degraded. Accordingly, in a preferred embodiment, the tissue or cells obtained from a subject is snap frozen as soon as possible.

RNA can be extracted from the tissue sample by a variety of methods, e.g., the guanidium thiocyanate lysis followed by CsCl centrifugation (Chirgwin et al., 1979, Biochemistry 18:5294-5299). RNA from single cells can be obtained as described in methods for preparing cDNA libraries from single cells, such as those described in Dulac, C. (1998) Curr. Top. Dev. Biol. 36, 245 and Jena et al. (1996) J. Immunol. Methods 190:199. Care to avoid RNA degradation must be taken, e.g., by inclusion of RNAsin.

The RNA sample can then be enriched in particular species. In one embodiment, poly(A)+RNA is isolated from the RNA sample. In general, such purification takes advantage of the poly-A tails on mRNA. In particular and as noted above, poly-T oligonucleotides may be immobilized within on a solid support to serve as affinity ligands for mRNA. Kits for this purpose are commercially available, e.g., the MessageMaker kit (Life Technologies, Grand Island, NY).

In a preferred embodiment, the RNA population is enriched in marker sequences. Enrichment can be undertaken, e.g., by primer-specific cDNA synthesis, or multiple rounds of linear amplification based on cDNA synthesis and template-directed in vitro transcription (see, e.g., Wang et al. (1989) *Proc. Natl. Acad. Sci. U.S.A.* 86: 9717; Dulac et al., supra, and Jena et al., supra).

The population of RNA, enriched or not in particular species or sequences, can further be amplified. As defined herein, an "amplification process" is designed to strengthen, increase, or augment a molecule within the RNA. For example, where RNA is mRNA, an amplification process such as RT-PCR can be utilized to amplify the mRNA, such that a signal is detectable or detection is enhanced. Such an amplification process is beneficial particularly when the biological, tissue, or tumor sample is of a small size or volume.

Various amplification and detection methods can be used. For example, it is within the scope of the present invention to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR) as described by R. L. Marshall, et al., PCR Methods and Applications 4: 80-84 (1994). Real time PCR may also be used.

Other known amplification methods which can be utilized herein include but are not limited to the so-called "NASBA" or "3SR" technique described in PNAS U.S.A. 87: 1874-1878 (1990) and also described in Nature 350 (No. 6313): 91-92 (1991); Q-beta amplification as described in published European Patent Application (EPA) No. 4544610; strand displacement amplification (as described in G. T. Walker et al., Clin. Chem. 42: 9-13 (1996) and European Patent Application No. 684315; target mediated amplification, as described by PCT Publication WO9322461; PCR; ligase chain reaction (LCR) (see, e.g., Wu and Wallace, Genomics 4, 560 (1989), Landegren et al., Science 241, 1077 (1988)); self-sustained sequence replication (SSR) (see, e.g., Guatelli et al., Proc. Nat. Acad. Sci. U.S.A., 87, 1874 (1990)); and transcription amplification (see, e.g., Kwoh et al., Proc. Natl. Acad. Sci. U.S.A. 86, 1173 (1989)).

Many techniques are known in the state of the art for determining absolute and relative levels of gene expression, commonly used techniques suitable for use in the present invention include Northern analysis, RNase protection assays (RPA), microarrays and PCR-based techniques, such as quantitative PCR and differential display PCR. For example, Northern blotting involves running a preparation of RNA on a denaturing agarose gel, and transferring it to a suitable support, such as activated cellulose, nitrocellulose or glass or nylon membranes. Radiolabeled cDNA or RNA is then hybridized to the preparation, washed and analyzed by autoradiography.

In situ hybridization visualization may also be employed, wherein a radioactively labeled antisense RNA probe is hybridized with a thin section of a biopsy sample, washed, cleaved with RNase and exposed to a sensitive emulsion for autoradiography. The samples may be stained with hematoxylin to demonstrate the histological composition of the sample, and dark field imaging with a suitable light filter shows the developed emulsion. Non-radioactive labels such as digoxigenin may also be used.

Alternatively, mRNA expression can be detected on a DNA array, chip or a microarray. Labeled nucleic acids of a test sample obtained from a subject may be hybridized to a solid surface comprising biomarker DNA. Positive hybridization signal is obtained with the sample containing biomarker transcripts. Methods of preparing DNA arrays and their use are well-known in the art (see, e.g., U.S. Pat. Nos. 6,618,6796; 6,379,897; 6,664,377; 6,451,536; 548,257; U.S. 20030157485 and Schena et al. (1995) *Science* 20, 467-470; Gerhold et al. (1999) *Trends In Biochem. Sci.* 24, 168-173; and Lennon et al. (2000) *Drug Discovery Today* 5, 59-65, which are herein incorporated by reference in their entirety). Serial Analysis of Gene Expression (SAGE) can also be performed (See for example U.S. Patent Application 20030215858).

To monitor mRNA levels, for example, mRNA is extracted from the biological sample to be tested, reverse transcribed, and fluorescently-labeled cDNA probes are generated. The microarrays capable of hybridizing to marker cDNA are then probed with the labeled cDNA probes, the slides scanned and fluorescence intensity measured. This intensity correlates with the hybridization intensity and expression levels.

Types of probes that can be used in the methods described herein include cDNA, riboprobes, synthetic oligonucleotides and genomic probes. The type of probe used will generally be dictated by the particular situation, such as riboprobes for in situ hybridization, and cDNA for Northern blotting, for example. In one embodiment, the probe is directed to nucleotide regions unique to the RNA. The probes may be as short as is required to differentially recognize marker mRNA transcripts, and may be as short as, for example, 15 bases; however, probes of at least 17, 18, 19 or 20 or more bases can be used. In one embodiment, the primers and probes hybridize specifically under stringent conditions to a DNA fragment having the nucleotide sequence corresponding to the marker. As herein used, the term "stringent conditions" means hybridization will occur only if there is at least 95% identity in nucleotide sequences. In another embodiment, hybridization under "stringent conditions" occurs when there is at least 97% identity between the sequences.

The form of labeling of the probes may be any that is appropriate, such as the use of radioisotopes, for example, $^{32}P$ and $^{35}S$. Labeling with radioisotopes may be achieved, whether the probe is synthesized chemically or biologically, by the use of suitably labeled bases.

In one embodiment, the biological sample contains polypeptide molecules from the test subject. Alternatively, the biological sample can contain mRNA molecules from the test subject or genomic DNA molecules from the test subject.

In another embodiment, the methods further involve obtaining a control biological sample from a control subject, contacting the control sample with a compound or agent capable of detecting marker polypeptide, mRNA, genomic DNA, or fragments thereof, such that the presence of the marker polypeptide, mRNA, genomic DNA, or fragments thereof, is detected in the biological sample, and comparing the presence of the marker polypeptide, mRNA, genomic DNA, or fragments thereof, in the control sample with the presence of the marker polypeptide, mRNA, genomic DNA, or fragments thereof in the test sample.

c. Methods for Detection of Biomarker Protein Expression

The activity or level of a biomarker protein can be detected and/or quantified by detecting or quantifying the expressed polypeptide. The polypeptide can be detected and quantified by any of a number of means well-known to those of skill in the art. Aberrant levels of polypeptide expression of the polypeptides encoded by a biomarker nucleic acid and functionally similar homologs thereof, including a fragment or genetic alteration thereof (e.g., in regulatory or promoter regions thereof) are associated with the likelihood of response of a cancer to inhibitor(s) of one or more biomarkers listed in Table 1, and immunotherapy combination treatments. Any method known in the art for detecting polypeptides can be used. Such methods include, but are not limited to, immunodiffusion, immunoelectrophoresis, radioimmunoassay (RIA), enzyme-linked immunosorbent assays (ELISAs), immunofluorescent assays, Western blotting, binder-ligand assays, immunohistochemical techniques, agglutination, complement assays, high performance liquid chromatography (HPLC), thin layer chromatography (TLC), hyperdiffusion chromatography, and the like (e.g., Basic and Clinical Immunology, Sites and Terr, eds., Appleton and Lange, Norwalk, Conn. pp 217-262, 1991 which is incorporated by reference). Preferred are binder-ligand immunoassay methods including reacting antibodies with an epitope or epitopes and competitively displacing a labeled polypeptide or derivative thereof.

For example, ELISA and RIA procedures may be conducted such that a desired biomarker protein standard is labeled (with a radioisotope such as $^{125}I$ or $^{35}S$, or an assayable enzyme, such as horseradish peroxidase or alkaline phosphatase), and, together with the unlabeled sample, brought into contact with the corresponding antibody, whereon a second antibody is used to bind the first, and radioactivity or the immobilized enzyme assayed (competitive assay). Alternatively, the biomarker protein in the sample is allowed to react with the corresponding immobilized antibody, radioisotope- or enzyme-labeled anti-biomarker protein antibody is allowed to react with the system, and radioactivity or the enzyme assayed (ELISA-sandwich assay). Other conventional methods may also be employed as suitable.

The above techniques may be conducted essentially as a "one-step" or "two-step" assay. A "one-step" assay involves contacting antigen with immobilized antibody and, without washing, contacting the mixture with labeled antibody. A "two-step" assay involves washing before contacting, the mixture with labeled antibody. Other conventional methods may also be employed as suitable.

In one embodiment, a method for measuring biomarker protein levels comprises the steps of: contacting a biological specimen with an antibody or variant (e.g., fragment) thereof which selectively binds the biomarker protein, and detecting whether said antibody or variant thereof is bound to said sample and thereby measuring the levels of the biomarker protein.

Enzymatic and radiolabeling of biomarker protein and/or the antibodies may be effected by conventional means. Such means will generally include covalent linking of the enzyme to the antigen or the antibody in question, such as by glutaraldehyde, specifically so as not to adversely affect the activity of the enzyme, by which is meant that the enzyme must still be capable of interacting with its substrate, although it is not necessary for all of the enzyme to be active, provided that enough remains active to permit the assay to be effected. Indeed, some techniques for binding enzyme are non-specific (such as using formaldehyde), and will only yield a proportion of active enzyme.

It is usually desirable to immobilize one component of the assay system on a support, thereby allowing other components of the system to be brought into contact with the component and readily removed without laborious and time-consuming labor. It is possible for a second phase to be immobilized away from the first, but one phase is usually sufficient.

It is possible to immobilize the enzyme itself on a support, but if solid-phase enzyme is required, then this is generally best achieved by binding to antibody and affixing the antibody to a support, models and systems for which are well-known in the art. Simple polyethylene may provide a suitable support.

Enzymes employable for labeling are not particularly limited, but may be selected from the members of the oxidase group, for example. These catalyze production of hydrogen peroxide by reaction with their substrates, and glucose oxidase is often used for its good stability, ease of availability and cheapness, as well as the ready availability of its substrate (glucose). Activity of the oxidase may be assayed by measuring the concentration of hydrogen peroxide formed after reaction of the enzyme-labeled antibody with the substrate under controlled conditions well-known in the art.

Other techniques may be used to detect biomarker protein according to a practitioner's preference based upon the present disclosure. One such technique is Western blotting (Towbin et at., Proc. Nat. Acad. Sci. 76:4350 (1979)), wherein a suitably treated sample is run on an SDS-PAGE gel before being transferred to a solid support, such as a nitrocellulose filter. Anti-biomarker protein antibodies (unlabeled) are then brought into contact with the support and assayed by a secondary immunological reagent, such as labeled protein A or anti-immunoglobulin (suitable labels including $^{125}$I, horseradish peroxidase and alkaline phosphatase). Chromatographic detection may also be used.

Immunohistochemistry may be used to detect expression of biomarker protein, e.g., in a biopsy sample. A suitable antibody is brought into contact with, for example, a thin layer of cells, washed, and then contacted with a second, labeled antibody. Labeling may be by fluorescent markers, enzymes, such as peroxidase, avidin, or radiolabeling. The assay is scored visually, using microscopy.

Anti-biomarker protein antibodies, such as intrabodies, may also be used for imaging purposes, for example, to detect the presence of biomarker protein in cells and tissues of a subject. Suitable labels include radioisotopes, iodine ($^{125}$I $^{121}$I), carbon ($^{14}$C), sulphur ($^{35}$S), tritium ($^{3}$H), indium ($^{112}$In), and technetium ($^{99m}$Tc), fluorescent labels, such as fluorescein and rhodamine, and biotin.

For in vivo imaging purposes, antibodies are not detectable, as such, from outside the body, and so must be labeled, or otherwise modified, to permit detection. Markers for this purpose may be any that do not substantially interfere with the antibody binding, but which allow external detection. Suitable markers may include those that may be detected by X-radiography, NMR or MRI. For X-radiographic techniques, suitable markers include any radioisotope that emits detectable radiation but that is not overtly harmful to the subject, such as barium or cesium, for example. Suitable markers for NMR and MRI generally include those with a detectable characteristic spin, such as deuterium, which may be incorporated into the antibody by suitable labeling of nutrients for the relevant hybridoma, for example.

The size of the subject, and the imaging system used, will determine the quantity of imaging moiety needed to produce diagnostic images. In the case of a radioisotope moiety, for a human subject, the quantity of radioactivity injected will normally range from about 5 to 20 millicuries of technetium-99. The labeled antibody or antibody fragment will then preferentially accumulate at the location of cells which contain biomarker protein. The labeled antibody or antibody fragment can then be detected using known techniques.

Antibodies that may be used to detect biomarker protein include any antibody, whether natural or synthetic, full length or a fragment thereof, monoclonal or polyclonal, that binds sufficiently strongly and specifically to the biomarker protein to be detected. An antibody may have a $K_d$ of at most about $10^{-6}$M, $10^{-7}$M, $10^{-8}$M, $10^{-9}$M, $10^{-10}$M, $10^{-11}$M, $10^{-12}$M. The phrase "specifically binds" refers to binding of, for example, an antibody to an epitope or antigen or antigenic determinant in such a manner that binding can be displaced or competed with a second preparation of identical or similar epitope, antigen or antigenic determinant. An antibody may bind preferentially to the biomarker protein relative to other proteins, such as related proteins.

Antibodies are commercially available or may be prepared according to methods known in the art.

Antibodies and derivatives thereof that may be used encompass polyclonal or monoclonal antibodies, chimeric, human, humanized, primatized (CDR-grafted), veneered or single-chain antibodies as well as functional fragments, i.e., biomarker protein binding fragments, of antibodies. For example, antibody fragments capable of binding to a biomarker protein or portions thereof, including, but not limited to, Fv, Fab, Fab' and F(ab') 2 fragments can be used. Such fragments can be produced by enzymatic cleavage or by recombinant techniques. For example, papain or pepsin cleavage can generate Fab or F(ab') 2 fragments, respectively. Other proteases with the requisite substrate specificity can also be used to generate Fab or F(ab') 2 fragments. Antibodies can also be produced in a variety of truncated forms using antibody genes in which one or more stop codons have been introduced upstream of the natural stop site. For example, a chimeric gene encoding a F(ab') 2 heavy chain portion can be designed to include DNA sequences encoding the CH, domain and hinge region of the heavy chain.

Synthetic and engineered antibodies are described in, e.g., Cabilly et al., U.S. Pat. No. 4,816,567 Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0451216 B1; and Padlan, E. A. et al., EP 0519596 A1. See also, Newman, R. et al., BioTechnology, 10: 1455-1460 (1992), regarding primatized antibody, and Ladner et al., U.S. Pat. No. 4,946,778 and Bird, R. E. et al., Science, 242: 423-426 (1988)) regarding single-chain antibodies. Antibodies produced from a library, e.g., phage display library, may also be used.

In some embodiments, agents that specifically bind to a biomarker protein other than antibodies are used, such as peptides. Peptides that specifically bind to a biomarker protein can be identified by any means known in the art. For example, specific peptide binders of a biomarker protein can be screened for using peptide phage display libraries.

d. Methods for Detection of Biomarker Structural Alterations

The following illustrative methods can be used to identify the presence of a structural alteration in a biomarker nucleic acid and/or biomarker polypeptide molecule in order to, for example, identify the one or more biomarkers listed in Table 1, or other biomarkers used in the immunotherapies described herein that are overexpressed, overfunctional, and the like.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. U.S.A. 91:360-364), the latter of which can be particularly useful for detecting point mutations in a biomarker nucleic acid such as a biomarker gene (see Abravaya et al. (1995) Nucleic Acids Res. 23:675-682). This method can include the steps of collecting a sample of cells from a subject, isolating nucleic acid (e.g., genomic, mRNA or both) from the cells of the sample, contacting the nucleic acid sample with one or more primers which specifically hybridize to a biomarker gene under conditions such that hybridization and amplification of the biomarker gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self-sustained sequence replication (Guatelli, J. C. et al. (1990) Proc. Natl. Acad. Sci. U.S.A. 87:1874-1878), transcriptional amplification system (Kwoh, D. Y. et al. (1989) Proc. Natl. Acad. Sci. U.S.A. 86:1173-1177), Q-Beta Replicase (Lizardi, P. M. et al. (1988) Bio-Technology 6:1197), or any other nucleic acid amplification method, followed by the detection of the amplified molecules using techniques well-known to those of skill in the art. These detection schemes are especially useful for the detection of nucleic acid molecules if such molecules are present in very low numbers.

In an alternative embodiment, mutations in a biomarker nucleic acid from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in biomarker nucleic acid can be identified by hybridizing a sample and control nucleic acids, e.g., DNA or RNA, to high density arrays containing hundreds or thousands of oligonucleotide probes (Cronin, M. T. et al. (1996) Hum. Mutat. 7:244-255; Kozal, M. J. et al. (1996) Nat. Med. 2:753-759). For example, biomarker genetic mutations can be identified in two dimensional arrays containing light-generated DNA probes as described in Cronin et al. (1996) supra. Briefly, a first hybridization array of probes can be used to scan through long stretches of DNA in a sample and control to identify base changes between the sequences by making linear arrays of sequential, overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene. Such biomarker genetic mutations can be identified in a variety of contexts, including, for example, germline and somatic mutations.

In yet another embodiment, any of a variety of sequencing reactions known in the art can be used to directly sequence a biomarker gene and detect mutations by comparing the sequence of the sample biomarker with the corresponding wild-type (control) sequence. Examples of sequencing reactions include those based on techniques developed by Maxam and Gilbert (1977) *Proc. Natl. Acad. Sci. U.S.A.* 74:560 or Sanger (1977) *Proc. Natl. Acad Sci. U.S.A.* 74:5463. It is also contemplated that any of a variety of automated sequencing procedures can be utilized when performing the diagnostic assays (Naeve (1995) *Biotechniques* 19:448-53), including sequencing by mass spectrometry (see, e.g., PCT International Publication No. WO 94/16101; Cohen et al. (1996) *Adv. Chromatogr.* 36:127-162; and Griffin et al. (1993) *Appl. Biochem. Biotechnol.* 38:147-159).

Other methods for detecting mutations in a biomarker gene include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes formed by hybridizing (labeled) RNA or DNA containing the wild-type biomarker sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with SI nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl. Acad. Sci. U.S.A.* 85:4397 and Saleeba et al. (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in biomarker cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662). According to an exemplary embodiment, a probe based on a biomarker sequence, e.g., a wild-type biomarker treated with a DNA mismatch repair enzyme, and the cleavage products, if any, can be detected from electrophoresis protocols or the like (e.g., U.S. Pat. No. 5,459,039.)

In other embodiments, alterations in electrophoretic mobility can be used to identify mutations in biomarker genes. For example, single strand conformation polymorphism (SSCP) may be used to detect differences in electrophoretic mobility between mutant and wild type nucleic acids (Orita et al. (1989) *Proc Natl. Acad. Sci U.S.A.* 86:2766; see also Cotton (1993) *Mutat. Res.* 285:125-144 and Hayashi (1992) *Genet. Anal. Tech. Appl.* 9:73-79). Single-stranded DNA fragments of sample and control biomarker nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163; Saiki et al. (1989) *Proc. Natd. Acad. Sci. U.S.A.* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci U.S.A.* 88:189). In such cases, ligation will occur only if there is a perfect match at the 3' end of the 5' sequence making it possible to detect the presence of a known mutation at a specific site by looking for the presence or absence of amplification.

3. Anti-Cancer Therapies

The efficacy of inhibitors of one or more biomarkers listed in Table 1, and immunotherapy combination treatment is predicted according to biomarker amount and/or activity associated with a cancer in a subject according to the methods described herein. In one embodiment, such inhibitor and immunotherapy combination treatments (e.g., one or more inhibitor and immunotherapy combination treatment in combination with one or more additional anti-cancer therapies, such as another immune checkpoint inhibitor) can be administered, particularly if a subject has first been indicated as being a likely responder to inhibitor and immunotherapy combination treatment. In another embodiment, such inhibitor and immunotherapy combination treatment can be avoided once a subject is indicated as not being a likely responder to inhibitor and immunotherapy combination treatment and an alternative treatment regimen, such as targeted and/or untargeted anti-cancer therapies can be administered. Combination therapies are also contemplated and can comprise, for example, one or more chemotherapeutic agents and radiation, one or more chemotherapeutic agents and immunotherapy, or one or more chemotherapeutic agents, radiation and chemotherapy, each combination of which can be with anti-immune checkpoint therapy. In addition, any representative embodiment of an agent to modulate a particular target can be adapted to any other target described herein by the ordinarily skilled artisn (e.g., direct and indirect PD-1 inhibitors described herein can be applied to other immune checkpoint inhibitors and/or one or more biomarkers listed in Table 1, such as monospecific antibodies, bispecific antibodies, non-activating forms, small molecules, peptides, interfering nucleic acids, and the like).

The term "targeted therapy" refers to administration of agents that selectively interact with a chosen biomolecule to thereby treat cancer. One example includes immunotherapies such as immune checkpoint inhibitors, which are well-known in the art. For example, anti-PD-1 pathway agents, such as therapeutic monoclonal blocking antibodies, which are well-known in the art and described above, can be used to target tumor microenvironments and cells expressing unwanted components of the PD-1 pathway, such as PD-1, PD-L1, and/or PD-L2.

For example, the term "PD-1 pathway" refers to the PD-1 receptor and its ligands, PD-L1 and PD-L2. "PD-1 pathway inhibitors" block or otherwise reduce the interaction between PD-1 and one or both of its ligands such that the immunoinhibitory signaling otherwise generated by the interaction is blocked or otherwise reduced. Anti-immune checkpoint inhibitors can be direct or indirect. Direct anti-immune checkpoint inhibitors block or otherwise reduce the interaction between an immune checkpoint and at least one of its ligands. For example, PD-1 inhibitors can block PD-1 binding with one or both of its ligands. Direct PD-1 combination inhibitors are well-known in the art, especially since the natural binding partners of PD-1 (e.g., PD-L1 and PD-L2), PD-L1 (e.g., PD-1 and B7-1), and PD-L2 (e.g., PD-1 and RGMb) are known.

For example, agents which directly block the interaction between PD-1 and PD-L1, PD-1 and PD-L2, PD-1 and both PD-L1 and PD-L2, such as a bispecific antibody, can prevent inhibitory signaling and upregulate an immune response (i.e., as a PD-1 pathway inhibitor). Alternatively, agents that indirectly block the interaction between PD-1 and one or both of its ligands can prevent inhibitory signaling and upregulate an immune response. For example, B7-1 or a soluble form thereof, by binding to a PD-L1 polypeptide indirectly reduces the effective concentration of PD-L1 polypeptide available to bind to PD-1. Exemplary agents include monospecific or bispecific blocking antibodies against PD-1, PD-L1, and/or PD-L2 that block the interaction between the receptor and ligand(s); a non-activating form of PD-1, PD-L1, and/or PD-L2 (e.g., a dominant negative or soluble polypeptide), small molecules or peptides that block the interaction between PD-1, PD-L1, and/or PD-L2; fusion proteins (e.g. the extracellular portion of PD-1, PD-L1, and/or PD-L2, fused to the Fc portion of an antibody or immunoglobulin) that bind to PD-1, PD-L1, and/or PD-L2 and inhibit the interaction between the receptor and ligand(s); a non-activating form of a natural PD-1, PD-L2, and/or PD-L2 ligand, and a soluble form of a natural PD-1, PD-L2, and/or PD-L2 ligand.

Indirect anti-immune checkpoint inhibitors block or otherwise reduce the immunoinhibitory signaling generated by the interaction between the immune checkpoint and at least one of its ligands. For example, an inhibitor can block the interaction between PD-1 and one or both of its ligands without necessarily directly blocking the interaction between PD-1 and one or both of its ligands. For example, indirect inhibitors include intrabodies that bind the intracellular portion of PD-1 and/or PD-L1 required to signal to block or otherwise reduce the immunoinhibitory signaling. Similarly, nucleic acids that reduce the expression of PD-1, PD-L1, and/or PD-L2 can indirectly inhibit the interaction between PD-1 and one or both of its ligands by removing the availability of components for interaction. Such nucleic acid molecules can block PD-L1, PD-L2, and/or PD-L2 transcription or translation.

Similar, agents which directly block the interaction between one or more biomarkers listed in Table 1, and the binding partners and/or substrates of such one or more biomarkers, and the like, can remove the inhibition to such one or more biomarkers-regulated signaling and its downstream immune responses, such as increasing sensitivity to interferon signaling. Alternatively, agents that indirectly block the interaction between such one or more biomarkers and its binding partners/substrates can remove the inhibition to such one or more biomarkers-regulated signaling and its downstream immune responses. For example, a truncated or dominant negative form of such one or more biomarkers, such as biomarker fragments without functional activity, by binding to a substrate of such one or more biomarkers and indirectly reducing the effective concentration of such substrate available to bind to the one or more biomarkers in cell. Exemplary agents include monospecific or bispecific blocking antibodies, especially intrbodies, against the one or more biomarkers and/or their substrate(s) that block the interaction between the one or more biomarkers and their substrate(s); a non-active form of such one or more biomarkers and/or their substrate(s) (e.g., a dominant negative polypeptide), small molecules or peptides that block the interaction between such one or more biomarkers and their substrate(s) or the activity of such one or more biomarkers; and a non-activating form of a natural biomarker and/or its substrate(s).

Immunotherapies that are designed to elicit or amplify an immune response are referred to as "activation immunotherapies." Immunotherapies that are designed to reduce or suppress an immune response are referred to as "suppression immunotherapies." Any agent believed to have an immune system effect on the genetically modified transplanted cancer cells can be assayed to determine whether the agent is an immunotherapy and the effect that a given genetic modification has on the modulation of immune response. In some embodiments, the immunotherapy is cancer cell-specific. In some embodiments, immunotherapy can be "untargeted," which refers to administration of agents that do not selectively interact with immune system cells, yet modulates immune system function. Representative examples of untargeted therapies include, without limitation, chemotherapy, gene therapy, and radiation therapy.

Immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer.

In one embodiment, immunotherapy comprises adoptive cell-based immunotherapies. Well-known adoptive cell-based immunotherapeutic modalities, including, without limitation, Irradiated autologous or allogeneic tumor cells, tumor lysates or apoptotic tumor cells, antigen-presenting cell-based immunotherapy, dendritic cell-based immunotherapy, adoptive T cell transfer, adoptive CAR T cell therapy, autologous immune enhancement therapy (AIET), cancer vaccines, and/or antigen presenting cells. Such cell-based immunotherapies can be further modified to express one or more gene products to further modulate immune responses, such as expressing cytokines like GM-CSF, and/or to express tumor-associated antigen (TAA) antigens, such as Mage-1, gp-100, patient-specific neoantigen vaccines, and the like.

In another embodiment, immunotherapy comprises non-cell-based immunotherapies. In one embodiment, compositions comprising antigens with or without vaccine-enhancing adjuvants are used. Such compositions exist in many well-known forms, such as peptide compositions, oncolytic viruses, recombinant antigen comprising fusion proteins, and the like. In still another embodiment, immunomodulatory interleukins, such as IL-2, IL-6, IL-7, IL-12, IL-17, IL-23, and the like, as well as modulators thereof (e.g., blocking antibodies or more potent or longer lasting forms) are used. In yet another embodiment, immunomodulatory cytokines, such as interferons, G-CSF, imiquimod, TNFalpha, and the like, as well as modulators thereof (e.g., blocking antibodies or more potent or longer lasting forms) are used. In another embodiment, immunomodulatory chemokines, such as CCL3, CCL26, and CXCL7, and the like, as well as modulators thereof (e.g., blocking antibodies or more potent or longer lasting forms) are used. In another embodiment, immunomodulatory molecules targeting immunosuppression, such as STAT3 signaling modulators, NFkappaB signaling modulators, and immune checkpoint modulators, are used. The terms "immune checkpoint" and "anti-immune checkpoint therapy" are described above.

In still another embodiment, immunomodulatory drugs, such as immunocytostatic drugs, glucocorticoids, cytostatics, immunophilins and modulators thereof (e.g., rapamycin, a calcineurin inhibitor, tacrolimus, ciclosporin (cyclosporin), pimecrolimus, abetimus, gusperimus, ridaforolimus, everolimus, temsirolimus, zotarolimus, etc.), hydrocortisone (cortisol), cortisone acetate, prednisone, prednisolone, methylprednisolone, dexamethasone, betamethasone, triamcinolone, beclometasone, fludrocortisone acetate, deoxycorticosterone acetate (doca) aldosterone, a non-glucocorticoid steroid, a pyrimidine synthesis inhibitor, leflunomide, teriflunomide, a folic acid analog, methotrexate, anti-thymocyte globulin, anti-lymphocyte globulin, thalidomide, lenalidomide, pentoxifylline, bupropion, curcumin, catechin, an opioid, an IMPDH inhibitor, mycophenolic acid, myriocin, fingolimod, an NF-xB inhibitor, raloxifene, drotrecogin alfa, denosumab, an NF-xB signaling cascade inhibitor, disulfiram, olmesartan, dithiocarbamate, a proteasome inhibitor, bortezomib, MG132, Prol, NPI-0052, curcumin, genistein, resveratrol, parthenolide, thalidomide, lenalidomide, flavopiridol, non-steroidal anti-inflammatory drugs (NSAIDs), arsenic trioxide, dehydroxymethylepoxyquinomycin (DHMEQ), I3C(indole-3-carbinol)/DIM(di-indolmethane) (13C/DIM), Bay 11-7082, luteolin, cell permeable peptide SN-50, IKBa.-super repressor overexpression, NFKB decoy oligodeoxynucleotide (ODN), or a derivative or analog of any thereo, are used. In yet another embodiment, immunomodulatory antibodies or protein are used. For example, antibodies that bind to CD40, Toll-like receptor (TLR), OX40, GITR, CD27, or to 4-1BB, T-cell bispecific antibodies, an anti-IL-2 receptor antibody, an anti-CD3 antibody, OKT3 (muromonab), otelixizumab, teplizumab, visilizumab, an anti-CD4 antibody, clenoliximab, keliximab, zanolimumab, an anti-CD11 a antibody, efalizumab, an anti-CD18 antibody, erlizumab, rovelizumab, an anti-CD20 antibody, afutuzumab, ocrelizumab, ofatumumab, pascolizumab, rituximab, an anti-CD23 antibody, lumiliximab, an anti-CD40 antibody, teneliximab, toralizumab, an anti-CD40L antibody, ruplizumab, an anti-CD62L antibody, aselizumab, an anti-CD80 antibody, galiximab, an anti-CD147 antibody, gavilimomab, a B-Lymphocyte stimulator (BLyS) inhibiting antibody, belimumab, an CTLA4-Ig fusion protein, abatacept, belatacept, an anti-CTLA4 antibody, ipilimumab, tremelimumab, an anti-eotaxin 1 antibody, bertilimumab, an anti-a4-integrin antibody, natalizumab, an anti-IL-6R antibody, tocilizumab, an anti-LFA-1 antibody, odulimomab, an anti-CD25 antibody, basiliximab, daclizumab, inolimomab, an anti-CD5 antibody, zolimomab, an anti-CD2 antibody, siplizumab, nerelimomab, faralimomab, atlizumab, atorolimumab, cedelizumab, dorlimomab aritox, dorlixizumab, fontolizumab, gantenerumab, gomiliximab, lebrilizumab, maslimomab, morolimumab, pexelizumab, reslizumab, rovelizumab, talizumab, telimomab aritox, vapaliximab, vepalimomab, aflibercept, alefacept, rilonacept, an IL-1 receptor antagonist, anakinra, an anti-IL-5 antibody, mepolizumab, an IgE inhibitor, omalizumab, talizumab, an IL12 inhibitor, an IL23 inhibitor, ustekinumab, and the like.

Nutritional supplements that enhance immune responses, such as vitamin A, vitamin E, vitamin C, and the like, are well-known in the art (see, for example, U.S. Pat. Nos. 4,981,844 and 5,230,902 and PCT Publ. No. WO 2004/004483) can be used in the methods described herein.

Similarly, agents and therapies other than immunotherapy or in combination thereof can be used with in combination with inhibitors of one or more biomarkers listed in Table 1, with or without immunotherapies to stimulate an immune response to thereby treat a condition that would benefit therefrom. For example, chemotherapy, radiation, epigenetic modifiers (e.g., histone deacetylase (HDAC) modifiers, methylation modifiers, phosphorylation modifiers, and the like), targeted therapy, and the like are well-known in the art.

The term "untargeted therapy" refers to administration of agents that do not selectively interact with a chosen biomolecule yet treat cancer. Representative examples of untargeted therapies include, without limitation, chemotherapy, gene therapy, and radiation therapy.

In one embodiment, chemotherapy is used. Chemotherapy includes the administration of a chemotherapeutic agent. Such a chemotherapeutic agent may be, but is not limited to, those selected from among the following groups of compounds: platinum compounds, cytotoxic antibiotics, antimetabolites, anti-mitotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: cisplatin, treosulfan, and trofosfamide; plant alkaloids: vinblastine, paclitaxel, docetaxol; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiments, PARP (e.g., PARP-1 and/or PARP-2) inhibitors are used and such inhibitors are well-known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1,8-naphthalimide; (Trevigen); 6(5H)-phenanthridinone (Trevigen); benzamide (U.S. Pat. Re. 36,397); and NU1025 (Bowman et al.). The mechanism of action is generally related to the ability of PARP inhibitors to bind PARP and decrease its activity. PARP catalyzes the conversion of.beta.-nicotinamide adenine dinucleotide (NAD+) into nicotinamide and poly-ADP-ribose (PAR). Both poly (ADP-ribose) and PARP have been linked to regulation of transcription, cell proliferation, genomic stability, and carcinogenesis (Bouchard V. J. et.al. Experimental Hematology, Volume 31, Number 6, June 2003, pp. 446-454(9); Herceg Z.; Wang Z.-Q. Mutation Research/Fundamental and Molecular Mechanisms of Mutagenesis, Volume 477, Number 1, 2 Jun. 2001, pp. 97-110(14)). Poly(ADP-ribose) polymerase 1 (PARP1) is a key molecule in the repair of DNA single-strand breaks (SSBs) (de Murcia J. et al. 1997. Proc Natl Acad Sci U.S.A. 94:7303-7307; Schreiber V, Dantzer F, Ame J C, de Murcia G (2006) Nat Rev Mol Cell Biol 7:517-528; Wang Z Q, et al. (1997) Genes Dev 11:2347-2358). Knockout of SSB repair by inhibition of PARP1 function induces DNA double-strand breaks (DSBs) that can trigger synthetic lethality in cancer cells with defective homology-directed DSB repair (Bryant H E, et al. (2005) Nature 434:913-917; Farmer H, et al. (2005) Nature 434:917-921). The foregoing examples of chemotherapeutic agents are illustrative, and are not intended to be limiting.

In another embodiment, radiation therapy is used. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In another embodiment, surgical intervention can occur to physically remove cancerous cells and/or tissues.

In still another embodiment, hormone therapy is used. Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

In yet another embodiment, hyperthermia, a procedure in which body tissue is exposed to high temperatures (up to 106° F.) is used. Heat may help shrink tumors by damaging cells or depriving them of substances they need to live. Hyperthermia therapy can be local, regional, and whole-body hyperthermia, using external and internal heating devices. Hyperthermia is almost always used with other forms of therapy (e.g., radiation therapy, chemotherapy, and biological therapy) to try to increase their effectiveness. Local hyperthermia refers to heat that is applied to a very small area, such as a tumor. The area may be heated externally with high-frequency waves aimed at a tumor from a device outside the body. To achieve internal heating, one of several types of sterile probes may be used, including thin, heated wires or hollow tubes filled with warm water; implanted microwave antennae; and radiofrequency electrodes. In regional hyperthermia, an organ or a limb is heated. Magnets and devices that produce high energy are placed over the region to be heated. In another approach, called perfusion, some of the patient's blood is removed, heated, and then pumped (perfused) into the region that is to be heated internally. Whole-body heating is used to treat metastatic cancer that has spread throughout the body. It can be accomplished using warm-water blankets, hot wax, inductive coils (like those in electric blankets), or thermal chambers (similar to large incubators). Hyperthermia does not cause any marked increase in radiation side effects or complications. Heat applied directly to the skin, however, can cause discomfort or even significant local pain in about half the patients treated. It can also cause blisters, which generally heal rapidly.

In still another embodiment, photodynamic therapy (also called PDT, photoradiation therapy, phototherapy, or photochemotherapy) is used for the treatment of some types of cancer. It is based on the discovery that certain chemicals known as photosensitizing agents can kill one-celled organisms when the organisms are exposed to a particular type of light. PDT destroys cancer cells through the use of a fixed-frequency laser light in combination with a photosensitizing agent. In PDT, the photosensitizing agent is injected into the bloodstream and absorbed by cells all over the body. The agent remains in cancer cells for a longer time than it does in normal cells. When the treated cancer cells are exposed to laser light, the photosensitizing agent absorbs the light and produces an active form of oxygen that destroys the treated cancer cells. Light exposure must be timed carefully so that it occurs when most of the photosensitizing agent has left healthy cells but is still present in the cancer cells. The laser light used in PDT can be directed through a fiber-optic (a very thin glass strand). The fiber-optic is placed close to the cancer to deliver the proper amount of light. The fiber-optic can be directed through a bronchoscope into the lungs for the treatment of lung cancer or through an endoscope into the esophagus for the treatment of esophageal cancer. An advantage of PDT is that it causes minimal damage to healthy tissue. However, because the laser light currently in use cannot pass through more than about 3 centimeters of tissue (a little more than one and an eighth inch), PDT is mainly used to treat tumors on or just under the skin or on the lining of internal organs. Photodynamic therapy makes the skin and eyes sensitive to light for 6 weeks or more after treatment. Patients are advised to avoid direct sunlight and bright indoor light for at least 6 weeks. If patients must go outdoors, they need to wear protective clothing, including sunglasses. Other temporary side effects of PDT are related to the treatment of specific areas and can include coughing, trouble swallowing, abdominal pain, and painful breathing or shortness of breath. In December 1995, the U.S. Food and Drug Administration (FDA) approved a photosensitizing agent called porfimer sodium, or Photofrin®, to relieve symptoms of esophageal cancer that is causing an obstruction and for esophageal cancer that cannot be satisfactorily treated with lasers alone. In January 1998, the FDA approved porfimer sodium for the treatment of early non-small cell lung cancer in patients for whom the usual treatments for lung cancer are not appropriate. The National Cancer Institute and other institutions are supporting clinical trials (research studies) to evaluate the use of photodynamic therapy for several types of cancer, including cancers of the bladder, brain, larynx, and oral cavity.

In yet another embodiment, laser therapy is used to harness high-intensity light to destroy cancer cells. This technique is often used to relieve symptoms of cancer such as bleeding or obstruction, especially when the cancer cannot be cured by other treatments. It may also be used to treat cancer by shrinking or destroying tumors. The term "laser" stands for light amplification by stimulated emission of radiation. Ordinary light, such as that from a light bulb, has many wavelengths and spreads in all directions. Laser light, on the other hand, has a specific wavelength and is focused in a narrow beam. This type of high-intensity light contains a lot of energy. Lasers are very powerful and may be used to cut through steel or to shape diamonds. Lasers also can be used for very precise surgical work, such as repairing a damaged retina in the eye or cutting through tissue (in place of a scalpel). Although there are several different kinds of lasers, only three kinds have gained wide use in medicine: Carbon dioxide ($CO_2$) laser—This type of laser can remove thin layers from the skin's surface without penetrating the deeper layers. This technique is particularly useful in treating tumors that have not spread deep into the skin and certain precancerous conditions. As an alternative to traditional scalpel surgery, the $CO_2$ laser is also able to cut the skin. The laser is used in this way to remove skin cancers. Neodymium:yttrium-aluminum-garnet (Nd:YAG) laser—Light from this laser can penetrate deeper into tissue than light from the other types of lasers, and it can cause blood to clot quickly. It can be carried through optical fibers to less accessible parts of the body. This type of laser is sometimes used to treat throat cancers. Argon laser—This laser can pass through only superficial layers of tissue and is therefore useful in dermatology and in eye surgery. It also is used with light-sensitive dyes to treat tumors in a procedure known as photodynamic therapy (PDT). Lasers have several advantages over standard surgical tools, including: Lasers are more precise than scalpels. Tissue near an incision is protected, since there is little contact with surrounding skin or other tissue. The heat produced by lasers sterilizes the surgery site, thus reducing the risk of infection. Less operating time may be needed because the precision of the laser allows for a smaller incision. Healing time is often shortened; since laser heat seals blood vessels, there is less bleeding, swelling, or scarring. Laser surgery may be less complicated. For example, with fiber optics, laser light can be directed to parts of the body without making a large incision. More procedures may be done on an outpatient basis. Lasers can be used in two ways to treat cancer: by shrinking or destroying a tumor with heat, or by activating a chemical—known as a photosensitizing agent—that destroys cancer cells. In PDT, a photosensitizing agent is retained in cancer cells and can be stimulated by light to cause a reaction that kills cancer cells. $CO_2$ and Nd:YAG lasers are used to shrink or destroy tumors. They may be used with endoscopes, tubes that allow physicians to see into certain areas of the body, such as the bladder. The light from some lasers can be transmitted through a flexible endoscope fitted with fiber optics. This allows physicians to see and work in parts of the body that could not otherwise be reached except by surgery and therefore allows very precise aiming of the laser beam. Lasers also may be used with low-power microscopes, giving the doctor a clear view of the site being treated. Used with other instruments, laser systems can produce a cutting area as small as 200 microns in diameter—less than the width of a very fine thread. Lasers are used to treat many types of cancer. Laser surgery is a standard treatment for certain stages of glottis (vocal cord), cervical, skin, lung, vaginal, vulvar, and penile cancers. In addition to its use to destroy the cancer, laser surgery is also used to help relieve symptoms caused by cancer (palliative care). For example, lasers may be used to shrink or destroy a tumor that is blocking a patient's trachea (windpipe), making it easier to breathe. It is also sometimes used for palliation in colorectal and anal cancer. Laser-induced interstitial thermotherapy (LITT) is one of the most recent developments in laser therapy. LITT uses the same idea as a cancer treatment called hyperthermia; that heat may help shrink tumors by damaging cells or depriving them of substances they need to live. In this treatment, lasers are directed to interstitial areas (areas between organs) in the body. The laser light then raises the temperature of the tumor, which damages or destroys cancer cells.

The duration and/or dose of treatment with therapies may vary according to the particular therapeutic agent or combination thereof. An appropriate treatment time for a particular cancer therapeutic agent will be appreciated by the skilled artisan. The present invention contemplates the continued assessment of optimal treatment schedules for each cancer therapeutic agent, where the phenotype of the cancer of the subject as determined by the methods of the present invention is a factor in determining optimal treatment doses and schedules.

Any means for the introduction of a polynucleotide into mammals, human or non-human, or cells thereof may be adapted to the practice of this invention for the delivery of the various constructs of the present invention into the intended recipient. In one embodiment of the present invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Felgner, et al., Ann NY Acad Sci 126-139, 1995). Formulation of DNA, e.g. with various lipid or liposome materials, may then be effected using known methods and materials and delivered to the recipient mammal. See, e.g., Canonico et al, Am J Respir Cell Mol Biol 10:24-29, 1994; Tsan et al, Am J Physiol 268; Alton et al., Nat Genet. 5:135-142, 1993 and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well-known and any can be selected for a particular application. In one embodiment of the present invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter may be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., Hum. Gene. Ther. 3:147-154, 1992. Other vehicles which can optionally be used include DNA-ligand (Wu et al., J. Biol. Chem. 264:16985-16987, 1989), lipid-DNA combinations (Felgner et al., Proc. Natl. Acad. Sci. U.S.A. 84:7413 7417, 1989), liposomes (Wang et al., Proc. Natl. Acad. Sci. 84:7851-7855, 1987) and microprojectiles (Williams et al., Proc. Natl. Acad. Sci. 88:2726-2730, 1991).

A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al., Cell 33:153, 1983, Cane and Mulligan, Proc. Nat'l. Acad. Sci. U.S.A. 81:6349, 1984, Miller et al., Human Gene Therapy 1:5-14, 1990, U.S. Pat. Nos. 4,405,712, 4,861,719, and 4,980,289, and PCT Application Nos. WO 89/02,468, WO 89/05,349, and WO 90/02, 806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777,127, GB 2,200,651, EP 0,345,242 and WO91/02805).

Other viral vector systems that can be used to deliver a polynucleotide of the present invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth,; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxivirus, an arena virus, a vaccinia virus, a polio virus, and the like. They offer several attractive features for various mammalian cells (Friedmann (1989) Science, 244:1275-1281; Ridgeway, 1988, supra; Baichwal and Sugden, 1986, supra; Coupar et al., 1988; Horwich et al.(1990) J. Virol., 64:642-650).

In other embodiments, target DNA in the genome can be manipulated using well-known methods in the art. For example, the target DNA in the genome can be manipulated by deletion, insertion, and/or mutation are retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis.

In other embodiments, recombinant biomarker polypeptides, and fragments thereof, can be administered to subjects. In some embodiments, fusion proteins can be constructed and administered which have enhanced biological properties. In addition, the biomarker polypeptides, and fragment thereof, can be modified according to well-known pharmacological methods in the art (e.g., pegylation, glycosylation, oligomerization, etc.) in order to further enhance desirable biological activities, such as increased bioavailability and decreased proteolytic degradation.

4. Clinical Efficacy

Clinical efficacy can be measured by any method known in the art. For example, the response to a therapy, such as inhibitors of one or more biomarkers listed in Table 1, and immunotherapy combination treatment, relates to any response of the cancer, e.g., a tumor, to the therapy, preferably to a change in tumor mass and/or volume after initiation of neoadjuvant or adjuvant chemotherapy. Tumor response may be assessed in a neoadjuvant or adjuvant situation where the size of a tumor after systemic intervention can be compared to the initial size and dimensions as measured by CT, PET, mammogram, ultrasound or palpation and the cellularity of a tumor can be estimated histologically and compared to the cellularity of a tumor biopsy taken before initiation of treatment. Response may also be assessed by caliper measurement or pathological examination of the tumor after biopsy or surgical resection. Response may be recorded in a quantitative fashion like percentage change in tumor volume or cellularity or using a semi-quantitative scoring system such as residual cancer burden (Symmans et al., J. Clin. Oncol. (2007) 25:4414-4422) or Miller-Payne score (Ogston et al., (2003) Breast (Edinburgh, Scotland) 12:320-327) in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of tumor response may be performed early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed.

In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular anti-immune checkpoint therapeutic regimen is at least 25%, 30%, 35%, 40%, 45%, 50%, 55%, 60%, 65%, 70%, 75%, 80%, 85%, or more.

Additional criteria for evaluating the response to immunotherapies, such as anti-immune checkpoint therapies, are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence.

For example, in order to determine appropriate threshold values, a particular anti-cancer therapeutic regimen can be administered to a population of subjects and the outcome can be correlated to biomarker measurements that were determined prior to administration of any immunotherapy, such as anti-immune checkpoint therapy. The outcome measurement may be pathologic response to therapy given in the neoadjuvant setting. Alternatively, outcome measures, such as overall survival and disease-free survival can be monitored over a period of time for subjects following immunotherapies for whom biomarker measurement values are known. In certain embodiments, the same doses of immunotherapy agents, if any, are administered to each subject. In related embodiments, the doses administered are standard doses known in the art for those agents used in immunotherapies. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of an immunotherapy can be determined using methods such as those described in the Examples section.

5. Further Uses and Methods of the Present Invention

The compositions described herein can be used in a variety of diagnostic, prognostic, and therapeutic applications. In any method described herein, such as a diagnostic method, prognostic method, therapeutic method, or combination thereof, all steps of the method can be performed by a single actor or, alternatively, by more than one actor. For example, diagnosis can be performed directly by the actor providing therapeutic treatment. Alternatively, a person providing a therapeutic agent can request that a diagnostic assay be performed. The diagnostician and/or the therapeutic interventionist can interpret the diagnostic assay results to determine a therapeutic strategy. Similarly, such alternative processes can apply to other assays, such as prognostic assays.

a. Screening Methods

One aspect of the present invention relates to screening assays, including non-cell based assays and xenograft animal model assays. In one embodiment, the assays provide a method for identifying whether a cancer is likely to respond to inhibitors of one or more biomarkers listed in Table 1, and immunotherapy combination treatments, such as in a human by using a xenograft animal model assay, and/or whether an agent can inhibit the growth of or kill a cancer cell that is unlikely to respond to inhibitors of one or more biomarkers listed in Table 1, and immunotherapy combination treatments.

In one embodiment, the present invention relates to assays for screening test agents which bind to, or modulate the biological activity of, at least one biomarker described herein (e.g., in the tables, figures, examples, or otherwise in the specification). In one embodiment, a method for identifying such an agent entails determining the ability of the agent to modulate, e.g. inhibit, the at least one biomarker described herein.

In one embodiment, an assay is a cell-free or cell-based assay, comprising contacting at least one biomarker described herein, with a test agent, and determining the ability of the test agent to modulate (e.g., inhibit) the enzymatic activity of the biomarker, such as by measuring direct binding of substrates or by measuring indirect parameters as described below.

For example, in a direct binding assay, biomarker protein (or their respective target polypeptides or molecules) can be coupled with a radioisotope or enzymatic label such that binding can be determined by detecting the labeled protein or molecule in a complex. For example, the targets can be labeled with $^{125}$I, $^{35}$S, $^{14}$C, or $^{3}$H, either directly or indirectly, and the radioisotope detected by direct counting of radioemission or by scintillation counting. Alternatively, the targets can be enzymatically labeled with, for example, horseradish peroxidase, alkaline phosphatase, or luciferase, and the enzymatic label detected by determination of conversion of an appropriate substrate to product. Determining the interaction between biomarker and substrate can also be accomplished using standard binding or enzymatic analysis assays. In one or more embodiments of the above described assay methods, it may be desirable to immobilize polypeptides or molecules to facilitate separation of complexed from uncomplexed forms of one or both of the proteins or molecules, as well as to accommodate automation of the assay.

Binding of a test agent to a target can be accomplished in any vessel suitable for containing the reactants. Non-limiting examples of such vessels include microtiter plates, test tubes, and micro-centrifuge tubes. Immobilized forms of the antibodies described herein can also include antibodies bound to a solid phase like a porous, microporous (with an average pore diameter less than about one micron) or macroporous (with an average pore diameter of more than about 10 microns) material, such as a membrane, cellulose, nitrocellulose, or glass fibers; a bead, such as that made of agarose or polyacrylamide or latex; or a surface of a dish, plate, or well, such as one made of polystyrene.

In an alternative embodiment, determining the ability of the agent to modulate the interaction between the biomarker and a substrate or a biomarker and its natural binding partner can be accomplished by determining the ability of the test agent to modulate the activity of a polypeptide or other product that functions downstream or upstream of its position within the signaling pathway (e.g., feedback loops). Such feedback loops are well-known in the art (see, for example, Chen and Guillemin (2009) *Int. J. Tryptophan Res.* 2:1-19).

The present invention further pertains to novel agents identified by the above-described screening assays. Accordingly, it is within the scope of this invention to further use an agent identified as described herein, such as in an appropriate animal model. For example, an agent identified as described herein can be used in an animal model to determine the efficacy, toxicity, or side effects of treatment with such an agent. Alternatively, an antibody identified as described herein can be used in an animal model to determine the mechanism of action of such an agent.

b. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining the amount and/or activity level of a biomarker described herein in the context of a biological sample (e.g., blood, serum, cells, or tissue) to thereby determine whether an individual afflicted with a cancer is likely to respond to inhibitors of one or more biomarkers listed in Table 1, and immunotherapy combination treatments, such as in a cancer. Such assays can be used for prognostic or predictive purpose alone, or can be coupled with a therapeutic intervention to thereby prophylactically treat an individual prior to the onset or after recurrence of a disorder characterized by or associated with biomarker polypeptide, nucleic acid expression or activity. The skilled artisan will appreciate that any method can use one or more (e.g., combinations) of biomarkers described herein, such as those in the tables, figures, examples, and otherwise described in the specification.

Another aspect of the present invention pertains to monitoring the influence of agents (e.g., drugs, compounds, and small nucleic acid-based molecules) on the expression or activity of a biomarker described herein. These and other agents are described in further detail in the following sections.

The skilled artisan will also appreciated that, in certain embodiments, the methods of the present invention implement a computer program and computer system. For example, a computer program can be used to perform the algorithms described herein. A computer system can also store and manipulate data generated by the methods of the present invention which comprises a plurality of biomarker signal changes/profiles which can be used by a computer system in implementing the methods of this invention. In certain embodiments, a computer system receives biomarker expression data; (ii) stores the data; and (iii) compares the data in any number of ways described herein (e.g., analysis relative to appropriate controls) to determine the state of informative biomarkers from cancerous or pre-cancerous tissue. In other embodiments, a computer system (i) compares the determined expression biomarker level to a threshold value; and (ii) outputs an indication of whether said biomarker level is significantly modulated (e.g., above or below) the threshold value, or a phenotype based on said indication.

In certain embodiments, such computer systems are also considered part of the present invention. Numerous types of computer systems can be used to implement the analytic methods of this invention according to knowledge possessed by a skilled artisan in the bioinformatics and/or computer arts. Several software components can be loaded into memory during operation of such a computer system. The software components can comprise both software components that are standard in the art and components that are special to the present invention (e.g., dCHIP software described in Lin et al. (2004) *Bioinformatics* 20, 1233-1240; radial basis machine learning algorithms (RBM) known in the art).

The methods of the present invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from MathSoft (Seattle, Wash.).

In certain embodiments, the computer comprises a database for storage of biomarker data. Such stored profiles can be accessed and used to perform comparisons of interest at a later point in time. For example, biomarker expression profiles of a sample derived from the non-cancerous tissue of a subject and/or profiles generated from population-based distributions of informative loci of interest in relevant populations of the same species can be stored and later compared to that of a sample derived from the cancerous tissue of the subject or tissue suspected of being cancerous of the subject.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

c. Diagnostic Assays

The present invention provides, in part, methods, systems, and code for accurately classifying whether a biological sample is associated with a cancer that is likely to respond to inhibitors of one or more biomarkers listed in Table 1, and immunotherapy combination treatments. In some embodiments, the present invention is useful for classifying a sample (e.g., from a subject) as associated with or at risk for responding to or not responding to inhibitors of one or more biomarkers listed in Table 1, and immunotherapy combination treatments using a statistical algorithm and/or empirical data (e.g., the amount or activity of a biomarker described herein, such as in the tables, figures, examples, and otherwise described in the specification).

An exemplary method for detecting the amount or activity of a biomarker described herein, and thus useful for classifying whether a sample is likely or unlikely to respond to inhibitors of one or more biomarkers listed in Table 1, and immunotherapy combination treatments involves obtaining a biological sample from a test subject and contacting the biological sample with an agent, such as a protein-binding agent like an antibody or antigen-binding fragment thereof, or a nucleic acid-binding agent like an oligonucleotide, capable of detecting the amount or activity of the biomarker in the biological sample. In some embodiments, at least one antibody or antigen-binding fragment thereof is used, wherein two, three, four, five, six, seven, eight, nine, ten, or more such antibodies or antibody fragments can be used in combination (e.g., in sandwich ELISAs) or in serial. In certain instances, the statistical algorithm is a single learning statistical classifier system. For example, a single learning statistical classifier system can be used to classify a sample as a based upon a prediction or probability value and the presence or level of the biomarker. The use of a single learning statistical classifier system typically classifies the sample as, for example, a likely immunotherapy responder or progressor sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Other suitable statistical algorithms are well-known to those of skill in the art. For example, learning statistical classifier systems include a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ). In certain embodiments, the method of the present invention further comprises sending the sample classification results to a clinician, e.g., an oncologist.

In another embodiment, the diagnosis of a subject is followed by administering to the individual a therapeutically effective amount of a defined treatment based upon the diagnosis.

In one embodiment, the methods further involve obtaining a control biological sample (e.g., biological sample from a subject who does not have a cancer or whose cancer is susceptible to inhibitors of one or more biomarkers listed in Table 1, and immunotherapy combination treatments), a biological sample from the subject during remission, or a biological sample from the subject during treatment for developing a cancer progressing despite inhibitors of one or more biomarkers listed in Table 1, and immunotherapy combination treatments.

d. Prognostic Assays

The diagnostic methods described herein can furthermore be utilized to identify subjects having or at risk of developing a cancer that is likely or unlikely to be responsive to inhibitors of one or more biomarkers listed in Table 1, and immunotherapy combination treatments. The assays described herein, such as the preceding diagnostic assays or the following assays, can be utilized to identify a subject having or at risk of developing a disorder associated with a misregulation of the amount or activity of at least one biomarker described herein, such as in cancer. Alternatively, the prognostic assays can be utilized to identify a subject having or at risk for developing a disorder associated with a misregulation of the at least one biomarker described herein, such as in cancer. Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat a disease or disorder associated with the aberrant biomarker expression or activity.

e. Treatment Methods

The therapeutic compositions described herein, such as the combination of inhibitors of one or more biomarkers listed in Table 1, and immunotherapy, can be used in a variety of in vitro and in vivo therapeutic applications using the formulations and/or combinations described herein. In one embodiment, the therapeutic agents can be used to treat cancers determined to be responsive thereto. For example, single or multiple agents that inhibit or block both an inhibitor of one or more biomarkers listed in Table 1, and a immunotherapy can be used to treat cancers in subjects identified as likely responders thereto.

Modulatory methods of the present invention involve contacting a cell, such as an immune cell with an agent that inhibits or blocks the expression and/or activity of such one or more biomarkers and an immunotherapy, such as an immune checkpoint inhibitor (e.g., PD-1). Exemplary agents useful in such methods are described above. Such agents can be administered in vitro or ex vivo (e.g., by contacting the cell with the agent) or, alternatively, in vivo (e.g., by administering the agent to a subject). As such, the present invention provides methods useful for treating an individual afflicted with a condition that would benefit from an increased immune response, such as an infection or a cancer like colorectal cancer.

Agents that upregulate immune responses can be in the form of enhancing an existing immune response or eliciting an initial immune response. Thus, enhancing an immune response using the subject compositions and methods is useful for treating cancer, but can also be useful for treating an infectious disease (e.g., bacteria, viruses, or parasites), a parasitic infection, and an immunosuppressive disease.

Exemplary infectious disorders include viral skin diseases, such as Herpes or shingles, in which case such an agent can be delivered topically to the skin. In addition, systemic viral diseases, such as influenza, the common cold, and encephalitis might be alleviated by systemic administration of such agents. In one preferred embodiment, agents that upregulate the immune response described herein are useful for modulating the arginase/iNOS balance during *Trypanosoma cruzi* infection in order to facilitate a protective immune response against the parasite.

Immune responses can also be enhanced in an infected patient through an ex vivo approach, for instance, by removing immune cells from the patient, contacting immune cells in vitro with an agent described herein and reintroducing the in vitro stimulated immune cells into the patient.

In certain instances, it may be desirable to further administer other agents that upregulate immune responses, for example, forms of other B7 family members that transduce signals via costimulatory receptors, in order to further augment the immune response. Such additional agents and therapies are described further below.

Agents that upregulate an immune response can be used prophylactically in vaccines against various polypeptides (e.g., polypeptides derived from pathogens). Immunity against a pathogen (e.g., a virus) can be induced by vaccinating with a viral protein along with an agent that upregulates an immune response, in an appropriate adjuvant.

In another embodiment, upregulation or enhancement of an immune response function, as described herein, is useful in the induction of tumor immunity.

In another embodiment, the immune response can be stimulated by the methods described herein, such that pre-existing tolerance, clonal deletion, and/or exhaustion (e.g., T cell exhaustion) is overcome. For example, immune responses against antigens to which a subject cannot mount a significant immune response, e.g., to an autologous antigen, such as a tumor specific antigens can be induced by administering appropriate agents described herein that upregulate the immune response. In one embodiment, an autologous antigen, such as a tumor-specific antigen, can be coadministered. In another embodiment, the subject agents can be used as adjuvants to boost responses to foreign antigens in the process of active immunization.

In one embodiment, immune cells are obtained from a subject and cultured ex vivo in the presence of an agent as described herein, to expand the population of immune cells and/or to enhance immune cell activation. In a further embodiment the immune cells are then administered to a subject. Immune cells can be stimulated in vitro by, for example, providing to the immune cells a primary activation signal and a costimulatory signal, as is known in the art. Various agents can also be used to costimulate proliferation of immune cells. In one embodiment immune cells are cultured ex vivo according to the method described in PCT Application No. WO 94/29436. The costimulatory polypeptide can be soluble, attached to a cell membrane, or attached to a solid surface, such as a bead.

6. Administration of Agents

The immune modulating agents of the invention are administered to subjects in a biologically compatible form suitable for pharmaceutical administration in vivo, to enhance immune cell mediated immune responses. By "biologically compatible form suitable for administration in vivo" is meant a form to be administered in which any toxic effects are outweighed by the therapeutic effects. The term "subject" is intended to include living organisms in which an immune response can be elicited, e.g., mammals. Examples of subjects include humans, dogs, cats, mice, rats, and transgenic species thereof. Administration of an agent as described herein can be in any pharmacological form including a therapeutically active amount of an agent alone or in combination with a pharmaceutically acceptable carrier.

Administration of a therapeutically active amount of the therapeutic composition of the present invention is defined as an amount effective, at dosages and for periods of time necessary, to achieve the desired result. For example, a therapeutically active amount of an agent may vary according to factors such as the disease state, age, sex, and weight of the individual, and the ability of peptide to elicit a desired response in the individual. Dosage regimens can be adjusted to provide the optimum therapeutic response. For example, several divided doses can be administered daily or the dose can be proportionally reduced as indicated by the exigencies of the therapeutic situation.

Inhibiting or blocking expression and/or activity of one or more biomarkers listed in Table 1, alone or in combination with an immunotherapy, can be accomplished by combination therapy with the modulatory agents described herein. Combination therapy describes a therapy in which such one or more biomarkers is inhibited or blocked with an immunotherapy simultaneously. This may be achieved by administration of the modulatory agent described herein swith the immunotherapy imultaneously (e.g., in a combination dosage form or by simultaneous administration of single agents) or by administration of single inhibitory agent for such one or more biomarkers and the immunotherapy, according to a schedule that results in effective amounts of each modulatory agent present in the patient at the same time.

The therapeutic agents described herein can be administered in a convenient manner such as by injection (subcutaneous, intravenous, etc.), oral administration, inhalation, transdermal application, or rectal administration. Depending on the route of administration, the active compound can be coated in a material to protect the compound from the action of enzymes, acids and other natural conditions which may inactivate the compound. For example, for administration of agents, by other than parenteral administration, it may be desirable to coat the agent with, or co-administer the agent with, a material to prevent its inactivation.

An agent can be administered to an individual in an appropriate carrier, diluent or adjuvant, co-administered with enzyme inhibitors or in an appropriate carrier such as liposomes. Pharmaceutically acceptable diluents include saline and aqueous buffer solutions. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEEP) and trasylol. Liposomes include water-in-oil-in-water emulsions as well as conventional liposomes (Sterna et al. (1984) *J. Neuroimmunol.* 7:27).

As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of an agent that modulates (e.g., inhibits) biomarker expression and/or activity, or expression and/or activity of the complex, or composition comprising an agent that modulates (e.g., inhibits) biomarker expression and/or activity, or expression and/or activity of the complex, which is effective for producing some desired therapeutic effect, e.g., cancer treatment, at a reasonable benefit/risk ratio.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that modulates (e.g., inhibits) biomarker expression and/or activity, or expression and/or activity of the complex encompassed by the present invention. These salts can be prepared in situ during the final isolation and purification of the therapeutic agents, or by separately reacting a purified therapeutic agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (See, for example, Berge et al. (1977) "Pharmaceutical Salts", J. Pharm. Sci. 66:1-19).

In other cases, the agents useful in the methods of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of agents that modulates (e.g., inhibits) biomarker expression and/or activity, or expression and/or activity of the complex. These salts can likewise be prepared in situ during the final isolation and purification of the therapeutic agents, or by separately reacting the purified therapeutic agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well-known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent that modulates (e.g., inhibits) biomarker expression and/or activity, with the carrier and, optionally, one or more accessory ingredients. In general, the formulations are prepared by uniformly and intimately bringing into association a therapeutic agent with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a therapeutic agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well-known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more therapeutic agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent that modulates (e.g., inhibits) biomarker expression and/or activity include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a therapeutic agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an agent that modulates (e.g., inhibits) biomarker expression and/or activity, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The agent that modulates (e.g., inhibits) biomarker expression and/or activity, can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a therapeutic agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more therapeutic agents in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the present invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of an agent that modulates (e.g., inhibits) biomarker expression and/or activity, in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

When the therapeutic agents of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions of this invention may be determined by the methods of the present invention so as to obtain an amount of the active ingredient, which is effective to achieve the desired therapeutic response for a particular subject, composition, and mode of administration, without being toxic to the subject.

The nucleic acid molecules of the present invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. U.S.A.* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

In one embodiment, an agent of the invention is an antibody. As defined herein, a therapeutically effective amount of antibody (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an antibody can include a single treatment or, preferably, can include a series of treatments. In a preferred example, a subject is treated with antibody in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody used for treatment may increase or decrease over the course of a particular treatment. Changes in dosage may result from the results of diagnostic assays.

7. Kits

The present invention also encompasses kits for detecting and/or modulating biomarkers described herein. A kit of the present invention may also include instructional materials disclosing or describing the use of the kit or an antibody of the disclosed invention in a method of the disclosed invention as provided herein. A kit may also include additional components to facilitate the particular application for which the kit is designed. For example, a kit may additionally contain means of detecting the label (e.g., enzyme substrates for enzymatic labels, filter sets to detect fluorescent labels, appropriate secondary labels such as a sheep anti-mouse-HRP, etc.) and reagents necessary for controls (e.g., control biological samples or standards). A kit may additionally include buffers and other reagents recognized for use in a method of the disclosed invention. Non-limiting examples include agents to reduce non-specific binding, such as a carrier protein or a detergent.

EXAMPLES

Example 1: Materials and Methods for Examples 2-6 a. In Vivo CRISPR Screening in B16 Tumor Cells

A Cas9-expressing version of the B16 melanoma cell line was created and confirmed that it could edit DNA efficiently with CRISPR using sgRNAs targeting the PD-L1 gene. For screening the B16-Cas9 cell line, a library of 9,992 optimized sgRNAs was created to target 2,398 genes, selected from the GO term categories: kinase, phosphatase, cell surface, plasma membrane, antigen processing and presentation, immune system process, and chromatin remodeling. The transcript abundance of the genes in these categories were then filtered to include only those that were expressed >RPKM ($\log_2$)=0.9. These genes were then ranked for expression in the B16 cell line using RNAseq to select for the top 2,398 expressed genes. The library was divided into 4 sub-pools, each containing one sgRNA per gene and 100 non-targeting control sgRNAs. The 4 sub-pools were screened individually and sgRNAs were delivered to B16-Cas9 cells via lentiviral infection at an infection rate of 30%. Transduced B16 cells were purified using a hCD19 reporter by positive magnetic selection (Miltenyi Biotech, Cambridge, MA) and then expanded in vitro before being implanted into animals. For each sub-pool, B16 cells were implanted into 10 TCRα$^{-/-}$ mice, 10 WT mice treated with GVAX, and 10 WT mice treated with GVAX and PD-1 blockade (see below for treatment protocols). B16 cells transduced with libraries were also grown in vitro at approximately 2000×library coverage for the same time period as the animal experiment. Mice were sacrificed 12-14 days after tumor implantation tumor genomic DNA was prepared from whole tumor tissue using the Qiagen DNA Blood Midi kit (Qiagen, Hilden, Germany). PCR was used to amplify the sgRNA region and sequencing to determine sgRNA abundance was performed on an Illumina HiSeq system (Illumina, San Diego, CA). Significantly enriched or depleted sgRNAs from any comparison of conditions were identified using the STARS algorithm (Doench et al. (2014) *Nat. Biotechnol.* 32:1262-1267).

b. Animal Treatment and Tumor Challenges

The designs of these animal studies and procedures were approved by the Dana Farber Cancer Institute IACUC committee. Dana Farber's specific-pathogen free facility was used for the storage and care of all mice. Seven-week old wild-type female C57BL/6J mice were obtained from Jackson laboratories (Bar Harbor, ME). A colony of B6.129S2-Tcra$^{tm1Mom}$/J (Tcra) T cell-deficient mice were bred on site. Mice were aged matched to be 7-12 weeks old at the time of tumor inoculation. For screening, $2.0\times10^6$ library-transduced B16-Cas9 cells resuspended in Hanks Balanced Salt Solution (Gibco, Thermo Fisher Scientific, Waltham, MA) were mixed 1:1 by volume with Matrigel© (Corning, Corning, NY) and subcutaneously injected into the right flank on day 0. Mice were vaccinated with $1.0\times10^6$ GM-CSF-secreting B16 (GVAX) cells that had been irradiated with 3500 Gy on days 1 and 4 to elicit an anti-tumor immune response. Subsequently, mice were treated with 100 µg of rat monoclonal anti-PD-1 antibody (clone: 29F.1A12) on days 9 and 12 via intraperitoneal injection. For validation assays, $5.0\times10^5$ tumor cells were subcutaneously injected into the right flank without matrigel. Tumors were measured every 3 days beginning on day 6 after challenge until time of death. Measurements were taken manually by collecting the longest dimension (length) and the longest perpendicular dimension (width). Tumor volume was estimated with the formula: $(L\times W^2)/2$. $CO_2$ inhalation was used to euthanize mice on the day of sacrifice.

c. Creation of CRISPR Edited Tumor Cell Lines

Transient transfection of Cas9-sgRNA plasmid (pX459, Addgene, Cambridge, MA) was used to edit B16 melanoma cell lines. pX459 was digested with the enzyme BpiI (Thermo Fisher Scientific) as per the manufacturer's instructions and sgRNA oligos were cloned in using standard molecular cloning. For B16 cells, $5\times10^5$ cells were plated in a well of a 6-well plate and were transfected the following day using 2 µg of pX459 plasmid DNA and Turbofect™ (3:1 ratio, Thermo Fisher Scientific). Twenty-four hours after transfection, transfectants were selected in puromycin (6 µg/mL, Thermo Fisher Scientific). After selection, cells were grown for 14 days in vitro before being implanted into mice.

d. Flow Cytometry Analysis of B16 Tumor Cells

B16 cells were dissociated with 5 mM EDTA. Qa-1b expression was evaluated by staining with anti-Qa-1b antibody (clone 6A8.6F10.1A6, Miltenyi Biotec) as per the manufacturer's instructions and then analyzed on an LSR Fortessa flow cytometry system (BD Biosciences).

e. Quantitative Reverse Transcription PCR Analysis of Tumor Cells

RNA was extracted from cell pellets of sgRNA-transfected B16 cells using the Qiagen RNeasy Mini kit according to manufacturer's instructions. cDNA was generated using the Im-Prom II reverse transcription system (Promega) as per manufacturers instructions. SPP transcript levels were measured via quantative reverse transcription reactions using the Taqman System (Applied Biosystems) with the Mm01241451_m1 Taqman probe. Beta actin transcript levels were measured similarly using the Mm00607939_s1 Taqman probe. Reactions were analyzed using a Viia7 Real-Time PCR System (Applied Biosystems). To calculate SPP knock out efficiency, delta CT values were calculated relative to β-actin.

f. CRISPR sgRNA sequences.

CRISPR sgRNA sequences uses are described in Table 3 as follows:

TABLE 3

| Gene Name/sg# | sgRNA Sequence | |
|---|---|---|
| Cd274 sgRNA 1 | GCCTGCTGTCACTTGCTACG | (SEQ ID NO: 46) |
| Cd274 sgRNA 2 | AATCAACCAGAGAATTTCCG | (SEQ ID NO: 47) |
| Cd274 sgRNA 3 | GGTCCAGCTCCCGTTCTACA | (SEQ ID NO: 48) |
| Cd274 sgRNA 4 | GTATGGCAGCAACGTCACGA | (SEQ ID NO: 49) |
| Cd47 sgRNA 1 | TATAGAGCTGAAAAACCGCA | (SEQ ID NO: 50) |
| Cd47 sgRNA 2 | CCACATTACGGACGATGCAA | (SEQ ID NO: 51) |
| Cd47 sgRNA 3 | TCTTACGAGGAGGAGAAAGG | (SEQ ID NO: 52) |
| Cd47 sgRNA 4 | GCAAGTGTAGTTTCCCACCA | (SEQ ID NO: 53) |
| control sgRNA 1 | GCGAGGTATTCGGCTCCGCG | (SEQ ID NO: 54) |
| control sgRNA 2 | GCTTTCACGGAGGTTCGACG | (SEQ ID NO: 55) |
| control sgRNA 3 | ATGTTGCAGTTCGGCTCGAT | (SEQ ID NO: 56) |
| control sgRNA 4 | ACGTGTAAGGCGAACGCCTT | (SEQ ID NO: 57) |
| control sgRNA 5 | ATTGTTCGACCGTCTACGGG | (SEQ ID NO: 58) |
| H2-T23 sgRNA 1 | TAGCCGACAATGATGAACCG | (SEQ ID NO: 59) |
| H2-T23 sgRNA 2 | AGGCCTCCTGACAATACCCG | (SEQ ID NO: 60) |
| H2-T23 sgRNA 3 | GGAACTTCAGAGTAAACCTG | (SEQ ID NO: 61) |
| H13 sgRNA 1 | ACTGGCTGTATCCTGCTCGG | (SEQ ID NO: 62) |
| H13 sgRNA 2 | GGCCACTGTCACCATCACGT | (SEQ ID NO: 63) |
| H13 sgRNA 3 | GCTGTCAGCGATCCGCACAA | (SEQ ID NO: 64) |
| H13 sgRNA 4 | TCCGCACAACGGCAGCGCCG | (SEQ ID NO: 65) |
| H13 sgRNA 5 | AGAAATACATGGACAGCAAG | (SEQ ID NO: 66) |

Examples 2-6 disclose the development of a pooled loss-of-function in vivo genetic screening approach that uses CRISPR-Cas9 genome editing to discover genes that increase sensitivity or cause resistance to immunotherapy in a mouse transplantable tumor model. About 2,400 genes expressed by tumor cells were screened in the B16 murine melanoma model to identify those that increase or decrease sensitivity to immunotherapy with tumor vaccination and PD-1 checkpoint blockade. The screen identified known immune evasion molecules PD-L1 and CD47, as tumor cells bearing sgRNAs for these targets were significantly depleted in animals treated with immunotherapy. In contrast, loss of function of any of the genes that sense or signal in response to interferon-γ (IFNγ) rendered cells resistant to immunotherapy with PD-1 checkpoint blockade and vaccination, recapitulating resistance mutations identified in melanoma patients (Zaretsky et al. (2016) *N. Engl. J. Med.* 375:819-829; Gao et al. (2016) *Cell* 167:397-404.e9). It was discovered and further validated that deletion of a signal peptide peptidase (SPP) sensitizes tumor cells to immunotherapy. These findings reveal that therapeutic strategies, such as SPP inhibition, are capable of increasing the efficacy of cancer immunotherapy. Moreover, this screening approach can discover new immunotherapy targets and prioritize their combination with existing immunotherapies.

Figure 3:
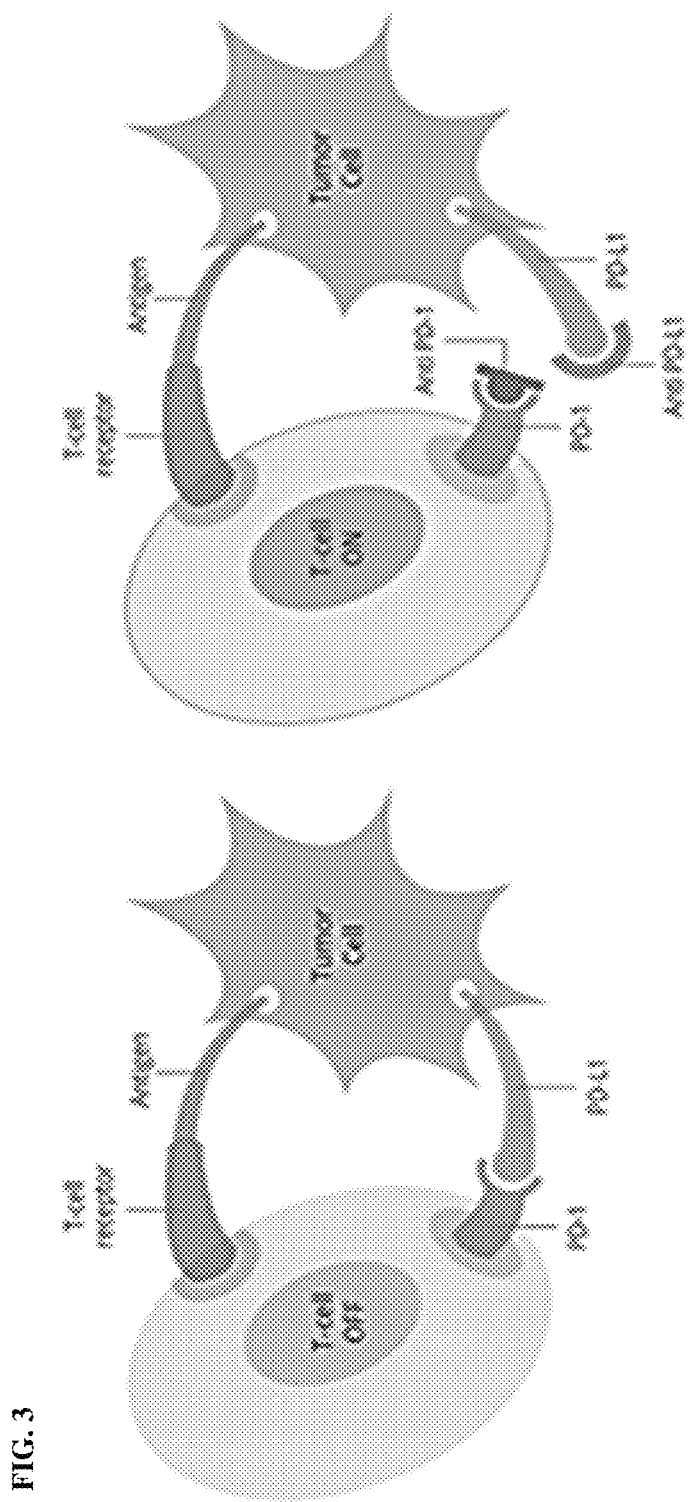
FIG. 3 shows the mechanism of action for PD-1 and PD-L1 blockades in cancer therapy. A schematic diagram on the left panel shows that the interaction between PD-1 on T cells, and PD-L1 on tumor cells turns off T cells, despite the recognition of a tumor antigen by the T-cell receptor. A schematic diagram on the right panel shows that disruption of the PD-1 and PD-L1 interaction by PD-1 and/or PD-L1 blockades results in activation of T cells. The figure is adapted from the drawing available on world wide web at smartpatients.com.

Example 2: A Pooled Loss-of-Function In Vivo Genetic Screen Recovers Known Immune Evasion Molecules Expressed by Tumors PD-1 and PD-L1 interaction turns off the activity of T cells, and prevents killing of tumor cells (FIG. 3). By contrast, PD-1 or PD-L1 blockades turn on the activity of T cells and allows T cell-mediated killing of the tumor cells. However, it is widely known that not all patients administered with PD-1 or PD-L1 blockades respond. Accordingly, there is a great need in the art for identification of the targets that enhance efficacy of immune therapies such as PD-1 or PD-L1 blockade.

Figure 1C:
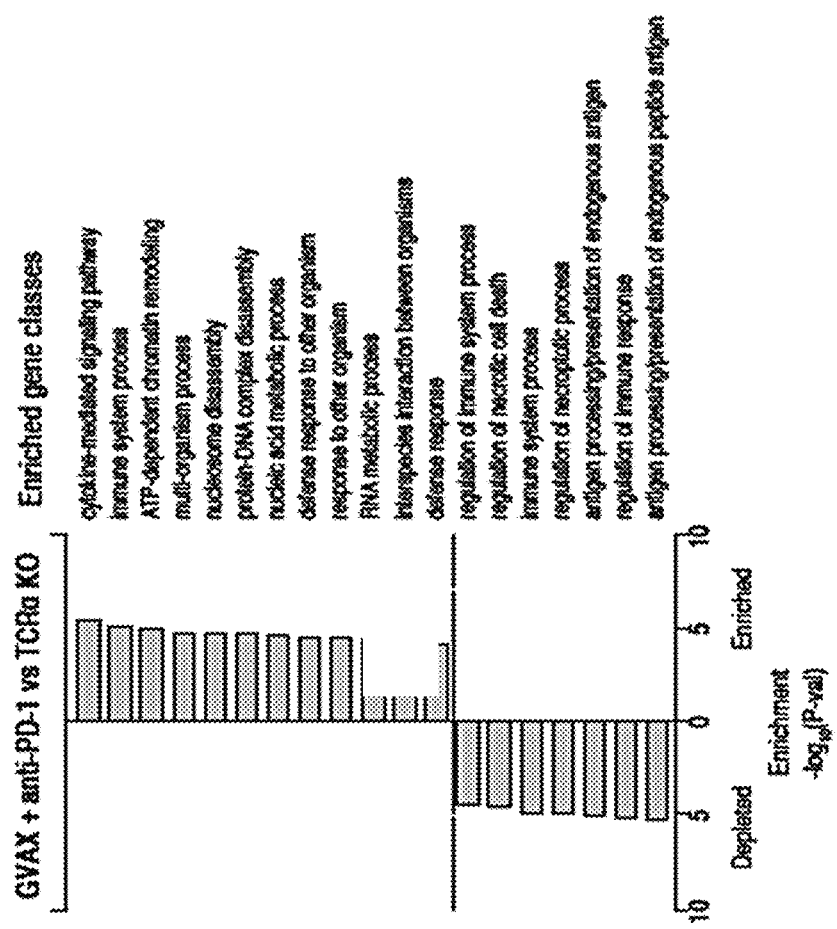
Figure 1E:
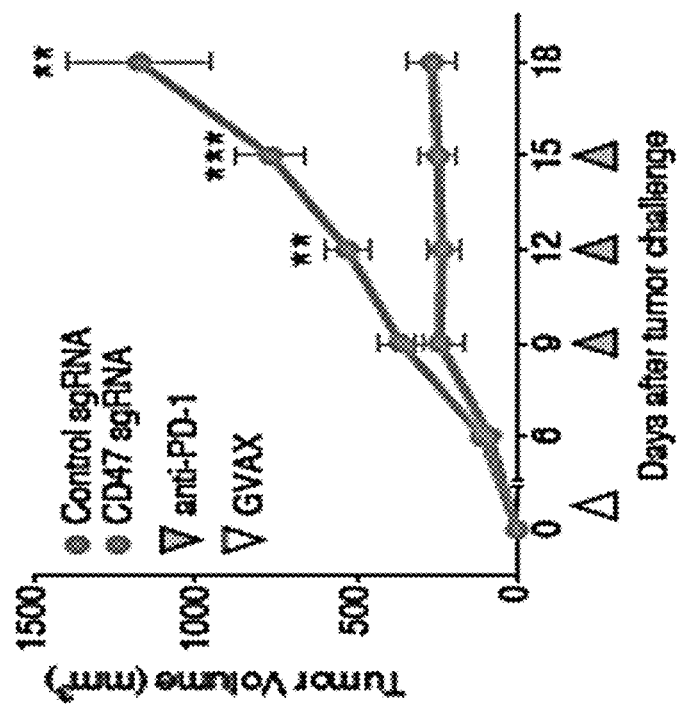
Figure 1F:
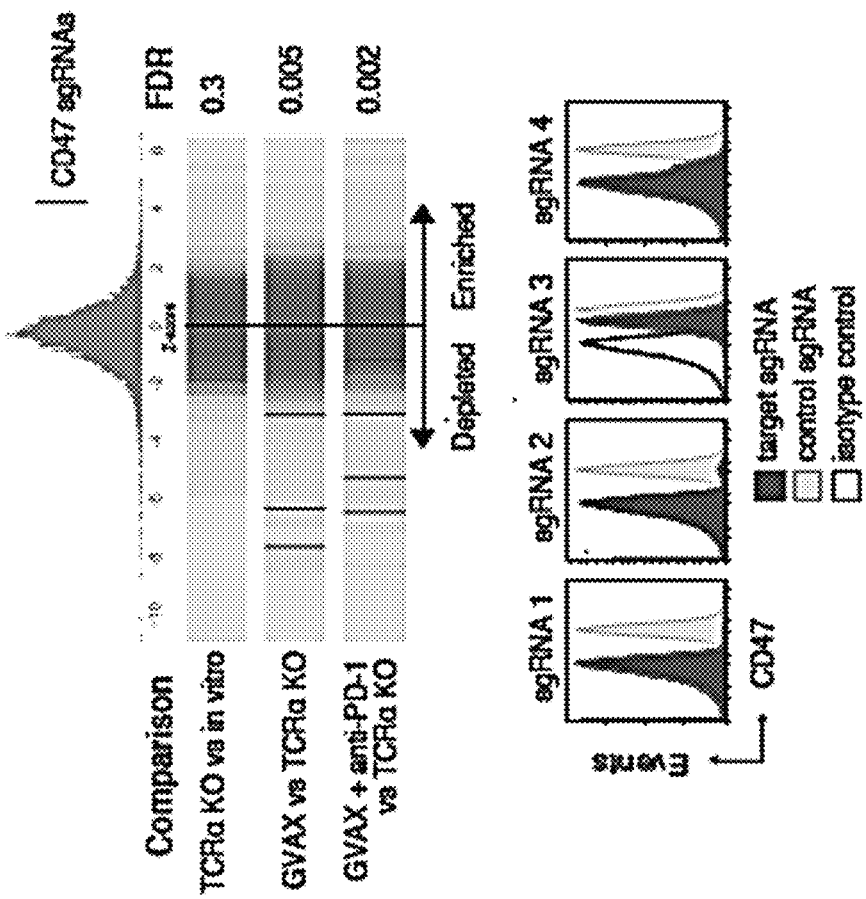
Figure 2B:
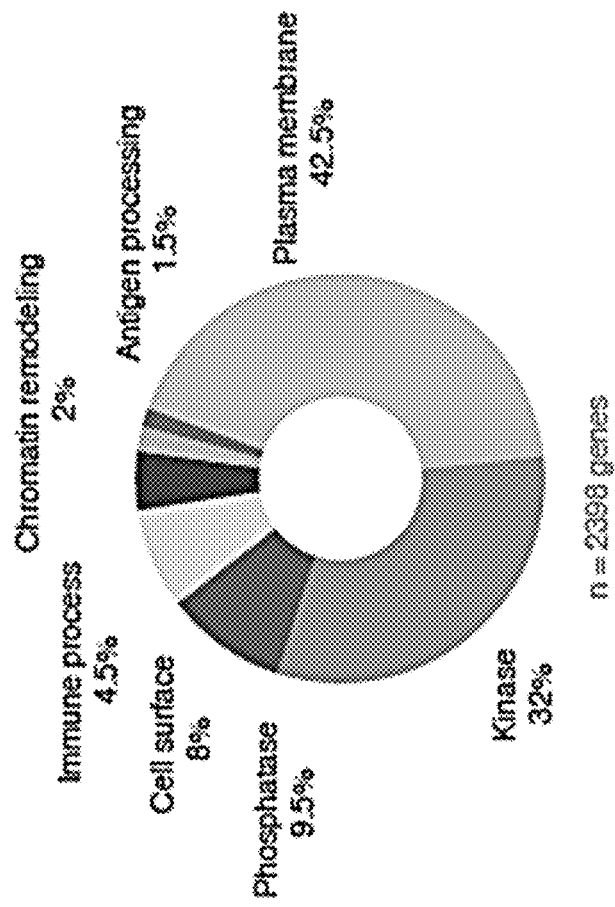
FIG. 2A-FIG. 2F show the performance analysis of the screening in FIG. 1.
Figure 2A:
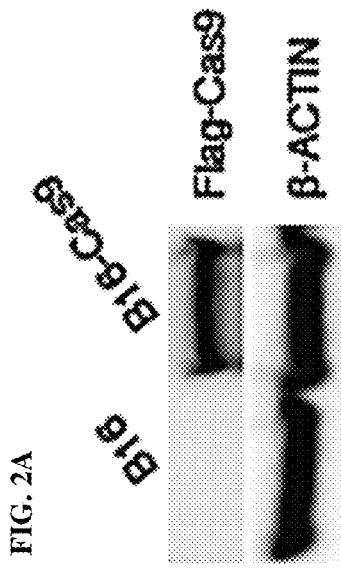
Figure 2C:
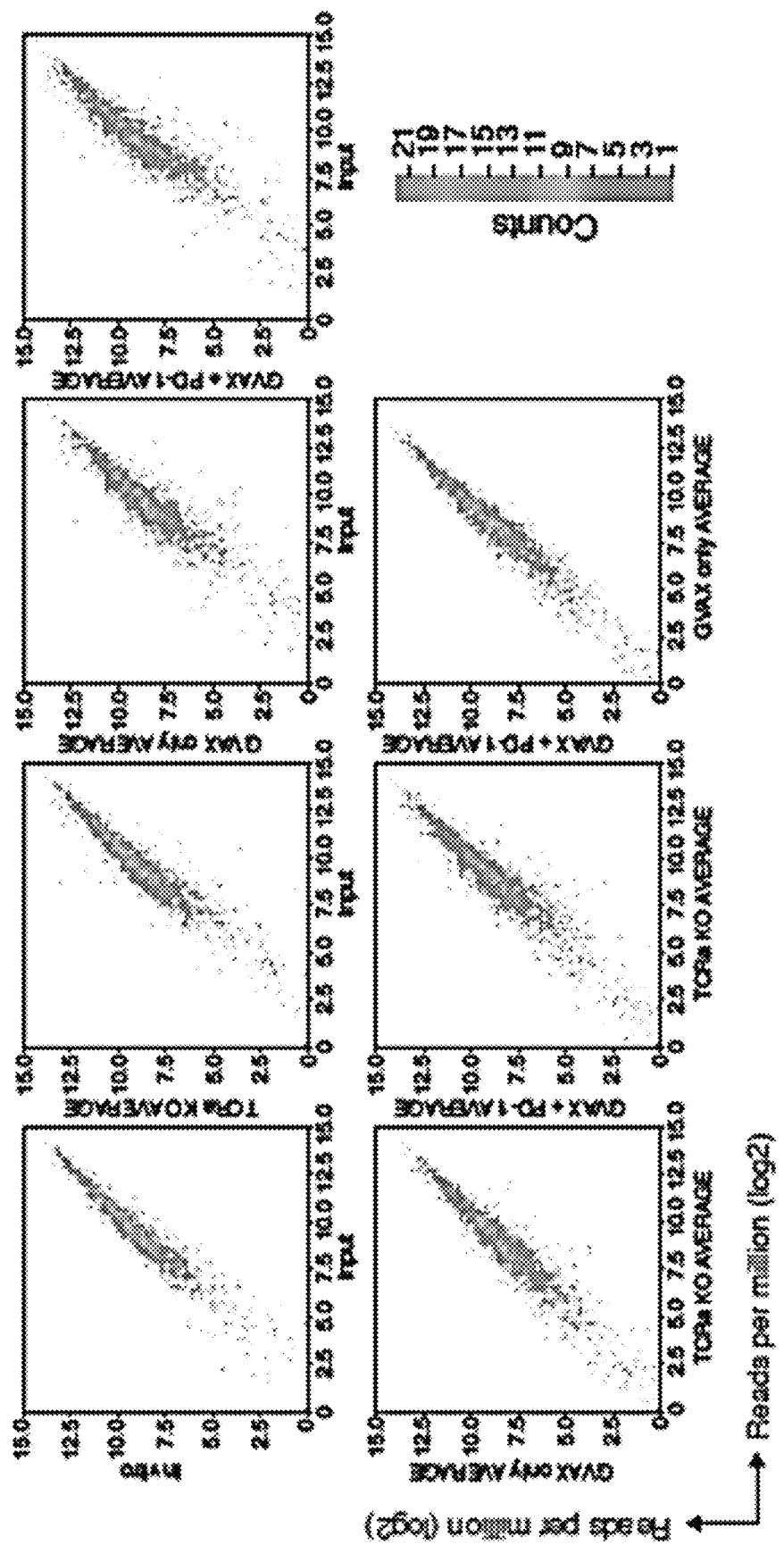
Figure 2D:
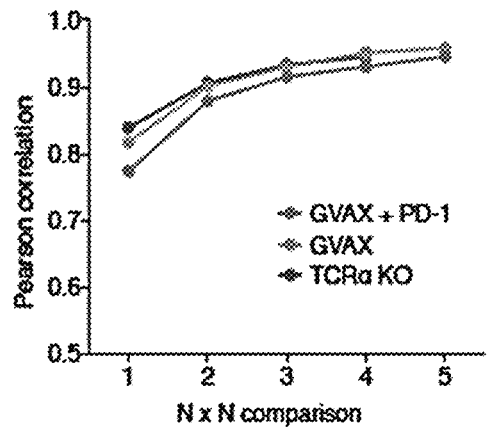
Figure 2F:
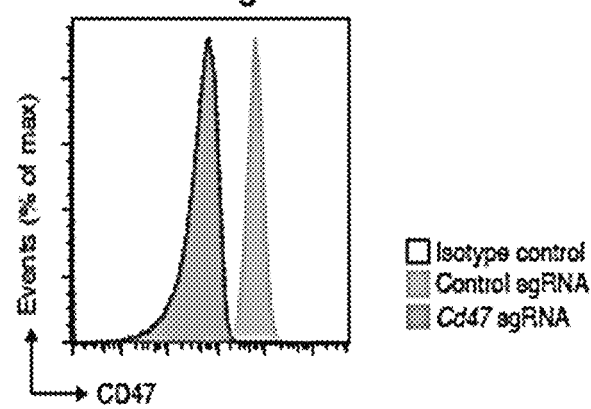
Figure 2E:
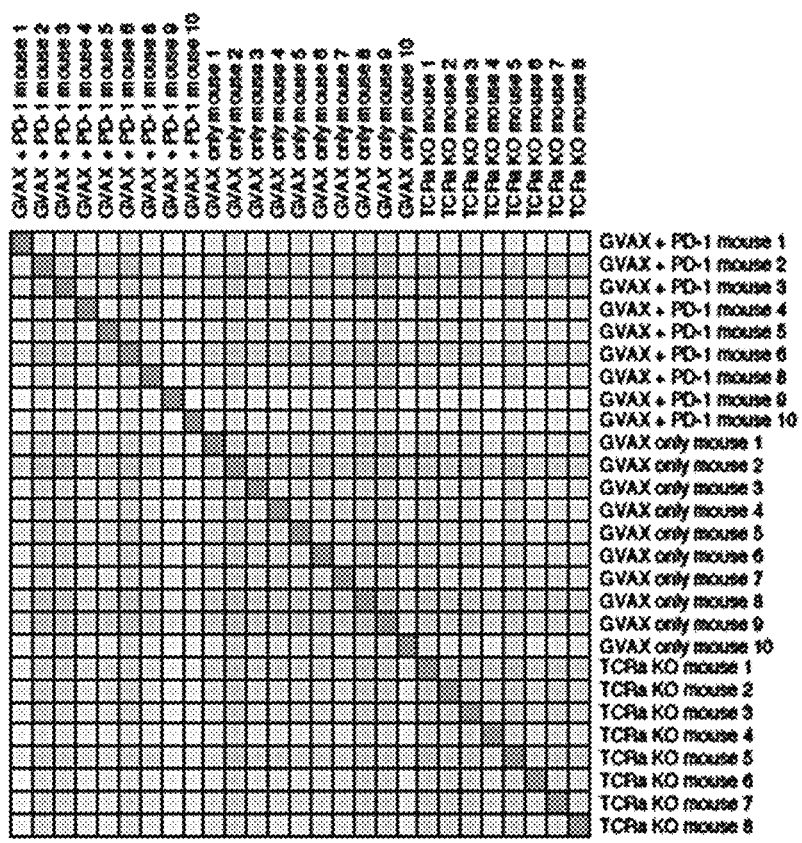

In order to systematically identify new cancer immunotherapy targets and resistance mechanisms, a pooled genetic screening approach was developed to identify genes that increase or decrease the fitness of tumor cells growing in vivo in animals treated with immunotherapy (FIG. 1). First, a B16 melanoma cell line was engineered to express Cas9 (FIG. 2A), confirmed of efficient DNA editing using sgRNAs targeting PD-L1 (FIG. 1D, bottom). Next, a library of lentiviral vectors was created to encode 9,992 sgRNAs targeting 2,398 genes from relevant functional classes that were expressed at detectable levels in the tumor cell line (FIG. 2B). After transduction and in vitro passage to allow gene editing to take place, the tumor cells were transplanted into animals that were then treated with either a GM-CSF-secreting, irradiated tumor cell vaccine (GVAX) or GVAX plus PD-1 blockade using a monoclonal antibody for PD-1, in order to apply immune selective pressure on the tumor cells (FIG. 1B) (see Dranoff (2003) *Oncogene* 22:3188-3192; Dranoff et al. (1993) *Proc. Natl. Acad. Sci. U.S.A.* 90:3539-3543; and Duraiswamy et al. (2013) *Cancer Res.* 73:3591-3603; Curran & Allison (2009) *Cancer Res* 69:7747-7755; Curran et al. (2010) *Proc. Natl. Acad. Sci. U.S.A.* 107:4275-4280). In parallel, the library-transduced tumor cells were transplanted into TCR$\alpha^{-/-}$ mice, which lack CD4$^+$ and CD8$^+$ T cells and were therefore unable to apply adaptive immune selective pressure on the tumors. This allowed to distinguish the effect of immune selective pressure on library representation from nonspecific effects on tumor cell viability. After 12-14 days, tumors were harvested (FIG. 1), with all sgRNAs recovered from each animal with good inter-animal reproducibility (FIG. 2C-FIG. 2E).

The library representation in tumors from immunotherapy-treated wild-type (WT) animals were compared with that found in tumors growing in TCR$\alpha^{-/-}$ mice, in which deletion of genes that result in resistance to immunotherapy would be expected to increase tumor sgRNA representation in WT animals, while deletion of genes that result in increased sensitivity of tumors to immunotherapy would decrease sgRNA representation. Analysis of sgRNAs enriched by immune selective pressure revealed those targeting genes involved in cytokine-mediating signaling and immune-system processes (FIG. 1C). sgRNAs depleted by immunotherapy included those targeting genes involved in antigen processing, necroptosis, and regulation of immune responses (FIG. 1C). These results indicate that the genetic screening approach used here identified genes expressed by tumors cells that play a role in interaction with the immune system.

Inspection of the list of genes targeted by sgRNAs depleted from tumors treated with immunotherapy revealed the known immune evasion molecule PD-L1, indicating that loss of PD-L1 increased the sensitivity of tumor cells to immune attack. sgRNAs targeting PD-L1 were not depleted from tumors in TCR$\alpha^{-/-}$ mice relative to cells growing in vitro, presumably due to the absence of T cell-mediated selective pressure (FIG. 1D), but were significantly depleted in WT mice treated with GVAX relative to TCR$\alpha^{-/-}$ mice (FDR=0.004). However, the depletion of PD-L1-targeting sgRNAs seen in GVAX-treated tumors was not observed in tumors treated with GVAX and anti-PD-1, indicating that loss of PD-L1 does not confer a selective disadvantage to tumors when PD-L1:PD-1 interactions are blocked (FIG. 1D).

It was also found that sgRNAs targeting CD47, which enables immune evasion by impairing engulfment of tumors cells by phagocytes (as in Liu et al. (2015) *Nat. Med.* 21:1209-1215; Weiskopf et al. (2016) *J. Clin. Invest.* 126:2610-2620; and Tseng et al. (2013) *Proc. Natl. Acad. Sci. U.S.A.* 110: 11103-11108), were markedly depleted in tumors treated with either GVAX or with GVAX plus PD-1 blockade (FDR=0.005, 0.002 respectively) (FIG. 1E). To confirm that CD47 null tumors were more susceptible to GVAX and PD-1 blockade, CD47 null B16 melanoma cells were generated using transient transfection of a Cas9-sgRNA plasmid (as in Ran et al. (2013) *Nat. Protoc.* 8:2281-2308) (FIG. 2F). It was found that loss of CD47 significantly improved control of tumor growth mediated by GVAX plus anti-PD-1 immunotherapy (FIG. 1F, p<0.01).

Using the pooled loss-of-function in vivo genetic screen for identifying immune evasion molecules expressed by tumors described above, genes that increase or decrease the fitness of MC38 colon cancer cells growing in vivo in animal treated with immunotherapy. Thus, in vivo genetic screening recovered genes known to confer tumor evasion properties on cancer cells.

Figure 4:
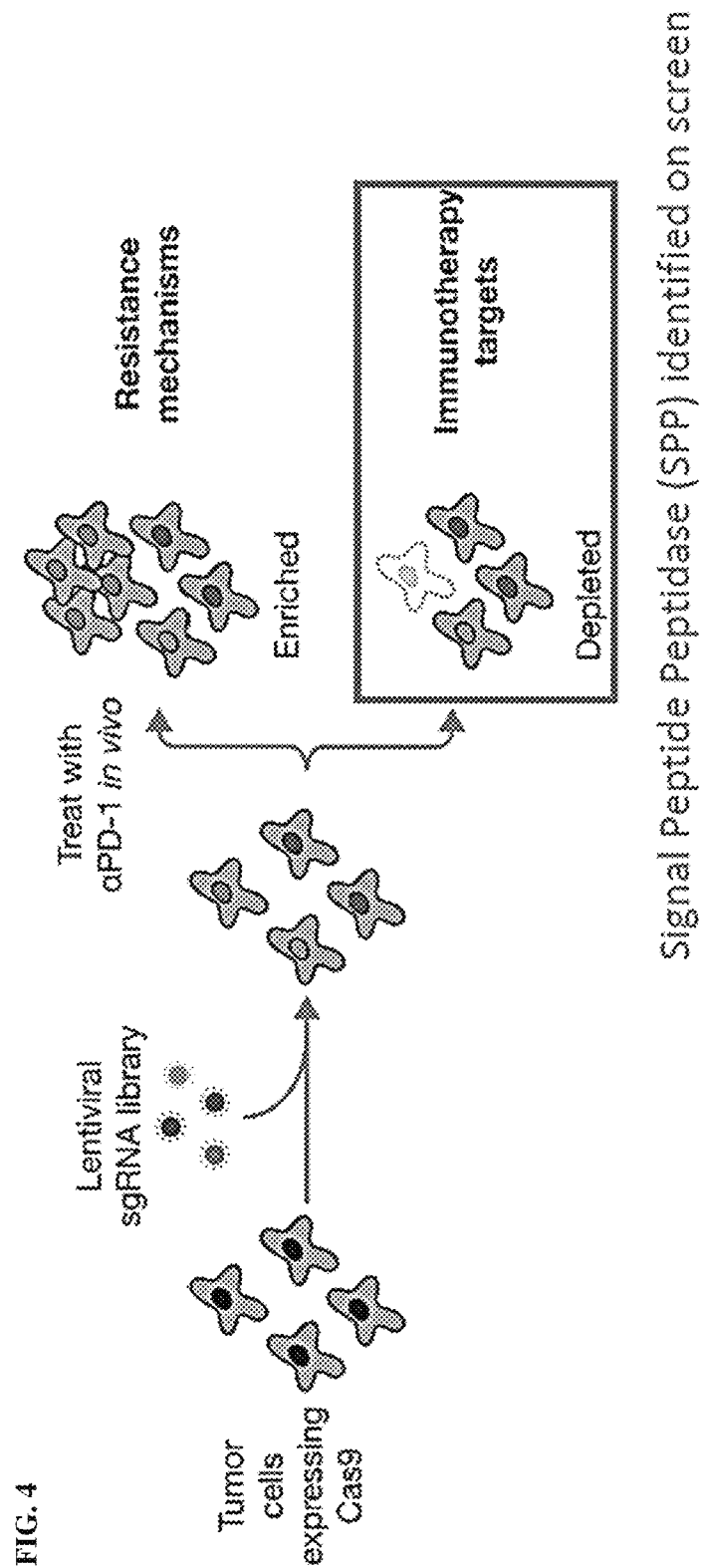
FIG. 4 shows that genetic CRISPR/Cas9 screen identifies synergistic immunotherapy targets, such as SPP. A schematic diagram of the in vivo pooled loss-of-function screening using CRISPR/Cas9 in B16 transplantable tumor cells, in combination with PD-1 blockade. The screen recovers SPP as a candidate molecule, when inhibited, sensitizes tumors to immunotherapy.
Figure 4:
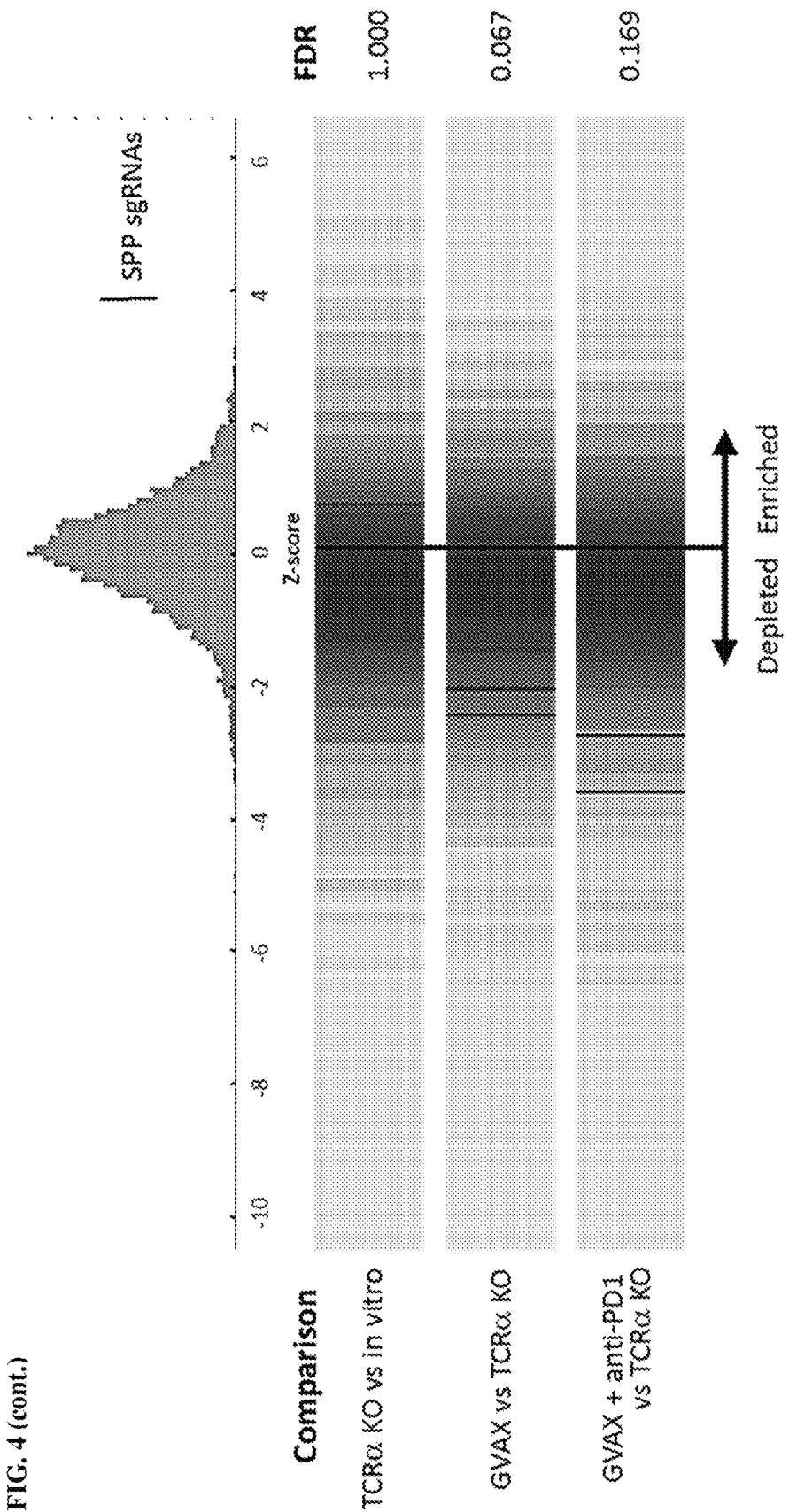

Example 3: Discovery of a New Gene Target to Increase the Efficacy of Immunotherapy Deletion of a new candidate immunotherapy target was found to increase sensitivity of tumor cells to immunotherapy. sgRNAs targeting signal peptide peptidase (SPP) was markedly depleted in mice treated with GVAX and PD-1 blockade relative to growth in TCR$\alpha^{-/-}$ mice (FIG. 4).

Figure 5A:
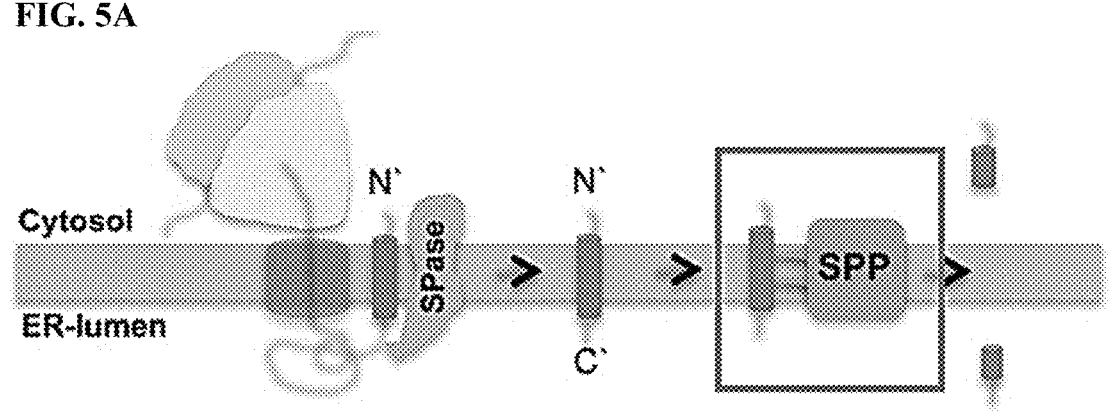
FIG. 5A-FIG. 5B show schematic diagrams depicting a mechanism of action for SPP. SPP is an intramembrane aspartyl protease in endoplasmic reticulum membrane. SPP cleaves remnant signal peptides left behind in membrane by the action of signal peptidases (SPases). SPP is conserved across mouse, human, and malaria. The GxGD-type aspartyl intramembrane-cleaving protease cleaves signal peptides in the ER membrane.
Figure 5B:
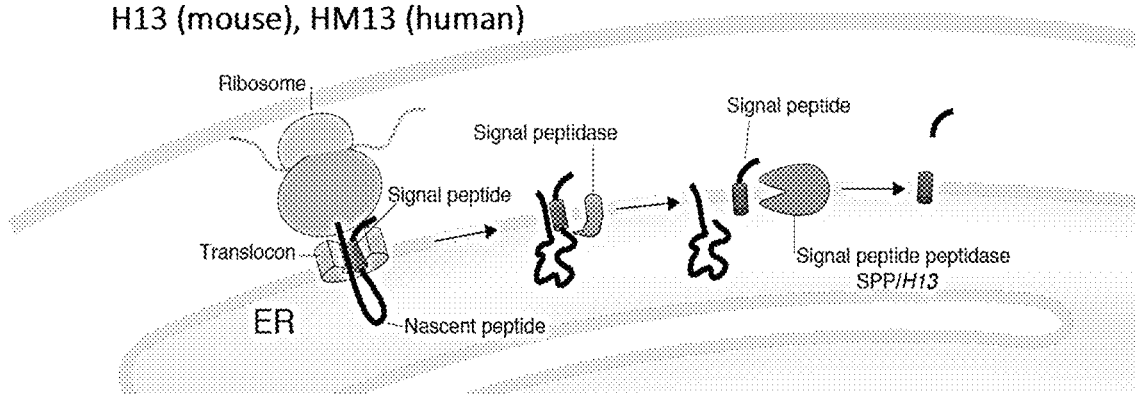

Example 4: In Vivo Validation of SPP as a Target for Combination with Immunotherapy A representative gene affecting protein cleavage and processing, e.g., SPP, was selected to validate based on their highest cumulative score as ranked by the STARS algorithm (Doench et al. (2014) *Nat. Biotechnol.* 32:1262-1267; FIG. 4). SPP is an intramembrane aspartyl protease that cleaves signal peptides in endoplasmic reticulum membrane (FIG. 5A-FIG. 5B) resulting in the release of the fragment from the ER membrane into the cytoplasm. It is highly conserved across mouse, human, and malaria (Schroder et al. (2010) *Biochem J.* 427:e1-e3).

Figure 6A:
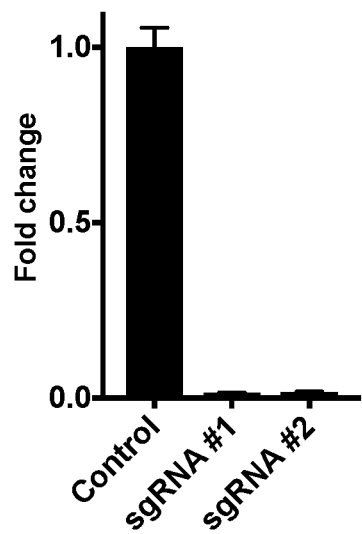
FIG. 6A-FIG. 6G show that deletion of SPP sensitizes tumor to anti-PD1 therapy, and synergistically improves immunotherapy efficacy.
Figure 6B:
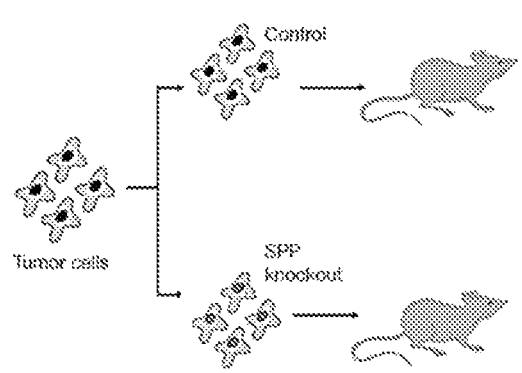
Figure 6C:
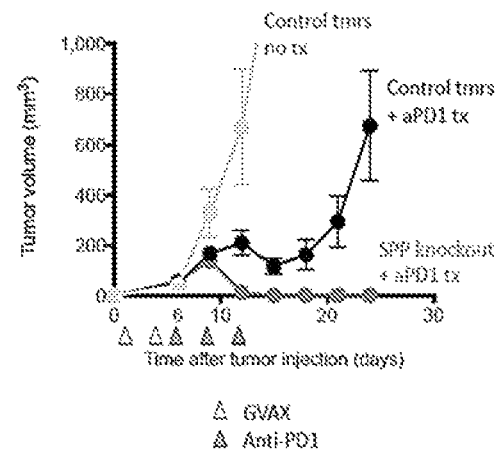
Figure 6D:
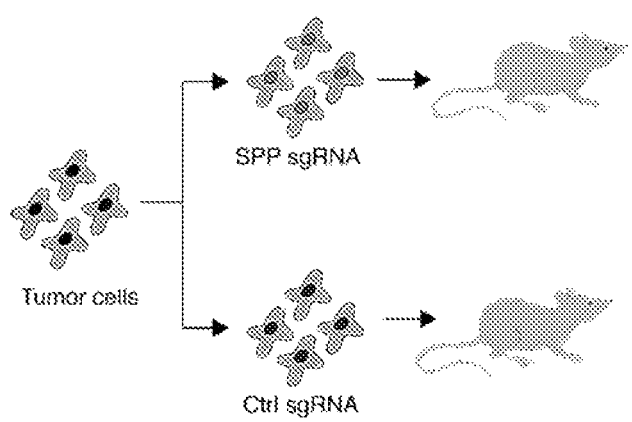
Figure 6E:
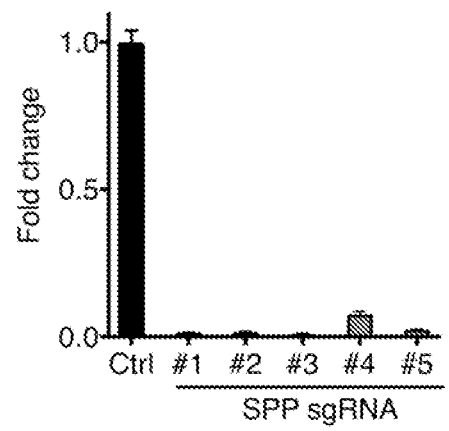
Figure 6F:
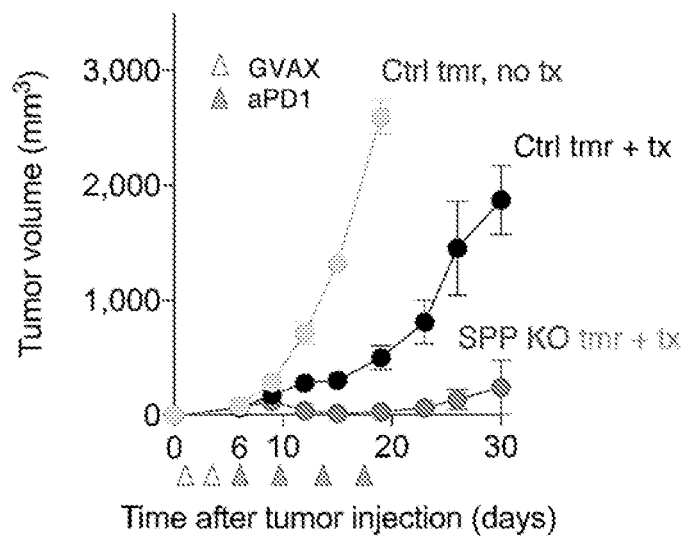
Figure 6G:
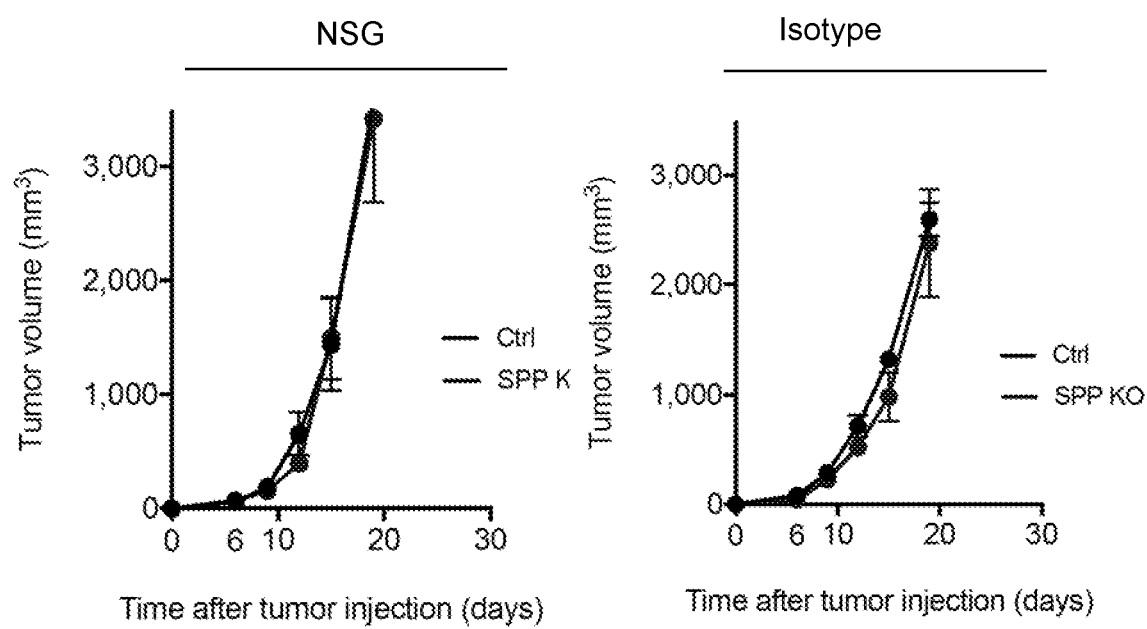

Ablation of SPP in murine B16 cancer cells dramatically improved in vivo efficacy of anti-PD-1 monoclonal antibody therapy in WT C57bl/6j mice (FIG. 6A-FIG. 6G). Mice injected with SPP-ablated tumor cells show significantly decreased tumor burden when treated with anti-PD-1 checkpoint blockade (FIG. 6C and FIG. 6F). In addition, the lack of tumor regression in NOD scid gamma mice bearing SPP deletion shows that the anti-tumor effect conferred by the SPP deletion requires immune response (FIG. 6G). Accordingly, SPP is synthetically lethal with an anti-tumor immune response and renders tumor cells more sensitive to immunotherapy without altering the cell growth or survival in the absence of T cells.

Figure 7A:
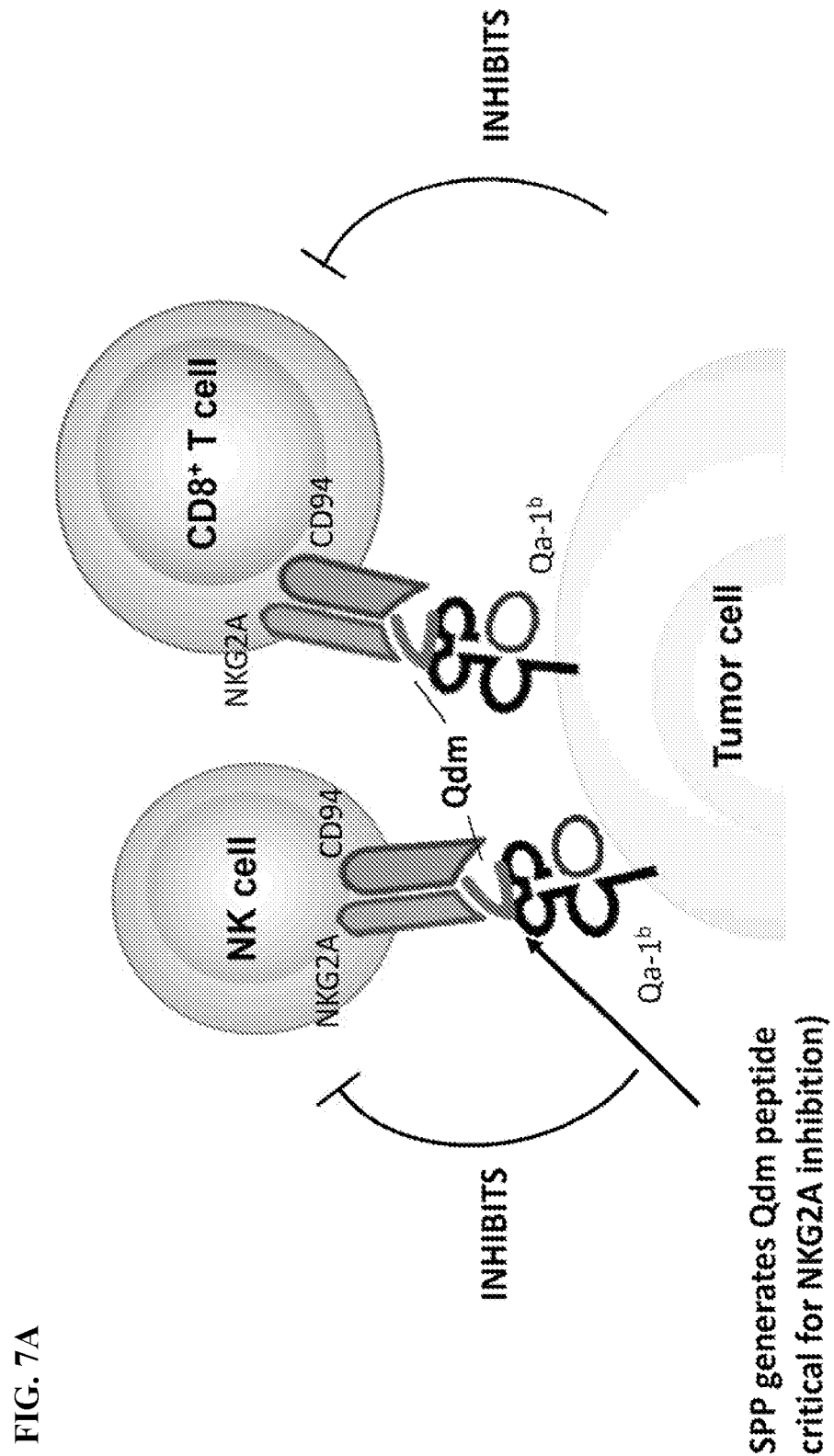
FIG. 7A-FIG. 7E show schematic diagrams depicting how Qa-1b/Qdm on tumor cells inhibit immune cells via NKG2A.
Figure 7B:
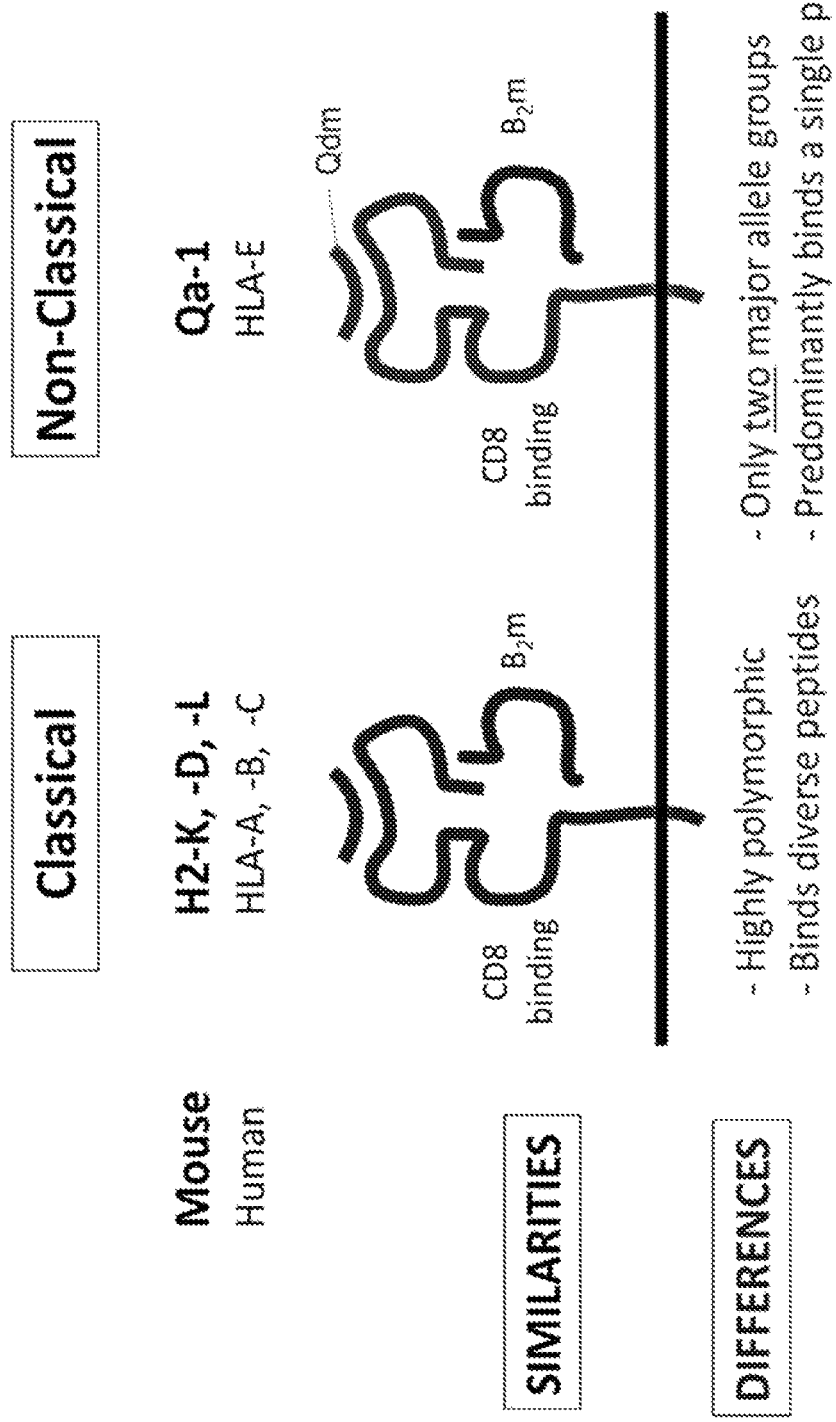
Figure 7C:
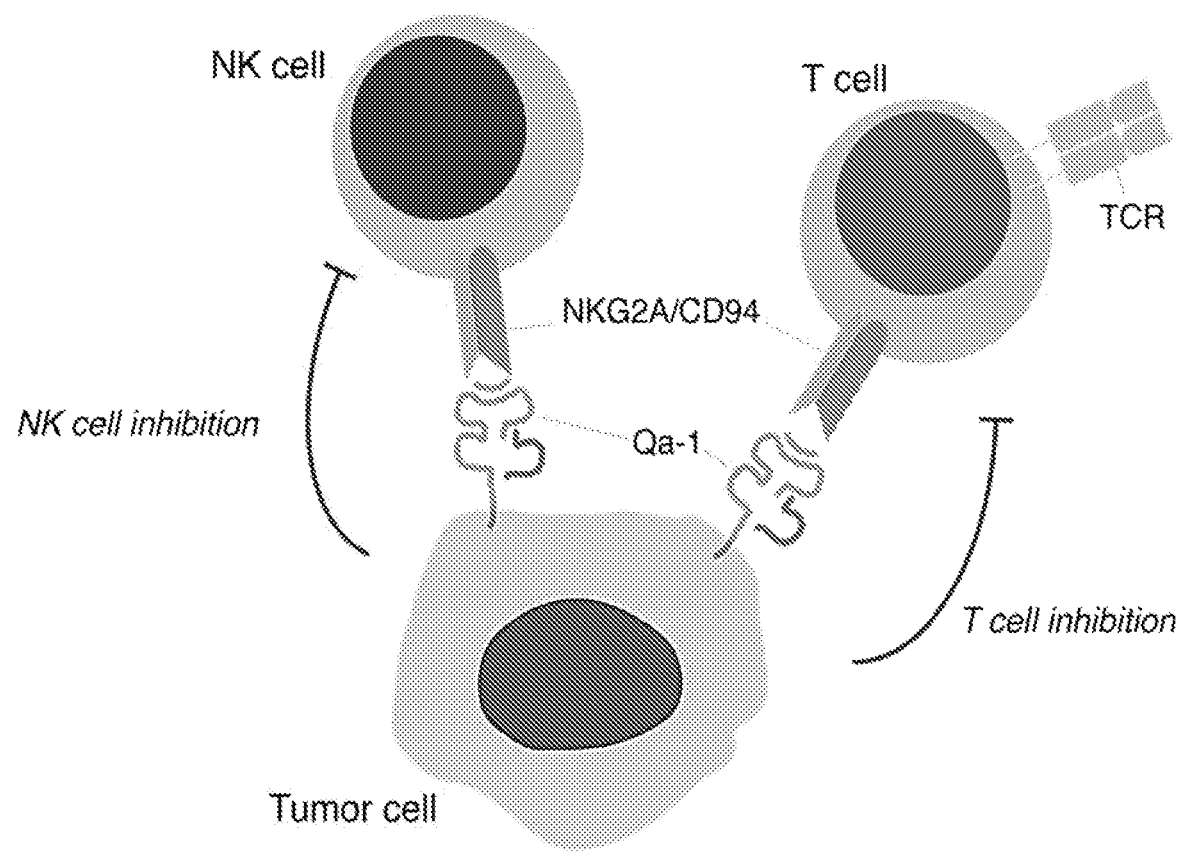
Figure 7D:
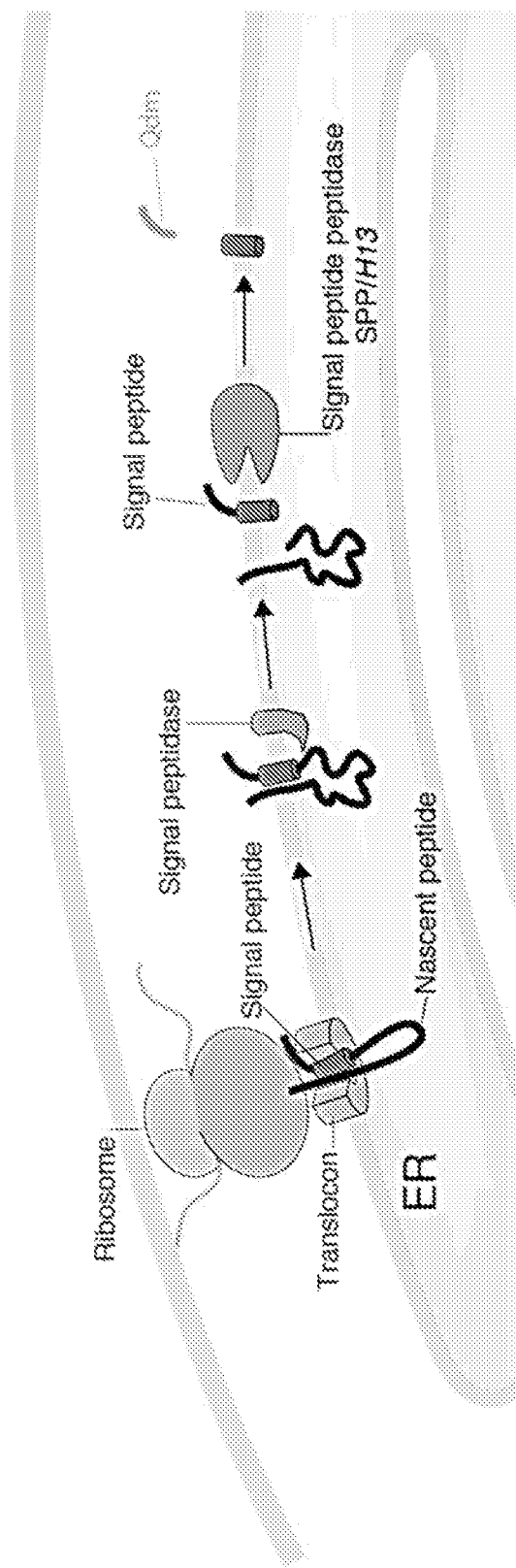
Figure 7E:
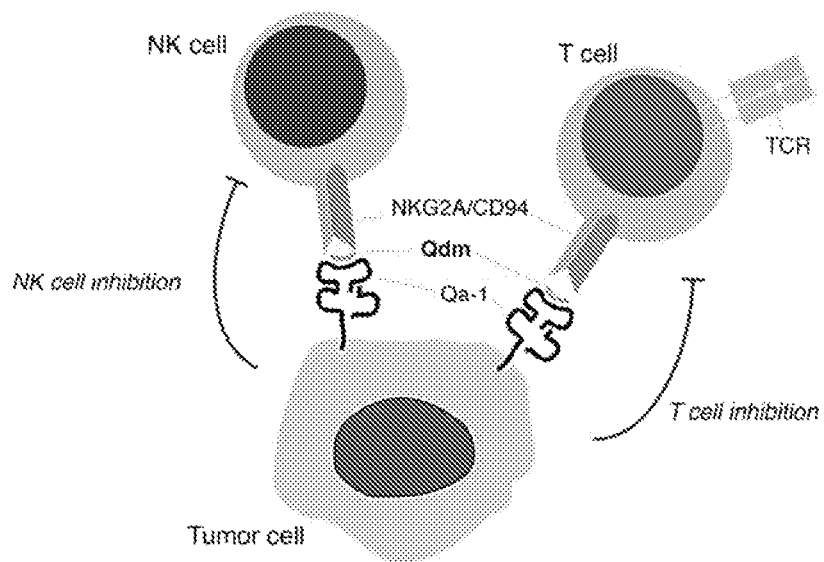
Figure 7E:
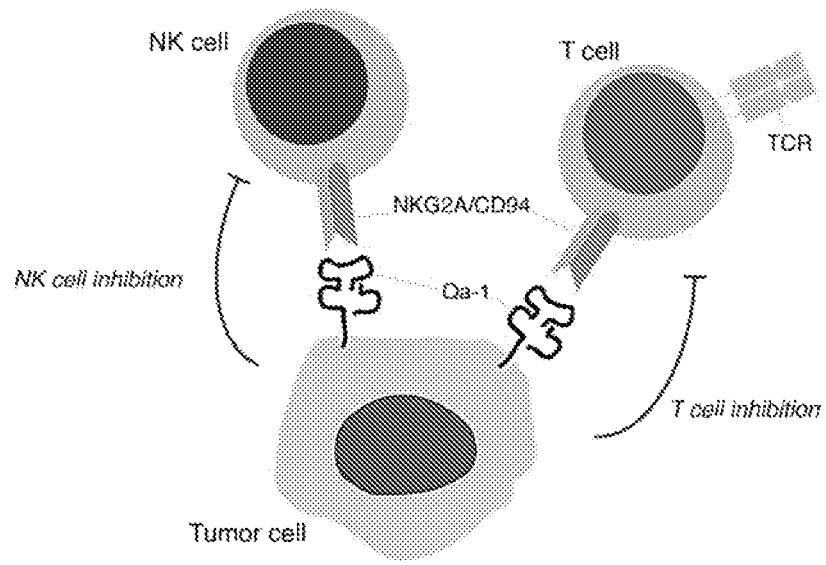
Figure 7E:
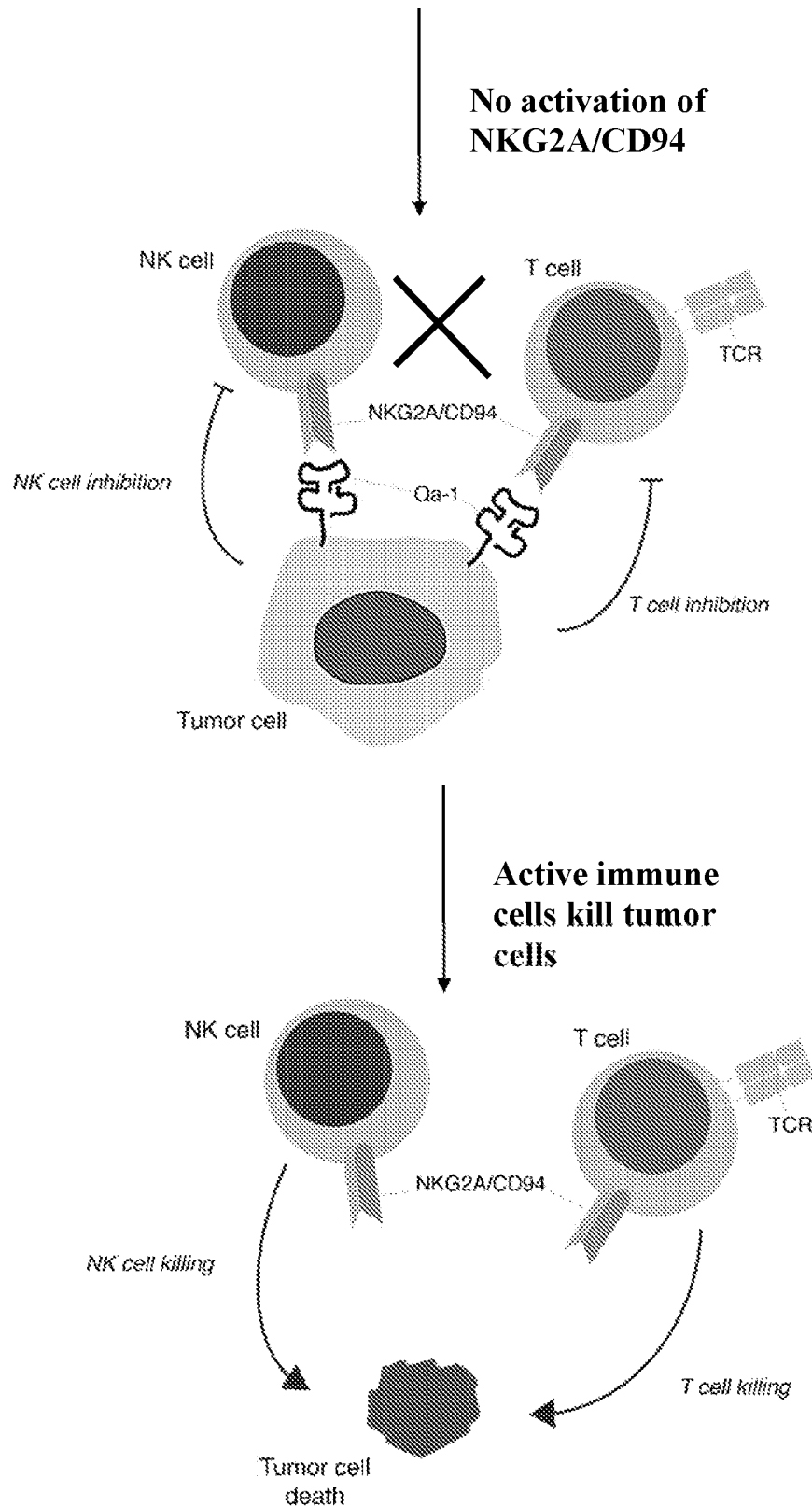

Example 5: Mechanistic Determination of the Sensitivity to Checkpoint Blockade Conferred by the SPP Deletion HLA-E in humans (or Qa-1b in mice) is a non-classical MHC molecule that binds the inhibitory receptors CD94/NKG2A on T cells and NK cells (Wada et al. (2004) *Eur J Immunol.* 34:81-90; see also FIG. 7A-FIG. 7D). HLA-E preferentially associates with a subset of peptides, including those derived from signal peptides of classical MHC class I molecules, namely HLA-A, B, C, G (Braud et al. (1997) *Eur. J. Immunol.* 27:1164-1169) (referred to herein as Qdm peptide(s)). Amino acid sequence of a representative set of such peptides is listed in Tables 1 and 2 (SEQ ID NOs: 17-45). Presentation of the the Qdm peptide by HLA-E facilitates the interaction between HLA-E and the CD94/NKG2A heterodimer (FIG. 7A). Upon engaging the HLA-E/associated peptide complex, CD94/NKG2A, a member of a family of lectin-like NK cell receptors, inhibits the activity of NK cells or CD8+ T cells against tumor cells. This inhibition allows efficient immune escape of tumors (FIG. 7A).

Figure 8A:
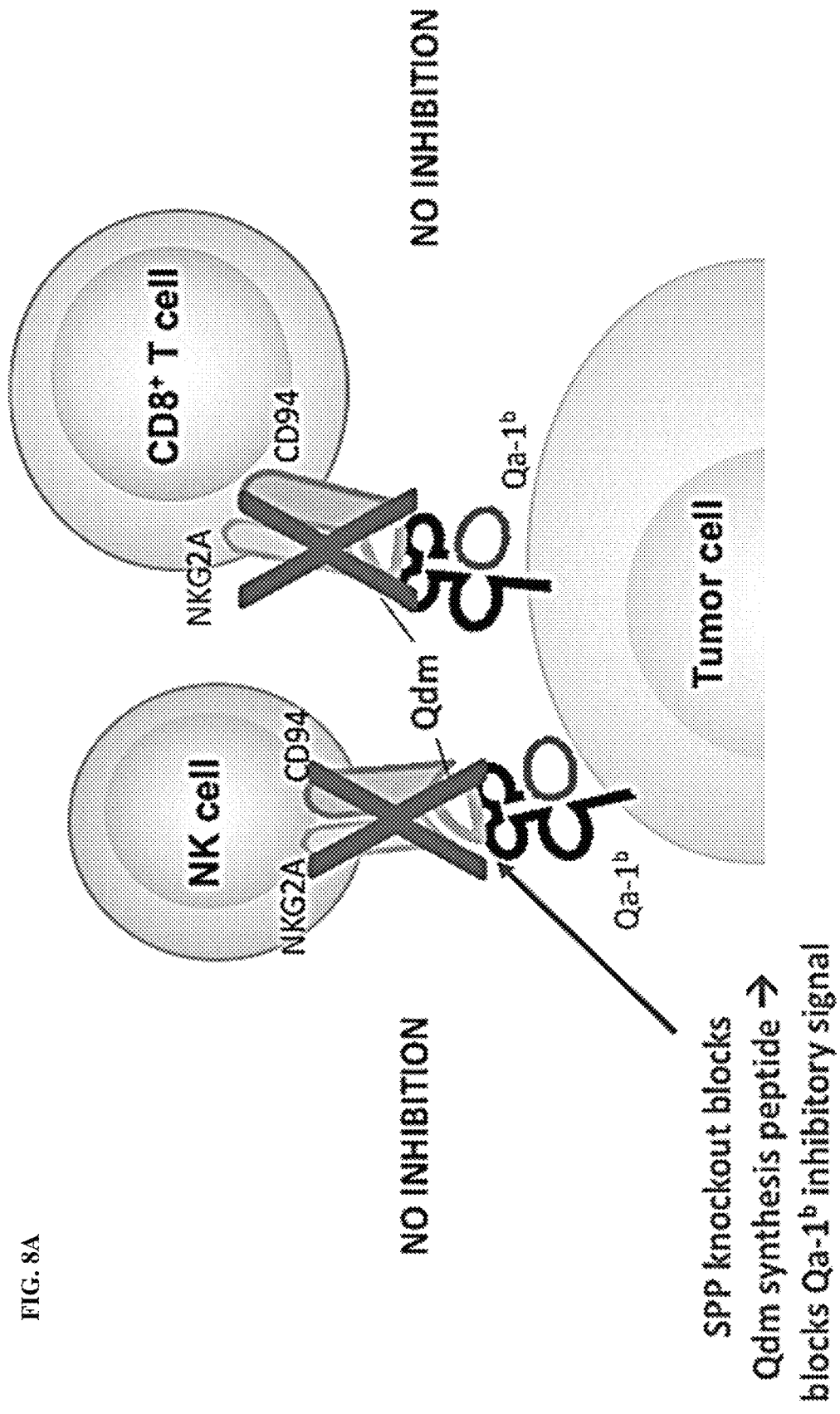
FIG. 8A-FIG. 8B shows a schematic diagram depicting two mechanism by which the deletion of SPP enhances immune response independently of the PD-1 pathway.
Figure 8B:
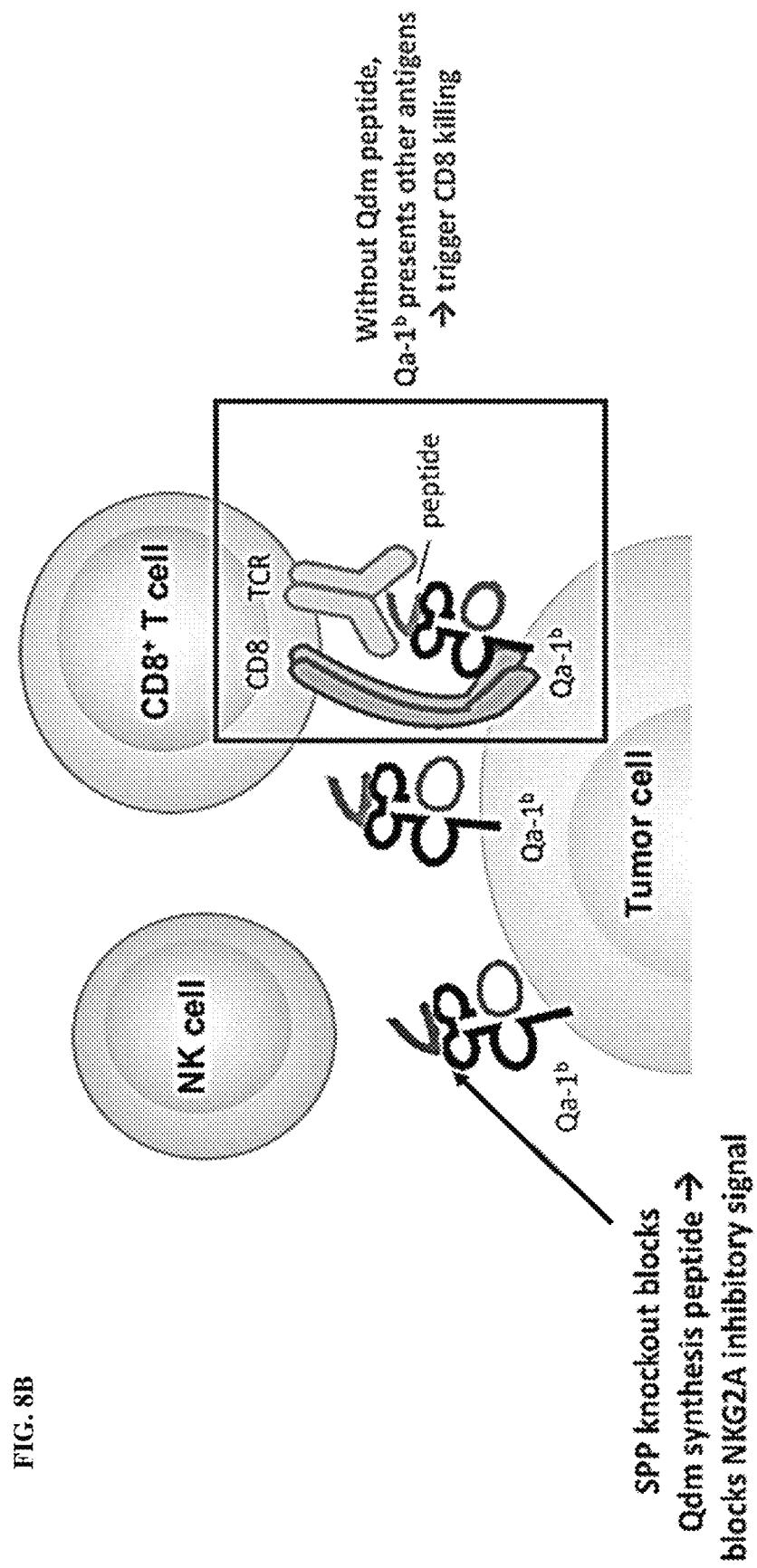
Figure 12:
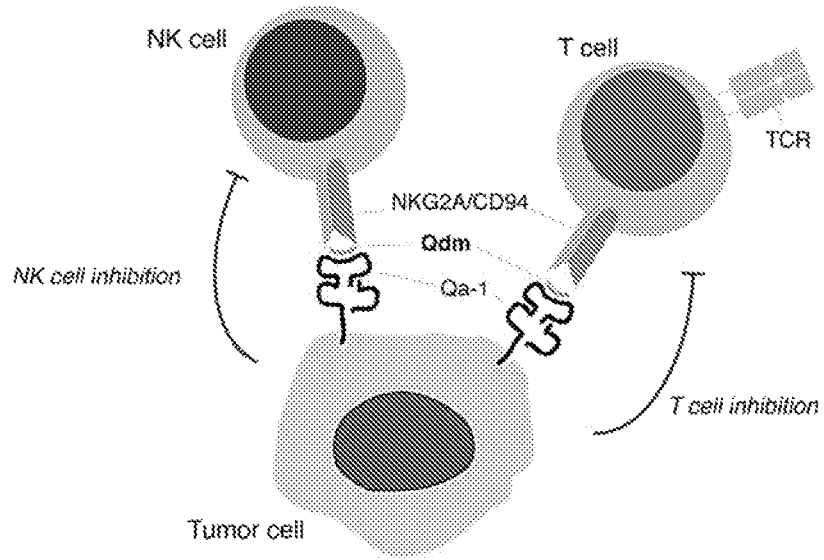
FIG. 12 shows a flow chart depicting a mechanism by which the peptides other than Qdm promotes the anti-tumor activity of CD8+ T cells by mediating the interaction between the T cell Receptor and Qa-1b.
Figure 12:
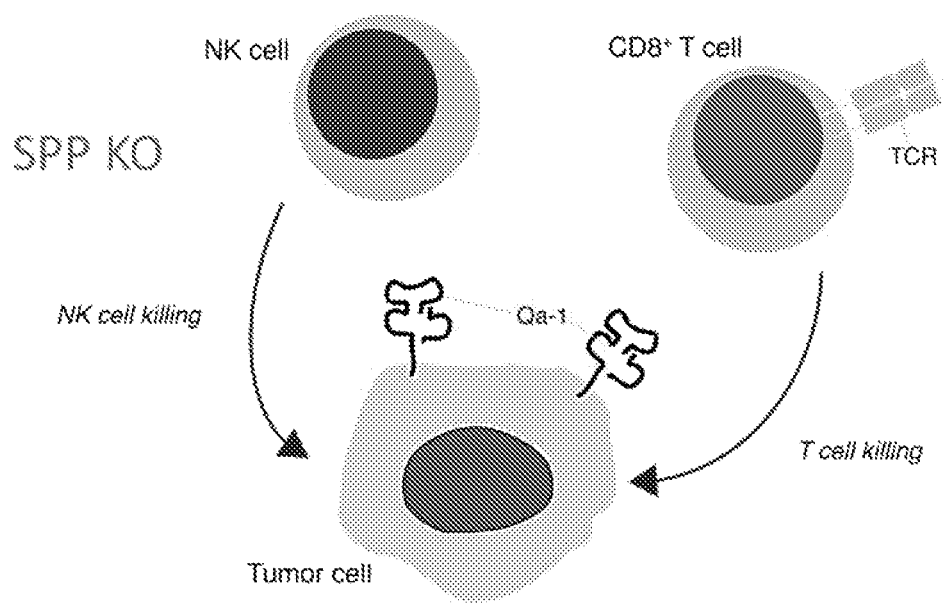
Figure 12:
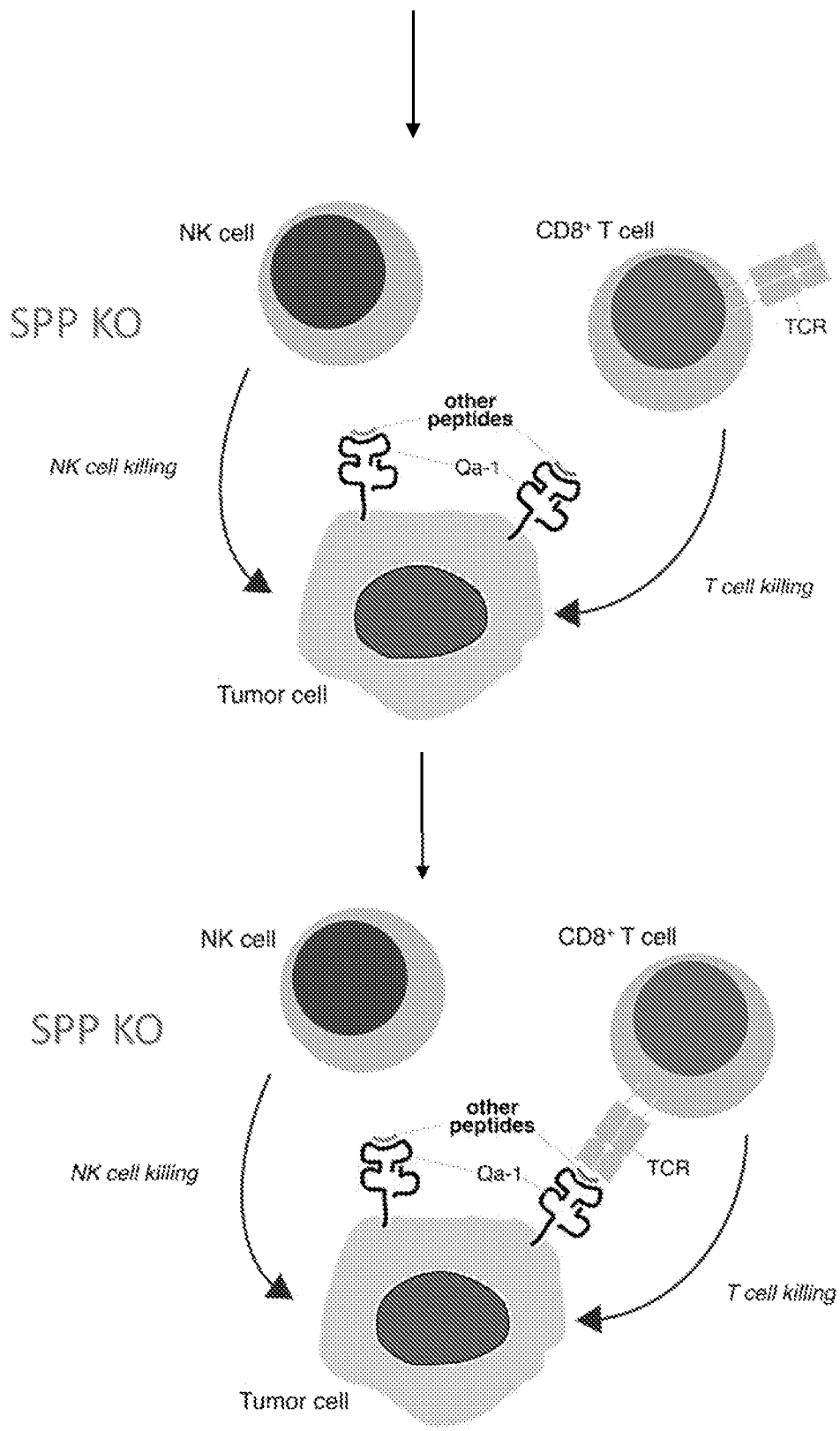
Figure 12:
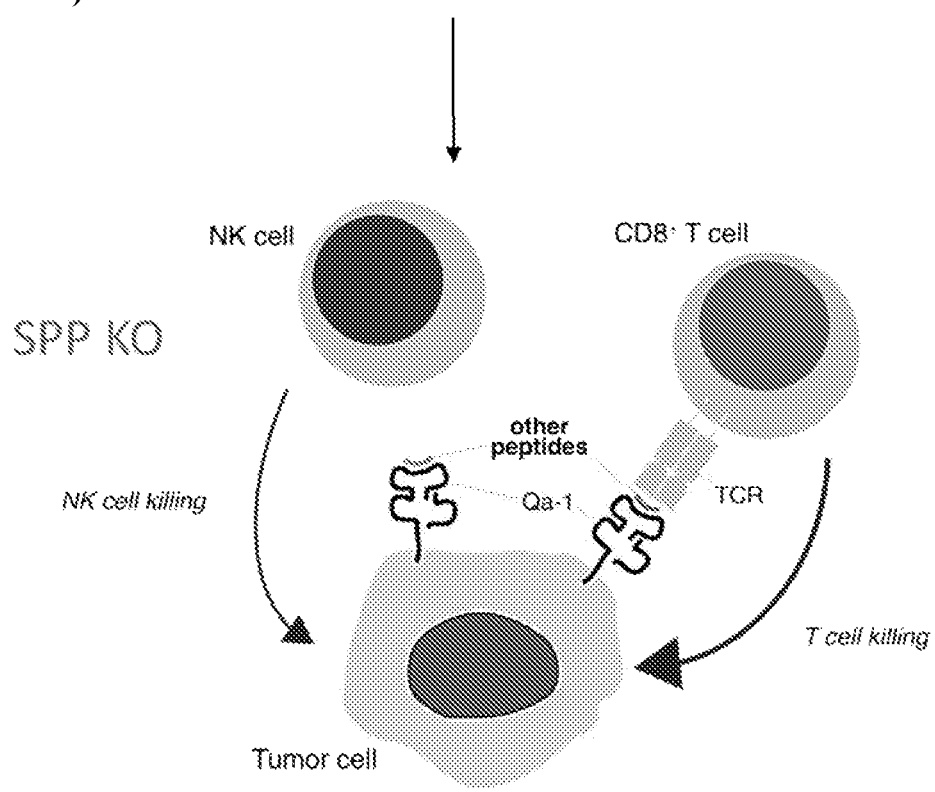

It is described herein that the deletion of SPP sensitizes tumor cells to checkpoint blockade or other immune therapies by two mechanisms (FIG. 7E-FIG. 8B, FIG. 12). First, as described above, SPP is required for the production of Qdm, which is critical for CD94/NKG2A inhibition of NK cells and CD8+ cells. Accordingly, deletion of SPP is believed to block the production of Qdm, and prevents the interaction between HLA-E and CD94/NKG2A (FIG. 8A). Without HLA-E, CD94/NKG2A cannot inhibit NK cells and T cells, and their killing of tumor cells. This activation of NK cells and T cells is independent of the PD-1 pathway such that PD-1 blockade and SPP deletion work synergistically. Second, without the Qdm peptide, it is believed that HLA-E can present other antigens that are tumor-derived, resulting in cytotoxic killing of the tumor cells by CD8+ T cells (FIG. 8B). Thus, SPP deletion is believed to enhance antigen presentation of novel tumor antigens (e.g., neoantigen) on the cell surface of tumors. In summary, the the SPP deletion is believed to provide a two-pronged method of promoting the immune system that improves tumor immunity and effectively synergizes with immunotherapies, such as PD-1 blockade (FIG. 6, FIG. 8, and FIG. 12).

The above mechanism is demonstrated in the in vivo efficacy study of FIG. 9. Specifically, deletion of Qa-1b (HLA-E in human) in tumor cells enhances tumor immunity, as evidenced by the efficacy data comparing the growth of HLA-E null B16 melanoma cells to control B16 tumors in mice treated with GVAX and PD-1 blockade (FIG. 9). Immunotherapy alone in control tumors did not eradicate tumors. By contrast, immunotherapy of Qa-1b null tumors was curative in all animals (FIG. 6; p<0.05, Student's t test). These results confirm that Qa-1b functions as an immune evasion molecule in tumors and that its loss of function improves tumor immunity, in a manner similar to deletion of SPP.

Example 6: Inhibition of SPP by Gamma Secretase Inhibitors (GSIs)

Figure 10:
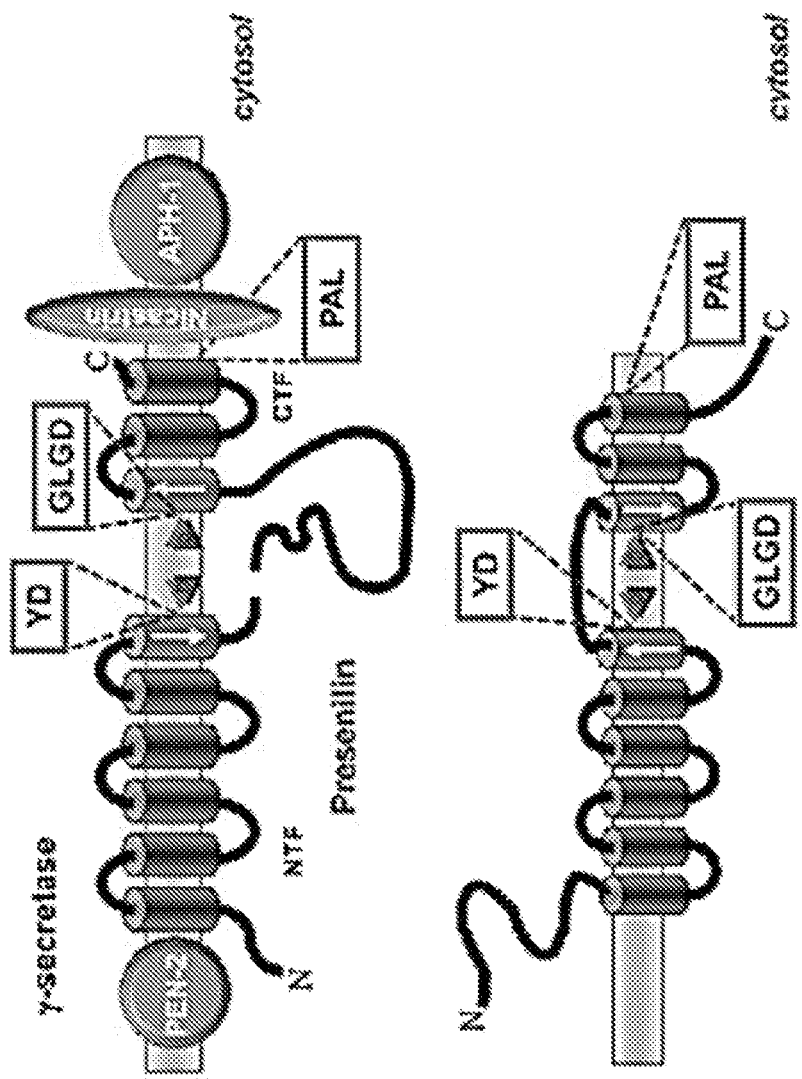
FIG. 10 shows a schematic diagram of the structural similarities between gamma secretases and SPP. Due to shared structures and motifs, inhibitors of gamma secretase (GSI) also inhibit SPP. The figure is adapted from Fluhrer et al. (2009) *J Biol Chem* 284:23975-9.

SPP is inhibited by gamma secretase inhibitors, largely owing to the structural similarities between gamma secretase and SPP (FIG. 10; Ran et al. (2015) *PLOS ONE* 10:e0128619). In addition to both proteins being membrane-bound, they share similar motifs, such as YD, GLGD, and PAL motifs (Fluhrer et al. (2009) *J Biol Chem* 284:23975-9; FIG. 10). Accordingly, this allows utility of gamma secretase inhibitors in inhibition of SPP, and provides pharmacological means to inhibit SPP in cancer treatment to enhance the efficacy of immune therapies.

Example 7: SPP and Qa-1b Function in the Same Pathway

Figure 9A:
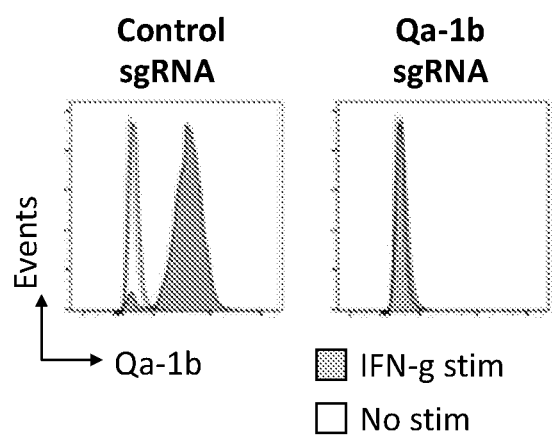
FIG. 9A-FIG. 9D show that deletion of Qa-1b in mice improves immunotherapy efficacy and that Qa-1b and SPP function in the same pathway.
Figure 9B:
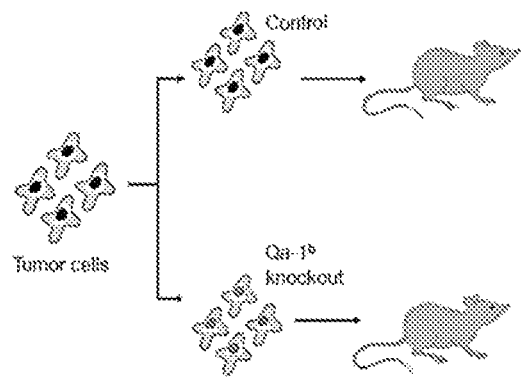
Figure 9C:
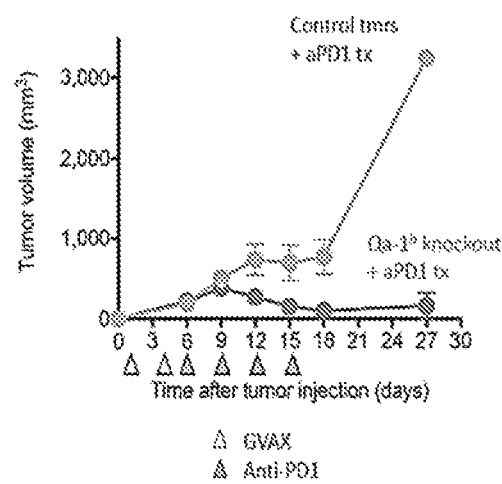
Figure 9D:
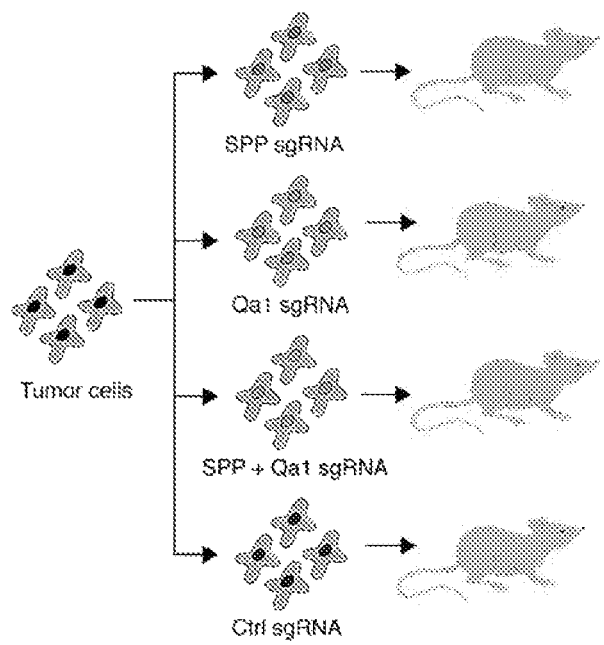
Figure 9D:
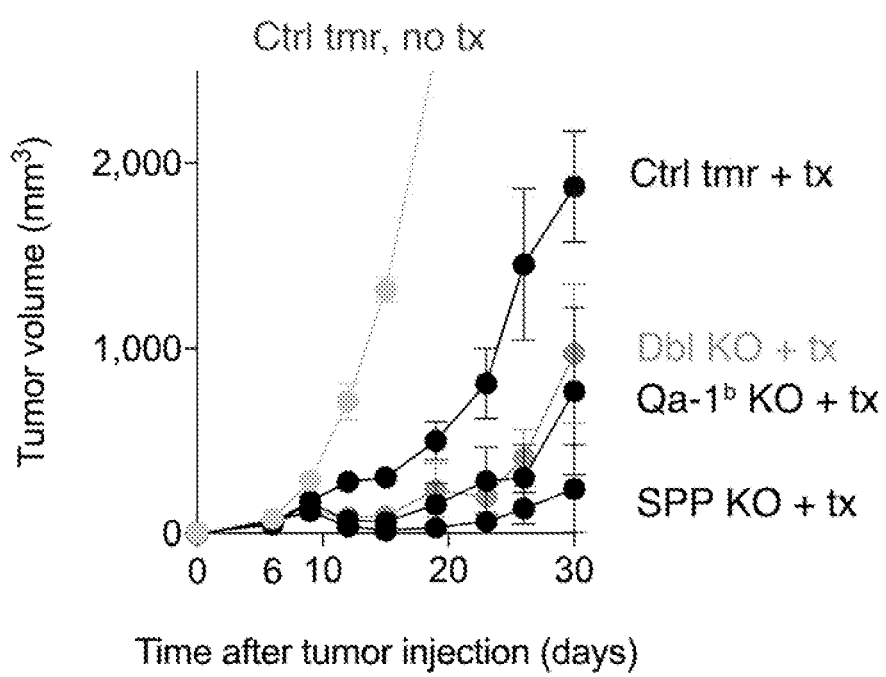

In order to determine the functional relationship between SPP and Qa-1b, their combined effect on tumor regression was tested in vivo. Specifically, the anti-tumor activity was compared for mice bearing tumors with the SPP deletion, the Qa-1b deletion, or the double deletion of SPP and Qa-1b (FIG. 9D). The similar growth rate displayed by these mutant tumors indicate a lack of synergism between the SPP and Qa-1b deletions (FIG. 9D). Thus, SPP and Qa-1b function cooperatively in the same pathway to sensitize tumor cells to immunotherapy.

Figure 11A:
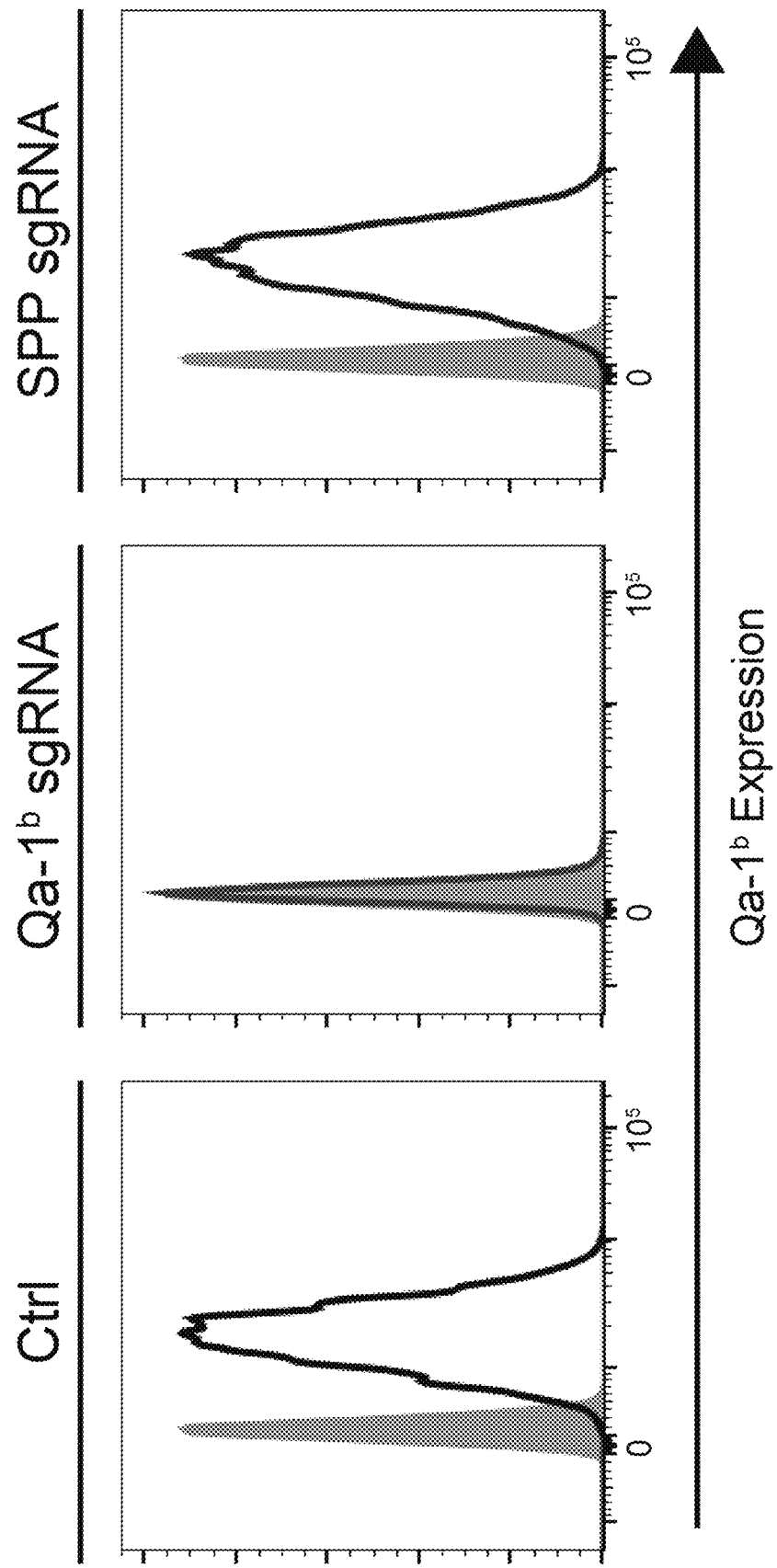
FIG. 11A-FIG. 11E show that when SPP is deleted and deprives the Qdm peptide, Qa-1b is then loaded with other peptides including Myo7a peptide, which in turn promotes CD8+ T cell-mediated killing of tumor cells.
Figure 11B:
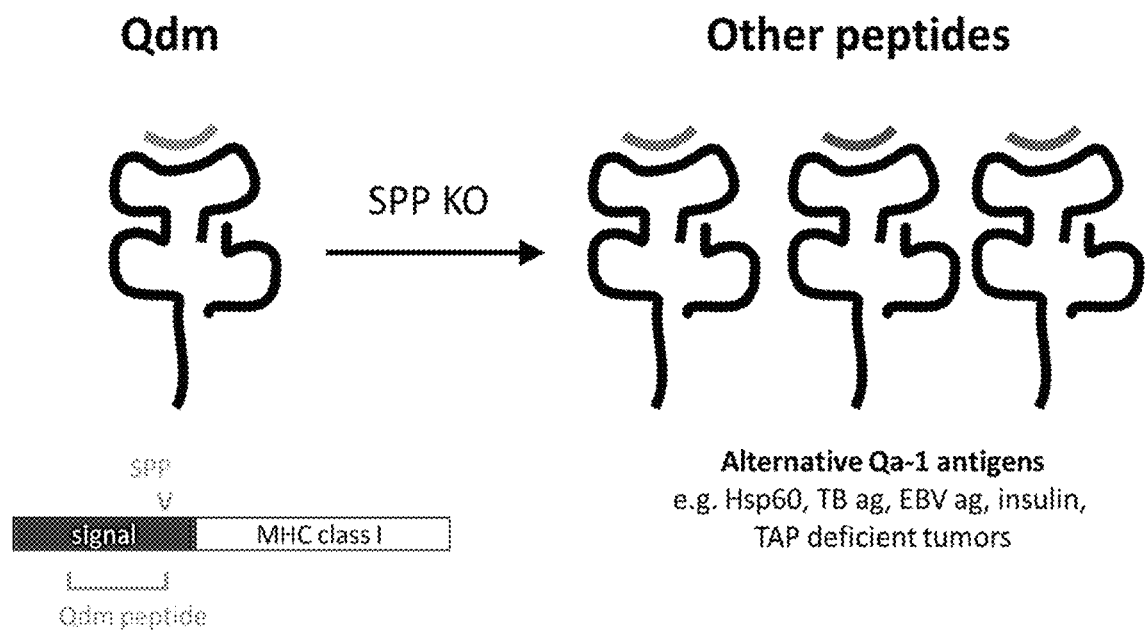
Figure 11C:
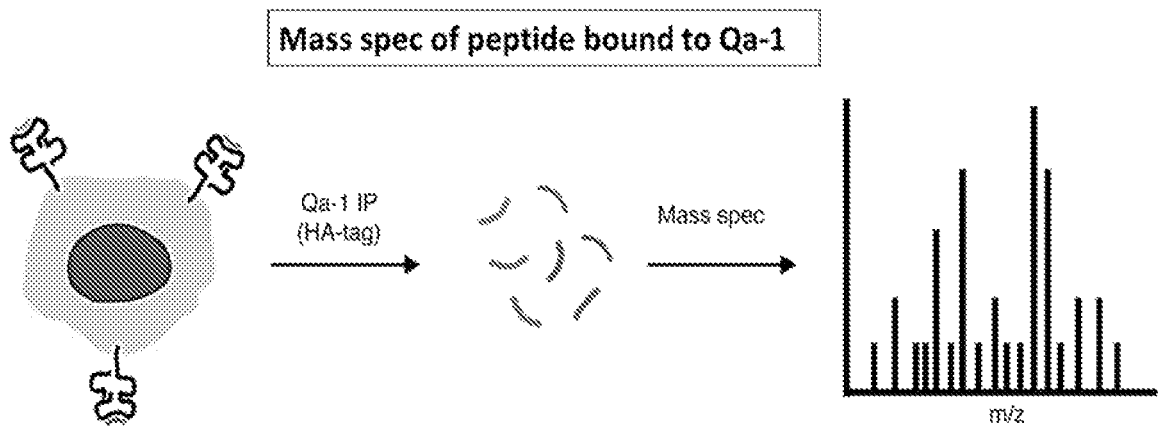
Figure 11D:
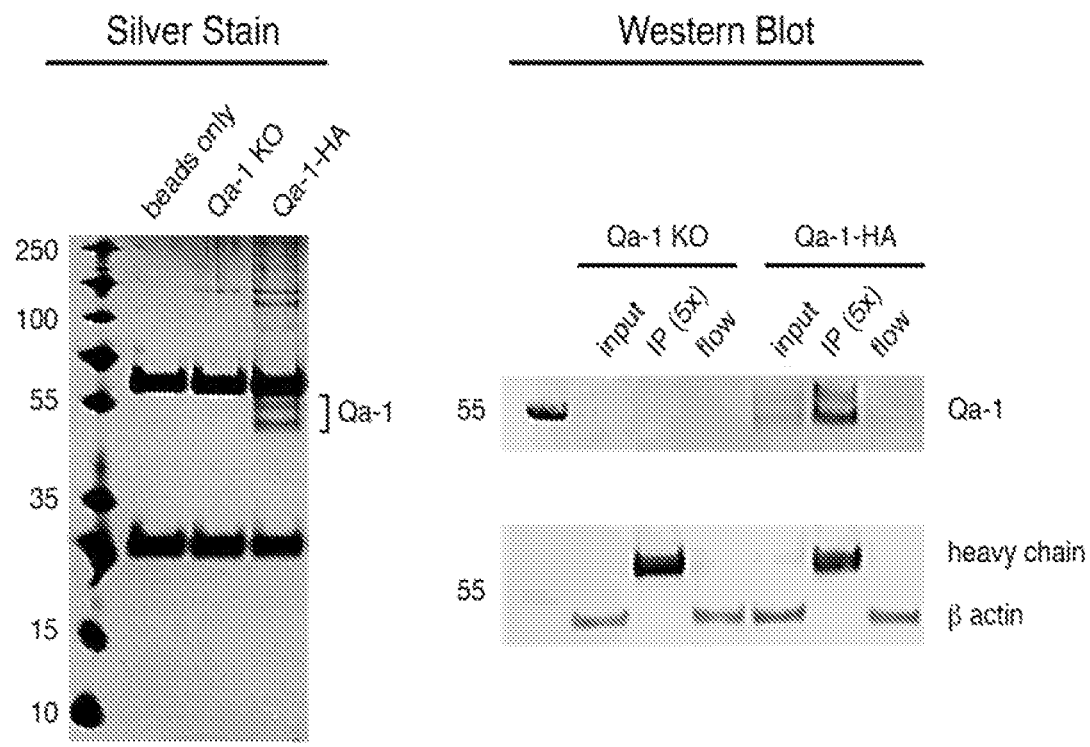
Figure 11E:
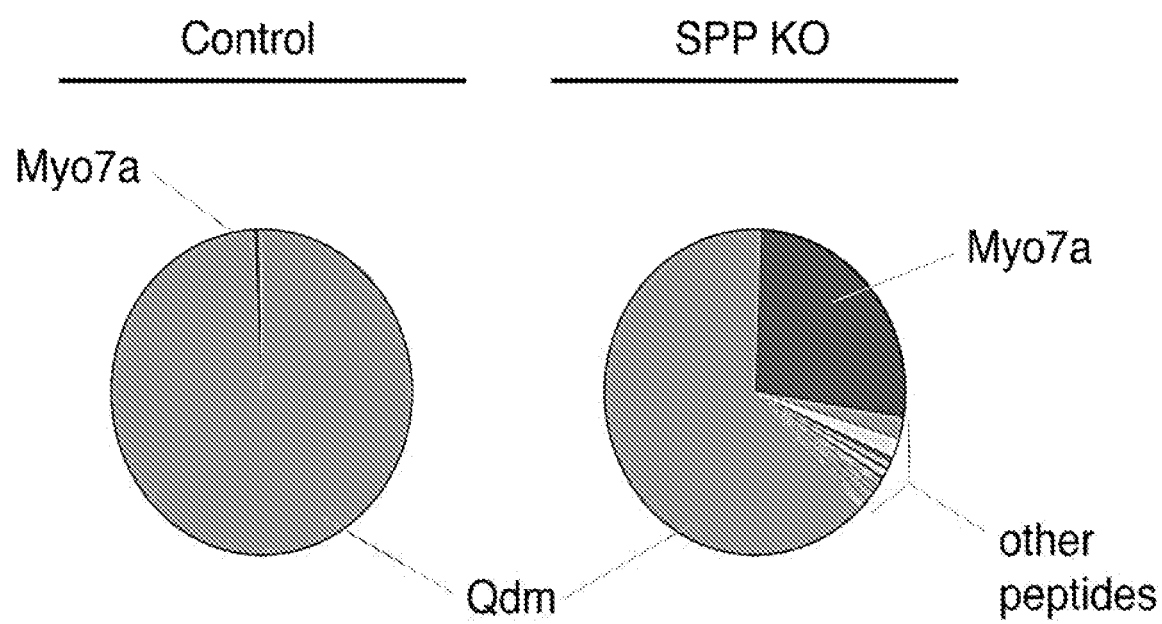

Example 8: In the Absence of SPP, the Qa-1b Preferentially Associates with Myo7a to Positively Regulate Immune Response As described above, in the absence of SPP and its consequential deprivation of the Qdm peptides, Qa-1b is believed to present other peptides and activate CD8+ T cells through T cell receptors (see Example 5; FIG. 7E-FIG. 8B). In order to identify the neoantigens, whose peptides associate with Qa-1b in the absene of SPP, Qa-1b was immunoprecipitated from tumor cells containing the SPP deletion. Silver staining and Western blotting of protein isolates from immunoprecipitation confirm pure and specific isolation of Qa-1b proteins (FIG. 11D). The Qa-1b-associated peptides were then recovered, and their identities were analyzed by mass spectrometry (FIG. 11A-FIG. 11C). The results show that a significant amount of Qa-1b associates with Myo7a in cells with the SPP deletion (FIG. 11E). Although Qa-1b-Myo7a complex is also present in the control sample, the amount of such complex is small, and over 99% of Qa-1b in the control sample is associated with the Qdm peptide (FIG. 11E). The surprising discovery of the preferential association between Qa-1b and Myo7a in cells containing the SPP deletion demonstrates the identity of a neoantigen whose peptides modulate the sensitivity of the tumor cells to immunotherapy (FIG. 12).

Example 9: SPP Deletion and Qa-1b Increase T Cell Reactivity to Tumor Cells

Figure 13:
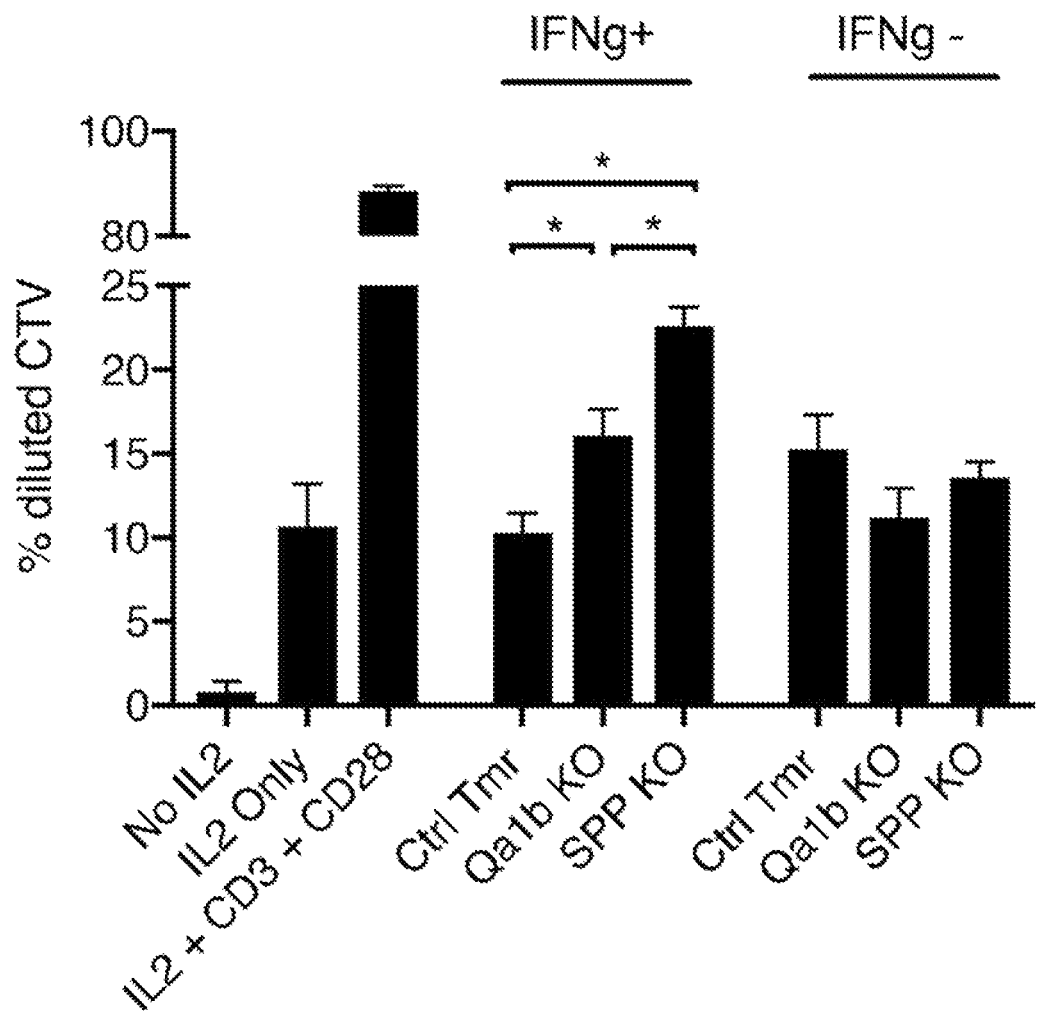
FIG. 13 shows that SPP deletion increases T cell reactivity to the tumor cells with SPP deletion. CD8+ T cells were isolated from whole spleens using negative selection magnetic bead isolation, and then stained with the proliferation tracer dye CellTrace™ Violet. CD8+ T cells were then co-incubated with either tumor cells expressing a wild-type copy of Qa-1b and wild-type copy of SPP, tumors with knock-out of Qa-1b, or tumors with knock out of SPP. These results demonstrate that tumor cells with Qa-1b deletion stimulate more proliferation than control tumor cells. Tumor cells with SPP deletion stimulation even more proliferation compared to those with either Qa-1b deletion or wild type tumors. Together, these results are consistent with a model where Qa-1b knock out provides loss of NKG2A inhibition in CD8 T cells, and SPP knock out provides both loss of NKG2A inhibition as well as the added increased activation due to increased reactivity to newly expressed antigens by Qa-1B.

Qa-1b deletion deletion increases the proliferative reactivity of CD8+ T cells to tumor cells (FIG. 13). Further, SPP deletion additionally increased the proliferative reactivity to a greater extent. Such surprising and unexpected finding demonstrates an that SPP knock out provides additional stimulation to CD8 T cells beyond loss of the Qa-1b/ NKG2A inhibitory signal.

TABLE 4

SEQ ID NO: 67 Human MYO7A Transcript Variant 1 cDNA Sequence
(NM_000260.4, CDS region from position 291-6938)

```
   1 agtgctggct ggacagctgc tctgggcagg agagagaggg agagacaaga gacacacaca
  61 gagagacggc gaggaaggga aagacccaga gggacgccta aacgagact tggagccaga
 121 cagaggaaga ggggacgtgt gtttgcagac tggctgggcc cgtgacccag cttcctgagt
 181 cctccgtgca ggtggcagct gtaccaggct ggcaggtcac tgagagtggg cagctgggcc
 241 ccagaactgt gcctggccca gtgggcagca ggagctcctg acttgggacc atggtgattc
 301 ttcagcaggg ggaccatgtg tggatggacc tgagattggg gcaggagttc gacgtgccca
 361 tcggggcggt ggtgaagctc tgcgactctg ggcaggtcca ggtggtggat gatgaagaca
 421 atgaacactg gatctctccg cagaacgcaa cgcacatcaa gcctatgcac cccacgtcgg
 481 tccacggcgt ggaggacatg atccgcctgg gggacctcaa cgaggcgggc atcttgcgca
 541 acctgcttat ccgctaccgg gaccacctca tctacacgta tacgggctcc atcctggtgg
 601 ctgtgaaccc ctaccagctg ctctccatct actcgccaga gcacatccgc cagtatacca
 661 acaagaagat tggggagatg ccccccccaca tctttgccat tgctgacaac tgctacttca
 721 acatgaaacg caacagccga gaccagtgct gcatcatcag tgggaatct ggggccggga
 781 agacggagag cacaaagctg atcctgcagt tcctggcagc catcagtggg cagcactcgt
 841 ggattgagca gcaggtcttg gaggccaccc ccattctgga agcatttggg aatgccaaga
 901 ccatccgcaa tgacaactca agccgtttcg gaaagtacat cgacatccac ttcaacaagc
 961 ggggcgccat cgagggcgcg aagattgagc agtacctgct ggaaaagtca cgtgtctgtc
1021 gccaggccct ggatgaaagg aactaccacg tgttctactg catgctggag ggtatgagtg
1081 aggatcagaa gaagaagctg ggcttgggcc aggcctctga ctacaactac ttggccatgg
1141 gtaactgcat aacctgtgag ggcgggtgg acagccagga gtacgccaac atccgctccg
1201 ccatgaaggt gctcatgttc actgacaccg agaactggga gatctcgaag ctcctggctg
1261 ccatcctgca cctgggcaac ctgcagtatg aggcacgcac atttgaaaac ctggatgcct
1321 gtgaggttct cttctcccca tcgctggcca cagctgcatc cctgcttgag gtgaacccc
1381 cagacctgat gagctgcctg actagccgca ccctcatcac ccgcggggag acggtgtcca
1441 ccccactgag cagggaacag gcactggacg tgcgcgacgc cttcgtaaag gggatctacg
1501 ggcggctgtt cgtgtggatt gtggacaaga tcaacgcagc aatttacaag cctccccccc
1561 aggatgtgaa gaactctcgc aggtccatcg gcctcctgga catctttggg tttgagaact
1621 ttgctgtgaa cagctttgag cagctctgca tcaacttcgc caatgacgac ctgcagcagt
1681 tctttgtgcg gcacgtgttc aagctgggc aggaggaata tgacctggag agcattgact
1741 ggctgcacat cgagttcact gacaaccagg atgccctgga catgattgcc aacaagccca
1801 tgaacatcat ctccctcatc gatgaggaga gcaagttccc caagggcaca gacaccacca
1861 tgttacacaa gctgaactcc cagcacaagc tcaacgccaa ctacatcccc cccaagaaca
1921 accatgagac ccagtttggc atcaaccatt ttgcaggcat cgtctactat gagacccaag
1981 gcttcctgga aagaaaccga gacacccctg atggggacat tatccagctg gtccactcct
2041 ccaggaacaa gttcatcaag cagatcttcc aggccgatgt cgccatgggc gccgagacca
2101 ggaagcgctc gcccacactt agcagccagt tcaagcggtc actggagctg ctgatgcgca
2161 cgctgggtgc ctgccagccc ttctttgtgc gatgcatcaa gcccaatgag ttcaagaagc
2221 ccatgctgtt cgaccggcac ctgtgcgtgc gccagctgcg gtactcagga atgatggaga
2281 ccatccgaat ccgccgagct ggctacccca tccgctacag cttcgtagag tttgtggagc
2341 ggtaccgtgt gctgctgcca ggtgtgaagc cggcctacaa gcagggcgac ctccgcggga
2401 cttgccagcg catggctgag gctgtgctgg gcacccacga tgactggcag ataggcaaaa
2461 ccaagatctt tctgaaggac caccatgaca tgctgctgga agtggagcgg gacaaagcca
2521 tcaccgacag agtcatcctc cttcagaaag tcatccgggg attcaaagac aggtctaact
2581 ttctgaagct gaagaacgct gccacactga tccagaggca ctggcggggt cacaactgta
2641 ggaagaacta cgggctgatg cgtctgggct tcctgcgcgt gcaggccctg caccgctccc
2701 ggaagctgca ccagcagtac cgcctggccc gccagcgcat catccagttc caggcccgct
2761 gccgcgccta tctggtgcgc aaggccttcc gccaccgcct ctgggctgtg ctcaccgtgc
2821 aggcctatgc ccggggcatg atcgcccgca ggctgcacca acgcctcagg gctgagtatc
2881 tgtggcgcct cgaggctgag aaaatgcggc tggcggaaga agagaagctt cggaaggaga
2941 tgagcgccaa gaaggccaag gaggaggccg agcgcaagca tcaggagcgc ctggccagc
3001 tggctcgtga ggacgctgag cgggagctga aggagaagga ggccgctcgg cggaagaagg
3061 agctcctgga gcagatggaa agggcccgcc atgagcctgt caatcactca gacatggtgg
3121 acaagatgtt tggcttcctg gggacttcag gtggcctgcc aggccaggag ggccaggcac
3181 ctagtggctt tgaggacctg gagcgagggc ggagggagat ggtggaggag gacctggatg
3241 cagccctgcc cctgcctgac gaggatgagg aggacctctc tgagtataaa tttgccaagt
3301 tcgcggccac ctacttccag gggacaacca cgcactccta cacccggcgg ccactcaaac
3361 agccactgct ctaccatgac gacagggtg accagctggc agcctggcg gtctggatca
3421 ccatcctccg cttcatgggg gacctccctg agcccaagta ccacacagcc atgagtgatg
3481 gcagtgagaa gatccctgtg atgaccaaga ttatgagac cctgggcaag aagacgtaca
3541 agagggagct gcaggccctg caggcgagg cgaggccca gctccccgag ggccagaaga
3601 agagcagtgt gaggcacaag ctggtgcatt tgactctgaa aaagaagtcc aagctcacag
3661 aggaggtgac caagaggctg catgacgggg agtccacagt gcaggcaac agcatgctgg
3721 aggaccggcc caccttccaa tctggagaagc tgcacttcat catcggcaat ggcatcctgc
3781 ggccagcact ccgggacgag atctactgcc agatcagcaa gcagctgacc cacaacccct
3841 ccaagagcag ctatgcccgg ggctggattc tcgtgtctct ctgcgtgggc tgtttcgccc
3901 cctccgagaa gtttgtcaag tacctgcgga acttcatcca cggggccg cccggctacg
3961 ccccgtactg tgaggagcgc ctgagaagga cctttgtcaa tggacacgg acacagccgc
4021 ccagctggct ggagctgcag gccaccaagt ccaagaagcc aatcatgttg cccgtgacat
4081 tcatggatgg gaccaccaag accctgctga cggactcggc aaccacgcc aaggagctct
4141 gcaacgcgct ggccgacaag atctctctca aggaccggtt cggttctcc ctctacattg
4201 ccctgtttga caaggtgtcc tccctgggca gcggcagtga ccacgtcatg gacgccatct
4261 cccagtgcga gcagtacgcc aaggagcagg gcgcccagga gcgcaacgcc cctggaggc
4321 tcttcttccg caaagaggtc ttcacgccct ggcacagccc ctccgaggac aacgtggcca
```

TABLE 4-continued

```
4381 ccaacctcat ctaccagcag gtggtgcgag gagtcaagtt tggggagtac aggtgtgaga
4441 aggaggacga cctggctgag ctggcctccc agcagtactt tgtagactat ggctctgaga
4501 tgatcctgga gcgcctcctg aacctcgtgc ccacctacat ccccgaccgc gagatcacgc
4561 ccctgaagac gctggagaag tgggcccagc tggccatcgc cgcccacaag aagggatttt
4621 atgcccagag gagaactgat gcccagaagg tcaaagagaa tgtggtcagt tatgcccgct
4681 tcaagtggcc ccttgctctt ccaggtttt atgaagccta caaattctca ggccccagtc
4741 tccccaagaa cgacgtcatc gtggccgtca actggacggg tgtgtacttt gtggatgagc
4801 aggagcaggt acttctggag ctgtcctcc cagagatcat ggccgtgtcc agcagcaggg
4861 agtgccgtgt ctggctctca ctgggctgct ctgatcttcg ctgtgctgcg cctcactcag
4921 gctgggcagg actgaccccg gcggggcccct gttctccgtg ttggtcctgc agggagcga
4981 aaacgacggc cccccagcttc acgctggcca ccatcaaggg ggacgaatac accttcacct
5041 ccagcaatgc tgaggacatt cgtgacctgg tggtcacctt cctagagggg ctccggaaga
5101 gatctaagta tgttgtggcc ctgcaggata accccaaccc cgcaggcgag gagtcaggct
5161 tcctcagctt tgccaaggga gacctcatca tcctggacca tgacacgggc gagcaggtca
5221 tgaactcggg ctgggccaac ggcatcaatg agaggaccaa gcagcgtggg gacttcccca
5281 ccgacagtgt gtacgtcatg cccactgtca ccatgccacc gcgggagatt gtggccctgg
5341 tcaccatgac tcccgatcag aggcaggacg ttgtccgaact cttgcagctg cgaaccggcgg
5401 agcccgaggt gcgtgccaag ccctacacgc tggaggagtt ttcctatgac tacttcaggc
5461 ccccacccaa gcacacgctg agccgtgtca tggtgtccaa ggcccgaggc aaggaccggc
5521 tgtggagcca cacgcgggaa ccgctcaagc aggcgctgct caagaagctc ctgggcagtg
5581 aggagctctc gcaggaggcc tgcctggcct tcattgctgt gctcaagtac atgggcgact
5641 acccgtccaa gaggacacgc tccgtcaacg agctcaccga ccagatcttt gagggtcccc
5701 tgaaagccga gccctgaag gacgaggcat atgtgcagat cctgaagcag ctgaccgaca
5761 accacatcag gtacagcgag gagcggggtt gggagctgct ctggctgtgc acgggccttt
5821 tccacccag caacatcctc tgccccacg tgcagcgctt cctgcagtcc cgaaagcact
5881 gcccactcgc catcgactgc ctgcaacggc tccagaaagc cctgagaaac gggtcccgga
5941 agtaccctcc gcacctggtg gaggtggagg ccatccagca caagaccacc cagatttcc
6001 acaaagtcta cttccctgat gacactgacg aggccttcga agtggagtcc agcaccaagg
6061 ccaaggactt ctgccagaac atcgccacca ggctgctcct caagtcctca gagggattca
6121 gcctcttttgt caaaattgca gacaaggtcc tcagcgttcc tgagaatgac ttcttcttg
6181 actttgttcg acacttgaca gactggataa agaaagctcg gcccatcaag gacggaattg
6241 tgccctcact cacctaccag gtgttcttca tgaagaagct gtggaccacc acggtgccag
6301 ggaaggatcc catggccgat tccatcttcc actattacca ggagttgccc aagtatctcc
6361 gaggctacca caagtgcacg cgggaggagg tgctgcagct ggggcgctg atctacaggg
6421 tcaagttcga ggaggacaag tcctacttcc ccagcatccc caagctgctg cgggagctgg
6481 tgccccagga ccttatccgg caggtctcac ctgatgactg gaagcggtcc atcgtcgcct
6541 acttcaacaa gcacgcaggg aagtccaagg aggaggccaa gctggccttc ctgaagctca
6601 tcttcaagtg gcccaccttt ggctcagcct tcttcgaggt gaagcaaact acggagccaa
6661 acttccctga gatcctccta attgccatca caagtatgg ggtcagcctc atcgatccca
6721 aaacgaagga tatcctcacc actcatccct tcaccaagat ctccaactgg agcagcggca
6781 acacctactt ccacatcacc attgggaact tggtgcgcgg gagcaaactg ctctgcgaga
6841 cgtcactggg ctacaagatg gatgacctcc tgacttccta cattagcag atgctcacag
6901 ccatgagcaa acagcggggc tccaggagcg gcaagtgaac agtcacgggg aggtgctggt
6961 tccatgcctg ctctcgaggc agcagtgggg tcaggcccat cagctacccc tgcagctggg
7021 gaagactata gccatcccgg cagcgaggct gggctggcca gccaccactg actataccaa
7081 ctgggcctct gatgttcttc cagtgaggca tctctctggg atgcagaact tccctccatc
7141 caccctcctg gcacctgggt tggtctaatc ctagttgct gtggcttcc cggttgtgag
7201 agcctgtgat ccttagatgt gtctcctgtt cagaccagc cccaccatgc aacttccttt
7261 gactttctgt gtaccactgg gatagaggaa tcaagaggac aatctagctc tccatacttt
7321 gaacaaccaa atgtgcattg aatactctga aaccgaaggg actggatctg caggtgggat
7381 gagggagaca gaccacttttt ctatattgca gtgtgaatgc tgggccctg ctcaagtcta
7441 ccctgatcac ctcagggcat aaagcatgtt tcattctctg gcc SEQ ID NO: 68 Human Myo7a Isoform 1 (Encoded by Transcript Variant 1)
Amino Acid Sequence (NP_000251.3)
   1 mvilqqgdhv wmdlrlgqef dvpigavvkl cdsgqvqvvd dednehwisp qnathikpmh
  61 ptsvhgvedm irlgdlneag ilrnlliryr dhliytytgs ilvavnpyql lsiyspehir
 121 qytnkkigem pphifaiadn cyfnmkrnsr dqcciisges gagktestkl ilqflaaisg
 181 qhswieqqvl eatpileafg naktirndns srfgkyidih fnkrgaiega kieqylleks
 241 rvcrqalder nyhvfycmle gmsedqkkkl glgqasdyny lamgncitce grvdsqeyan
 301 irsamkvlmf tdtenweisk llaailhlgn lqyeartfen ldacevlfsp slataaslle
 361 vnppdlmscl tsrtlitrge tvstplsreq aldvrdafvk giygrlfvwi vdkinaaiyk
 421 ppsqdvknsr rsiglldifg fenfavnsfe qlcinfaneh lqqffvrhvf kleqeeydle
 481 sidwlhieft dnqdaldmia nkpmniisli deeskfpkgt dttmlhkIns qhklnanyip
 541 pknnhetqfg inhfagivyy etqgfleknr dtlhgdiiql vhssrnkfik qifqadvamg
 601 aetrkrsptl ssqfkrslel lmrtlgacqp ffvrcikpne fkkpmlfdrh lcvrqlrysg
 661 mmetirirra gypirysfve fveryrvllp gvkpaykqgd lrgtcqrmae avlgthddwq
 721 igktkifkld hhdmllever dkaitdrvil lqkvirgfkd rsnflklkna atliqrhwrg
 781 hncrknyglm rlgflrlqal hrsrklhqqy rlarqriiqf qarcraylvr kafrhrlwav
 841 ltvqayargm iarrlhqrlr aeylwrleae kmrlaeeekl rkemsakkak eeaerkhqer
 901 laglaredae relkekeaar rkkelleqme rarhepvnhs dmvdkmfgfl gtsgglpgqe
 961 gqapsgfedl ergrremvee dldaalplpd edeedlseyk fakfaatyfq gttthsytrr
1021 plkqpllyhd degdqlaala vwitilrfmg dlpepkyhta msdgsekipv mtkiyetlgk
1081 ktykrelqal qgegeaqlpe gqkkssvrhk lvhltlkkks klteevtkrl hdgestvqgn
1141 smledrptsn leklhfiign gilrpalrde iycqiskqlt hnpskssyar gwilvslcvg
1201 cfapsekfvk ylrnfihgpp pgyapyceer lrrtfvngtr tqppswlelq atkskkpiml
1261 pvtfmdgttk tlltdsatta kelcnaladk islkdrfgfs lyialfdkvs slgsgsdhvm
1321 daisqceqya keqgagerna pwrlfffrkev ftpwhspsed nvatnliyqq vvrgvkfgey
1381 rcekeddlae lasqqyfvdy gsemilerll nlvptyipdr eitplktlek waqlaiaahk
1441 kgiyaqrrtd aqkvkedvvs yarfkwpllf srfyeaykfs gpslpkndvi vavnwtgvyf
```

TABLE 4-continued

```
1501 vdeqeqvlle lsfpeimavs ssrecrvwls lgcsdlgcaa phsgwagltp agpcspcwsc
1561 rgakttapsf tlatikgdey tftssnaedi rdlvvtfleg lrkrskyvva lqdnpnpage
1621 esgflsfakg dliildhdtg eqvmnsgwan ginertkqrg dfptdsvyvm ptvtmpprei
1681 valvtmtpdq rqdvvrllql rtaepevrak pytleefsyd yfrpppkhtl srvmvskarg
1741 kdrlwshtre plkqallkkl lgseelsqea clafiavlky mgdypskrtr svneltdqif
1801 egplkaeplk deayvqilkq ltdnhiryse ergwellwlc tglfppsnil lphvqrflqs
1861 rkhcplaidc lqrlqkalrn gsrkypphlv eveaiqhktt qifhkvyfpd dtdeafeves
1921 stkakdfcqn iatrlllkss egfslfvkia dkvlsvpend fffdfvrhlt dwikkarpik
1981 dgivpsltyq vffmkklwtt tvpgkdpmad sifhyyqelp kylrgyhkct reevlqlgal
2041 iyrvkfeedk syfpsipkll relvpqdlir qvspddwkrs ivayfnkhag kskeeaklaf
2101 lklifkwptf gsaffevkqt tepnfpeill iainkygvsl idpktkdilt thpftkisnw
2161 ssgntyfhit ignlvrgskl lcetslgykm ddlltsyisq mltamskqrg srsgk
```

SEQ ID NO: 69 Human MYO7A Transcript Variant 2 cDNA Sequence
(NM_001127180.1, CDS region from position 267-6794)

```
   1 ggcaggagag agagggagag acaagagaca cacacagaga gacggcgagg aagggaaaga
  61 cccagaggga cgcctagaac gagacttgga gccagacaga ggaagagggg acgtgtgttt
 121 gcagactggc tgggcccgtg acccagcttc ctgagtcctc cgtgcaggtg cagctgtac
 181 caggctggca ggtcactgag agtgggcagc tgggccccag aactgtgcct ggcccagtgg
 241 gcagcaggag ctcctgactt gggaccatgg tgattcttca gcaggggggac catgtgtgga
 301 tggacctgag attggggcag gagttcgacg tgcccatcgg ggcggtggtg aagctctgcg
 361 actctgggca ggtccaggtg gtggatgatg aagacaatga acactgggatc tctccgcaga
 421 acgcaacgca catcaagcct atgcacccca cgtcggtcca cggcgtggag acatgatcc
 481 gcctggggga cctcaacgag gcgggcatct tgcgcaacct gcttatccgc taccgggacc
 541 acctcatcta cacgtatacg ggctccatcc tggtggctgt cagctgctct
 601 ccatctactc gccagagcac atccgccagt ataccaacaa gaagattggg gagatgcccc
 661 cccacatctt tgccattgct gacaactgct acttcaacat gaaacgcaac agccgagacc
 721 agtgctgcat catcagtggg gaatctgggg ccgggaagac ggagagcaca aagctgatcc
 781 tgcagttcct ggcagccatc agtgggcagc actcgtggat tgagcagcag gtcttggagg
 841 ccaccccat tctggaagca tttgggaatg ccaagaccat ccgcaatgac aactcaagcc
 901 gtttcggaaa gtacatcgac atccacttca caaagcgggg cgccatcgac ggcgcgaaga
 961 ttgagcagta cctgctggaa aagtcacgtg tctgtcgcca ggcctggat aaggaact
1021 accacgtgtt ctactgcatg ctggaggta tgagtgagga tcagaagaag aagctgggct
1081 tgggccaggc ctctgactac aactacttgg ccatgggtaa ctgcataacc tgtgagggcc
1141 gggtggacag ccaggagtac gccaacatcc gctccgccat gaaggtgctc atgttcactg
1201 acaccgagaa ctgggagatc tcgaagctcc tggctgccat cctgcacctg gcaacctgc
1261 agtatgaggc acgcacattt gaaaacctgg atgcctgtga ggttctcttc tccccatcgc
1321 tggccacagc tgcatccctg cttgaggtga accccccaga cctgatgagc tgcctgacta
1381 gccgcacccct catcacccgc ggggagacgg tgtccacccc actgagcagg gaacaggcac
1441 tggacgtgcg cgacgccttc gtaaaggggg tctacgggcg gctgttcgtg tggattgtgg
1501 acaagatcaa cgcagcaatt tacaagcctc cctcccagga tgtgaagaac tctcgcaggt
1561 ccatcggcct cctggacatc tttgggtttg agaactttgc tgtgaacagc tttgagcagc
1621 tctgcatcaa cttcgccaat gagcacctgc agcagttctt tgtgcggcac gtgttcaagc
1681 tggagcagga ggaatatgac ctggagagca ttgactggct gcacatcgag ttcactgaca
1741 accaggatgc cctggacatg attgccaaca gcccatgaa catcatctcc ctcatcgatg
1801 aggagagcaa gttccccaag ggcacagaca ccaccatgtt acacaagctg aactcccagc
1861 acaagctcaa cgccaactac atccccccca agaacaacca tgagacccag tttggcatca
1921 accattttgc aggcatcgtc tactatgaga cccaaggctt cctggagaag aaccgagaca
1981 ccctgcatgg ggacattatc cagctggtcc actcctccag gaacaagttc atcaagcaga
2041 tcttccaggc cgatgtcgcc atgggcgccg agaccaggga gcgctcgccc acacttagca
2101 gccagttcaa gcggtcactg gagctgctga tgcgcacgct gggtgcctgc cagcccttct
2161 ttgtgcgatg catcaagccc aatgagttca gaagcccat gctgttcgac cggcacctgt
2221 gcgtgcgcca gctgcggtac tcaggaatga tggagaccat ccgaatccgc cgagctggct
2281 accccatccg ctacagcttc gtagagttttg tggagcggta ccgtgtgctg ctgcctgg
2341 tgaagccggc ctacaagcag ggcgacccc gcgggacttg ccagcgcatg gctgaggcctg
2401 tgctgggcac ccacgatgac tggcagatag gcaaaaccaa gatctttctg aaggaccacc
2461 atgacatgct gctggaagtg gagcgggaca agccatcac cgacagagtc atcctccttc
2521 agaaagtcat ccggggattc aaagacaggt ctaacttct gaagctgaag aacgctgcca
2581 cactgatcca gaggcactgg cgggggtcaca actgtaggaa gaactacgag ctgatgcgtc
2641 tgggcttcct gcggctgcag gccctgcacc gctcccggaa gctgcaccag cagtaccgcc
2701 tggcccgcca gcgcatcatc cagttccagg cccgctgccg cgcctatctg gtgcgcaagg
2761 ccttccgcca ccgcctctgg gctgtgctca ccgtgcaggc ctatgcccgg gcatgatcg
2821 cccgcaggct gcaccaacgc ctcagggctg agtatctgtg gcgcctcgag gctgagaaaa
2881 tgcggctggc ggaggaagag aagcttcgga aggagatgag cgccaagaag gccaaggagg
2941 aggccgagcg caagcatcag gagcgcctgg cccagctggc tcgtgaggac gctgagcggg
3001 agctgaagga gaaggaggcc gctcggcgga agaaggagct cctggagcag atggaaaggg
3061 cccgccatga gcctgtcaat cactcagaca tggtggacaa ggtgtttggc ttcctgggga
3121 cttcaggtgg cctgccaggc caggaggcc aggcacctag tggctttgag gacctggagc
3181 gagggcggag ggagatggtg gaggaggacc tggatgcagc cctgcccctg cctgacgagg
3241 atgaggagga cctctctgag tataaatttg ccaagttcgc ggccacctac ttccagggga
3301 caaccacgca ctcctacacc cggcggccac tcaaacagcc actgctctac catgacgacg
3361 agggtgacca gctggcagcc ctggcggtct ggatcaccat cctccgcttc atggggggacc
3421 tccctgagcc caagtaccac acagccatga gtgatggcag tgagaagatc cctgtgatga
3481 ccaagattta tgagaccctg ggcaagaaga gatacaagag ggagctgcag gccctgcagg
3541 gcgagggcga ggcccgactc ccggagggcc agaagaagag cagtgtgagg accaagctgg
3601 tgcatttgac tctgaaaaag aagtccaagc tcacagacca ggtgaccaag aggctgcatg
3661 acggggagtc cacagtgcag ggcaacagca tgctggagga ccgcccacc tccaacctgg
3721 agaagctgca cttcatcatc ggcaatgca tcctgcggcc agcactccgg gacgagatct
3781 actgccagat cagcaagcag ctgacccaca acccctccaa gagcagctat gcccggggct
3841 ggattctcgt gtctctctgc gtgggctgtt tcgcccctc cgagaagtttt gtcaagtacc
```

TABLE 4-continued

```
3901 tgcggaactt catccacggg ggcccgcccg gctacgcccc gtactgtgag gagcgcctga
3961 gaaggacctt tgtcaatggg acacggacac agccgcccag ctggctgagg ctgcaggcca
4021 ccaagtccaa gaagccaatc atgttgcccg tgacattcat ggatgggacc accaagaccc
4081 tgctgacgga ctcggcaacc acggccaagg agctctgcac cgcgctggcc gacaagatct
4141 ctctcaagga ccggttcggg ttctccctct acattgccct gtttgacaag gtgtcctccc
4201 tgggcagcgg cagtgaccac gtcatggacg ccatctccca gtgcgagcag tacgccaagg
4261 agcaggcgc ccaggagcgc aacgcccct ggaggctctt cttccgcaaa gaggtcttca
4321 cgccctggca cagcccctcc gaggacaacg tggccaccaa cctcatctac cagcaggtgg
4381 tgcgaggagt caagtttggg gagtacaggt gtgagaagga gacgacctg gctgagctgg
4441 cctcccagca gtactttgta gactatggct ctgagatgat cctggagcgc ctcctgaacc
4501 tcgtgcccac ctacatcccc gaccgcgaga tcacgcccct gaagacgctg gagaagtggg
4561 cccagctggc catcgccgcc cacaagaagg ggattttatgc ccagaggaga actgatgccc
4621 agaaggtcaa agaggatgtg gtcagttatg cccgcttcaa gtggcccttg ctcttctcca
4681 ggttttatga agcctacaaa ttctcaggcc ccagtctccc caagaacgac gtcatcgtgg
4741 ccgtcaactg gacgggtgtg tactttgtgg atgagcagga gcaggtactt ctggagctgt
4801 ccttcccaga gatcatggcc gtgtccagca gcaggggagc gaaaacgacg gcccccagct
4861 tcacgctggc caccatcaag ggggacgaat acaccttcac ctccagcaat gctgaggaca
4921 ttcgtgacct ggtggtcacc ttcctagagg ggctccggaa gagatctaag tatgttgtgg
4981 ccctgcagga taaccccaac cccgcaggcg aggagtcagg cttcctcagc tttgccaagg
5041 gagacctcat catcctggac catgacacgg gcgagcaggt catgaactcg ggctgggcca
5101 acggcatcaa tgagaggacc aagcagcgtg gggacttccc caccgacgt gtgtacgtca
5161 tgcccactgt caccatgcca ccgcgggaga ttgtggccct ggtcaccatg actcccgatc
5221 agaggcagga cgttgtccgg ctccttgcagc tgcgaacggc ggagcccgag gtgcgtgcca
5281 agccctacac gctggaggag ttttcctatg actacttcag gcccccaccc aagcacacgc
5341 tgagccgtgt catggtgtcc aaggcccgag gcaaggaccg gctgtggagc cacacgcggg
5401 aaccgctcaa gcaggcgctg ctcaagaagc tcctggaccg tgaggagctc tcgcaggagg
5461 cctgcctggc cttcattgct gtgctcaagt acatgggcga ctaccgtcc aagaggacac
5521 gctccgtcaa cgagctcacc gaccagatct ttgagggtcc cctgaaagcc gagccctga
5581 aggacgaggc atatgtgcag atcctgaagc agctgaccga caaccacatc aggtacagcg
5641 aggagcgggg ttgggagctg ctctggctgt gcacgggcct tttcccaccc agcaacatcc
5701 tcctgccccca cgtgcagcgc ttcctgcagt cccgaaagca ctgcccactc gccatcgact
5761 gcctgcaacg gctccagaaa gccctgagaa acgggtcccg gaagtaccct ccgcacctgg
5821 tggaggtgga ggccatccag cacaagacca cccagatttt ccacaaagtc tacttccctg
5881 atgacactga cgaggccttc gaagtggagt ccagcaccaa ggccaaggac ttctgccaga
5941 acatcgccac caggctgctc ctcaagtcct cagagggatt cagcctcttt gtcaaaattg
6001 cagacaaggt cctcagcgtt cctgagaatg acttcttctt tgactttgtt cgacacttga
6061 cagactggat aaagaaagct cggcccatca aggacgggaat tgtgccctca ctcacctacc
6121 aggtgttctt catgaagaag ctgtggacca ccacggtgcc agggaaggat cccatggccg
6181 attccatctt ccactattac caggagttgc ccaagtatcc ccgaggctac cacaagtgca
6241 cgcggggagga ggtgctgcag ctgggggcgc tgatctacag ggtcaagttc gaggaggaca
6301 agtcctactt ccccagcatc cccaagctgc tgcgggagct ggtgccccag gaccttatcc
6361 ggcaggtctc acctgatgac tggaagcggt ccatcgtcgc ctacttcaac aagcacgcag
6421 ggaagtccaa ggaggaggcc aagctggcct tcctgaagct catcttcaag tggcccacct
6481 ttggctcagc cttcttcgag caaactacgg agccaaactt ccctgagatc ctcctaattg
6541 ccatcaacaa gtatgggtc agcctcatcg atcccaaaac gaaggatatc ctcaccactc
6601 atcccttcac caagatctcc aactggagca gcggcaacac ctacttccac atcaccattg
6661 ggaacttggt gcgcgggagc aaactgctct gcgagacgct actgggctac aagatggatg
6721 acctcctgac ttcctacatt agccagatgc tcacagccat gagcaaacag cggggctcca
6781 ggagcggcaa gtgaacagtc acggggaggt gctggttcca tgcctgctct cgaggcagca
6841 gtgggttcag gcccatcagc tacccctgca gctgggaagg acttatgcca tcccggcagc
6901 gaggctgggc tggccagcca ccactgacta taccaactgg gcctctgatg ttcttccagt
6961 gaggcatctc tctgggatgc agaacttccc tccatccacc cctctggcac ctgggttggt
7021 ctaatcctag tttgctgtgg ccttcccggt tgtgagagcc tgtgatcctt agatgtgtct
7081 cctgtttcag accagcccca ccatgcaact tcctttgact ttctgtgtac cactgggata
7141 gaggaatcaa gaggacaatc tagctctcca tactttgaac aaccaaatgt gcattgaata
7201 ctctgaaacc gaagggactg gatctgcagg tgggatgagg gagacagacc acttttctat
7261 attgcagtgt gaatgctggg cccctgctca agtctaccct gatcacctca gggcataaag
7321 catgtttcat tctctggcc
```

SEQ ID 70 Human Myo7a Isoform 2 (Encoded by Transcript Variant 2)
Amino Acid Sequence (NP_001120652.1)

```
   1 mvilqqgdhv wmdlrlgqef dvpigavvkl cdsgqvqvvd dednehwisp qnathikpmh
  61 ptsvhgvedm irlgdlneag ilrnlliryr dhliytytgs ilvavnpyql lsiyspehir
 121 qytnkkigem pphifaiadn cyfnmkrnsr dqccisges gagktestkl ilqfflaaisg
 181 qhswieqqvl eatpileafg naktirndns srfgkyidih fnkrgaiega kieqylleks
 241 rvcrqalder nyhvfycmle gmsedqkkkl glgqasdyny lamgncitce grvdsqeyan
 301 irsamkvlmf tdtenweisk llaailhlgn lqyeartfen ldacevlfsp slataaslle
 361 vnppdlmscl tsrtlitrge tvstplsreq aldvrdafvk giygrlfvwi vdkinaaiyk
 421 ppsqdvknsr rsiglldifg fenfavnsfe qlcinfaneh lqqffvrhvf kleqeeydle
 481 sidwlhieft dnqdaldmia nkpmniisli deeskfpkgt dttmlhklns qhklnanyip
 541 pknnhetqfg inhfagivyy etqgfleknr dtlhgdiiql vhssrnkfik qifqadvamg
 601 aetrkrsptl ssqfkrslel lmrtlgacqp ffvrcikpne fkkpmlfdrh lcvrqlrysg
 661 mmetirirra gypirysfve fveryrvllp gvkpaykqgd lrgtcqrmae avlgthddwq
 721 igktkiflkd hhdmllever dkaitdrvil qkvirgfkd rsnflklkna atliqrhwrg
 781 hncrknyglm rlgflrlqal hrsrklhqqy rlarqriiqf qarcraylvr kafrhrlwav
 841 ltvqayargm iarrlhqrlr aeylwrleae kmrlaeeekl rkemsakkak eeaerkhqer
 901 laqlaredae relkekeaar rkkelleqme rarhepvnhs dmvdkmfgfl gtsgglpgqe
 961 gqapsgfedl ergrremvee dldaalplpd edeedlseyk fakfaatyfq gttthsytrr
1021 plkqpllyhd degdqlaala vwitilrfmg dlpepkyhta msdgsekipv mtkiyetlgk
1081 ktykrelqal qgegeaqlpe gqkkssvrhk lvhltlkkks klteevtkrl hdgestvqgn
```

TABLE 4-continued

```
1141 smledrptsn leklhfiign gilrpalrde iycqiskqlt hnpskssyar gwilvslcvg
1201 cfapsekfvk ylrnfihggp pgyapyceer lrrtfvngtr tqppswlelq atkskkpiml
1261 pvtfmdgttk tlltdsatta kelcnaladk islkdrfgfs lyialfdkvs slgsgsdhvm
1321 daisqceqya keqgaqerna pwrlffrkev ftpwhspsed nvatnliyqq vvrgvkfgey
1381 rcekeddlae lasqqyfvdy gsemilerll nlvptyipdr eitplktlek waqlaiaahk
1441 kgiyaqrrtd aqkvkedvvs yarfkwpllf srfyeaykfs gpslpkndvi vavnwtgvyf
1501 vdeqeqvlle lsfpeimavs ssrgakttap sftlatikgd eytftssnae dirdlvvtfl
1561 eglrkrskyv valqdnpnpa geesgflsfa kgdliildhd tgeqvmnsgw anginertkq
1621 rgdfptdsvy vmptvtmppr eivalvtmtp dqrqdvvrll qlrtaepevr akpytleefs
1681 ydyfrpppkh tlsrvmvska rgkdrlwsht replkqallk kllgseelsq eaclafiavl
1741 kymgdypskr trsvneltdq ifegplkaep lkdeayvqil kqltdnhiry seergwellw
1801 lctglfppsn illphvqrfl qsrkhcplai dclqrlqkal rngsrkypph lveveaiqhk
1861 ttqifhkvyf pddtdeafev esstkakdfc qniatrlllk ssegfslfvk iadkvlsvpe
1921 ndfffdfvrh ltdwikkarp ikdgivpslt yqvffmkklw tttvpgkdpm adsifhyyqe
1981 lpkylrgyhk ctreevlqlg aliyrvkfee dksyfpsipk llrelvpqdl irqvspddwk
2041 rsivayfnkh agkskeeakl aflklifkwp tfgsaffeqt tepnfpeill iainkygvsl
2101 idpktkdilt thpftkisnw ssgntyfhit ignlvrgskl lcetslgykm ddlltsyisq
2161 mltamskqrg srsgk
```

SEQ ID NO: 71 Mouse MYO7A Transcript Variant 1 cDNA Sequence
(NM_001256081.1, CDS region from position 261-6908)

```
   1 agtgcaggct ggacagctgc cctgaacaga aagaaagagt gacccaggga gacaagaaac
  61 agagtagccc aagggaagcc cacagcagca gcagatcaag gctcaagctg gagctgaaaa
 121 tttgcaggct ccagcctcag cttccagagt cctcctgacc tgtgacccct ggctcctggc
 181 tgggaggtgg tgactcggag ggtgtggata aaacccgagg ctgtgtctgg tcactccggc
 241 aggtgtgctg acgtagaagc atggttattc tgcagaaggg ggactatgta tggatggacc
 301 tgaagtcagg ccaggagttt gatgtgccca tcggggccgt ggtgaagctc tgcgactcgg
 361 gccagatcca ggtggtggat gatgaagaca atgaacactg gatatcccct cagaatgcca
 421 cgcacatcaa gccaatgcac cccacatcgg tgcacggcgt ggaggacatg atccgcactgg
 481 gggatctcaa cgaggcaggc atccttcgaa accttctcat tcgctaccgg gaccacctca
 541 tctatacgta cacaggttcc atcctggtgg ccgtgaaccc ctaccagctg ctctccatct
 601 actcgccaga gcacatccgc cagtacacca acaagaagat aggggagatg cccccccaca
 661 tcttcgccat tgctgacaac tgctacttca acatgaaacg caacaaccgg gaccagtgct
 721 gtattatcag cggggagtcg ggagctggca agacagagac cacaaagttg atcctgcagt
 781 tcctggcagc catcagtgga cagcactcat ggatcgagca gcaggtgctg gaggccaccc
 841 cgatcctgga agcatttggg aacgccaaga ccatccgcaa cgacaactct agccgctttg
 901 gcaagtacat tgacatccac tttaacaagc gtggtgccat cgagggcgcc aaaatagagc
 961 aatacctgct ggagaagtca cgtgtctgcc gccaggcccc tgacgagagg aactatcacg
1021 tgttctactg tatgctggag ggcatgaatg aggaggagaa gaagaaactg ggcctaggcc
1081 aggccgctga ctacaactac ttggccatgg gtaactgcat cacctgtgag ggccgcgtgg
1141 acagtcagga gtatgccaac atccgctctg ccatgaaggt tctcatgttc acagacacgg
1201 agaactggga gatctcgaag cttctggctg ccatcctaca catgggcaat ctgcagtatg
1261 aggcccggac atttgagaac ttggatgcgt gtgaagtcct cttctcccca tcgctggcca
1321 cggcagcttc tctgctcgag gtgaaccccc cagacctgat gagctgcctc accagccgca
1381 ccctcatcac ccgtggggag acggtgtcca ccctctcag cagggaacag gcgctggatg
1441 tgcgagatgc ctttgtcaag ggcatctatg ggcggctctt tgtgtggatt gtggagagaa
1501 tcaacgcagc aatctacaag ccaccccccc tggaagtgaa gaactctcgc cggtccatcg
1561 gtctcctgga catctttgga tttgagaact tcactgtgaa cagcttcgag cagctctgca
1621 ttaactttgc caatgagcac ctgcagcaat tcttcgtgcg gcacgtgttc aagctggagc
1681 aggaggagta cgacctggag agcatcgact ggttgcacat tgagttcact gacaaccagg
1741 aagcactgga catgattgcc aaccggccta tgaacgtcat ctccctcatc gatgaggaga
1801 gcaagttccc caagggcacg gatgccacca tgctgcataa gctgaactca cagcacaagc
1861 tcaatgccaa ctacgtgcca cccaagaaca gccacgagac ccagtttgga atcaaccact
1921 ttgcgggtgt tgtctattat gagagtcaag gcttcctgga gaagaaccga gacaccctgc
1981 atggggacat catccagctg gtccactctt cccggaacaa gttcataaag cagatttttcc
2041 aagctgacgt tgccatgggt gccgagacca ggaagcgctc gcctacactc agcagccagt
2101 tcaagcggtc tctggagctg ctgatgcgca cactgggcgc ctgccagccc ttctttgtgc
2161 gttgtatcaa acccaatgag ttcaagaagc ccatgctctt cgaccggcac ttgtgtgtac
2221 gccagctgcg atattcggcc atgatggaga caatccgcat ccgccacgca ggctacccca
2281 ttcgctacag cttttgtggag tttgtggagc gctaccgggt actgctgcct ggtgtgaagc
2341 cagcatacaa gcaggtgac ctccgaggga catgccagcg catggctgag gctgtgctgg
2401 gcacgcacga tgactggcag attggcaaaa ccaagatctt tctgaaggac caccatgaca
2461 tgttgctgga ggtggacgg gacaaggcca tcacagacag agtcattctc ctccagaagg
2521 ttatccgggg cttcaaagac aggtccaact tcctgagact gaagagtgct gccacactga
2581 tccagaggca ctggcgggc caccactgta ggaaaaacta tgagctgatt cgtcttggct
2641 tcctgcggct gcaggccctg caccgctccc ggaagctgca caagcagtac cgcctggcca
2701 gacagcgcat aatagagttc aggcccgct gccgggccta tctggtgcgc aaggcctcc
2761 gccaccgcct ctgggccgtg atcaccgtgc aggcctatgc ccgaggcatg attgcccgcc
2821 ggctacaccg ccgcctccgg gttgagtacc agcggcgcct cgaggcagag aggatgcgtc
2881 tggcagagga ggagaaactc cgaaaggaga tgagtgccaa gaaggccaaa gaggaggctg
2941 agcgcaagca tcaggagcgc ctggctcagc tacccgcgga ggatgcggag cgggaactga
3001 aggagaagga ggaggctcgg aggaagaagg aactgctgga gcagatggag aaggcccgcc
3061 acgaacccat caaccactca gatatggtgg acaagatgtt tggcttcctg gggacttcag
3121 gcagcctgcc aggccaggaa ggccaggcgc ctagtggctt tgaggaccta gagcgcggac
3181 ggagggagat ggtggaagag gatgttgacg ctgccctgcc cctgcctgat gaagacgagg
3241 aggacctttc tgagtacaaa ttcgccaagt ttgctgccac ctacttccag ggcacaacca
3301 cacactccta cacccggagg cctctcaagc agccgctgct ctaccacgac gatgagggtg
3361 accagctggc ggcgctggct gtctggatca ccatcctccg gttcatgggg acctcccag
3421 agcccaagta ccacacagcc atgagcgacg gcagtgagaa gatcccagtg atgactaaga
3481 tctacgagac cctaggcaag aagacatata agagggagct gcaggccttg cagggcgagg
```

TABLE 4-continued

```
3541 gcgagaccca gctccctgag gggcagaaga agaccagtgt gagacacaag ttggtacact
3601 tgacactgaa gaaaaagtcc aaactcacag aagaggtgac caagaggctg aacgatgggg
3661 aatccacggt acagggcaac agcatgctgg aggatcggcc cacctcaaat ctagagaagc
3721 tgcacttcat catcggcaac ggcatcctgc ggcctgcgct gcgggacgag atttactgcc
3781 agatcagtaa gcagctcaca cacaacccat ccaagagcag ctatgccagg ggctggatcc
3841 tcgtgtcgct ctgtgtgggc tgcttcgccc cctctgagaa gttcgttaag tacctgcgga
3901 acttcatcca cggaggccca cctggctatg ctccttactg tgaggagcgc ctgaggagga
3961 cctttgtcaa cggaactcgg acacagccac ccagctggct ggagctgcag gccaccaagt
4021 ccaagaagcc catcatgttg cccgtgacct tcatggatgg gaccaccaag accctgctaa
4081 cagattcagc aactacagcc agggagctgt gcaatgctct ggctgacaag atctcactca
4141 aggaccgctt tggcttctcc ctctacatcg ctctgttcga taaggtgtcc tccctgggca
4201 gcggcagtga ccatgtcatg gatgccatct ctcagtgtga gcagtacgcc aaggagcagg
4261 gtgctcagga gcgcaacgcc ccatggaggc tcttctttag aaaggaggtc ttcacaccct
4321 ggcacaaccc ctcggaggac aacgtggcca cgaacctcat ctaccagcag gtggtgcgag
4381 gagtcaagtt tggggagtac aggtgtgaga aggaggacga cctggctgag ctggcttctc
4441 agcagtactt tgtggactat ggttctgaga tgattctgga gcgcctgctg agcctcgtgc
4501 ccacttacat ccctgaccgt gagatcacac cgctgaagaa tcttgagaag tgggcacagc
4561 tggccattgc tgcccacaag aagggaattt atgcccagag gagaactgac tcccagaagg
4621 tcaaagagga tgtggtcaat tatgcccgtt tcaagtggcc cttgctcttc tccaggtttt
4681 acgaagctta caaattctca ggccctcccc tccccaagag cgacgtcatc gtggctgtca
4741 actggacggg tgtgtacttc gtggacgagc aggagcaggt gcttctggag ctgtccttcc
4801 cggagatcat ggctgtgtcc agcagtaggg agtgccgcgt cttgctctca ctgggctgct
4861 ctgacttggg ctgtgctact tgtcaatcgg gccgggcagg gctgaccccg gctggaccct
4921 gttctccgtg ttggtcctgt aggggaacaa agatgatggc ccccagcttt accctggcca
4981 ccatcaaagg agatgagtac accttcacat ccagcaatgc tggaggacat cgtgacctgg
5041 tggtcacctt tctggagggg ctacggaaga ggtctaagta tgtggtggca ctgcaggaca
5101 atcctaaccc tgctggtgag gagtcaggct tcctcagctt cgccaaggga gacctcatca
5161 tccttgacca tgatactggt gagcaggtca tgaactcagg ctgggccaac ggcatcaacg
5221 agaggaccaa gcagcgcggc gacttcccca ctgactgtgt atacgtcatg cccactgtca
5281 ccttgccacc aagggagatt gtgggcctgg tcactatgac cccagaccag aggcaggatg
5341 tcgtccggct cctgcagctt cgcacagcag agccagaggt gcgcgccaag ccctacacgc
5401 tagaggagtt ctcctacgac tacttcaggc cccccaccca gcacacgctg agccgtgtca
5461 tggtgtccaa ggcccgcggt aaggacaggc tgtggagcca cacgcgagag cccctcaagc
5521 aggccctgct caagaagatc ctgggcagtg aagaactctc ccaggaagcc tgcatggcct
5581 ttgtagctgt gctcaagtac atgggcgact acccatccaa gaggatgcga tccgtcaatg
5641 agctcactga ccagatcttt gagtgggcac tcaaggctga gccctcaag gatgaggcct
5701 acgtgcagat cctgaagcag ctgactgaca atcacatcag gtacagcgaa gagaggggct
5761 gggaactgct gtggctgtgc acgggcctct tcccgcccag caacatcctc ctgcctcatg
5821 ttcagcggtt tctgcagtcc cgcaagcact gtcctcttgc cattgactgc ctgcagaggc
5881 tccagaaagc cctgagaaat ggctcccgga agtaccctcc gcacctggtg gaggtggagg
5941 ccatccaaca taagactacc cagatcttcc acaaggtcta cttccccgat gacacggacg
6001 aggcttttga ggtggagtcc agcaccaagg ccaaggactt ctgccagaac atcgccaggg
6061 ggctgctgct caagtcttcc gagggattca gcctttttgt caaaatcgca gataaggtca
6121 tcagcgtccc agagaatgat ttcttctttg actttgtccg acacctgaca gactggataa
6181 agaaagcacg gcccatcaag gacggaatcg tgccctcact aacctaccag gtgttcttca
6241 tgaagaagct gtggaccaac acagtgccgg gcaaggaccc catggctgac tccatcttcc
6301 actattacca ggaactgccc aaatatctcc gaggctacca caagtgcacc cgggaggagg
6361 tgctgcagct gggcgcactc atctacaggg tcaagtttga ggaggacaaa tcctacttcc
6421 ctagcatccc caagttgctg agggagctgg tacccagga cctaatccgg caggtctcac
6481 ctgatgactg gaaacggtct attgtcgcct acttcaacaa acatggggg aagtccaagg
6541 aggaagccaa gctggccttc ctcaaactca tcttcaagtg gcccacctt ggctcagcct
6601 tctttgaggt gaagcaaact acagaaccaa acttcccaga gattctctta attgccatca
6661 acaagtacgg ggtcagcctc atcgatccca gaaccaagga catcctgact actcaccct
6721 tcaccaagat ctccaactgg agtagtggca acacctactt ccacatcacc attgggaact
6781 tggtccgtgg gagcaaactg ctctgtgaga catcgctggg atacaaaatg gatgatcttc
6841 tgacttccta catcagccag atgctcacag ccatgagcaa gcagaggaac tccaggagtg
6901 gaaggtgaac ctcagaggag acgctggctc aggccttggc cctctaggca gggaagctgg
6961 actgaccata tctgctgggc atctgatctg cctgccacga ggtccagact cttctgcatc
7021 cacctatggc atctgggttt gctgtcaccc tacttttgttg tggccttcct ggttgtaagag
7081 tctgtgttcc ttggtcacct ctcctgattc agaccagtgc catcaagcaa cctcttttga
7141 ctttctgtat atggatggca cagaggaatc aaggacaact tagctctctg catacttgga
7201 acaaccaaac tatttgtaca ttgaacggat gctctgaaac ccaagggact gggctcaggg
7261 tcctcagcac tggcccctgt cataagcact accactaagg actctctgga ggactcctca
7321 gtatcatctg ctccaggaag cccccctagac tacctcctga gtctggacaa agcctcctga
7381 ttctacctgg atcactcctg ttatgtgaca gttatgtggt gggtccctgc taaaatctcc
7441 ctgaccacct gagggcataa agcatgtgtc ttattctctg g
```

SEQ ID NO: 72 Mouse Myo7a Isoform 1 (Encoded by Transcript Variant 1) Amino Acid Sequence (NP_001243010.1)

```
  1 mvilqkgdyv wmdlksgqef dvpigavvkl cdsgqiqvvd dednehwisp qnathikpmh
 61 ptsvhgvedm irlgdlneag ilrnlliryr dhliytytgs ilvavnpyql lsiyspehir
121 qytnkkigem pphifaiadn cyfnmkrnnr dqccisges gagktestkl ilqflaaisg
181 qhswieqqvl eatpileafg naktirndns srfgkyidih fnkrgaiega kieqylleks
241 rvcrqapder nyhvfycmle gmneeekkkl glgqaadyny lamgncitce grvdsqeyan
301 irsamkvlmf tdtenweisk llaailhmgn lqyeartfen ldacevlfsp slataaslle
361 vnppdlmscl tsrtlitrge tvstplsreq aldvrdafvk giygrlfvwi vekinaaiyk
421 ppplevknsr rsiglldifg fenftvnsfe qlcinfaneh lqqffvrhvf kleqeeydle
481 sidwlhieft dnqealdmia nrpmnvisli deeskfpkgt datmlhklns qhklnanyvp
541 pknshetqfg inhfagvvyy esqgflekn rdtlhgdiiql vhssrnkfik qifqadvamg
601 aetrkrsptl ssqfkrslel lmrtlgacqp ffvrcikpne fkkpmlfdrh lcvrqlrysg
```

TABLE 4-continued

```
 661 mmetirirha gypirysfve fveryrvllp gvkpaykqgd lrgtcqrmae avlgthddwq
 721 igktkiflkd hhdmllever dkaitdrvil lqkvirgfkd rsnflrlksa atliqrhwrg
 781 hhcrknyeli rlgflrlqal hrsrklhkqy rlarqriief qarcraylvr kafrhrlwav
 841 itvqayargm iarrlhrrlr veyqrrleae rmrlaeeekl rkemsakkak eeaerkhqer
 901 laqlaredae relkekeear rkkellecme karhepinhs dmvdkmfgfl gtsgslpgqe
 961 gqapsgfedl ergrremvee dvdaalplpd edeedlseyk fakfaatyfq gttthsytrr
1021 plkqpllyhd degdqlaala vwitilrfmg dlpepkyhta msdgsekipv mtkiyetlgk
1081 ktykrelqal qgegetqlpe gqkktsvrhk lvhltlkkks klteevtkrl ndgestvqgn
1141 smledrptsn leklhfiign gilrpalrde iycqiskqlt hnpskssyar gwilvslcvg
1201 cfapsekfvk ylrnfihggp pgyapyceer lrrtfvngtr tqppswlelq atkskkpiml
1261 pvtfmdgttk tlltdsatta relcnaladk islkdrfgfs lyialfdkvs slgsgsdhvm
1321 daisqceqya keqgaqerna pwrlffrkev ftpwhnpsed nvatnliyqq vvrgvkfgey
1381 rcekeddlae lasqqyfvdy gsemilerll slvptyipdr eitplknlek waqlaiaahk
1441 kgiyaqrrtd sqkvkedvvn yarfkwpllf srfyeaykfs gpplpksdvi vavnwtgvyf
1501 vdeqeqvlle lsfpeimavs ssrecrvlls lgcsdlgcat cqsgragltp agpcspcwsc
1561 rgtkmmapsf tlatikgdey tftssnaedi rdlvvtfleg lrkrskyvva lqdnpnpage
1621 esgflsfakg dliildhdtg eqvmnsgwan ginertkqrg dfptdcvyvm ptvtlpprei
1681 valvtmtpdq rqdvvrllql rtaepevrak pytleefsyd yfrpppkhtl srvmvskarg
1741 kdrlwshtre plkqallkki lgseelsqea cmafvavlky mgdypskrmr svneltdqif
1801 ewalkaeplk deayvqilkq ltdnhiryse ergwellwlc tglfppsnil lphvqrflqs
1861 rkhcplaidc lqrlqkalrn gsrkypphlv eveaiqhktt qifhkvyfpd dtdeafeves
1921 stkakdfcqn iasrllllkss egfslfvkia dkvisvpend ffffdfvrhlt dwikkarpik
1981 dgivpsltyq vffmkklwtt tvpgkdpmad sifhyyqelp kylrgyhkct reevlqlgal
2041 iyrvkfeedk syfpsipkll relvpqdlir qvspddwkrs ivayfnkhag kskeeaklaf
2101 lklifkwptf gsaffevkqt tepnfpeill iainkygvsl idprtkdilt thpftkisnw
2161 ssgntyfhit ignlvrgskl lcetslgykm ddlltsyisq mltamskqrn srsgr
```

SEQ ID NO: 73 Mouse MYO7A Transcript Variant 2 cDNA Sequence
(NM_008663.2, CDS region from position 261-6794)

```
   1 agtgcaggct ggacagctgc cctgaacaga aagaaagagt gacccaggga gacaagaaac
  61 agagtagccc aagggaagcc cacagcagca gcagatcaag gctcaagctg gagctgaaaa
 121 tttgcaggct ccagcctcag cttccagagt cctcctgacc tgtgacccct ggctcctggc
 181 tgggaggtgg tgactcggag ggtgtggata aacccagag ctgtgtctgg tcactccggc
 241 aggtgtgctg acgtagaagc atggttattc tgcagaaggg ggactatgta tggatggacc
 301 tgaagtcagg ccaggagttt gatgtgccca tcggggccgt ggtgaagctc tgcgactcgg
 361 gccagatcca ggtggtggat gatgaagaca atgaacactg gatatcccct cagaatgcca
 421 cgcacatcaa gccaatgcac cccacatcgg tgcacgcgt ggaggacatg atccgcctgg
 481 gggatctcaa cgaggcagge atccttcgaa accttctcat tcgctaccgg gaccacctca
 541 tctatacgta cacaggttcc atcctggtgg ccgtgaaccc ctaccagctg ctctccatct
 601 actcgccaga gcacatccgc cagtacacca acaagaagat aggggagatg ccccccacca
 661 tcttcgccat tgctgacaac tgctacttca acatgaaacg caacaaccgg gaccagtgct
 721 gtattatcag cggggagtcg ggagctggca agacagagag cacaaagttg atcctgcagt
 781 tcctggcagc catcagtgga cagcactcat ggatcgagca gcaggtgctg gaggccaccc
 841 cgatcctgga agcatttggg aacgccaaga ccatccgcaa cgacaactct agccgctttg
 901 gcaagtacat tgacatccac tttaacaagc gtggtgccat cgagggcgcc aaaatagagc
 961 aatacctgct ggagaagtca cgtgtctgcc gccaggcccc tgacgagagg aactatcacg
1021 tgttctactg tatgctggag ggcatgaatg aggaggagaa gaagaaactg ggctaggcc
1081 aggccgctga ctacaactac ttggccatgg gtaactgcat cacctgtgag ggccgcgtgg
1141 acagtcagga gtatgccaac atccgctctg ccatgaaggt tctcatgttc acagacacgg
1201 agaactggga gatctcgaga cttctggctg ccatcctaca catgggcaat ctgcagtatg
1261 aggcccggac atttgagaac ttggatgcgt gtgaagtcct cttctcccca tcgctggcca
1321 cggcagcttc tctgctcgag gtgaaccccc cagacctgat gagctgcctc accagccgca
1381 ccctcatcac ccgtggggag acggtgtcca ccctctcag cagggaacag cgcctggatg
1441 tgcgagatgc cttttgtcaag ggcatctatg gcggctctt tgtgtggatt gtggagaaga
1501 tcaacgcagc aatctacaag ccacccccc tggaagtgaa gaactctcgc cggtccatcg
1561 gtctcctgga catctttgga tttgagaact tcactgtgaa cagcttcgag cagctctgca
1621 ttaactttgc caatgagcac ctgcagcaat tcttcgtgcg gcacgtgttc aagctggagc
1681 aggaggagta cgacctggag agcatcgact ggttgcacat tgagttcact gacaaccagg
1741 aagcactgga catgattgcc aaccggccta tgaacgtcat ctccctcatc gatgaggaga
1801 gcaagttccc caagggcacg gatgccacca tgctgcataa gctgaactca cagcacaagc
1861 tcaatgccaa ctacgtgcca cccaagaaca gccacgagac ccagtttgga atcaaccact
1921 ttgcgggtgt tgtctattat gagagtcaag gcttcctgga gaagaaccga gacacccctgc
1981 atggggacat catccagctg tgccatgggt gccgagacca ggaagcgctc gcctacactc agcagccagt
2101 tcaagcggtc tctggagctg ctgatgcgca cactgggcgc ctgccagccc ttcttttgtgc
2161 gttgtatcaa acccaatgag ttcaagaagc ccatgctctt cgaccggcac ttgtgtgtac
2221 gccagctgcg atattcgggc atgatggaga caatccgcat ccgccacgca ggctacccca
2281 ttcgctacag ctttgtggag tttgtggagc gctaccgggt actgctgcct ggtgtgaagc
2341 cagcatacaa gcaggtgac ctcgaggga catgccagcg catggctgag gctgtgctgg
2401 gcacgcacga tgactggcag attggcaaaa ccaagatctt tctgaaggac caccatgaca
2461 tgttgctgga ggtggagcgg acaaggcca tcacagacag agtcattctc ctccagaagg
2521 ttatccgggg cttcaaagac aggtccaact tcctgagact gaagagtgct gccacactga
2581 tccagaggca ctggcgggc caccactgta ggaaaaacta tgagctgatt cgtcttggct
2641 tcctgcggct gcaggccctg caccgctccc ggaagctgca caagcagtac cgcctggcca
2701 gacagcgcat aatagagttc caagcgcctg ccgggtcta tctggtgcga aaggccttcc
2761 gccaccgcct ctgggccgtg atcaccgtgc aggcctatgc ccgaggcatg attgcccgcc
2821 ggctacaccg ccgcctccgg gttgagtacc agcggcgcct cgaggcagag aggatgcgtc
2881 tggcagagga ggagaaactc cgaaaggaga tgagtgccaa gaaggccaaa gaggaggctg
2941 agcgcaagca tcaggagcgc ctggctcagc tagcccgcga ggatgcggag cgggaactga
3001 aggagaagga ggaggctcgg aggaagaagg aactgctgga gcagatggag aaggccccgcc
```

TABLE 4-continued

```
3061 acgaacccat caaccactca gatatggtgg acaagatgtt tggcttcctg gggacttcag
3121 gcagcctgcc aggccaggaa ggccaggcgc ctagtggctt tgaggaccta gagcgcggac
3181 ggagggagat ggtggaagag gatgttgacg ctgccctgcc cctgcctgat gaagacgagg
3241 aggaccttc tgagtacaaa ttcgccaagt ttgctgccac ctacttccag ggcacaacca
3301 cacactccta cacccggagg cctctcaagc agccgctgct ctaccacgac gatgagggtg
3361 accagctggc ggcgctggct gtctggatca ccatcctccg gttcatgggg gacctcccag
3421 agcccaagta ccacacagcc atgagcgacg gcagtgagaa gatcccagtg atgactaaga
3481 tctacgagac cctaggcaag aagacatata agagggagct gcaggccttg cagggcgagg
3541 gcgagaccca gctccctgag gggcagaaga agaccagtgt gagacacaga ttggtacact
3601 tgacactgaa gaaaaagtcc aaactcacag aagaggtgca caagaggctg aacgatgggg
3661 aatccacggt acagggcaac agcatgctgg aggatcggcc cacctcaaat ctagagaagc
3721 tgcacttcat catcggcaac ggcatcctgc ggcctgcgct gcgggacgag atttactgcc
3781 agatcagtaa gcagctcaca cacaacccat ccaagacgag ctatgccagg ggctggatcc
3841 tcgtgtcgct ctgtgtgggc tgcttcgccc cctctgagaa gttcgttaag tacctgcgga
3901 acttcatcca cggaggccca cctggctatg ctccttactg tgaggagcgc ctgaggagga
3961 cctttgtcaa cggaactcgg acacagccac ccagctggct ggagctgcag gccaccaagt
4021 ccaagaagcc catcatgttg cccgtgacct tcatggatgg gaccaccaag accctgctaa
4081 cagattcagc aactacagcc agggagctgt gcaatgctct ggctgacaag atctcactca
4141 aggaccgctt tggcttctcc ctctacatcg ctctgttcga taaggtgtcc tccctgggca
4201 gcggcagtga ccatgtcatg gatgccatct ctcagtgtga gcagtacgcc aaggagcagg
4261 gtgctcagga gcgcaacgcc ccatggaggc tcttctttag aaaggaggtc ttcacaccct
4321 ggcacaaccc ctcggaggac aacgtggcca cgaacctcat ctaccagcag gtggtgcgag
4381 gagtcaagtt tggggagtac aggtgtgaga aggaggacga cctggctgag ctggcttctc
4441 agcagtactt tgtggactat ggttctgaga tgattctgga gcgcctgctg agcctcgtgc
4501 ccacttacat ccctgaccgt gagatcacac cgctgaagaa tcttgagaag tgggcagag
4561 tggccattgc tgcccacaag aagggaattt atgcccagag gagaactgac tcccagaagg
4621 tcaaagagga tgtggtcaat tatgcccgtt caagtggcc cttgctcttc tccaggtttt
4681 acgaagctta caaattctca ggccctcccc tccccaagag cgacgtcatc gtggctgtca
4741 actggacggg tgtgtacttc gtggacgagc aggagcaggt gcttctggag ctgtccttcc
4801 cggagatcat ggctgtgtcc agcagtaggg gaacaaagat gatggcccc agctttaccc
4861 tggccaccat caaaggagat gagtacacct tcacatccag caatgctgag gacatccgtg
4921 acctggtggt caccttctg gagggctac ggaagaggtc taagtatgtg gtggcactgc
4981 aggacaatcc taaccctgct ggtgaggagt caggcttcct cagcttcgcc aagggagacc
5041 tcatcatcct tgaccatgat actggtgagc aggtcatgaa ctcaggctgg gccaacggca
5101 tcaacgagag gaccaagcag cgcggcgact tccccactga ctgtgtatac gtcatgccca
5161 ctgtcacctt gccaccaagg gagattgtgg ccctggtcac tatgaccccca gaccagaggc
5221 aggatgtcgt ccggctcctg cagcttcgca cagcagagcc agaggtgcgc gccaagccct
5281 acacgctaga ggagttctcc tacgactact tcaggccccc acccaagcac acgctgagcc
5341 gtgtcatggt gtccaaggcc cgcggtaagg acaggctgtg gagccacaca cgagagcccc
5401 tcaagcaggc cctgctcaag aagatcctgg gcagtgaaga actctcccag gaagcctgca
5461 tggcctttgt agctgtgctc aagtacatgg gcgactaccc atccaagagg atgcgatccg
5521 tcaatgagct cactgaccag atctttgagt gggcactcaa ggctgagccc ctcaaggatg
5581 aggcctacgt gcagatcctg aagcagctga ctgacaatca catcaggtac agcgaagaga
5641 ggggctggga actgctgtgg ctgtgcacgg gcctcttccc gcccagcaac atcctcctgc
5701 ctcatgttca gcggtttctg cagtcccgca agcactgtcc tcttgccatt gactgcctgc
5761 agaggctcca gaaagccctg agaaatggct cccggaagta ccctccgcac ctggtgggga
5821 tggaggccat ccaacataag actacccaga tcttccacaa ggtctacttc cccgatgaca
5881 cggacgaggc ttttgaggtg gagtccagca ccaaggccaa ggacttctgc agaacatcg
5941 ccagccggct gctgctcaag tcttccgagg gattcagcct ttttgtcaaa atcgcagata
6001 aggtcatcag cgtcccagag aatgatttct tctttgactt tgtccgacac ctgacagact
6061 ggataaagaa agcacggccc atcaaggacg gaatcgtgcc ctcactaacc taccaggtgt
6121 tcttcatgaa gaagctgtgg accaccacag tgccgggcaa ggaccccatg gctgactcca
6181 tcttccacta ttaccaggaa ctgcccaaat atctccgagg ctaccacaag tgcacccggg
6241 aggaggtgct gcagctgggc gcactcatct acaggtgtaa gtttgaggag gacaaatcct
6301 acttccctag catcccccaag ttgctgaggg agctggtacc ccaggaccta atccggcagg
6361 tctcacctga tgactggaaa cggtctattg tcgcctactt caacaaacat gcggggaagt
6421 ccaaggagga agcaagctg gccttcctca aactcatctt caagtggccc acctttggct
6481 cagccttctt tgaggtgaag caaactacag aaccaaactt cccagagatt ctcttaattg
6541 ccatcaacaa gtacggggtc agcctcatcg atccccagaac caaggacatc ctgactactc
6601 acccccttcac caagatctcc aactggagta gtgccaacac ctacttccac atcaccattg
6661 ggaacttggt ccgtggggagc aaactgctct gtgagacatc gctgggatac aaaatggatg
6721 atcttctgac ttcctacatc agccagatgc tcacagccat gagcaagcag aggaactcca
6781 ggagtggaag gtgaacctca gaggagacgc tggctcaggc cttggccctc taggcaggga
6841 agctggactg accatatctg ctgggcatct gatctgcctg ccacgaggtc cagactcttc
6901 tgcatccacc tatggcatct gggtttgctg tcacccact ttgttgtggc cttcctggtg
6961 taagagtctg tgttccttgg tcacctctcc tgattcagac cagctccatc aagcaacctc
7021 ttttgacttt ctgtatatgg atggcacaga ggaatcaagg acaacttagc tctctgcata
7081 cttggaacaa ccaaactatt tgtacattga acggatgctc tgaaacccaa gggactgggc
7141 tcagggtcct cagcactggc ccctgtcata agcactacca ctaaggactc tctgaggac
7201 tcctcagtat catctgctcc aggaagcccc ctagactacc tcctgagtct ggacaaagcc
7261 tcctgattct acctggatca ctcctgttat gtgacagtta tgtggtgggt ccctgctaaa
7321 atctccctga ccacctgagg gcataaagca tgtgtcttat t
```

SEQ ID NO: 74 Mouse Myo7a Isoform 2 (Encoded by Transcript Variant 2)
Amino Acid Sequence (NP_032689.2)

```
  1 mvilqkgdyv wmdlksgqef dvpigavvkl cdsgqiqvvd dednehwisp qnathikpmh
 61 ptsvhgvedm irlgdlneag ilrnlliryr dhliytytgs ilvavnpyql lsiyspehir
121 qytnkkigem pphifaiadn cyfnmkrnnr dqcciisges gagktestkl ilqflaaisg
181 qhswieqqvl eatpileafg naktirndns srfgkyidih fnkrgaiega kieqyllleks
241 rvcrqapder nyhvfycmle gmneeekkkl glgqaadyny lamgncitce grvdsqeyan
```

TABLE 4-continued

```
 301 irsamkvlmf tdtenweisk llaailhmgn lqyeartfen ldacevlfsp slataaslle
 361 vnppdlmscl tsrtlitrge tvstplsreq aldvrdafvk giygrlfvwi vekinaaiyk
 421 ppplevknsr rsiglldifg fenftvnsfe qlcinfaneh lqqffvrhvf kleqeeydle
 481 sidwlhieft dnqealdmia nrpmnvisli deeskfpkgt datmlhklns qhklnanyvp
 541 pknshetqfg inhfagvvyy esqgfleknr dtlhgdiiql vhssrnkfik qifqadvamg
 601 aetrkrsptl ssqfkrslel lmrtlgacqp ffvrcikpne fkkpmlfdrh lcvrqlrysg
 661 mmetirirha gypirysfve fveryrvllp gvkpaykqgd lrgtcqrmae avlgthddwq
 721 igktkiflkd hhdmllever dkaitdrvil lqkvirgfkd rsnflrlksa atliqrhwrg
 781 hhcrknyeli rlgflrlqal hrsrklhkqy rlarqriief qarcraylvr kafrhrlwav
 841 itvqayargm iarrlhrrlr veyqrrleae rmrlaeeekl rkemsakkak eeaerkhqer
 901 laglaredae relkekeear rkkelleqme karhepinhs dmvdkmfgfl gtsgslpgqe
 961 gqapsgfedl ergrremvee dvdaalplpd edeedlseyk fakfaatyfq gttthsytrr
1021 plkqpllyhd degdqlaala vwitilrfmg dlpepkyhta msdgsekipv mtkiyetlgk
1081 ktykrelqal qgegetqlpe gqkktsvrhk lvhltlkkks klteevtkrl ndgestvqgn
1141 smledrptsn leklhfiign gilrpalrde iycqiskqlt hnpskssyar gwilvslcvg
1201 cfapsekfvk ylrnfihgp pgyapyceer lrrtfvngtr tqppswlelq atkskkpiml
1261 pvtfmdgttk tlltdsatta relcnaladk islkdrfgfs lyialfdkvs slgsgsdhvm
1321 daisqceqya keqgaqerna pwrlffrkev ftpwhnpsed nvatnliyqq vvrgvkfgey
1381 rcekeddlae lasqqyfvdy gsemilerll slvptyipdr eitplknlek waqlaiaahk
1441 kgiyaqrrtd sqkvkedvvn yarfkwpllf srfyeaykfs gpplpksdvi vavnwtgvyf
1501 vdeqeqvlle lsfpeimavs ssrgtkmmap sftlatikgd eytftssnae dirdlvvtfl
1561 eglrkrskyv valqdnpnpa geesgflsfa kgdliildhd tgeqvmnsgw anginertkq
1621 rgdfptdcvy vmptvtlppr eivalvtmtp dqrqdvvrll qlrtaepevr akpytleefs
1681 ydyfrpppkh tlsrvmvska rgkdrlwsht replkqallk kilgseelsq eacmafvavl
1741 kymgdypskr mrsvneltdq ifewalkaep lkdeayvqil kqltdnhiry seergwellw
1801 lctglfppsn illphvqrfl qsrkhcplai dclqrlqkal rngsrkypph lveveaiqhk
1861 ttqifhkvyf pddtdeafev esstkakdfc qniasrlllk ssegfslfvk iadkvisvpe
1921 ndfffdfvrh ltdwikkarp ikdgivpslt yqvffmkklw tttvpgkdpm adsifhyyqe
1981 lpkylrgyhk ctreevlqlg aliyrvkfee dksyfpsipk llrelvpqdl irqvspddwk
2041 rsivayfnkh agkskeeakl aflklifkwp tfgsaffevk qttepnfpei lliainkygv
2101 slidprtkdi ltthpfktkis nwssgntyfh itignlvrgs kllcetslgy kmddlltsyi
2161 sqmltamskq rnsrsgr SEQ ID NO: 75 Mouse MYO7A Transcript Variant 3 cDNA Sequence
(NM_001256082.1, CDS region from position 123-6641)
    1 gcgctaggc tgtgagatca tcagaggact ccgttaccca cacagctgcc agaggggagt
   61 tgtcaaagtg aaaccccagg gactgggggt gtagtttgtg gggtcagggg gactatgtat
  121 ggatggacct gaagtcaggc caggagtttg atgtgcccat cggggccgtg gtgaagctct
  181 gcgactcggg ccagatccag gtggtggatg atgaagacaa tgaacactgg atatccctc
  241 agaatgccac gcacatcaag ccaatgcacc ccacatcggt gcacggcgtg gaggacatga
  301 tccgcctggg ggatctcaac gaggcaggca tccttcgaaa ccttctcatt cgctaccggg
  361 accacctcat ctataccagc tgtgaggac ggacgtacac aggttccatc ctggtggccg
  421 tgaacccta ccagctgctc tccatctact cgccagagca catccgccag tacaccaaca
  481 agaagatagg ggagatgccc ccccacatct tcgccattgc tgacaactgc tacttcaaca
  541 tgaaacgcaa caaccgggac cagtgctgta ttatcagcgg ggagtcggga gctggcaaga
  601 cagagagcac aaagttgatc ctgcagttcc tggcagccat cagtggacag cactcatgga
  661 tcgagcagca ggtgctggag gccacccccga tcctggaagc attgggaac gccaagacca
  721 tccgcaacga caactctagc cgctttggca agtacattga catccacttt aacaagcgtg
  781 gtgccatcga gggcgccaaa atagagcaat acctgctgga gaagtcacgt gtctgccgcc
  841 aggccctga cgagaggaac tatcacgtgt tctactgtat gctggagggc atgaatgagg
  901 aggagaagaa gaaactgggc ctaggccagg ccgctgacta caactacttg gccatgggta
  961 actgcatcac ctgtgagggc cgcgtggaca gtcaggagta tgccaacatc cgctctgcca
 1021 tgaaggttct catgttcaca gacacggaga actgggagat ctcgaagctt ctggctgcca
 1081 tcctacacat gggcaatctg cagtatgagg cccgacatt tgaaacttg gatgcgtgtg
 1141 aagtcctctt ctcccccatcg ctggccacgg cagcttctct gctcgaggtg aacccccag
 1201 acctgatgag ctgcctcacc agccgcaccc tcatcacccg tggggagacg tgtccaccc
 1261 ctctcagcag ggaacaggcg ctggatgtgc gagatgcctt tgtcaagggc atctatgggc
 1321 ggctcttttgt gtggattgtg gagaagatca acgcagcaat ctacaagcca ccccccctgg
 1381 aagtgaagaa ctctcgcgg tccatcggtc tcctggacat ctttggattt ggaacttca
 1441 ctgtgaacag cttcgagcag ctctgcatta actttgccaa tgagcacctt cagcaattct
 1501 tcgtgcggca cgtgttcaag ctggagcagg aggagtacga cctggagagc atcgactggt
 1561 tgcacattga gttcactgac aaccaggaag cactggacat gattgccaac cggcctatga
 1621 acgtcatctc cctcatcgat gaggagagca agttcccaa cagcacggat gccaccatgc
 1681 tgcataagct gaactcacag cacaagctca atgccaacta cgtgccaccc aagaacagcc
 1741 acgagaccca gtttggaatc aaccactttg cgggtgttgt ctattatgag agtcaaggct
 1801 tcctggagaa gaaccgagac accctgcatg gggacatcat ccagctggtc cactcttccc
 1861 ggaacaagtt cataaagcag attttccaag tgcacagctc agtggtgcc gagaccagga
 1921 agcgctcgcc tacactcagc agccagttca agcggtctct ggagctgctg atgcgcacac
 1981 tgggcgcctg ccagccctc tttgtgcgtt gtatcaaacc caatgagttc aagaagccca
 2041 tgctcttcga ccggcacttg tgtgtacgcc agctgcgata tcgggcatg atggagacaa
 2101 tccgcatccg ccacgcaggc tacccccattc gctacagctt tgtggagttt gtggagcgcc
 2161 accgggtact gctgcctggt gtgaagccag catacaagca gggtgacctc cgagggacat
 2221 gccagcgcat ggctgaggct gtgctgggca cgcacgatga ctggcagatt ggcaaaacca
 2281 agatctttct gaaggaccac catgacatgt tgctggaggt ggagcgggac aaggccatca
 2341 cagacagagt cattctcctc cagaaggtta ccaaagacag tccaacttcc
 2401 tgagactgaa gagtgctgcc acactggatcc agaggcactg gcggggccac cactgtagga
 2461 aaaactatga gctgattcgt cttggcttcc tgccggctga ggcccttgcac cgtcccggaa
 2521 agctgcacaa gcagtaccgc ctggccgac agcgcataat agagttccag gcccgctgcc
 2581 gggcctatct ggtgcgcaag gccttccgcc accgcctctg ggccgtgatc accgtgcagg
 2641 cctatgcccg aggcatgatt gccgccggc tacaccgccc cctccgggtt gagtaccagc
```

TABLE 4-continued

```
2701 ggcgcctcga ggcagagagg atgcgtctgg cagaggagga gaaactccga aaggagatga
2761 gtgccaagaa ggccaaagag gaggctgagc gcaagcatca ggagcgcctg gctcagctag
2821 cccgcgagga tgcggagcgg gaactgaagg agaaggagga ggctcggagg aagaaggaac
2881 tgctggagca gatggagaag gcccgccacg aacccatcaa ccactcagat atggtggaca
2941 agatgtttgg cttcctgggg acttcaggca gcctgccagg ccaggaaggc caggcgccta
3001 gtggctttga ggacctagag cgcggacgga gggagatggt ggaagaggat gttgacgctg
3061 ccctgcccct gcctgatgaa gacgaggagg acctttctga gtacaaattc gccaagtttg
3121 ctgccaccta cttccagggc acaaccacac actcctacac ccggaggcct ctcaagcagc
3181 cgctgctcta ccacgacgat gagggtgacc agctggcggc gctggctgtc tggatcacca
3241 tcctccggtt catggggggac ctcccagagc ccaagtacca cacagccatg agcgacggca
3301 gtgagaagat cccagtgatg actaagatct acgagaccct aggcaagaag acatataaga
3361 gggagctgca ggccttgcag ggcgagggcg agacccagct ccctgagggg cagaagaaga
3421 ccagtgtgag acacaagttg gtacacttga cactgaagaa aaagtccaaa ctcacagaag
3481 aggtgaccaa gaggctgaac gatgggggaat ccacggtaca gggcaacagc atgctggagg
3541 atcggcccac ctcaaatcta gagaagctgc acttcatcat cggcaacggc atcctgcggc
3601 ctgcgctgcg ggacgagatt tactgccaga tcagtaagca gctcacacac aacccatcca
3661 agagcagcta tgccaggggc tggatcctcg tgtcgctctg tgtgggctgc ttcgcccct
3721 ctgagaagtt cgttaagtac ctgcggaact tcatccacgg aggcccacct ggctatgctc
3781 cttactgtga ggagcgcctg aggaggacct ttgtcaacgg aactcggaca cagccaccca
3841 gctggctgga gctgcaggcc accaagtcca agaagcccat catgttgccc gtgaccttca
3901 tggatgggac caccaagacc ctgctaacag attcagcaac tacagccagg gagctgtgca
3961 atgctctggc tgacaagatc tcactcaagg accgctttgg cttctccctc tacatcgctc
4021 tgttcgataa ggtgtcctcc ctgggcagcg gcagtgacca tgtcatggat gccatctctc
4081 agtgtgagca gtacgccaag gagcagggtg ctcaggagcg caacgcccca tggaggctct
4141 tctttagaaa ggaggtcttc acaccctggc acaaccctc ggaggacaac gtggccacga
4201 acctcatcta ccagcaggtg gtgcgaggag tcaagtttgg ggagtacagg tgtgagaagg
4261 aggacgacct ggctgagctg gcttctcagc agtactttgt ggactatggt tctgagatga
4321 ttctggagcg cctgctgagc ctcgtgccca cttcatccc tgaccgtgag atcacaccgc
4381 tgaagaatct tgagaagtgg ccacgactgg ccattgctgc ccacaagaag ggaatttatg
4441 cccagaggag aactgactcc cagaaggtca aagaggatgt ggtcaattat gcccgtttca
4501 agtggccctt gctcttctcc aggtttacg aagcttacaa attctcaggc cctcccctcc
4561 ccaagagcga cgtcatcgtg gctgtcaact ggacgggtgt gtacttcgtg gacgagcagg
4621 agcaggtgct tctggagctg tccttccgg agatcatggc tgtgtccagc agtagggggaa
4681 caaagatgat ggccccccagc tttaccctgg ccaccatcaa aggagatgag tacaccttca
4741 catccagcaa tgctgaggac atccgtgacc tggtggtcac cttctggag gggctacgga
4801 agaggtctaa gtatgtggtg gcactgcagg acaatcctaa ccctgctggt gaggagtcag
4861 gcttcctcag cttcgccaag ggagacctca tcatccttga ccatgatact ggtgagcagg
4921 tcatgaactc aggctgggcc aacggcatca acgagaggac caagcagcgc ggcgacttcc
4981 ccactgactg tgtatacgtc atgcccactg tcaccttgcc accaagggag attgtggccc
5041 tggtcactat gaccccagac cagaggcagg atgtcgtccg gctcctgcag cttcgcacag
5101 cagagccaga ggtgcgcgcc aagccctaca cgctagagga gttctcctac gactacttca
5161 ggccccccacc caagcacacg ctgagccgtg tcatggtgtc caaggcccgc ggtaaggaca
5221 ggctgtggag ccacacacga gagcccctca gcaggccct gctcaagaag atcctgggca
5281 gtgaagaact ctcccaggaa gcctgcatgg cctttgtagc tgtgctcaag tacatgggcg
5341 actacccatc caagaggatg cgatccgtca atgagctcac tgaccagatc tttgagtggg
5401 cactcaaggc tgagccctc aaggatgagg cctacgtcga gatcctgaag cagctgactg
5461 acaatcacat caggtacagc gaagagaggg gctgggaact gctgtggctg tgcacgggcc
5521 tcttcccgcc cagcaacatc ctcctgcctc atgttcagcg gtttctgcag tcccgcaagc
5581 actgtcctct tgccattgac tgcctgcaga ggctccagaa agccctgaga aatggctccc
5641 ggaagtaccc tccgcacctg gtggaggtgg aggccatcca acataagact acccagatct
5701 tccacaaggt ctacttcccc gatgacacgg acgaggcttt tgaggtggag tccagcacca
5761 aggccaagga cttctgccag aacatcgcca gccggctgct gctcaagtct tccgagggat
5821 tcagcctttt tgtcaaaatc gcagataagg tcatcagcgt cccagagaat gatttcttct
5881 ttgactttgt ccgacacctg acagactgga taaagaaagc acggcccatc aaggacggaa
5941 tcgtgccctc actaacctac caggtgttct tcatgaagaa gctgtggacc accacagtgc
6001 cgggcaagga ccccatggct gactccatct tccactatta ccaggaactg cccaaatatc
6061 tccgaggcta ccacagtgc acccgggagg aggtgctgca gctgggcgca ctcatcctaca
6121 gggtcaagtt tgaggaggac aaatcctact tccctagcat ccccaagttg ctgagggagc
6181 tggtacccca ggacctaatc cggcaggtct cacctgatga ctgaaacgg tctattgtcg
6241 cctacttcaa caaacatgcg gggaagtcca aggaggaagc caagctggcc ttcctcaaac
6301 tcatcttcaa gtggcccacc tttggctcag ccttctttga ggtgaagcaa actacagaac
6361 caaacttccc agagattctc ttaattgcca tcaacaagta cggggtcagc ctcatcgatc
6421 ccagaaccaa ggacatcctg actactcacc ccttcaccaa gatctccaac tggagtagtg
6481 gcaacaccta cttccacatc accattggga acttggtccg tgggagcaaa ctgctctgtg
6541 agacatcgct gggatacaaa atggatgatc ttctgacttc ctacatccac cagatgtcca
6601 cagccatgag caagcagagg aactccagga gtggaaggtg aacctcagag gagacgctgg
6661 ctcaggcctt ggccctctag gcagggaagc tggactgacc atatctgctg ggcatctgat
6721 ctgcctgcca cgaggtccag actcttctgc atccacctat ggcatctggg tttgctgtca
6781 ccctactttg ttgtggcctt cctggtgtaa gagtctgtgt tccttggtca cctctcctga
6841 ttcagaccag ctccatcaag caacctcttt tgactttctg tatatggatg gcacagagga
6901 atcaaggaca acttagctct ctgcatactt ggaacaacca actatttgt acattgaacg
6961 gatgctctga aacccaaggg actgggctca gggtcctcag cactggcccc tgtcataagc
7021 actaccacta aggactctct ggaggactcc tcagtatcat ctgctccagg aagcccccta
7081 gactacctcc tgagtctgga caaagcctcc tgattctacc tggatcactc ctgttatgtg
7141 acagttatgt ggtgggtccc tgctaaaatc tccctgacca cctgagggca taaagcatgt
7201 gtcttattct ctgg
```

TABLE 4-continued

SEQ ID NO: 76 Mouse Myo7a Isoform 3 (Encoded by Transcript Variant 3)
Amino Acid Sequence (NP_001243011.1)

```
   1 mdlksgqefd vpigavvklc dsgqiqvvdd ednehwispq nathikpmhp tsvhgvedmi
  61 rlgdlneagi lrnlliryrd hliytscggr tytgsilvav npyqllsiys pehirqytnk
 121 kigempphif aiadncyfnm krnnrdqcci isgesgagkt estklilqfl aaisgqhswi
 181 eqqvleatpi leafgnakti rndnssrfgk yidihfnkrg aiegakieqy lleksrvcrq
 241 apdernyhvf ycmlegmnee ekkklglgqa adynylamgn citcegrvds qeyanirsam
 301 kvlmftdten weiskllaai lhmgnlqyea rtfenldace vlfspslata asllevnppd
 361 lmscltsrtl itrgetvstp lsreqaldvr dafvkgiygr lfwivekin aaiykppple
 421 vknsrrsigl ldifgfenft vnsfeqlcin fanehlqqff vrhvfklege eydlesidwl
 481 hieftdnqea ldmianrpmn vislideesk fpkgtdatml hklnsqhkln anyvppknsh
 541 etqfginhfa gvvyyesqgf leknrdtlhg diiqlvhssr nkfikqifqa dvamgaetrk
 601 rsptlssqfk rslellmrtl gacqpffvrc ikpnefkkpm lfdrhlcvrq lrysgmmeti
 661 rirhagypir ysfvefvery rvllpgvkpa ykqgdlrgtc qrmaeavlgt hddwqigktk
 721 iflkdhhdml leverdkait drvillqkvi rgfkdrsnfl rlksaatliq rhwrghhcrk
 781 nyelirlgfl rlqalhrsrk lhkqyrlarq riiefqarcr aylvrkafrh rlwavitvqa
 841 yargmiarrl hrrlrveyqr rleaermrla eeeklrkems akkakeeaer khqerlaqla
 901 redaerelke keearrkkel leqmekarhe pinhsdmvdk mfgflgtsgs lpgqegqaps
 961 gfedlergrr emveedvdaa lplpdedeed lseykfakfa atyfqgttth sytrrplkqp
1021 llyhddegdq laalavwiti lrfmgdlpep kyhtamsdgs ekipvmtkiy etlgkktykr
1081 elqalqgege tqlpegqkkt svrhklvhlt lkkkskltee vtkrlndges tvqqnsmled
1141 rptsnleklh fiigngilrp alrdeiycqi skqlthnpsk ssyargwilv slcvgcfaps
1201 ekfvkylrnf ihggppgyap yceerlrrtf vngtrtqpps wlelqatksk kpimlpvtfm
1261 dgttktlltd sattarelcn aladkislkd rfgfslyial fdkvsslgsg sdhvmdaisq
1321 ceqyakeqga qernapwrlf frkevftpwh npsednvatn liyqqvvrgv kfgeyrceke
1381 ddlaelasqq yfvdygsemi lerllslvpt yipdreitpl knlekwaqla iaahkkgiya
1441 qrrtdsqkvk edvvnyarfk wpllfsrfye aykfsgpplp ksdvivavnw tgvyfvdeqe
1501 qvllelsfpe imavsssrgt kmmapsftla tikgdeytft ssnaedirdl vvtfleglrk
1561 rskyvvalqd npnpageesg flsfakgdli ildhdtgeqv mnsgwangin ertkqrgdfp
1621 tdcvyvmptv tlppreival vtmtpdqrqd vvrllqlrta epevrakpyt leefsydyfr
1681 pppkhtlsrv mvskargkdr lwshtreplk qallkkilgs eelsqeacma fvavlkymgd
1741 ypskrmrsvn eltdqifewa lkaeplkdea yvqilkqltd nhiryseerg wellwlctgl
1801 fppsnillph vqrflqsrkh cplaidclqr lqkalrngsr kypphlveve aiqhkttqif
1861 hkvyfpddtd eafevesstk akdfcqnias rlllkssegf slfvkiadkv isvpendfff
1921 dfvrhltdwi kkarpikdgi vpsltyqvff mkklwtttvp gkdpmadsif hyyqelpkyl
1981 rgyhkctree vlqlgaliyr vkfeedksyf psipkllrel vpqdlirqvs pddwkrsiva
2041 yfnkhagksk eeaklaflkl ifkwptfgsa ffevkqttep nfpeilliai nkygvslidp
2101 rtkdiltthp ftkisnwssg ntyfhitign lvrgskllce tslgykmddl ltsyisqmlt
2161 amskqrnsrs gr
```

SEQ ID NO: 77 Mouse MYO7A Transcript Variant 4 cDNA Sequence
(NM_001256083.1, CDS region from position 123-6623)

```
   1 ggcgctaggc tgtgagatca tcagaggact ccgttaccca cacagctgcc agaggggagt
  61 tgtcaaagtg aaaccccagg gactgggggt gtagtttgtg gggtcagggg gactatgtat
 121 ggatggacct gaagtcaggc caggagtttg atgtgcccat cggggccgtg gtgaagctct
 181 gcgactcggg ccagatccag gtggtggatg atgaagacaa tgaacactgg atatcccctc
 241 agaatgccac gcacatcaag ccaatgcacc ccacatcggt gcacggcgtg gaggacatga
 301 tccgcctggg ggatctcaac gaggcaggca tccttcgaaa ccttctcatt cgctaccggg
 361 accacctcat ctatacgtac acaggttcca tcctggtggc cgtgaaccgc taccagctgc
 421 tctccatcta ctcgccagag cacatccgcc agtacaccaa caagaagata ggggagatgc
 481 cccccacat cttcgccatt gctgacaact gctacttcaa catgaaacgc aacaaccggg
 541 accagtgctg tattatcagc ggggagtcgg gagctggcaa gacagagagc acaaagttga
 601 tcctgcagtt cctggcagcc atcagtggac agcactcatg gatcgagcag caggtgctgg
 661 aggccacccc gatcctggaa gcatttggga acgccaagac catccgcaac gacaactcta
 721 gccgctttgg caagtacatt gacatccact ttaacaagcg tggtgccatc gagggcgcca
 781 aaatagagca atacctgctg gagaagtcac gtgtctgccg ccaggcccct gacgagagga
 841 actatcacgt gttctactgt atgctggagg gcatgaatga ggaggagaag aagaaactgg
 901 gcctaggcca ggccgctgca tacaactact tggccatggg taactgcatc acctgtgagg
 961 gccgcgtgga cagtcaggag tatgccaaca tccgctctgc catgaaggtt ctcatgttca
1021 cagacacgga gaactgggag atctcgaagc ttctggctgc catcctacac atgggcaatc
1081 tgcagtatga ggcccggaca tttgagaact ggatgcgtga tgaagtcctc ttctccccat
1141 cgctggccac ggcagcttct ctgctcgagg tgaaccccc agacctgatg agctgctca
1201 ccagccgcac cctcatcacc cgtgggaga cggtgtccac ccctctcagc agggaacagg
1261 cgctggatgt gcgagatgcc tttgtcaagg gcatctatgg gcggctcttt gtgtggattg
1321 tggagaagat caacgcagca atctacaagc caccccccct ggaagtgaag aactctcgcc
1381 ggtccatcgg tctcctggac atctttggat ttgagaactt cgtgaactcc agctcttgcc
1441 agctctgcat taactttgcc aatgagcacc tgcagcaatt cttcgtgcgg cacgtgttca
1501 agctgggagca ggaggagtac gacctggaga gcatcgactg gttgcacatt gagttcactg
1561 acaaccagga agcactggac atgattgcca accggcctat gaacgtcatc tccctcatcg
1621 atgaggagag caagttcccc aagggcacgg atgccacgat gctgcataag ctgaactcac
1681 agcacaagct caatgccaac tacgtgccac ccaagaacac ccacgagacc cagtttggaa
1741 tcaaccactt tgcgggtgtt gtctattatg agagtcaagg cttcctggag aagaaccgag
1801 acaccctgca tggggacatc atccagctgg tccactcttc ccggaacaag ttcataaagc
1861 agattttcca agctgacgtt gccatggtgt cggagaccag gaagcgctcg cctacactca
1921 gcagccagtt caagcggtct ctggagctgc tgatgcgcac actgggcgcc tgccagccct
1981 tcttttgcgg ttgtatcaaa cccaatgagt tcaagaagcc catgctcttc gaccggcact
2041 tgtgtgtacg ccagctgcga tattcggca tgatggagac aatccgcatc cgccacgcag
2101 gctaccccat tcgctacagc tttgtggagt tgtggagcg ctaccgggta ctgctgcctg
2161 gtgtgaagcc agcatacaag cagggtgacc tcgagggac atgccagcgc atggctgagg
```

TABLE 4-continued

```
2221 ctgtgctggg cacgcacgat gactggcaga ttggcaaaac caagatcttt ctgaaggacc
2281 accatgacat gttgctggag gtggagcggg acaaggccat cacagacaga gtcattctcc
2341 tccagaaggt tatccggggc ttcaaagaca ggtccaactt cctgagactg aagagtgctg
2401 ccacactgat ccagaggcac tggcggggcc accactgtag gaaaaactat gagctgattc
2461 gtcttggctt cctgcggctg caggccctgc accgctcccg gaagctgcac aagcagtacc
2521 gcctggccag acagcgcata atagagttcc aggcccgctg ccgggcctat ctggtgcgca
2581 aggccttccg ccaccgcctc tgggccgtga tcaccgtgca ggcctatgcc cgaggcatga
2641 ttgcccgccg gctacaccgc cgcctccggg ttgagtacca gcggcgcctc gaggcagaga
2701 ggatgcgtct ggcagaggag gagaaactcc gaaaggagat gagtgccaag aaggccaaag
2761 aggaggctga gcgcaagcat caggagcgcc tggctcagct agcccgcgag gatgcggagc
2821 gggaactgaa ggagaaggag gaggctcgga ggaagaagga actgctggag cagatggaga
2881 aggcccgcca cgaacccatc aaccactcag atatggtgga caagatgttt ggcttcctgg
2941 ggacttcagg cagcctgcca ggccaggaag gccaggcgcc tagtggcttt gaggacctag
3001 agcgcggacg gagggagatg gtggaagagg atgttgacgc tgccctgccc ctgcctgatg
3061 aagacgagga ggacctttct gagtacaaat tcgccaagtt tgctgccacc tacttccagg
3121 gcacaaccac acactcctac acccggaggc ctctcaagca gccgctgctc taccacgacg
3181 atgagggtga ccagctggcg gcgctggctg tctggatcac catcctccgg ttcatggggg
3241 acctcccaga gcccaagtac cacacagcca tgagcgacga cagtgagaag atcccagtga
3301 tgactaagat ctacgagacc ctaggcaaga agacatataa gagggagctg caggccttgc
3361 agggcgaggg cgagacccag ctccctgagg ggcagaagaa gaccagtgtg agacacaagt
3421 tggtacactt gacactgaag aaaaagtcca aactcacaga agaggtgacc aagaggctga
3481 acgatgggga atccacggta cagggcaaca gcatgctgga ggatcggccc acctcaaatc
3541 tagagaagct gcacttcatc atcggcacg gcatcctgcg gcctgcgctg cgggacgaga
3601 tttactgcca gatcagtaag cagctcacac acaacccatc caagagcagc tatgccaggg
3661 gctggatcct cgtgtcgctc tgtgtgggct gcttcgcccc ctctgagaag ttcgttaagt
3721 acctgcggaa cttcatccac ggaggcccac ctggctatgc tccttactgt gaggagcgcc
3781 tgaggaggac ctttgtcaac ggaactcgga cacagccacc cagctggctg gagctgcagg
3841 ccaccaagtc caagaagccc atcatgttgc ccgtgacctt catggatggg accaccaaga
3901 ccctgctaac agattcagca actacagcca gggagctgtg caatgctctg gctgacaaga
3961 tctcactcaa ggaccgcttt ggcttctccc tctacatcgc tctgttcgat aaggtgtcct
4021 ccctgggcag cggcagtgac catgtcatgg atgccatctc tcagtgtgag cagtacgcca
4081 aggagcaggg tgctcaggag cgcaacgccc catggaggct cttctttaga aaggaggtct
4141 tcacaccctg gcacaacccc tcggaggaca acgtggccac gaacctcatc taccagcagg
4201 tggtgcgagg agtcaagttt ggggagtaca ggtgtgagaa ggaggacgac ctggctgagg
4261 tggcttctca gcagtacttt gtggactatg gttctgagat gattctggag cgcctgctga
4321 gcctcgtgcc cacttacatc cctgaccgtg agatcacacc gctgaagaat cttgagaagt
4381 gggcacagct ggccattgct gcccacaaga agggaattta tgcccagagg agaactgact
4441 cccagaaggt caaagaggat gtggtcaatt atgcccgttt caagtggccc ttgctcttct
4501 ccaggtttta cgaagcttac aaattctcag gccctcccct ccccaagagc gacgtcatcg
4561 tggctgtcaa ctggacgggt gtgtacttcg tggacgagca ggagcaggtg cttctggagc
4621 tgtccttccc ggagatcatg gctgtgtcca gcagtagggg aacaaagatg atggcccca
4681 gctttaccct ggccaccatc aaaggagatg agtacacctt cacatccagc aatgctgagg
4741 acatccgtga cctggtggtc accttctctg aggggctacg gaagaggtct aagtatgtgg
4801 tggcactgca ggacaatcct aaccctgctg tgagggagtc aggcttcctc agcttcgcca
4861 agggagacct catcatcctt gaccatgata ctggtgagca ggtcatgaac tcaggctggg
4921 ccaacggcat caacgagagg accaagcagc gcggcgactt ccccactgac tgtgtatacg
4981 tcatgcccac tgtcaccttg ccaccaaggg agattgtggc cctggtcact atgaccccag
5041 accagaggca ggatgtcgtc cggctcctgc agcttcgcac agcagagcca gaggtgcgcg
5101 ccaagcccta cacgctagag gagttctcct acgactactt caggccccca cccaagcaca
5161 cgctgagccg tgtcatgatg tccaaggccc gcggtaagga caggctgtgg agccacacac
5221 gagagcccct caagcaggcc ctgctcaaga agatctgggg cagtgaagaa ctctcccagg
5281 aagcctgcat ggcctttgta gctgtgctca agtacatggg cgactaccca tccaagagga
5341 tgcgatccgt caatgagctc actgaccaga tctttgagtg ggcactcaag gctgagcccc
5401 tcaaggatga ggcctacgtg cagatcctga agcagctgac tgacaatcac atcaggtaca
5461 gcgaagagag gggctgggaa ctgctgtggg tgtgcacggg cctcttcccg cccagcaaca
5521 tcctcctgcc tcatgttcag cggtttctgc agtcccgcaa gcactgtcct cttgccattg
5581 actgcctgca gaggctccag aaagccctga gaaatggctc ccggaagtac cctccgcacc
5641 tggtggaggt ggaggccatc caacataaga ctacccagat cttccacaag gtctacttcc
5701 ccgatgacac ggacgaggct tttgaggtgg agtccgacac caggccaag gacttctgcc
5761 agaacatcgc cagccggctg ctgctcaagt cttccgaggg attcagcctt tttgtcaaaa
5821 tcgcagataa ggtcatcagc gtcccagaga atgatttctt ctttgacttt gtccgacacc
5881 tgacagactg gataaagaaa gcacggccca tcaaggacgg aatcgtgccc tcactaacct
5941 accaggtgtt cttcatgaag aagctgtgga ccaccacagt gccgggcaag gacccatgcc
6001 ctgactccat cttccactat taccaggaac tgcccaaata tctccgaggc taccacaagt
6061 gcaccccggga ggaggtgctg cagctgggcg cactcatcta cagggtcaag tttgaggagg
6121 acaaatccta cttccctagc atcccaagt tgctgaggga gctggtaccc caggacctaa
6181 tccggcaggt ctcacctgat gactggaaac ggtctattgt cgcctacttc aacaaacatg
6241 cggggaagtc caaggaggaa gccaagctgg ccttcctcaa actcatcttc aagtggccca
6301 cctttggctc agccttcttt gaggtgaagc aaactacaga accaaacttc ccagagattc
6361 tcttaattgc catcaacaag tacggggtca gcctcatcga tcccagaacc aaggacatcc
6421 tgactactca cccctcacc aagatctcca actggagtag tggcaacacc tacttccaca
6481 tcaccattgg gaacttggtc cgtgggagca aactgctctg tgagacatcg ctgggataca
6541 aaatggatga tcttctgact tcctacatca gccagatgct cacagccatg agcaagcaga
6601 ggaactccag gagtggaagg tgaacctcag aggagacgct ggctcaggcc ttggccctct
6661 aggcagggaa gctggactga ccatatctgc tgggcatctg atctgcctgc cacgaggtcc
6721 agactcttct gcatccacct atggcatctg ggtttgctgt cacctactt tgttgtggcc
6781 ttcctggtgt aagagtctgt gttccttggt cacctctcct gattcagacc agctccatca
6841 agcaacctct tttgactttc tgtatatgga tggcacagag gaatcaagga caacttagct
6901 ctctgcatac ttgaacaac caaactattt gtacattgaa cggatgctct gaaacccaag
6961 ggactgggct cagggtcctc agcactggcc cctgtcataa gcactaccac taaggactct
```

TABLE 4-continued

```
7021 ctggaggact cctcagtatc atctgctcca ggaagccccc tagactacct cctgagtctg
7081 gacaaagcct cctgattcta cctggatcac tcctgttatg tgacagttat gtggtgggtc
7141 cctgctaaaa tctccctgac cacctgaggg cataaagcat gtgtcttatt ctctgg
```

SEQ ID NO: 78 Mouse Myo7a Isoform 4 (Encoded by Transcript Variant 4)
Amino Acid Sequence (NP_001243012.1)

```
   1 mdlksgqefd vpigavvklc dsgqiqvvdd ednehwispq nathikpmhp tsvhgvedmi
  61 rlgdlneagi lrnlliryrd hliytytgsi lvavnpyqll siyspehirq ytnkkigemp
 121 phifaiadnc yfnmkrnnrd qcciisgesg agktestkli lqflaaisgq hswieqqvle
 181 atpileafgn aktirndnss rfgkyidihf nkrgaiegak ieqylleksr vcrqapdern
 241 yhvfycmleg mneeekkklg lgqaadynyl amgncitceg rvdsqeyani rsamkvlmft
 301 dtenweiskl laailhmgnl qyeartfenl dacevlfsps lataasllev nppdlmsclt
 361 srtlitrget vstplsreqa ldvrdafvkg iygrlfvwiv ekinaaiykp pplevknsrr
 421 siglldifgf enftvnsfeq lcinfanehl qqffvrhvfk leqeeydles idwlhieftd
 481 nqealdmian rpmnvislid eeskfpkgtd atmlhklnsq hklnanyvpp knshetqfgi
 541 nhfagvvyye sqgfleknrd tlhgdiiqlv hssrnkfikq ifqadvamga etrkrsptls
 601 sqfkrslell mrtlgacqpf fvrcikpnef kkpmlfdrhl cvrqlrysgm metirirhag
 661 ypirysfvef veryrvllpg vkpaykqgdl rgtcqrmaea vlgthddwqi gktkiflkdh
 721 hdmlleverd kaitdrvill qkvirgfkdr snflrlksaa tliqrhwrgh hcrknyelir
 781 lgflrlqalh rsrklhkqyr larqriiefq arcraylvrk afrhrlwavi tvqayargmi
 841 arrlhrrlrv eyqrrleaer mrlaeeeklr kemsakkake eaerkhqerl aqlaredaer
 901 elkekeearr kkelleqmek arhepinhsd mvdkmfgflg tsgslpgqeg qapsgfedle
 961 rgrremveed vdaalplpde deedlseykf akfaatyfqg ttthsytrrp lkqpllyhdd
1021 egdqlaalav witilrfmgd lpepkyhtam sdgsekipvm tkiyetlgkk tykrelqalq
1081 gegetqlpeg qkktsvrhkl vhltlkkksk lteevtkrln dgestvqqns mledrptsnl
1141 eklhfiigng ilrpalrdei ycqiskqlth npskssyarg wilvslcvgc fapsekfvky
1201 lrnfihggpp gyapyceerl rrtfvngtrt qppswlelqa tkskkpimlp vtfmdgttkt
1261 lltdsattar elcnaladki slkdrfgfsl yialfdkvss lgsgsdhvmd aisqceqyak
1321 eqgagernap wrlffrkevf tpwhnpsedn vatnliyqqv vrgvkfgeyr cekeddlael
1381 asqqyfvdyg semilerlls lvptyipdre itplknlekw aqlaiaahkk giyaqrrtds
1441 qkvkedvvny arfkwpllfs rfyeayksfg pplpksdviv avnwtgvyfv deqeqvllel
1501 sfpeimavss srgtkmmaps ftlatikgde ytftssnaed irdlvvtfle glrkrskyvv
1561 alqdnpnpag eesgflsfak gdliildhdt geqvmnsgwa nginertkqr gdfptdcvyv
1621 mptvtlppre ivalvtmtpd qrqdvvrllq lrtaepevra kpytleefsy dyfrpppkht
1681 lsrvmvskar gkdrlwshtr eplkqallkk ilgseelsqe acmafvavlk ymgdypskrm
1741 rsvneltdqi fewalkaepl kdeayvqilk qltdnhirys eergwellwl ctglfppsni
1801 llphvqrflq srkhcplaid clqrlqkalr ngsrkypphl veveaiqhkt tqifhkvyfp
1861 ddtdeafeve sstkakdfcq niasrlllks segfslfvki adkvisvpen dfffdfvrhl
1921 tdwikkarpi kdgivpslty qvffmkklwt ttvpgkdpma dsifhyyqel pkylrgyhkc
1981 treevlqlga liyrvkfeed ksyfpsipkl lrelvpqdli rqvspddwkr sivayfnkha
2041 gkskeeakla flklifkwpt fgsaffevkq ttepnfpeil liainkygvs lidprtkdil
2101 tthpftkisn wssgntyfhi tignlvrgsk llcetslgyk mddlltsyis qmltamskqr
2161 nsrsgr
```

SEQ ID NO: 79 Rat MYO7A cDNA Sequence (NM_153473.1, CDS region from
position 272-6805)

```
   1 ggccggtgcc attgcaggct ggacagctgc cccgaacaga gagaaagagt gacccaggga
  61 gacaagaaac agagtagccc aagggaaccc cacagcaaca tcagagcaag actcaagctg
 121 gggcaaagta tttgcaggct ccagcctcag cttccagagt cctccagacc tgtgaccct
 181 ggcctgaggc tgggggggtg gtgacccaga gggtgtggat aagaccaga acggtgtctg
 241 gtcactcagg caggtgctct gacgtagaac catggttatt ctacaaaagg gggactacgt
 301 gtggatggac ctgaagtcgg gccaggagtt cgatgtgccc atcggggcca tggtaaagct
 361 ctgtgagtct gggcagatcc aggtggtgga tgatgaaggc aatgaacact ggatttcccc
 421 tcaaaatgcc acgcacatca agccaatgca ccccacatcg gtgcatggtg tggaggacat
 481 gatccgcctg ggggatctca acgaggcagg cattcttcga aaccttctca ttcgctaccg
 541 ggaccatctc atctacacat acgggttc catcctggtg gccgtgaacc cctaccagct
 601 gctgtccatc tactcgtcag agcacatccg ccagtatacc aacaagaaga taggggagat
 661 gcccccccac atctttgcca ttgccgacaa ttgctacttc aacatgaaac gcaacaaccg
 721 ggaccagtgc tgtatcatca gcggggaatc aggagctggc agtcagaga gcacaaagct
 781 gatcctgcag ttcctggcgg ctatcagtgg acagcactca tggatcgagc agcaggtgct
 841 ggaggccacc ccgatcctgg aagcatttgg gaatgccaag accatccgca atgacaactc
 901 cagccgcttt ggcaagtaca ttgacatcca ctttaacaag cgtggtgcca ttgagggcgc
 961 aaaaatagag cagtacctgc tggagaagtc acgagctcgc gccaggccc ctgatgagga
1021 gaactatcac gtgttctact gtatgctgga gggcatgaat gaggaggaga agaagagct
1081 aggcctaggc caggccgctg actacaacta tttggcaatg gtaactgca tcacctgtga
1141 gggccgtgtg gacagtcagg agtatgccaa catccgctca gccatgaagg tgctcatgtt
1201 cacagacacg gagaactggg agatcttgaa gcttctggcc tgccatcctac acatgggcaa
1261 tctgcagtac gaggcccgta cgtttgaaa cttggatgcg tgcgaagtcc tcttctcccc
1321 atcgctggcc acggcagctt ctcatctcga ggtgaatccc ccagacctga tgagctgcct
1381 caccagccgc accctcatca cccgtgggga acggtctcc accccctctca gcagggagca
1441 gccgctggat gtgcgagatg cctttgtcaa gggcatctat gggcgcctt ttgtatgat
1501 tgtggagaag atcaatgcag caatctacaa accaccctct caggaagtga cgaactctcg
1561 ccggtccatc ggtctcctgg acatttttgg gtttgagaac ttcaccgtga acagctttga
1621 gcagctctgc attaactttg ccaatgagca cctgcagcag tttttcgtgc gacacgtgtt
1681 caagttggag caggaggagt atgacttgga gacattgaca tggctgcaca tcgagttcac
1741 tgacaaccac gaggccctgg acatgatcgc caaccggcct atgaacgtca tctccctcat
1801 tgacgaaagg agcaagttcc caagggcac ggatgccacc atgctgcata gttgaactc
1861 acagcacagg ctcaatgcca actacgtccc cccaagaaac agccatgaga cccagtttgg
1921 aatcaaccac tttgcgggca ttgtctacta tgagagtcaa gcttcctgg agaagaacag
1981 agacaccctg catggggaca tcatccagct ggtccactct tcccggaaca gtttgtaaa
```

TABLE 4-continued

```
2041 gcagattttc caggccgacg ttgctatggg tgcagagacc aggaagcgct cgcctacact
2101 cagcagccag ttcaagcggt ctctggagct gctgatgcgc acactgggcg cctgccagcc
2161 cttctttgta cgatgcatca aacccaatga gttcaagaag cccatgctct tcgaccggca
2221 cctgtgtgta cgccagctgc gctattcggg catgatggag actatccgca tccgccacgc
2281 aggctacccc attcgctaca gctttgtgga gtttgtggag cgctaccgcg tgctgctgcc
2341 tggggtgaaa ccagcataca agcaggatga cctccaaggg acatgccagc gcatggctga
2401 ggccgtgctg ggcactcacg atgactggca gattggcaaa accaagatct ttctgaagga
2461 ccaccatgac atgttgctgg aggtggagcg ggacaaggcc atcacagaca gagtcattct
2521 cctccagaag gtcatccggg gcttcaaaga caggtccaac ttcctgagat tgaagagtgc
2581 agccacactg atccagaggc attggcgggg ccaccactgt aggaaaaact atgagctgat
2641 tcgtcttggc ttcctgcggt tgcaggccct gcaccgctcc cggaaactgc acaaacagta
2701 ccgcctggcc agacagcgca taataaagtt ccaggcccgc tgccgggcct acctggtgcg
2761 cagggccttc cgccaccgcc tctgggccgt gatcaccgtg caggcctatg cccggggcat
2821 gattgcgcgc cggctacacc ggcgcctccg agttgagtac tggcggcgcc ttgaggcaga
2881 gaggatgcgg ctggcagagg aggagaagct aagaaaggag atgagtgcca agaaggccaa
2941 ggaggagggcg gagcgcaagc atcaggagcg cctggcccaa ctagcccgcg aggatgcaga
3001 gcgggaactg aaggagaagg aagaggctcg gcggaagaag gagctgttac agcagatgga
3061 gagggcccgc catgagccta tcaaccactc agatatggtg gacaagatgt ttggcttcct
3121 ggggacttca agtggcctgc caggccagga gggccaggca cctagtggct tgaggacct
3181 ggagcgaggg cggagggaga tggtggaaga ggatgtcgat gctgccctgc ccctgcctga
3241 cgaggatgag gaggaccttt ctgagtacaa attcgccaaa tttgctgcca cctacttcca
3301 gggcacaacc acacactcct acacccggag gcccctcaag cagccactgc tctaccacga
3361 tgatgagggt gaccagctgg cggcactggc tgtctggatc accatcctcc ggttcatggg
3421 ggacctccca gagcccaagt accacacagc catgagcgat ggcagtgaga gatccctgt
3481 gatgactaag atctatgaga ccctgggcaa gaagacatac aagagggagc tgcaggccct
3541 gcagggcgag ggcgaggccc agctctctga ggggcagaag aagaccagtg tgaaacacaa
3601 gttggtacac ttgacactga agaagaagtc caaactcaca gaagaggtga ccaagagct
3661 gcatgatggg gagtccatgg tacagggcaa cagcatgctg gaggaccggc ccacctcaaa
3721 tctagagaag ctgcacttca tcattggcaa cggtatcctg cgacctgcac tgcgggatga
3781 gatttactgc cagatcagca gcaactcac acacaaccca tccaagagca gctatgccag
3841 gggctggatc cttgtgtctc tgtgtgtggg atgcttcgcc ccttctgaga gtttgttaa
3901 gtacctacgg aacttcatcc atggaggccc accggctat gccccctact gtgaggagcg
3961 cctgagaagg acctttgtca atggaactcg gacacagcca cccagttggc tggaactgca
4021 ggccaccaag tccaagaagc ccatcatgtt gcccgtgacc ttcatggacg ggaccactaa
4081 gaccctgcta gcagattcag caaccacagc caaggaacta tgcaatgctc tggctgacaa
4141 gatctcactc aaggaccgct ttggcttctc cctctacatt gctctgttcg ataaggtatc
4201 ctccctgggc agtggcagtg accacgtcat ggacgcaatc tcccagtgcg agcagtatgc
4261 caaggagcag ggtgcacagg agcgcaacgc cccctggagg ctcttcttca gaaaggaggt
4321 cttcacaccc tggcacaacc cctcggagga caacgtggcc accaacctca tctaccagca
4381 ggtggtgcga ggagtcaagt ttggggagta caggtgtgag aaggaggatg acctggccga
4441 gttgcctcc cagcagtact ttgtggacta tggttctgag atgattctgg agcgtctgct
4501 gagcctcgtg cccacttaca ttcctgaccg tgagatccaa ccgctaaaga atcttgagaa
4561 gtgggcacag ctggctattg ctgcccacaa gaagggaatt tatgcccaga ggagaactga
4621 tgcccagaag gtcaaacagg atgtggtcaa ttatgcccgt ttcaagtggc ccttgctctt
4681 ttccaggtttt tatgaagcct acaaattctc aggccctccc ctcctaaga gtgacgtcat
4741 cgtggctgtg aactggacgg gcgtctactt cgtggacgag caggagcagg tgcttctgga
4801 gctgtccttt ccggagatca tggctgtgtc cagcagtagg ggagcaaaac tgatggcccc
4861 cagctttaca ctggccacca tcaaaggggga tgagtacaacc ttcacatcta gcaatgctga
4921 ggacatccgt gacctggtgg tcaccttctc tggaggggctc cggaagaggt ctaagtatgt
4981 ggtggcactg caggacaatc ccaaccctgc tggtgaggag tcgggcttcc tcagctttgc
5041 caagggagac ctcatcattc tcgaccatga taccggcgag caggtcatga attcaggctg
5101 ggccaatggc atcaacgaga gaaccaagca gcgtggagac ttccccaccg actgtgtcta
5161 cgtcatgccc actgtcacct tgccaccag ggaaattgtg gccctggtca ctatgacccc
5221 agaccagagg caggatgttg tccggcttct gcagctgcgc acagcagagc cagaggtgcg
5281 caccaagccc tacacgctgg aggagttctc ctatgactac ttcaggtccc cacccaagca
5341 cacgctgagc cgtgtcatgg tgtccaaggc ccgagggaag gaccgactgt ggagtcacac
5401 acgagagccc ctcaagcagg ccctgctcaa gaagatcgtg ggcagcgagg aactctccca
5461 ggaagcctgc atgtccttca tagctgtgct caagtacatg ggtgactacc catccaagag
5521 gacacgctct gtcaatgagc tcactgacca gatcttcgag tgggcagtga aggccgagcc
5581 cctcaaagat gaggcctacg tgcagatcct gaagcagctg actgacaatc atatcaggta
5641 cagcgaagag aagggttggg agctgctgtg gctgtgcaca ggcctcttcc cacccagcaa
5701 catcctcctg cctcatgttc agcgtttcct gcagtcccgc aaacactgtc ctcttgccat
5761 tgactgccta caaaggctcc agaaagccct gaaaacgggg tcccggaagt accctccaca
5821 cctggtggag gtagaggcca tccagcacaa gactacccag atttttccaca aggtctactt
5881 ccctgacgac acgatgagg cttttgaggt agagtccagc accaaggcca aggacttctg
5941 ccagaacatc gccagccggc tgctcctcaa gtcttctgag ggattcagcc ttttgtcaa
6001 aatcgcagat aaggtcatca gcgtccctga aatgacttc ttctttgact tgttcgaca
6061 cctgacagac tggataaaga aggcacggcc catcaaggat ggaatctgac cctcactgac
6121 ctaccaggtg ttcttcatga agaagctgtg gaccaccacc gtgcctggca aggacccat
6181 ggccgactcc atattccact attaccagga actgccaag tatctccgag ctaccacaa
6241 gtgcacccgg gaggaggtgc tacagctggg cgcgctcatc tacagggtca gtttgagga
6301 ggacaaatcc tacttcccta gcatcccaa gttgctgagg gagctggtgc cccaggacct
6361 aatccggcag gtctcacctg atgactgaa acggtctatt gtcgcctact tcaacaagca
6421 tgcagggaag tccaaggagg aggccaagct ggccttcctc aagctcatct tcaagtggcc
6481 cacctttgga tcagccttct ttgaggtgaa gcaaacgaca gaaccaaact tcccagagat
```

TABLE 4-continued

```
6541 tctcttaatt gccatcaaca agtatgggat cagcctcatc gatcccagaa ccaaggacat
6601 cttgactact caccccttca ccaagatctc caactggagt agtggcaaca cctacttcca
6661 catcaccatt gggaacttgg tccgtgggag caaactgctc tgtgagacat cactgggata
6721 caaaatggat gatcttctga cttcctacat cagccagatg ctcactgcca tgagcaaaca
6781 gaggaactcc aggagcggga ggtgaac SEQ ID NO: 80 Rat Myo7a Amino Acid Sequence (NP_703203.1)
    1 mvilqkgdyv wmdlksgqef dvpigamvkl cesgqiqvvd degnehwisp qnathikpmh
   61 ptsvhgvedm irlgdlneag ilrnlliryr dhliytytgs ilvavnpyql lsiyssehir
  121 qytnkkigem pphifaiadn cyfnmkrnnr dqcciisges gagktestkl ilqflaaisg
  181 qhswieqqvl eatpileafg naktirndns srfgkyidih fnkrgaiega kieqylleks
  241 rvcrqapder nyhvfycmle gmneeekkkl glgqaadyny lamgncitce grvdsqeyan
  301 irsamkvlmf tdtenweilk llaailhmgn lqyeartfen ldacevlfsp slataashle
  361 vnppdlmscl tsrtlitrge tvstplsreq aldvrdafvk giygrlfvwi vekinaaiyk
  421 ppsqevtnsr rsiglldifg fenftvnsfe qlcinfaneh lqqffvrhvf kleqeeydle
  481 sidwlhieft dnqealdmia nrpmnvisli deeskfpkgt datmlhklns qhrlnanyvp
  541 pknshetqfg inhfagivyy esqgfleknr dtlhgdiiql vhssrnkfvk qifqadvamg
  601 aetrkrsptl ssqfkrslel lmrtlgacqp ffvrcikpne fkkpmlfdrh lcvrqlrysg
  661 mmetirirha gypirysfve fveryrvllp gvkpaykqdd lqgtcqrmae avlgthddwq
  721 igktkiflkd hhdmllever dkaitdrvil lqkvirgfkd rsnflrlksa atliqrhwrg
  781 hhcrknyeli rlgflrlqal hrsrklhkqy rlarqriikf qarcraylvr rafrhrlwav
  841 itvqayargm iarrlhrrlr veywrrleae rmrlaeeekl rkemsakkak eeaerkhqer
  901 laqlaredae relkekeear rkkellqqme rarhepinhs dmvdkmfgfl gtssglpgqe
  961 gqapsgfedl ergrremvee dvdaalplpd edeedlseyk fakfaatyfq gttthsytrr
 1021 plkqpllyhd degdqlaala vwitilrimg dlpepkyhta msdgsekipv mtkiyetlgk
 1081 ktykrelqal qgegeaqlse gqkktsvkhk lvhltlkkks klteevtkrl hdgesmvqgn
 1141 smledrptsn leklhfiign gilrpalrde iycqiskqlt hnpsksssyar gwilvslcvg
 1201 cfapsekfvk ylrnfihggp pgyapyceer lrrtfvngtr tqppswlelq atkskkpiml
 1261 pvtfmdgttk tlladsatta kelcnaladk islkdrfgfs lyialfdkvs slgsgsdhvm
 1321 daisqceqya keqgaqerna pwrlffrkev ftpwhnpsed nvatnliyqq vvrgvkfgey
 1381 rcekeddlae lasqqyfvdy gsemilerll slvptyipdr eitplknlek waqlaiaahk
 1441 kgiyaqrrtd aqkvkqdvvn yarfkwpllf srfyeaykfs gpplpksdvi vavnwtgvyf
 1501 vdeqeqvlle lsfpeimavs ssrgaklmap sftlatikgd eytftssnae dirdlvvtfl
 1561 eglrkrskyv valqdnpnpa geesgflsfa kgdliildhd tgeqvmnsgw anginertkq
 1621 rgdfptdcvy vmptvtlppr eivalvtmtp dqrqdvvrll qlrtaepevr tkpytleefs
 1681 ydyfrsppkh tlsrvmvska rgkdrlwsht replkqallk kivgseelsq eacmsfiavl
 1741 kymgdypskr trsvneltdq ifewavkaep lkdeayvqil kqltdnhiry seekgwellw
 1801 lctglfppsn illphvqrfl qsrkhcplai dclqrlqkal rngsrkypph lveveaiqhk
 1861 ttqifhkvyf pddtdeafev esstkakdfc qniasrlllk ssegfslfvk iadkvisvpe
 1921 ndfffdfvrh ltdwikkarp ikdgivpslt yqvffmkklw tttvpgkdpm adsifhyyqe
 1981 lpkylrgyhk ctreevlqlg aliyrvkfee dksyfpsipk llrelvpqdl irqvspddwk
 2041 rsivayfnkh agkskeeakl aflklifkwp tfgsaffevk qttepnfpei lliainkygi
 2101 slidprtkdi ltthpftkis nwssgntyfh itignlvrgs kllcetslgy kmddlltsyi
 2161 sqmltamskq rnsrsgr SEQ ID NO: 46 Representative Myo7a peptides associated with Qa-1b
AITDRVILL
(corresponding to residues 743-751 from UniProtKB/Swiss-Prot: P97479.2
available on the World Wide Web at uniprot.org/uniprot/P97479.2)
```

Binding of HLA-E to Myo7a peptides allows HLA-E to bind to T cell receptor and activate CD8+ T cells.

* Included in Table 4 are RNA nucleic acid molecules (e.g., thymines replaced with uridines), nucleic acid molecules encoding orthologs of the encoded proteins, as well as DNA or RNA nucleic acid sequences comprising a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with the nucleic acid sequence of any SEQ ID NO listed in Table 4, or a portion thereof. Such nucleic acid molecules can have a function of the full-length nucleic acid as described further herein.

* Included in Table 4 are orthologs of the proteins, as well as polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of any SEQ ID NO listed in Table 4, or a portion thereof. Such polypeptides can have a function of the full-length polypeptide as described further herein.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web at tigr.org and/or the National Center for Biotechnology Information (NCBI) on the World Wide Web at ncbi.nlm.nih.gov.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating a subject afflicted with a cancer comprising administering to the subject a therapeutically effective amount of a nucleic acid agent that inhibits the copy number or the expression level of signal peptide peptidase (SPP) in combination with an immunotherapy, wherein the immunotherapy inhibits an immune checkpoint.

2. The method of claim 1, wherein the agent:
   i) decreases CD94/NKG2A-mediated inhibition of NK cells or T cells in the subject;
   ii) decreases HLA-E-mediated inhibition of NK cells or T cells in the subject;
   iii) increases HLA-E-mediated killing of cancer cells by CD8+ T cells in the subject;
   iv) increases the sensitivity of the cancer cells to the immunotherapy; or
   v) increases the number of CD8+ T cells or NK cells in a tumor comprising the cancer cells in the subject.

3. The method of claim 1, wherein the agent is a CRISPR single-guide RNA (sgRNA), RNA interfering agent, or an antisense oligonucleotide.

4. The method of claim 3, wherein the gRNA comprises a nucleic acid sequence selected from the group consisting of SEQ ID NOs: 62-66.

5. The method of claim 1, wherein the SPP is encoded by a nucleic acid encoding an amino acid sequence having at least 95% identity to an amino acid sequence comprising a nucleic acid sequence selected from the group consisting of SEQ ID NOs: 2, 4, 6, 8, 10, 12, 14, and 16.

6. The method of claim 1, wherein the SPP comprises an amino acid sequence having at least 95% identity to an amino acid sequence selected from the group consisting of SEQ ID NOs: 2, 4, 6, 8, 10, 12, 14, and 16.

7. The method of claim 1, wherein the immunotherapy is administered concurrently with the agent.

8. The method of claim 1, wherein the immunotherapy is administered after the agent.

9. The method of claim 1, wherein the cancer is selected from the group consisting of melanoma, glioblastoma, lung cancer, prostate cancer, squamous cell carcinoma, adenocarcinoma, cervical carcinoma, head and neck carcinoma, and gastric cancer.

10. The method of claim 1, wherein the subject is selected from the group consisting of a human, a mouse, and an animal model of the cancer.

11. A method of killing cancer cells comprising contacting the cancer cell with qanila nucleic acid agent that inhibits the copy number or the expression level of SPP in combination with contacting immune cells with an immunotherapy, wherein the immunotherapy inhibits an immune checkpoint and the immune cells are i) selected from the group consisting of NK cells and T cells and ii) located in the presence of the cancer cells.

12. The method of claim 11, wherein the agent:
   i) decreases CD94/NKG2A-mediated inhibition of the NK cells or T cells;
   ii) decreases HLA-E-mediated inhibition of the NK cells or T cells;
   iii) increases HLA-E-mediated killing of cancer cells by CD8+ T cells;
   iv) increases the sensitivity of the cancer cells to the immunotherapy; or
   v) increases the number of the CD8+ T cells or NK cells in a tumor comprising the cancer cells.

13. The method of claim 11, wherein the agent is a CRISPR single-guide RNA (sgRNA), RNA interfering agent, or an antisense oligonucleotide.

14. The method of claim 13, wherein the gRNA comprises a nucleic acid sequence selected from the group consisting of SEQ ID NOs: 62-66.

15. The method of claim 11, wherein the SPP is encoded by a nucleic acid encoding an amino acid sequence having at least 95% identity to an amino acid sequence comprising a nucleic acid sequence selected from the group consisting of SEQ ID NOs: 2, 4, 6, 8, 10, 12, 14, and 16.

16. The method of claim 11, wherein the SPP comprises an amino acid sequence having at least 95% identity to an amino acid sequence selected from the group consisting of SEQ ID NOs: 2, 4, 6, 8, 10, 12, 14, and 16.

17. The method of claim 11, wherein the immunotherapy contacts the immune cells concurrently with contacts of the cancer cells with the agent.

18. The method of claim 11, wherein the immunotherapy contacts the immune cells after contact of the cancer cells with the agent.

19. The method of claim 11, wherein the cancer is selected from the group consisting of melanoma, glioblastoma, lung cancer, prostate cancer, squamous cell carcinoma, adenocarcinoma, cervical carcinoma, head and neck carcinoma, and gastric cancer.

20. The method of claim 11, wherein the cancer cells are human cancer cells, mouse cancer cells, or cancer cells of an animal model of the cancer.

\* \* \* \* \*